US012577546B2

(12) United States Patent (10) Patent No.: US 12,577,546 B2
Sontheimer et al. (45) Date of Patent: Mar. 17, 2026

(54) PROGRAMMABLE DNA BASE EDITING BY Nme2Cas9-DEAMINASE FUSION PROTEINS

(71) Applicant: UNIVERSITY OF MASSACHUSETTS, Boston, MA (US)

(72) Inventors: Erik J Sontheimer, Auburndale, MA (US); Xin Gao, Maynard, MA (US); Aamir Mir, Pleasanton, CA (US); Alireza Edraki, Worcester, MA (US); Scot A Wolfe, Winchester, MA (US); Pengpeng Liu, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 1305 days.

(21) Appl. No.: 17/285,440

(22) PCT Filed: Oct. 15, 2019

(86) PCT No.: PCT/US2019/056341
§ 371 (c)(1),
(2) Date: Apr. 14, 2021

(87) PCT Pub. No.: WO2020/081568
PCT Pub. Date: Apr. 23, 2020

(65) Prior Publication Data
US 2022/0290113 A1     Sep. 15, 2022

Related U.S. Application Data

(60) Provisional application No. 62/745,666, filed on Oct. 15, 2018.

(51) Int. Cl.
C12N 9/22     (2006.01)
A61P 3/00     (2006.01)
C12N 9/78     (2006.01)
C12N 15/11    (2006.01)
C12N 15/62    (2006.01)
C12N 15/86    (2006.01)

(52) U.S. Cl.
CPC .................. *C12N 9/22* (2013.01); *A61P 3/00* (2018.01); *C12N 9/78* (2013.01); *C12N 15/11* (2013.01); *C12N 15/625* (2013.01); *C12N 15/86* (2013.01); *C12Y 305/04004* (2013.01); *C12Y 305/04005* (2013.01); *C07K 2319/09* (2013.01); *C12N 2310/20* (2017.05); *C12N 2750/14122* (2013.01); *C12N 2750/14142* (2013.01); *C12N 2750/14171* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 3,817,837 | A | 6/1974 | Rubenstein et al. | 435/7.9 |
| 3,850,752 | A | 11/1974 | Schuurs et al. | 435/7.93 |
| 3,939,350 | A | 2/1976 | Kronick et al. | 250/365 |
| 3,996,345 | A | 12/1976 | Ullman et al. | 436/537 |
| 4,275,149 | A | 6/1981 | Litman et al. | 435/7.91 |
| 4,277,437 | A | 7/1981 | Maggio | 422/401 |
| 4,366,241 | A | 12/1982 | Tom et al. | 435/7.91 |
| 2015/0166980 | A1 | 6/2015 | Liu et al. | 435/227 |
| 2017/0121693 | A1 | 5/2017 | Liu et al. | |

FOREIGN PATENT DOCUMENTS

| | | |
|---|---|---|
| WO | WO 2017/070633 A | 4/2017 |
| WO | WO 2017/070633 B | 4/2017 |
| WO | WO 2018/027078 | 8/2018 |
| WO | WO 2018/027078 B | 8/2018 |
| WO | WO 2018/027078 C | 8/2018 |
| WO | WO 2018/149915 | 8/2018 |
| WO | WO 2018/152197 | 8/2018 |
| WO | WO 2018/176009 | 9/2018 |

OTHER PUBLICATIONS

Amrani, et al., "NmeCas9 Is an Intrinsically High-Fidelity Genome Editing Platform." bioRxiv:https://doi.org/10.1101/172650 (1-58) (2018).
Barrangou, et al., "CRISPR Provides Acquired Resistance against Viruses in Prokaryotes." *Science*, 315(5819):1709-1712 (2007).
Bisaria, et al., "Lessons from Enzyme Kinetics Reveal Specificity Principles for RNA-Guided Nucleases in RNA Interference and CRISPR-Based Genome Editing." *Cell Syst.*, 4(1):21-29 (2017).
Bolukbasi, et al., "DNA-Binding-Domain Fusions Enhance the Targeting Range and Precision of Cas9." *Nat. Methods*, 12(12):1150-1156 (2015a).
Bolukbasi, et al., "Creating and Evaluating Accurate CRISPR-Cas9 Scalpels for Genomic Surgery." *Nat. Methods*, 13(1):41-50 (2015b).
Brinkman, et al., "Easy Quantitative Assessment of Genome Editing by Sequence Trace Decomposition." *Nucleic Acids Res.*, 42(22):e168 (pp. 1-8) (2014).
Brouns, et al., "Small CRISPR RNAs Guide Antiviral Defense in Prokaryotes." *Science*, 321(5891):960-964 (2008).
Casini, et al., "A Highly Specific SpCas9 Variant Is Identified by in Vivo Screening in Yeast." *Nat Biotechnol*, 36(3):265-271 (2018).
(Continued)

*Primary Examiner* — Michael D Burkhart
(74) *Attorney, Agent, or Firm* — Medlen & Carroll, LLP

(57) ABSTRACT

The present invention is related to the field of gene editing. In particular, the gene editing is directed toward single nucleotide base editing. For example, such single nucleotide base editing results in a conversion of a OG base pair to a T*A base pair. The high accuracy and precision of the presently disclosed single nucleotide base gene editor is accomplished by an NmeCas9 nuclease that is fused to a nucleotide deaminase protein. The compact nature of the NmeCas9 coupled with a larger number of compatible protospacer adjacent motifs provide the Cas9 fusion constructs contemplated herein to have a gene editing window that can edit sites that are not targetable by other conventional SpCas9 base editor platforms.

11 Claims, 45 Drawing Sheets

Specification includes a Sequence Listing.

(56) References Cited

OTHER PUBLICATIONS

Certo, et al., "Tracking Genome Engineering Outcome at Individual DNA Breakpoints." *Nat. Methods*, 8(8):671-676 (2011).
Chen, et al., "Enhanced Proofreading Governs CRISPR-Cas9 Targeting Accuracy." *Nature*, 550(7676):407-410 (2017).
Cho, et al., "Targeted Genome Engineering in Human Cells with the Cas9 RNA-Guided Endonuclease." *Nat Biotechnol*, 31(3):230-232 (2013).
Cho, et al., "Analysis of Off-Target Effects of CRISPR/Cas-Derived RNA-Guided Endonucleases and Nickases." *Genome Res*, 24(1):132-141 (2014).
Cong, et al., "Multiplex Genome Engineering Using CRISPR/Cas Systems." *Science*, 339(6121):819-823 (2013).
Deltcheva, et al., "CRISPR RNA Maturation by Trans-Encoded Small RNA and Host Factor RNAse III." *Nature*, 471(7340):602-607 (2011).
Deveau, et al., "Phage Response to CRISPR-Encoded Resistance in *Streptococcus thermophilus.*" *J Bacteriol*, 190(4):1390-1400 (2008).
Dominguez, et al., "Beyond Editing: Repurposing CRISPR-Cas9 for Precision Genome Regulation and Interrogation." *Nat. Rev. Mol. Cell Biol.*, 17(1):5-15 (2016).
Dong, et al., "Structural Basis of CRISPR-SpyCas9 Inhibition by an Anti-CRISPR Protein." *Nature*, 546(7658):436-439 (2017).
Esvelt, et al., "Orthogonal Cas9 Proteins for RNA-Guided Gene Regulation and Editing." *Nat. Methods*, 10(11):1116-1121 (2013).
Fonfara, et al., "Phylogeny of Cas9 Determines Functional Exchange-ability of Dual-RNA and Cas9 among Orthologous Type II CRISPR-Cas Systems." *Nucleic Acids Res.*, 42(4):2577-2590 (2014).
Friedland, et al., "Characterization of *Staphylococcus aureus* Cas9: A Smaller Cas9 for All-in-One Adeno-Associated Virus Delivery and Paired Nickase Applications." *Genome Biol.*, 16:257 (pp. 1-10) (2015).
Friedrich and Soriano, "Promoter Traps in Embryonic Stem Cells: A Genetic Screen to Identify and Mutate Developmental Genes in Mice." *Genes Dev.*, 5(9):1513-1523 (1991).
Fu, et al., "Improving CRISPR-Cas Nuclease Specificity Using Truncated Guide RNAs." *Nat Biotechnol*, 32(3):279-284 (2014).
Gallagher and Haber, "Repair of a Site-Specific DNA Cleavage: Old-School Lessons for Cas9-Mediated Gene Editing." *ACS Chem. Biol.*, 13(2):397-405 (2018).
Garneau, et al., "The CRISPR/Cas Bacterial Immune System Cleaves Bacteriophage and Plasmid DNA." *Nature*, 468(7320):67-71 (2010).
Gasiunas, et al., "Cas9-CrRNA Ribonucleoprotein Complex Mediates Specific DNA Cleavage for Adaptive Immunity in Bacteria." *Proc Natl Acad Sci USA*, 109(39):E2579-2586 (2012).
Gaudelli, et al., "Programmable Base Editing of a *T to G*C in Genomic DNA without DNA Cleavage." *Nature*, 551(7681):464-471 (2017).
Ghanta, et al., "5' Modifications Improve Potency and Efficacy of DNA Donors for Precision Genome Editing." bioRxiv:354480 (2021).
Gorski, et al., "RNA-Based Recognition and Targeting: Sowing the Seeds of Specificity." *Nat. Rev. Mol. Cell Biol.*, 18(4):215-228 (2017).
Harrington, et al., "A Broad-Spectrum Inhibitor of CRISPR-Cas9." *Cell*, 170(6):1224-1233 (2017a).
Harrington, et al., "A Thermostable Cas9 with Increased Lifetime in Human Plasma." *Nat. Commun.*, 8(1):1424 (2017b).
Hou, et al., "Efficient Genome Engineering in Human Pluripotent Stem Cells Using Cas9 from *Neisseria meningitidis.*" *Proc Natl Acad Sci USA*, 110(39):15644-15649 (2013).
Hu, et al., "Evolved Cas9 Variants with Broad Pam Compatibility and High DNA Specificity." *Nature*, 556(7699):57-63 (2018).
Hwang, et al., "Efficient Genome Editing in Zebrafish Using a CRISPR-Cas System." *Nat Biotechnol*, 31(3):227-229 (2013).
Hynes, et al., "An Anti-CRISPR from a Virulent Streptococcal Phage Inhibits *Streptococcus pyogenes* Cas9." *Nat. Microbiol.*, 2:1374-1380 (2017).

Ibraheim, et al., "All-in-One Adeno-Associated Virus Delivery and Genome Editing by Neisseria Meningitidis Cas9 in Vivo." bioRxiv:https://doi.org/10.1101/295055 (1-36) (2018).
Jiang, et al., "RNA-Guided Editing of Bacterial Genomes Using CRISPR-Cas Systems." *Nat Biotechnol*, 31(3):233-239 (2013).
Jiang and Doudna, "CRISPR-Cas9 Structures and Mechanisms." *Annu Rev Biophys*, 46:505-529 (2017).
Jinek, et al., "A Programmable Dual-RNA-Guided DNA Endonuclease in Adaptive Bacterial Immunity." *Science*, 337(6096):816-821 (2012).
Jinek, et al., "RNA-Programmed Genome Editing in Human Cells." *eLife*, 2:e00471 (1-9) (2013).
Karvelis, et al., "Rapid Characterization of CRISPR-Cas9 Protospacer Adjacent Motif Sequence Elements." *Genome Biol.*, 16:253 (1-13) (2015).
Keeler, et al., "Gene Therapy 2017: Progress and Future Directions." *Clin. Transl. Sci.*, 10(4):242-248 (2017).
Kim, et al., "Highly Efficient RNA-Guided Genome Editing in Human Cells Via Delivery of Purified Cas9 Ribonucleoproteins." *Genome Res*, 24(6):1012-1019 (2014).
Kim, et al., "In Vivo Genome Editing with a Small Cas9 Ortholog Derived from *Campylobacter jejuni.*" *Nat. Commun.*, 8:14500 (1-12) (2017a).
Kim, et al., "Increasing the Genome-Targeting Scope and Precision of Base Editing with Engineered Cas9-Cytidine Deaminase Fusions." *Nat Biotechnol*, 35(4):371-376 (2017b).
Kleinstiver, et al., "Broadening the Targeting Range of *Staphylococcus aureus* CRISPR-Cas9 by Modifying PAM Recognition." *Nat Biotechnol*, 33(12):1293-1298 (2015).
Kluesner, et al., "EditR: A Method to Quantify Base Editing from Sanger Sequencing." *CRISPR J*, 1(3):239-250 (2018).
Koblan, et al., "Improving Cytidine and Adenine Base Editors by Expression Optimization and Ancestral Reconstruction." *Nature Biotechnology*, 36(9):843-846 (2018).
Komor, et al., "Programmable Editing of a Target Base in Genomic DNA without Double-Stranded DNA Cleavage." *Nature*, 533(7603):420-424 (2016).
Komor, et al., "CRISPR-Based Technologies for the Manipulation of Eukaryotic Genomes." *Cell*, 168(1-2):20-36 (2017).
Lee, et al., "The *Neisseria meningitidis* CRISPR-Cas9 System Enables Specific Genome Editing in Mammalian Cells." *Mol. Ther.*, 24(3):645-654 (2016).
Lee, et al., "Potent Cas9 Inhibition in Bacterial and Human Cells by ACRIIC4 and ACRIIC5 Anti-Crispr Proteins." *mBio*, 9(6)(1-26) (2018).
Ma, et al., "Single-Stranded DNA Cleavage by Divergent CRISPR-Cas9 Enzymes." *Mol. Cell*, 60(3):398-407 (2015).
Mali, et al., "Cas9 Transcriptional Activators for Target Specificity Screening and Paired Nickases for Cooperative Genome Engineering." *Nat Biotechnol*, 31(9):833-838 (2013a).
Mali, et al., "RNA-Guided Human Genome Engineering Via Cas9." *Science*, 339(6121):823-826 (2013b).
Marraffini and Sontheimer, "CRISPR Interference Limits Horizontal Gene Transfer in Staphylococci by Targeting DNA." *Science*, 322(5909):1843-1845 (2008).
Mir, et al., "Type II-C CRISPR-Cas9 Biology, Mechanism and Application." *ACS Chem. Biol.*, 13(2):357-365 (2018).
Mojica, et al., "Short Motif Sequences Determine the Targets of the Prokaryotic CRISPR Defence System." *Microbiology*, 155(Pt 3):733-740 (2009).
Paez-Espino, et al., "CRISPR Immunity Drives Rapid Phage Genome Evolution in *Streptococcus thermophilus.*" *MBio*, 6(2):6 (1-9) (2015).
Pawluk, et al., "A New Group of Phage Anti-CRISPR Genes Inhibits the Type I-E CRISPR-Cas System of Pseudomonas Aeruginosa." *mBio*, 5(2):e00896 (1-7) (2014).
Pawluk, et al., "Naturally Occurring Off-Switches for CRISPR-Cas9." *Cell*, 167(7):1829-1838 e1829 (2016).
Pinello, et al., "Analyzing CRISPR Genome-Editing Experiments with CRISPResso." *Nat Biotechnol*, 34(7):695-697 (2016).
Racanelli and Rehermann, "The Liver as an Immunological Organ." *Hepatology*, 43(2 Suppl 1):S54-62 (2006).
Ran, et al., "Double Nicking by RNA-Guided CRISPR Cas9 for Enhanced Genome Editing Specificity." *Cell*, 154(6):1380-1389 (2013).

(56) References Cited

OTHER PUBLICATIONS

Ran, et al., "In Vivo Genome Editing Using *Staphylococcus aureus* Cas9." *Nature*, 520(7546):186-191 (2015).

Rashid, et al., "Decreased Plasma Cholesterol and Hypersensitivity to Statins in Mice Lacking Pcsk9." *Proc Natl Acad Sci USA*, 102(15):5374-5379 (2005).

Rauch, et al., "Inhibition of CRISPR-Cas9 with Bacteriophage Proteins." *Cell*, 168(1-2):150-158 e110 (2017).

Sapranauskas, et al., "The *Streptococcus thermophilus* CRISPR/Cas System Provides Immunity in *Escherichia coli.*" *Nucleic Acids Res.*, 39(21):9275-9282 (2011).

Schumann, et al., "Generation of Knock-in Primary Human T Cells Using Cas9 Ribonucleoproteins." *Proc Natl Acad Sci USA*, 112(33):10437-10442 (2015).

Seidah, et al., "The Secretory Proprotein Convertase Neural Apoptosis-Regulated Convertase 1 (Narc-1): Liver Regeneration and Neuronal Differentiation." *Proc Natl Acad Sci U S A*, 100(3):928-933 (2003).

Shin, et al., "Disabling Cas9 by an Anti-CRISPR DNA Mimic." *Sci. Adv.*, 3(7):e1701620 (1-9) (2017).

Tsai, et al., "GUIDE-Seq Enables Genome-Wide Profiling of Off-Target Cleavage by CRISPR-Cas Nucleases." *Nat Biotechnol*, 33:187-197 (2014).

Tsai and Joung, "Defining and Improving the Genome-Wide Specificities of CRISPR-Cas9 Nucleases." *Nat. Rev. Genet.*, 17(5):300-312 (2016).

Tycko, et al., "Methods for Optimizing CRISPR-Cas9 Genome Editing Specificity." *Mol. Cell*, 63(3):355-370 (2016).

Yang and Patel, "Inhibition Mechanism of an Anti-CRISPR Suppressor ACRIIA4 Targeting Spycas9." *Mol Cell*, 67(1):117-127 e115 (2017).

Yin, et al., "Partial DNA-Guided Cas9 Enables Genome Editing with Reduced Off-Target Activity." *Nat. Chem. Biol.*, 14(3):311-316 (2018).

Yokoyama, et al., "Conserved Cysteine to Serine Mutation in Tyrosinase Is Responsible for the Classical Albino Mutation in Laboratory Mice." *Nucleic Acids Res.*, 18(24):7293-7298 (1990).

Yoon, et al., "Streamlined Ex Vivo and in Vivo Genome Editing in Mouse Embryos Using Recombinant Adeno-Associated Viruses." *Nat. Commun.*, 9(1):412 (1-12) (2018).

Zhang, et al., "Strand-Specific Libraries for High Throughput RNA Sequencing (RNA-Seq) Prepared without Poly(A) Selection." *Silence*, 3(1):9 (1-9) (2012).

Zhang, et al., "Processing-Independent CRISPR RNAs Limit Natural Transformation in *Neisseria meningitidis.*" *Mol. Cell*, 50(4):488-503 (2013).

Zhang, et al., "DNAse H Activity of *Neisseria meningitidis* Cas9." *Mol. Cell*, 60:242-255 (2015).

Zhu, et al., "CRISPRseek: A Bioconductor Package to Identify Target-Specific Guide RNAs for CRISPR-Cas9 Genome-Editing Systems." *PloS one*, 9(9):e108424 (1-7) (2014).

Zhu, et al., "GUIDEseq: A Bioconductor Package to Analyze GUIDE-Seq Datasets for CRISPR-Cas Nucleases." *BMC Genomics*, 18:379 (1-10) (2017).

Zuris, et al., "Cationic Lipid-Mediated Delivery of Proteins Enables Efficient Protein-Based Genome Editing in Vitro and in Vivo." *Nat Biotechnol*, 33(1):73-80 (2015).

Edraki, et al., "A Compact, High-Accuracy Cas9 with a Dinucleotide PAM for In vivo Genome Editing." *Mol Cell*, 73(4):714-726 e714 (2019).

Eid, et al., "CRISPR Base Editors: Genome Editing without Double-Stranded Breaks." *Biochem J*, 475(11):1955-1964 (2018).

Kleinstiver, et al., "Engineered CRISPR-Cas9 Nucleases with Altered PAM Specificities." *Nature*, 523(7561):481-485 (2015b).

Rousseau, et al., "Programmable RNA Cleavage and Recognition by a Natural CRISPR-Cas9 System from *Neisseria meningitidis.*" *Mol Cell*, 69(5):906-914 e904 (2018).

Endogenous Genomic Site - TS25

```
                  1 2 3 4 5 6 7 8 9 10 11 12 13 14 15 16 17 18 19 20 21 22 23
                  ACTCACTCACCCACACAGACACAC
SEQ ID NO: 969    ::CACAC              ::ACGTCCTCAC:::
SEQ ID NO: 970    ::GTGTGTGAGTGAGTGGGTGTGTCTGTGTGCAGGAGTG:::
SEQ ID NO: 971    5'--GCUCACU CACCCACACAGACACAC ACGUUGU••• GN23
```

```
C T C A C T C A C C C A C A C A G A C A C A C A C G T C C T
```

Fig. 3E c-fos site 3 (nNmeCas9-YE1-BE3)

|  | 1 2 3 4 5 6 7 8 9 10 11 12 13 14 15 16 17 18 19 20 21 22 23 | PAM | 3' | reference |
|---|---|---|---|---|
| SEQ ID NO: 900 | aGCCTTTCCCTGTAGCCCTGGGG | GGAGCCA | | |
| SEQ ID NO: 901 | aGCCTTTCCCTGTAGCCCTGGGG | GGAGCCA | | 42.44% |
| SEQ ID NO: 902 | aGCCTTTCCCTGTAGCCCTGGGG | GGAGCCA | | 32.50% |
| SEQ ID NO: 903 | aGCCTTTTCTGTAGCCCTGGGG | GGAGCCA | | 9.79% |
| SEQ ID NO: 904 | aGCCTTTACCTGTAGCCCTGGGG | GGAGCCA | | 3.15% |
| SEQ ID NO: 905 | aGCCTTTTTTGTAGCCCTGGGG | GGAGCCA | | 2.92% |
| SEQ ID NO: 906 | aGCCTTTTGCCTGTAGCCCTGGGG | GGAGCCA | | 1.03% |
| SEQ ID NO: 907 | aGCCTTTTCTTGTAGCCCTGGGG | GGAGCCA | | 1.04% |
| SEQ ID NO: 908 | aGCCTTT-CCTGTAGCCCTGGGG | GGAGCCA | | 0.60% |
| SEQ ID NO: 909 | aGCCTTTCCTTGTAGCCCTGGGG | GGAGCCA | | 0.59% |
| SEQ ID NO: 910 | aGCCTTTCTCTGTAGCCCTGGGG | GGAGCCA | | 0.31% | c-fos site 10: ABE7.10-nNme2Cas9 (D16A)

|  | reference |
|---|---|
|  | 98.47% |
|  | 0.53% | c-fos site 10: ABEmax-nNme2Cas9 (D16A)

|  | reference |
|---|---|
|  | 96.54% |
|  | 2.33% |

SEQ ID NO: 911
SEQ ID NO: 912
SEQ ID NO: 913

SEQ ID NO: 914
SEQ ID NO: 915
SEQ ID NO: 916

Fig. 4

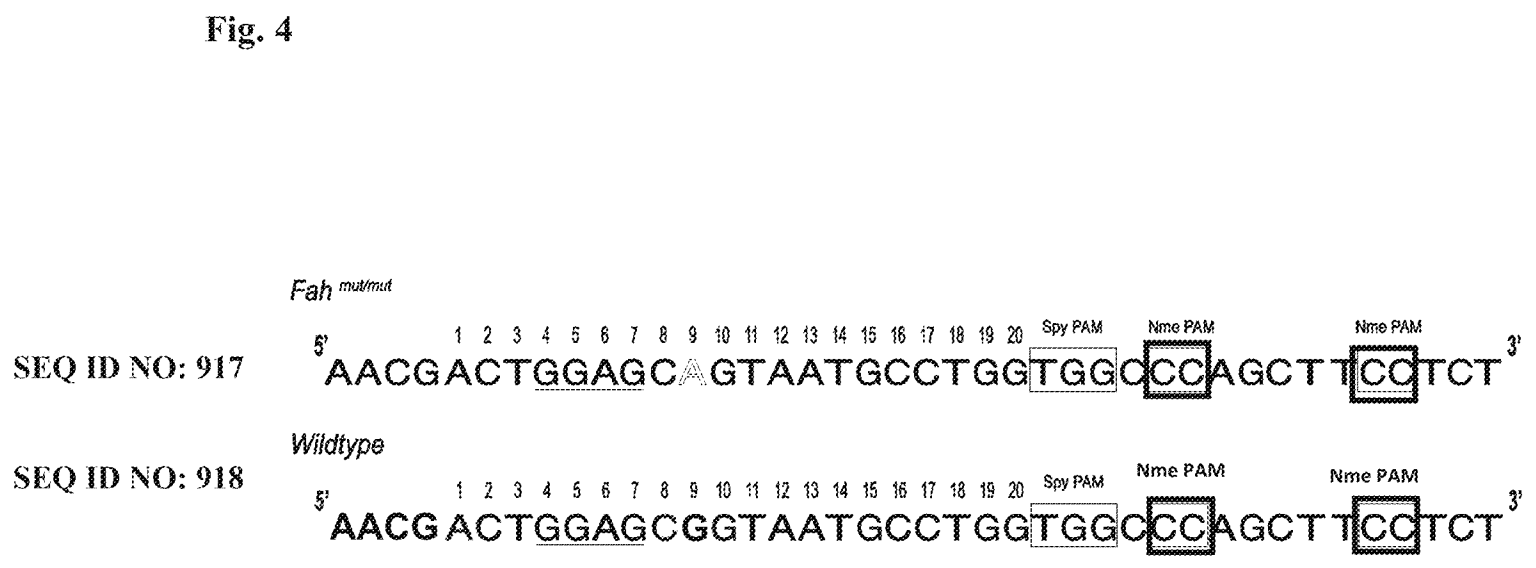

*Fah* ^mut/mut^

5′ AACG ACTGGAGCAGTAATGCCTGG TGG CCAGCT TCCT TCT 3′
     1 2 3 4 5 6 7 8 9 10 11 12 13 14 15 16 17 18 19 20 Spy PAM  Nme PAM  Nme PAM

SEQ ID NO: 917

*Wildtype*

5′ AACG ACTGGAGCGGTAATGCCTGG TGG CCAGCT TCCT TCT 3′
     1 2 3 4 5 6 7 8 9 10 11 12 13 14 15 16 17 18 19 20 Spy PAM  Nme PAM  Nme PAM

SEQ ID NO: 918

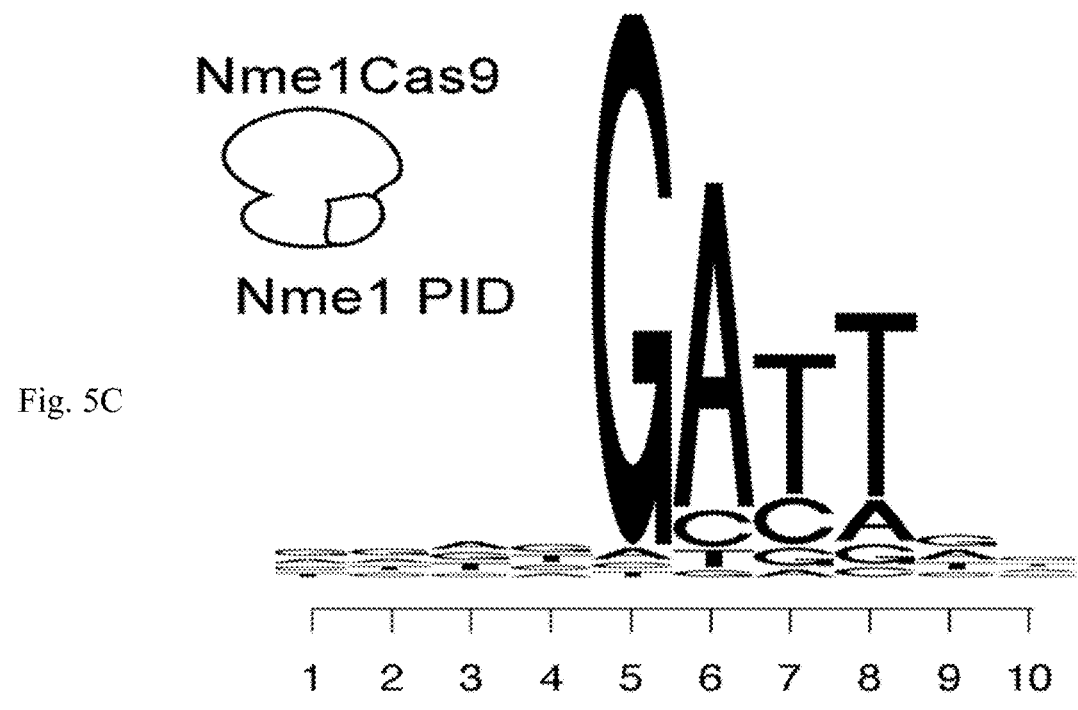
Fig. 5C
Fig. 5D
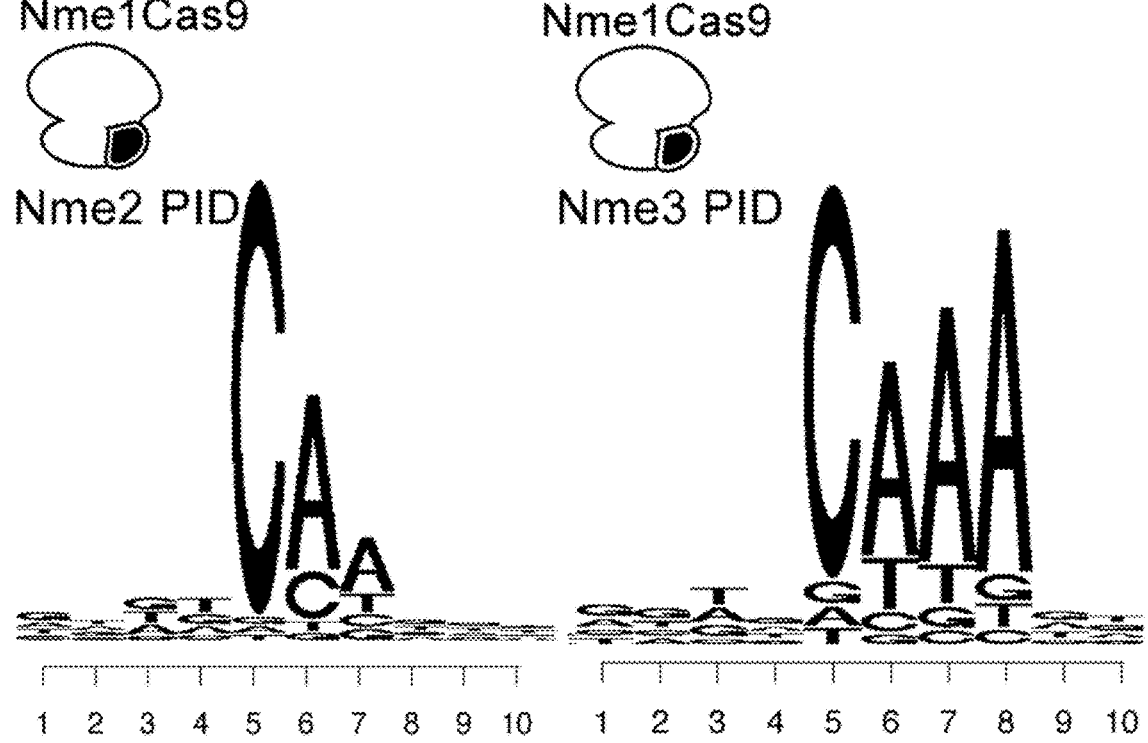

SEQ ID NO: 943
SEQ ID NO: 944
SEQ ID NO: 945
SEQ ID NO: 946

SEQ ID NO: 947
SEQ ID NO: 948
SEQ ID NO: 949
SEQ ID NO: 950
SEQ ID NO: 951

Fig. 14E

Rosa26|On: TGAGGACCGGCCCTGGGGCCTGGGGAGAATCCCT    SEQ ID NO: 953

Rosa26|OT1: GAAGGACCACCCTAGGCCTGGGGAGACTCCCT    SEQ ID NO: 954

Fig. 15A
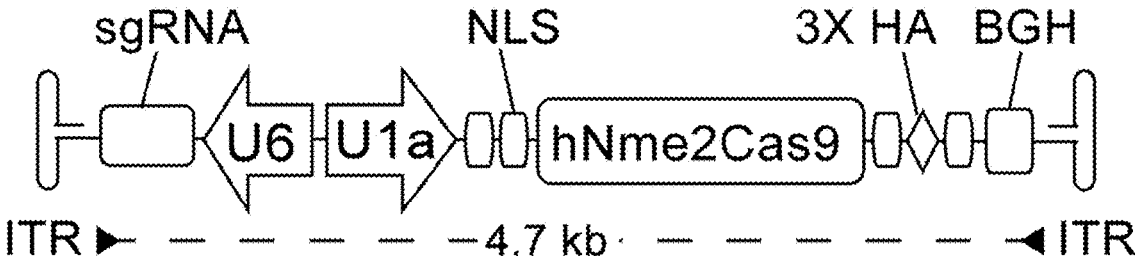
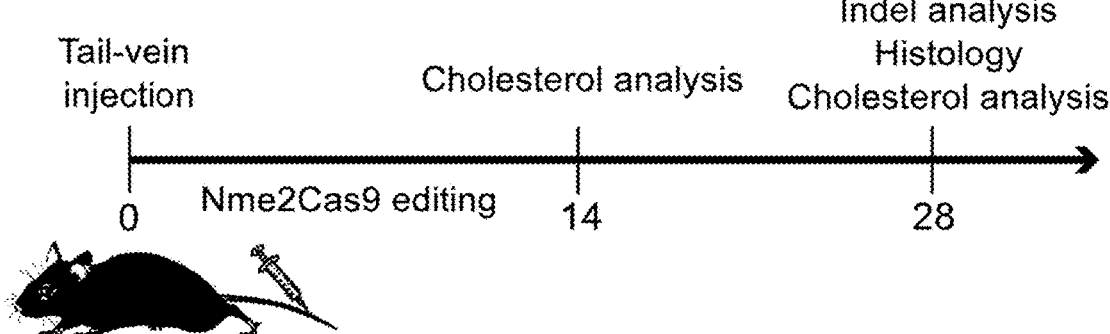
Fig. 15B
Fig. 15C
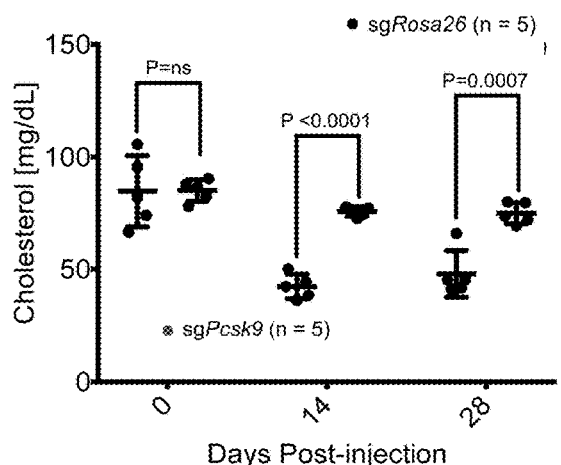

PCSK9 →
(mature)

GAPDH sg*Pcsk*9                    sg*Rosa*26

| Mouse ID | AAV dosage | Indels (%) | Coat color |
|----------|-----------|-----------|-----------|
| 9-1 | $3 \times 10^9$ GCs | 100 | Albino |
| 9-2 | $3 \times 10^9$ GCs | 100 | Albino |
| 9-3 | $3 \times 10^9$ GCs | 84 | mosaic and hypomorphic |
| 9-4 | $3 \times 10^9$ GCs | 98 | mosaic and hypomorphic |
| 9-5 | $3 \times 10^9$ GCs | 100 | mosaic and hypomorphic |
| 8-1 | $3 \times 10^8$ GCs | 100 | mosaic and hypomorphic |
| 8-2 | $3 \times 10^8$ GCs | 96 | mosaic and hypomorphic |

KANK3

GACTCTTCTGCATGGGTGATGTCAATGCC

SEQ ID NO: 967

Negative

Nme2Cas9-CBE

PLXNB2

CCGCCAGAACCGAGCCGGCTACTCGGCCC

SEQ ID NO: 968

Negative

Fig. 22 (continued)

Nme2Cas9-ABE

Fig. 22 (continued)

Nme2Cas9-CBE

PROGRAMMABLE DNA BASE EDITING BY Nme2Cas9-DEAMINASE FUSION PROTEINS

CROSS-REFERENCE TO RELATED APPLICATION

This application claims priority to the co-pending PCT/US19/56341 application, filed Oct. 15, 2019 and the U.S. Provisional Patent Application No. 62/745,666, filed Oct. 15, 2018, herein incorporated by reference in its entirety.

A Sequence Listing has been submitted in an ASCII text file named "19482.txt" created on Sep. 17, 2021, consisting of 342,134 bytes, the entire content of which is herein incorporated by reference.

FIELD OF THE INVENTION

The present invention is related to the field of gene editing. In particular, the gene editing is directed toward single nucleotide base editing. For example, such single nucleotide base editing results in a conversion of a C•G base pair to a T•A base pair. The high accuracy and precision of the presently disclosed single nucleotide base gene editor is accomplished by an NmeCas9 nuclease that is fused to a nucleotide deaminase protein. The compact nature of the NmeCas9 coupled with a larger number of compatible protospacer adjacent motifs provide the Cas9 fusion constructs contemplated herein to have a gene editing window that can edit sites that are not targetable by other conventional SpyCas9 base editor platforms.

BACKGROUND

Many human diseases arise due to the mutation of a single base. The ability to correct such genetic aberrations is paramount in treating these genetic disorders. Clustered regularly interspaced short palindromic repeats (CRISPR) along with CRISPR associated (Cas) proteins comprise an RNA-guided adaptive immune system in archaea and bacteria. These systems provide immunity by targeting and inactivating nucleic acids that originate from foreign genetic elements.

SpyCas9 base editing platforms cannot be used to target all single-base mutations due to their limited editing windows. The editing window is constrained in part by the requirement for an NGG PAM and by the requirement that the edited base(s) be a very precise distance from the PAM. SpyCas9 is also intrinsically associated with high off-targeting effects in genome editing.

What is needed in the art is a highly accurate Cas9 single base editing platform having a programmable target specificity due to recognition of a diverse population of PAM sites.

SUMMARY OF THE INVENTION

The present invention is related to the field of gene editing. In particular, the gene editing is directed toward single nucleotide base editing. For example, such single nucleotide base editing results in a conversion of a C•G base pair to a T•A base pair. The high accuracy and precision of the presently disclosed single nucleotide base gene editor is accomplished by an NmeCas9 nuclease that is fused to a nucleotide deaminase protein. The compact nature of the NmeCas9 coupled with a larger number of compatible protospacer adjacent motifs provide the Cas9 fusion constructs contemplated herein to have a gene editing window that is superior to other conventional SpyCas9 base editor platforms.

In one embodiment, the present invention contemplates a mutated NmeCas9 protein comprising a fused nucleotide deaminase and a binding region for an $N_4CC$ nucleotide sequence. In one embodiment, said protein is Nme2Cas9. In one embodiment, said protein further comprises a nuclear localization signal protein. In one embodiment, said nucleotide deaminase is a cytidine deaminase. In one embodiment, said nucleotide deaminase is an adenosine deaminase. In one embodiment, the protein further comprises a uracil glycosylase inhibitor. In one embodiment, the said nuclear localization signal protein includes, but is not limited to, nucleoplasmin (NLS) and/or SV40 NLS and/or C-myc NLS. In one embodiment, said binding region is a protospacer accessory motif interacting domain. In one embodiment, said protospacer accessory motif interacting domain comprises said mutation. In one embodiment, said mutation is a D16A mutation. In one embodiment, said mutated NmeCas9 protein further comprises CBE4. In one embodiment, said mutated NmeCas9 protein further comprises a linker. In one embodiment, said linker is a 73aa linker. In one embodiment, said linker is a 3×HA-tag.

In one embodiment, the present invention contemplates a construct, wherein said construct is an optimized nNme2Cas9-ABEmax.

In one embodiment, the present invention contemplates a construct, wherein said construct is a nNme2Cas9-CBE4.

In one embodiment, the present invention contemplates a construct, wherein said construct is a YE1-BE3-nNme2Cas9 (D16A)-UGI.

In one embodiment, the present invention contemplates an adeno-associated virus comprising a mutated NmeCas9 protein, said mutated NmeCas9 protein comprising a fused nucleotide deaminase and a binding region for an $N_4CC$ nucleotide sequence. In one embodiment, said virus is an adeno-associated virus 8. In one embodiment, said virus is an adeno-associated virus 6. In one embodiment, said protein is Nme2Cas9. In one embodiment, said protein further comprises a nuclear localization signal protein. In one embodiment, said nucleotide deaminase is a cytidine deaminase. In one embodiment, said nucleotide deaminase is an adenosine deaminase. In one embodiment, the protein further comprises a uracil glycosylase inhibitor. In one embodiment, the nuclear localization signal protein includes, but is not limited to, nucleoplasmin (NLS) and/or SV40 NLS and/or C-myc NLS. In one embodiment, said binding region is a protospacer accessory motif interacting domain. In one embodiment, said protospacer accessory motif interacting domain comprises said mutation. In one embodiment, said mutation is a D16A mutation. In one embodiment, said mutated NmeCas9 protein further comprises CBE4. In one embodiment, said mutated NmeCas9 protein further comprises a linker. In one embodiment, said linker is a 73aa linker. In one embodiment, said linker is a 3×HA-tag.

In one embodiment, the present invention contemplates a construct, wherein said construct is an optimized nNme2Cas9-ABEmax.

In one embodiment, the present invention contemplates a construct, wherein said construct is a nNme2Cas9-CBE4.

In one embodiment, the present invention contemplates a construct, wherein said construct is a YE1-BE3-nNme2Cas9 (D16A)-UGI.

In one embodiment, the present invention contemplates a method, comprising: a) providing; i) a nucleotide sequence comprising a gene with a mutated single base, wherein said gene is flanked by an $N_4CC$ nucleotide sequence; ii) a mutated NmeCas9 protein comprising a fused nucleotide deaminase and a binding region for said $N_4CC$ nucleotide sequence; b) contacting said nucleotide sequence with said mutated NmeCas9 protein under conditions such that said binding region attaches to said $N_4CC$ nucleotide sequence; and c) replacing said mutated single base with a wild type base with said mutated NmeCas9 protein. In one embodiment, said protein is Nme2Cas9. In one embodiment, said protein further comprises a nuclear localization signal protein. In one embodiment, said nucleotide deaminase is a cytidine deaminase. In one embodiment, said nucleotide deaminase is an adenosine deaminase. In one embodiment, the protein further comprises a uracil glycosylase inhibitor. In one embodiment, the nuclear localization signal protein includes, but is not limited to, nucleoplasmin (NLS) and/or SV40 NLS and/or C-myc NLS. In one embodiment, said binding region is a protospacer accessory motif interacting domain. In one embodiment, said protospacer accessory motif interacting domain comprises said mutation. In one embodiment, said mutation is a D16A mutation. In one embodiment, said mutated NmeCas9 protein further comprises CBE4. In one embodiment, said mutated NmeCas9 protein further comprises a linker. In one embodiment, said linker is a 73aa linker. In one embodiment, said linker is a 3×HA-tag. In one embodiment, said gene encodes a tyrosinase. In one embodiment, said gene is Fah. In one embodiment, said gene is c-fos.

In one embodiment, the present invention contemplates a method, comprising: a) providing; i) a patient comprising a nucleotide sequence comprising a gene with a mutated single base, wherein said gene is flanked by an $N_4CC$ nucleotide sequence, wherein said mutated gene causes a genetically-based medical condition; ii) an adeno-associated virus comprising a mutated NmeCas9 protein, said mutated NmeCas9 protein comprising a fused nucleotide deaminase and a binding region for said $N_4CC$ nucleotide sequence; b) treating said patient with said adeno-associated virus under conditions such that said mutated NmeCas9 protein replaces said mutated single base with a wild type single base, such that said genetically-based medical condition does not develop. In one embodiment, said gene encodes a tyrosinase protein. In one embodiment, said genetically-based medical condition is tyrosinemia. In one embodiment, said virus is an adeno-associated virus 8. In one embodiment, said virus is an adeno-associated virus 6. In one embodiment, said protein is Nme2Cas9. In one embodiment, said protein further comprises a nuclear localization signal protein. In one embodiment, said nucleotide deaminase is a cytidine deaminase. In one embodiment, said nucleotide deaminase is an adenosine deaminase. In one embodiment, the protein further comprises a uracil glycosylase inhibitor. In one embodiment, the nuclear localization signal protein includes, but is not limited to, nucleoplasmin (NLS) and/or SV40 NLS and/or C-myc NLS. In one embodiment, said binding region is a protospacer accessory motif interacting domain. In one embodiment, said protospacer accessory motif interacting domain comprises said mutation. In one embodiment, said mutation is a D16A mutation. In one embodiment, said mutated NmeCas9 protein further comprises CBE4. In one embodiment, said mutated NmeCas9 protein further comprises a linker. In one embodiment, said linker is a 73aa linker. In one embodiment, said linker is a 3×HA-tag. In one embodiment, said gene encodes a tyrosinase. In one embodiment, said gene is Fah. In one embodiment, said gene is c-fos.

In one embodiment, the present invention contemplates a method, comprising: a) providing; i) a patient comprising a nucleotide sequence comprising a gene with a mutated single base, wherein said gene is flanked by an $N_4CC$ nucleotide sequence, wherein said mutated gene causes a genetically-based medical condition; ii) an optimized nNme2Cas9-ABEmax, comprising a mutated NmeCas9 protein, said mutated NmeCas9 protein comprising a fused nucleotide deaminase and a binding region for said $N_4CC$ nucleotide sequence; b) treating said patient with said optimized nNme2Cas9-ABEmax under conditions such that said mutated NmeCas9 protein replaces said mutated single base with a wild type single base, such that said genetically-based medical condition does not develop.

In one embodiment, the present invention contemplates a method, comprising: a) providing; i) a patient comprising a nucleotide sequence comprising a gene with a mutated single base, wherein said gene is flanked by an $N_4CC$ nucleotide sequence, wherein said mutated gene causes a genetically-based medical condition; ii) a nNme2Cas9-CBE4, comprising a mutated NmeCas9 protein, said mutated NmeCas9 protein comprising a fused nucleotide deaminase and a binding region for said $N_4CC$ nucleotide sequence; b) treating said patient with said nNme2Cas9-CBE4 under conditions such that said mutated NmeCas9 protein replaces said mutated single base with a wild type single base, such that said genetically-based medical condition does not develop.

In one embodiment, the present invention contemplates a method, comprising: a) providing; i) a patient comprising a nucleotide sequence comprising a gene with a mutated single base, wherein said gene is flanked by an $N_4CC$ nucleotide sequence, wherein said mutated gene causes a genetically-based medical condition; ii) a YE1-BE3-nNme2Cas9 (D16A)-UGI, comprising a mutated NmeCas9 protein, said mutated NmeCas9 protein comprising a fused nucleotide deaminase and a binding region for said $N_4CC$ nucleotide sequence; b) treating said patient with said nNme2Cas9-CBE4 under conditions such that said mutated NmeCas9 protein replaces said mutated single base with a wild type single base, such that said genetically-based medical condition does not develop.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target. Such a specific genomic target includes, but is not limited to, a chromosomal region, a gene, a promoter, an open reading frame or any nucleic acid sequence.

As used herein, the term "single base" refers to one, and only one, nucleotide within a nucleic acid sequence. When used in the context of single base editing, it is meant that the base at a specific position within the nucleic acid sequence is replaced with a different base. This replacement may occur by many mechanisms, including but not limited to, substitution or modification.

As used herein, the term "target" or "target site" refers to a pre-identified nucleic acid sequence of any composition and/or length. Such target sites include, but is not limited to, a chromosomal region, a gene, a promoter, an open reading frame or any nucleic acid sequence. In some embodiments, the present invention interrogates these specific genomic target sequences with complementary sequences of gRNA.

The term "on-target binding sequence" as used herein, refers to a subsequence of a specific genomic target that may be completely complementary to a programmable DNA binding domain and/or a single guide RNA sequence.

The term "off-target binding sequence" as used herein, refers to a subsequence of a specific genomic target that may be partially complementary to a programmable DNA binding domain and/or a single guide RNA sequence.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "viral vector" encompasses any nucleic acid construct derived from a virus genome capable of incorporating heterologous nucleic acid sequences for expression in a host organism. For example, such viral vectors may include, but are not limited to, adeno-associated viral vectors, lentiviral vectors, SV40 viral vectors, retroviral vectors, adenoviral vectors. Although viral vectors are occasionally created from pathogenic viruses, they may be modified in such a way as to minimize their overall health risk. This usually involves the deletion of a part of the viral genome involved with viral replication. Such a virus can efficiently infect cells but, once the infection has taken place, the virus may require a helper virus to provide the missing proteins for production of new virions. Preferably, viral vectors should have a minimal effect on the physiology of the cell it infects and exhibit genetically stable properties (e.g., do not undergo spontaneous genome rearrangement). Most viral vectors are engineered to infect as wide a range of cell types as possible. Even so, a viral receptor can be modified to target the virus to a specific kind of cell. Viruses modified in this manner are said to be pseudotyped. Viral vectors are often engineered to incorporate certain genes that help identify which cells took up the viral genes. These genes are called marker genes. For example, a common marker gene confers antibiotic resistance to a certain antibiotic.

As used herein the "ROSA26 gene" or "Rosa26 gene" refers to a human or mouse (respectively) locus that is widely used for achieving generalized expression in the mouse. Targeting to the ROSA26 locus may be achieved by introducing a desired gene into the first intron of the locus, at a unique XbaI site approximately 248 bp upstream of the original gene trap line. A construct may be constructed using an adenovirus splice acceptor followed by a gene of interest and a polyadenylation site inserted at the unique XbaI site. A neomycin resistance cassette may also be included in the targeting vector.

As used herein the "PCSK9 gene" or "Pcsk9 gene" refers to a human or mouse (respectively) locus that encodes a PCSK9 protein. The PCSK9 gene resides on chromosome 1 at the band 1p32.3 and includes 13 exons. This gene may produce at least two isoforms through alternative splicing.

The term "proprotein convertase subtilisin/kexin type 9" and "PCSK9" refers to a protein encoded by a gene that modulates low density lipoprotein levels. Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation" Proc. Natl. Acad. Sci. U.S.A. 100 (3): 928-933 (2003). Similar genes (orthologs) are found across many species. Many enzymes, including PSCK9, are inactive when they are first synthesized, because they have a section of peptide chains that blocks their activity; proprotein convertases remove that section to activate the enzyme. PSCK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

The term "hypercholesterolemia" as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 70 mg/dl. Alternatively, if cholesterol is measured using free plasma cholesterol, hypercholesterolemia may exist if the measured free cholesterol levels are above, for example, approximately 200-220 mg/dl.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by 30 or so base pairs known as "spacer DNA". The spacers are short segments of DNA from a virus and may serve as a 'memory' of past exposures to facilitate an adaptive defense against future invasions.

As used herein, the term "Cas" or "CRISPR-associated (cas)" refers to genes often associated with CRISPR repeat-spacer arrays.

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence.

The term "protospacer adjacent motif" (or PAM) as used herein, refers to a DNA sequence that may be required for a Cas9/sgRNA to form an R-loop to interrogate a specific DNA sequence through Watson-Crick pairing of its guide RNA with the genome. The PAM specificity may be a function of the DNA-binding specificity of the Cas9 protein (e.g., a "protospacer adjacent motif recognition domain" at the C-terminus of Cas9).

As used herein, the term "sgRNA" refers to single guide RNA used in conjunction with CRISPR associated systems (Cas). sgRNAs are a fusion of crRNA and tracrRNA and contain nucleotides of sequence complementary to the desired target site. Jinek et al., "A programmable dual-RNA-guided DNA endonuclease in adaptive bacterial immunity" Science 337 (6096): 816-821 (2012) Watson-Crick pairing of the sgRNA with the target site permits R-loop formation, which in conjunction with a functional PAM permits DNA cleavage or in the case of nuclease-deficient Cas9 allows binds to the DNA at that locus.

As used herein, the term "fluorescent protein" refers to a protein domain that comprises at least one organic compound moiety that emits fluorescent light in response to the appropriate wavelengths. For example, fluorescent proteins may emit red, blue and/or green light. Such proteins are readily commercially available including, but not limited to: i) mCherry (Clonetech Laboratories): excitation: 556/20 nm (wavelength/bandwidth); emission: 630/91 nm; ii) sfGFP (Invitrogen): excitation: 470/28 nm; emission: 512/23 nm; iii) TagBFP (Evrogen): excitation 387/11 nm; emission 464/23 nm.

As used herein, the term "sgRNA" refers to single guide RNA used in conjunction with CRISPR associated systems (Cas). sgRNAs contains nucleotides of sequence complementary to the desired target site. Watson-crick pairing of the sgRNA with the target site recruits the nuclease-deficient Cas9 to bind the DNA at that locus.

As used herein, the term "orthogonal" refers targets that are non-overlapping, uncorrelated, or independent. For example, if two orthogonal nuclease-deficient Cas9 gene fused to different effector domains were implemented, the sgRNAs coded for each would not cross-talk or overlap. Not all nuclease-deficient Cas9 genes operate the same, which enables the use of orthogonal nuclease-deficient Cas9 gene fused to a different effector domains provided the appropriate orthogonal sgRNAs.

As used herein, the term "phenotypic change" or "phenotype" refers to the composite of an organism's observable characteristics or traits, such as its morphology, development, biochemical or physiological properties, phenology, behavior, and products of behavior. Phenotypes result from the expression of an organism's genes as well as the influence of environmental factors and the interactions between the two.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 μg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the T$_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., Co t or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277, 437; 4,275,149; and 4,366,241 (all herein incorporated by reference in their entirety). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE DRAWINGS

FIG. 1A shows an exemplary YE1-BE3-nNme2Cas9 (D16A)-UGI construct.

FIG. 1B shows an exemplary ABE7.10 nNme2Cas9 (D16A) construct.

FIG. 1C shows an exemplary ABE7.10-nNme2Cas9 (D16A) construct comprising two SV40 NLS sequences.

FIG. 2A shows exemplary sequences for a TS25 endogenous target site (within the black rectangle). GN23 sgRNA base-pairs with the target DNA strand, leaving the displaced DNA strand for cytidine deaminase to edit (e.g. new underlined nucleotides).

FIG. 2B shows exemplary sequencing data showing a doublet nucleotide peak (7th position from 5' end; arrow) demonstrating the successful single base editing of a cytidine to a thymidine (e.g., a C•G base pair conversion to a T•A base pair).

FIG. 2C shows an exemplary quantitation of the data shown in FIG. 2B plotting the percent conversion of C→T single base editing. The percentage of C converted to T is about 40% in the base editor- and sgRNA-treated sample (p-value=6.88×10-6). The "no sgRNA" control displays the background noise due to Sanger sequencing. EditR (Kluesner et al., 2018) was used to perform the analysis.

FIG. 3A-F presents exemplary specific UGI target sites that were respectively integrated into YE1-BE3-nNme2Cas9/D16A mutant fusion proteins and co-expressed with enhanced green fluorescent protein (EGFP) in a stable K562-derived cell line. Converted bases are highlighted in black boxes with thick lines. Background signals were filtered using negative control samples (YE1-BE3-nNme2Cas9 nucleofected K562 cells without sgRNA constructs). $N_4CC$ PAMs are boxed with thin lines. The percentage of total reads exhibiting mutations in base-editor-targeted sites is shown in the right column.

FIG. 3A shows an exemplary EGFP-Site 1.

FIG. 3B shows an exemplary EGFP-Site 2.

FIG. 3C shows an exemplary EGFP-Site 3.

FIG. 3D shows an exemplary EGFP-Site 4.

FIG. 3E shows an exemplary deep-sequencing analysis indicating where YE1-BE3-nNme2Cas9 converts C residues to T residues at endogenous c-fos promoter region. The percentage of total reads exhibiting mutations in base-editor-targeted sites is shown in the right column. The converted bases are highlighted with black boxes outside of the PAM areas. Background signals were filtered using negative control samples. The highest percentage of editing is 32.50%.

FIG. 3F shows an exemplary deep-sequencing analysis indicating where ABE7.10-nNme2Cas9 or ABEmax (Koblan et al., 2018)-nNme2Cas9 converts A residues to G residues at endogenous c-fos promoter region. The percentage of total reads exhibiting mutations in base-editor-targeted sites is shown in the right column. The converted bases are highlighted as black boxes outside of the PAM areas. Background signals were filtered using negative control samples. The percentage of editing is 0.53% by ABE7.10-nNme2Cas9 or 2.33% by ABEmax-nNme2Cas9 (D16A).

FIG. 4 presents an exemplary alignment of the wildtype Fah gene with the tyrosinemia Fah mutant gene showing an A-G single base gene editing target site (position 9). The respective SpyCas9 single PAM site and NmeCas9 double PAM sites are indicated for demonstrating the suboptimal targeting window relative to the SpyCas9 PAM site.

FIG. 5A-E illustrates exemplary three closely related *Neisseria meningitidis* Cas9 orthologs that have distinct PAMs.

FIG. 5A shows an exemplary schematic showing mutated residues (black spheres) between Nme2Cas9 (left) and Nme3Cas9 (right) mapped onto the predicted structure of Nme1Cas9, revealing the cluster of mutations in the PID (black areas).

FIG. 5B shows an exemplary experimental workflow of the in vitro PAM discovery assay with a 10-bp randomized PAM region. Following in vitro digestion, adapters were ligated to cleaved products for library construction and sequencing.

FIG. 5C shows exemplary sequence logos resulting from in vitro PAM discovery reveal the enrichment of a $N_4GATT$ PAM for Nme1Cas9, consistent with its previously established specificity.

FIG. 5D shows exemplary sequence logos indicating that Nme1Cas9 with its PID swapped with that of Nme2Cas9 (left) or Nme3Cas9 (right) requires a C at PAM position 5. The remaining nucleotides were not determined with high confidence due to the modest cleavage efficiency of the PID-swapped protein chimeras (see FIG. 6C).

FIG. 5E shows an exemplary sequence logo showing that full-length Nme2Cas9 recognizes an $N_4CC$ PAM, based on efficient substrate cleavage of a target pool with a fixed C at PAM position 5, and with PAM nts 1~4 and 6-8 randomized.

FIG. 6A shows an exemplary unrooted phylogenetic tree of NmeCas9 orthologs that are >80% identical to Nme1Cas9. Three distinct branches emerged, with the majority of mutations clustered in the PID. Groups 1 (black), 2 (red), and 3 (green) have PIDs with >98%, ~52%, and ~86% identity to Nme1Cas9, respectively. Three representative Cas9 orthologs (one from each group) (Nme1Cas9, Nme2Cas9 and Nme3Cas9) are indicated.

FIG. 6B shows an exemplary schematic showing the CRISPR-cas loci of the strains encoding the three Cas9 orthologs (Nme1Cas9, Nme2Cas9, and Nme3Cas9) from (A). Percent identities of each CRISPR-Cas component with *N. meningitidis* 8013 (encoding Nme1Cas9) are shown. Black arrows denote pre-crRNA and tracrRNA transcription initiation sites, respectively.

FIG. 6C shows an exemplary normalized read counts (% of total reads) from cleaved DNAs from the in vitro assays for intact Nme1Cas9 (grey), for chimeras with Nme1Cas9's PID swapped with those of Nme2Cas9 and Nme3Cas9 (small black regions), and for full-length Nme2Cas9 (large with small black regions), are plotted. The reduced normalized read counts indicate lower cleavage efficiencies in the chimeras.

FIG. 6D shows an exemplary sequence logos from the in vitro PAM discovery assay on an NNNNCNNN PAM pool by Nme1Cas9 with its PID swapped with those of Nme2Cas9 (left) or Nme3Cas9 (right).

FIG. 7A shows an exemplary schematic diagram depicting transient transfection and editing of HEK293T TLR2.0 cells, with mCherry+ cells detected by flow cytometry 72 hours after transfection.

FIG. 7B shows an exemplary Nme2Cas9 editing of the TLR2.0 reporter. Sites with $N_4CC$ PAMs were targeted with varying efficiencies, while no Nme2Cas9 targeting was observed at an $N_4GATT$ PAM or in the absence of sgRNA. SpyCas9 (targeting a previously validated site with an NGG PAM) and Nme1Cas9 (targeting $N_4GATT$) were used as positive controls.

FIG. 7C shows an exemplary effect of spacer length on the efficiency of Nme2Cas9 editing. An sgRNA targeting a single TLR2.0 site, with spacer lengths varying from 24 to 20 nts (including the 5'-terminal G required by the U6 promoter), indicate that highest editing efficiencies are obtained with 22-24 nt spacers.

FIG. 7D shows an exemplary An Nme2Cas9 dual nickase can be used in tandem to generate NHEJ- and HDR-based edits in TLR2.0. Nme2Cas9- and sgRNA-expressing plasmids, along with an 800-bp dsDNA donor for homologous repair, were electroporated into HEK293T TLR2.0 cells, and both NHEJ (mCherry+) and HDR (GFP+) outcomes were scored by flow cytometry. HNH nickase, $Nme2Cas9^{D16A}$; RuvC nickase, $Nme2Cas9^{H588A}$. Cleavage sites 32 bp and 64 bp apart were targeted using either nickase. The HNH nickase ($Nme2Cas9^{D16A}$) yielded efficient editing, particularly with the cleavage sites that were separated by 32 bp, whereas the RuvC nickase ($Nme2Cas9^{H588A}$) was not effective. Wildtype Nme2Cas9 was used as a control.

FIG. 8A shows an exemplary Nme2Cas9 targeting at $N_4CD$ sites in TLR2.0, with editing estimated based on mCherry+ cells. Four sites for each non-C nucleotide at the tested position ($N_4CA$, $N_4CT$ and $N_4CG$) were examined, and an $N_4CC$ site was used as a positive control.

FIG. 8B shows an exemplary Nme2Cas9 targeting at $N_4DC$ sites in TLR2.0 [similar to (A)].

FIG. 8C shows exemplary guide truncations on a TLR2.0 site (distinct from that in FIG. 2C) with a $N_4CCA$ PAM, revealing similar length requirements as those observed at the other site.

FIG. 8D shows exemplary Nme2Cas9 targeting efficiency is differentially sensitive to single-nucleotide mismatches in the seed region of the sgRNA. Data show the effects of walking single-nucleotide sgRNA mismatches along the 23-nt spacer in a TLR2.0 target site.

FIG. 9A shows an exemplary Nme2Cas9 genome editing of endogenous human sites in HEK293T cells following transient transfection of Nme2Cas9- and sgRNA-expressing plasmids. 40 sites were screened initially (Table 1); the 14 sites shown (selected to include representatives of varying editing efficiencies, as measured by TIDE) were then re-analyzed in triplicate. An Nme1Cas9 target site (with an $N_4GATT$ PAM) was used as a negative control.

FIG. 9B shows exemplary data charts: Left panel: Transient transfection of a single plasmid expressing both Nme2Cas9 and sgRNA (targeting the Pcsk9 and Rosa26 loci) enables editing in Hepa1-6 mouse cells, as detected by TIDE. Right panel: Electroporation of sgRNA plasmids into K562 cells stably expressing Nme2Cas9 from a lentivector results in efficient indel formation.

FIG. 9C shows exemplary Nme2Cas9 can be electroporated as an RNP complex to induce genome editing. 40 picomoles Cas9 along with 50 picomoles of in vitro-transcribed sgRNAs targeting three different loci were electroporated into HEK293T cells. Indels were measured after 72 h using TIDE.

FIG. 10A shows exemplary increasing the dose of electroporated Nme2Cas9 plasmid (500 ng, vs. 200 ng in FIG. 3A) improves editing efficiency at two sites (TS16 and TS6). Data provided in black are re-used from FIG. 9A.

FIG. 10B shows exemplary Nme2Cas9 can be used to create precise segmental deletions. Two TLR2.0 targets with cleavage sites 32 bp apart were targeted simultaneously with Nme2Cas9. The majority of lesions created were deletions of exactly 32 bp (patterns).

FIG. 11A shows exemplary In vitro cleavage assay of Nme1Cas9 and Nme2Cas9 in the presence of five previously characterized anti-CRISPR proteins (10:1 ratio of Acr: Cas9). Top: Nme1Cas9 efficiently cleaves a fragment containing a protospacer with an $N_4GATT$ PAM in the absence of an Acr or in the presence of a negative control Acr (AcrE2). All five previously characterized type II-C Acr families inhibited Nme1Cas9, as expected. Bottom: Nme2Cas9 inhibition mirrors that of Nme1Cas9, except for the lack of inhibition by $AcrIIC5_{Smu}$.

FIG. 11B shows exemplary genome editing in the presence of the five previously described anti-CRISPR families. Plasmids expressing Nme2Cas9 (200 ng), sgRNA (100 ng) and each respective Acr (200 ng) were co-transfected into HEK293T cells, and genome editing was measured using Tracking of Indels by Decompostion (TIDE) 72 hr post transfection. Consistent with our in vitro analyses, all type II-C anti-CRISPRs except $AcrIIC5_{Smu}$ inhibited genome editing, albeit with different efficiencies.

FIG. 11C shows exemplary Acr inhibition of Nme2Cas9 is dose-dependent with distinct apparent potencies. Nme2Cas9 is fully inhibited by $AcrIIC1_{Nme}$ and $AcrIIC4_{Hpa}$ at 2:1 and 1:1 mass ratios of cotransfected Acr and Nme2Cas9 plasmids, respectively.

FIG. 13A shows exemplary Nme2Cas9 and SpyCas9 guides are orthogonal. TIDE results show the frequencies of indels created by both nucleases targeting DS2 with either their cognate sgRNAs or with the sgRNAs of the other ortholog.

FIG. 13B shows exemplary Nme2Cas9 and SpyCas9 exhibiting comparable on-target editing efficiencies as assessed by GUIDE-seq. Bars indicate on-target read counts from GUIDE-Seq at the three dual sites targeted by each ortholog. White bars represent Nme2Cas9 and black bars represent SpyCas9.

FIG. 13C shows an exemplary SpyCas9's on-target vs. off-target read counts for each site. White bars represent the on-target reads while black bars represent off-targets.

FIG. 13D shows exemplary Nme2Cas9's on-target vs. off-target reads for each site.

FIG. 13E bar graphs showing exemplary indel efficiencies (measured by TIDE) at potential off-target sites predicted by CRISPRSeek. On- and off-target site sequences are shown on the left, with the PAM region underlined and sgRNA mismatches and non-consensus PAM nucleotides are boxed.

FIG. 14A-E presents exemplary data showing that Nme2Cas9 exhibits little or no detectable off-targeting in mammalian cells.

FIG. 14A shows an exemplary schematic depicting dual sites (DSs) targetable by both SpyCas9 and Nme2Cas9 by virtue of their non-overlapping PAMs. The Nme2Cas9 PAM (orange) and SpyCas9 PAM (blue) are highlighted. A 24nt Nme2Cas9 guide sequence is indicated in yellow; the corresponding guide sequence for SpyCas9 would be 4nt shorter at the 5' end.

FIG. 14B shows an exemplary Nme2Cas9 and SpyCas9 that both induce indels at DSs. Six DSs in VEGFA (with $GN_3GN_{19}NGGNCC$ sequences) were selected for direct comparisons of editing by the two orthologs. Plasmids expressing each Cas9 (with the same promoter, linkers, tags and NLSs) and its cognate guide were transfected into HEK293T cells. Indel efficiencies were determined by TIDE 72 hrs post transfection. Nme2Cas9 editing was detectable at all six sites and was marginally or significantly more efficient than SpyCas9 at two sites (DS2 and DS6, respectively). SpyCas9 edited four out of the six sites (DS1, DS2, DS4 and DS6), with two sites showing significantly higher editing efficiencies than Nme2Cas9 (DS1 and DS4). DS2, DS4 and DS6 were selected for GUIDE-Seq analysis as Nme2Cas9 was equally efficient, less efficient and more efficient than SpyCas9, respectively, at these sites.

FIG. 14C shows exemplary Nme2Cas9 genome editing that is highly accurate in human cells. Numbers of off-target sites detected by GUIDE-Seq for each nuclease at individual target sites are shown. In addition to dual sites, we analyzed TS6 (because of its high on-target editing efficiency) and Pcsk9 and Rosa26 sites in mouse Hepa1-6 cells (to measure accuracy in another cell type).

FIG. 14D shows an exemplary targeted deep sequencing to detect indels in edited cells confirms the high Nme2Cas9 accuracy indicated by GUIDE-seq.

FIG. 14E shows an exemplary sequence for the validated off-target site of the Rosa26 guide, showing the PAM region (underlined), the consensus CC PAM dinucleotide (bold), and three mismatches in the PAM-distal portion of the spacer (bold outside of the underlined region).

FIG. 15A-C presents exemplary data showing Nme2Cas9 genome editing in vivo via all-in-one AAV delivery.

FIG. 15A shows exemplary workflow for delivery of AAV8.sgRNA.Nme2Cas9 to lower cholesterol levels in mice by targeting Pcsk9. Top: schematic of the all-in-one AAV vector expressing Nme2Cas9 and the sgRNA (individual genome elements not to scale). BGH, bovine growth hormone poly (A) site; HA, epitope tag; NLS, nuclear localization sequence; h, human-codon-optimized. Bottom: Timeline for AAV8.sgRNA.Nme2Cas9 tail-vein injections $(4 \times 10^{11}$ GCs), followed by cholesterol measurements at day 14 and indel, histology and cholesterol analyses at day 28 post-injection.

FIG. 15B shows an exemplary TIDE analysis to measure indels in DNA extracted from livers of mice injected with AAV8.Nme2Cas9+sgRNA targeting Pcsk9 and Rosa26 (control) loci. Indel efficiency at the lone off-target site identified by GUIDE-seq for these two sgRNAs (Rosa26|OT1) were also assessed by TIDE.

FIG. 15C shows an exemplary reduced serum cholesterol levels in mice injected with the Pcsk9-targeting guide (left values in the pairs of values) compared to the Rosa26-targeting controls (right values in the pairs of values). P values are calculated by unpaired two-tailed t-test.

FIG. 16A shows exemplary Western blotting using anti-PCSK9 antibody reveals strongly reduced levels of PCSK9 in the livers of mice treated with sgPcsk9, compared to mice treated with sgRosa26. 2 ng of recombinant PCSK9 was used as a mobility standard (left-most lane), and a cross-reacting band in the liver samples is indicated by an asterisk. GAPDH was used as loading control (bottom panel).

FIG. 16B shows exemplary H&E staining from livers of mice injected with AAV8.Nme2Cas9+sgRosa26 (left) or AAV8.Nme2Cas9+sgPcsk9 (right) vectors. Scale bars, 25 μm.

FIG. 17A shows an exemplary two sites in Tyr, each with $N_4CC$ PAMs, were tested for editing in Hepa1-6 cells. The sgTyr2 guide exhibited higher editing efficiency and was selected for further testing.

FIG. 17B shows an exemplary seven mice that survived post-natal development, and each exhibited coat color phenotypes as well as on-target editing, as assayed by TIDE.

FIG. 17C shows an exemplary Indel spectra from tail DNA of each mouse from (B), as well as an unedited C57BL/6NJ mouse, as indicated by TIDE analysis. Efficiencies of insertions (positive) and deletions (negative) of various sizes are indicated.

FIG. 18A shows an exemplary workflow for single-AAV Nme2Cas9 editing ex vivo to generate albino C57BL/6NJ mice by targeting the Tyr gene. Zygotes are cultured in KSOM containing AAV6.Nme2Cas9:sgTyr for 5-6 hours, rinsed in M2, and cultured for a day before being transferred to the oviduct of pseudo-pregnant recipients.

FIG. 18B shows exemplary albino (left) and chinchilla or variegated (white areas with black-middle) mice generated by $3 \times 10^9$ GCs, and chinchilla or variegated mice (white areas with black-right) generated by $3 \times 10^8$ GCs of zygotes with AAV6.Nme2Cas9:sgTyr.

FIG. 18C shows an exemplary summary of Nme2Cas9.sgTyr single-AAV ex vivo Tyr editing experiments at two AAV doses.

FIG. 19A shows exemplary sequence information of sequence information of ABE-mCherry reporter. There is a TAG stop codon in mCherry coding region. In the reporter-integrated stable cell line, there is no mCherry signal. The mCherry signal will show up if the nSpCas9-ABEmax or optimized ABEmax-nNme2Cas9 (D16A) can convert TAG to CAG (which is encoded Gln).

FIG. 19B shows an exemplary mCherry signals light up since SpCas9-ABE or ABEmax-nNme2Cas9 (D16A) is active in the specific region of the mCherry reporter. Upper panel is the negative control, middle panel shows the mCherry signals light up in reporter cells treated with nSpCas9-ABEmax, bottom panel shows the mCherry signals light up in reporter cells treated with optimized ABEmax-nNme2Cas9 (D16A).

FIG. 19C shows an exemplary FACs Quantitation of base editing events in mCherry reporter cells transfected with the SpCas9-ABE or ABEmax-nNme2Cas9 (D16A). N=6; error bars represent S.D. Results are from biological replicates performed in technical duplicates.

FIG. 20A shows exemplary sequence information of CBE-GFP reporter. There is a mutation in the fluorophore core region of the GFP reporter line, which converts GYG to GHG. Therefore, there is no GFP signal. The GFP signal will show up if the nSpCas9-CBE4 or CBE4-nNme2Cas9 (D16A)-UGI-UGI can convert CAC to TAC/TAT (Histidine to Tyrosine).

FIG. 20B shows an exemplary GFP signal (green) since nSpCas9-CBE4 or CBE4-nNme2Cas9 (D16A)-UGI-UGI is active in the specific region of the GFP reporter. Upper panel is the negative control. Middle panel shows that the mCherry signals light up in the reporter cells treated with CBE4-nNme2Cas9 (D16A)-UGI-UGI. Bottom panel shows that the GFP signals light up in the reporter cells treated with CBE4-nNme2Cas9 (D16A)-UGI-UGI.

FIG. 20C shows an exemplary FACs Quantitation of base editing events in GFP reporter cells transfected with nSpCas9-CBE4 or CBE4-nNme2Cas9 (D16A)-UGI-UGI. N=6; error bars represent S.D. Results are from biological replicates performed in technical duplicates.

DETAILED DESCRIPTION OF THE INVENTION

Figures 1A, 1B, 1C:
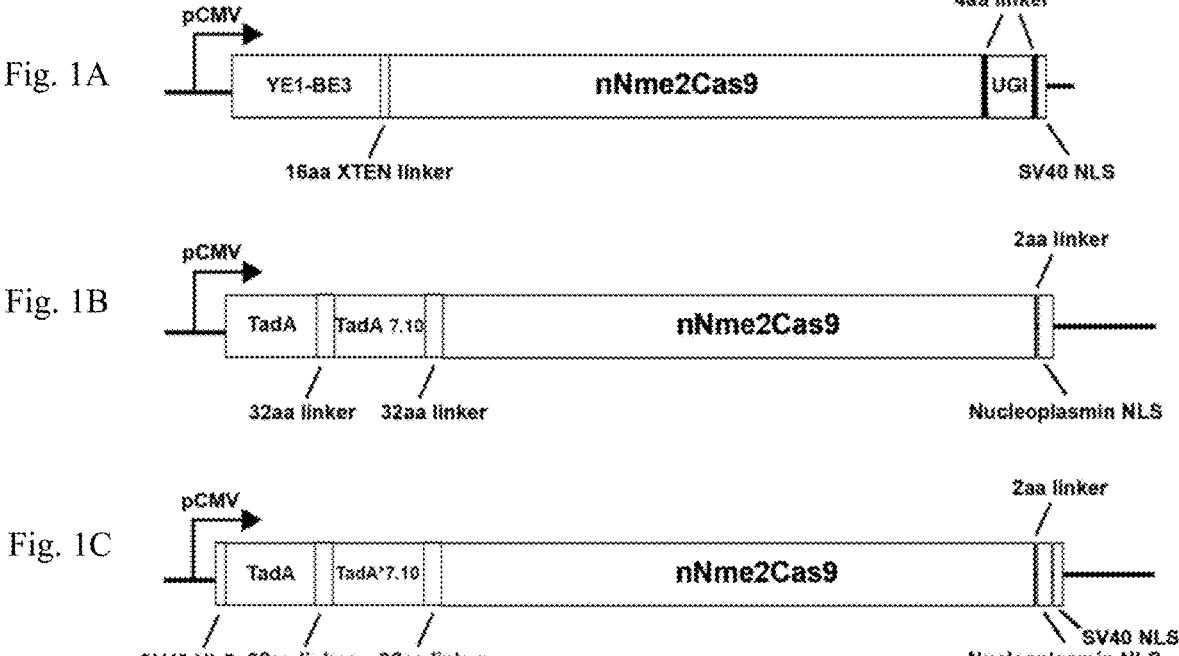
FIG. 1A-C illustrates exemplary schematic embodiments of an NmeCas9 deaminase fusion protein single base editor and exemplary constructed plasmids of base editors.

The present invention is related to the field of gene editing. In particular, the gene editing is directed toward single nucleotide base editing. For example, such single nucleotide base editing results in a conversion of a C•G base pair to a T•A base pair. The high accuracy and precision of the presently disclosed single nucleotide base gene editor is accomplished by an NmeCas9 nuclease that is fused to a nucleotide deaminase protein. The compact nature of the NmeCas9 coupled with a larger number of compatible protospacer adjacent motifs provide the Cas9 fusion constructs contemplated herein can edit sites that are not targetable by conventional SpyCas9 base editor platforms.

A. NmeCas9 Single Base Editing

Cas9 is a programmable nuclease that uses a guide RNA to create a double-stranded break at any desired genomic locus. This programmability has been harnessed for biomedical and therapeutic approaches. However, Cas9-induced breaks often lead to imprecise repair by the cellular machinery, hindering its therapeutic application for single-base corrections as well as uniform and precise gene knockouts. Moreover, it is extremely challenging to combine Cas9-induced DNA double strand breaks and a repair template for homologous directed repair (HDR) for correcting genetic mutations in post-mitotic cells (e.g. neuronal cells).

Single nucleotide base editing is a genome editing approach where a nuclease-dead or-impaired Cas9 (e.g., dead Cas9 (dCas9) or nickase Cas9 (nCas9)) is fused to another enzyme capable of base-editing nucleotides without causing DNA double strand breaks. To date, two broad classes of Cas9 base editors have been developed: i) cytidine deaminase (edits a C•G base pair to a T•A base pair) SpyCas9 fusion protein; and ii) adenosine deaminase (edits a A•T base pair to a G•C base pair) SpyCas9. Liu et al., "Nucleobase editors and uses thereof" US 2017/0121693; and Lui et al., "Fusions of cas9 domains and nucleic acid-editing domains" US 2015/0166980; (both herein incorporated by reference).

However as mentioned above, SpyCas9 base editing platforms cannot be used to target all single-base mutations due to their limited editing windows. The editing window is constrained by the requirement for an NGG PAM. SpyCas9 is also intrinsically associated with high off-targeting effects in genome editing.

In one embodiment, the present invention contemplates a deaminase fusion protein with a compact and hyper-accurate Nme2Cas9 (*Neisseria meningitidis* spp.). This Nme2Cas9 has 1,082 amino acids as compared to SpyCas9 that has 1,368 amino acids. This Nme2Cas9 ortholog functions efficiently in mammalian cells, recognizes an N₄CC PAM, and is intrinsically hyper-accurate. Edraki et al., Mol Cell. (in preparation).

Although it is not necessary to understand the mechanism of an invention, it is believed that the compactness and hyper-accuracy of an NmeCas9 base editor targets single-base mutations that could not be reached previously by other Cas9 platforms currently known in the art. It is further believed that the NmeCas9 base editors contemplated herein target pathogenic mutations that are not feasible via current base editor platforms, and with an increased base editing accuracy.

In one embodiment, the present invention contemplates a fusion protein comprising a Nme2Cas9 and a deaminase protein, exemplary examples including ABE7.10-nNme2Cas9 (D16A); Optimized nNme2Cas9-ABEmax; nNme2Cas9-CBE4 (equals BE4-nNme2Cas9 (D16A)-UGI-UGI) as well as ABEmax-nNme2Cas9 (D16A). See, FIG. 1A, FIG. 1B, and FIG. 1C.

FIG. 1A-C illustrates exemplary schematic embodiments of an NmeCas9 deaminase fusion protein single base editor and exemplary constructed plasmids of base editors. FIG. 1A shows an exemplary YE1-BE3-nNme2Cas9 (D16A)-UGI construct. FIG. 1B shows an exemplary ABE7.10 nNme2Cas9 (D16A) construct. FIG. 1C shows an exemplary ABE7.10-nNme2Cas9 (D16A) construct. FIG. 1C shows an exemplary ABE7.10-nNme2Cas9 (D16A) construct comprising two SV40 NLS sequences.

In one embodiment, the deaminase protein is Apobec1 (YE1-BE3). It is not intended to limit Apobec1 to one organism. In one embodiment, the Apobec1 is derived from a rat species. Kim et al., "Increasing the genome-targeting scope and precision of base editing with engineered Cas9-cytidine deaminase fusions". *Nature Biotechnology* 35 (2017). In one embodiment, the Nme2Cas9 comprises an nNme2Cas9 D16A mutant. In one embodiment, the fusion protein further comprises a uracil glycosylase inhibitor protein (UGI). In one embodiment, the fusion protein comprises a YE1-BE3-nNme2Cas9 (D16A)-UGI construct. In one embodiment, the YE1-BE3-nNme2Cas9 (D16A)-UGI construct has the sequence of:

```
                                      (SEQ ID NO: 1)
MSSETGPVAVDPTLRRRIEPHEFEVFFDPRELRKETCLLYEINWGGRHS

IWRHTSQNTNKHVEVNFIEKFTTERYFCPNTRCSITWFLSYSPCGECSR

AITEFLSRYPHVTLFIYIARLYHHADPENRQGLRDLISSGVTIQIMTEQ

ESGYCWRNFVNYSPSNEAHWPRYPHLWVRLYVLELYCIILGLPPCLNIL

RRKQPQLTFFTIALQSCHYQRLPPHILWATGLKSGSETPGTSESATPES

MAAFKPNPINYILGLAIGIASVGWAMVEIDEEENPIRLIDLGVRVFERA

EVPKTGDSLAMARRLARSVRRLTRRRAHRLLRARRLLKREGVLQAADFD

ENGLIKSLPNTPWQLRAAALDRKLTPLEWSAVLLHLIKHRGYLSQRKNE

GETADKELGALLKGVANNAHALQTGDFRTPAELALNKFEKESGHIRNQR

GDYSHTFSRKDLQAELILLFEKQKEFGNPHVSGGLKEGIETLLMTQRPA

LSGDAVQKMLGHCTFEPAEPKAAKNTYTAERFIWLTKLNNLRILEQGSE

RPLTDTERATLMDEPYRKSKLTYAQARKLLGLEDTAFFKGLRYGKDNAE

ASTLMEMKAYHAISRALEKEGLKDKKSPLNLSSELQDEIGTAFSLFKTD

EDITGRLKDRVQPEILEALLKHISFDKFVQISLKALRRIVPLMEQGKRY

DEACAEIYGDHYGKKNTEEKIYLPPIPADEIRNPVVLRALSQARKVING

VVRRYGSPARIHIETAREVGKSFKDRKEIEKRQEENRKDREKAAAKFRE

YFPNFVGEPKSKDILKLRLYEQQHGKCLYSGKEINLVRLNEKGYVEIDA
```

-continued

```
ALPFSRTWDDSFNNKVLVLGSENQNKGNQTPYEYFNGKDNSREWQEFKA

RVETSRFPRSKKQRILLQKFDEDGFKECNLNDTRYVNRFLCQFVADHIL

LTGKGKRRVFASNGQITNLLRGFWGLRKVRAENDRHHALDAVVVACSTV

AMQQKITRFVRYKEMNAFDGKTIDKETGKVLHQKTHFPQPWEFFAQEVM

IRVFGKPDGKPEFEEADTPEKLRTLLAEKLSSRPEAVHEYVTPLFVSRA

PNRKMSGAHKDTLRSAKRFVKHNEKISVKRVWLTEIKLADLENMVNYKN

GREIELYEALKARLEAYGGNAKQAFDPKDNPFYKKGGQLVKAVRVEKTQ

ESGVLLNKKNAYTIADNGDMVRVDVFCKVDKKGKNQYFIVPIYAWQVAE

NILPDIDCKGYRIDDSYTFCFSLHKYDLIAFQKDEKSKVEFAYYINCDS

SNGRFYLAWHDKGSKEQQFRISTQNLVLIQKYQVNELGKEIRPCRLKKR

PPVRSGGSTNLSDIIEKETGKQLVIQESILMLPEEVEEVIGNKPESDIL

VHTAYDESTDENVMLLTSDAPEYKPWALVIQDSNGENKIKMLSGGSPKK

KRKV*
```

YE1-BE3 (underlined); linker (bold), nNme2Cas9
(italics), UGI (bold/underlined), SV40 NLS
(plain).

In one embodiment, the YE1-BE3-nNme2Cas9 (D16A)-
UGI construct has the sequence of:

(SEQ ID NO: 2)
```
MSSETGPVAVDPTLRRRIEPHEFEVFFDPRELRKETCLLYEINWGGRHS

IWRHTSQNTNKHVEVNFIEKFTTERYFCPNTRCSITWFLSYSPCGECSR

AITEFLSRYPHVTLFIYIARLYHHADPENRQGLRDLISSGVTIQIMTEQ

ESGYCWRNFVNYSPSNEAHWPRYPHLWVRLYVLELYCIILGLPPCLNIL

RRKQPQLTFFTIALQSCHYQRLPPHILWATGLKSGSETPGTSESATPES

MAAFKPNPINYILGLAIGIASVGWAMVEIDEEENPIRLIDLGVRVFERA

EVPKTGDSLAMARRLARSVRRLTRRRAHRLLRARRLLKREGVLQAADFD

ENGLIKSLPNTPWQLRAAAALDRKLTPLEWSAVLLHLIKHRGYLSQRKNE

GETADKELGALLKGVANNAHALQTGDFRTPAELALNKFEKESGHIRNQR

GDYSHTFSRKDLQAELILLFEKQKEFGNPHVSGGLKEGIETLLMTQRPA

LSGDAVQKMLGHCTFEPAEPKAAKNTYTAERFIWLTKLNNLRILEQGSE

RPLTDTERATLMDEPYRKSKLTYAQARKLLGLEDTAFFKGLRYGKDNAE

ASTLMEMKAYHAISRALEKEGLKDKKSPLNLSSELQDEIGTAFSLFKTD

EDITGRLKDRVQPEILEALLKHISFDKFVQISLKALRRIVPLMEQGKRY

DEACAEIYGDHYGKKNTEEKIYLPPIPADEIRNPVVLRALSQARKVING

VVRRYGSPARIHIETAREVGKSFKDRKEIEKRQEENRKDREKAAAKFRE

YFPNFVGEPKSKDILKLRLYEQQHGKCLYSGKEINLVRLNEKGYVEIDA

ALPFSRTWDDSFNNKVLVLGSENQNKGNQTPYEYFNGKDNSREWQEFKA

RVETSRFPRSKKQRILLQKFDEDGFKECNLNDTRYVNRFLCQFVADHIL

LTGKGKRRVFASNGQITNLLRGFWGLRKVRAENDRHHALDAVVVACSTV

AMQQKITRFVRYKEMNAFDGKTIDKETGKVLHQKTHFPQPWEFFAQEVM

IRVFGKPDGKPEFEEADTPEKLRTLLAEKLSSRPEAVHEYVTPLFVSRA

PNRKMSGAHKDTLRSAKRFVKHNEKISVKRVWLTEIKLADLENMVNYKN
```

-continued

```
GREIELYEALKARLEAYGGNAKQAFDPKDNPFYKKGGQLVKAVRVEKTQ

ESGVLLNKKNAYTIADNGDMVRVDVFCKVDKKGKNQYFIVPIYAWQVAE

NILPDIDCKGYRIDDSYTFCFSLHKYDLIAFQKDEKSKVEFAYYINCDS

SNGRFYLAWHDKGSKEQQFRISTQNLVLIQKYQVNELGKEIRPCRLKKR

PPVRSGGSTNLSDIIEKETGKQLVIQESILMLPEEVEEVIGNKPESDIL

VHTAYDESTDENVMLLTSDAPEYKPWALVIQDSNGENKIKMLSGGSPKK

KRKV*
```

YE1-BE3 (underlined); linker (bold), nNme2Cas9
(italics), UGI (bold/underlined), SV40 NLS
(plain).

In one embodiment, the present invention contemplates a
fusion protein comprising an NmeCas9/ABE7.10 deaminase
protein. In one embodiment, the deaminase protein is TadA.
In one embodiment, the deaminase protein is TadA 7.10. In
one embodiment, the ABE7.10-nNme2Cas9 (D16A) con-
struct has the following sequence:

(SEQ ID NO: 3)
```
MSEVEFSHEYWMRHALTLAKRAWDEREVPVGAVLVHNNRVIGEGWNRPI

GRHDPTAHAEIMALRQGGLVMQNYRLIDATLYVTLEPCVMCAGAMIHSR

IGRVVFGARDAKTGAAGSLMDVLHHPGMNHRVEITEGILADECAALLSD

FFRMRRQEIKAQKKAQSSTDSGGSSGGSSGSETPGTSESATPESSGGSS

GGSSEVEFSHEYWMRHALTLAKRARDEREVPVGAVLVLNNRVIGEGWNR

AIGLHDPTAHAEIMALRQGGLVMQNYRLIDATLYVTFEPCVMCAGAMIH

SRIGRVVFGVRNAKTGAAGSLMDVLHYPGMNHRVEITEGILADECAALL

CYFFRMPRQVENAQKKAQSSTDSGGSSGGSSGSETPGTSESATPESSGG

SSGGSMAAFKPNPINYILGLAIGIASVGWAMVEIDEEENPIRLIDLGVR

VFERAEVPKTGDSLAMARRLARSVRRLTRRRAHRLLRARRLLKREGVLQ

AADFDENGLIKSLPNTPWQLRAAAALDRKLTPLEWSAVLLHLIKHRGYLS

QRKNEGETADKELGALLKGVANNAHALQTGDFRTPAELALNKFEKESGH

IRNQRGDYSHTFSRKDLQAELILLFEKQKEFGNPHVSGGLKEGIETLLM

TQRPALSGDAVQKMLGHCTFEPAEPKAAKNTYTAERFIWLTKLNNLRIL

EQGSERPLTDTERATLMDEPYRKSKLTYAQARKLLGLEDTAFFKGLRYG

KDNAEASTLMEMKAYHAISRALEKEGLKDKKSPLNLSSELQDEIGTAFS

LFKTDEDITGRLKDRVQPEILEALLKHISFDKFVQISLKALRRIVPLME

QGKRYDEACAEIYGDHYGKKNTEEKIYLPPIPADEIRNPVVLRALSQAR

KVINGVVRRYGSPARIHIETAREVGKSFKDRKEIEKRQEENRKDREKAA

AKFREYFPNFVGEPKSKDILKLRLYEQQHGKCLYSGKEINLVRLNEKGY

VEIDHALPFSRTWDDSFNNKVLVLGSENQNKGNQTPYEYFNGKDNSREW

QEFKARVETSRFPRSKKQRILLQKFDEDGFKECNLNDTRYVNRFLCQFV

ADHILLTGKGKRRVFASNGQITNLLRGFWGLRKVRAENDRHHALDAVVV

ACSTVAMQQKITRFVRYKEMNAFDGKTIDKETGKVLHQKTHFPQPWEFF

AQEVMIRVFGKPDGKPEFEEADTPEKLRTLLAEKLSSRPEAVHEYVTPL

FVSRAPNRKMSGAHKDTLRSAKRFVKHNEKISVKRVWLTEIKLADLENM
```

-continued

*VNYKNGREIELYEALKARLEAYGGNAKQAFDPKDNPFYKKGGQLVKAVR*

*VEKTQESGVLLNKKNAYTIADNGDMVRVDVFCKVDKKGKNQYFIVPIYA*

*WQVAENILPDIDCKGYRIDDSYTFCFSLHKYDLIAFQKDEKSKVEFAYY*

*INCDSSNGRFYLAWHDKGSKEQQFRISTQNLVLIQKYQVNELGKEIRPC*

*RLKKRPPVR*EDKRPAATKKAGQAKKKK*

TadA (underlined), TadA 7.10 (underlined/bold),
linker (bold), nNme2Cas9 (italics), In one embodiment, an ABE7.10-nNme2Cas9 (D16A)
construct has the following amino acid sequence:

(SEQ ID NO: 4)
MSEVEFSHEYWMRHALTLAKRAWDEREVPVGAVLVHNNRVIGEGWNRPI

GRHDPTAHAEIMALRQGGLVMQNYRLIDATLYVTLEPCVMCAGAMIHSR

IGRVVFGARDAKTGAAGSLMDVLHHPGMNHRVEITEGILADECAALLSD

FFRMRRQEIKAQKKAQSSTDSGGSSGGSSGSETPGTSESATPESSGGSS

GGSSEVEFSHEYWMRHALTLAKRARDEREVPVGAVLVLNNRVIGEGWNR

AIGLHDPTAHAEIMALRQGGLVMQNYRLIDATLYVTFEPCVMCAGAMIH

SRIGRVVFGVRNAKTGAAGSLMDVLHYPGMNHRVEITEGILADECAALL

CYFFRMPRQVENAQKKAQSSTD*SGGSSGGSSGSETPGTSESATPESSGG*

*SSGGSMAAFKPNPINYILGLAIGIASVGWAMVEIDEEENPIRLIDLGVR*

*VFERAEVPKTGDSLAMARRLARSVRRLTRRRAHRLLRARRLLKREGVLQ*

*AADFDENGLIKSLPNTPWQLRAAALDRKLTPLEWSAVLLHLIKHRGYLS*

*QRKNEGETADKELGALLKGVANNAHALQTGDFRTPAELALNKFEKESGH*

*IRNQRGDYSHTFSRKDLQAELILLFEKQKEFGNPHVSGGLKEGIETLLM*

*TQRPALSGDAVQKMLGHCTFEPAEPKAAKNTYTAERFIWLTKLNNLRIL*

*EQGSERPLTDTERATLMDEPYRKSKLTYAQARKLLGLEDTAFFKGLRYG*

*KDNAEASTLMEMKAYHAISRALEKEGLKDKKSPLNLSSELQDEIGTAFS*

*LFKTDEDITGRLKDRVQPEILEALLKHISFDKFVQISLKALRRIVPLME*

*QGKRYDEACAEIYGDHYGKKNTEEKIYLPPIPADEIRNPVVLRALSQAR*

*KVINGVVRRYGSPARIHIETAREVGKSFKDRKEIEKRQEENRKDREKAA*

*AKFREYFPNFVGEPKSKDILKLRLYEQQHGKCLYSGKEINLVRLNEKGY*

*VEIDHALPFSRTWDDSFNNKVLVLGSENQNKGNQTPYEYFNGKDNSREW*

*QEFKARVETSRFPRSKKQRILLQKFDEDGFKECNLNDTRYVNRFLCQFV*

*ADHILLTGKGKRRVFASNGQITNLLRGFWGLRKVRAENDRHHALDAVVV*

*ACSTVAMQQKITRFVRYKEMNAFDGKTIDKETGKVLHQKTHFPQPWEFF*

*AQEVMIRVFGKPDGKPEFEEADTPEKLRTLLAEKLSSRPEAVHEYVTPL*

*FVSRAPNRKMSGAHKDTLRSAKRFVKHNEKISVKRVWLTEIKLADLENM*

*VNYKNGREIELYEALKARLEAYGGNAKQAFDPKDNPFYKKGGQLVKAVR*

*VEKTQESGVLLNKKNAYTIADNGDMVRVDVFCKVDKKGKNQYFIVPIYA*

*WQVAENILPDIDCKGYRIDDSYTFCFSLHKYDLIAFQKDEKSKVEFAYY*

-continued
*INCDSSNGRFYLAWHDKGSKEQQFRISTQNLVLIQKYQVNELGKEIRPC*

*RLKKRPPVR*EDKRPAATKKAGQAKKKK*

TadA (underlined), TadA 7.10 (underlined/bold),
linker (bold italics), nNme2Cas9 (italics),
Nucleoplasmin NLS (plain).

In one embodiment, an ABEmax-nNme2Cas9 (D16A)
construct has the following amino acid sequence (SEQ ID NO: 5)
MKRTADGSEFESPKKKRKVSEVEFSHEYWMRHALTLAKRAWDEREVPVG

AVLVHNNRVIGEGWNRPIGRHDPTAHAEIMALRQGGLVMQNYRLIDATL

YVTLEPCVMCAGAMIHSRIGRVVFGARDAKTGAAGSLMDVLHHPGMNHR

VEITEGILADECAALLSDFFRMRRQEIKAQKKAQSSTD*SGGSSGGSSGS*

*ETPGTSESATPESSGGSSGGS*SEVEFSHEYWMRHALTLAKRARDEREVP

VGAVLVLNNRVIGEGWNRAIGLHDPTAHAEIMALRQGGLVMQNYRLIDA

TLYVTFEPCVMCAGAMIHSRIGRVVFGVRNAKTGAAGSLMDVLHYPGMN

HRVEITEGILADECAALLCYFFRMPRQVFNAQKKAQSSTD*SGGSSGGSS*

*GSETPGTSESATPESSGGSSGGS*MAAFKPNPINYILGLAIGIASVGWAM

*VEIDEEENPIRLIDLGVRVFERAEVPKTGDSLAMARRLARSVRRLTRRR*

*AHRLLRARRLLKREGVLQAADFDENGLIKSLPNTPWQLRAAALDRKLTP*

*LEWSAVLLHLIKHRGYLSQRKNEGETADKELGALLKGVANNAHALQTGD*

*FRTPAELALNKFEKESGHIRNQRGDYSHTFSRKDLQAELILLFEKQKEF*

*GNPHVSGGLKEGIETLLMTQRPALSGDAVQKMLGHCTFEPAEPKAAKNT*

*YTAERFIWLTKLNNLRILEQGSERPLTDTERATLMDEPYRKSKLTYAQA*

*RKLLGLEDTAFFKGLRYGKDNAEASTLMEMKAYHAISRALEKEGLKDKK*

*SPLNLSSELQDEIGTAFSLFKTDEDITGRLKDRVQPEILEALLKHISFD*

*KFVQISLKALRRIVPLMEQGKRYDEACAEIYGDHYGKKNTEEKIYLPPI*

*PADEIRNPVVLRALSQARKVINGVVRRYGSPARIHIETAREVGKSFKDR*

*KEIEKRQEENRKDREKAAAKFREYFPNFVGEPKSKDILKLRLYEQQHGK*

*CLYSGKEINLVRLNEKGYVEIDHALPFSRTWDDSFNNKVLVLGSENQNK*

*GNQTPYEYFNGKDNSREWQEFKARVETSRFPRSKKQRILLQKFDEDGFK*

*ECNLNDTRYVNRFLCQFVADHILLTGKGKRRVFASNGQITNLLRGFWGL*

*RKVRAENDRHHALDAVVVACSTVAMQQKITRFVRYKEMNAFDGKTIDKE*

*TGKVLHQKTHFPQPWEFFAQEVMIRVFGKPDGKPEFEEADTPEKLRTLL*

*AEKLSSRPEAVHEYVTPLFVSRAPNRKMSGAHKDTLRSAKRFVKHNEKI*

*SVKRVWLTEIKLADLENMVNYKNGREIELYEALKARLEAYGGNAKQAFD*

*PKDNPFYKKGGQLVKAVRVEKTQESGVLLNKKNAYTIADNGDMVRVDVF*

*CKVDKKGKNQYFIVPIYAWQVAENILPDIDCKGYRIDDSYTFCFSLHKY*

*DLIAFQKDEKSKVEFAYYINCDSSNGRFYLAWHDKGSKEQQFRISTQNL*

*VLIQKYQVNELGKEIRPCRLKKRPPVR*EDKRPAATKKAGQAKKKKFEPK

KKRKV\*

TadA (underlined), TadA* 7.10 (underlined/bold),
linker (bold italics), nNme2Cas9 (italics),
Nucleoplasmin NLS (plain) and SV40 NLS (BOLD).

In one embodiment, a CBE4-nNme2Cas9 (D16A)-UGI-UGI construct has the following amino acid sequence:

(SEQ ID NO: 6)
PAAKRVKLDGGSGGGSGGGSGPAAKRVKLD*GGSGGGSGGGSGPLEPKKK*

*RKVPW*SSETGPVAVDPTLRRRIEPHEFEVFFDPRELRKETCLLYEINWG

GRHSIWRHTSQNTNKHVEVNFIEKFTTERYFCPNTRCSITWFLSWSPCG

ECSRAITEFLSRYPHVTLFIYIARLYHHADPRNRQGLRDLISSGVTIQI

MTEQESGYCWRNFVNYSPSNEAHWPRYPHLWVRLYVLELYCIILGLPPC

LNILRRKQPQLTFFTIALQSCHYQRLPPHILWATGLK*SGGSSGGSSGSE*

*TPGTSESATPESSGGSSGGSSIDKL*AAFKPNPINYILGLAIGIASVGWAM

*VEIDEEENPIRLIDLGVRVFERAEVPKTGDSLAMARRLARSVRRLTRRR*

*AHRLLRARRLLKREGVLQAADFDENGLIKSLPNTPWQLRAAALDRKLTP*

*LEWSAVLLHLIKHRGYLSQRKNEGETADKELGALLKGVANNAHALQTGD*

*FRTPAELALNKFEKESGHIRNQRGDYSHTFSRKDLQAELILLFEKQKEF*

*GNPHVSGGLKEGIETLLMTQRPALSGDAVQKMLGHCTFEPAEPKAAKNT*

*YTAERFIWLTKLNNLRILEQGSERPLTDTERATLMDEPYRKSKLTYAQA*

*RKLLGLEDTAFFKGLRYGKDNAEASTLMEMKAYHAISRALEKEGLKDKK*

*SPLNLSSELQDEIGTAFSLFKTDEDITGRLKDRVQPEILEALLKHISFD*

*KFVQISLKALRRIVPLMEQGKRYDEACAEIYGDHYGKKNTEEKIYLPPI*

*PADEIRNPVVLRALSQARKVINGVVRRYGSPARIHIETAREVGKSFKDR*

*KEIEKRQEENRKDREKAAAKFREYFPNFVGEPKSKDILKLRLYEQQHGK*

*CLYSGKEINLVRLNEKGYVEIDHALPFSRTWDDSFNNKVLVLGSENQNK*

*GNQTPYEYFNGKDNSREWQEFKARVETSRFPRSKKQRILLQKFDEDGFK*

*ECNLNDTRYVNRFLCQFVADHILLTGKGKRRVFASNGQITNLLRGFWGL*

*RKVRAENDRHHALDAVVVACSTVAMQQKITRFVRYKEMNAFDGKTIDKE*

*TGKVLHQKTHFPQPWEFFAQEVMIRVFGKPDGKPEFEEADTPEKLRTLL*

*AEKLSSRPEAVHEYVTPLFVSRAPNRKMSGAHKDTLRSAKRFVKHNEKI*

*SVKRVWLTEIKLADLENMVNYKNGREIELYEALKARLEAYGGNAKQAFD*

*PKDNPFYKKGGQLVKAVRVEKTQESGVLLNKKNAYTIADNGDMVRVDVF*

*CKVDKKGKNQYFIVPIYAWQVAENILPDIDCKGYRIDDSYTFCFSLHKY*

*DLIAFQKDEKSKVEFAYYINCDSSNGRFYLAWHDKGSKEQQFRISTQNL*

*VLIQKYQVNELGKEIRPCRLKKRPPVR**VYPYDVPDYAGYPYDVPDYAGS*

*YPYDVPDYAGSAAPAAKKKKLDFESGEFLQPGIDLSQLGGDSGGSGGSG*

*GS*TNLSDIIEKETGKQLVIQESILMLPEEVEEVIGNKPESDILVHTAYD

ESTDENVMLLTSDAPEYKPWALVIQDSNGENKIKML*SGGSGGSGGS*TNL

SDIIEKETGKQLVIQESILMLPEEVEEVIGNKPESDILVHTAYDESTDE

NVMLLTSDAPEYKPWALVIQDSNGENKIKML*SGGS*PKKKRKVSRGSAAP

AAKRVKLD*GGSGGGSGGGSGS*GPAAKRVKLD rApobec1 (underlined), UGI (underlined/bold),
linker (bold italics), nNme2Cas9 (D16A) (italics),
Cmyc-NLS (plain) and SV40 NLS (BOLD).

In one embodiment, an optimized nNme2Cas9-ABEmax construct refers to an optimized version with improved promoter, NLS sequences, and linker sequences. In some embodiments, an optimized nNme2Cas9-ABEmax construct comprises, 5' to 3', a C-myc NLS, 12aa linker, 15aa linker, SV40 NLS, TadA, TadA*7.10, 48aa linker, nNme2Cas9, a 73aa linker (3×HA-tag), 15aa linker, and a C-myc NLS. In some embodiments, an optimized nNme2Cas9-ABEmax construct further comprises at least two each alternating C-myc NLS and a 12aa linker at the 3' end. In some embodiments, an optimized nNme2Cas9-ABEmax construct further comprises at least two each alternating 15aa linker and C-myc NLS at the 5' end.

In one embodiment, an optimized nNme2Cas9-ABEmax construct has the following amino acid sequence (SEQ ID NO: 7):
PAAKRVKLD*GGSGGGSGGGSG*PAAKRVKLD*GGSGGGSGGGSGPLEPKKK*

*RKV*SEVEFSHEYWMRHALTLAKRAWDEREVPVGAVLVHNNRVIGEGWNR

PIGRHDPTAHAEIMALRQGGLVMQNYRLIDATLYVTLEPCVMCAGAMIH

SRIGRVVFGARDAKTGAAGSLMDVLHHPGMNHRVEITEGILADECAALL

SDFFRMRRQEIKAQKKAQSSTD*SGGSSGGSSGSETPGTSESATPESSGG*

*SSGGSS*EVEFSHEYWMRHALTLAKRARDEREVPVGAVLVLNNRVIGEGW

NRAIGLHDPTAHAEIMALRQGGLVMQNYRLIDATLYVTFEPCVMCAGAM

IHSRIGRVVFGVRNAKTGAAGSLMDVLHYPGMNHRVEITEGILADECAA

LLCYFFRMPRQVFNAQKKAQSSTD*SGGSSGGSSGSETPGTSESATPESS*

*GGSSGGSMAAFKPNPINYDIDKL*AAFKPNPINYILGLAIGIASVGWAMV

*EIDEEENPIRLIDLGVRVFERAEVPKTGDSLAMARRLARSVRRLTRRRA*

*HRLLRARRLLKREGVLQAADFDENGLIKSLPNTPWQLRAAALDRKLTPL*

*EWSAVLLHLIKHRGYLSQRKNEGETADKELGALLKGVANNAHALQTGDF*

*RTPAELALNKFEKESGHIRNQRGDYSHTFSRKDLQAELILLFEKQKEFG*

*NPHVSGGLKEGIETLLMTQRPALSGDAVQKMLGHCTFEPAEPKAAKNTY*

*TAERFIWLTKLNNLRILEQGSERPLTDTERATLMDEPYRKSKLTYAQAR*

*KLLGLEDTAFFKGLRYGKDNAEASTLMEMKAYHAISRALEKEGLKDKKS*

*PLNLSSELQDEIGTAFSLFKTDEDITGRLKDRVQPEILEALLKHISFDK*

*FVQISLKALRRIVPLMEQGKRYDEACAEIYGDHYGKKNTEEKIYLPPIP*

*ADEIRNPVVLRALSQARKVINGVVRRYGSPARIHIETAREVGKSFKDRK*

*EIEKRQEENRKDREKAAAKFREYFPNFVGEPKSKDILKLRLYEQQHGKC*

*LYSGKEINLVRLNEKGYVEIDHALPFSRTWDDSFNNKVLVLGSENQNKG*

*NQTPYEYFNGKDNSREWQEFKARVETSRFPRSKKQRILLQKFDEDGFKE*

*CNLNDTRYVNRFLCQFVADHILLTGKGKRRVFASNGQITNLLRGFWGLR*

*KVRAENDRHHALDAVVVACSTVAMQQKITRFVRYKEMNAFDGKTIDKET*

*GKVLHQKTHFPQPWEFFAQEVMIRVFGKPDGKPEFEEADTPEKLRTLLA*

*EKLSSRPEAVHEYVTPLFVSRAPNRKMSGAHKDTLRSAKRFVKHNEKIS*

*VKRVWLTEIKLADLENMVNYKNGREIELYEALKARLEAYGGNAKQAFDP*

*KDNPFYKKGGQLVKAVRVEKTQESGVLLNKKNAYTIADNGDMVRVDVFC*

*KVDKKGKNQYFIVPIYAWQVAENILPDIDCKGYRIDDSYTFCFSLHKYD*

*LIAFQKDEKSKVEFAYYINCDSSNGRFYLAWHDKGSKEQQFRISTQNLV*

-continued

*LIQKYQVNELGKEIRPCRLKKRP*PVR*VYPYDVPDYAGYPYDVPDYAGSY*

*PYDVPDYAGSAAPAAKKKKLDFESGEFLQPGGSTSSRGSAA**PAAKRVKL*

D*GGSGGGSGGGSGS**G*PAAKRVKLD hTadA7.10 (underlined), hTadA*7.10 (underlined/
bold), linker (bold italics), nNme2Cas9 (italics),
Cmyc-NLS (plain), SV40-NLS (bold).

In some embodiments, a plasmid nSpCas9-ABEmax (Addgene ID: 112095) was used for experimental controls and for molecular cloning. In some embodiments, a plasmid nSpCas9-CBE4 (Addgene ID: 100802) was used for experimental controls and for molecular cloning.

Electroporation of HEK293T cells with DNA plasmids comprising a YE1-BE3-Nme2Cas9 nucleotide deaminase fusion protein achieved robust single-base editing of a C•G base pair to a T•A base pair at an endogenous target site (TS25). See, FIGS. 2A-C.

Figures 2A, 2B:
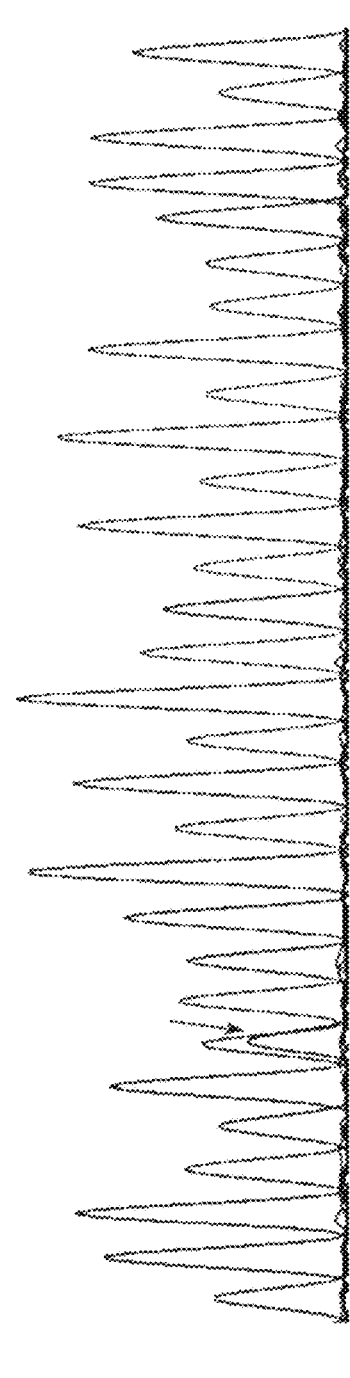
FIG. 2A-C presents exemplary data of the electroporation of HEK293T cells with DNA plasmids comprising a YE1-BE3-nNme2Cas9 (D16A)-UGI fusion protein efficiently converting C to T at endogenous target site 25 (TS25) in HEK293T cells via nucleofection.
Figure 2C:
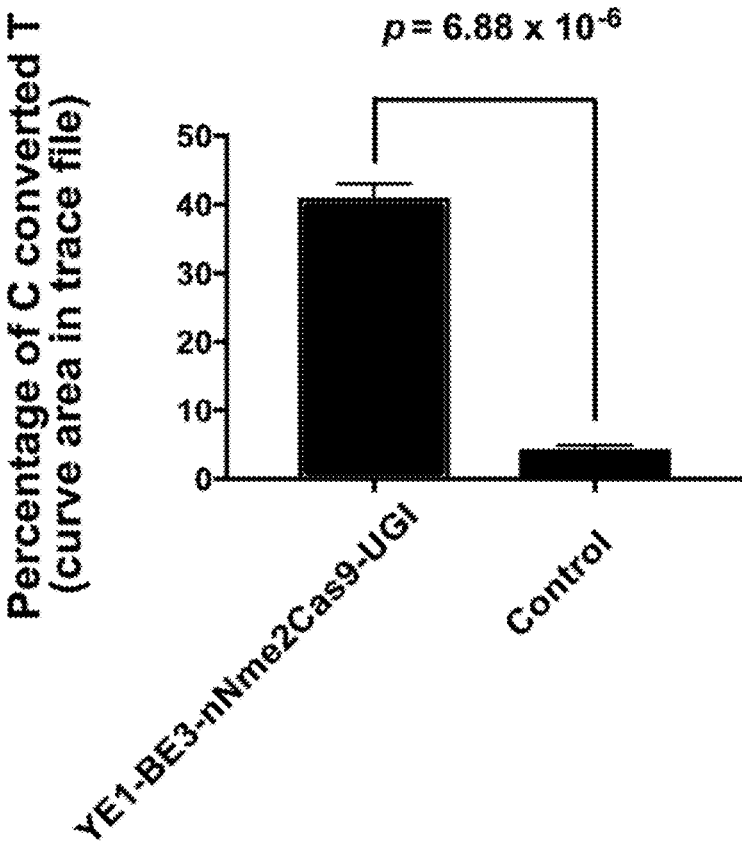

FIG. 2A-C presents exemplary data of the electroporation of HEK293T cells with DNA plasmids comprising a YE1-BE3-nNme2Cas9 (D16A)-UGI fusion protein efficiently converting C to T at endogenous target site 25 (TS25) in HEK293T cells via nucleofection. FIG. 2A shows exemplary sequences for a TS25 endogenous target site (within the black rectangle). GN23 sgRNA base-pairs with the target DNA strand, leaving the displaced DNA strand for cytidine deaminase to edit (e.g. new underlined nucleotides). FIG. 2B shows exemplary sequencing data showing a doublet nucleotide peak (7″ position from 5′ end; arrow) demonstrating the successful single base editing of a cytidine to a thymidine (e.g., a C•G base pair conversion to a T•A base pair). FIG. 2C shows an exemplary quantitation of the data shown in FIG. 2B plotting the percent conversion of C→T single base editing. The percentage of C converted to T is about 40% in the base editor- and sgRNA-treated sample (p-value=$6.88 \times 10^{-6}$). The "no sgRNA" control displays the background noise due to Sanger sequencing. EditR (Kluesner et al., 2018) was used to perform the analysis.

Four other YE1-BE3-nNme2Cas9/D16A mutant fusion proteins were co-expressed with enhanced green fluorescent protein (EGFP) in a stable K562-derived cell line expressing enhanced green fluorescent protein (EGFP). Each YE1-BE3-nNme2Cas9/D16A mutant fusion protein had a specific UGI target site. See, FIGS. 3A-D.

Deep-sequencing analysis indicates YE1-BE3-nNme2Cas9 converts C residues to T residues at each of the four EGFP target sites. The percentage of editing ranged from 0.24% to 2%. The potential base editing window is from nucleotides 2-8 in the displaced DNA strand, counting the nucleotide at the 5′ (PAM-distal) end as nucleotide #1. See, FIGS. 3A-D.

Figures 3A, 3B, 3C, 3D:
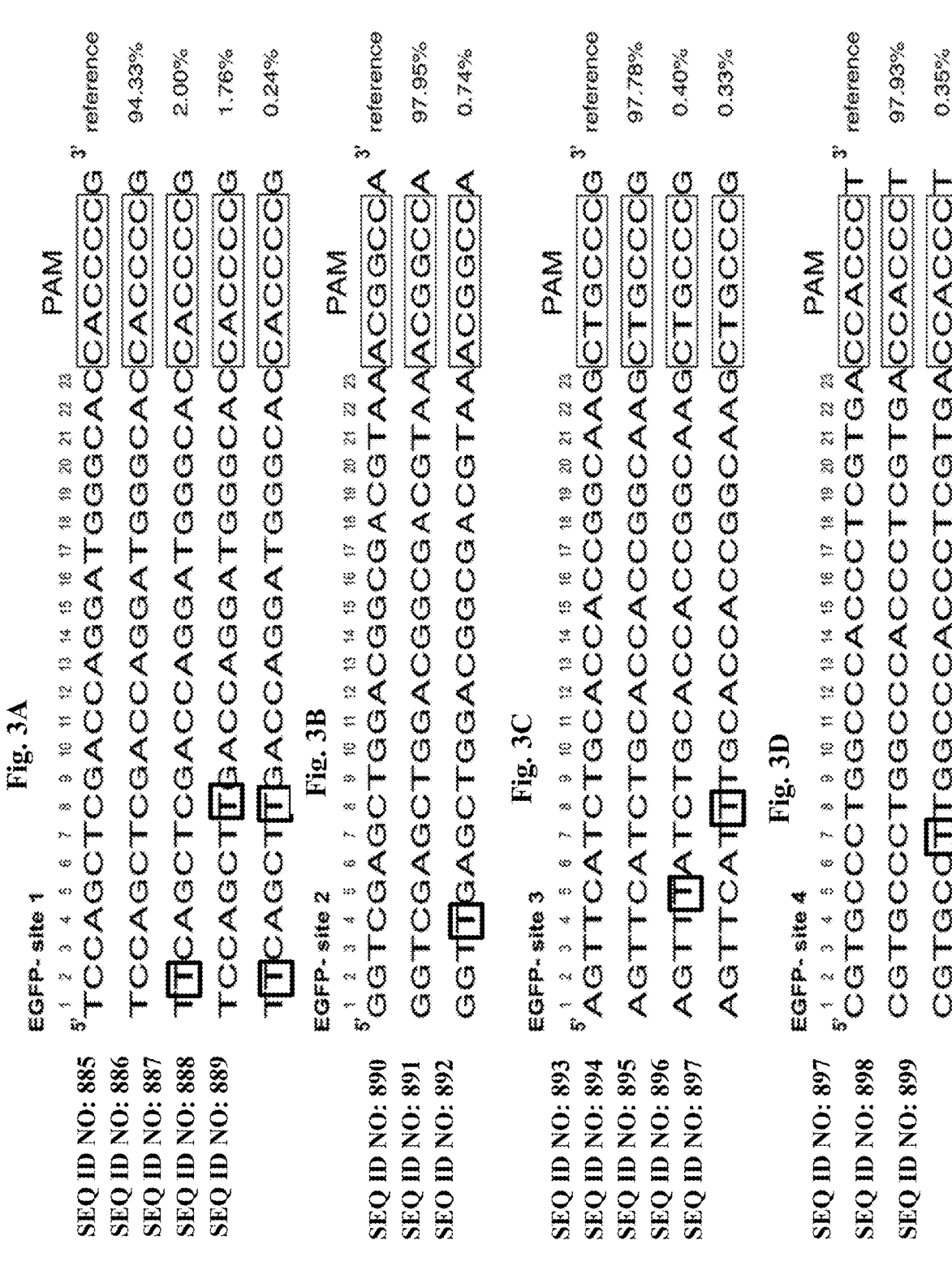

FIG. 3A-F presents exemplary specific UGI target sites that were respectively integrated into YE1-BE3-nNme2Cas9/D16A mutant fusion proteins and co-expressed with enhanced green fluorescent protein (EGFP) in a stable K562-derived cell line. Converted bases are highlighted using boxes. Background signals were filtered using negative control samples (YE1-BE3-nNme2Cas9 nucleofected K562 cells without sgRNA constructs). $N_4CC$ PAMs are boxed. The percentage of total reads exhibiting mutations in base-editor-targeted sites is shown in the right column. FIG. 3A shows an exemplary EGFP-Site 1. FIG. 3B shows an exemplary EGFP-Site 2. FIG. 3C shows an exemplary EGFP-Site 3. FIG. 3D shows an exemplary EGFP-Site 4.

Figure 3F:

Electroporation of HEK293T cells with DNA plasmids comprising a YE1-BE3-nNme2Cas9c-fos promoter achieved robust single-base editing of a C•G base pair to a T•A base pair at endogenous target sites in the c-fos promoter (FIG. 3E). FIG. 3E shows an exemplary deep-sequencing analysis indicating where YE1-BE3-nNme2Cas9 converts C residues to T residues at endogenous c-fos promoter region. The percentage of total reads exhibiting mutations in base-editor-targeted sites is shown in the right column. The converted bases outside of the PAM region are boxed. Background signals were filtered using negative control samples. The highest percentage of editing is 32.50%. FIG. 3F shows an exemplary deep-sequencing analysis indicating where ABE7.10-nNme2Cas9 or ABEmax (Koblan et al., 2018)-nNme2Cas9 converts A residues to G residues at endogenous c-fos promoter region. The percentage of total reads exhibiting mutations in base-editor-targeted sites is shown in the right column. The converted bases outside of the PAM region are boxed. Background signals were filtered using negative control samples. The percentage of editing is 0.53% by ABE7.10-nNme2Cas9 or 2.33% by ABEmax-nNme2Cas9 (D16A).

In one embodiment, the present invention contemplates the expression of an ABE7.10-nNme2Cas9 (D16A) fusion protein for base editing. Although it is not necessary to understand the mechanism of an invention, it is believed that Nme2Cas9 base editing may be an effective treatment for tyrosinemia by reversing a G-to-A point mutation in the Fah gene with an ABE7.10-nNme2Cas9 (D16A) fusion protein.

G-to-A mutation (outlined A) at the last nucleotide of exon 8 in Fah gene, causing exon skipping. FAH deficiency leads to toxin accumulation and severe liver damage. The position of a SpyCas9 PAM (thin black rectangular box) downstream of the mutation is not optimal for designing the sgRNA since the A mutation is out of the efficient base editing window of ABE7.10, which is 4-7th nt at the 5′ (PAM-distal) end (underlined) (Gaudelli et al., 2017).

However, there are two Nme2Cas9 PAMs (thick black rectangular box) in the downstream sequences that can potentially correct the mutation and revert DNA sequence to wildtype via ABE7.10-nNme2Cas9 (D16A). See, FIG. 4.

FIG. 4 presents an exemplary alignment of the wildtype Fah gene with the tyrosinemia Fah mutant gene showing an A-G single base gene editing target site (position 9). The respective SpyCas9 single PAM site and NmeCas9 double PAM sites are indicated for demonstrating the suboptimal targeting window relative to the SpyCas9 PAM site. This figure serves as a potential example of a site where Nme2Cas9 could overcome limitations of existing base editors. It is further believed that the NmeCas9 base editor described herein can perform precise base editing that cannot be achieved with conventional SpyCas9-derived base editors due to a suboptimal base editing window relative to available PAMs nearby.

Furthermore, we contemplate extending base editing to a tyrosinemia mouse model for reversing the G-to-A point mutation by viral delivery methods using ABEmax-nNme2Cas9 (D16A), where the desired editing cannot be achieved with SpyCas9-derived base editors due to a suboptimal base editing window relative to available PAMs nearby (e.g. FIG. 4).

B. NmeCas9 Constructs: Compact & Hyperaccurate

Clustered, regularly interspaced, short, palindromic repeats (CRISPR) along with CRISPR-associated (Cas) proteins constitute bacterial and archaeal adaptive immune pathways against phages and other mobile genetic elements (MGEs) (Barrangou et al., 2007; Brouns et al., 2008; Marraffini and Sontheimer, 2008). In Type II CRISPR systems, CRISPR RNA (crRNA) is bound to a trans-activating crRNA (tracrRNA) and loaded onto a Cas9 effector protein that cleaves MGE nucleic acids complementary to the crRNA (Garneau et al., 2010; Deltcheva et al., 2011; Sapranauskas et al., 2011; Gasiunas et al., 2012; Jinek et al., 2012). The crRNA: tracrRNA hybrid can be fused into a single-guide RNA (sgRNA) (Jinek et al., 2012). The RNA programmability of Cas9 endonucleases has made it a powerful genome editing platform in biotechnology and medicine (Cho et al., 2013; Cong et al., 2013; Hwang et al., 2013; Jiang et al., 2013; Jinek et al., 2013; Mali et al., 2013b).

In addition to sgRNA, Cas9 target recognition is usually associated with a 1-5 nucleotide signature downstream of the complementary DNA sequence, called a protospacer adjacent motif (PAM) (Deveau et al., 2008; Mojica et al., 2009). Cas9 orthologs exhibit considerable diversity in PAM length and sequence. Among Cas9 orthologs that have been characterized, *Streptococcus pyogenes* Cas9 (SpyCas9) is the most widely used, in part because it recognizes a short NGG PAM (Jinek et al., 2012) (N represents any nucleotide) that affords a high density of targetable sites. Nevertheless, Spy's relatively large size (i.e., 1,368 amino acids) makes this Cas9 difficult to package (along with sgRNA and promoters) into a single recombinant adeno-associated virus (rAAV). This has been shown to be a drawback for therapeutic applications given the promise shown by AAV vectors for in vivo gene delivery (Keeler et al., 2017). Moreover, SpyCas9 and its RNA guides have required extensive characterization and engineering to minimize the tendency to edit near-cognate, off-target sites. (Bolukbasi et al., 2015b; Tsai and Joung, 2016; Tycko et al., 2016; Chen et al., 2017; Casini et al., 2018; Yin et al., 2018). To date, subsequent engineering efforts have not overcome these size limitations.

Several Cas9 orthologs of less than 1,100 amino acids in length obtained from diverse species have been validated for mammalian genome editing, including strains of *N. meningitidis* (NmeCas9, 1,082 aa) (Esvelt et al., 2013; Hou et al., 2013), *Staphylococcus aureus* (SauCas9, 1,053 aa) (Ran et al., 2015), *Campylobacter jejuni* (CjeCas9, 984 aa) (Kim et al., 2017), and *Geobacillus stearothermophilus* (GeoCas9, 1,089 aa) (Harrington et al., 2017b). NmeCas9, CjeCas9, and GeoCas9 are representatives of type II-C Cas9s (Mir et al., 2018), most of which are <1,100 aa. With the exception of GeoCas9, each of these shorter sequence orthologs has been successfully deployed for in vivo editing via all-in-one AAV delivery (in which a single vector expresses both guide and effector) (Ran et al., 2015; Kim et al., 2017; Ibraheim et al., 2018, submitted). Furthermore, NmeCas9 and CjeCas9 have been shown to be naturally resistant to off-target editing (Lee et al., 2016; Kim et al., 2017; Amrani et al., 2018, submitted). However, the PAMs that are recognized by compact Cas9s are usually longer than that of SpyCas9, substantially reducing the number of targetable sites at or near a given locus; for example, i) $N_4$GAYW/$N_4$GYTT/$N_4$GTCT for NmeCas9 (Esvelt et al., 2013; Hou et al., 2013; Lee et al., 2016; Amrani et al., 2018); ii) $N_2$GRRT for SauCas9 (Ran et al., 2015); iii) $N_4$RYAC for CjeCas9 (Kim et al., 2017); and iv) $N_4$CRAA/$N_4$GMAA for GeoCas9s (Harrington et al., 2017b) (Y=C, T; R=A, G; M=A, C; W=A, T). A smaller subset of target sites is advantageous for highly accurate and precise gene editing tasks including, but not limited to: i) editing of small targets (e.g. miRNAs); ii) correction of mutations by base editing which alters a very narrow window of bases relative to the PAM (Komor et al., 2016; Gaudelli et al., 2017); or iii) precise editing via homology-directed repair (HDR) which is most efficient when the rewritten bases are close to the cleavage site (Gallagher and Haber, 2018). Because of PAM restrictions, many editing sites cannot be targeted using all-in-one AAV vectors for in vivo delivery even with these shorter Cas9 proteins. For example, A SauCas9 mutant (SauCas9$^{KKH}$) has been developed that has reduced PAM constraints ($N_3$RRT), though this increase in targeting range often comes at the cost of reduced on-target editing efficacy, and off-target edits are still observed. (Kleinstiver et al., 2015).

Safe and effective CRISPR-based therapeutic gene editing will be greatly enhanced by Cas9 orthologs and variants that are highly active in human cells, resistant to off-targeting, sufficiently compact for all-in-one AAV delivery, and capable of accessing a high density of genomic sites. In one embodiment, the present invention contemplates a compact, hyper-accurate Cas9 (Nme2Cas9) from a distinct strain of *N. meningitidis*. In one embodiment, the present invention contemplates a method for single-AAV delivery of Nme2Cas9 and its sgRNA to perform efficient genome editing in vivo and/or ex vivo. Although it is not necessary to understand the mechanism of an invention, it is believed that this ortholog functions efficiently in mammalian cells and recognizes an $N_4$CC PAM that affords a target site density identical to that of wild-type SpyCas9 (e.g., every 8 bp on average, when both DNA strands are considered).

1. PAM Interacting Domains and Anti-CRISPR Proteins

PAM recognition by Cas9 orthologs occurs predominantly through protein-DNA interactions between the PAM Interacting Domain (PID) and the nucleotides adjacent to the protospacer (Jiang and Doudna, 2017). PAM mutations often enable phage escape from type II CRISPR immunity (Paez-Espino et al., 2015), placing these systems under selective pressure not only to acquire new CRISPR spacers, but also to evolve new PAM specificities via PID mutations. In addition, some phages and MGEs express anti-CRISPR (Acr) proteins that inhibit Cas9 (Pawluk et al., 2016; Hynes et al., 2017; Rauch et al., 2017). PID binding is an effective inhibitory mechanism adopted by some Acrs (Dong et al., 2017; Shin et al., 2017; Yang and Patel, 2017), suggesting that PID variation may also be driven by selective pressure to escape Acr inhibition. Cas9 PIDs can evolve such that closely-related orthologs recognize distinct PAMs, as illustrated recently in two species of *Geobacillus*. The Cas9 encoded by *G. stearothermophilus* recognizes a $N_4$CRAA PAM, but when its PID was swapped with that of strain LC300's Cas9, its PAM requirement changed to $N_4$GMAA (Harrington et al., 2017b).

In one embodiment, the present invention contemplates a plurality of *N. meninigitidis* Cas9 orthologs with divergent PIDs that recognize different PAMs. In one embodiment, the present invention contemplates a Cas9 protein with a high sequence identity (>80% along their entire lengths) to that of NmeCas9 strain 8013 (Nme1Cas9) (Zhang et al., 2013). Nme1Cas9 also has a small size and naturally high accuracy as discussed above. (Lee et al., 2016; Amrani et al., 2018). Alignments revealed three clades of meningococcal Cas9 orthologs, each with >98% identity in the N-terminal ~820 amino acid (aa) residues, which includes all regions of the protein other than the PID. See, FIG. 5A and FIG. 6A.

All of these Cas9 orthologs are 1,078-1,082 aa in length. The first clade (group 1) includes orthologs in which the >98% aa sequence identity with Nme1Cas9 extends through the PID. In contrast, the other two groups had PIDs that were significantly diverged from that of Nme1Cas9, with group 2 and group 3 orthologs averaging ~52% and ~86% PID sequence identity with Nme1Cas9, respectively. One meningococcal strain was selected from each group: i) De11444 from group 2; and ii) 98002 from group 3 for detailed analysis, which are referred to herein as Nme2Cas9 (1,082 aa) and Nme3Cas9 (1,081 aa), respectively. The CRISPR-cas loci from these two strains have repeat sequences and spacer lengths that are identical to those of strain 8013. See, FIG. 6B. This strongly suggested that their mature crRNAs also have 24nt guide sequences and 24 nt repeat sequences (Zhang et al., 2013). Similarly, the tracrRNA sequences of De11444 and 98002 were 100% identical to the 8013 tracrRNA. See, FIG. 6B. These observations imply that the same sgRNA sequence scaffold can guide DNA cleavage by all three Cas9s.

To determine whether these Cas9 orthologs have distinct PAMs, the PID of Nme1Cas9 was replaced with that of either Nme2Cas9 or Nme3Cas9. To identify the corresponding PAM requirements, these protein chimeras were expressed in *Escherichia coli*, purified, and used for in vitro PAM identification (Karvelis et al., 2015; Ran et al., 2015; Kim et al., 2017). Briefly, a pool of DNA fragments containing a protospacer followed by a 10-nt randomized sequence was cleaved in vitro using recombinant Cas9 and a cognate, in vitro-transcribed sgRNA. See, FIG. 5B. Only those DNAs containing a Cas9 PAM sequence were expected to be cleaved. Cleavage products were then sequenced to identify the PAMs. See, FIGS. 5C-D.

The expected N$_4$GATT PAM consensus was validated in the recovered full-length Nme1Cas9. See, FIG. 5C. Chimeric PID-swapped derivatives exhibited a strong preference for a C residue in the 5th position in place of the G recognized by Nme1Cas9. See, FIG. 5D. In one embodiment, ABE7.10-nNme2Cas9 (D16A) is used for single-base editing of A•T base pair to a G•C base pair. In one embodiment, BEmax-nNme2Cas9 (D16A) is used for single-base editing of A•T base pair to a G•C base pair. (See, FIG. 3F).

Figure 5A:
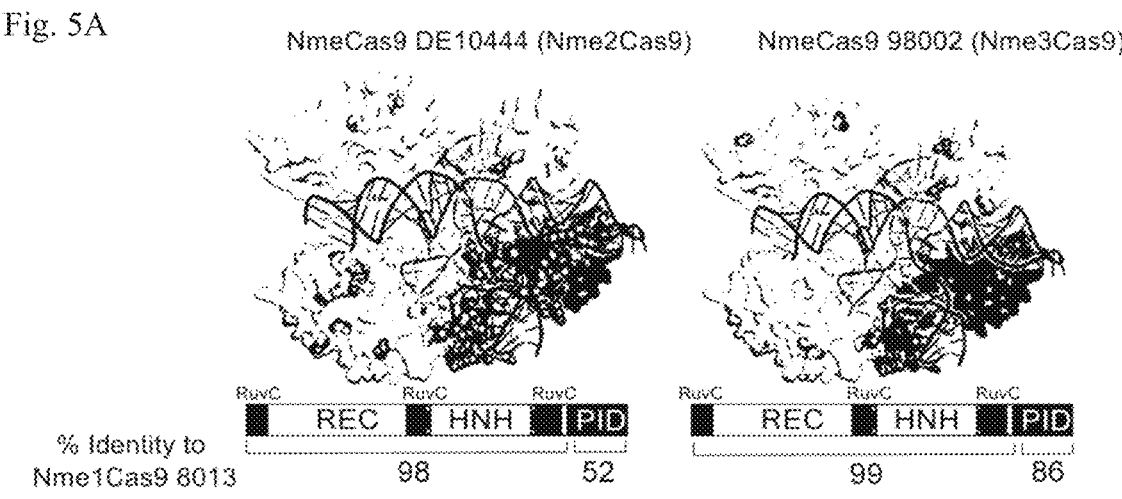
Figure 5B:
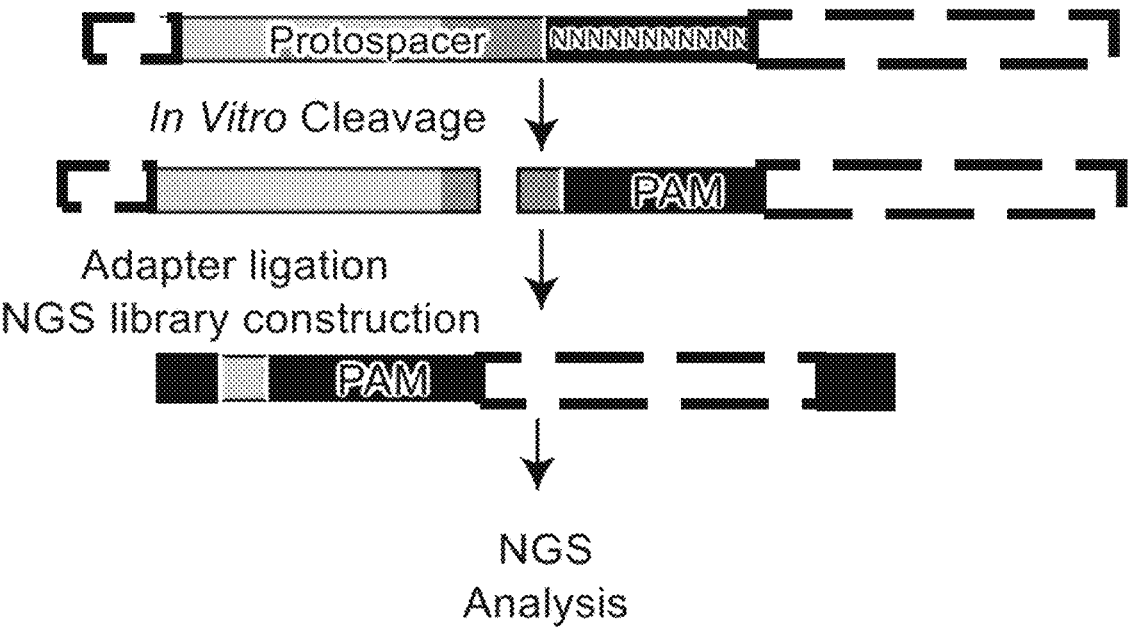
Figure 5E:
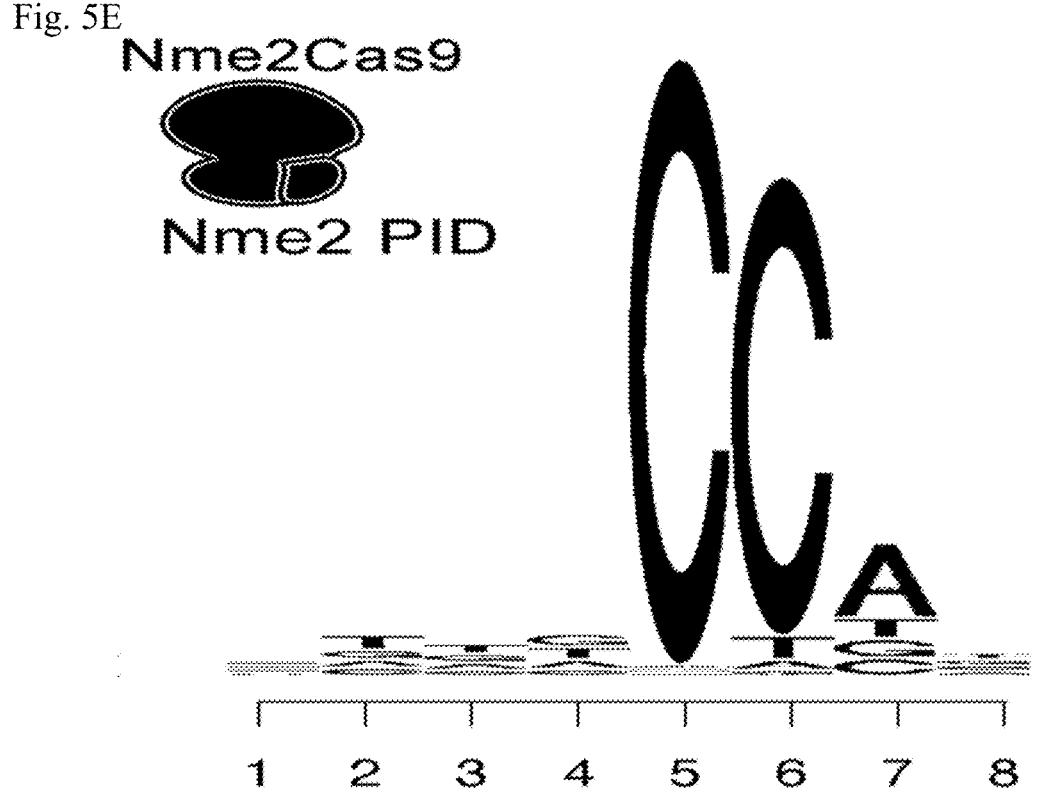

FIG. 5A-E illustrates exemplary three closely related *Neisseria meningitidis* Cas9 orthologs that have distinct PAMs. FIG. 5A shows an exemplary schematic showing mutated residues (black spheres) between Nme2Cas9 (left) and Nme3Cas9 (right) mapped onto the predicted structure of Nme1Cas9, revealing the cluster of mutations in the PID (black). FIG. 5B shows an exemplary experimental workflow of the in vitro PAM discovery assay with a 10-bp randomized PAM region. Following in vitro digestion, adapters were ligated to cleaved products for library construction and sequencing. FIG. 5C shows exemplary sequence logos resulting from in vitro PAM discovery reveal the enrichment of a N$_4$GATT PAM for Nme1Cas9, consistent with its previously established specificity. FIG. 5D shows exemplary sequence logos indicating that Nme1Cas9 with its PID swapped with that of Nme2Cas9 (left) or Nme3Cas9 (right) requires a C at PAM position 5. The remaining nucleotides were not determined with high confidence due to the modest cleavage efficiency of the PID-swapped protein chimeras (see FIG. 6C). FIG. 5E shows an exemplary sequence logo showing that full-length Nme2Cas9 recognizes an N$_4$CC PAM, based on efficient substrate cleavage of a target pool with a fixed C at PAM position 5, and with PAM nts 1~4 and 6-8 randomized.

Any remaining PAM nucleotides could not be confidently assigned due to the low cleavage efficiencies of the chimeric proteins under the conditions used. See, FIG. 6C. To further resolve the PAMs, in vitro assays were performed on a library with a 7-nt randomized sequence possessing an invariant C at the 5th PAM position (e.g., 5'-NNNNCNNN-3' on the sgRNA-noncomplementary strand). This strategy yielded a much higher cleavage efficiency and the results indicated that the Nme2Cas9 and Nme3Cas9 PIDs recognize NNNNCC (A) and NNNNCAAA PAMs, respectively. See, FIGS. 6C-D. The Nme3Cas9 consensus is similar to that of GeoCas9 (Harrington et al., 2017b).

These tests were repeated using a full-length Nme2Cas9 (rather than a PID-swapped chimera) with the NNNNCNNN DNA pool, and again a NNNNCC (A) consensus was recovered. See, FIG. 5E. It was noted that this test had more efficient cleavage. See, FIG. 6C. These data suggest that one or more of the 15 amino acid changes in Nme2Cas9 (relative to Nme1Cas9) outside of the PID support efficient DNA cleavage activity. See, FIG. 6C. Because the unique, 2-3 nt PAM of Nme2Cas9 affords a higher density of potential target sites than the previously described compact Cas9 orthologs, it was selected for further analyses.

Figure 6A:
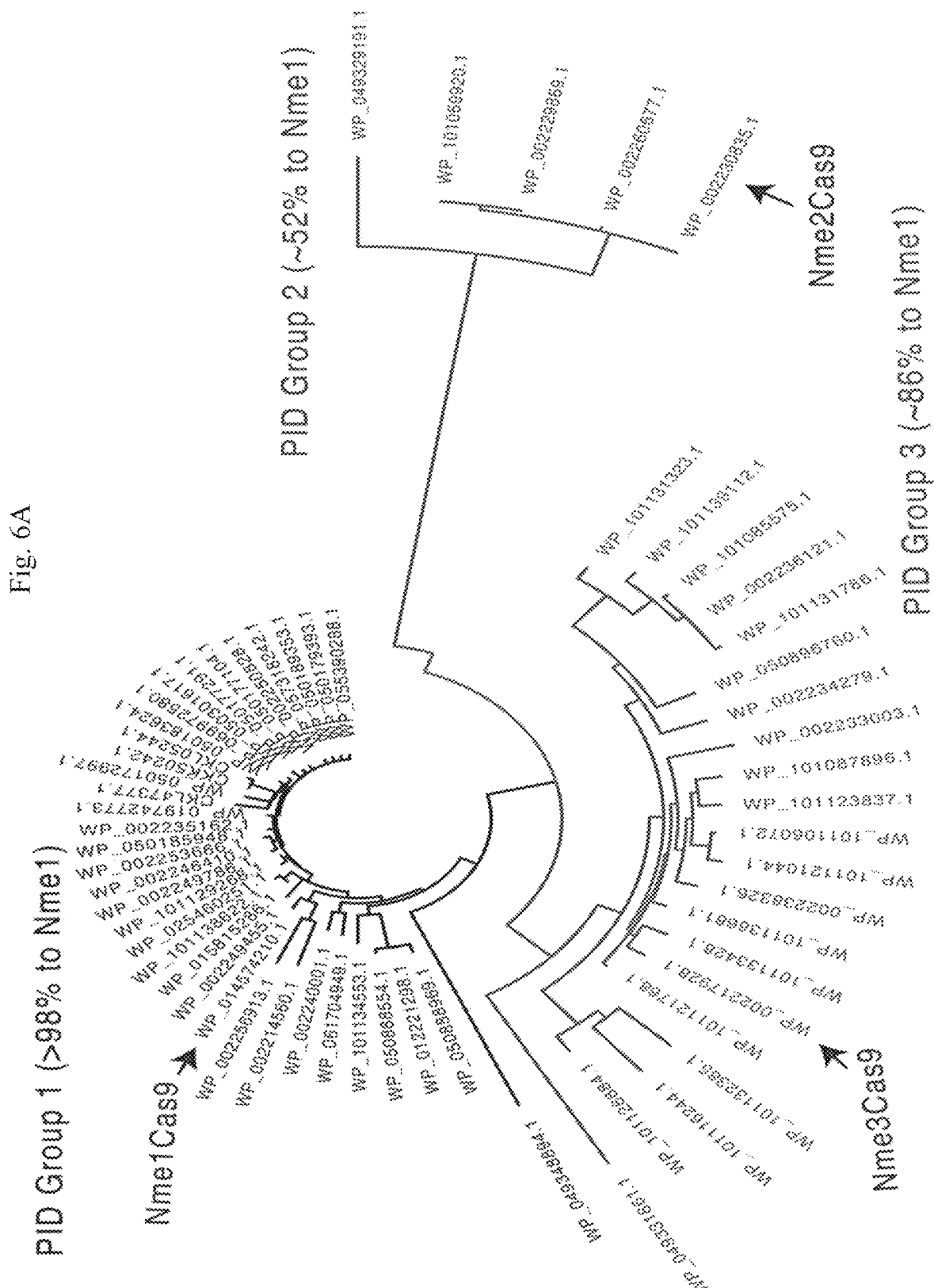
FIG. 6A-D presents a characterization of *Neisseria meningitidis* Cas9 orthologs with rapidly-evolving PIDs, as related to FIG. 5A-E.
Figure 6B:
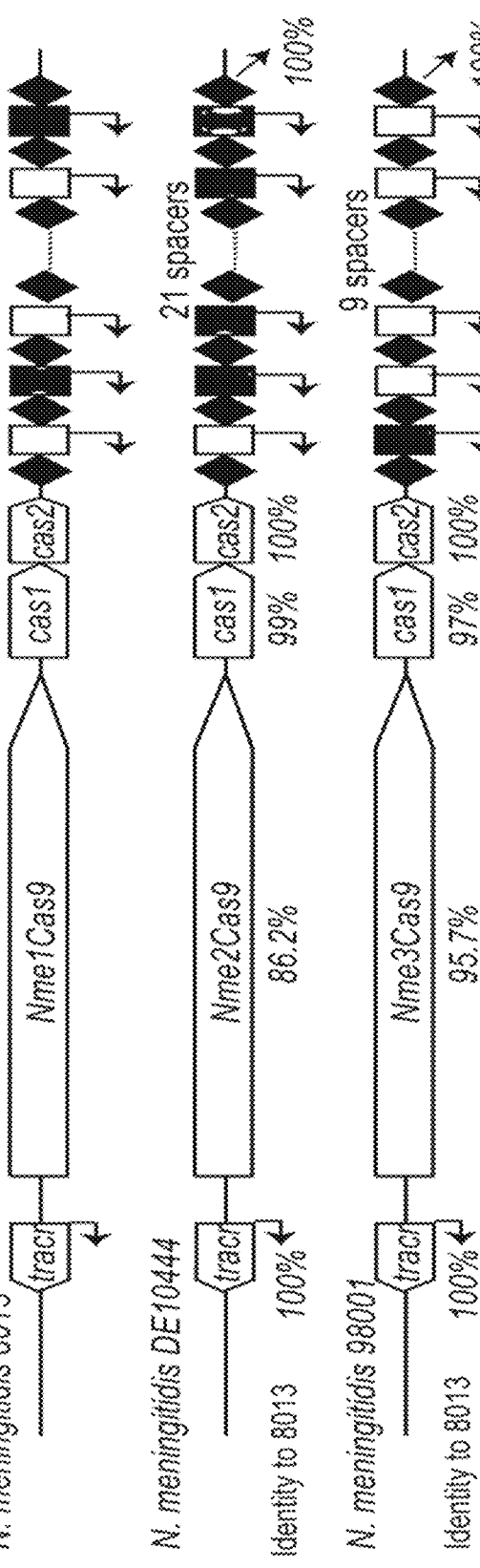
Figure 6C:
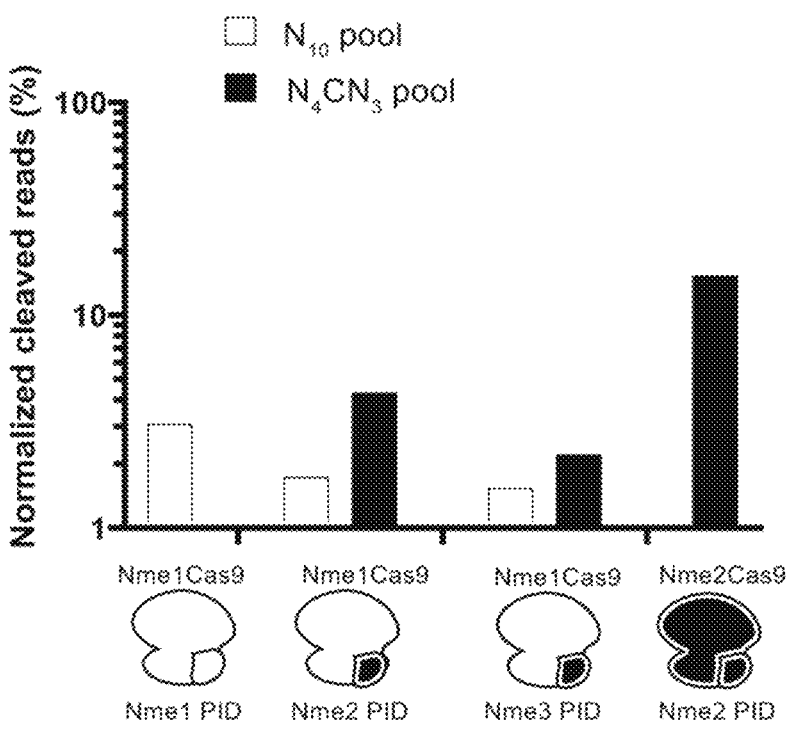
Figure 6D:
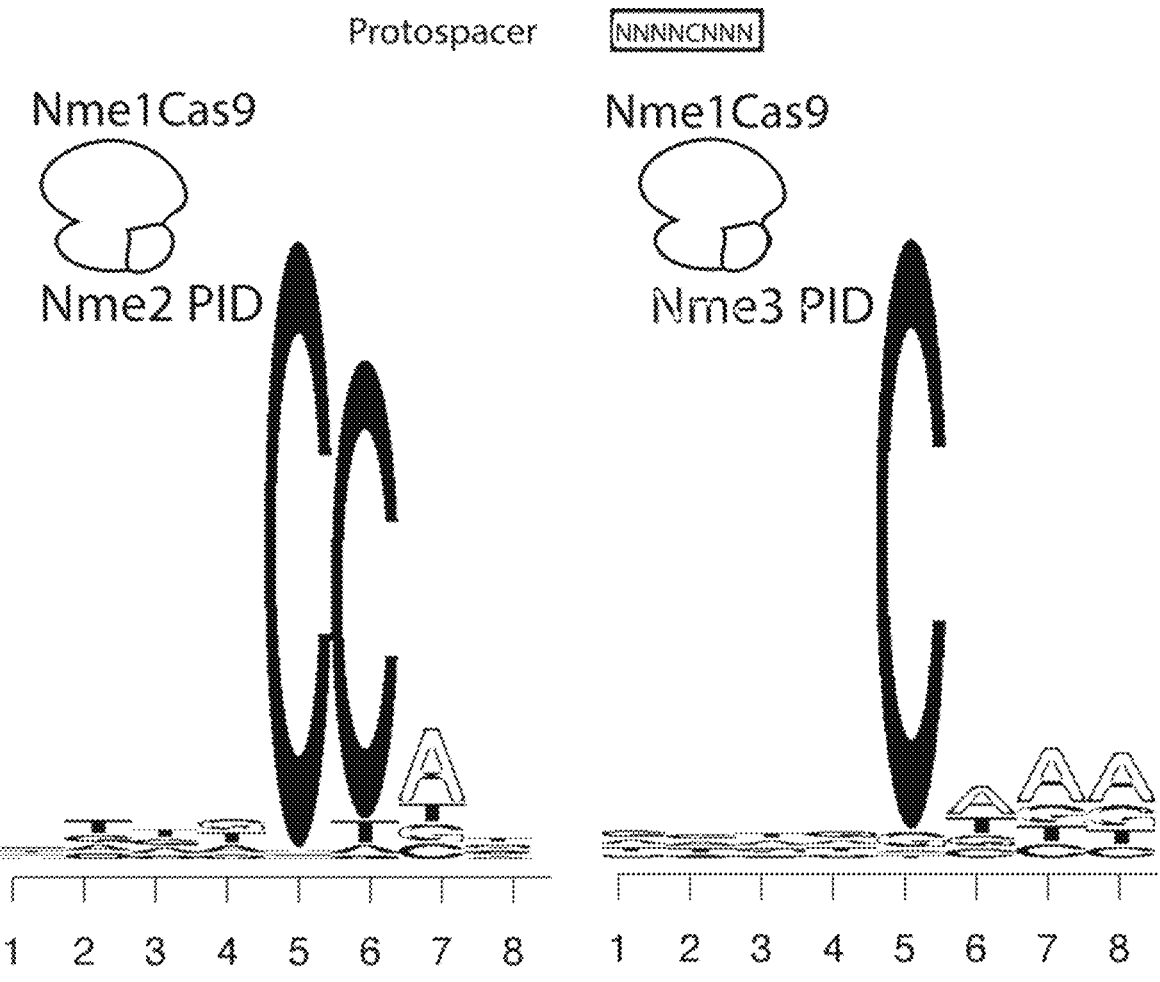

FIG. 6A-C presents a characterization of *Neisseria meningitidis* Cas9 orthologs with rapidly-evolving PIDs, as related to FIG. 5A-E. FIG. 6A shows an exemplary unrooted phylogenetic tree of NmeCas9 orthologs that are >80% identical to Nme1Cas9. Three distinct branches emerged, with the majority of mutations clustered in the PID. Groups 1 (black), 2 (red), and 3 (green) have PIDs with >98%, approximately 52%, and approximately 86% identity to Nme1Cas9, respectively. Three representative Cas9 orthologs (one from each group) (Nme1Cas9, Nme2Cas9 and Nme3Cas9) are indicated. FIG. 6B shows an exemplary schematic showing the CRISPR-cas loci of the strains encoding the three Cas9 orthologs (Nme1Cas9, Nme2Cas9, and Nme3Cas9) from (FIG. 6A). Percent identities of each CRISPR-Cas component with *N. meningitidis* 8013 (encoding Nme1Cas9) are shown. Black arrows denote pre-crRNA and tracrRNA transcription initiation sites, respectively. FIG. 6C shows an exemplary normalized read counts % of total reads) from cleaved DNAs from the in vitro assays for intact Nme1Cas9 (white), for chimeras with Nme1Cas9's PID swapped with those of Nme2Cas9 and Nme3Cas9 (black colors), and for full-length Nme2Cas9 (black), are plotted. The reduced normalized read counts indicate lower cleavage efficiencies in the chimeras. FIG. 6D shows an exemplary sequence logos from the in vitro PAM discovery assay on an NNNNCNNN PAM pool by Nme1Cas9 with its PID swapped with those of Nme2Cas9 (left) or Nme3Cas9 (right).

2. N$_4$CC PAM-Directed Gene Editing

To test the efficacy of Nme2Cas9 in human genome editing, a full-length (e.g., not PID-swapped) human-codon-optimized Nme2Cas9 construct was cloned into a mammalian expression plasmid with appended nuclear localization signals (NLSs) and linkers validated previously for Nme1Cas9 (Amrani et al., 2018). For initial tests, a modified, fluorescence-based Traffic Light Reporter (TLR2.0) was used (Certo et al., 2011). Briefly, a disrupted GFP is followed by an out-of-frame T2A peptide and mCherry cassette. When DNA double-strand breaks (DSBs) are introduced in the broken-GFP cassette, a subset of non-homologous end joining (NHEJ) repair events leave +1-frame-shifted indels, placing mCherry in frame and yielding red fluorescence that can be easily quantified by flow cytometry See, FIG. 7A. Homology-directed repair (HDR) outcomes can also be scored simultaneously by including a DNA donor that restores the functional GFP sequence, yielding a green fluorescence (Certo et al., 2011). Because some indels do not introduce a +1 frameshift, the fluorescence readout generally provides an underestimate of the true editing efficiency. Nonetheless, the speed, simplicity, and low cost of the assay makes it useful as an initial, semi-quantitative measure of genome editing in HEK293T cells carrying a single TLR2.0 locus incorporated via lentivector. For initial tests, Nme2Cas9 plasmid was transiently co-transfected with one of fifteen sgRNA plasmids carrying spacers that target TLR2.0 sites with $N_4CC$ PAMs. No HDR donor was included, so only NHEJ-based editing (mCherry) was scored. Most sgRNAs were in a G23 format (i.e. a 5'-terminal G to facilitate transcription, followed by a 23nt guide sequence), as used routinely for Nme1Cas9 (Lee et al., 2016; Pawluk et al., 2016; Amrani et al., 2018; Ibraheim et al., 2018). No sgRNA and an sgRNA targeting an $N_4GATT$ PAM were used as negative controls, and SpyCas9+sgRNA and Nme1Cas9+sgRNA co-transfections (targeting NGG and $N_4GATT$ protospacers, respectively) were included as positive controls. Editing by SpyCas9 and Nme1Cas9 was readily detectable (~28% and 10% mCherry, respectively). See, FIG. 7B.

For Nme2Cas9, all 15 targets with $N_4CC$ PAMs were functional, though to various extents ranging from 4% to 20% mCherry. These fifteen sites include examples with each of the four possible nucleotides in the 7th PAM position (e.g., after the CC dinucleotide), indicating that a slight preference for an A residue was observed in vitro (FIG. 5E) does not reflect a PAM requirement for editing applications in human cells. The $N_4GATT$ PAM control yielded mCherry signal similar to no-sgRNA control. See, FIG. 7B.

To determine whether both C residues in the $N_4CC$ PAM are involved in editing, a series of $N_4DC$ (D=A, T, G) and $N_4CD$ PAM sites were tested in TLR2.0 reporter cells. See, FIGS. 8A and 8B. No detectable editing was found at any of these sites, providing an initial indication that both C residues of the $N_4CC$ PAM consensus are required for efficient Nme2Cas9 activity.

The length of the spacer in the crRNA differs among Cas9 orthologs and can affect on-vs. off-target activity (Cho et al., 2014; Fu et al., 2014). SpyCas9's optimal spacer length is 20 nts, with truncations down to 17 nts tolerated (Fu et al., 2014). In contrast, Nme1Cas9 usually has 24-nt spacers (Hou et al., 2013; Zhang et al., 2013), and tolerates truncations down to 18-20 nts (Lee et al., 2016; Amrani et al., 2018). To test spacer length requirements for Nme2Cas9, guide RNA plasmids were created for each targeted single TLR2.0 site, but with varying spacer lengths. See, FIG. 7C and FIG. 8C. Comparable activities were observed with G23, G22 and G21 guides, but significantly decreased activity upon further truncation to G20 and G19 lengths. See, FIG. 7C. These results validate Nme2Cas9 as a genome editing platform, with 22-24 nt guide sequences, at $N_4CC$ PAM sites in cultured human cells.

Figure 7A:
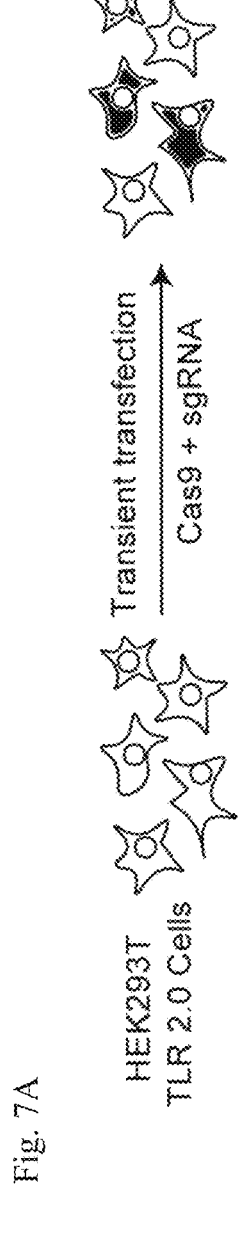
FIG. 7A-D presents exemplary data showing that Nme2Cas9 uses a 22-24 nt spacer to edit sites adjacent to an $N_4CC$ PAM. All experiments were done in triplicate, and error bars represent the standard error of the mean (s.e.m.).
Figure 7B:
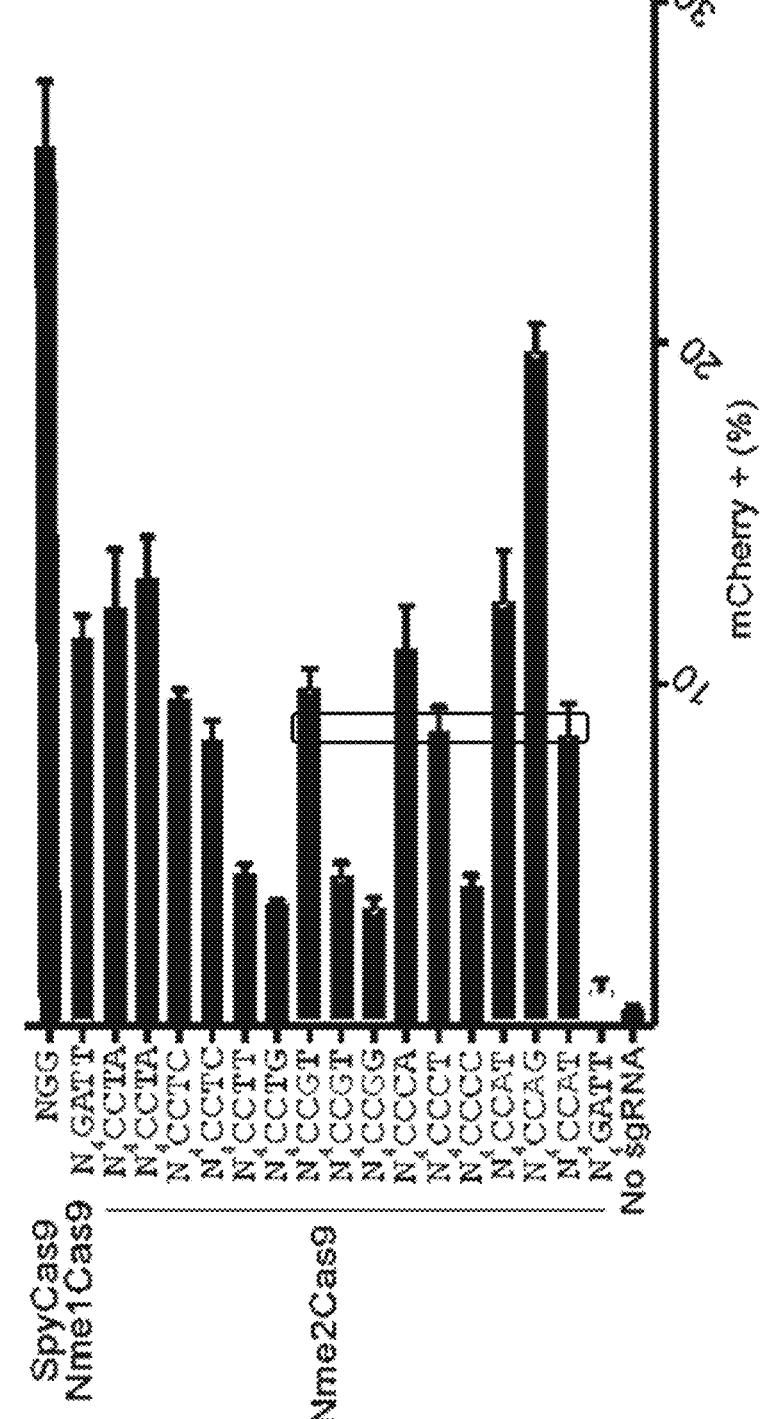
Figure 7C:
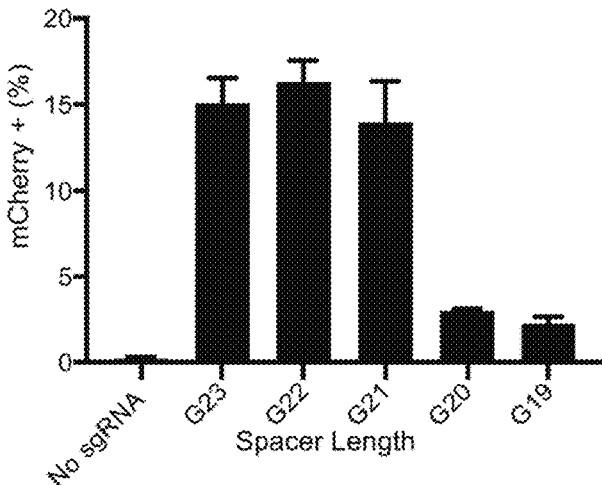
Figure 7D:
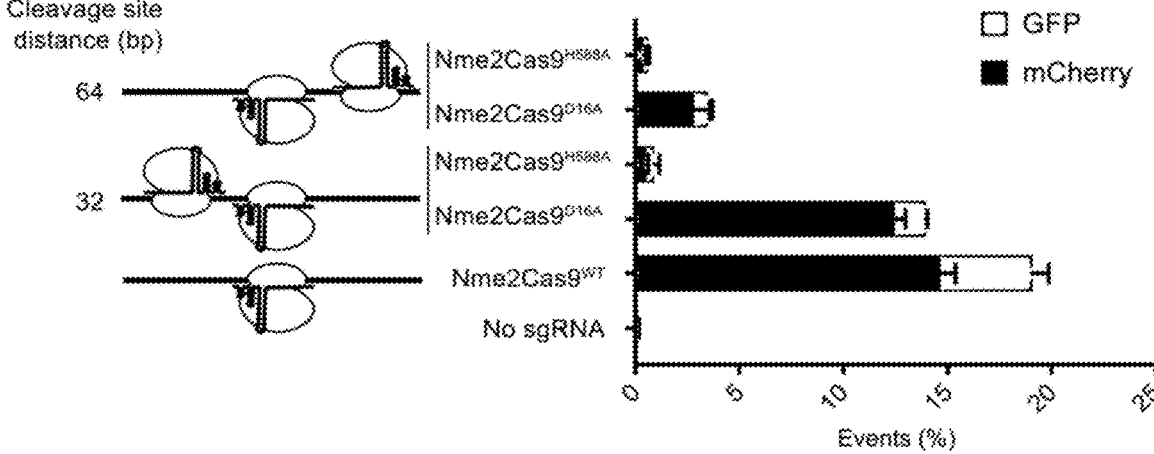

FIG. 7A-D presents exemplary data showing that Nme2Cas9 uses a 22-24 nt spacer to edit sites adjacent to an $N_4CC$ PAM. All experiments were done in triplicate, and error bars represent the standard error of the mean (s.e.m.). FIG. 7A shows an exemplary schematic diagram depicting transient transfection and editing of HEK293T TLR2.0 cells, with mCherry+ cells detected by flow cytometry 72 hours after transfection. FIG. 7B shows an exemplary Nme2Cas9 editing of the TLR2.0 reporter. Sites with $N_4CC$ PAMs were targeted with varying efficiencies, while no Nme2Cas9 targeting was observed at an $N_4GATT$ PAM or in the absence of sgRNA. SpyCas9 (targeting a previously validated site with an NGG PAM) and Nme1Cas9 (targeting $N_4GATT$) were used as positive controls. FIG. 7C shows an exemplary effect of spacer length on the efficiency of Nme2Cas9 editing. An sgRNA targeting a single TLR2.0 site, with spacer lengths varying from 24 to 20 nts (including the 5'-terminal G required by the U6 promoter), indicate that highest editing efficiencies are obtained with 22-24 nt spacers. FIG. 7D shows an exemplary An Nme2Cas9 dual nickase can be used in tandem to generate NHEJ- and HDR-based edits in TLR2.0. Nme2Cas9- and sgRNA-expressing plasmids, along with an 800-bp dsDNA donor for homologous repair, were electroporated into HEK293T TLR2.0 cells, and both NHEJ (mCherry+) and HDR (GFP+) outcomes were scored by flow cytometry. HNH nickase, $Nme2Cas9^{D16A}$, RuvC nickase, $Nme2Cas9^{H588A}$. Cleavage sites 32 bp and 64 bp apart were targeted using either nickase. The HNH nickase ($Nme2Cas9^{D16A}$ yielded efficient editing, particularly with the cleavage sites that were separated by 32 bp, whereas the RuvC nickase ($Nme2Cas9^{H588A}$) was not effective. Wildtype Nme2Cas9 was used as a control.

3. Precise Editing by HDR and HNH Nickase

Cas9 enzymes use their HNH and RuvC domains to cleave the guide-complementary and non-complementary strand of the target DNA, respectively. SpyCas9 nickases (nCas9s), in which either the HNH or RuvC domain is mutationally inactivated, have been used to induce homology-directed repair (HDR) and to improve genome editing specificity via DSB induction by dual nickases (Mali et al., 2013a; Ran et al., 2013).

To test the efficacy of Nme2Cas9 as a nickase, a $Nme2Cas9^{D16A}$ (HNH nickase) and $Nme2Cas9^{H588A}$ (RuvC nickase) were created, which possess alanine mutations in catalytic residues of the RuvC and HNH domains, respectively (Esvelt et al., 2013; Hou et al., 2013; Zhang et al., 2013). TLR2.0 cells, along with a GFP donor dsDNA, were used to determine whether Nme2Cas9-induced nicks can induce precise edits via HDR. Target sites within TLR2.0 were used to test the functionality of each nickase using guides targeting cleavage sites spaced 32 bp and 64 bp apart. See, FIG. 7D. Wildtype Nme2Cas9 targeting a single site showed efficient editing, with both NHEJ and HDR as outcomes of repair. For nickases, cleavage sites 32 bp and 64 bp apart showed editing using the $Nme2Cas9^{D16A}$ (HNH nickase), but neither target pair worked with $Nme2Cas9^{H588A}$. These results suggest that Nme2Cas9 HNH nickase can be used for efficient genome editing, as long as the sites are in close proximity.

Studies in previously characterized Cas9s have identified a specific region proximal to the PAM where Cas9 activity is highly sensitive to sequence mismatches. This 8 to 12-nt region is known as the seed sequence and has been observed among all Cas9s characterized to date (Gorski et al., 2017). To determine whether Nme2Cas9 also possesses a seed sequence, a series of transient transfections was performed, each targeting the same locus in TLR2.0, but with a single-nucleotide mismatch at different positions of the guide. See, FIG. 8D. A significant decrease in the number of mCherry-positive cells was observed for mismatches in the first 10-12 nts proximal to the PAM, suggesting that Nme2Cas9 possesses a seed sequence in this region.

Figure 8A:
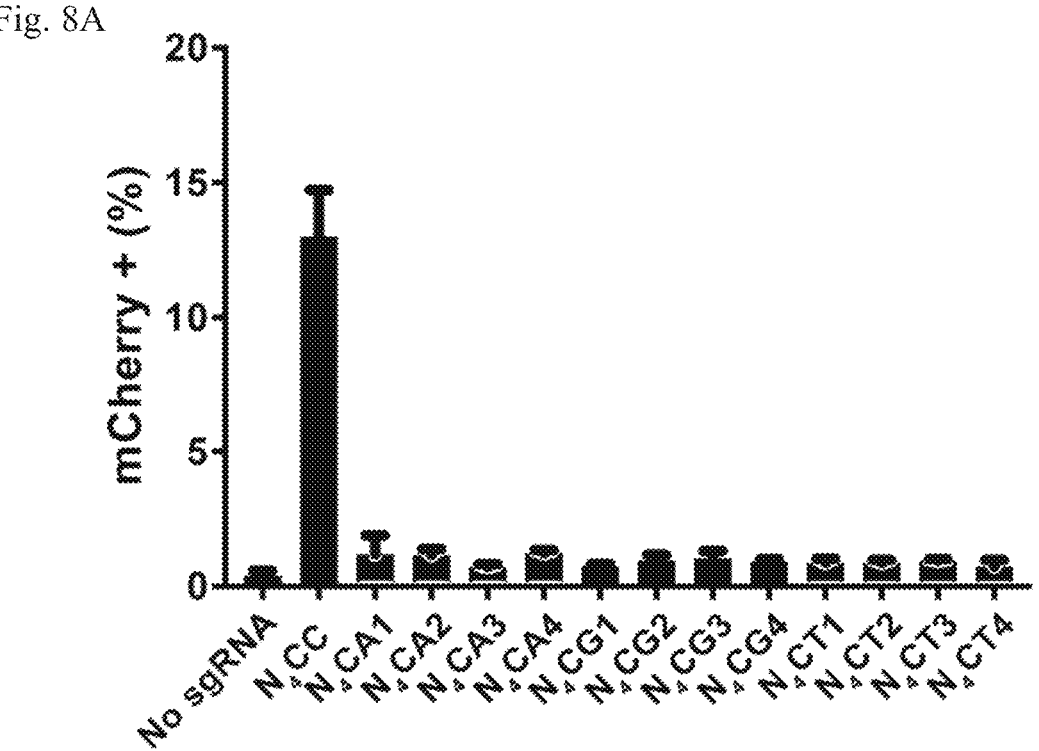
FIG. 8A-D presents exemplary data showing PAM, spacer, and seed requirements for Nme2Cas9 targeting in mammalian cells, as related to FIG. 7A-D. All experiments were done in triplicate and error bars represent s.e.m.

FIG. 8A-D presents exemplary data showing PAM, spacer, and seed requirements for Nme2Cas9 targeting in mammalian cells, as related to FIG. 7A-D. All experiments were done in triplicate and error bars represent s.e.m. FIG. 8A shows an exemplary Nme2Cas9 targeting at $N_4CD$ sites in TLR2.0, with editing estimated based on mCherry+ cells.

Figure 8B:
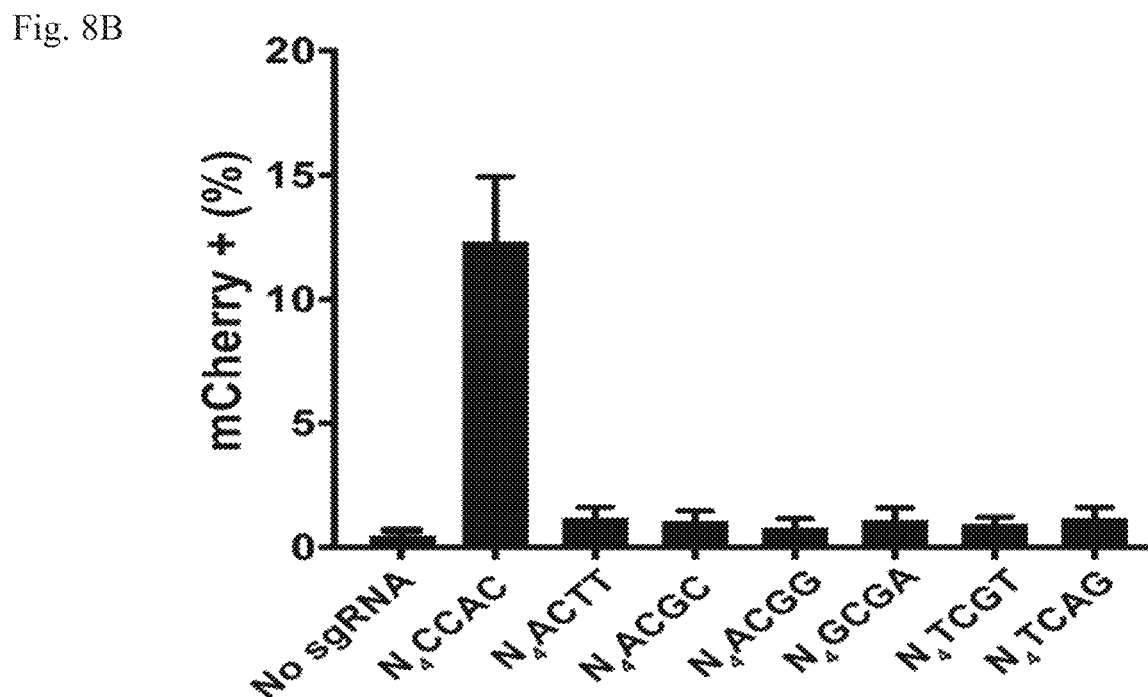
Figure 8C:
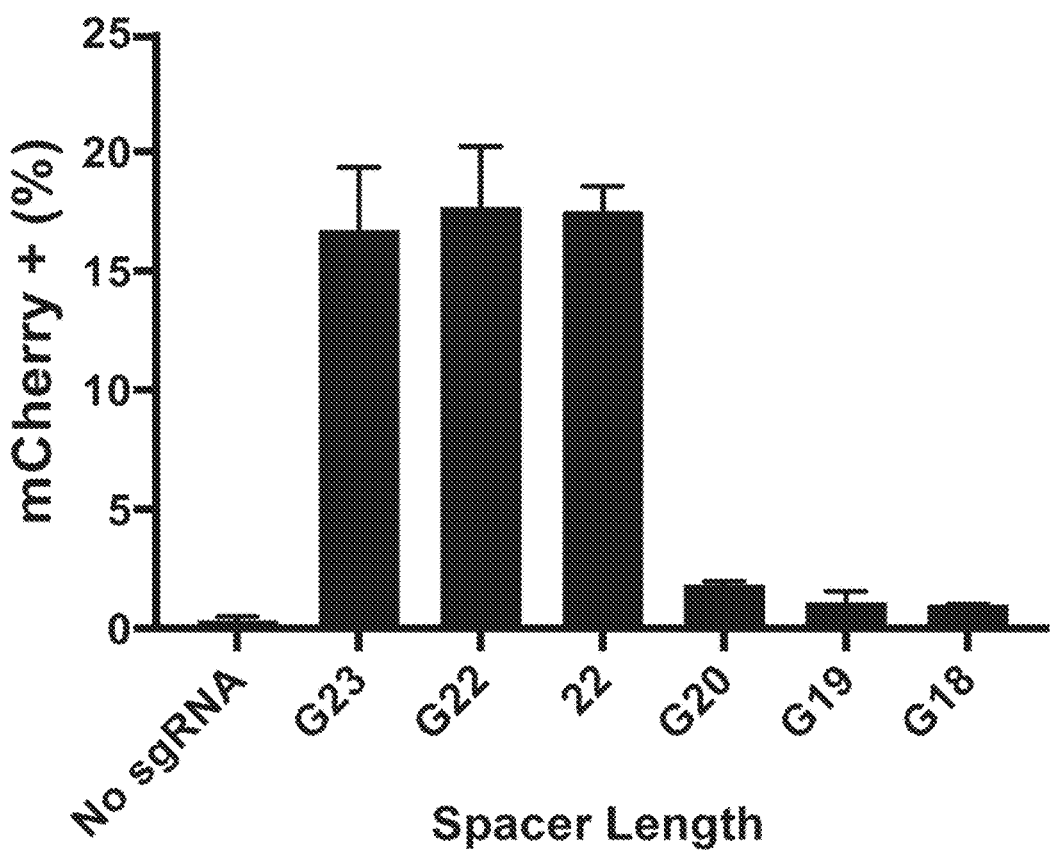
Figure 8D:
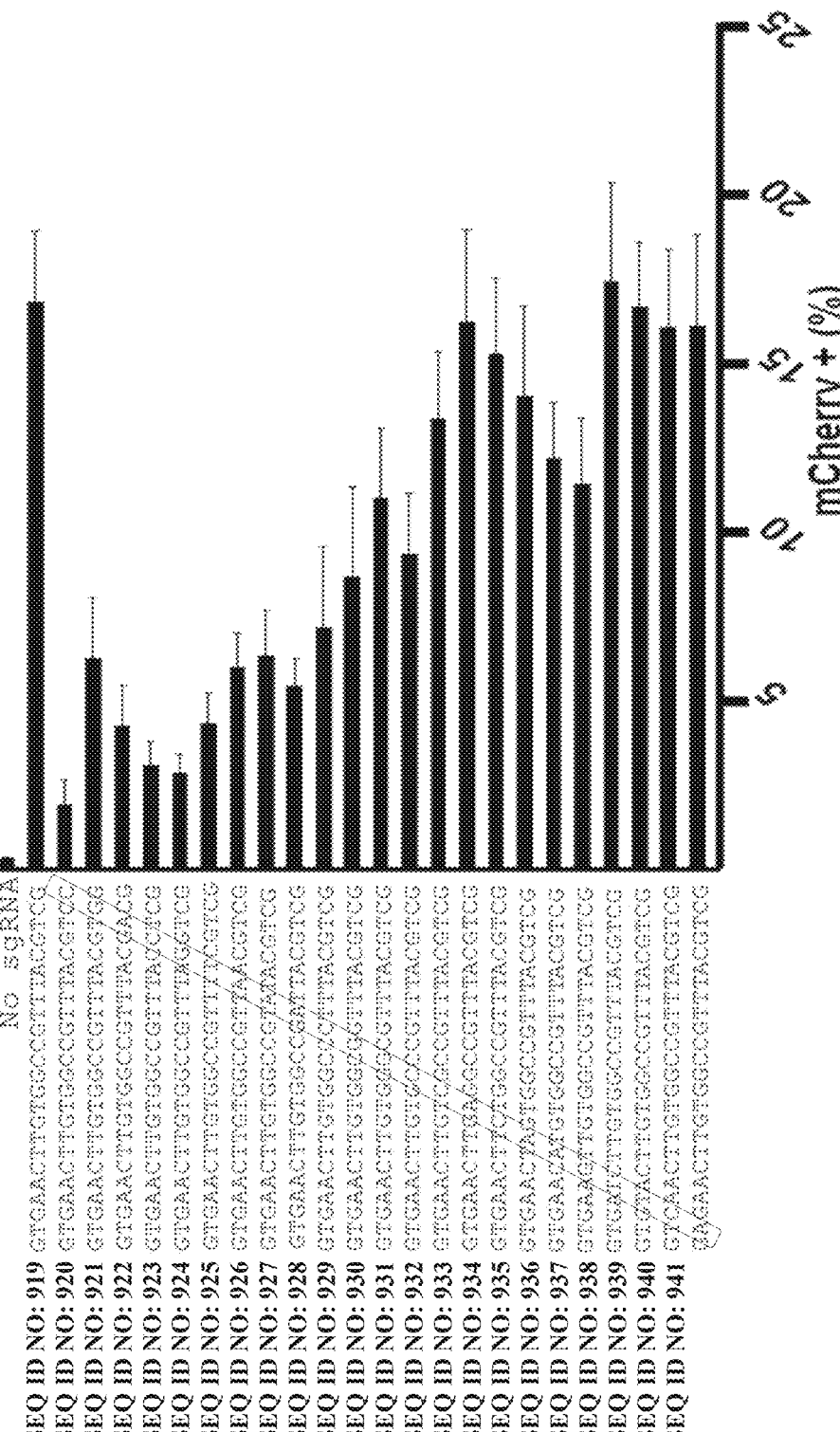

Four sites for each non-C nucleotide at the tested position (N$_4$CA, N$_4$CT and N$_4$CG) were examined, and an N$_4$CC site was used as a positive control. FIG. 8B shows an exemplary Nme2Cas9 targeting at N$_4$DC sites in TLR2.0 [similar to (A)]. FIG. 8C shows exemplary guide truncations on a TLR2.0 site (distinct from that in FIG. 2C) with a N$_4$CCA PAM, revealing similar length requirements as those observed at the other site. FIG. 8D shows exemplary Nme2Cas9 targeting efficiency is differentially sensitive to single-nucleotide mismatches in the seed region of the sgRNA. Data show the effects of walking single-nucleotide sgRNA mismatches along the 23-nt spacer in a TLR2.0 target site.

4. Delivery Methods to Mammalian Cell Types

Nme2Cas9's ability to function in different mammalian cell lines was tested using various delivery methods. As an initial test, forty (40) different sites (29 with a N$_4$CC PAM, and 11 sites were tested with a N$_4$CD PAM). Several loci were selected (AAVS1, VEGFA, etc.), and target sites with N$_4$CC PAMs were randomly chosen for editing with Nme2Cas9. Editing (%) was determined by transiently transfecting 150 ng of Nme2Cas9 along with 150 ng of sgRNA plasmids followed by TIDE analysis 72 hours post-transfection. A subset of sites exhibiting a range of editing efficiencies in this initial screen was selected for repeat analyses in triplicate. See, FIG. 9A; and Table 1.

Figure 9A:
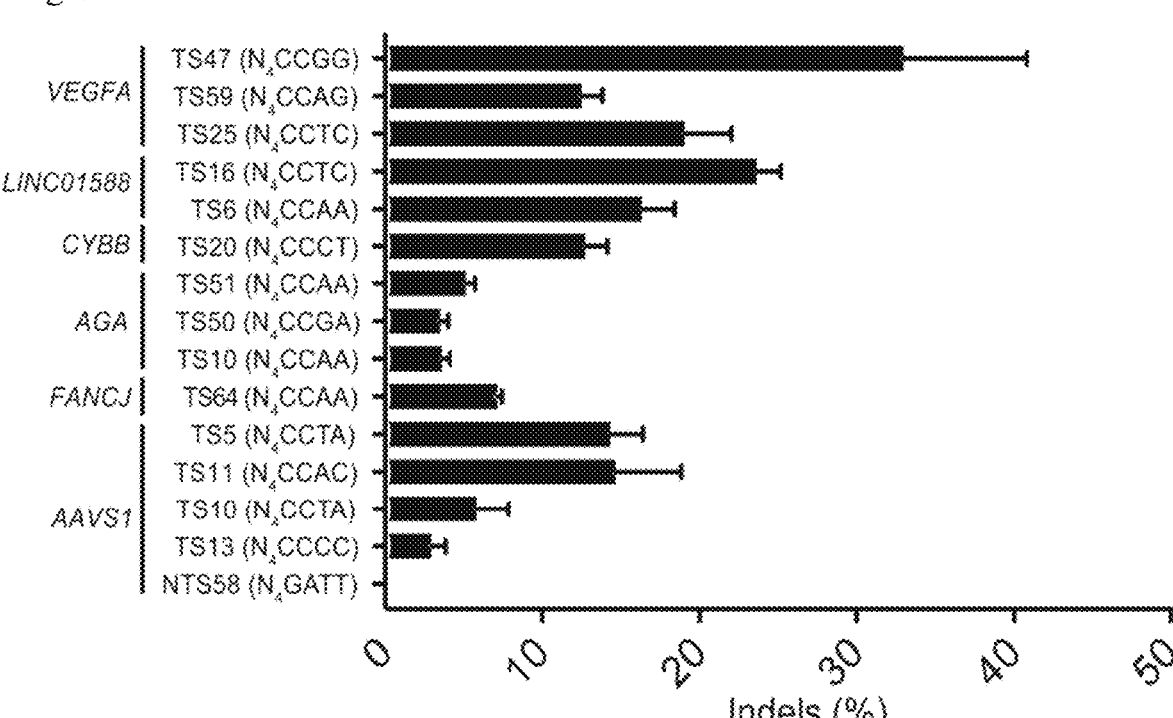
FIG. 9A-C presents exemplary data showing Nme2Cas9 genome editing at endogenous loci in mammalian cells via multiple delivery methods. All results represent 3 independent biological replicates, and error bars represent s.e.m.
Figure 9B:
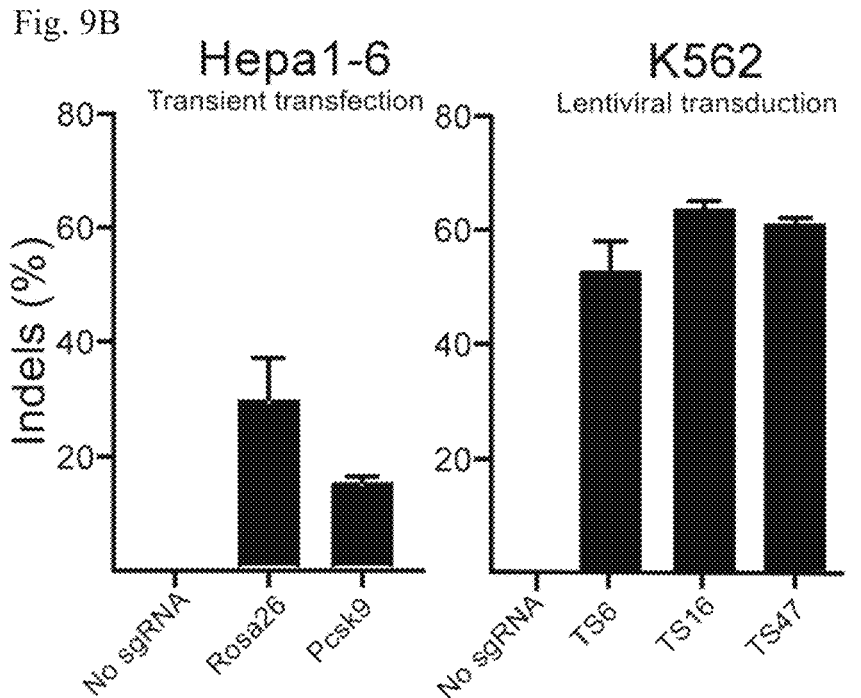
Figure 9C:
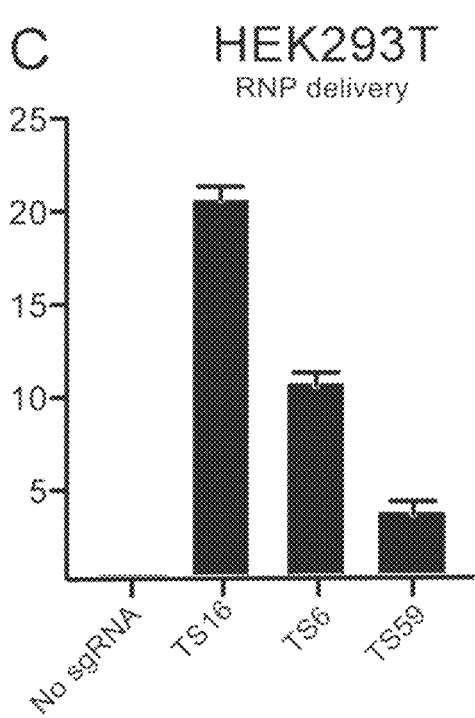

FIG. 9A-C presents exemplary data showing Nme2Cas9 genome editing at endogenous loci in mammalian cells via multiple delivery methods. All results represent 3 independent biological replicates, and error bars represent s.e.m. FIG. 9A shows an exemplary Nme2Cas9 genome editing of endogenous human sites in HEK293T cells following transient transfection of Nme2Cas9- and sgRNA-expressing plasmids. 40 sites were screened initially (Table 1); the 14 sites shown (selected to include representatives of varying editing efficiencies, as measured by TIDE) were then re-analyzed in triplicate. An Nme1Cas9 target site (with an N$_4$GATT PAM) was used as a negative control. FIG. 9B shows exemplary data charts: Left panel: Transient transfection of a single plasmid expressing both Nme2Cas9 and sgRNA (targeting the Pcsk9 and Rosa26 loci) enables editing in Hepa1-6 mouse cells, as detected by TIDE. Right panel: Electroporation of sgRNA plasmids into K562 cells stably expressing Nme2Cas9 from a lentivector results in efficient indel formation. FIG. 9C shows exemplary Nme2Cas9 can be electroporated as an RNP complex to induce genome editing. 40 picomoles Cas9 along with 50 picomoles of in vitro-transcribed sgRNAs targeting three different loci were electroporated into HEK293T cells. Indels were measured after 72 h using TIDE.

TABLE 1

| | | | | | | |
|---|---|---|---|---|---|---|
| Exemplary Endogenous human genome editing sites targeted by Nme2Cas9. | | | | | | |
| SEQ ID NOS. | No. | Site Name | Spacer Seq | PAM | Locus | Editing (%) |
| 8, 9 | 1 | TS1 | GGTTCTGGGTACTTTTATCTGTCC | CCTCCACC | AAVS1 | ND |
| 12, 13 | 2 | TS4 | GTCTGCCTAACAGGAGGTGGGGGT | TAGACGAA | AAVS1 | 11 |
| 16, 17 | 3 | TSS | GAATATCAGGAGACTAGGAAGGAG | GAGGCCTA | AAVSI | 15 |
| 20, 21 | 4 | TS6 | GCCTCCCTGCAGGGCTGCTCCC | CAGCCCAA | LINC01588 | 20 |
| 24, 25 | 5 | TS10 | GAGCTAGTCTTCTTCCTCCAACCC | GGGCCCTA | AAVS1 | 3.5 |
| 28, 29 | 6 | TS11 | GATCTGTCCCCTCCACCCCACAGT | GGGGCCAC | AAVS1 | 9 |
| 32, 33 | 7 | TS12 | GGCCCAAATGAAAGGAGTGAGAGG | TGACCCGA | AAVS1 | 10 |
| 36, 37 | 8 | TS13 | GCATCCTCTTGCTTTCTTTGCCTG | GACACCCA | AVSI | 2 |
| 40, 41 | 9 | TS16 | GGAGTCGCCAGAGGCCGGTGGTGG | ATTTCCTC | LINC01588 | 28 |
| 44, 45 | 10 | TS17 | GCCCAGCGGCCGGATATCAGCTGC | CACGCCCG | LINC01588 | ND |
| 48, 49 | 11 | TS18 | GGAAGGGAACATATTACTATTGC | TTTCCCTC | CYBB | 1 |
| 52, 53 | 12 | TS19 | GTGGAGTGGCCTGCTATCAGCTAC | CTATCCAA | CYBB | 6 |
| 56, 57 | 13 | TS20 | GAGGAAGGGAACATATTACTATTG | CTTTCCCT | CYBB | 11.2 |
| 60, 61 | 14 | TS21 | GTGAATTCTCATCAGCTAAAATGC | CAAGCCTT | CYBB | 1 |
| 64, 65 | 15 | TS25 | GCTCACTCACCCACACAGACACAC | ACGTCCTC | VEGFA | 15.6 |
| 68, 69 | 16 | TS26 | GGAAGAATTTCATTCTGTTCTCAG | TTTTCCTG | CFTR | 2 |
| 72, 73 | 17 | TS27 | GCTCAGTTTTCCTGGATTATGCCT | GGCACCAT | CFTR | 4 |
| 76, 77 | 18 | TS31 | GCGTTGGAGCGGGGAGAAGGCCAG | GGGTCACT | VEGFA | 9 |
| 80, 81 | 19 | TS34 | GGGCCGCGGAGATAGCTGCAGGGC | GGGGCCCC | LINC01588 | ND |
| 84, 85 | 20 | TS35 | GCCCACCCGGCGGCGCCTCCCTGC | AGGGCTGC | LINC01588 | ND |
| 88, 89 | 21 | TS36 | GCGTGGCAGCTGATATCCGGCCGC | TGGGCGTC | LINC01588 | ND |

TABLE 1-continued

Exemplary Endogenous human genome editing sites targeted by Nme2Cas9.

| | | | | | | | |
|---|---|---|---|---|---|---|---|
| 92, 93 | 22 | TS37 | GCCGCGGCGCGACGTGGAGCCAGC | CCCGCAAA | LINC01588 | ND |
| 96, 97 | 23 | TS38 | GTGCTCCCCAGCCCAAACCGCCGC | GGCGCGAC | LINC01588 | 2 |
| 100, 101 | 24 | TS41 | GTCAGATTGGCTTGCTCGGAATTG | CCAGCCAA | AGA | 3 |
| 104, 105 | 25 | TS44 | GCTGGGTGAATGGAGCGAGCAGCG | TCTTCGAG | VEGFA | 3 |
| 108, 109 | 26 | TS45 | GTCCTGGAGTGACCCCTGGCCTTC | TCCCCGCT | VEGFA | 7.4 |
| 112, 113 | 27 | TS46 | GATCCTGGAGTGACCCCTGGCCTT | CTCCCCGC | VEGFA | 6 |
| 116, 117 | 28 | TS47 | GTGTGTCCCTCTCCCCACCCGTCC | CTGTCCGG | VEGFA | 23.1 |
| 120, 121 | 29 | TS48 | GTTGGAGCGGGGAGAAGGCCAGGG | GTCACTCC | VEGFA | 2 |
| 124, 125 | 30 | TS49 | GCGTTGGAGCGGGGAGAAGGCCAG | GGGTCACT | VEGFA | 4 |
| 128, 129 | 31 | TS50 | GTACCCTCCAATAATTTGGCTGGC | AATTCCGA | AGA | 6 |
| 132, 133 | 32 | TS51 | GATAATTTGGCTGGCAATTCCGAG | CAAGCCAA | AGA | 4.5 |
| 136, 137 | 33 | TS58 (DS1) | GCAGGGGCCAGGTGTCCTTCTCTG | GGGGCCTC | VEGFA | 5 |
| 140, 141 | 34 | TS59 (DS2) | GAATGGCAGGCGGAGGTTGTACTG | GGGGCCAG | VEGFA | 11.5 |
| 144, 145 | 35 | TS60 (DS3) | GAGTGAGAGAGTGAGAGAGAGACA | CGGGCCAG | VEGFA | 3 |
| 148, 149 | 36 | TS61 (DS4) | GTGAGCAGGCACCTGTGCCAACAT | GGGCCCGC | VEGFA | 3.5 |
| 152, 153 | 37 | TS62 (DS5) | GCGTGGGGGCTCCGTGCCCCACGC | GGGTCCAT | VEGFA | 3.4 |
| 156,157 | 38 | TS63 (DS6) | GCATGGGCAGGGGCTGGGGTGCAC | AGGCCCAG | VEGFA | 16 |
| 160, 161 | 39 | TS64 | GAAAATTGTGATTTCCAGATCCAC | AAGCCCAA | FANCJ | 7 |
| 164, 165 | 40 | TS65 | GAGCAGAAAAAATTGTGATTTCC | AGATCCAC | FANCJ | ND |

| SEQ ID NOS. | No. | Site Name | TIDE Primer name | FW TIDE primer | RV TIDE primer |
|---|---|---|---|---|---|
| 10. 11 | 1 | TS1 | AAVS1_ TIDE1 | TGGCTTAGCACCTCTC CAT | AGAACTCAGGACCAACTTATTCTG |
| 14, 15 | 2 | TS4 | AAVS1_ TIDE1 | TGGCTTAGCACCTCTC CAT | AGAACTCAGGACCAACTTATTCTG |
| 18, 19 | 3 | TSS | AAVS1_ TIDE1 | TGGCTTAGCACCTCTC CAT | AGAACTCAGGACCAACTTATTCTG |
| 22, 23 | 4 | TS6 | LINC01588_ TIDE | AGAGGAGCCTTCTGAC TGCTGCAGA | ATGACAGACACAACCAGAGGGCA |
| 26, 27 | 5 | TS10 | AAVS1_ TIDE1 | TGGCTTAGCACCTCTC CAT | AGAACTCAGGACCAACTTATTCTG |
| 30, 31 | 6 | TS11 | AAVS1_ TIDE1 | TGGCTTAGCACCTCTC CAT | AGAACTCAGGACCAACTTATTCTG |
| 34, 35 | 7 | TS12 | AAVS1_ TIDE2 | TCCGTCTTCCTCCACTC C | TAGGAAGGAGGAGGCCTAAG |
| 38, 39 | 8 | TS13 | AAVS1_ TIDE2 | TCCGTCTTCCTCCACTC C | TAGGAAGGAGGAGGCCTAAG |
| 42, 43 | 9 | TS16 | LINC01588_ TIDE | AGAGGAGCCTTCTGAC TGCTGCAGA | ATGACAGACACAACCAGAGGGCA |
| 46, 47 | 10 | TS17 | LINC01588_ TIDE | AGAGGAGCCTTCTGAC TGCTGCAGA | ATGACAGACACAACCAGAGGGCA |

TABLE 1-continued

| | | | | Exemplary Endogenous human genome editing sites targeted by Nme2Cas9. | | |
|---|---|---|---|---|---|---|
| 50, 51 | 11 | TS18 | NTS55_TIDE | TAGAGAACTGGGTAGT GTG | CCAATATTGCATGGGATGG |
| 54, 55 | 12 | TS19 | NTS55_TIDE | TAGAGAACTGGGTAGT GTG | CCAATATTGCATGGGATGG |
| 58, 59 | 13 | TS20 | NTS55_TIDE | TAGAGAACTGGGTAGT GTG | CCAATATTGCATGGGATGG |
| 62, 63 | 14 | TS21 | NTS55_TIDE | TAGAGAACTGGGTAGT GTG | CCAATATTGCATGGGATGG |
| 66, 67 | 15 | TS25 | VEGF_ TIDE3 | GTACATGAAGCAACTC CAGTCCCA | ATCAAATTCCAGCACCGAGCGC |
| 70, 71 | 16 | TS26 | hCFTR_ TIDE1 | TGGTGATTATGGGAGA ACTGGAGC | ACCATTGAGGACGTTTGTCTCAC |
| 74, 75 | 17 | TS27 | hCFTR_ TIDE1 | TGGTGATTATGGGAGA ACTGGAGC | ACCATTGAGGACGTTTGTCTCAC |
| 78, 79 | 18 | TS31 | VEGF_ TIDE3 | GTACATGAAGCAACTC CAGTCCCA | ATCAAATTCCAGCACCGAGCGC |
| 82, 83 | 19 | TS34 | LINC01588_ TIDE | AGAGGAGCCTTCTGAC TGCTGCAGA | ATGACAGACACAACCAGAGGGCA |
| 86, 87 | 20 | TS35 | LINC01588_ TIDE | AGAGGAGCCTTCTGAC TGCTGCAGA | ATGACAGACACAACCAGAGGGCA |
| 90. 91 | 21 | TS36 | LINC01588_ TIDE | AGAGGAGCCTTCTGAC TGCTGCAGA | ATGACAGACACAACCAGAGGGCA |
| 94, 95 | 22 | TS37 | LINC01588_ TIDE | AGAGGAGCCTTCTGAC TGCTGCAGA | ATGACAGACACAACCAGAGGGCA |
| 98, 99 | 23 | TS38 | LINC01588_ TIDE | AGAGGAGCCTTCTGAC TGCTGCAGA | ATGACAGACACAACCAGAGGGCA |
| 102, 103 | 24 | TS41 | AGA_ TIDE1 | GGCATAAGGAAATCGA AGGTC | CATGTCCTCAAGTCAAGAACAAG |
| 106, 107 | 25 | TS44 | VEGF_ TIDE3 | GTACATGAAGCAACTC CAGTCCCA | ATCAAATTCCAGCACCGAGCGC |
| 110,111 | 26 | TS45 | VEGF_ TIDE3 | GTACATGAAGCAACTC CAGTCCCA | ATCAAATTCCAGCACCGAGCGC |
| 114, 115 | 27 | TS46 | VEGF_ TIDE3 | GTACATGAAGCAACTC CAGTCCCA | ATCAAATTCCAGCACCGAGCGC |
| 118, 119 | 28 | TS47 | VEGF_ TIDE3 | GTACATGAAGCAACTC CAGTCCCA | ATCAAATTCCAGCACCGAGCGC |
| 122, 124 | 29 | TS48 | VEGF_ TIDE3 | GTACATGAAGCAACTC CAGTCCCA | ATCAAATTCCAGCACCGAGCGC |
| 126, 127 | 30 | TS49 | VEGF_ TIDE3 | GTACATGAAGCAACTC CAGTCCCA | ATCAAATTCCAGCACCGAGCGC |
| 130, 131 | 31 | TS50 | AGA_TIDE1 AGGTC | GGCATAAGGAAATCGA | CATGTCCTCAAGTCAAGAACAAG |
| 134, 135 | 32 | TS51 | AGA_TIDE1 AGGTC | GGCATAAGGAAATCGA | CATGTCCTCAAGTCAAGAACAAG |
| 138, 139 | 33 | TS58 (DS1) | VEGF_ TIDE4 | ACACGGGCAGCATGGG AATAGTC | GCTAGGGGAGAGTCCCACTGTCCA |
| 142, 143 | 34 | TS59 (DS2) | VEGF_ TIDE5 | CCTGTGTGGCTTTGCTT TGGTC | GGTAGGGTGTGATGGGAGGCTAA GC |
| 146, 147 | 35 | TS60 (DS3) | VEGF_ TIDE5 | CCTGTGTGGCTTTGCTT TGGTC | GGTAGGGTGTGATGGGAGGCTAA GC |
| 150, 151 | 36 | TS61 (DS4) | VEGF TIDE5 | CCTGTGTGGCTTTGCTT TGGTC | GGTAGGGTGTGATGGGAGGCTAA GC |

TABLE 1-continued

| | | | | Exemplary Endogenous human genome editing sites targeted by Nme2Cas9. | |
|---|---|---|---|---|---|
| 154, 155 | 37 | TS62 (DS5) | VEGF_TIDE6 | GGAGGAAGAGTAGCTC GCCGAGG | AGACCGAGTGGCAGTGACAGCAA G |
| 158, 159 | 38 | TS63 (DS6) | VEGF_TIDE7 | AGGGAGAGGGAAGTG TGGGGAAGG | GTCTTCCTGCTCTGTGCGCACGAC |
| 162, 163 | 39 | TS64 | FancJ_TIDE5 | GTTGGGGGCTCTAAGT TATGTAT | CTTCATCTGTATCTTCAGGATCA |
| 166, 167 | 40 | TS65 | FancJ_TIDE5 | GTTGGGGGCTCTAAGT TATGTAT | CTTCATCTGTATCTTCAGGATCA |

HEK293T cells were used to support transient transfections and at 72-hours post transfection the, cells were harvested, followed by genomic DNA extraction and selective amplification of the targeted locus. TIDE analysis was used to measure indel efficiency at each locus (Brinkman et al., 2014). Nme2Cas9 editing was detectable at most of these sites, even though efficiencies varied depending on the target sequence. Table 1. Interestingly, Nme2Cas9 induced indels at several genomic sites with $N_4CD$ PAMs, albeit less consistently and at lower levels. Table 1. Fourteen (14) sites with $N_4CC$ PAMs were analyzed in triplicate, and consistent editing was observed. See, FIG. 9A. In addition, editing efficiency could be improved significantly by increasing the quantity of the Nme2Cas9 plasmid delivered, and this high efficiency could be extended to precise segmental deletion with two guides. See, FIGS. 10A and 10B.

The ability of Nme2Cas9 to function was tested in mouse Hepa1-6 cells (hepatoma-derived). For Hepa1-6 cells, a single plasmid encoding both Nme2Cas9 and an sgRNA (targeting either Rosa26 or Pcsk9) was transiently transfected and indels were measured after 72 hrs. Editing was readily observed at both sites. See, FIG. 9B, left. Nme2Cas9's functionality was also tested when stably expressed in human leukemia K562 cells. To this end, a lentiviral construct was created expressing Nme2Cas9 and transduced cells to stably express Nme2Cas9 under the control of the SFFV promoter. This stable cell line did not show any visible differences with respect to growth and morphology in comparison to untransduced cells, suggesting that Nme2Cas9 is not toxic when stably expressed. These cells were transiently electroporated with plasmids expressing sgRNAs and analyzed by TIDE after 72 hours to measure indel efficiencies. Efficient (>50%) editing was observed at all three sites tested, validating Nme2Cas9's ability to function upon lentiviral delivery in K562 cells. See, FIG. 9B.

Ribonucleoprotein (RNP) delivery of Cas9 and its sgRNA is also useful for some genome editing applications, and the greater transience of Cas9's presence can minimize off-target editing (Kim et al., 2014; Zuris et al., 2015). Moreover, some cell types (e.g. certain immune cells) are recalcitrant to DNA transfection-based editing (Schumann et al., 2015). To test whether Nme2Cas9 is functional by RNP delivery, a 6×His-tagged Nme2Cas9 (fused to three NLSs) was cloned into a bacterial expression construct and the recombinant protein was purified. The recombinant protein was then loaded with T7 RNA polymerase-transcribed sgRNAs targeting three previously validated sites. Electroporation of the Nme2Cas9: sgRNA complex induced successful editing at each of the three target sites in HEK293T cells, as detected by TIDE. See, FIG. 9C. Collectively these results indicate that Nme2Cas9 can be delivered effectively via plasmid or lentivirus, or as an RNP complex, in multiple cell types.

5. Anti-CRISPR Regulation

To date, five families of Acrs from diverse bacterial species have been shown to inhibit Nme1Cas9 in vitro and in human cells (Pawluk et al., 2016; Lee et al., 2018, submitted). Considering the high sequence identity between Nme1Cas9 and Nme2Cas9, at least some of these Acr families should inhibit Nme2Cas9. To test this, all five families of recombinant Acrs were expressed, purified and tested for Nme2Cas9's ability to cleave a target in vitro in the presence of a member of each family (10:1 Acr:Cas9 molar ratio). An inhibitor was used for the type I-E CRISPR system in E. coli (AcrE2) as a negative control, while Nme1Cas9 was used as a positive control. (Pawluk et al., 2014); (Pawluk et al., 2016). As expected, all 5 families inhibited Nme1Cas9, while AcrE2 failed to do so. See, FIG. 11A, top. $AcrIIC1_{Nme}$, $AcrIIC2_{Nme}$, $AcrIIC3_{Nme}$, and $AcrIIC4_{Hpa}$ completely inhibited Nme2Cas9. Strikingly, however, $AcrIIC5_{Smu}$ which has been previously reported as the most potent of the Nme1Cas9 inhibitors (Lee et al., 2018), did not inhibit Nme2Cas9 in vitro even at a 10-fold molar excess. This suggests that it likely inhibits Nme1Cas9 by interacting with its PID.

Figure 10A:
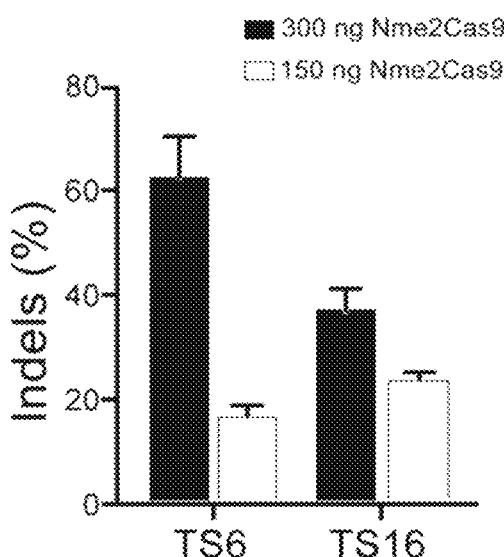
FIG. 10A-B presents exemplary data showing dose dependence and segmental deletions by Nme2Cas9, as related to FIG. 9A-C.
Figure 10B:
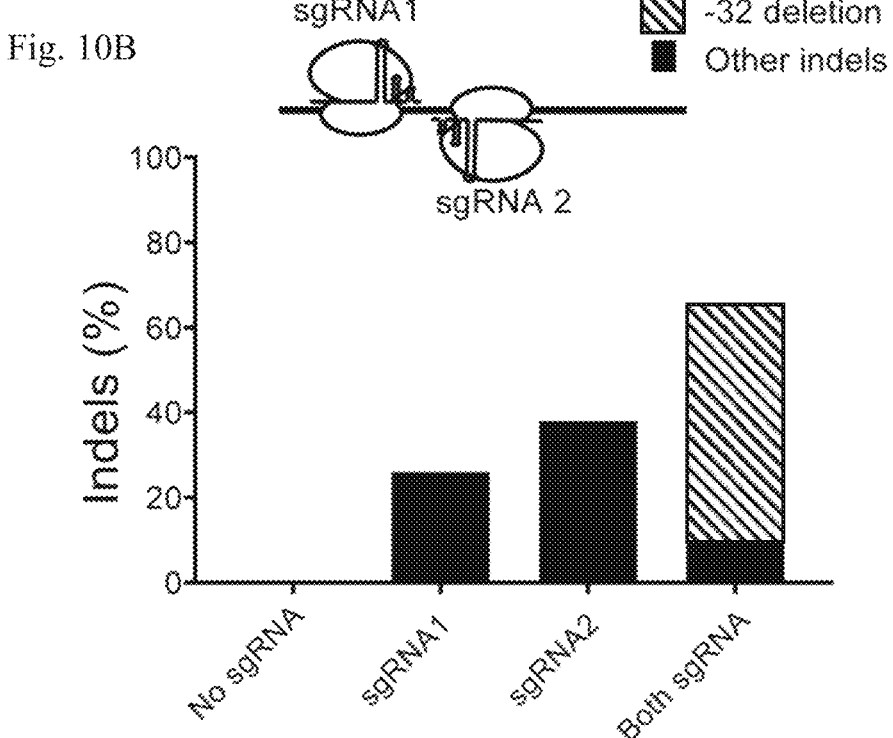

FIG. 10A-B presents exemplary data showing dose dependence and segmental deletions by Nme2Cas9, as related to FIG. 9A-C. FIG. 10A shows exemplary increasing the dose of electroporated Nme2Cas9 plasmid (500 ng, vs. 200 ng in FIG. 3A) improves editing efficiency at two sites (TS16 and TS6). Data provided in black are re-used from FIG. 9A. FIG. 10B shows exemplary Nme2Cas9 can be used to create precise segmental deletions. Two TLR2.0 targets with cleavage sites 32 bp apart were targeted simultaneously with Nme2Cas9. The majority of lesions created were deletions of exactly 32 bp (pattern).

Figure 11A:
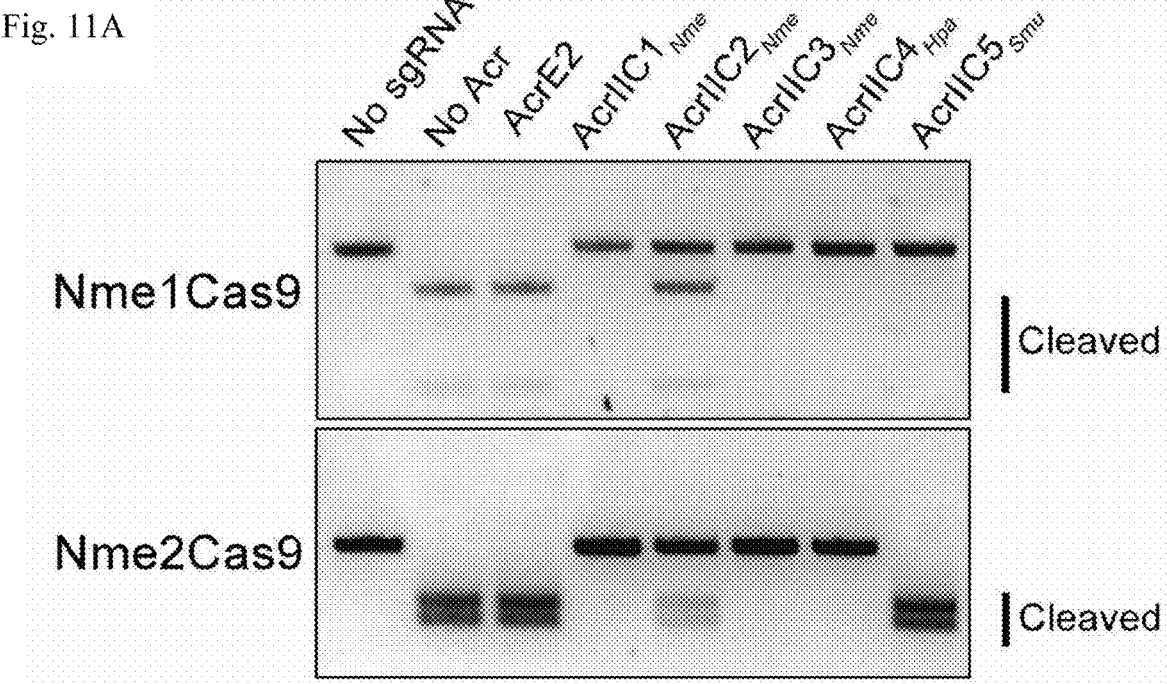
FIG. 11A-C presents exemplary data showing that Nme2Cas9 is subject to inhibition by a subset of type II-C anti-CRISPR families in vitro and in cells. All experiments were done in triplicate and error bars represent s.e.m.
Figure 11B:
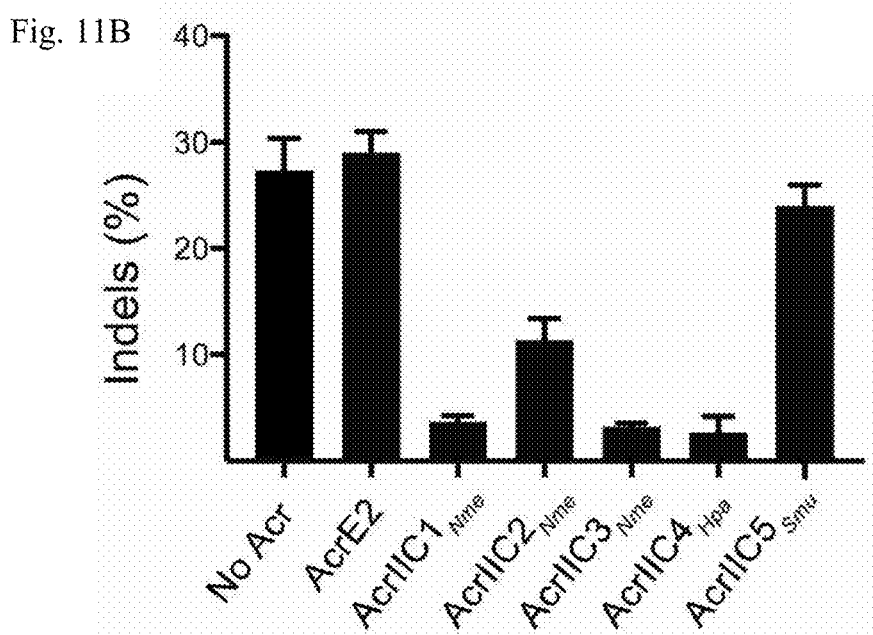
Figure 11C:
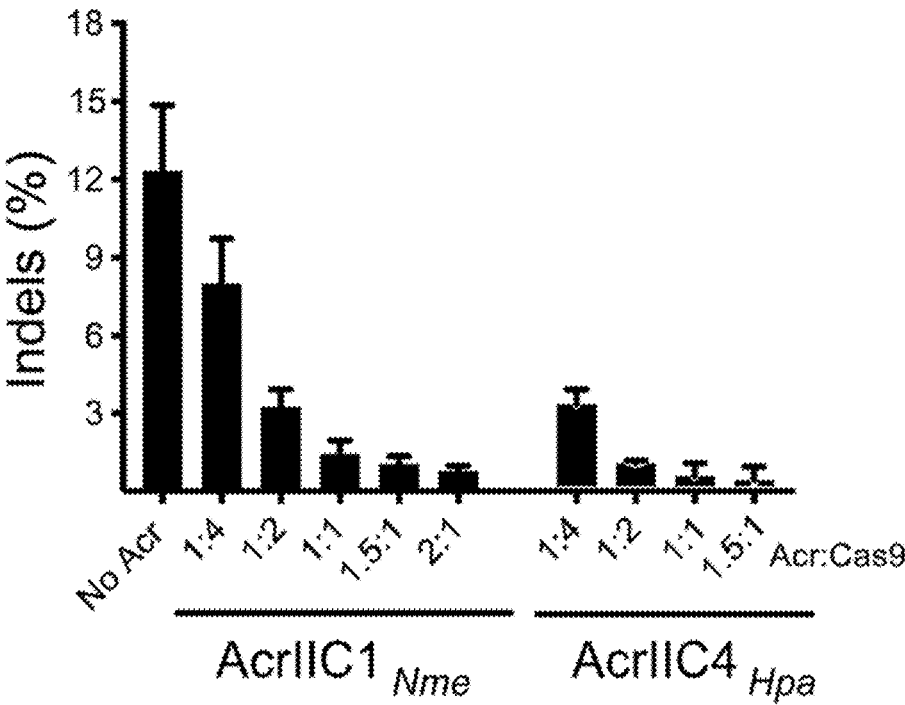

FIG. 11A-C presents exemplary data showing that Nme2Cas9 is subject to inhibition by a subset of type II-C anti-CRISPR families in vitro and in cells. All experiments were done in triplicate and error bars represent s.e.m. FIG. 11A shows exemplary In vitro cleavage assay of Nme1Cas9 and Nme2Cas9 in the presence of five previously characterized anti-CRISPR proteins (10:1 ratio of Acr:Cas9). Top: Nme1Cas9 efficiently cleaves a fragment containing a protospacer with an $N_4GATT$ PAM in the absence of an Acr or in the presence of a negative control Acr (AcrE2). All five previously characterized type II-C Acr families inhibited Nme1Cas9, as expected. Bottom: Nme2Cas9 inhibition mirrors that of Nme1Cas9, except for the lack of inhibition by $AcrIIC5_{Smu}$. FIG. 11B shows exemplary genome editing in the presence of the five previously described anti-CRISPR families. Plasmids expressing Nme2Cas9 (200 ng), sgRNA (100 ng) and each respective Acr (200 ng) were co-transfected into HEK293T cells, and genome editing was measured using Tracking of Indels by Decompostion (TIDE) 72 hr post transfection. Consistent with our in vitro analyses, all type II-C anti-CRISPRs except AcrIIC5$_{Smu}$ inhibited genome editing, albeit with different efficiencies. FIG. 11C shows exemplary Acr inhibition of Nme2Cas9 is dose-dependent with distinct apparent potencies. Nme2Cas9 is fully inhibited by AcrIIC1$_{Nme}$ and AcrIIC4$_{Hpa}$ at 2:1 and 1:1 mass ratios of cotransfected Acr and Nme2Cas9 plasmids, respectively.

To further test this, a Nme1Cas9/Nme2Cas9 chimera with the PID of Nme2Cas9 was tested. See, FIG. 5D and FIG. 6D. Due to the reduced activity of this hybrid, a ~30× higher concentration of Cas9 was used to achieve a similar cleavage efficiency while maintaining the 10:1 Cas9: Acr molar ratio. No inhibition was observed by AcrIIC5$_{Smu}$ on this protein chimera. See, FIG. 12. This data provides further evidence that AcrIIC5$_{Smu}$ likely interacts with the PID of Nme1Cas9. Regardless of the mechanistic basis for the differential inhibition by AcrIIC5$_{Smu}$, these results indicate that Nme2Cas9 is subject to inhibition by the other four type II-C Acr families.

Figure 12:
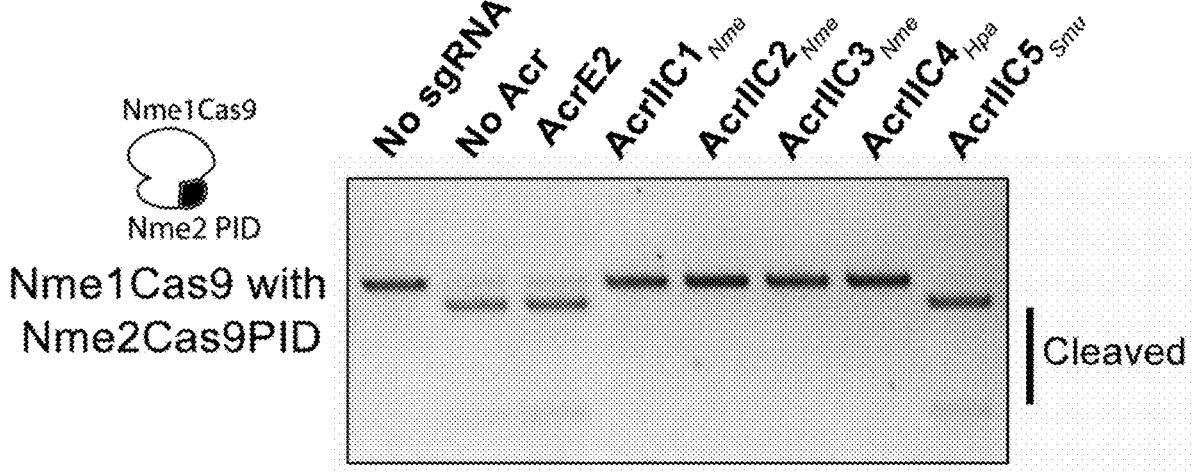
FIG. 12 presents exemplary data showing that a Nme2Cas9 PID swap renders Nme1Cas9 insensitive to $AcrIIC5_{Smu}$ inhibition, as related to FIG. 11A-C. In vitro cleavage by the Nme1Cas9-Nme2Cas9PID chimera in the presence of previously characterized Acr proteins (10 uM Cas9-sgRNA+100 uM Acr).

FIG. 12 presents exemplary data showing that a Nme2Cas9 PID swap renders Nme1Cas9 insensitive to AcrIIC5$_{Smu}$ inhibition, as related to FIG. 11A-C. In vitro cleavage by the Nme1Cas9-Nme2Cas9PID chimera in the presence of previously characterized Acr proteins (10 uM Cas9-sgRNA+100 uM Acr).

Based on the above in vitro data, it was hypothesized that AcrIIC1$_{Nme}$, AcrIIC2$_{Nme}$, AcrIIC3$_{Nme}$, and AcrIIC4$_{Hpa}$ could be used as off-switches for Nme2Cas9 genome editing. To test this, Nme2Cas9/sgRNA plasmid transfections (150 ng of each plasmid) targeting TS16 were performed in HEK293T cells in the presence or absence of Acr expression plasmids, as it has been reported that most Acrs inhibited Nme1Cas9 at those plasmid ratios (Pawluk et al., 2016). As expected, AcrIIC1$_{Nme}$, AcrIIC2$_{Nme}$, AcrIIC3$_{Nme}$ and AcrIIC4$_{Hpa}$ inhibited Nme2Cas9 genome editing, while AcrIIC5$_{Smu}$ had no effect. See, FIG. 11B. Complete inhibition was observed by AcrIIC3$_{Nme}$ and AcrIIC4$_{Hpa}$, suggesting that they have high potency against Nme2Cas9 as compared to AcrIIC1$_{Nme}$ and AcrIIC2$_{Nme}$. To further compare the potency of AcrIIC1$_{Nme}$ and AcrIIC4$_{Hpa}$, we repeated the experiments at various ratios of Acr plasmid to Cas9 plasmid. See, FIG. 11C. The data show that the AcrIIC4$_{Hpa}$ plasmid is especially potent against Nme2Cas9. Together, these data suggest that several Acr proteins can be used as off-switches for Nme2Cas9-based applications.

6. Hyper-Accuracy

Nme1Cas9 demonstrates remarkable editing fidelity in cells and mouse models (Lee et al., 2016; Amrani et al., 2018; Ibraheim et al., 2018). Furthermore, the similarity of Nme2Cas9 to Nme1Cas9 over most of its length suggests that it may likewise be hyper-accurate. However, the higher number of sites sampled in the genome as a result of the dinucleotide PAM could create more opportunities for Nme2Cas9 off-targeting in comparison with Nme1Cas9 and its less frequently encountered 4-nucleotide PAM. To assess the off-target profile of Nme2Cas9, GUIDE-seq (genome-wide, unbiased identification of double-stranded breaks enabled by sequencing) was used to identify potential off-target sites empirically and in an unbiased fashion (Tsai et al., 2014). Even the best off-target prediction algorithms are prone to false negatives necessitating empirical target site profiling methods (Bolukbasi et al., 2015b; Tsai and Joung, 2016; Tycko et al., 2016). GUIDE-seq relies on the incorporation of double-stranded oligodeoxynucleotides (dsODNs) into DNA double-stranded break sites throughout the genome. These insertion sites are then detected by amplification and high-throughput sequencing.

Because SpyCas9 is a well-characterized Cas9 ortholog it is useful for multiplexed applications with other Cas9s, and as a benchmark for their editing properties (Jiang and Doudna, 2017; Komor et al., 2017). SpyCas9 and Nme2Cas9 were cloned into identical plasmid backbones, with the same UTRs, linkers, NLSs, and promoters, for parallel transient transfections (along with similarly matched sgRNA-expressing plasmids) into HEK293T cells. First, it was confirmed that the RNA guides for SpyCas9 and Nme2Cas9 are orthogonal, i.e. that Nme2Cas9 sgRNAs do not direct editing by SpyCas9, and vice versa. See, FIG. 13A. This was in contrast to earlier reported results with Nme1Cas9 (Esvelt et al., 2013; Fonfara et al., 2014).

Next, to identify a use of SpyCas9 as a benchmark for GUIDE-seq, because SpyCas9 and Nme2Cas9 have non-overlapping PAMs its can therefore potentially edit any dual site (DS) flanked by a 5'-NGGNCC-3' sequence, which simultaneously fulfills the PAM requirements of both Cas9's. This permits side-by-side comparisons of off-targeting with RNA guides that facilitate an edit of the exact same on-target site. See, FIG. 14A. Six (6) DSs in VEGFA were targeted, each of which also has a G at the appropriate positions 5' of the PAM such that both SpyCas9 and Nme2Cas9 guides (driven by the U6 promoter) were 100% complementary to the target site. Seventy-two (72) hours after transfection, a TIDE analysis was performed on these sites targeted by each nuclease. Nme2Cas9 induced indels at all six sites, albeit at low efficiencies at two of them, while SpyCas9 induced indels at four of the six sites. See, FIG. 14B. At two of the four sites (DS1 and DS4) at which SpyCas9 was effective, it induced ~7-fold more indels than Nme2Cas9, while Nme2Cas9 induced a ~3-fold higher frequency of indels than SpyCas9 at DS6. Both Cas9 orthologs edited DS2 with approximately equal efficiency.

For GUIDE-seq, DS2, DS4 and DS6 were selected to sample off-target cleavage with Nme2Cas9 guides that direct on-target editing as efficiently, less efficiently, or more efficiently than the corresponding SpyCas9 guides, respectively. In addition to the three dual sites, TS6 was added as it has been observed to be an efficiently edited Nme2Cas9 target sites, having an approximate 30-50% indel efficiency depending on the cell type. See, FIGS. 9A and 10A. Similar data is seen with the mouse Pcsk9 and Rosa26$_{Nme}$2Cas9 sites. See, FIG. 9B.

Plasmid transfections were performed for each Cas9 along with their cognate sgRNAs and the dsODNs. Subsequently, GUIDE-seq libraries were prepared as described previously (Amrani et al., 2018). A GUIDE-seq analysis revealed efficient on-target editing for both Cas9 orthologs, with relative efficiencies (as reflected by GUIDE-seq read counts) that are similar to those observed by TIDE. FIG. 13B and Table 2. (Tsai et al., 2014; Zhu et al., 2017).

Figure 13A:
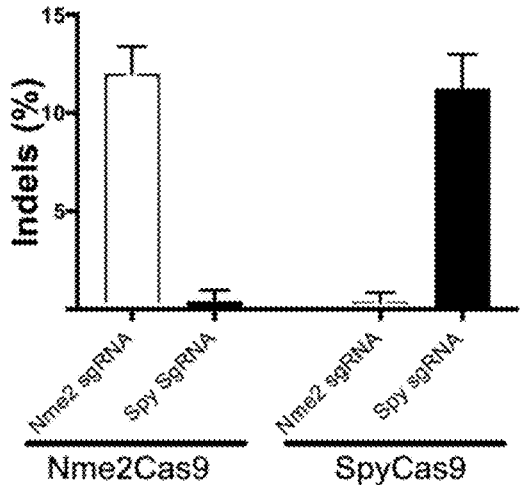
FIG. 13A-E presents exemplary data showing orthogonality and relative accuracy of Nme2Cas9 and SpyCas9 at dual target sites, as related to FIG. 12.
Figure 13B:
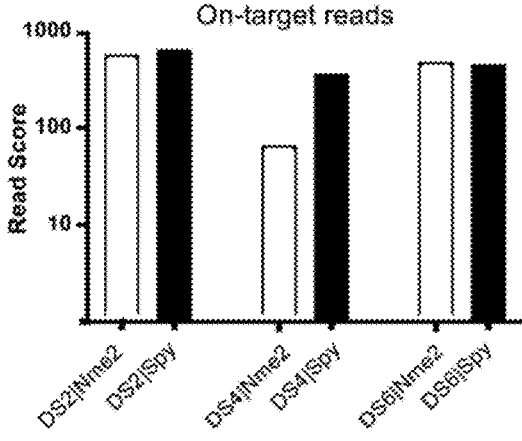
Figure 13C:
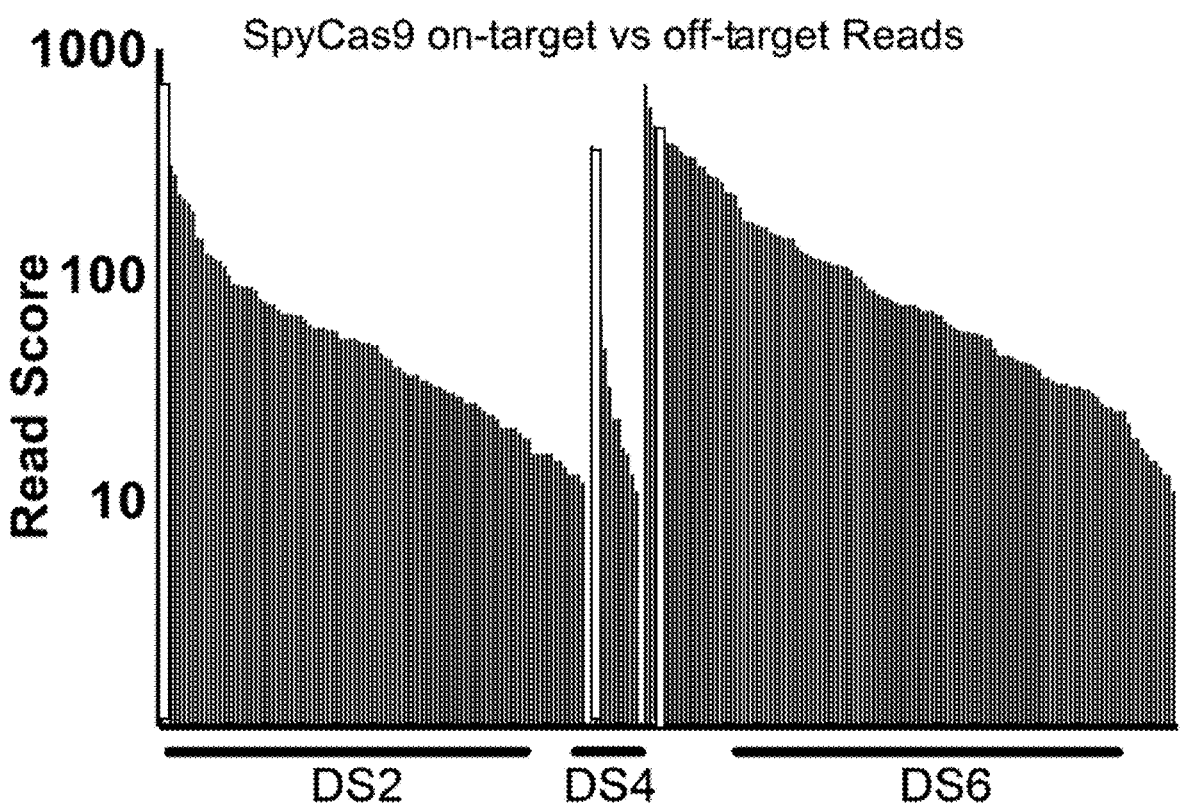
Figure 13D:
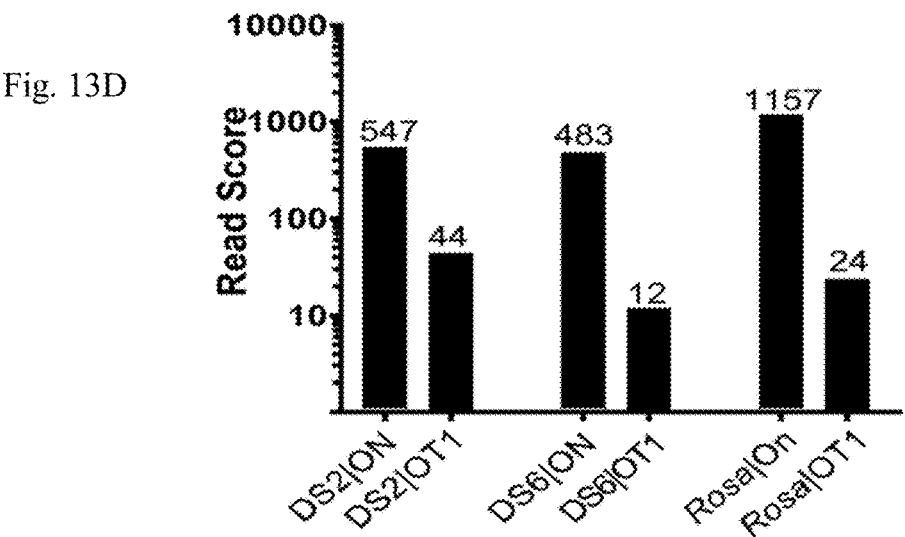

FIG. 13A-E presents exemplary data showing orthogonality and relative accuracy of Nme2Cas9 and SpyCas9 at dual target sites, as related to FIG. 12. FIG. 13A shows exemplary Nme2Cas9 and SpyCas9 guides are orthogonal. TIDE results show the frequencies of indels created by both nucleases targeting DS2 with either their cognate sgRNAs or with the sgRNAs of the other ortholog. FIG. 13B shows exemplary Nme2Cas9 and SpyCas9 exhibiting comparable on-target editing efficiencies as assessed by GUIDE-seq. Bars indicate on-target read counts from GUIDE-Seq at the three dual sites targeted by each ortholog. White bars represent Nme2Cas9 and black bars represent SpyCas9. FIG. 13C shows an exemplary SpyCas9's on-target vs. off-target read counts for each site. White bars represent the on-target reads while black bars represent off-targets. FIG.

Figure 13E:
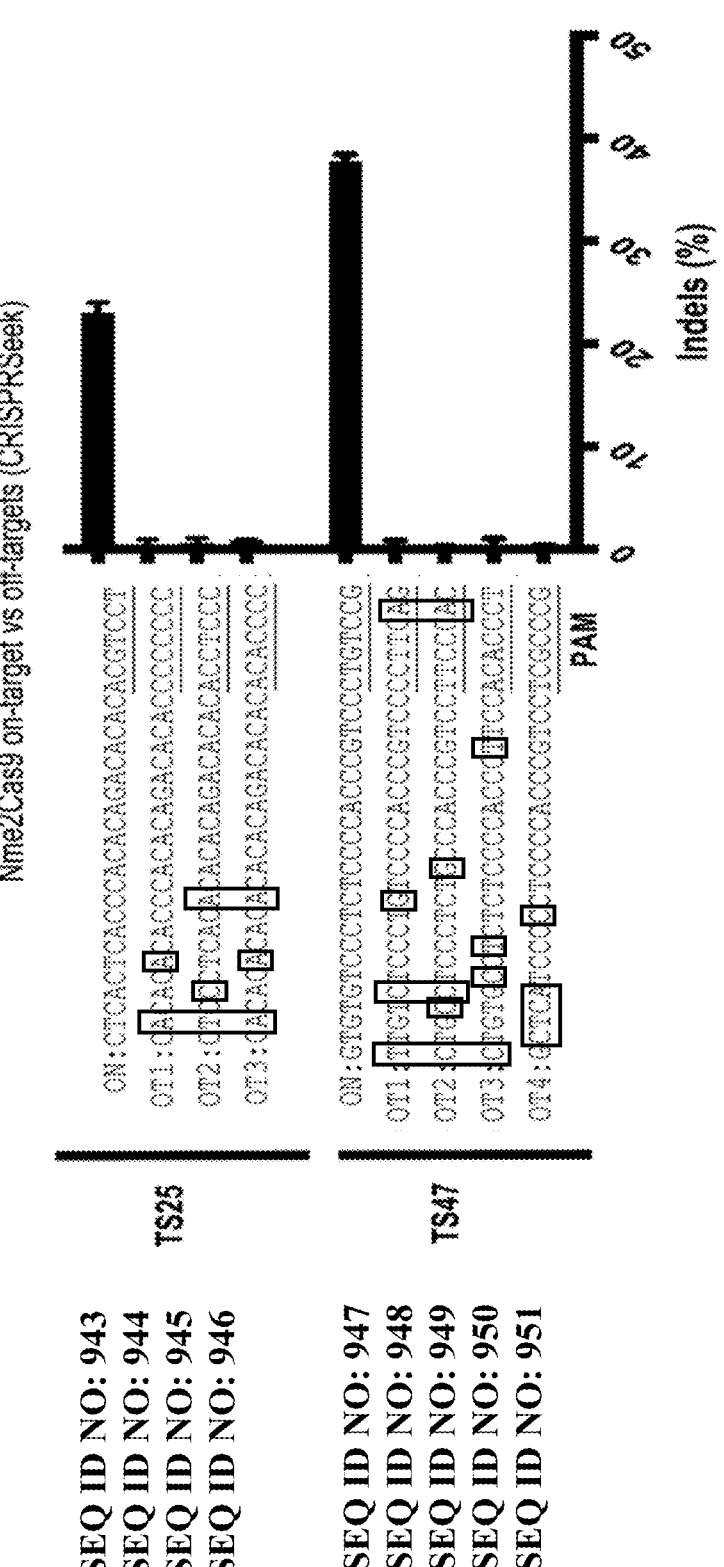

13D shows exemplary Nme2Cas9's on-target vs. off-target reads for each site. FIG. 13E bar graphs showing exemplary indel efficiencies (measured by TIDE) at potential off-target sites predicted by CRISPRSeek. On- and off-target site sequences are shown on the left, with the PAM region underlined and sgRNA mismatches and non-consensus PAM nucleotides are boxed.

TABLE 2

| GUIDE-seq Data | | |
| --- | --- | --- |
| SpyDS2 (gRNA.name SpyDS2) | | |
| offTarget | peak_score | predicted_cleavage_score |
| chr6:-:43748587:<br>43748609 | 652 | 100 |
| chr1:+:82004618:<br>82004640 | 304 | 4.1 |
| chr1:-:31140567:<br>31140589 | 275 | 19.6 |
| chr16:+:30357052:<br>30357074 | 226 | 0.6 |
| chr5:-:33453895:<br>33453917 | 217 | 4 |
| chr11:+:116600352:<br>116600374 | 206 | 0.4 |
| chr17:-:46938649:<br>46938671 | 191 | 0.6 |
| chr9:-:130859778:<br>130859800 | 146 | 5.4 |
| chr15:+:59837681:<br>59837703 | 143 | 2.6 |
| chr22:-:19135541:<br>19135563 | 124 | 0.3 |
| chrX:+:49057600:<br>49057622 | 122 | 0.6 |
| chr7:-:72751388:<br>72751410 | 117 | 2.6 |
| chr3:-:51652045:<br>51652067 | 115 | 0.3 |
| chr1:-:9544334:<br>9544356 | 109 | 0.7 |
| chr3:-:47868006:<br>47868028 | 99 | 2.6 |
| chr9:+:140670069:<br>140670091 | 91 | 0.4 |
| chr2:-:149516035:<br>149516057 | 90 | 0.3 |
| chr22:-:18245713:<br>18245735 | 89 | 0.2 |
| chr3:+:154744438:<br>154744460 | 89 | 2.6 |
| chr17:-:73320669:<br>73320691 | 88 | 0.7 |
| chr1:-:38479457:<br>38479479 | 85 | 2.6 |

TABLE 2-continued

| GUIDE-seq Data | | |
| --- | --- | --- |
| chr7:+:33058792:<br>33058814 | 78 | 0.3 |
| chr9:+:108299833:<br>108299855 | 76 | 1 |
| chr1:-:23627429:<br>23627451 | 74 | 0.5 |
| chr2:-:63393272:<br>63393294 | 74 | 0.5 |
| chr16:+:71467786:<br>71467808 | 70 | 0.6 |
| chr1:-:111638773:<br>111638795 | 67 | 0.3 |
| chr1:-:213393740:<br>213393762 | 67 | 0.5 |
| chr7:+:38284425:<br>38284447 | 67 | 0.3 |
| chr7:-:134511606:<br>134511628 | 66 | 0.7 |
| chr7:+:152293366:<br>152293388 | 66 | 0.7 |
| chr17:+:60243345:<br>60243367 | 63 | 0.5 |
| chrX:-:48007735:<br>48007757 | 60 | 0.6 |
| chr1:+:52768707:<br>52768729 | 58 | 5.4 |
| chr19:-:38805324:<br>38805346 | 58 | 0.3 |
| chrX:-:41283776:<br>41283798 | 58 | 2.6 |
| chr11:-:14539718:<br>14539740 | 57 | 2.6 |
| chr6:+:32895093:<br>32895115 | 57 | 0.7 |
| chr7:-:138957343:<br>138957365 | 56 | 98.6 |
| chr3:-:63900682:<br>63900704 | 52 | 0.4 |
| chr5:-:79624954:<br>79624976 | 52 | 9.6 |
| chr7:+:76012229:<br>76012251 | 52 | 0.7 |
| chrX:+:39889198:<br>39889220 | 52 | 2.6 |
| chr4:-:99897525:<br>99897547 | 51 | 5.4 |
| chr1:-:25822709:<br>25822731 | 50 | 0.7 |
| chr5:+:17293204:<br>17293226 | 50 | 0.7 |
| chr13:-:66697991:<br>66698013 | 49 | 0.1 |

TABLE 2-continued

| GUIDE-seq Data | | |
|---|---|---|
| chr5:-:80796103:80796125 | 49 | 2.6 |
| chr16:+:49239128:49239150 | 45 | 1.9 |
| chr3:+:69489884:69489906 | 43 | 0.5 |
| chr8:+:113712655:113712677 | 42 | 0.3 |
| chr2:-:24502672:24502694 | 39 | 2.6 |
| chr7:-:65642349:65642371 | 39 | 2.6 |
| chrX:-:135700076:135700098 | 37 | 2.6 |
| chr1:-:99795756:99795778 | 36 | 6.2 |
| chr19:+:1821377:1821399 | 36 | 0.2 |
| chr4:-:75501534:75501556 | 36 | 0.3 |
| chr18:+:74828740:74828762 | 34 | 0.3 |
| chrX:+:133975784:133975806 | 34 | 6.2 |
| chr14:+:55717904:55717926 | 33 | 98.6 |
| chr13:+:49522615:49522637 | 32 | 0.3 |
| chr3:-:77788415:77788437 | 32 | 0.7 |
| chr11:-:48230825:48230847 | 31 | 6.2 |
| chr1:-:1280441:1280463 | 30 | 0.3 |
| chr7:+:44602379:44602401 | 30 | 5.4 |
| chr12:-:108166294:108166316 | 29 | 5.4 |
| chr7:-:111929850:111929872 | 29 | 4 |
| chr12:-:122404237:122404259 | 27 | 0.2 |
| chr12:-:79123453:79123475 | 27 | 0.7 |
| chr22:-:46412541:46412563 | 27 | 6.2 |
| chr5:+:93889070:93889092 | 26 | 0.3 |
| chr10:-:97776548:97776570 | 25 | 0.6 |
| chr2:-:56533335:56533357 | 24 | 98.6 |

TABLE 2-continued

| GUIDE-seq Data | | |
|---|---|---|
| chr3:+:149843401:<br>149843423 | 24 | 0.1 |
| chr1:-:232769157:<br>232769179 | 23 | 2.6 |
| chr15:-:75100050:<br>75100072 | 21 | 2.6 |
| chr18:+:37252965:<br>37252987 | 21 | 0.6 |
| chr2:-:44506208:<br>44506230 | 21 | 7.6 |
| chr4:+:182389352:<br>182389374 | 21 | 0.6 |
| chr11:+:9360929:<br>9360951 | 20 | 98.6 |
| chr12:+:23638452:<br>23638474 | 19 | 0.4 |
| chr7:-:66498753:<br>66498775 | 19 | 1.4 |
| chr13:+:32055862:<br>32055884 | 16 | 6.2 |
| chr15:-:59331986:<br>59332008 | 16 | 6.2 |
| chr2:+:126196868:<br>126196890 | 16 | 0.7 |
| chrX:-:77359566:<br>77359588 | 16 | 0 |
| chrX:+:24652788:<br>24652810 | 16 | 6.2 |
| chr17:-:17667857:<br>17667879 | 15 | 0.4 |
| chr21:+:34751155:<br>34751177 | 15 | 2.6 |
| chr2:-:48734975:<br>48734997 | 14 | 5.4 |
| chr1:-:69755048:<br>69755070 | 13 | 2.6 |
| chr16:+:90013282:<br>90013304 | 13 | 1.1 |
| chr18:-:630757:<br>630779 | 13 | 5.4 |
| chr3:-:163905630:<br>163905652 | 12 | 0.6 |

| SEQ<br>ID<br>NOS: | gRNAPlusPAM | SEQ<br>ID<br>NOS: | offTarget sequence |
|---|---|---|---|
| 168 | GGCAGGCGGAGGTTGTACTGNGG | 169 | GGCAGGCGGAGGTTGTACTGGGG |
| 168 | GGCAGGCGGAGGTTGTACTGNGG | 170 | GGAAGGCGGAAGTTGTACTGAGG |
| 168 | GGCAGGCGGAGGTTGTACTGNGG | 171 | GGCAGGCGGAGGTTGTAGTGGGG |
| 168 | GGCAGGCGGAGGTTGTACTGNGG | 172 | AGGAGGCGGAGGTTGCACTGAGG |
| 168 | GGCAGGCGGAGGTTGTACTGNGG | 173 | GGGAGGTGGAGGTTGTACTGAGG |
| 168 | GGCAGGCGGAGGTTGTACTGNGG | 174 | GGCAGGGGGAAGCTGTACTGTGG |

TABLE 2-continued

| | GUIDE-seq Data | | |
|---|---|---|---|
| 168 | GGCAGGCGGAGGTTGTACTGNGG | 175 | AGGAGGCGGAGGTTGCACTGAGG |
| 168 | GGCAGGCGGAGGTTGTACTGNGG | 176 | AGGAGGCGGAGGTTGTACTGAGC |
| 168 | GGCAGGCGGAGGTTGTACTGNGG | 177 | GGGAGGCGGAGGTTGTAATGAGG |
| 168 | GGCAGGCGGAGGTTGTACTGNGG | 178 | GGCAAGAGGAGGTTGGACTGGGG |
| 168 | GGCAGGCGGAGGTTGTACTGNGG | 179 | AGGAGGCGGAGGTTGCACTGAGG |
| 168 | GGCAGGCGGAGGTTGTACTGNGG | 180 | GGGAGGCGGAGGTTGTAGTGAGG |
| 168 | GGCAGGCGGAGGTTGTACTGNGG | 181 | AGGAAGCGGAGGTTGTAATGAGG |
| 168 | GGCAGGCGGAGGTTGTACTGNGG | 182 | AGGAGGCGGAGGTTGTAATGAGG |
| 168 | GGCAGGCGGAGGTTGTACTGNGG | 183 | GGGAGGCGGAGGTTGTAGTGAGG |
| 168 | GGCAGGCGGAGGTTGTACTGNGG | 184 | TCCAGGTGGAGGCTGTACTGAGG |
| 168 | GGCAGGCGGAGGTTGTACTGNGG | 185 | AGGAGGCAGAGGTTGCACTGGGG |
| 168 | GGCAGGCGGAGGTTGTACTGNGG | 186 | GGGAGGCGGAGGATGTAATGAGG |
| 168 | GGCAGGCGGAGGTTGTACTGNGG | 187 | CACAGGCAGAGGTTGTACTGAGC |
| 168 | GGCAGGCGGAGGTTGTACTGNGG | 188 | AGGAGGCGGAGGTTGTAGTGAGG |
| 168 | GGCAGGCGGAGGTTGTACTGNGG | 189 | GGGAGGCGGAGGTTGTAGTGAGG |
| 168 | GGCAGGCGGAGGTTGTACTGNGG | 190 | AGGAGGCAGAGGTTGAACTGAGG |
| 168 | GGCAGGCGGAGGTTGTACTGNGG | 191 | GGCAAGGGGAAGTTGTACTGTGG |
| 168 | GGCAGGCGGAGGTTGTACTGNGG | 192 | GGGAGGCAGAGGTTGCACTGAGG |
| 168 | GGCAGGCGGAGGTTGTACTGNGG | 193 | GAGAGGCGGAGGTTGCACTGAGG |
| 168 | GGCAGGCGGAGGTTGTACTGNGG | 194 | AGGAGGCGGAGGTTGCACTGAGG |
| 168 | GGCAGGCGGAGGTTGTACTGNGG | 195 | AGGAGGCAGAGGTTGCACTGAGG |
| 168 | GGCAGGCGGAGGTTGTACTGNGG | 196 | GGGAGGCAGAGGTTGCACTGAGG |
| 168 | GGCAGGCGGAGGTTGTACTGNGG | 197 | CAGAGGCGGAGGTTGTAGTGAGG |
| 168 | GGCAGGCGGAGGTTGTACTGNGG | 198 | AGCAGGTAGAGGTTGGACTGAGG |
| 168 | GGCAGGCGGAGGTTGTACTGNGG | 199 | AGGAGGCGGAGGTTGTAGTGAGG |
| 168 | GGCAGGCGGAGGTTGTACTGNGG | 200 | GGGAGGCAGAGGTTGCACTGAGG |
| 168 | GGCAGGCGGAGGTTGTACTGNGG | 201 | AGGAGGCGGAGGTTGCACTGAGG |
| 168 | GGCAGGCGGAGGTTGTACTGNGG | 202 | TGGAGGCGGAGGTTGTACTGAGC |
| 168 | GGCAGGCGGAGGTTGTACTGNGG | 203 | AGGAGGCAGAGGTTGCACTGAGG |
| 168 | GGCAGGCGGAGGTTGTACTGNGG | 204 | GGGAGGCGGAGGTTGTAGTGAGG |
| 168 | GGCAGGCGGAGGTTGTACTGNGG | 205 | AGGAGGCAGAGGTTGTACTGAGC |
| 168 | GGCAGGCGGAGGTTGTACTGNGG | 206 | AGGAGGCGGAGGTTGTAGTGAGG |
| 168 | GGCAGGCGGAGGTTGTACTGNGG | 207 | GGGAGGCGGAGGTTGTACTGAGC |
| 168 | GGCAGGCGGAGGTTGTACTGNGG | 208 | GGGAGGTGGAGGTTGCACTGAGG |
| 168 | GGCAGGCGGAGGTTGTACTGNGG | 209 | GGGAGGCGGAGGTTGTAGTGAGG |
| 168 | GGCAGGCGGAGGTTGTACTGNGG | 210 | AGGAGGCGGAGGTTGTAGTGAGG |
| 168 | GGCAGGCGGAGGTTGTACTGNGG | 211 | GGGAGGCGGAGGTTGTAGTGAGG |
| 168 | GGCAGGCGGAGGTTGTACTGNGG | 212 | AGGAGGCGGAGGTTGTACTGAGC |
| 168 | GGCAGGCGGAGGTTGTACTGNGG | 213 | AGAAGGCGGAGGTTGTAGTGAGG |

TABLE 2-continued

| | GUIDE-seq Data | | |
|---|---|---|---|
| 168 | GGCAGGCGGAGGTTGTACTGNGG | 214 | AGGAGGCGGAGGTTGTAGTGAGG |
| 168 | GGCAGGCGGAGGTTGTACTGNGG | 215 | AGGAGGCGGAGGCTGCACTGAGG |
| 168 | GGCAGGCGGAGGTTGTACTGNGG | 216 | GGGAGGCGGAGGTTGTAGTGAGG |
| 168 | GGCAGGCGGAGGTTGTACTGNGG | 217 | GGGAGGCGGAGGTTGCACTGAGG |
| 168 | GGCAGGCGGAGGTTGTACTGNGG | 218 | GGGAGGCAGAGGTTGCACTGAGG |
| 168 | GGCAGGCGGAGGTTGTACTGNGG | 219 | AGGAGGCAGAGGTTGTAATGAGG |
| 168 | GGCAGGCGGAGGTTGTACTGNGG | 220 | GGGAGGCGGAGGTTGTAGTGAGG |
| 168 | GGCAGGCGGAGGTTGTACTGNGG | 221 | GGAAGGCGGAGGTTGTAGTGAGG |
| 168 | GGCAGGCGGAGGTTGTACTGNGG | 222 | AGGAGGCAGAGGTTGTACTGAGC |
| 168 | GGCAGGCGGAGGTTGTACTGNGG | 223 | GGGAGGCAGAGGTTGTACTGAGC |
| 168 | GGCAGGCGGAGGTTGTACTGNGG | 224 | GGAAGGTGAAGGCTGTACTGCGG |
| 168 | GGCAGGCGGAGGTTGTACTGNGG | 225 | AGAAGGCAGAGGTTGCACTGAGG |
| 168 | GGCAGGCGGAGGTTGTACTGNGG | 226 | AGTAGGCAGAGGTTGCACTGAGG |
| 168 | GGCAGGCGGAGGTTGTACTGNGG | 227 | GGGAGGCAGAGGTTGTACTGAGC |
| 168 | GGCAGGCGGAGGTTGTACTGNGG | 228 | GGGAGGCGGAGGTTGTACTGAGC |
| 168 | GGCAGGCGGAGGTTGTACTGNGG | 229 | AGGAGGCAGAGGTTGTAATGAGG |
| 168 | GGCAGGCGGAGGTTGTACTGNGG | 230 | AGGAGGCGGAGGTTGTAGTGAGG |
| 168 | GGCAGGCGGAGGTTGTACTGNGG | 231 | GGGAGGCAGAGGTTGTACTGAGC |
| 168 | GGCAGGCGGAGGTTGTACTGNGG | 232 | GCCAGGCGGGTGCTGTACTGGGG |
| 168 | GGCAGGCGGAGGTTGTACTGNGG | 233 | AGGAGGCGGAGGTTGTACTGGGC |
| 168 | GGCAGGCGGAGGTTGTACTGNGG | 234 | TGGAGGCGGAGGTTGTACTGAGC |
| 168 | GGCAGGCGGAGGTTGTACTGNGG | 235 | GGGAGGTGGAGGTTGTACTGAGC |
| 168 | GGCAGGCGGAGGTTGTACTGNGG | 236 | AGGAGGTGGAGGTTGTAATGAGG |
| 168 | GGCAGGCGGAGGTTGTACTGNGG | 237 | AGGAGGCGGAGGTTGTAGTGAGG |
| 168 | GGCAGGCGGAGGTTGTACTGNGG | 238 | GGGAGGCAGAGGTTGTACTGAGC |
| 168 | GGCAGGCGGAGGTTGTACTGNGG | 239 | AGGAGGCAGAGGTTGCACTGAGG |
| 168 | GGCAGGCGGAGGTTGTACTGNGG | 240 | GGGAGGCAGAGGTTGTAGTGAGG |
| 168 | GGCAGGCGGAGGTTGTACTGNGG | 241 | GGGAGGCGGAGGTTGTACTGAGC |
| 168 | GGCAGGCGGAGGTTGTACTGNGG | 242 | GGTAGGCAAAGGTTGTACCAGGG |
| 168 | GGCAGGCGGAGGTTGTACTGNGG | 243 | GGGAGGCGGAGGTTGTAGTGAGG |
| 168 | GGCAGGCGGAGGTTGTACTGNGG | 244 | AGGAGGCAGAGGTTGTACTGAGC |
| 168 | GGCAGGCGGAGGTTGTACTGNGG | 245 | GGGAGGCAGAGGTTGTAGTGAGG |
| 168 | GGCAGGCGGAGGTTGTACTGNGG | 246 | GGGAGGCGGAGGTTGTAGTGAGG |
| 168 | GGCAGGCGGAGGTTGTACTGNGG | 247 | GGGAGGCAGAGGTTGTAGTGAGG |
| 168 | GGCAGGCGGAGGTTGTACTGNGG | 248 | GGGAGGCGGAGGTTGTACTGAGC |
| 168 | GGCAGGCGGAGGTTGTACTGNGG | 249 | GGGAGGTGGAGGTTGCACTGAGG |
| 168 | GGCAGGCGGAGGTTGTACTGNGG | 250 | CAGAGGCAGAGGTTGTACTGAGC |
| 168 | GGCAGGCGGAGGTTGTACTGNGG | 251 | GGGAGGCAGAGGTTGTACTGAGT |
| 168 | GGCAGGCGGAGGTTGTACTGNGG | 252 | GGGAGGCAGAGGTTGTACTGAGC |

TABLE 2-continued

| GUIDE-seq Data | | | |
| --- | --- | --- | --- |
| 168 | GGCAGGCGGAGGTTGTACTGNGG | 253 | AGAAGGCGGAGGTTGTAGTGAGG |
| 168 | GGCAGGCGGAGGTTGTACTGNGG | 254 | CGTCTGCGAGGGTACTAGTGAGA |
| 168 | GGCAGGCGGAGGTTGTACTGNGG | 255 | GGGAGGCAGAGGTTGTACTGAGC |
| 168 | GGCAGGCGGAGGTTGTACTGNGG | 256 | GGGAGACGGAGGTTGTAGTGAGG |
| 168 | GGCAGGCGGAGGTTGTACTGNGG | 257 | AGGAGGCAGAGGTTGTACTGAGC |
| 168 | GGCAGGCGGAGGTTGTACTGNGG | 258 | AGGAGGCGGAGGTTGTACTGAGC |
| 168 | GGCAGGCGGAGGTTGTACTGNGG | 259 | AGAAGGCAGAGGTTGTACTGAGC |
| 168 | GGCAGGCGGAGGTTGTACTGNGG | 260 | GCCAGGCTGAGGATGTACTGTGG |
| 168 | GGCAGGCGGAGGTTGTACTGNGG | 261 | AGGAGGCGGAGGTTGTACTGAGC |
| 168 | GGCAGGCGGAGGTTGTACTGNGG | 262 | GGGAGGCAGAGGTTGTAGTGAGG |

| guideAlignment2 OffTarget | SEQ ID NOS: | offTarget Strand | mismatch.distance2PAM |
| --- | --- | --- | --- |
| .................. | | - | — |
| ..A.......A......... | | + | 18, 10 |
| ................G.. | | - | 3 |
| A.G...........C.... | | + | 20, 18, 5 |
| ..G...T............ | | - | 18, 14 |
| ......G...A.C....... | | + | 14, 10, 8 |
| A.G...........C.... | | - | 20, 18, 5 |
| A.G................ | | - | 20, 18 |
| ..G.............A.. | | + | 18, 3 |
| ....A.A........G.... | | - | 16, 14, 5 |
| A.G...........C.... | | + | 20, 18, 5 |
| ..G.............G.. | | - | 18, 3 |
| A.G.A...........A.. | 263 | - | 20, 18, 16, 3 |
| A.G.............A.. | | - | 20, 18, 3 |
| ..G.............G.. | | - | 18, 3 |
| TC....T.....C....... | 264 | + | 20, 19, 14, 8 |
| A.G....A.......C.... | 265 | - | 20, 18, 13, 5 |
| ..G.........A....A.. | | - | 18, 8, 3 |
| CA.....A............ | | + | 20, 19, 13 |
| A.G.............G.. | | - | 20, 18, 3 |
| ..G.............G.. | | - | 18, 3 |
| A.G....A.......A.... | 266 | + | 20, 18, 13, 5 |
| ....A.G...A......... | | + | 16, 14, 10 |
| ..G....A.......C.... | | - | 18, 13, 5 |
| .AG...........C.... | | - | 19, 18, 5 |
| A.G...........C.... | | + | 20, 18, 5 |
| A.G....A.......C.... | 267 | - | 20, 18, 13, 5 |

TABLE 2-continued

| GUIDE-seq Data | | | |
|---|---|---|---|
| ..G....A.......C.... | | - | 18, 13, 5 |
| CAG.............G.. | 268 | + | 20, 19, 18, 3 |
| A.....TA.......G.... | 269 | - | 20, 14, 13, 5 |
| A.G.............G.. | | + | 20, 18, 3 |
| ..G....A.......C.... | | + | 18, 13, 5 |
| A.G...........C.... | | - | 20, 18, 5 |
| T.G............... | | + | 20, 18 |
| A.G....A.......C.... | 270 | - | 20, 18, 13, 5 |
| ..G.............G.. | | - | 18, 3 |
| A.G....A.......... | | - | 20, 18, 13 |
| A.G.............G.. | | + | 20, 18, 3 |
| ..G............... | | - | 18 |
| ..G...T........C.... | | - | 18, 14, 5 |
| ..G.............G.. | | - | 18, 3 |
| A.G.............G.. | | + | 20, 18, 3 |
| ..G.............G.. | | + | 18, 3 |
| A.G............... | | - | 20, 18 |
| A.A.............G.. | | - | 20, 18, 3 |
| A.G.............G.. | | + | 20, 18, 3 |
| A.G.........C..C.... | 271 | - | 20, 18, 8, 5 |
| ..G.............G.. | | - | 18, 3 |
| ..G...........C.... | | + | 18, 5 |
| ..G....A.......C.... | | + | 18, 13, 5 |
| A.G....A.........A.. | 272 | + | 20, 18, 13, 3 |
| ..G.............G.. | | - | 18, 3 |
| ..A.............G.. | | - | 18, 3 |
| A.G...............A | | - | 20, 18, 13 |
| ..G....A........... | | - | 18, 13 |
| ..A...T.A...C....... | 273 | + | 18, 14, 12, 8 |
| A.A....A.......C.... | 274 | - | 20, 18, 13, 5 |
| A.T....A.......C.... | 275 | + | 20, 18, 13, 5 |
| ..G....A........... | | + | 18, 13 |
| ..G............... | | + | 18 |
| A.G....A.........A.. | 276 | + | 20, 18, 13, 3 |
| A.G.............G.. | | - | 20, 18, 3 |
| ..G....A........... | | - | 18, 13 |
| .C.......GT.C....... | 277 | - | 19, 11, 10, 8 |
| A.G............... | | + | 20, 18 |
| T.G............... | | - | 20, 18 |

TABLE 2-continued

| GUIDE-seq Data | | | |
|---|---|---|---|
| ..G...T............ | | - | 18, 14 |
| A.G...T.........A.. | 278 | - | 20, 18, 14, 3 |
| A.G............G.. | | - | 20, 18, 3 |
| ..G....A........... | | - | 18, 13 |
| A.G....A.......C.... | 279 | + | 20, 18, 13, 5 |
| ..G....A........G.. | | - | 18, 13, 3 |
| ..G................ | | - | 18 |
| ..T....AA.........CA | 280 | + | 18, 13, 12, 2, 1 |
| ..G.............G.. | | - | 18, 3 |
| A.G....A........... | | - | 20, 18, 13 |
| ..G....A........G.. | | + | 18, 13, 3 |
| ..G.............G.. | | - | 18, 3 |
| ..G....A........G.. | | + | 18, 13, 3 |
| ..G................ | | + | 18 |
| ..G...T........C.... | | + | 18, 14, 5 |
| CAG....A............ | 281 | - | 20, 19, 18, 13 |
| ..G....A........... | | + | 18, 13 |
| ..G....A........... | | - | 18, 13 |
| A.A.............G.. | | + | 20, 18, 3 |
| C.TCT...AG...AC..G.. | 282 | - | 20, 18, 17, 16, 12, 11, 7, 6, 3 |
| ..G....A........... | | + | 18, 13 |
| ..G..A..........G.. | | - | 18, 15, 3 |
| A.G....A........... | | + | 20, 18, 13 |
| A.G................ | | - | 20, 18 |
| A.A....A........... | | - | 20, 18, 13 |
| .C...........T....A | | + | 19, 13, 8 |
| A.G................ | | - | 20, 18 |
| ..G....A........G.. | | - | 18, 13, 3 |

| n.PAM.mismatch | n.guide.mismatch | PAM.sequence |
|---|---|---|
| 0 | 0 | GGG |
| 0 | 2 | AGG |
| 0 | 1 | GGG |
| 0 | 3 | AGG |
| 0 | 2 | AGG |
| 0 | 3 | TGG |
| 0 | 3 | AGG |
| 1 | 2 | AGC |
| 0 | 2 | AGG |
| 0 | 3 | GGG |

TABLE 2-continued

| | GUIDE-seq Data | |
|---|---|---|
| 0 | 3 | AGG |
| 0 | 2 | AGG |
| 0 | 4 | AGG |
| 0 | 3 | AGG |
| 0 | 2 | AGG |
| 0 | 4 | AGG |
| 0 | 4 | GGG |
| 0 | 3 | AGG |
| 1 | 3 | AGC |
| 0 | 3 | AGG |
| 0 | 2 | AGG |
| 0 | 4 | AGG |
| 0 | 3 | TGG |
| 0 | 3 | AGG |
| 0 | 3 | AGG |
| 0 | 3 | AGG |
| 0 | 4 | AGG |
| 0 | 3 | AGG |
| 0 | 4 | AGG |
| 0 | 4 | AGG |
| 0 | 3 | AGG |
| 0 | 3 | AGG |
| 0 | 3 | AGG |
| 1 | 2 | AGC |
| 0 | 4 | AGG |
| 0 | 2 | AGG |
| 1 | 3 | AGC |
| 0 | 3 | AGG |
| 1 | 1 | AGC |
| 0 | 3 | AGG |
| 0 | 2 | AGG |
| 0 | 3 | AGG |
| 0 | 2 | AGG |
| 1 | 2 | AGC |
| 0 | 3 | AGG |
| 0 | 3 | AGG |
| 0 | 4 | AGG |
| 0 | 2 | AGG |
| 0 | 2 | AGG |

TABLE 2-continued

| | | GUIDE-seq Data | | |
|---|---|---|---|---|
| 0 | 3 | AGG |
| 0 | 4 | AGG |
| 0 | 2 | AGG |
| 0 | 2 | AGG |
| 1 | 3 | AGC |
| 1 | 2 | AGC |
| 0 | 4 | CGG |
| 0 | 4 | AGG |
| 0 | 4 | AGG |
| 1 | 2 | AGC |
| 1 | 1 | AGC |
| 0 | 4 | AGG |
| 0 | 3 | AGG |
| 1 | 2 | AGC |
| 0 | 4 | GGG |
| 1 | 2 | GGC |
| 1 | 2 | AGC |
| 1 | 2 | AGC |
| 0 | 4 | AGG |
| 0 | 3 | AGG |
| 1 | 2 | AGC |
| 0 | 4 | AGG |
| 0 | 3 | AGG |
| 1 | 1 | AGC |
| 0 | 5 | GGG |
| 0 | 2 | AGG |
| 1 | 3 | AGC |
| 0 | 3 | AGG |
| 0 | 2 | AGG |
| 0 | 3 | AGG |
| 1 | 1 | AGC |
| 0 | 3 | AGG |
| 1 | 4 | AGC |
| 1 | 2 | AGT |
| 1 | 2 | AGC |
| 0 | 3 | AGG |
| 1 | 9 | AGA |
| 1 | 2 | AGC |
| 0 | 3 | AGG |

TABLE 2-continued

| | | | |
|---|---|---|---|
| GUIDE-seq Data | | | |
| 1 | 3 | | AGC |
| 1 | 2 | | AGC |
| 1 | 3 | | AGC |
| 0 | 3 | | TGG |
| 1 | 2 | | AGC |
| 0 | 3 | | AGG |

| offTarget_Start | offTarget_End | chromosome |
|---|---|---|
| 43748587 | 43748609 | chr6 |
| 82004618 | 82004640 | chr1 |
| 31140567 | 31140589 | chr1 |
| 30357052 | 30357074 | chr16 |
| 33453895 | 33453917 | chr5 |
| 116600352 | 116600374 | chr11 |
| 46938649 | 46938671 | chr17 |
| 130859778 | 130859800 | chr9 |
| 59837681 | 59837703 | chr15 |
| 19135541 | 19135563 | chr22 |
| 49057600 | 49057622 | chrX |
| 72751388 | 72751410 | chr7 |
| 51652045 | 51652067 | chr3 |
| 9544334 | 9544356 | chr1 |
| 47868006 | 47868028 | chr3 |
| 140670069 | 140670091 | chr9 |
| 149516035 | 149516057 | chr2 |
| 18245713 | 18245735 | chr22 |
| 154744438 | 154744460 | chr3 |
| 73320669 | 73320691 | chr17 |
| 38479457 | 38479479 | chr1 |
| 33058792 | 33058814 | chr7 |
| 108299833 | 108299855 | chr9 |
| 23627429 | 23627451 | chr1 |
| 63393272 | 63393294 | chr2 |
| 71467786 | 71467808 | chr16 |
| 111638773 | 111638795 | chr1 |
| 213393740 | 213393762 | chr1 |
| 38284425 | 38284447 | chr7 |
| 134511606 | 134511628 | chr7 |
| 152293366 | 152293388 | chr7 |
| 60243345 | 60243367 | chr17 |

TABLE 2-continued

| | GUIDE-seq Data | |
|---|---|---|
| 48007735 | 48007757 | chrX |
| 52768707 | 52768729 | chr1 |
| 38805324 | 38805346 | chr19 |
| 41283776 | 41283798 | chrX |
| 14539718 | 14539740 | chr11 |
| 32895093 | 32895115 | chr6 |
| 138957343 | 138957365 | chr7 |
| 63900682 | 63900704 | chr3 |
| 79624954 | 79624976 | chr5 |
| 76012229 | 76012251 | chr7 |
| 39889198 | 39889220 | chrX |
| 99897525 | 99897547 | chr4 |
| 25822709 | 25822731 | chr1 |
| 17293204 | 17293226 | chr5 |
| 66697991 | 66698013 | chr13 |
| 80796103 | 80796125 | chr5 |
| 49239128 | 49239150 | chr16 |
| 69489884 | 69489906 | chr3 |
| 113712655 | 113712677 | chr8 |
| 24502672 | 24502694 | chr2 |
| 65642349 | 65642371 | chr7 |
| 135700076 | 135700098 | chrX |
| 99795756 | 99795778 | chr1 |
| 1821377 | 1821399 | chr19 |
| 75501534 | 75501556 | chr4 |
| 74828740 | 74828762 | chr18 |
| 133975784 | 133975806 | chrX |
| 55717904 | 55717926 | chr14 |
| 49522615 | 49522637 | chr13 |
| 77788415 | 77788437 | chr3 |
| 48230825 | 48230847 | chr11 |
| 1280441 | 1280463 | chr1 |
| 44602379 | 44602401 | chr7 |
| 108166294 | 108166316 | chr12 |
| 111929850 | 111929872 | chr7 |
| 122404237 | 122404259 | chr12 |
| 79123453 | 79123475 | chr12 |
| 46412541 | 46412563 | chr22 |
| 93889070 | 93889092 | chr5 |

TABLE 2-continued

| GUIDE-seq Data | | |
| --- | --- | --- |
| 97776548 | 97776570 | chr10 |
| 56533335 | 56533357 | chr2 |
| 149843401 | 149843423 | chr3 |
| 232769157 | 232769179 | chr1 |
| 75100050 | 75100072 | chr15 |
| 37252965 | 37252987 | chr18 |
| 44506208 | 44506230 | chr2 |
| 182389352 | 182389374 | chr4 |
| 9360929 | 9360951 | chr11 |
| 23638452 | 23638474 | chr12 |
| 66498753 | 66498775 | chr7 |
| 32055862 | 32055884 | chr13 |
| 59331986 | 59332008 | chr15 |
| 126196868 | 126196890 | chr2 |
| 77359566 | 77359588 | chrX |
| 24652788 | 24652810 | chrX |
| 17667857 | 17667879 | chr17 |
| 34751155 | 34751177 | chr21 |
| 48734975 | 48734997 | chr2 |
| 69755048 | 69755070 | chr 1 |
| 90013282 | 90013304 | chr16 |
| 630757 | 630779 | chr18 |
| 163905630 | 163905652 | chr3 |

| inExon | entrez_id | symbol |
| --- | --- | --- |
| TRUE | 7422 | VEGFA |
| — | 23266 | ADGRL2 |
| — | — | — |
| — | — | — |
| — | 6897 | TARS |
| — | - | |
| — | 10241 | CALCOCO2 |
| — | 114789 | SLC25A25 |
| — | — | — |
| — | — | — |
| — | — | — |
| — | 8468 | FKBP6 |
| — | 23132 | RAD54L2 |
| — | — | — |

TABLE 2-continued

| | GUIDE-seq Data | |
| --- | --- | --- |
| — | 22907 | DHX30 |
| — | 79813 | EHMT1 |
| — | 26122 | EPC2 |
| — | 637 | BID |
| — | 4311 | MME |
| — | 2885 | GRB2 |
| — | 51118 | UTP11 |
| — | 51251 | NT5C3A |
| — | 83856 | FSD1L |
| — | — | — |
| — | 51057 | WDPCP |
| — | — | — |
| — | — | — |
| — | 26750 | RPS6KC1 |
| — | 445347 | TARP |
| — | 800 | CALD1 |
| — | — | — |
| — | — | — |
| — | — | — |
| — | 9372 | ZFYVE9 |
| — | 90522 | YIF1B |
| — | — | — |
| — | 5682 | PSMA1 |
| — | — | — |
| — | 254048 | UBN2 |
| — | 6314 | ATXN7 |
| — | — | — |
| — | — | — |
| — | — | — |
| — | 55219 | MACO1 |
| — | — | — |
| — | — | — |
| — | 23635 | SSBP2 |
| — | 23150 | FRMD4B |
| — | 114788 | CSMD3 |
| — | 50618 | ITSN2 |
| — | — | — |
| — | — | — |
| — | — | — |

TABLE 2-continued

| | GUIDE-seq Data | |
| --- | --- | --- |
| — | 57455 | REXO1 |
| — | — | — |
| — | 4155 | MBP |
| — | 159091 | FAM122C |
| — | — | — |
| — | — | — |
| — | 1855 | DVL1 |
| — | — | — |
| — | — | — |
| — | 11179 | ZNF277 |
| — | 144406 | WDR66 |
| — | — | — |
| — | — | — |
| — | 285600 | KIAA0825 |
| — | 728558 | ENTPD1-AS1 |
| — | 114800 | CCDC85A |
| — | — | — |
| — | — | — |
| — | — | — |
| — | 647946 | MIR924HG |
| — | 6519 | SLC3A1 |
| — | — | — |
| — | — | — |
| — | — | — |
| — | 55253 | TYW1 |
| — | — | — |
| — | 54778 | RNF111 |
| — | — | — |
| — | — | — |
| — | 9468 | PCYT1B |
| — | 10743 | RAI1 |
| — | — | — |
| — | 129285 | PPP1R21 |
| — | — | — |
| — | — | — |
| — | 27098 | CLUL1 |

TABLE 2-continued

| GUIDE-seq Data | | |
|---|---|---|
| SpyDS4 (gRNA.name SpyDS4) | | |
| predicted_ cleavage_score | SEQ ID NOS: | gRNAPlusPAM |
| 100 | 283 | GCAGGCACCTGTGCCAACATNGG |
| 0.1 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |
| 0 | 283 | GCAGGCACCTGTGCCAACATNGG |

| SEQ ID NOS. | offTarget_sequence | SEQ ID NOS. | guideAlignment2OffTarget |
|---|---|---|---|
| 284 | GCAGGCACCTGTGCCAACATGGG | | .................... |
| 285 | ACAGGCACTGATGCCAACTTTGG | 295 | A.......TGA.......T. |
| 286 | TAATGCCCTGGAGCCTCCCTGGC | 296 | TA.T..C.TG.A...TC.C. |
| 287 | GCAGGGCGCGCCGAGAGCAGCGG | 297 | .....GCG.GCC.AG.G..G |
| 288 | CCAGCCACCCAGCCCCTCCTCCC | 298 | C...C....CAGC..CT.C. |
| 289 | GTAAGCATATGATAGTCCATTTT | 299 | .T.A...TA..ATAGTC... |
| 290 | CCGCGTCCCTGCGCAAACCCAGG | 300 | C.GC.TC....C..A....CC |
| 291 | GTGCACCCCTGCTCCTACCCCCC | 301 | .TGCA.C....CT..T..CC |
| 292 | CCAGGGAGCAATGGCAGCGCGCC | 302 | C....G.G.AA..G..G.GC |
| 293 | GGCGGAAGTTGTACTGAGGTGAG | 303 | .GC..A.GT...A.TG.GG. |
| 294 | GCAGGAACTGGAGTGCACAGGTG | 304 | .....A..TG.A.TGC...G |

| offTarget Strand | mismatch.distance2PAM | n.guide.mismatch |
|---|---|---|
| — | — | 0 |
| + | 20, 12, 11, 10, 2 | 5 |
| + | 20, 19, 17, 14, 12, 11, 9, 5, 4, 2 | 10 |
| + | 15, 14, 13, 11, 10, 9, 7, 6, 4, | 10 |
| - | 20, 16, 11, 10, 9, 8, 5, 4, 2 | 9 |
| + | 19, 17, 13, 12, 9, 8, 7, 6, 5, 4 | 10 |
| - | 20, 18, 17, 15, 14, 9, 6, 2, 1 | 9 |
| + | 19, 18, 17, 16, 14, 9, 8, 5, 2, 1 | 10 |
| + | 20, 15, 13, 11, 10, 7, 4, 2, 1 | 9 |
| + | 19, 18, 15, 13, 12, 8, 6, 5, 3, 2 | 10 |
| - | 15, 12, 11, 9, 7, 6, 5, 1 | 8 |

TABLE 2-continued

GUIDE-seq Data

| PAM.sequence | offTarget_Start | offTarget_End |
|---|---|---|
| GGG | 43748848 | 43748870 |
| TGG | 41551021 | 41551043 |
| GGC | 43748564 | 43748586 |
| CGG | 77359654 | 77359676 |
| CCC | 43741999 | 43742021 |
| TTT | 68132445 | 68132467 |
| AGG | 77359345 | 77359367 |
| CCC | 22774978 | 22775000 |
| GCC | 77359596 | 77359618 |
| GAG | 82004622 | 82004644 |
| GTG | 80003891 | 80003913 |

| chromosomeinExon | | entrez_id | symbol |
|---|---|---|---|
| chr6 | NA | 7422 | VEGFA |
| chr22 | TRUE | 2033 | EP300 |
| chr6 | TRUE | 7422 | VEGFA |
| chrX | TRUE | 5230 | PGK1 |
| chr6 | — | 7422 | VEGFA |
| chr15 | — | — | — |
| chrX | — | — | — |
| chr6 | — | — | — |
| chrX | — | — | — |
| chr11 | — | 23266 | ADGRL2 |
| chr12 | — | 5074 | PAWR |

SpyDS6 (gRNA.name SpyDS6)

| offTarget | peak_score | predicted_cleavage_score |
|---|---|---|
| chr6:+:80816457:80816479 | 699 | 0.2 |
| chr6:-:22774975:22774997 | 553 | 1.4 |
| chr6:-:43742023:43742045 | 458 | 100 |
| chr7:-:124498153:124498175 | 449 | 0.2 |
| chr1:-:79194307:79194329 | 386 | 0.2 |
| chr17:+:77835740:77835762 | 383 | 5.2 |
| chr19:+:15313634:15313656 | 382 | 0.7 |
| chr12:+:96650610:96650632 | 374 | 3.7 |

TABLE 2-continued

| GUIDE-seq Data | | |
|---|---|---|
| chr10:-:79681895:<br>79681917 | 352 | 1.5 |
| chr6:+:20250488:<br>20250510 | 338 | 0.2 |
| chr13:-:49117083:<br>49117105 | 334 | 0.1 |
| chr12:-:80003893:<br>80003915 | 330 | 0.1 |
| chr17:-:77543039:<br>77543061 | 302 | 1.6 |
| chr8:-:65972642:<br>65972664 | 299 | 0.1 |
| chr20:-:35488683:<br>35488705 | 277 | 2.4 |
| chr11:+:100275645:<br>100275667 | 271 | 1.6 |
| chr22:+:38338356:<br>38338378 | 268 | 0.4 |
| chr13:+:45356854:<br>45356876 | 255 | 0.2 |
| chr20:-:31061319:<br>31061341 | 231 | 1.9 |
| chr11:-:66051111:<br>66051133 | 229 | 0.7 |
| chr17:-:72637693:<br>72637715 | 225 | 2.4 |
| chr11:+:128772408:<br>128772430 | 198 | 0.5 |
| chr1:-:99257317:<br>99257339 | 172 | 0.1 |
| chr15:-:39243269:<br>39243291 | 171 | 0.3 |
| chr14:-:22258408:<br>22258430 | 170 | 0.2 |
| chr21:-:42506703:<br>42506725 | 166 | 2.1 |
| chr7:-:150036050:<br>150036072 | 163 | 0.2 |
| chr7:-:1140569:<br>1140591 | 162 | 1.5 |
| chr4:+:40239842:<br>40239864 | 154 | 0.4 |
| chr22:-:50743552:<br>50743574 | 151 | 0.9 |
| chr2:-:241904500:<br>241904522 | 149 | 3.1 |
| chr9:-:136776149:<br>136776171 | 146 | 1 |
| chr8:+:22487688:<br>22487710 | 145 | 0.3 |
| chr1:-:110032844:<br>110032866 | 144 | 4.6 |

TABLE 2-continued

| GUIDE-seq Data | | |
| --- | --- | --- |
| chr1:-:182626625: 182626647 | 133 | 0.9 |
| chr5:-:134908150: 134908172 | 127 | 0.1 |
| chr20:-:61928182: 61928204 | 123 | 9.1 |
| chr10:-:88042752: 88042774 | 120 | 0.4 |
| chr17:-:6131626: 6131648 | 118 | 0.2 |
| chr4:-:1002743: 1002765 | 117 | 0.2 |
| chr22:+:19106203: 19106225 | 115 | 0.2 |
| chr1:+:44003969: 44003991 | 114 | 1.5 |
| chr1:-:114792469: 114792491 | 110 | 0.4 |
| chr19:+:38997988: 38998010 | 110 | 1.6 |
| chr2:-:46897354: 46897376 | 109 | 0.1 |
| chr12:+:121011672: 121011694 | 108 | 0.1 |
| chr17:-:75891020: 75891042 | 105 | 0.6 |
| chr9:+:139220931: 139220953 | 98 | 5.7 |
| chr14:+:24168625: 24168647 | 97 | 0.1 |
| chr15:-:74949775: 74949797 | 92 | 0.1 |
| chr19:+:44199443: 44199465 | 86 | 0.4 |
| chr12:+:75214528: 75214550 | 85 | 0.3 |
| chr17:-:46058760: 46058782 | 82 | 0.2 |
| chr16:-:90077745: 90077767 | 80 | 1.3 |
| chr20:+:62023611: 62023633 | 79 | 2.1 |
| chr12:+:121013758: 121013780 | 77 | 0.1 |
| chrX:+:106755923: 106755945 | 75 | 1 |
| chr10:+:44417540: 44417562 | 73 | 0.3 |
| chr11:-:118193407: 118193429 | 73 | 1.4 |
| chr16:-:13411476: 13411498 | 73 | 0.2 |

TABLE 2-continued

| GUIDE-seq Data | | |
|---|---|---|
| chr4:-:8206405:<br>8206427 | 73 | 0.6 |
| chr16:+:1517259:<br>1517281 | 71 | 0.1 |
| chr1:-:150849202:<br>150849224 | 69 | 0 |
| chr19:-:2057711:<br>2057733 | 69 | 1.1 |
| chr9:-:136075308:<br>136075330 | 69 | 0.1 |
| chr12:+:29935821:<br>29935843 | 67 | 0.1 |
| chr11:-:70812278:<br>70812300 | 66 | 0.2 |
| chr13:-:89703965:<br>89703987 | 62 | 2.3 |
| chr1:+:110166721:<br>110166743 | 60 | 0.6 |
| chr11:-:114079332:<br>114079354 | 58 | 0.2 |
| chr10:-:71813737:<br>71813759 | 57 | 0.4 |
| chr19:-:17414518:<br>17414540 | 56 | 0.3 |
| chr3:-:184289395:<br>184289417 | 56 | 0.3 |
| chr14:-:94566714:<br>94566736 | 55 | 0.2 |
| chr5:+:178665449:<br>178665471 | 55 | 0.1 |
| chr5:+:149568491:<br>149568513 | 54 | 0.3 |
| chr11:-:70242709:<br>70242731 | 52 | 0.1 |
| chr21:-:45132035:<br>45132057 | 52 | 0.1 |
| chr17:-:827977:<br>827999 | 47 | 0.2 |
| chr18:-:35056448:<br>35056470 | 44 | 0 |
| chr6:+:12990616:<br>12990638 | 44 | 0.2 |
| chr8:-:17955569:<br>17955591 | 44 | 0.1 |
| chr1:-:148932239:<br>148932261 | 43 | 0.3 |
| chr19:-:32734619:<br>32734641 | 42 | 0.2 |
| chr1:+:228330887:<br>228330909 | 41 | 0.1 |
| chr3:+:140221489:<br>140221511 | 41 | 3.3 |

TABLE 2-continued

| GUIDE-seq Data | | |
|---|---|---|
| chr5:-:139938346: 139938368 | 40 | 0.2 |
| chr22:+:23744878: 23744900 | 39 | 1.6 |
| chr10:-:16388635: 16388657 | 38 | 0.1 |
| chr17:+:34824953: 34824975 | 35 | 0.1 |
| chr3:-:129656921: 129656943 | 35 | 0.4 |
| chr14:-:93351573: 93351595 | 34 | 0 |
| chr1:+:33169255: 33169277 | 33 | 0.1 |
| chr18:+:29253123: 29253145 | 33 | 0 |
| chr6:+:20984444: 20984466 | 33 | 0 |
| chr10:-:77256682: 77256704 | 32 | 2.5 |
| chr15:+:89196634: 89196656 | 32 | 1.7 |
| chr18:-:73391522: 73391544 | 32 | 0 |
| chr10:-:72512814: 72512836 | 31 | 0 |
| chr8:+:80980935: 80980957 | 31 | 0.1 |
| chr11:+:37704008: 37704030 | 30 | 0.1 |
| chr12:+:52539310: 52539332 | 29 | 1.7 |
| chr14:-:56431001: 56431023 | 27 | 0.3 |
| chr15:-:66949803: 66949825 | 26 | 1.6 |
| chr7:+:100879116: 100879138 | 26 | 98.6 |
| chr11:-:94784149: 94784171 | 25 | 0.2 |
| chr12:+:111548733: 111548755 | 25 | 0.8 |
| chr19:+:2212199: 2212221 | 25 | 0.2 |
| chr13:-:22824517: 22824539 | 22 | 0.1 |
| chr13:-:84196623: 84196645 | 19 | 0.2 |
| chr15:+:96534271: 96534293 | 19 | 0.1 |
| chr21:-:21304105: 21304127 | 17 | 0.2 |

TABLE 2-continued

| GUIDE-seq Data | | |
|---|---|---|
| chr17:-:39705337:<br>39705359 | 16 | 0.2 |
| chr20:-:56582544:<br>56582566 | 15 | 0.9 |
| chr20:+:49479068:<br>49479090 | 15 | 0.1 |
| chr1:+:89258185:<br>89258207 | 14 | 0.1 |
| chr15:-:51386687:<br>51386709 | 13 | 0.1 |
| chr19:+:38724286:<br>38724308 | 13 | 0.3 |
| chr16:-:2286384:<br>2286406 | 11 | 0.2 |

| SEQ<br>ID<br>NOS. | gRNAPlusPAM | SEQ<br>ID<br>NOS. | offTarget_sequence |
|---|---|---|---|
| 305 | GGGCAGGGGCTGGGGTGCACNGG | 306 | CGGCAGGGGCTGAGGGGCACTGG |
| 305 | GGGCAGGGGCTGGGGTGCACNGG | 307 | GGGTAGGAGCAGGGGTGCACTGG |
| 305 | GGGCAGGGGCTGGGGTGCACNGG | 308 | GGGCAGGGGCTGGGGTGCACAGG |
| 305 | GGGCAGGGGCTGGGGTGCACNGG | 309 | GGGCAGGAACTGGAGTGCACAGG |
| 305 | GGGCAGGGGCTGGGGTGCACNGG | 310 | GGGCAGGAACTGGAGTGCACAGG |
| 305 | GGGCAGGGGCTGGGGTGCACNGG | 311 | CAGCAGGGGCTGGGGTGCACAGG |
| 305 | GGGCAGGGGCTGGGGTGCACNGG | 312 | GGGAAGGGCCTGGGGTACACGGG |
| 305 | GGGCAGGGGCTGGGGTGCACNGG | 313 | GGGCCGGGGCAGGGGTGCACAGG |
| 305 | GGGCAGGGGCTGGGGTGCACNGG | 314 | AGACAGGGGCCGGGGTGCACAGG |
| 305 | GGGCAGGGGCTGGGGTGCACNGG | 315 | GGGCAGGAACTGGAGTGCACCGG |
| 305 | GGGCAGGGGCTGGGGTGCACNGG | 316 | AGGCAGGAACTGGAGTGCACGGG |
| 305 | GGGCAGGGGCTGGGGTGCACNGG | 317 | AGGCAGGAACTGGAGTGCACAGG |
| 305 | GGGCAGGGGCTGGGGTGCACNGG | 318 | AGGAAGGGACTGGGGTGCACTGG |
| 305 | GGGCAGGGGCTGGGGTGCACNGG | 319 | AGGCAGGAACTGGAGTGCACAGG |
| 305 | GGGCAGGGGCTGGGGTGCACNGG | 320 | AGGTGGGGGCTGGGGTGCACAGG |
| 305 | GGGCAGGGGCTGGGGTGCACNGG | 321 | AGGCAGGAACTGGGGTGCACGGG |
| 305 | GGGCAGGGGCTGGGGTGCACNGG | 322 | TGGCAGGGGCAGGGGTGAACTGG |
| 305 | GGGCAGGGGCTGGGGTGCACNGG | 323 | GGGCAGGAACTGGAGTGCACGGG |
| 305 | GGGCAGGGGCTGGGGTGCACNGG | 324 | GGCCAGGGGCTGGGGAGCACAGG |
| 305 | GGGCAGGGGCTGGGGTGCACNGG | 325 | GGGCAGGGCTGGGGGTGCACAGG |
| 305 | GGGCAGGGGCTGGGGTGCACNGG | 326 | TGGGTGGGGCTGGGGTGCACTGG |
| 305 | GGGCAGGGGCTGGGGTGCACNGG | 327 | GGGAGGGGGCTGGGGAGCACAGG |
| 305 | GGGCAGGGGCTGGGGTGCACNGG | 328 | GGGCAGGAACTGGAGTACACGGG |
| 305 | GGGCAGGGGCTGGGGTGCACNGG | 329 | GAGAAGGAGCTGGGGAGCACTGG |
| 305 | GGGCAGGGGCTGGGGTGCACNGG | 330 | GGGCAGGAACTGGAGTGCACCAG |
| 305 | GGGCAGGGGCTGGGGTGCACNGG | 331 | GGGCAAGGGCAGGGGTGCACCAG |
| 305 | GGGCAGGGGCTGGGGTGCACNGG | 332 | AAGAAGGGGCAAGGGTGCACAGG |

TABLE 2-continued

GUIDE-seq Data

| 305 | GGGCAGGGGCTGGGGTGCACNGG | 333 | GGCCAGGAGCAGGGGTGCACGGG |
| 305 | GGGCAGGGGCTGGGGTGCACNGG | 334 | TGGCAGCGGCTGGGGAGCACTGG |
| 305 | GGGCAGGGGCTGGGGTGCACNGG | 335 | GGGCGTGGGCAGGGGTGCACTGG |
| 305 | GGGCAGGGGCTGGGGTGCACNGG | 336 | GGGCAGTGGCTGGGGTGCATTGG |
| 305 | GGGCAGGGGCTGGGGTGCACNGG | 337 | GGCCAGGAGCTGGGGTGCTCAGG |
| 305 | GGGCAGGGGCTGGGGTGCACNGG | 338 | CCTCAGGGGCTGGGGTGAACAGG |
| 305 | GGGCAGGGGCTGGGGTGCACNGG | 339 | TGGCAGGGTCTGGGGTGCACAGA |
| 305 | GGGCAGGGGCTGGGGTGCACNGG | 340 | GAGCAGGGTCTGGGGTGCATGGG |
| 305 | GGGCAGGGGCTGGGGTGCACNGG | 341 | GAGCAGGGACTGAGGGCACAGG |
| 305 | GGGCAGGGGCTGGGGTGCACNGG | 342 | GAGCAGGGGCTGGGGGGCACTGG |
| 305 | GGGCAGGGGCTGGGGTGCACNGG | 343 | TGGCAGGGGTAAGGGTGCACTGG |
| 305 | GGGCAGGGGCTGGGGTGCACNGG | 345 | AGACAGAGGCTGGAGTGCACTGG |
| 305 | GGGCAGGGGCTGGGGTGCACNGG | 346 | AGGCAGGGGCTGGAGTTCACAGG |
| 305 | GGGCAGGGGCTGGGGTGCACNGG | 347 | AGGAAGGGACCAGGGTGCACCAG |
| 305 | GGGCAGGGGCTGGGGTGCACNGG | 348 | GGCCAGGAGCAGGGGTGCACAGG |
| 305 | GGGCAGGGGCTGGGGTGCACNGG | 349 | GGGCCGGGGCTGGGGTGCCAGGG |
| 305 | GGGCAGGGGCTGGGGTGCACNGG | 350 | GGGCGGGGGCTGGGGAGCACAGG |
| 305 | GGGCAGGGGCTGGGGTGCACNGG | 351 | AGGCAGGAGCCAGGGTGCAGAGG |
| 305 | GGGCAGGGGCTGGGGTGCACNGG | 352 | GGGCAGAGGCTGGAGTGCCCAGG |
| 305 | GGGCAGGGGCTGGGGTGCACNGG | 353 | GGACAGGGGCAGGGGTGCCCGGG |
| 305 | GGGCAGGGGCTGGGGTGCACNGG | 354 | AGGGAGGGGCTGGGGTGCACGGA |
| 305 | GGGCAGGGGCTGGGGTGCACNGG | 355 | GGGCAGGAACTGGAGTGCATAGG |
| 305 | GGGCAGGGGCTGGGGTGCACNGG | 356 | AGGCAGGAACTGGAGTGCACAAG |
| 305 | GGGCAGGGGCTGGGGTGCACNGG | 357 | GGGCAGAGGCTAGGGTGCAGTGG |
| 305 | GGGCAGGGGCTGGGGTGCACNGG | 358 | AGGTAGGGGTTGGGGGGCACAGG |
| 305 | GGGCAGGGGCTGGGGTGCACNGG | 359 | GGGCAGAAGCAGGGGTGCTCAGG |
| 305 | GGGCAGGGGCTGGGGTGCACNGG | 360 | GGGGAGGGGTGGGGGTGCACCGG |
| 305 | GGGCAGGGGCTGGGGTGCACNGG | 361 | GAGCAGGGGCTGGGGGGCACTGG |
| 305 | GGGCAGGGGCTGGGGTGCACNGG | 362 | GGGCAGAGGCTGGAGTGCCCAGG |
| 305 | GGGCAGGGGCTGGGGTGCACNGG | 363 | GGGTGGGGGCTGGGGTGCCCAGG |
| 305 | GGGCAGGGGCTGGGGTGCACNGG | 364 | GGGCAAGGGCAGGGGTGCCCTGG |
| 305 | GGGCAGGGGCTGGGGTGCACNGG | 365 | GAGAGGGAGCTGGGGTGCACGGG |
| 305 | GGGCAGGGGCTGGGGTGCACNGG | 366 | AGGCAGGGACTGAGGTGCATAGG |
| 305 | GGGCAGGGGCTGGGGTGCACNGG | 367 | GGGCCAGGGCTGAGGTGCACAGG |
| 305 | GGGCAGGGGCTGGGGTGCACNGG | 368 | TGGGAGGGGCTAGAGTGCACAGG |
| 305 | GGGCAGGGGCTGGGGTGCACNGG | 369 | CCGCAGGGGCTGGGATGCTGGGG |
| 305 | GGGCAGGGGCTGGGGTGCACNGG | 371 | GAGGAGGGGCTGGGGTGCCCTGG |
| 305 | GGGCAGGGGCTGGGGTGCACNGG | 372 | GGGCAAAGGCCGGGGTGCCCAGG |
| 305 | GGGCAGGGGCTGGGGTGCACNGG | 373 | AGGCGGGGGCTGGGGGGCTCGGG |

TABLE 2-continued

| | GUIDE-seq Data | | |
|---|---|---|---|
| 305 | GGGCAGGGGCTGGGGTGCACNGG | 374 | AGGCAGGGGCCAGGGTCCACAGG |
| 305 | GGGCAGGGGCTGGGGTGCACNGG | 376 | GGGTTGGGGTTGGGGTGCACAGG |
| 305 | GGGCAGGGGCTGGGGTGCACNGG | 377 | AGGCAGGGGCCGGGGTGCGCAGG |
| 305 | GGGCAGGGGCTGGGGTGCACNGG | 378 | GGGCACAGACTGGGGTGCATTGG |
| 305 | GGGCAGGGGCTGGGGTGCACNGG | 379 | GGGCTGGGGCTGAGGTGCGCCGG |
| 305 | GGGCAGGGGCTGGGGTGCACNGG | 380 | AGGCAGGGGCTGGGGGGCAAGGG |
| 305 | GGGCAGGGGCTGGGGTGCACNGG | 381 | GAGCGGGAGCTGGGGGGCACAGG |
| 305 | GGGCAGGGGCTGGGGTGCACNGG | 382 | GGGCAGGGACTGGGGTGCTTAGG |
| 305 | GGGCAGGGGCTGGGGTGCACNGG | 383 | GGGAAGGGGCTGGAGGGCACAGG |
| 305 | GGGCAGGGGCTGGGGTGCACNGG | 384 | GGGCAGGGGAAGGGGTGGACTGG |
| 305 | GGGCAGGGGCTGGGGTGCACNGG | 385 | AGACAGGGGCTGGAGTGCAGTGG |
| 305 | GGGCAGGGGCTGGGGTGCACNGG | 386 | GGGCAGAGGCTGGAGTGCAATGG |
| 305 | GGGCAGGGGCTGGGGTGCACNGG | 387 | GGGCTGGGGCTGGGGAGCAGGGG |
| 305 | GGGCAGGGGCTGGGGTGCACNGG | 388 | AGGAAAGGGCTGGAGTGCAGGGG |
| 305 | GGGCAGGGGCTGGGGTGCACNGG | 389 | GGGCAGGAACTGGAGTGCACCAG |
| 305 | GGGCAGGGGCTGGGGTGCACNGG | 390 | AGGCAGGAACTGGAGTGCACAAG |
| 305 | GGGCAGGGGCTGGGGTGCACNGG | 391 | AGGCAGAGCCTGGGGTGCAGGGG |
| 305 | GGGCAGGGGCTGGGGTGCACNGG | 392 | GGGCAGGGCCAGGGGAGCACAGG |
| 305 | GGGCAGGGGCTGGGGTGCACNGG | 393 | AGCCAGGGGCTGGGGGGAACAGG |
| 305 | GGGCAGGGGCTGGGGTGCACNGG | 394 | GGGCAGGGGATGGGGTGCAGTGG |
| 305 | GGGCAGGGGCTGGGGTGCACNGG | 395 | AGGCAAGGCCTGGGGTGCCCAGG |
| 305 | GGGCAGGGGCTGGGGTGCACNGG | 396 | GGGCTGGGGCTGGGGAGCACGGG |
| 305 | GGGCAGGGGCTGGGGTGCACNGG | 397 | GAGAAGGGGCTGGGAAGCACAGG |
| 305 | GGGCAGGGGCTGGGGTGCACNGG | 398 | AGGCAGGAACTGGAGTGCACAAG |
| 305 | GGGCAGGGGCTGGGGTGCACNGG | 399 | GGGGAGGGGCTGGGGTGCCAGGG |
| 305 | GGGCAGGGGCTGGGGTGCACNGG | 400 | AGGAAGGGGCTGGGGAAAACAGG |
| 305 | GGGCAGGGGCTGGGGTGCACNGG | 401 | CCCCAGGGGCTGGGGTGCCTGGG |
| 305 | GGGCAGGGGCTGGGGTGCACNGG | 402 | AAGCAGAGGCTGAAGTGCACAGG |
| 305 | GGGCAGGGGCTGGGGTGCACNGG | 403 | AGGCAGGAACTAGAGTGCACAGG |
| 305 | GGGCAGGGGCTGGGGTGCACNGG | 404 | GGGCAGGGGGGTGGGGTCCACAGG |
| 305 | GGGCAGGGGCTGGGGTGCACNGG | 406 | GGGGAGGGGCTGGGGAGCACGGA |
| 305 | GGGCAGGGGCTGGGGTGCACNGG | 407 | AGGCAGAGGCTGGAGTGGACCGG |
| 305 | GGGCAGGGGCTGGGGTGCACNGG | 408 | GGGTAGGGGCTGGGGGATACCGG |
| 305 | GGGCAGGGGCTGGGGTGCACNGG | 409 | GGGAAGGGTCTGGAGTCCACTGG |
| 305 | GGGCAGGGGCTGGGGTGCACNGG | 410 | GGGCAGGAACTAGAGTGCACGGG |
| 305 | GGGCAGGGGCTGGGGTGCACNGG | 411 | GGGCAGGGACTGGGGTGCTCTGG |
| 305 | GGGCAGGGGCTGGGGTGCACNGG | 412 | GAGTAGGGGCAGGGGTGCTCTGG |
| 305 | GGGCAGGGGCTGGGGTGCACNGG | 413 | AGGAAGGGCCTGGGGTGCACAGA |
| 305 | GGGCAGGGGCTGGGGTGCACNGG | 414 | GGCCAGGGGCTGGGGTGCACGGT |

TABLE 2-continued

| | | GUIDE-seq Data | |
|---|---|---|---|
| 305 | GGGCAGGGGCTGGGGTGCACNGG | 415 | AGGCAGGGGCCAGGGTGCATGGG |
| 305 | GGGCAGGGGCTGGGGTGCACNGG | 416 | GGGCAGAGGATGGGGTGCAGGGG |
| 305 | GGGCAGGGGCTGGGGTGCACNGG | 417 | CGGCAGGGGCTGGAGTGCAGTGG |
| 305 | GGGCAGGGGCTGGGGTGCACNGG | 418 | AGGCAGGATCTGGAGTGCACAGG |
| 305 | GGGCAGGGGCTGGGGTGCACNGG | 419 | AGACAGGAGCTGGAGTGCACAAG |
| 305 | GGGCAGGGGCTGGGGTGCACNGG | 420 | TGGCAGGGGCAGGGATGCTCTGG |
| 305 | GGGCAGGGGCTGGGGTGCACNGG | 421 | CCTCAGGGGTTGGGATGCACTGG |
| 305 | GGGCAGGGGCTGGGGTGCACNGG | 422 | GAGCAGGGTCAGGGGTGCAGAGG |
| 305 | GGGCAGGGGCTGGGGTGCACNGG | 423 | CAGGAGTGGCTGGGGTGCACAGG |
| 305 | GGGCAGGGGCTGGGGTGCACNGG | 424 | GGGCCTGGGCTGAGATGCACGGG |
| 305 | GGGCAGGGGCTGGGGTGCACNGG | 425 | ACGCAGGGGCTAGGGAGCACAAG |
| 305 | GGGCAGGGGCTGGGGTGCACNGG | 426 | GGGCTGGGGCTGGGGAGGACGGG |
| 305 | GGGCAGGGGCTGGGGTGCACNGG | 427 | GGGCAGGGATTGGGGGGCACAGG |
| 305 | GGGCAGGGGCTGGGGTGCACNGG | 428 | AGGGAGGGGCCGGGCTGCACTGG |

| SEQ ID NOS. | guideAlignment2OffTarget | offTargetStrand | mismatch.distance2PAM |
|---|---|---|---|
| | C...........A..G.... | + | 20, 8, 5 |
| | ...T...A A.......... | - | 17, 13, 10 |
| | .................. | - | — |
| | .............AA....A | - | 13, 12, 7 |
| | .............AA....A | - | 13, 12, 7 |
| | CA................. | + | 20, 19 |
| | ...A....C.......A... | + | 17, 12, 4 |
| | ....C.....A......... | + | 16, 10 |
| | A.A.......C......... | - | 20, 18, 10 |
| | .......AA....A...... | + | 13, 12, 7 |
| 429 | A......AA....A...... | - | 20, 13, 12, 7 |
| 430 | A......AA....A...... | - | 20, 13, 12, 7 |
| | A..A....A.......... | - | 20, 17, 12 |
| 431 | A......AA....A...... | - | 20, 13, 12, 7 |
| | A..TG.............. | - | 20, 17, 16 |
| | A......AA.......... | + | 20, 13, 12 |
| | T.........A......A.. | + | 20, 10, 3 |
| | .......AA....A...... | + | 13, 12, 7 |
| | ..C..............A. | - | 18, 5 |
| | ........CTG......... | - | 12, 11, 10 |
| | T..GT.............. | - | 20, 17, 16 |
| | ...AG.........A.... | + | 17, 16, 5 |

TABLE 2-continued

| | GUIDE-seq Data | | |
|---|---|---|---|
| 432 | .......AA....A..A... | - | 13, 12, 7, 4 |
| 433 | .A.A...A.......A.... | - | 19, 17, 13, 5 |
| | .......AA....A...... | - | 13, 12, 7 |
| | .....A....A......... | - | 15, 10 |
| 434 | AA.A......AA........ | - | 20, 19, 17, 10, 9 |
| | ..C....A..A......... | - | 18, 13, 10 |
| | T.....C........A.... | + | 20, 14, 5 |
| | ....GT....A......... | - | 16, 15, 10 |
| | ......T...........T | - | 14, 1 |
| | ..C....A.........T. | - | 18, 13, 2 |
| 435 | CCT.............A.. | + | 20, 19, 18, 3 |
| | T......T........... | - | 20, 12 |
| | .A......T.........T | - | 19, 12, 1 |
| 436 | .A......A...A..G.... | - | 19, 12, 8, 5 |
| | .A.............G.... | - | 19, 5 |
| 437 | T........TAA........ | - | 20, 11, 10, 9 |
| 438 | A.A...A......A...... | - | 20, 18, 14, 7 |
| | A...........A..T... | - | 20, 7, 4 |
| 439 | A..A....A.CA........ | + | 20, 17, 12, 10, 9 |
| | ..C....A..A......... | + | 18, 13, 10 |
| | ....C..............CA | - | 16, 2, 1 |
| | ....G..........A.... | + | 16, 5 |
| 440 | A......A..CA.......G | - | 20, 13, 10, 9, 1 |
| | ......A......A....C. | + | 14, 7, 2 |
| | ..A.......A.......C. | - | 18, 10, 2 |
| | A..G............... | + | 20, 17 |
| 441 | .......AA....A.....T | + | 13, 12, 7, 1 |
| 442 | A......AA....A...... | - | 20, 13, 12, 7 |
| | ......A....A.......G | + | 14, 9, 1 |
| 443 | A..T.....T.....G.... | + | 20, 17, 11, 5 |
| 444 | ......AA..A.......T. | - | 14, 13, 10, 2 |
| | ...G.....TG......... | - | 17, 11, 10 |
| | .A..........  G.... | + | 19, 5 |
| | ......A......A....C. | + | 14, 7, 2 |
| | ...TG.............C. | + | 17, 16, 2 |
| | ......A....A.....C. | + | 15, 10, 2 |
| 445 | .A.AG..A............ | - | 19, 17, 16, 13 |
| 446 | A.......A...A......T | - | 20, 12, 8, 1 |
| | ....CA......A....... | - | 16, 15, 8 |

TABLE 2-continued

| | GUIDE-seq Data | | |
|---|---|---|---|
| 447 | T..G.......A.A...... | + | 20, 17, 9, 7 |
| | CC............A...TG | - | 20, 19, 6, 2, 1 |
| | .A.G..............C. | - | 19, 17, 2 |
| 448 | .....AA...C.......C. | - | 15, 14, 10, 2 |
| 449 | A...G.........G..T. | + | 20, 16, 5, 2 |
| 450 | A.........CA....C... | - | 20, 10, 9, 4 |
| | ...TT....T.......... | - | 17, 16, 11 |
| | A.........C.......G. | + | 20, 10, 2 |
| 451 | .....CA.A.........T | - | 15, 14, 12, 1 |
| | ....T.......A.....G. | - | 16, 8, 2 |
| | A..............G...A | - | 20, 5, 1 |
| 452 | .A..G..A.......G... | - | 19, 16, 13, 5 |
| | .......A.........TT | - | 12, 2, 1 |
| | ...A.........A.G.... | + | 17, 7, 5 |
| | .........AA......G.. | + | 11, 10, 3 |
| 453 | A.A.........A.....G | - | 20, 18, 7, 1 |
| | ......A......A....A | - | 14, 7, 1 |
| | ....T..........A...G | - | 16, 5, 1 |
| 454 | A..A.A.......A.....G | - | 20, 17, 15, 7, 1 |
| | .......AA....A...... | + | 13, 12, 7 |
| 455 | A......AA...A....... | - | 20, 13, 12, 7 |
| 456 | A.....A.C..........G | - | 20, 14, 12, 1 |
| | .......C.A....A.... | - | 12, 10, 5 |
| 457 | A.C............G.A.. | + | 20, 18, 5, 3 |
| | .........A.........G | + | 11, 1 |
| 458 | A....A..C........C. | - | 20, 15, 12, 2 |
| | ....T..........A.... | + | 16, 5 |
| 459 | .A.A..........AA.... | - | 19, 17, 6, 5 |
| 460 | A......AA....A...... | + | 20, 13, 12, 7 |
| | ...G..............CA | - | 17, 2, 1 |
| 461 | A..A...........AAA.. | - | 20, 17, 5, 4, 3 |
| 462 | CCC..............CT | + | 20, 19, 18, 2, 1 |
| 463 | AA....A......AA...... | + | 20, 19, 14, 8, 7 |
| 464 | A......AA..A.A...... | + | 20, 13, 12, 9, 7 |
| | .........G......C... | - | 11, 4 |
| | ...G...........A.... | + | 17, 5 |
| 465 | A.....A......A...G.. | - | 20, 14, 7, 3 |
| 466 | ...T..........GAT.. | - | 17, 5, 4, 3 |

TABLE 2-continued

| | GUIDE-seq Data | | |
|---|---|---|---|
| 467 | ...A....T....A..C... | + | 17, 12, 7, 4 |
| 468 | .......AA..A.A...... | + | 13, 12, 9, 7 |
| | .......A.........T. | + | 12, 2 |
| 469 | .A.T......A.......T. | - | 19, 17, 10, 2 |
| | A..A....C........... | - | 20, 17, 12 |
| | ..C................. | + | 18 |
| 470 | A........CA.......T | - | 20, 10, 9, 1 |
| | ......A..A.........G | + | 14, 11, 1 |
| | C...........A.....G | + | 20, 7, 1 |
| 471 | A......AT....A...... | - | 20, 13, 12, 7 |
| 472 | A.A....A.....A...... | - | 20, 18, 13, 7 |
| 473 | T.........A...A...T. | + | 20, 10, 6, 2 |
| 474 | CCT......T....A..... | - | 20, 19, 18, 11, 6 |
| 475 | .A......T.A........G | - | 19, 12, 10, 1 |
| 476 | CA.G..T............. | - | 20, 19, 17, 14 |
| 477 | ....CT......A.A..... | + | 16, 15, 8, 6 |
| 478 | AC.........A...A.... | + | 20, 19, 9, 5 |
| | ....T..........A.G.. | - | 16, 5, 3 |
| | ........AT.....G.... | + | 12, 11, 5 |
| 479 | A..G......C...C..... | - | 20, 17, 10, 6 |

| n.PAM.mismatch | n.guide.mismatch | PAM.sequence |
|---|---|---|
| 0 | 3 | TGG |
| 0 | 3 | TGG |
| 0 | 0 | AGG |
| 0 | 3 | AGG |
| 0 | 3 | AGG |
| 0 | 2 | AGG |
| 0 | 3 | GGG |
| 0 | 2 | AGG |
| 0 | 3 | AGG |
| 0 | 3 | CGG |
| 0 | 4 | GGG |
| 0 | 4 | AGG |
| 0 | 3 | TGG |
| 0 | 4 | AGG |
| 0 | 3 | AGG |
| 0 | 3 | GGG |
| 0 | 3 | TGG |
| 0 | 3 | GGG |

TABLE 2-continued

| GUIDE-seq Data | | |
| --- | --- | --- |
| 0 | 9 | AGG |
| 0 | 3 | AGG |
| 0 | 3 | TGG |
| 0 | 3 | AGG |
| 0 | 4 | GGG |
| 0 | 4 | TGG |
| 1 | 3 | CAG |
| 1 | 2 | CAG |
| 0 | 5 | AGG |
| 0 | 3 | GGG |
| 0 | 3 | TGG |
| 0 | 3 | TGG |
| 0 | 2 | TGG |
| 0 | 3 | AGG |
| 0 | 4 | AGG |
| 1 | 2 | AGA |
| 0 | 3 | GGG |
| 0 | 4 | AGG |
| 0 | 2 | TGG |
| 0 | 4 | TGG |
| 0 | 4 | TGG |
| 0 | 3 | AGG |
| 1 | 5 | CAG |
| 0 | 3 | AGG |
| 0 | 3 | GGG |
| 0 | 2 | AGG |
| 0 | 5 | AGG |
| 0 | 3 | AGG |
| 0 | 3 | GGG |
| 1 | 2 | GGA |
| 0 | 4 | AGG |
| 1 | 4 | AAG |
| 0 | 3 | TGG |
| 0 | 4 | AGG |
| 0 | 4 | AGG |
| 0 | 3 | CGG |
| 0 | 2 | TGG |
| 0 | 3 | AGG |
| 0 | 3 | AGG |

TABLE 2-continued

| GUIDE-seq Data | | |
|---|---|---|
| 0 | 3 | TGG |
| 0 | 4 | GGG |
| 0 | 4 | AGG |
| 0 | 3 | AGG |
| 0 | 4 | AGG |
| 0 | 5 | GGG |
| 0 | 3 | TGG |
| 0 | 4 | AUG |
| 0 | 4 | GGG |
| 0 | 4 | AGG |
| 0 | 3 | AGG |
| 0 | 3 | AGG |
| 0 | 4 | TGG |
| 0 | 3 | CGG |
| 0 | 3 | GGG |
| 0 | 4 | AGG |
| 0 | 3 | AGG |
| 0 | 3 | AGG |
| 0 | 3 | TGG |
| 0 | 4 | TGG |
| 0 | 3 | TGG |
| 0 | 3 | GGG |
| 0 | 5 | GGG |
| 1 | 3 | CAG |
| 1 | 4 | AAG |
| 0 | 4 | GGG |
| 0 | 3 | AGG |
| 0 | 4 | AGG |
| 0 | 2 | TGG |
| 0 | 4 | AGG |
| 0 | 2 | GGG |
| 0 | 4 | AGG |
| 1 | 4 | AAG |
| 0 | 3 | GGG |
| 0 | 5 | AGG |
| 0 | 5 | GGG |
| 0 | 5 | AGG |
| 0 | 5 | AGG |
| 0 | 2 | AGG |

TABLE 2-continued

| GUIDE-seq Data | | |
| --- | --- | --- |
| 1 | 2 | GGA |
| 0 | 4 | CGG |
| 0 | 4 | CGG |
| 0 | 4 | TGG |
| 0 | 4 | GGG |
| 0 | 2 | TGG |
| 0 | 4 | TGG |
| 1 | 3 | AGA |
| 1 | 1 | GGT |
| 0 | 4 | GGG |
| 0 | 3 | GGG |
| 0 | 3 | TGG |
| 0 | 4 | AGG |
| 1 | 4 | AAG |
| 0 | 4 | TGG |
| 0 | 5 | TGG |
| 0 | 4 | AGG |
| 0 | 4 | AGG |
| 0 | 4 | GGG |
| 1 | 4 | AAG |
| 0 | 3 | GGG |
| 0 | 3 | AGG |
| 0 | 4 | TGG |

| offTarget_Start | offTarget_End | chromosome |
| --- | --- | --- |
| 80816457 | 80816479 | chr6 |
| 22774975 | 22774997 | chr6 |
| 43742023 | 43742045 | chr6 |
| 124498153 | 124498175 | chr7 |
| 79194307 | 79194329 | chr1 |
| 77835740 | 77835762 | chr17 |
| 15313634 | 15313656 | chr19 |
| 96650610 | 96650632 | chr12 |
| 79681895 | 79681917 | chr10 |
| 20250488 | 20250510 | chr6 |
| 49117083 | 49117105 | chr13 |
| 80003893 | 80003915 | chr12 |
| 77543039 | 77543061 | chr17 |
| 65972642 | 65972664 | chr8 |
| 35488683 | 35488705 | chr20 |

TABLE 2-continued

| | GUIDE-seq Data | |
|---|---|---|
| 100275645 | 100275667 | chr11 |
| 38338356 | 38338378 | chr22 |
| 45356854 | 45356876 | chr13 |
| 31061319 | 31061341 | chr20 |
| 66051111 | 66051133 | chr11 |
| 72637693 | 72637715 | chr17 |
| 128772408 | 128772430 | chr11 |
| 99257317 | 99257339 | chr1 |
| 39243269 | 39243291 | chr15 |
| 22258408 | 22258430 | chr14 |
| 42506703 | 42506725 | chr21 |
| 150036050 | 150036072 | chr7 |
| 1140569 | 1140591 | chr7 |
| 40239842 | 40239864 | chr4 |
| 50743552 | 50743574 | chr22 |
| 241904500 | 241904522 | chr2 |
| 136776149 | 136776171 | chr9 |
| 22487688 | 22487710 | chr8 |
| 110032844 | 110032866 | chr1 |
| 182626625 | 182626647 | chr1 |
| 134908150 | 134908172 | chr5 |
| 61928182 | 61928204 | chr20 |
| 88042752 | 88042774 | chr10 |
| 6131626 | 6131648 | chr17 |
| 1002743 | 1002765 | chr4 |
| 19106203 | 19106225 | chr22 |
| 44003969 | 44003991 | chr1 |
| 114792469 | 114792491 | chr1 |
| 38997988 | 38998010 | chr19 |
| 46897354 | 46897376 | chr2 |
| 121011672 | 121011694 | chr12 |
| 75891020 | 75891042 | chr17 |
| 139220931 | 139220953 | chr9 |
| 24168625 | 24168647 | chr14 |
| 74949775 | 74949797 | chr15 |
| 44199443 | 44199465 | chr19 |
| 75214528 | 75214550 | chr12 |
| 46058760 | 46058782 | chr17 |
| 90077745 | 90077767 | chr16 |

TABLE 2-continued

| | GUIDE-seq Data | |
|---|---|---|
| 62023611 | 62023633 | chr20 |
| 121013758 | 121013780 | chr12 |
| 106755923 | 106755945 | chrX |
| 44417540 | 44417562 | chr10 |
| 118193407 | 118193429 | chr11 |
| 13411476 | 13411498 | chr16 |
| 8206405 | 8206427 | chr4 |
| 1517259 | 1517281 | chr16 |
| 150849202 | 150849224 | chr1 |
| 2057711 | 2057733 | chr19 |
| 136075308 | 136075330 | chr9 |
| 29935821 | 29935843 | chr12 |
| 70812278 | 70812300 | chr11 |
| 89703965 | 89703987 | chr13 |
| 110166721 | 110166743 | chr1 |
| 114079332 | 114079354 | chr11 |
| 71813737 | 71813759 | chr10 |
| 17414518 | 17414540 | chr19 |
| 184289395 | 184289417 | chr3 |
| 94566714 | 94566736 | chr14 |
| 178665449 | 178665471 | chr5 |
| 149568491 | 149568513 | chr5 |
| 70242709 | 70242731 | chr11 |
| 45132035 | 45132057 | chr21 |
| 827977 | 827999 | chr17 |
| 35056448 | 35056470 | chr18 |
| 12990616 | 12990638 | chr6 |
| 17955569 | 17955591 | chr8 |
| 148932239 | 148932261 | chr1 |
| 32734619 | 32734641 | chr19 |
| 228330887 | 228330909 | chr1 |
| 140221489 | 140221511 | chr3 |
| 139938346 | 139938368 | chr5 |
| 23744878 | 23744900 | chr22 |
| 16388635 | 16388657 | chr10 |
| 34824953 | 34824975 | chr17 |
| 129656921 | 129656943 | chr3 |
| 93351573 | 93351595 | chr14 |
| 33169255 | 33169277 | chr1 |

TABLE 2-continued

| | GUIDE-seq Data | |
|---|---|---|
| 29253123 | 29253145 | chr18 |
| 20984444 | 20984466 | chr6 |
| 77256682 | 77256704 | chr10 |
| 89196634 | 89196656 | chr15 |
| 73391522 | 73391544 | chr18 |
| 72512814 | 72512836 | chr10 |
| 80980935 | 80980957 | chr8 |
| 37704008 | 37704030 | chr11 |
| 52539310 | 52539332 | chr12 |
| 56431001 | 56431023 | chr14 |
| 66949803 | 66949825 | chr15 |
| 100879116 | 100879138 | chr7 |
| 94784149 | 94784171 | chr11 |
| 111548733 | 111548755 | chr12 |
| 2212199 | 2212221 | chr19 |
| 22824517 | 22824539 | chr13 |
| 84196623 | 84196645 | chr13 |
| 96534271 | 96534293 | chr15 |
| 21304105 | 21304127 | chr21 |
| 39705337 | 39705359 | chr17 |
| 56582544 | 56582566 | chr20 |
| 49479068 | 49479090 | chr20 |
| 89258185 | 89258207 | chr1 |
| 51386687 | 51386709 | chr15 |
| 38724286 | 38724308 | chr19 |
| 2286384 | 2286406 | chr16 |
| TRUE | 594 | BCKDHB |
| — | — | — |
| — | 7422 | VEGFA |
| — | 25913 | POT1 |
| — | — | — |
| — | — | — |
| — | — | — |
| — | 2004 | ELK3 |
| — | 9231 | DLG5 |
| — | — | — |
| — | — | — |

TABLE 2-continued

| | GUIDE-seq Data | |
| --- | --- | --- |
| — | 5074 | PAWR |
| — | — | — |
| — | — | — |
| — | 140710 | SOGA1 |
| — | — | — |
| TRUE | 85377 | MICALL1 |
| — | — | — |
| — | 140688 | NOL4L |
| TRUE | 254263 | CNIH2 |
| — | — | — |
| TRUE | 3762 | KCNJ5 |
| — | — | — |
| — | — | — |
| — | — | — |
| — | 5919 | RARRES2 |
| — | 84310 | C7orf50 |
| — | 399 | RHOH |
| — | 23654 | PLXNB2 |
| — | 200772 | LOC200772 |
| — | 7410 | VAV2 |
| — | 55909 | BIN3 |
| — | 127002 | ATXN7L2 |
| — | 85397 | RGS8 |
| — | 9547 | CXCL14 |
| — | 57642 | COL20A1 |
| — | 2894 | GRID1 |
| — | — | — |
| — | — | — |
| — | 9993 | DGCR2 |
| — | 5792 | PTPRF |
| — | — | — |
| — | 6261 | RYR1 |
| — | — | — |
| — | 9921 | RNF10 |
| — | — | — |
| TRUE | 26102 | DKEZP434A062 |
| — | — | — |

TABLE 2-continued

| | GUIDE-seq Data | |
| --- | --- | --- |
| — | 80153 | EDC3 |
| — | — | — |
| — | — | — |
| — | 80279 | CDK5RAP3 |
| — | 79007 | DBNDD1 |
| — | — | — |
| — | 9921 | RNF10 |
| — | — | — |
| — | 283033 | LINC00841 |
| — | — | — |
| — | — | — |
| — | 54436 | SH3TC1 |
| — | 1186 | CLCN7 |
| TRUE | 405 | ARNT |
| — | — | — |
| — | — | — |
| TRUE | 83857 | TMTC1 |
| — | 22941 | SHANK2 |
| — | — | — |
| — | 271 | AMPD2 |
| — | 7704 | ZBTB16 |
| — | 55506 | H2AFY2 |
| — | — | — |
| — | 2049 | EPHB3 |
| — | 122509 | IFI27L1 |
| — | 9509 | ADAMTS2 |
| — | — | — |
| — | — | — |
| — | — | — |
| — | 64359 | NXN |
| — | 56853 | CELF4 |
| — | 221692 | PHACTR1 |
| — | — | — |
| — | 645166 | LOC645166 |
| — | — | — |
| — | 2987 | GUK1 |
| — | 64084 | CLSTN2 |

TABLE 2-continued

| GUIDE-seq Data | | |
|---|---|---|
| TRUE | 10307 | APBB3 |
| — | — | — |
| — | — | — |
| — | — | — |
| — | — | — |
| — | — | — |
| — | — | — |
| — | 9331 | B4GALT6 |
| — | 54901 | CDKAL1 |
| — | — | — |
| — | 3669 | ISG20 |
| — | — | — |
| — | 140766 | ADAMTS14 |
| — | 7163 | TPD52 |
| — | — | — |
| — | — | — |
| — | — | — |
| — | 24146 | CLDN15 |
| — | — | — |
| — | 23316 | CUX2 |
| TRUE | 84444 | DOT1L |
| — | — | — |
| — | 3728 | JUP |
| — | — | — |
| — | 55653 | BCAS4 |
| — | 5586 | PKN2 |
| — | 388121 | TNFAIP8L3 |
| — | — | — |

| Nme2DS2 | | |
|---|---|---|
| offTarget | peak_score | predicted_cleavage_score |
| chr6:-:43748582: 43748613 | 547 | 100 |
| chrX:+:77359550: 77359581 | 44 | 0 |

| gRNA.name | SEQ ID NOS: | gRNAPlusPAM | SEQ ID NOS; | offTarget_sequence |
|---|---|---|---|---|
| Nme2DS2 | 480 | GAATGGCAGGCGGAGG TTGTACTGNNNCCNN | 481 | GAATGGCAGGCGGAGGTT GTACTGGGGGCCAG |
| Nme2DS2 | 480 | GAATGGCAGGCGGAGG TTGTACTGNNNNCCNN | 482 | AAACGGAAGC CGCACGTCTC ACTAGTACCC TC |

TABLE 2-continued

| GUIDE-seq Data | | |
| --- | --- | --- |

| SEQ ID NO: | guideAlignment2OffTarget | offTargetStrand | mismatch.distance2PAM |
| --- | --- | --- | --- |
| | ...................... | - | — |
| 483 | A..C..A..C..C.C..CTC...A | + | 24, 21, 18, 15, 12, 10, 7, 6, 5, 1 |

| n.PAM.mismatch | n.guide.mismatch | PAM.sequence |
| --- | --- | --- |
| 0 | 0 | GGGGCCAG |
| 0 | 10 | GTACCCTC |

| offTarget_Start | offTarget_End | chromosome |
| --- | --- | --- |
| 43748582 | 43748613 | chr6 |
| 77359550 | 77359581 | chrX |

| inExon | entrez_id | symbol |
| --- | --- | --- |
| TRUE | 7422 | VEGFA |
| — | — | — |

| Nme2DS4 | | |
| --- | --- | --- |

| offTarget | peak_score | gRNA.name |
| --- | --- | --- |
| chr6:-:43748843: 43748874 | 66 | c_DeCas9_human_TS14 |

| gRNAPlusPAM | |
| --- | --- |

| SEQ ID NO: 486 | GTGAGCAGGCACCTGTGCCAACATNNNNCCNN |
| --- | --- |

| | offTarget_sequence | guideAlignment2Off Target |
| --- | --- | --- |
| SEQ ID NO: 487 | GTGAGCAGGCACCTGTGCCAACATGGGCCCGC | ................... ...... |

| offTargetStrand | predicted_cleavage_score | mismatch.distance2PAM |
| --- | --- | --- |
| — | 100 | — |

| n.PAM.mismatch | n.guide.mismatch | | PAM.sequence |
| --- | --- | --- | --- |
| 0 | 0 | SEQ ID NO: 488 | GGGCCCGC |

| offTarget_Start | offTarget_End | chromosome |
| --- | --- | --- |
| 43748843 | 43748874 | chr6 |

| inExon | entrez_id | symbol |
| --- | --- | --- |
| — | 7422 | VEGFA |

| Nme2DS6 | | |
| --- | --- | --- |

| offTarget | peak_score | predicted_cleavage_score |
| --- | --- | --- |
| chr6:-:43742018: 43742049 | 483 | 100 |
| chrX:-:77359465: 77359496 | 12 | 0 |

| gRNA.name | gRNAPlusPAM | |
| --- | --- | --- |
| d_DeCas9_human_TS16 | SEQ ID NO: 489 | GCATGGGCAGGGGCTGGGGTGCAC NNNNCCNN |
| d_DeCas9_human_TS16 | SEQ ID NO: 489 | GCATGGGCAGGGGCTGGGGTGCAC NNNNC |

TABLE 2-continued

| GUIDE-seq Data | | |
|---|---|---|
| offTarget_sequence | guideAlignment2OffTarget | offTargetStrand |
| SEQ ID NO: 490 GCATGGGCA GGGGCTGGG GTGCACAGG CCCAG | ........................ | — |
| SEQ ID NO: 491 GCAGGAAGC GTCGCCGGG GGGCCCACA AGGGT | SEQ ID NO: 492 ...G.AAGC.TC ..C....G..C. | 21,19,18,17,16,14,13,10,5,2 |

| n.PAM.mismatch | PAM.sequence | PAM.sequence |
|---|---|---|
| 0 | SEQ ID NO: 493 AGGCCCAG | SEQ ID NO: 499 AATCCCTT |
| 10 | SEQ ID NO: 494 ACAAGGGT | SEQ ID NO: 500 ACTCCCTC |

| offTarget_Start | offTarget_End | chromosome |
|---|---|---|
| 43742018 | 43742049 | chr6 |
| 77359465 | 77359496 | chrX |

| inExon | entrez_id | symbol |
|---|---|---|
| — | 7422 | VEGFA |
| — | — | VEGFA |

| Rosa26 | | |
|---|---|---|
| offTarget | peak_score | predicted_cleavage_score |
| chr6:- :113076072:113076103 | 1175 | 100 |
| chr1 1:- :73171296:73171327 | 24 | 1.4 |

| gRNA.name | gRNAPlusPAM | |
|---|---|---|
| Nme2Rosa | SEQ ID NO: 495 | TGAGGACCGCCCTGGGCCTGGGAGNNNNCC NN |
| Nme2Rosa | SEQ ID NO: 495 | TGAGGACCGCCCTGGGCCTGGGAGNNNNCC NN |

| offTarget_sequence | guideAlignment2OffTarget | offTargetStrand |
|---|---|---|
| SEQ ID NO: 496 TGAGGACC GCCCTGGG CCTGGGAG AATCCCTT | ........................ | — |
| SEQ ID NO: 497 GAAGGACC ACCCTAGG CCTGGGAG ACTCCCT | SEQ ID NO: 498 GA......A....A.... ...... | — |

| mismatch.distance2PAM | n.PAM.mismatch | n.guide.mismatch |
|---|---|---|
| — | 0 | 0 |
| 24, 23, 16, 11 | 0 | 4 |

| PAM.sequence | offTarget_Start | offTarget_End |
|---|---|---|
| SEQ ID NO: 499 AATCCCTT | 113076072 | 113076103 |
| SEQ ID NO: 500 ACTCCCTC | 73171296 | 73171327 |

TABLE 2-continued

| GUIDE-seq Data | | |
|---|---|---|
| chromosome | inExon | entrez_id |
| chr6 | – | 14910 |
| chr11 | – | 94045 |

| PCSK9 | | |
|---|---|---|
| off-Target | peak_score | gRNA.name |
| chr4:-:106463720:<br>106463751 | 266 | Nme2PCSK9 |

| gRNAPlusPAM | | offTarget_sequence | |
|---|---|---|---|
| SEQ ID<br>NO: 501 | GGCCTGGCTGAT<br>GAGGCCGCACAT<br>NNNNCCNN | SEQ ID<br>NO: 502 | GGCCTGGCTGATGAGGCCGC<br>ACATGTGGCCAC |

| guideAlignment2<br>OffTarget | offTargetStrand | predicted_cleavage_score |
|---|---|---|
| . . . . . . . . . . . .<br>. . . . . . . . . . .<br>mismatch. | – | 100 |

| distance2PAM | n.PAM.mismatch | n.guide.mismatch |
|---|---|---|
| – | 0 | 0 |

| PAM.sequence | offTarget_Start | offTarget_End |
|---|---|---|
| SEQ ID     GTGGCCAC<br>NO: 503 | 106463720 | 106463751 |

| chromosome | inExon | entrez_id |
|---|---|---|
| chr4 | TRUE | 100102 |

For off-target identification, the analysis revealed that the DS2, DS4, and DS6 SpyCas9 sgRNAs appeared to direct editing at 93, 10, and 118 candidate off-target sites, respectively, in the normal range of off-targets when plasmid-based SpyCas9 editing is analyzed by GUIDE-seq (Fu et al., 2014; Tsai et al., 2014). In striking contrast, the DS2, DS4, and DS6$_{Nme}$2Cas9 sgRNAs appeared to direct editing at 1, 0, and 1 off-target sites, respectively. FIG. 14C and Table 2. When compared to the GUIDE-seq read counts for the SpyCas9 off-targets, those of Nme2Cas9 were very low, further suggesting that Nme2Cas9 is highly specific. FIG. 13C cf. FIG. 13D. Nme2Cas9 GUIDE-seq analyses with the TS6, Pcsk9, and Rosa26 yielded similar results (0, 0, and 1 off-target sites, respectively, with a modest read count for the Rosa26-OT1 off-target site). FIG. 13C, FIG. 14D, and Table 2.

Figure 14A:
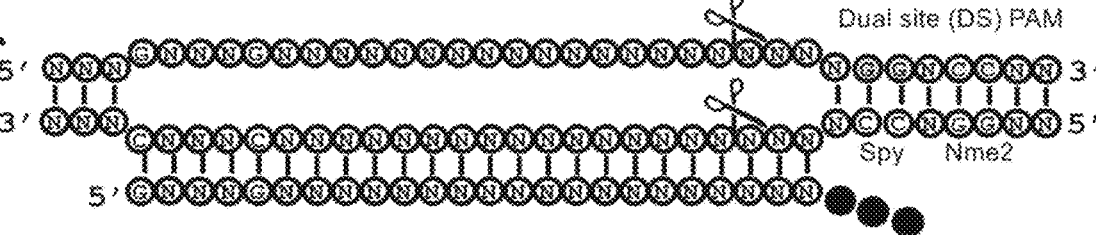
Figure 14B:
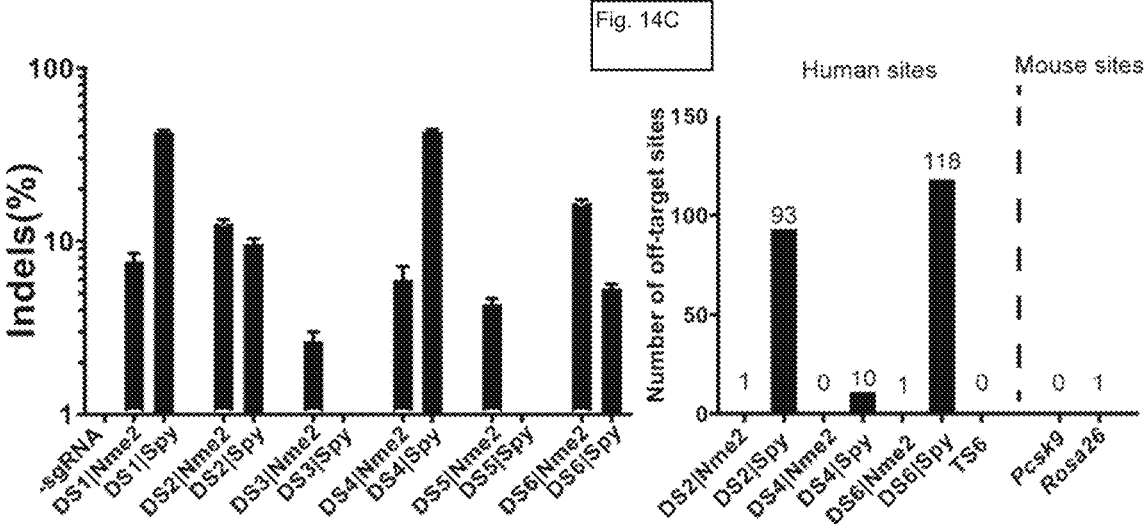
Figure 14D:
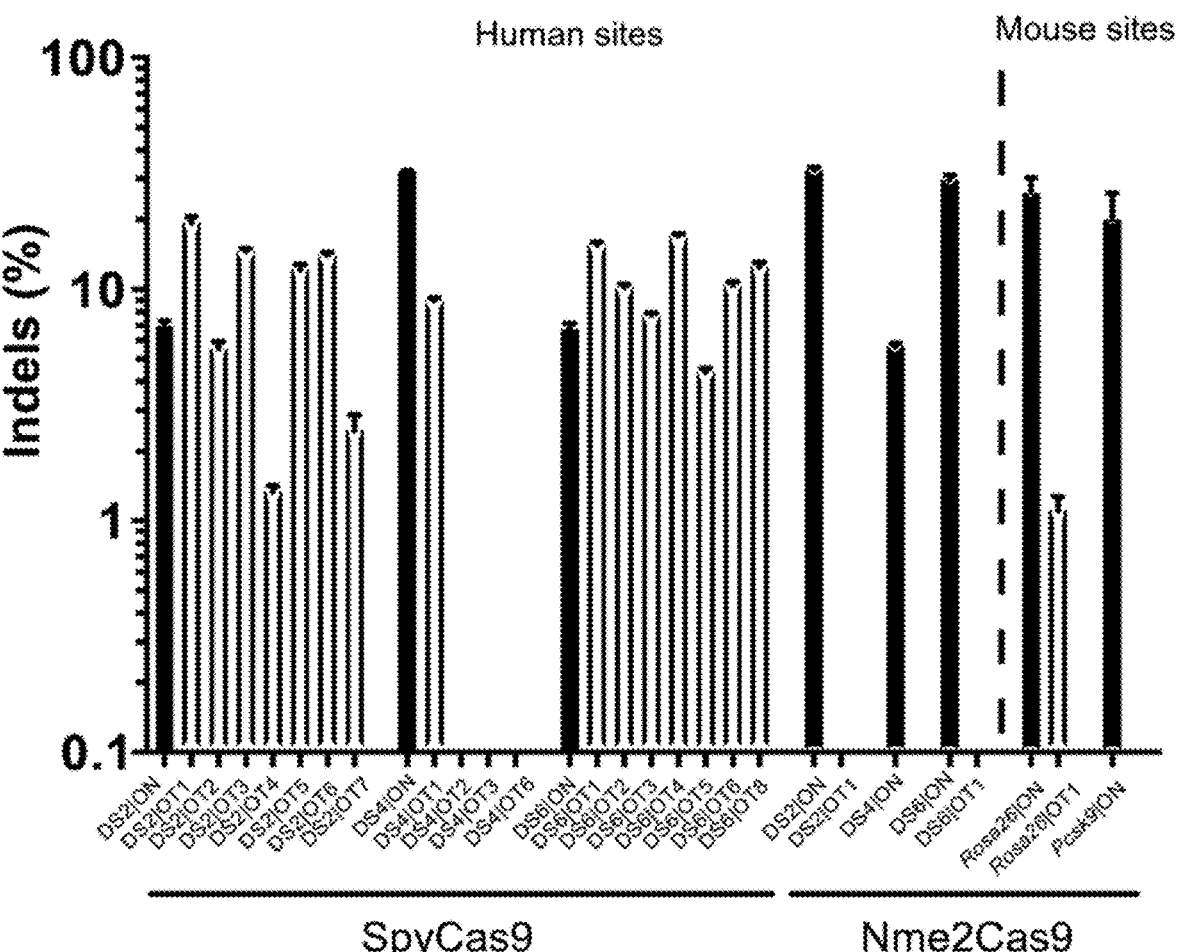

FIG. 14A-E presents exemplary data showing that Nme2Cas9 exhibits little or no detectable off-targeting in mammalian cells. FIG. 14A shows an exemplary schematic depicting dual sites (DSs) targetable by both SpyCas9 and Nme2Cas9 by virtue of their non-overlapping PAMs. The Nme2Cas9 PAM (orange) and SpyCas9 PAM (blue) are highlighted. A 24nt Nme2Cas9 guide sequence is indicated in yellow; the corresponding guide sequence for SpyCas9 would be 4nt shorter at the 5' end. FIG. 14B shows an exemplary Nme2Cas9 and SpyCas9 that both induce indels at DSs. Six DSs in VEGFA (with GN3GN19NGGNCC sequences) were selected for direct comparisons of editing by the two orthologs. Plasmids expressing each Cas9 (with the same promoter, linkers, tags and NLSs) and its cognate guide were transfected into HEK293T cells. Indel efficiencies were determined by TIDE 72 hrs post transfection. Nme2Cas9 editing was detectable at all six sites and was marginally or significantly more efficient than SpyCas9 at two sites (DS2 and DS6, respectively). SpyCas9 edited four out of the six sites (DS1, DS2, DS4 and DS6), with two sites showing significantly higher editing efficiencies than Nme2Cas9 (DS1 and DS4). DS2, DS4 and DS6 were selected for GUIDE-Seq analysis as Nme2Cas9 was equally efficient, less efficient and more efficient than SpyCas9, respectively, at these sites. FIG. 14C shows exemplary Nme2Cas9 genome editing that is highly accurate in human cells. Numbers of off-target sites detected by GUIDE-Seq for each nuclease at individual target sites are shown. In addition to dual sites, we analyzed TS6 (because of its high on-target editing efficiency) and Pcsk9 and Rosa26 sites in mouse Hepa1-6 cells (to measure accuracy in another cell type). FIG. 14D shows an exemplary targeted deep sequencing to detect indels in edited cells confirms the high Nme2Cas9 accuracy indicated by GUIDE-seq. FIG. 14E shows an exemplary sequence for the validated off-target site of the Rosa26 guide, showing the PAM region (underlined), the consensus CC PAM dinucleotide (bold), and three mismatches in the PAM-distal portion of the spacer (red).

To validate the off-target sites detected by GUIDE-seq, a targeted deep sequencing was performed to measure indel formation at the top off-target loci following GUIDE-seq-independent editing (i.e. without co-transfection of the dsODN). While SpyCas9 showed considerable editing at most off-target sites tested and, in some instances, was more efficient than that at the corresponding on-target site, Nme2Cas9 exhibited no detectable indels at the lone DS2 and DS6 candidate off-target sites. See, FIG. 14D. With the Rosa26 sgRNA, Nme2Cas9 induced ~1% editing at the Rosa26-OT1 site in Hepa1-6 cells, compared to ~30% on-target editing. See, FIG. 14D. It is noteworthy that this off-target site has a consensus Nme2Cas9 PAM (ACTCCCT) with only 3 mismatches at the PAM-distal end of the guide-complementary region (i.e. outside of the seed). See, FIG. 14E. These data support and reinforce our GUIDE-seq results indicating a high degree of accuracy for Nme2Cas9 genome editing in mammalian cells.

To further corroborate the above GUIDE-Seq results, CRISPRseek was used to computationally predict potential off-target sites for two active Nme2Cas9 sgRNAs that targeted TS25 and TS47, both of which are also in VEGFA See, FIG. 9A; (Zhu et al., 2014). Three (TS25) or four (TS47) of the most closely matched predicted sites, five with $N_4CC$ PAMs and two with $N_4CA$ PAMs; each had 2-5 mismatches, mostly in their PAM-distal, non-seed regions. See, FIG. 13E. On- vs. off-target editing was compared after Nme2Cas9+sgRNA plasmid transfections into HEK293T cells by targeted amplification of each locus, followed by TIDE analysis. Consistently, no indels could be detected at those off-target sites for either sgRNA by TIDE, while efficient on-target editing was readily detected in DNA from the same populations of cells. Taken together, our data indicate that Nme2Cas9 is a naturally hyper-accurate genome editing platform in mammalian cells.

7. Associated Adenovirus Delivery

The compact size, small PAM, and high fidelity of Nme2Cas9 offer major advantages for in vivo genome editing using Associated Adenovirus (AAV) delivery. To test whether effective Nme2Cas9 genome editing can be achieved via single-AAV delivery, Nme2Cas9 was cloned with its sgRNA and their promoters (Ula and U6, respectively) into an AAV vector backbone. See, FIG. 15A. An all-in-one AAV was prepared with an sgRN-. Nme2Cas9 packaged into a hepatotropic AAV8 capsid to target two genes in the mouse liver: i) Rosa26 (a commonly used safe harbor locus for transgene insertion) (Friedrich and Soriano, 1991) as a negative control; and ii) Pcsk9, a major regulator of circulating cholesterol homeostasis (Rashid et al., 2005), as a phenotypic target.

SauCas9- or Nme1Cas9-induced indels in Pesk9 in the mouse liver results and reduced cholesterol levels providing a useful and easy-to-score in vivo benchmark for new editing platforms (Ran et al., 2015; Ibraheim et al., 2018). The Nme2Cas9 RNA guides were the same as those used above. See, FIG. 9B, FIG. 13D, and FIG. 14A-E. As Rosa26-OT1 was the only Nme2Cas9 off-target site that has been validated in cultured mammalian cells, the Rosa26 guide also provided us with an opportunity to assess on-vs. off-target editing in vivo. See, FIGS. 14D-E). The tail veins of two groups of mice (n=5) were injected with $4 \times 10^{11}$ AAV8.sgRNA.Nme2Cas9 genome copies (GCs) targeting either Pcsk9 or Rosa26. Serum was collected at 0, 14 and 28 days post-injection for cholesterol level measurement. Mice were sacrificed at 28 days post-injection and liver tissues were harvested. See, FIG. 15A. Targeted deep sequencing of each locus revealed ~38% and ~46% indel induction at the Pcsk9 and Rosa26 editing sites, respectively, in the liver. See, FIG. 15B. Because hepatocytes constitute only 65-70% of total cellular content in the adult liver, Nme2Cas9 AAV-induced hepatocyte editing efficiencies with sgPcsk9 and sgRosa were approximately 54-58% and 66-71%, respectively (Racanelli and Rehermann, 2006).

Only 2.25% liver indels overall (~3-3.5% in hepatocytes) were detected at the Rosa26-OT1 off-target site, comparable to the 1% editing that we observed at this site in transfected Hepa1-6 cells. FIG. 15B cf FIG. 14D. At both 14 and 28 days post-injection, Pcsk9 editing was accompanied by a ~44% reduction in serum cholesterol levels, whereas mice treated with the sgRosa26-expressing AAV maintained normal level of cholesterol throughout the study. See, FIG. 15C. The ~44% reduction in serum cholesterol in the Nme2Cas9/sgPcsk9 AAV-treated mice compares well with the ~40% reduction reported with SauCas9 all-in-one AAV when targeting the same gene (Ran et al., 2015).

Figure 16A:
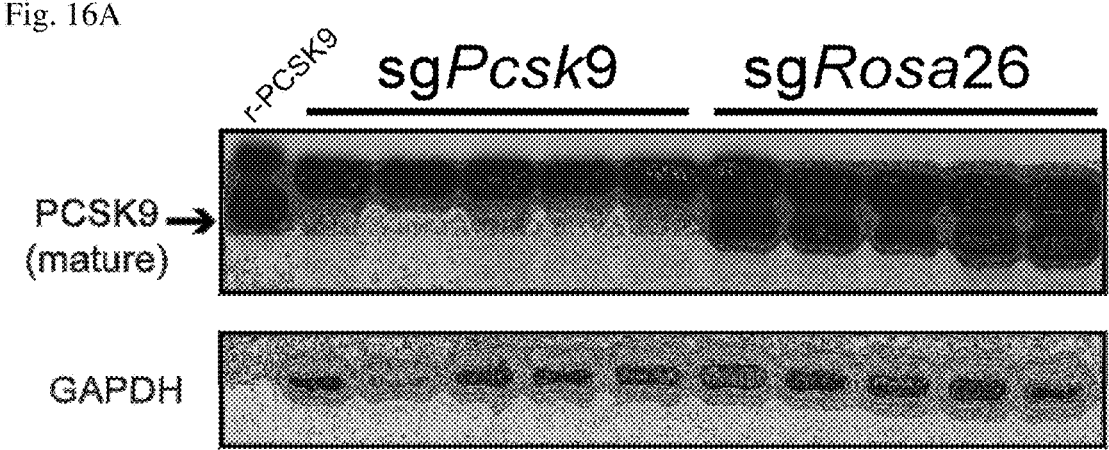
FIG. 16A-B presents exemplary data showing PCSK9 knockdown and liver histology following Nme2Cas9 AAV delivery and editing, related to FIG. 15A-C.
Figure 16B:
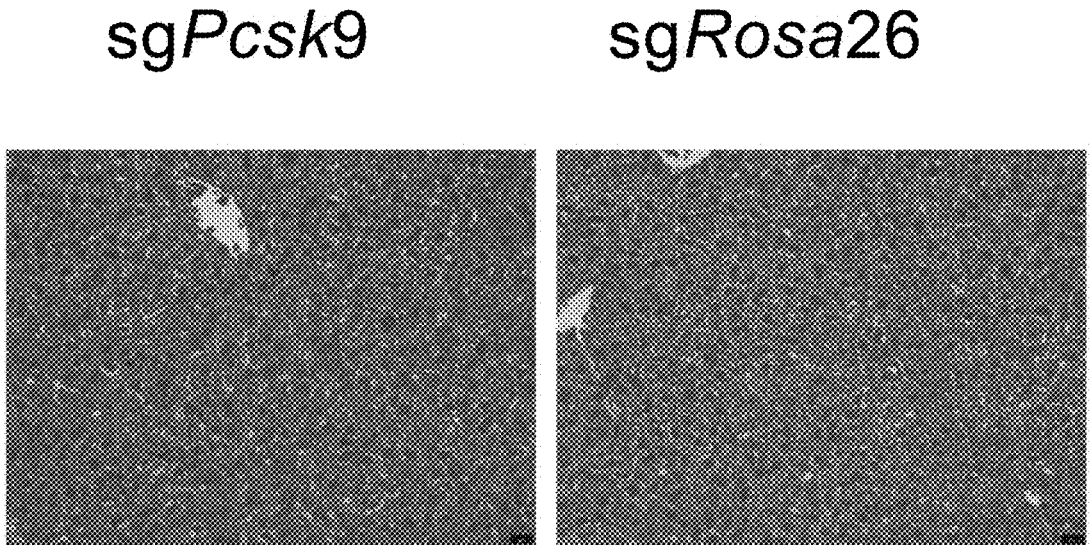

FIG. 15A-C presents exemplary data showing Nme2Cas9 genome editing in vivo via all-in-one AAV delivery. FIG. 15A shows exemplary workflow for delivery of AAV8.sgRNA.Nme2Cas9 to lower cholesterol levels in mice by targeting Pcsk9. Top: schematic of the all-in-one AAV vector expressing Nme2Cas9 and the sgRNA (individual genome elements not to scale). BGH, bovine growth hormone poly (A) site; HA, epitope tag; NLS, nuclear localization sequence; h, human-codon-optimized. Bottom: Timeline for AAV8.sgRNA.Nme2Cas9 tail-vein injections $(4 \times 10^{11} \text{ GCs})$, followed by cholesterol measurements at day 14 and indel, histology and cholesterol analyses at day 28 post-injection. FIG. 15B shows an exemplary TIDE analysis to measure indels in DNA extracted from livers of mice injected with AAV8.Nme2Cas9+sgRNA targeting Pcsk9 and Rosa26 (control) loci. Indel efficiency at the lone off-target site identified by GUIDE-seq for these two sgRNAs (Rosa26|OT1) were also assessed by TIDE. FIG. 15C shows an exemplary reduced serum cholesterol levels in mice injected with the Pcsk9-targeting guide compared to the Rosa26-targeting controls. P values are calculated by unpaired two-tailed t-test. FIG. 16A-B presents exemplary data showing PCSK9 knockdown and liver histology following Nme2Cas9 AAV delivery and editing, related to FIG. 15A-C. FIG. 16A shows exemplary Western blotting using anti-PCSK9 antibody reveals strongly reduced levels of PCSK9 in the livers of mice treated with sgPcsk9, compared to mice treated with sgRosa26. 2 ng of recombinant PCSK9 was used as a mobility standard (left-most lane), and a cross-reacting band in the liver samples is indicated by an asterisk. GAPDH was used as loading control (bottom panel). FIG. 16B shows exemplary H&E staining from livers of mice injected with AAV8.Nme2Cas9+sgRosa26 (left) or AAV8.Nme2Cas9+sgPcsk9 (right) vectors. Scale bars, 25 μm.

Western blotting was performed using an anti-PCSK9 antibody to estimate PCSK9 protein levels in the livers of mice treated with sgPcsk9 and sgRosa26. Liver PCSK9 was below the detection limit in mice treated with sgPcsk9, whereas sgRosa26-treated mice exhibited normal levels of PCSK9. See, FIG. 16A. Hematoxylin and eosin (H&E) staining and histology revealed no signs of toxicity or tissue damage in either group after Nme2Cas9 expression. See, FIG. 16B. These data validate Nme2Cas9 as a highly effective genome editing system in vivo, including when delivered by single-AAV vectors.

AAV vectors have recently been used for the generation of genome-edited mice, without the need for microinjection or electroporation, simply by soaking the zygotes in culture medium containing AAV vector(s), followed by reimplantation into pseudopregnant females (Yoon et al., 2018). Editing was obtained previously with a dual-AAV system in which SpyCas9 and its sgRNA were delivered in separate vectors (Yoon et al., 2018). To test whether Nme2Cas9 could perform accurate and efficient editing in mouse zygotes with an all-in-one AAV delivery system, we targeted Tyrosinase (Tyr). A bi-allelic inactivation of Tyr disrupts melanin production resulting in an albino phenotype (Yokoyama et al., 1990).

An efficient Tyr sgRNA was validated that cleaves the Tyr locus only seventeen (17) bp from the site of the classic albino mutation in Hepa1-6 cells by transient transfections. See, FIG. 17A. Next, C57BL/6NJ zygotes were incubated for 5-6 hours in culture medium containing $3\times10^9$ or $3\times10^8$ GCs of an all-in-one AAV6 vector expressing Nme2Cas9 along with the Tyr sgRNA. After overnight culture in fresh media, those zygotes that advanced to the two-cell stage were transferred to the oviduct of pseudopregnant recipients and allowed to develop to term. See, FIG. 18A. Coat color analysis of pups revealed mice that were albino, chinchilla (indicating a hypomorphic allele of Tyrosinase), or that had variegated coat color composed of albino and chinchilla spots but lacking black pigmentation. See, FIGS. 18B-C. These results suggest a high frequency of biallelic mutations since the presence of a wild-type Tyrosinase allele should render black pigmentation. A total of five pups (10%) were born from the $3\times10^9$ GCs experiment. All of them carried indels; phenotypically, two were albino, one was chinchilla, and two had variegated pigmentation, indicating mosaicism.

From the $3\times10^8$ GCs experiment, four (4) pups (14%) were obtained, two of which died at birth, preventing a coat color or genome analysis. Coat color analysis of the remaining two pups revealed one chinchilla and one mosaic pup. These results indicate that single-AAV delivery of Nme2Cas9 and its guide can be used to generate mutations in mouse zygotes without microinjection or electroporation.

Figures 17A, 17B:
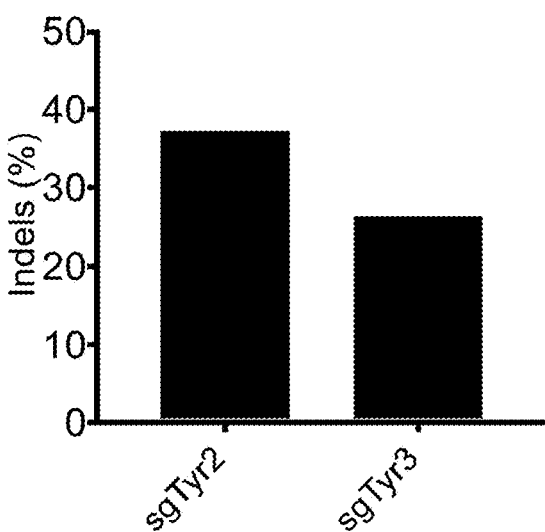
FIG. 17A-C presents exemplary data showing Tyr editing ex vivo in mouse zygotes, related to FIG. 16A-B.
Figure 17C:
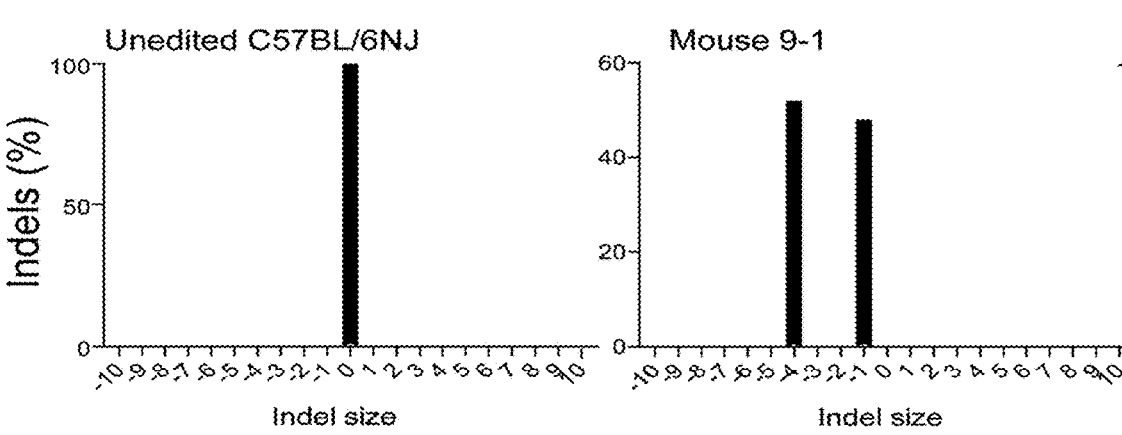
Figure 17C:
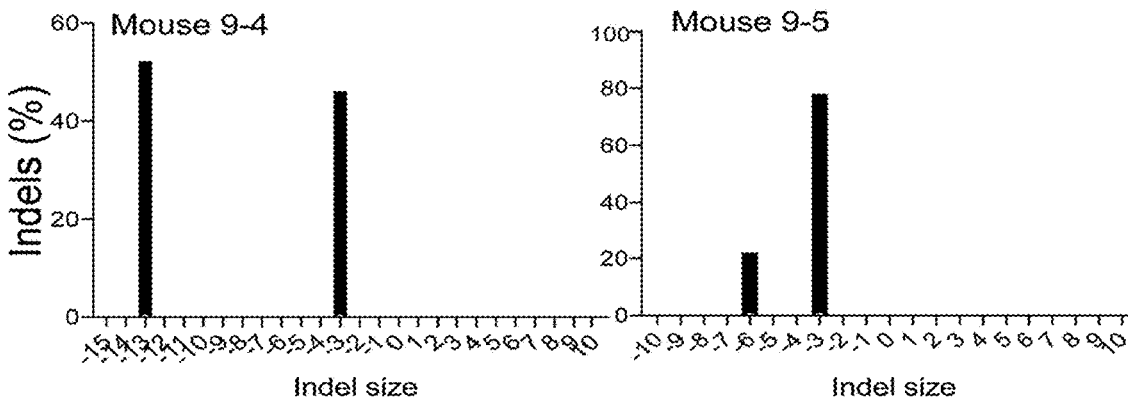
Figure 17C:
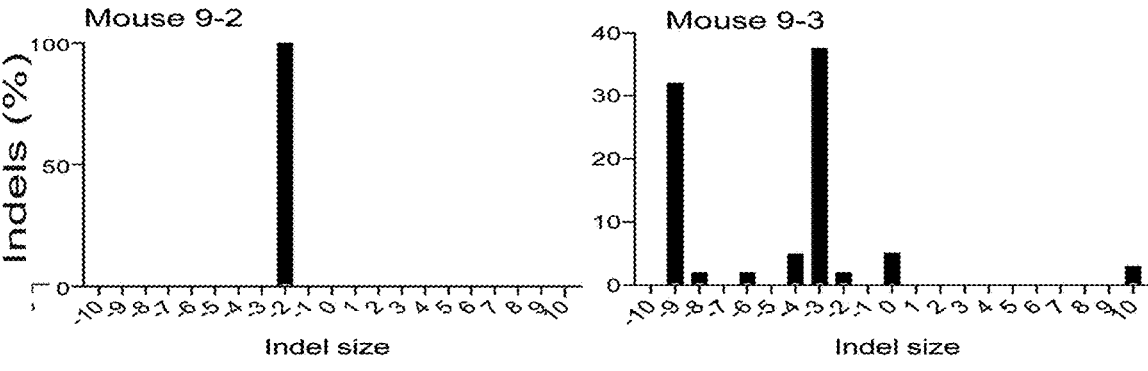
Figure 17C:
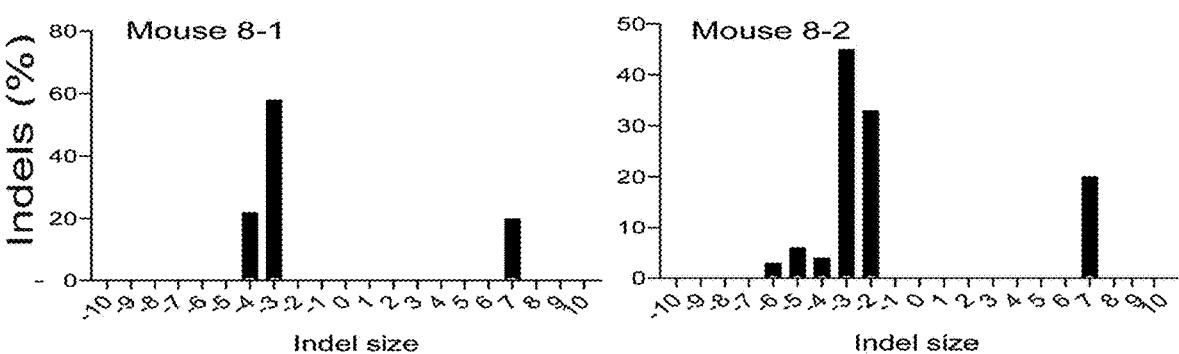

To measure on-target indel formation in the Tyr gene, DNA was isolated from the tails of each mouse, the locus was amplified and upon which a TIDE analysis was performed. All mice had high levels of on-target editing by Nme2Cas9, varying from 84% to 100%. See, FIGS. 17B-C. Most lesions in albino mouse 9-1 were either a 1- or a 4-bp deletion, suggesting either mosaicism or trans-heterozygosity, but albino mouse 9-2 exhibited a uniform 2-bp deletion. See, FIG. 17C. FIG. 17 presents exemplary data showing Tyr editing ex vivo in mouse zygotes, related to FIG. 16A-B. FIG. 17A shows an exemplary two sites in Tyr, each with $N_4CC$ PAMs, were tested for editing in Hepa1-6 cells. The sgTyr2 guide exhibited higher editing efficiency and was selected for further testing. FIG. 17B shows an exemplary seven mice that survived post-natal development, and each exhibited coat color phenotypes as well as on-target editing, as assayed by TIDE. FIG. 17C shows an exemplary Indel spectra from tail DNA of each mouse from (B), as well as an unedited C57BL/6NJ mouse, as indicated by TIDE analysis. Efficiencies of insertions (positive) and deletions (negative) of various sizes are indicated.

Figures 18A, 18B, 18C:
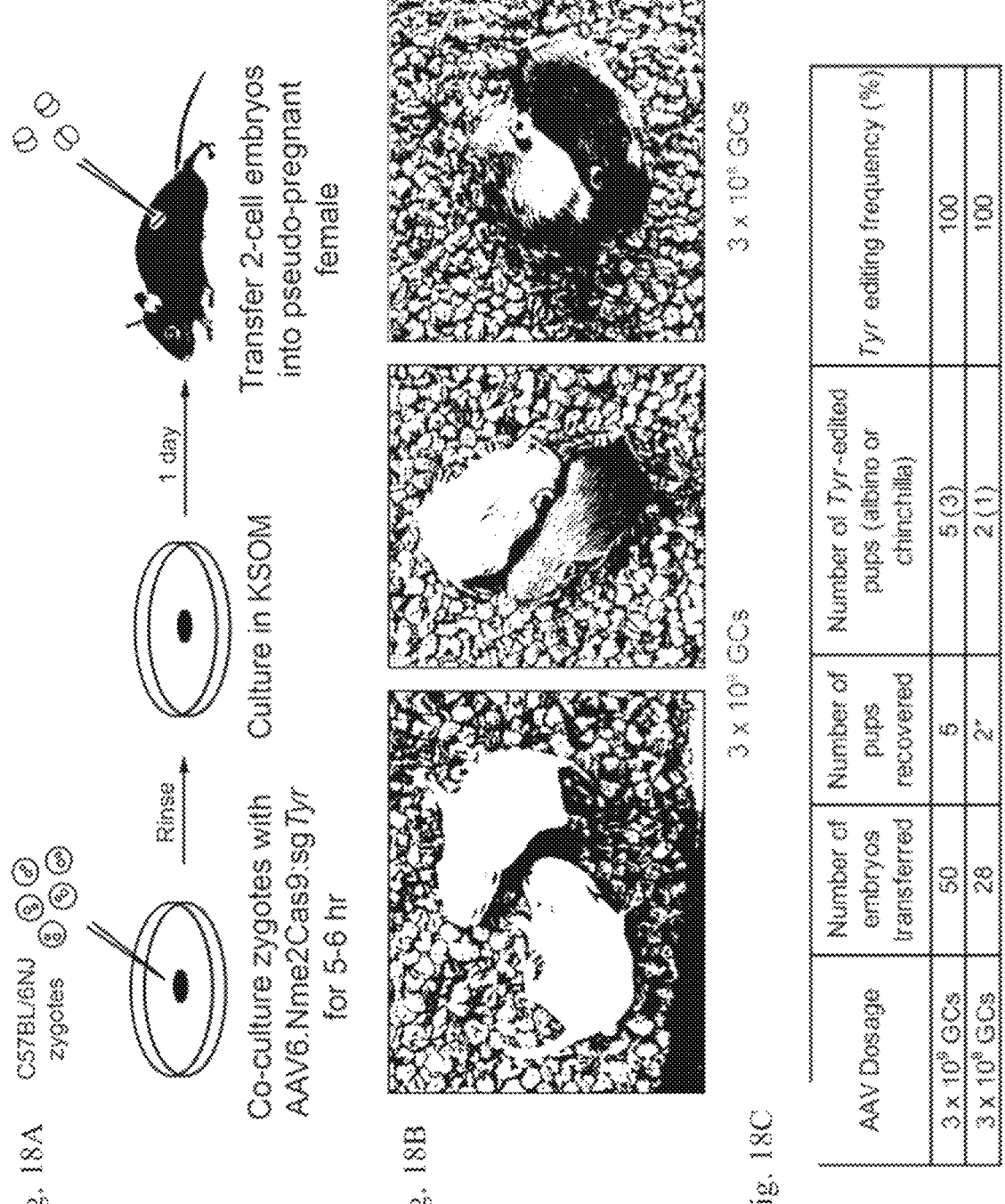
FIG. 18A-C presents exemplary data showing Nme2Cas9 genome editing ex vivo via all-in-one AAV delivery.

FIG. 18A-C presents exemplary data showing Nme2Cas9 genome editing ex vivo via all-in-one AAV delivery. FIG. 18A shows an exemplary workflow for single-AAV Nme2Cas9 editing ex vivo to generate albino C57BL/6NJ mice by targeting the Tyr gene. Zygotes are cultured in KSOM containing AAV6.Nme2Cas9:sgTyr for 5-6 hours, rinsed in M2, and cultured for a day before being transferred to the oviduct of pseudo-pregnant recipients. FIG. 18B shows exemplary albino (left) and chinchilla or variegated (middle) mice generated by $3\times10^9$ GCs, and chinchilla or variegated mice (right) generated by $3\times10^8$ GCs of zygotes with AAV6.Nme2Cas9:sgTyr. FIG. 18C shows an exemplary summary of Nme2Cas9.sgTyr single-AAV ex vivo Tyr editing experiments at two AAV doses.

The data is inconclusive as to whether there was no mosaicism in mouse 9-2, or that additional alleles were absent from mouse 9-1, because only tail samples were sequenced and other tissues could have distinct lesions. Analysis of tail DNA from chinchilla mice revealed the presence of in-frame mutations that are potentially the cause of the chinchilla coat color. The limited mutational complexity suggests that editing occurred early during embryonic development in these mice. These results provide a streamlined route toward mammalian mutagenesis through the application of a single AAV vector, in this case delivering both Nme2Cas9 and its sgRNA.

Figure 19A:
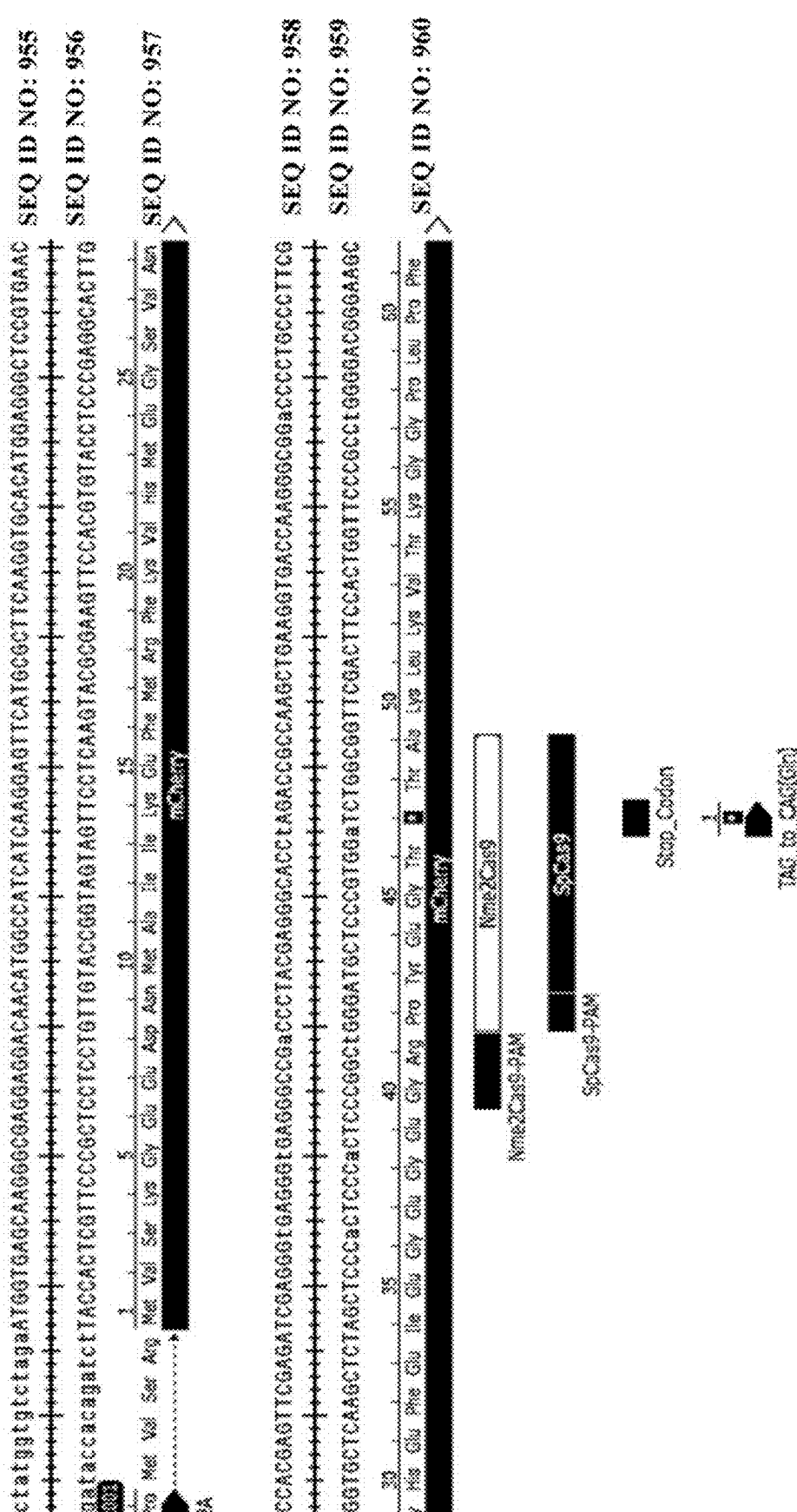
FIG. 19A-C shows an exemplary mCherry reporter assay for nSpCas9-ABEmax and optimized ABEmax-nNme2Cas9 (D16A) activities.
Figure 19C:
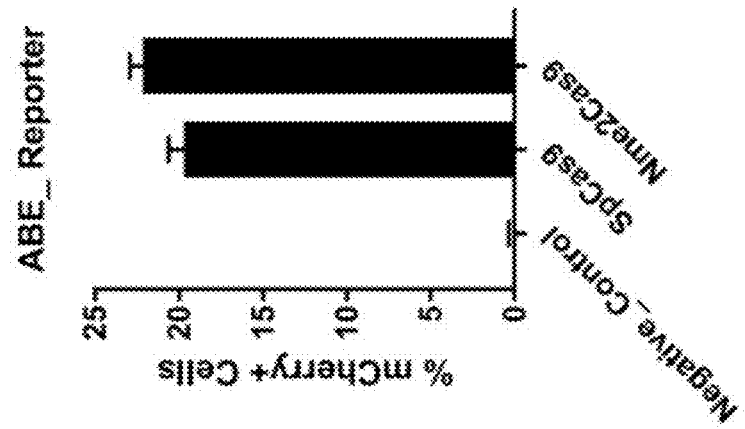
Figure 19B:
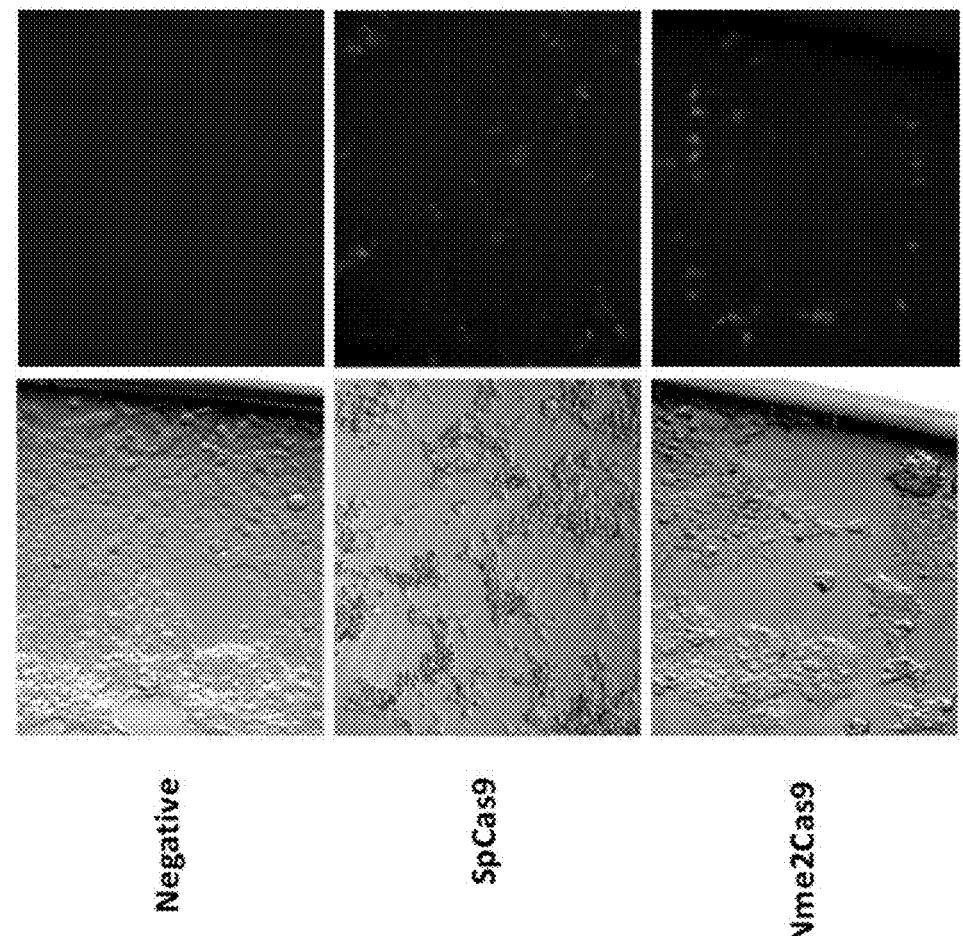

FIG. 19A-B shows an exemplary mCherry reporter assay for nSpCas9-ABEmax and optimized nNme2Cas9-ABEmax activities. FIG. 19A shows exemplary sequence information of ABE-mCherry reporter. There is a TAG stop codon in the mCherry coding region. In the reporter-integrated stable cell line, there is no mCherry signal due to this stop codon. The mCherry signal will be activated if the nSpCas9-ABEmax or optimized nNme2Cas9-ABEmax can convert TAG to CAG, which encodes a glutamine residue. FIG. 19B shows an exemplary mCherry signal is activated due to SpCas9-ABE or Nme2Cas9-ABE activity. Upper panel: negative control (no editing); middle panel: mCherry activation by nSpCas9-ABEmax; bottom panel: mCherry activation by optimized nNme2Cas9-ABEmax. FIG. 19C shows an exemplary FACS quantitation of base editing events in mCherry reporter cells transfected with the SpCas9-ABE or Nme2Cas9-ABE. N=6; error bars represent S.D. Results are from three biological replicates performed in technical duplicates.

Figure 20A:
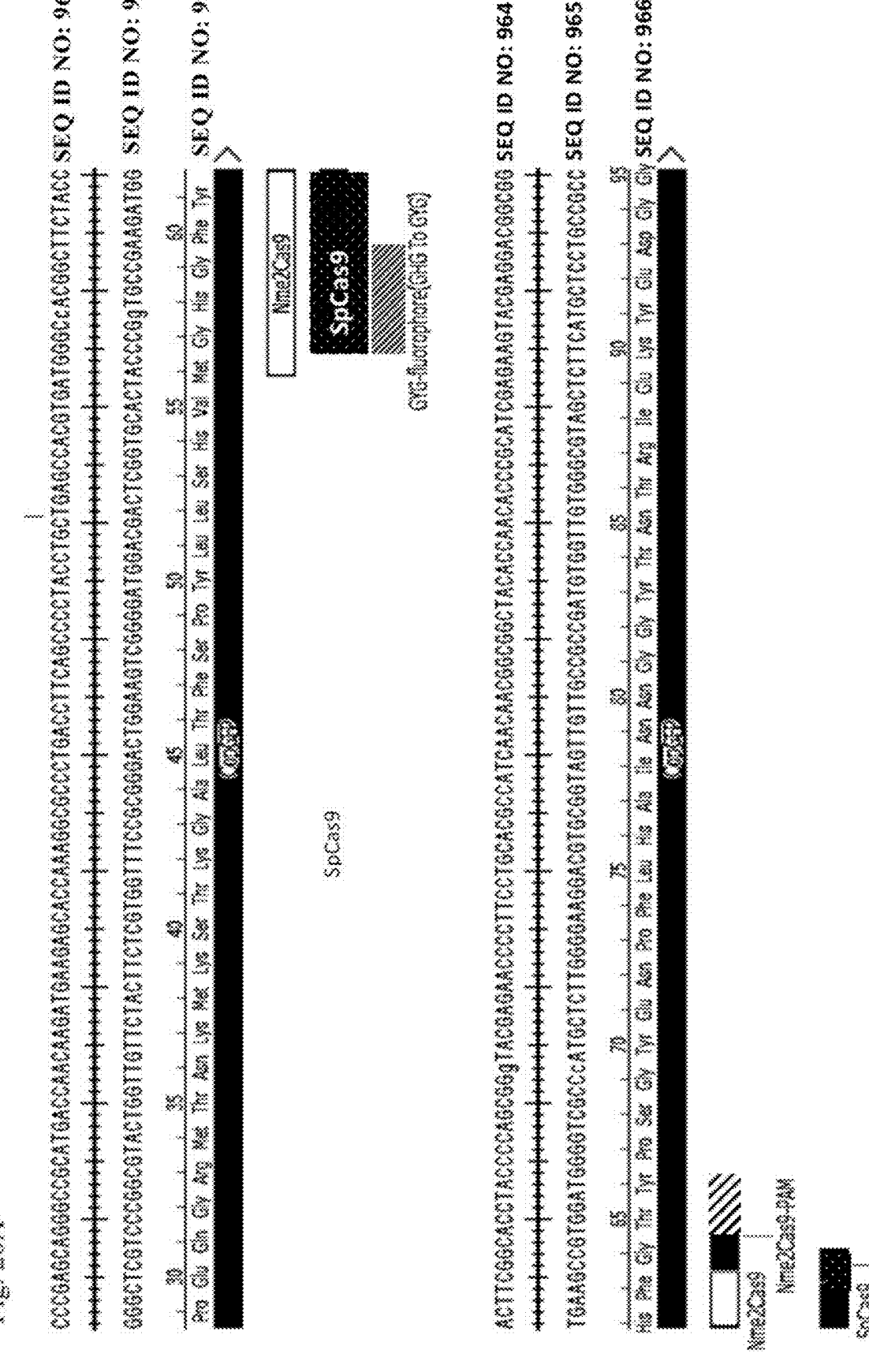
FIG. 20A-C shows an exemplary GFP reporter assay for nSpCas9-CBE4 (Addgene #100802) and CBE4-nNme2Cas9 (D16A)-UGI-UGI (CBE4 was cloned from Addgene #100802) activities.
Figure 20C:
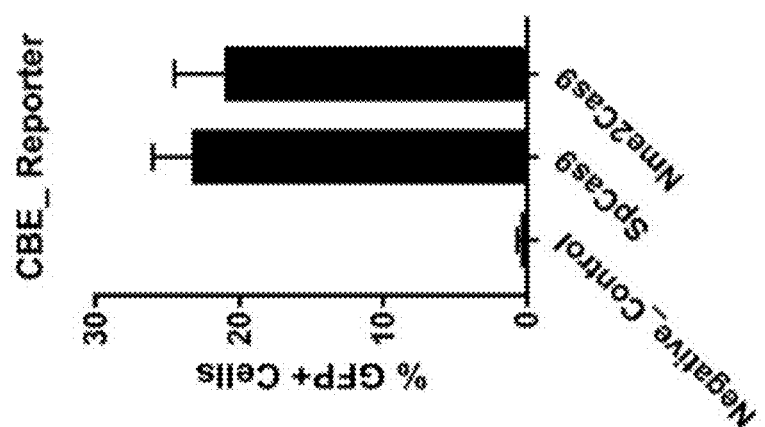
Figure 20B:
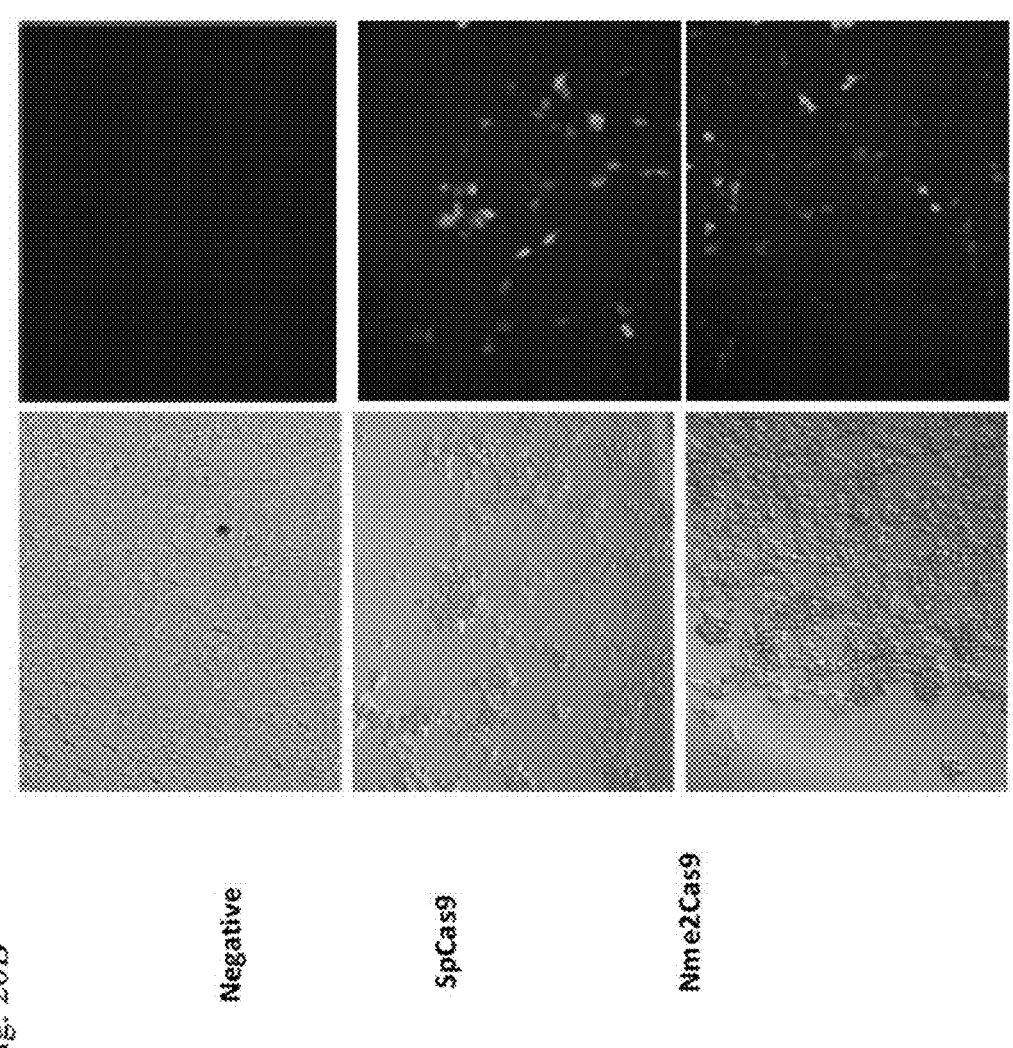

FIG. 20A-C shows an exemplary GFP reporter assay for nSpCas9-CBE4 (Addgene #100802) and nNme2Cas9-CBE4 (same plasmid backbone as Addgene #100802) activities. FIG. 20A shows exemplary sequence information of the CBE-GFP reporter. There is a mutation that converts GYG to GHG in the fluorophore core region of the GFP reporter line. There is no GFP signal due to this mutation. The GFP signal will be activated if the nSpCas9-CBE4 or nNme2Cas9-CBE4 can convert CAC (encoding histidine) to TAC/TAT (encoding tyrosine). FIG. 20B shows an exemplary GFP signal is activated due to nSpCas9-CBE4 or nNme2Cas9-CBE4 activity. Upper panel: negative control (no editing); middle panel: GFP activation by nSpCas9-CBE4; bottom panel: GFP activation by nNme2Cas9-CBE4). FIG. 20C shows an exemplary FACS quantitation of base editing events in GFP reporter cells transfected with nSpCas9-CBE4 or nNme2Cas9-CBE4. N=6; error bars represent S.D. Results are from biological replicates performed in technical duplicates.

Figure 21:
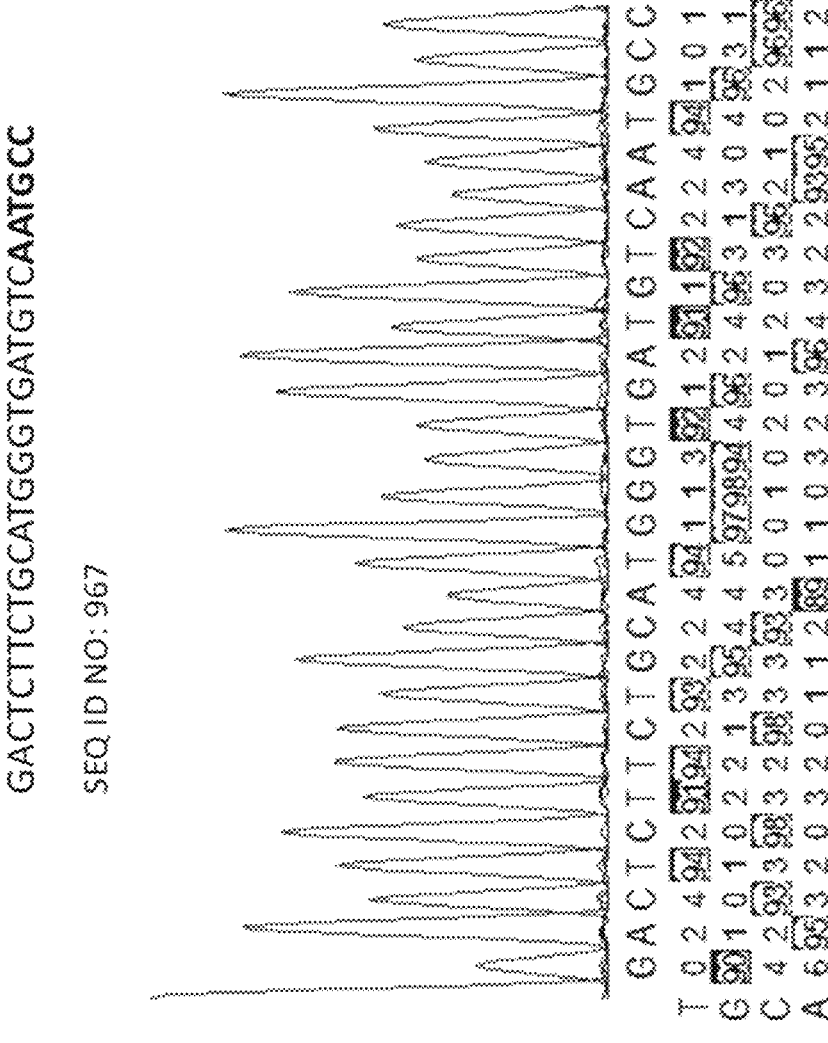
FIG. 21 shows exemplary cytosine editing by CBE4-nNme2Cas9 (D16A)-UGI-UGI. Upper panel shows the KANK3 targeting sequence information (PAM sequences are indicated in bold) of Nme2Cas9 and base editing in the negative control samples. Bottom panel shows the quantification of the substitution rate of each type of base in the CBE4-nNme2Cas9 (D16A)-UGI-UGI editing window of the KANK3 target sequences. Sequence tables show nucleotide frequencies at each position. Frequencies of expected C-to-T conversion are highlighted in black.
Figure 21:
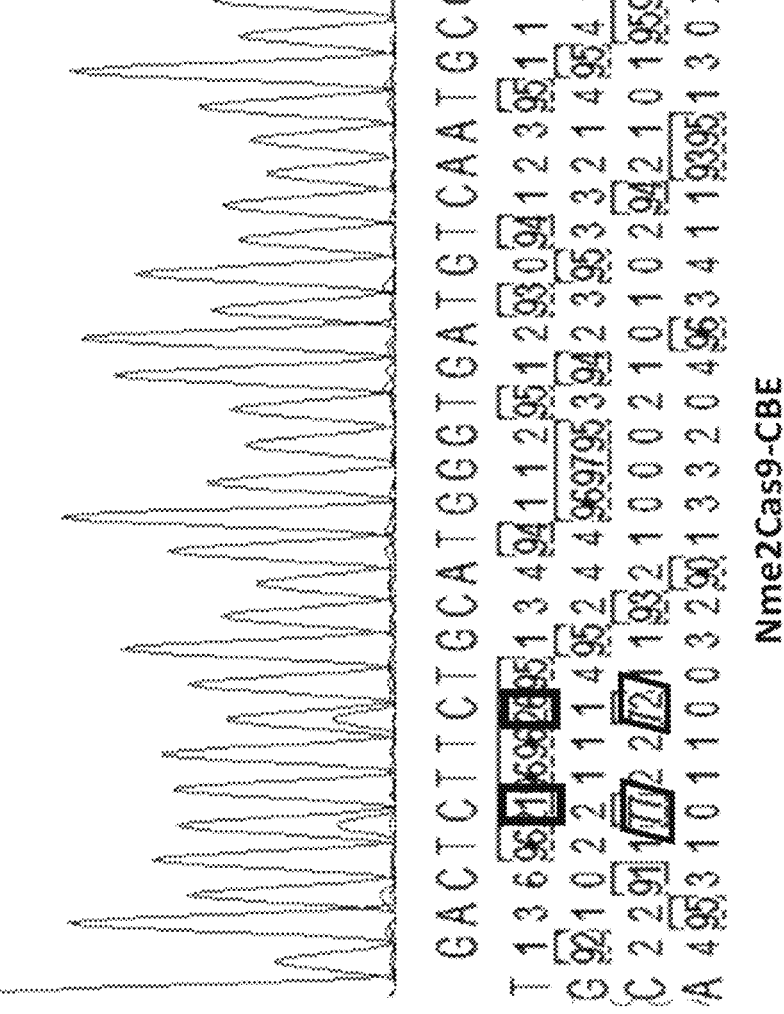
Figure 22:
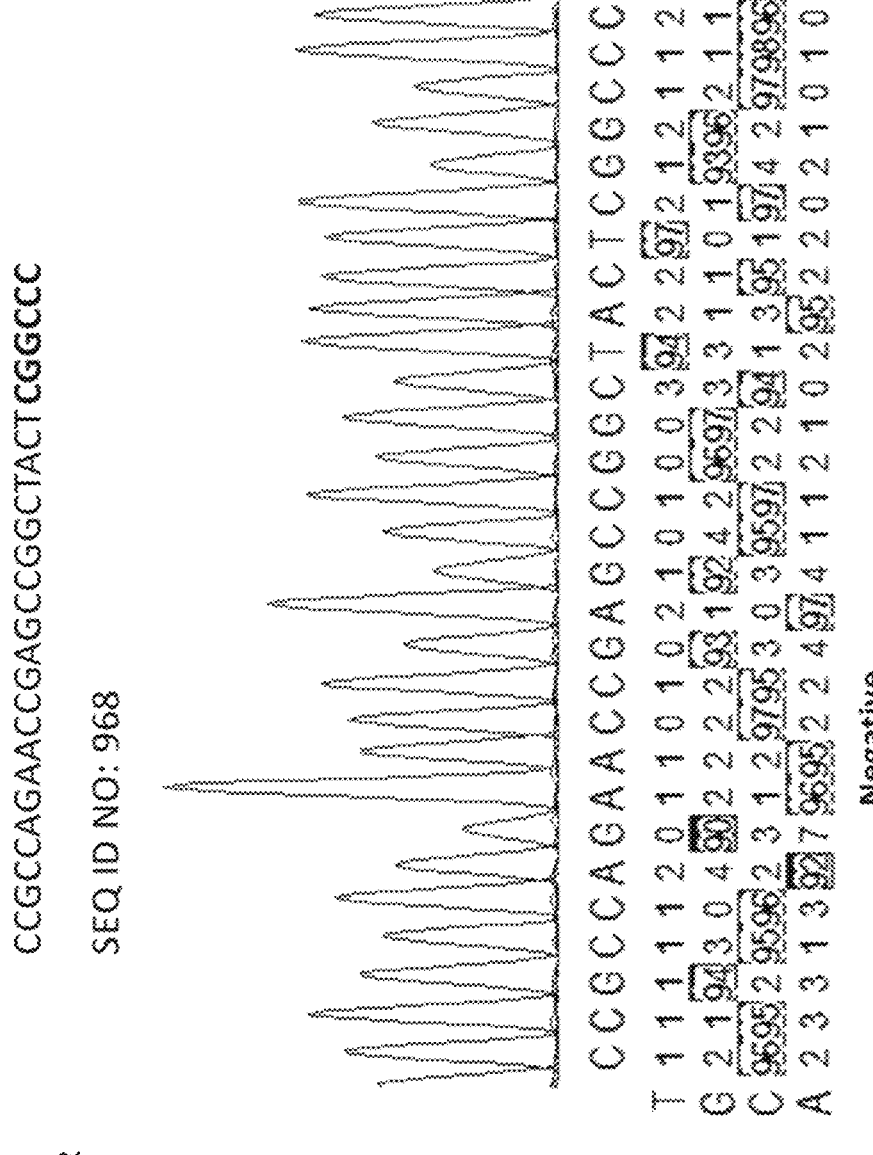
FIG. 22 shows exemplary cytosine and adenine editing by CBE4-nNme2Cas9 (D16A)-UGI-UGI and optimized ABEmax-nNme2Cas9 (D16A), respectively. Upper panel shows the PLXNB2 targeting sequence information (PAM sequences are indicated in bold) of Nme2Cas9 and base editing in the negative control samples. Middle panel shows the quantification of the substitution rate of each type of base in the optimized ABEmax-nNme2Cas9 (D16A) editing windows of the PLXNB2 target sequences. Sequence tables show nucleotide frequencies at each position. Frequencies of expected A-to-G conversion are boxed in thick black lines. Bottom panel shows the quantification of the substitution rate of each type of base in the CBE4-nNme2Cas9 (D16A)-UGI-UGI editing windows of the PLXNB2 target sequences. Sequence tables show nucleotide frequencies at each position. Frequencies of expected C-to-T conversion are boxed in thick black lines.

FIG. 21 shows exemplary cytosine editing by nNme2Cas9-CBE4. Upper panel shows the KANK3 targeting sequence information (PAM sequences are indicated in bold) of Nme2Cas9 and base editing in the negative control samples. Bottom panel shows the quantification of the substitution efficiency of each type of base in the nNme-Cas9-CBE4 editing window of the KANK3 target sequences. Sequence tables show nucleotide frequencies at each position. Frequencies of expected C-to-T conversion are indicated as nucleotides highlighted in bold. FIG. 22 shows exemplary cytosine and adenine editing by nNme2Cas9-CBE4 and nNme2Cas9-ABEmax, respectively. Upper panel shows the PLXNB2 targeting sequence information (PAM sequences are indicated as nucleotides highlighted in bold) of Nme2Cas9 and base editing in the negative control samples. Middle panel shows the quantification of the substitution rate of each type of base in the nNmeCas9-ABEmax editing windows of the PLXNB2 target sequence. Sequence tables show nucleotide frequencies at each position. Frequencies of expected A-to-G conversion are highlighted as nucleotides highlighted in bold. Bottom panel shows the quantification of the substitution efficiency of each type of base in the nNmeCas9-CBE4 editing windows of the PLXNB2 target sequence. Sequence tables show nucleotide frequencies at each position. Frequencies of expected C-to-T conversion are highlighted as nucleotides highlighted in bold.

```
8. Sequences
Alignment of Nme1Cas9 and Nme2Cas9
Non-PID aa differences (teal-underlined); PID aa
differences (yellow-underlined bold); active
site residues (red-bold).
Nme1Cas9 (1-60)
                                      (SEQ ID NO: 652)
MAAFKPNSINYILGLDIGIASVGWAMVEIDEEENPIRLIDLGVRVFERAEVPKTGDSLAM Nme2Cas9 (1-60)
                                      (SEQ ID NO: 883)
MAAFKPNPINYILGLDIGIASVGWAMVEIDEEENPIRLIDLGVRVFERAEVPKTGDSLAM Nme1Cas9 (61-120)
                                      (SEQ ID NO: 653)
ARRLARSVRRLTRRRAHRLLRTRRLLKREGVLQAANFDENGLIKSLPNTPWQLRAAALDR Nme2Cas9 (61-120)
                       (SEQ ID NO: 654)(SEQ ID NO: 653)
ARRLARSVRRLTRRRAHRLLRARRLLKREGVLQAADFDENGLIKSLPNTPWQLRAAALDR Nme1Cas9 (121-180)
                                      (SEQ ID NO: 655)
KLTPLEWSAVLLHLIKHRGYLSQRKNEGETADKELGALLKGVAGNAHALQTGDFRTPA
EL Nme2Cas9 (121-180)
                                      (SEQ ID NO: 656)
KLTPLEWSAVLLHLIKHRGYLSQRKNEGETADKELGALLKGVANNAHALQTGDFRTPA
EL Nme1Cas9 (181-240)
                                      (SEQ ID NO: 657)
ALNKFEKESGHIRNQRSDYSHTFSRKDLQAELILLFEKQKEFGNPHVSGGLKEGIETLLM Nme2Cas9 (181-240)
                                      (SEQ ID NO: 658)
ALNKFEKESGHIRNQRGDYSHTFSRKDLQAELILLFEKQKEFGNPHVSGGLKEGIETLLM Nme1Cas9 (241-300)
                                      (SEQ ID NO: 659)
TQRPALSGDAVQKMLGHCTFEPAEPKAAKNTYTAERFIWLTKLNNLRILEQGSERPLTDT Nme2Cas9 (241-300)
                                      (SEQ ID NO: 660)
TQRPALSGDAVQKMLGHCTFEPAEPKAAKNTYTAERFIWLTKLNNLRILEQGSERPLTD
T Nme1Cas9 (301-360)
                                      (SEQ ID NO: 661)
ERATLMDEPYRKSKLTYAQARKLLGLEDTAFFKGLRYGKDNAEASTLMEMKAYHAISR
AL Nme2Cas9 (301-360)
                                      (SEQ ID NO: 662)
ERATLMDEPYRKSKLTYAQARKLLGLEDTAFFKGLRYGKDNAEASTLMEMKAYHAISRAL Nme1Cas9 (361-420)
                                      (SEQ ID NO: 663)
EKEGLKDKKSPLNLSPELQDEIGTAFSLFKTDEDITGRLKDRIQPEILEALLKHISFDKF Nme2Cas9 (361-420)
                                      (SEQ ID NO: 664)
EKEGLKDKKSPLNLSSELQDEIGTAFSLFKTDEDITGRLKDRVQPEILEALLKHISFDKF Nme1Cas9 (421-480)
                                      (SEQ ID NO: 665)
VQISLKALRRIVPLMEQGKRYDEACAEIYGDHYGKKNTEEKIYLPPIPADEIRNPVVLRA Nme2Cas9 (421-480)
```

-continued (SEQ ID NO: 666)
VQISLKALRRIVPLMEQGKRYDEACAEIYGDHYGKKNTEEKIYLPPIPADEIRNPVVLRA Nme1Cas9 (481-540)

(SEQ ID NO: 667)
LSQARKVINGVVRRYGSPARIHIETAREVGKSFKDRKEIEKRQEENRKDREKAAAKFREY

Nme2Cas9 (481-540)

(SEQ ID NO: 668)
LSQARKVINGVVRRYGSPARIHIETAREVGKSFKDRKEIEKRQEENRKDREKAAAKFREY

Nme1Cas9 (541-600)

(SEQ ID NO: 669)
FPNFVGEPKSKDILKLRLYEQQHGKCLYSGKEINLGRLNEKGYVEIDHALPFSRTWDDSF

Nme2Cas9 (541-600)

(SEQ ID NO: 670)
FPNFVGEPKSKDILKLRLYEQQHGKCLYSGKEINLVRLNEKGYVEIDHALPFSRTWDDSF

Nme1Cas9 (601-660)

(SEQ ID NO: 671)
NNKVLVLGSENQNKGNQTPYEYFNGKDNSREWQEFKARVETSRFPRSKKQRILLQKFDED

Nme2Cas9 (601-660)

(SEQ ID NO: 672)
NNKVLVLGSENQNKGNQTPYEYFNGKDNSREWQEFKARVETSRFPRSKKQRILLQKFDED

Nme1Cas9 (661-720)

(SEQ ID NO: 673)
GFKERNLNDTRYVNRFLCQFVADRMRLTGKGKKRVFASNGQITNLLRGFWGLRKVRAEND

Nme2Cas9 (661-720)

(SEQ ID NO: 674)
GFKECNLNDTRYVNRFLCQFVADHILLTGKGKRRVFASNGQITNLLRGFWGLRKVRAEND

Nme1Cas9 (721-780)

(SEQ ID NO: 675)
RHHALDAVVVACSTVAMQQKITRFVRYKEMNAFDGKTIDKETGEVLHQKTHFPQPWEFFA

Nme2Cas9 (721-780)

(SEQ ID NO: 676)
RHHALDAVVVACSTVAMQQKITRFVRYKEMNAFDGKTIDKETGKVLHQKTHFPQPWEFFA

Nme1Cas9 (781-840)

(SEQ ID NO: 677)
QEVMIRVFGKPDGKPEFEEADTLEKLRTLLAEKLSSRPEAVHEYVTPLFVSRAPNRKMSG

Nme2Cas9 (781-840)

(SEQ ID NO: 678)
QEVMIRVFGKPDGKPEFEEADTPEKLRTLLAEKLSSRPEAVHEYVTPLFVSRAPNRKMSG

Nme1Cas9 (841-895)

(SEQ ID NO: 679)
QGHMETVKSAK---RLDEGVSVLRVPLTQLKLKDLEKMVNR--

EREPKLYEALKARLEAH

Nme2Cas9 (841-899)

(SEQ ID NO: 680)
AHM-DTLSSAKRFVKHNNEKISVKRVWLTEIKLADLNMVNYKNGREIE

LYEALKARLEAY

Nme1Cas9 (896-950)

(SEQ ID NO: 681)
KDDPAKAFAE---PFYKYDKAGNRTQQVKAVRVEQVVQKTGVWVRNH--

NGIADNATMVRV

Nme2Cas9 (900-954)

(SEQ ID NO: 682)
GGNAKQAFDPKDNPFYKK---G--

GQLVKAVRVEKTQESGVLLNKKNAYTIADNGDMVRV

Nme1Cas9 (951-1005)

(SEQ ID NO: 683)

DVFEKG-----

DKYYLVPIYSWQVAKGILPDRAVVQGKDEEDWQLIDDSFNFKFSLHPND

Nme2Cas9 (955-1007)

(SEQ ID NO: 684)

DVFCKVDKKGKNQYFIVPIYAWQVAENILPDIDCKG-------YRIDDSYTFC

FSLHKYD

Nme1Cas9 (1006-1063)

(SEQ ID NO: 685)

LVEVIT--KKARMFGYFASCHRGTGNINIRIHDLDHKIGKNGILEG**

IGVKTALSFQKYQI

Nme2Cas9 (1008-1063)

(SEQ ID NO: 686)

LIAFQKDEKSKVEFAYYINCDSSNGRFYLAWHDKGSKEQ----

QFRISTQNLVLIQKYQV

Nme1Cas9 (1064-1082)

(SEQ ID NO: 687)

DELGKEIRPCRLKKRPPVR

Nme2Cas9 (1064-1082)

(SEQ ID NO: 688)

NELGKEIRPCRLKKRPPVR

Alignment of Nme1Cas9 and Nme3Cas9
Non-PID aa differences (teal-underlined); PID aa
differences (yellow-underlined bold); active
site residues (red-bold).
Nme1Cas9 1

(SEQ ID NO: 689)

MAAFKPNSINYILGLDIGIASVGWAMVEIDEEENPIRLIDLGVRVFERAE    50

Nme3Cas9 1

(SEQ ID NO: 690)

MAAFKPNPINYILGLDIGIASVGWAMVEIDEEENPIRLIDLGVRVFERAE    50

Nme1Cas9 51

(SEQ ID NO: 691)

VPKTGDSLAMARRLARSVRRLTRRRAHRLLRTRRLLKREGVLQAANFDEN   100

Nme3Cas9 51

(SEQ ID NO: 692)

VPKTGDSLAMARRLARSVRRLTRRRAHRLLRARRLLKREGVLQAADFDEN   100

Nme1Cas9 101

(SEQ ID NO: 693)

GLIKSLPNTPWQLRAAALDRKLTPLEWSAVLLHLIKHRGYLSQRKNEGET   150

Nme3Cas9 101

(SEQ ID NO: 694)

GLIKSLPNTPWQLRAAALDRKLTPLEWSAVLLHLIKHRGYLSQRKNEGET   150

Nme1Cas9 151

(SEQ ID NO: 695)

ADKELGALLKGVAGNAHALQTGDFRTPAELALNKFEKESGHIRNQRSDYS   200

Nme3Cas9 151

(SEQ ID NO: 696)

ADKELGALLKGVADNAHALQTGDFRTPAELALNKFEKECGHIRNQRGDYS   200

Nme1Cas9 201

(SEQ ID NO: 697)

HTFSRKDLQAELILLFEKQKEFGNPHVSGGLKEGIETLLMTQRPALSGDA   250

Nme3Cas9 201

(SEQ ID NO: 698)

HTFSRKDLQAELNLLFEKQKEFGNPHVSGGLKEGIETLLMTQRPALSGDA   250

Nme1Cas9 251

(SEQ ID NO: 699)

VQKMLGHCTFEPAEPKAAKNTYTAERFIWLTKLNNLRILEQGSERPLTDT   300

-continued

```
Nme3Cas9 251
                                              (SEQ ID NO: 700)
VQKMLGHCTFEPAEPKAAKNTYTAERFIWLTKLNNLRILEQGSERPLTDT  300

Nme1Cas9 301
                                              (SEQ ID NO: 701)
ERATLMDEPYRKSKLTYAQARKLLGLEDTAFFKGLRYGKDNAEASTLMEM  350

Nme3Cas9 301
                                              (SEQ ID NO: 702)
ERATLMDEPYRKSKLTYAQARKLLSLEDTAFFKGLRYGKDNAEASTLMEM  350

Nme1Cas9 351
                                              (SEQ ID NO: 703)
KAYHAISRALEKEGLKDKKSPLNLSPELQDEIGTAFSLFKTDEDITGRLK  400

Nme3Cas9 351
                                              (SEQ ID NO: 704)
KAYHTISRALEKEGLKDKKSPLNLSPELQDEIGTAFSLFKTDEDITGRLK  400

Nme1Cas9 401
                                              (SEQ ID NO: 705)
DRIQPEILEALLKHISFDKFVQISLKALRRIVPLMEQGKRYDEACAEIYG  450

Nme1Cas9 401
                                              (SEQ ID NO: 706)
DRIQPEILEALLKH1SFDKFVQISLKALRRIVPLMEQGKRYDEACAEIYG  450

Nme1Cas9 451
                                              (SEQ ID NO: 707)
DHYGKKNTEEKIYLPPIPADLIRNPVVLRALSQARKVINGVVRRYGSPAR  500

Nme3Cas9 451
                                              (SEQ ID NO: 708)
DHYGKKNTEEKIYLPPIPADEIRNPVVLRALSQARKVINGVVRRYGSPAR  500

Nme1Cas9 501
                                              (SEQ ID NO: 709)
IHIETAREVGKSFKDRKEIEKRQEENRKDREKAAAKFREYFPNEVGEPKS  550

Nme3Cas9 501
                                              (SEQ ID NO: 710)
IHIETAREVGKSFKDRKEIEKRQEENRKDREKAAAKFREYFPNEVGEPKS  550

Nme1Cas9 551
                                              (SEQ ID NO: 711)
KDILKLRLYEQQHGKCLYSGKEINLGRLNEKGYVEIDHALPFSRTWDDSF  600

Nme3Cas9 551
                                              (SEQ ID NO: 712)
KDILKLRLYEQQHGKCLYSGKEINLGRLNEKGYVEIDHALPFSRTWDDSF  600

Nme1Cas9 601
                                              (SEQ ID NO: 713)
NNKVLVLGSENQNKGNQTPYEYFNGKDNSREWQEFKARVETSRFPRSKKQ  650

Nme3Cas9 601
                                              (SEQ ID NO: 714)
NNKVLVLGSENQNKGNQFPYEYENGKDNSREWQEFKARVETSRFPRSKKQ  650

Nme1Cas9 651
                                              (SEQ ID NO: 715)
RILLQKFDEDGEKERNLNDTRYVNRFICQFVADRMRLIGKGKKRVFASNG  700

Nme3Cas9 651
                                              (SEQ ID NO: 716)
RILLQKFDEDGEKERNLNDTRYVNRFLCQFVADRMRLTGKGKKRVFASNG  700

Nme1Cas9 701
                                              (SEQ ID NO: 717)
QITNLLRGFWGLRKVRAENDRHHALDAVVVACSTVAMQQKITREVRYKEM  750

Nme3Cas9 701
                                              (SEQ ID NO: 718)
QITNLLRGFWGLRKVRAENDRHHALDAVVVACSINAMQQKITREVRYKEM  750

Nme1Cas9 751
                                              (SEQ ID NO: 719)
NAFDGKTIDKETGEVLHQKTHFPQPWEFFAQEVMIRVFGKPDGKPEFEEA  800
```

-continued

```
Nme3Cas9  751
                                                        (SEQ ID NO: 720)
NAFDGKTIDKETGEVLHQKTHFPQPWEFFLQEVMIRVFGKPDGKPEFEEA  800

Nme1Cas9  801
                                                        (SEQ ID NO: 721)
DTLEKLRTLLAEKLSSRPEAVHEYVTPLFVSRAPNRKMSGQGHMETVKSA  850

Nme3Cas9  801
                                                        (SEQ ID NO: 722)
DTPEKLRTLLAEKLSSRPEAVHEYVTPLFVSRAPNRKMSGQGHMETVKSA  850

Nme1Cas9  851
                                                        (SEQ ID NO: 723)
KRLDEGVSVLRVPLTQLKLKDLEKMVNREREPKLYEALKARLEAHKDDPA  900

Nme3Cas9  851
                                                        (SEQ ID NO: 724)
KRLDEGVSVLRVPLTQLKLKDLEKMVNREREPKLYEALKARLEAHKDDPA  900

Nme1Cas9  901
                                                        (SEQ ID NO: 725)
KAFAEPFYKYDKAGNRTQQVKAVRVEQVQKTGVWVRNHNGIADNATMVRV  950

Nme3Cas9  901
                                                        (SEQ ID NO. 726)
KAFAEPFYKYDKAGNRTQQVKAVRVEQVQKTGVWVRNFINGIADNATMVRV 950

Nme1Cas9  951
                                                        (SEQ ID NO: 727)
DVFEKGDKYYLVPIYSWQVAKGILPDRAQGKGKDEEDWQLLIDDSFNFKFS 1000

Nme3Cas9  951
                                                        (SEQ ID NO: 728)
DVFEKGDKYYLVPIYSWQVAKGILPDRAVVAYADEEDWTVIDESERFKEV 1000

Nme1Cas9 1001
                                                        (SEQ ID NO: 729)
LHPNDLVEVITKKARMFGYFASCHRGTGNININIRIHDLDHKIGKNGILEGI 1050

Nme3Cas9 1001
                                                        (SEQ H) NO: 884)
LYSNDLIKVQLKKDFSLGYFSGLDRATGAISLREHDLEKSKGKDG-MHRI 1049

Nme1Cas9 1051
                                                        (SEQ ID NO: 730)
GVKTALSEQKYQIDELGKEIRPCRLKKRPPVR                     1082

Nme3Cas9 1050
                                                        (SEQ ID NO: 731)
GVKTALSFQKYQIDEMGKEIRPCRLKKRPPVR                     1081

Plasmid-Expressed Nme2Cas9
SV40 NLS (yellow-BOLD); 3X-HA-Tag (green-(underlined/bold);
cMyc-like NLS (teal-plain); Linker (magenta-bold italics)
and Nme2Cas9 (italics).
                                                        (SEQ ID NO: 732)
MAAFKPNPINYILGLDIGIASVGWAMVEIDEEENPIRLIDLGVRVF

ERAEVPKTGDSLAMARRLARSVRRLTRRRAHRLLRARRLLKREGV

LQAADFDENGLIKSLPNTPWQLRAAALDRKLTPLEWSAVLLHLIK

HRGYLSQRKNEGETADKELGALLKGVANNAHALQTGDFRTPAELA

LNKFEKESGHIRNQRGDYSHTFSRKDLQAELILLFEKQKEFGNPH

VSGGLKEGIETLLMTQRPALSGDAVQKMLGHCTFEPAEPKAAKNT

YTAERFIWLTKLNNLRILEQGSERPLTDTERATLMDEPYRKSKLT

YAQARKLLGLEDTAFFKGLRYGKDNAEASTLMEMKAYHAISRALE

KEGLKDKKSPLNLSSELQDEIGTAFSLFKTDEDITGRLKDRVQPE

ILEALLKHISFDKFVQISLKALRRIVPLMEQGKRYDEACAEIYGD

HYGKKNTEEKIYLPPIPADEIRNPWLRALSQARKVINGWRRYGSP

ARIHIETAREVGKSFKDRKEIEKRQEENRKDREKAAAKFREYFPN
```

-continued

*FVGEPKSKDILKLRLYEQQHGKCLYSGKEINLVRLNEKGYVEIDH*

*ALPFSRTWDDSFNNKVLVLGSENQNKGNQTPYEYFNGKDNSREWQ*

*EFKARVETSRFPRSKKQRILLQKFDEDGFKECNLNDTRYVNRFLC*

*QFVADHILLTGKGKRRVFASNGQITNLLRGFWGLRKVRAENDRHH*

*ALDAVWACSTVAMQQKITRFVRYKEMNAFDGKTIDKETGKVLHQK*

*TIIFPQPWEFFAQEVMIRVFGKPDGKPEFEEADTPEKLRTLLAEK*

*LSSRPEAVHEYVTPLFVSRAPNRKMSGAHKDTLRSAKRFVKHNEK*

*ISVKRVWLTEIKLADLENMVNYKNGREIELYEALKARLEAYGGNA*

*KQAFDPKDNPFYKKGGQLVKAVRVEKTQESGVLLNKKNAYTIADN*

*GDMVRVDVFCKVDKKGKNQYFIVPIYAWQVAENILPDIDCKGYRI*

*DDSYTFCFSLHKYDLIAFQKDEKSKVEFAYYINCDSSNGRFYLAW*

*HDKGSKEQQFRISTQNLVLIQKYQVNELGKEIRPCRLKKRPPVRG

***TGG*PKKKRKVPYDVPDYAGYPYYDVPDYAGSYPYDVPDYAGSAA*

AAPAAKKKKLDFESG*

AAV-expressed Nme2Cas9
SV40 NLS (yellow-BOLD); 3X-HA-Tag (green-(underlined/bold);
Nucleoplasmin-like NLS (red-underline); c-myc NLS (teal-plain);
Linker (magenta-bold italics) and Nme2Cas9 (italics).

(SEQ ID NO: 733)

*MVPKKKRKVEDKRPAATKKAGQAKKKKMAAFKPNPINYILGLDIGI*

*ASVGWAMVEIDEEENPIRLIDLGVRVFERAEVPKTGDSLAMARRL*

*ARSVRRLTRRRAHRLLRARRLLKREGVLQAADFDENGLIKSLPNT*

*PWQLRAAALDRKLTPLEWSAVLLHLIKHRGYLSQRKNEGETADKE*

*LGALLKGVANNAHALQTGDFRTPAELALNKFEKESGHIRNQRGDY*

*SHTFSRKDLQAELILLFEKQKEFGNPHVSGGLKEGIETLLMTQRP*

*ALSGDAVQKMLGHCTFEPAEPKAAKNTYTAERFIWLTKLNNLRIL*

*EQGSERPLTDTERATLMDEPYRKSKLTYAQARKLLGLEDTAFFKG*

*LRYGKDNAEASTLMEMKAYHAISRALEKEGLKDKKSPLNLSSELQ*

*DEIGTAFSLFKTDEDITGRLKDRVQPEILEALLKHISFDKFVQIS*

*LKALRRIVPLMEQGKRYDEACAEIYGDHYGKKNTEEKIYLPPIPA*

*DEIRNPVVLRALSQARKVINGVVRRYGSPARIHIETAREVGKSFK*

*DRKEIEKRQEENRKDREKAAAKFREYFPNFVGEPKSKDILKLRLY*

*EQQHGKCLYSGKEINLVRLNEKGYVEIDHALPFSRTWDDSFNNKV*

*LVLGSENQNKGNQTPYEYFNGKDNSREWQEFKARVETSRFPRSKK*

*QRILLQKFDEDGFKECNLNDTRYVNRFLCQFVADHILLTGKGKRR*

*VFASNGQITNLLRGFWGLRKVRAENDRHHALDAVVVACSTVAMQQ*

*KITRFVRYKEMNAFDGKTIDKETGKVLHQKTHFPQPWEFFAQEVM*

*IRVFGKPDGKPEFEEADTPEKLRTLLAEKLSSRPEAVHEYVTPLF*

*VSRAPNRKMSGAHKDTLRSAKRFVKHNEKISVKRVWLTEIKLADL*

*ENMVNYKNGREIELYEALKARLEAYGGNAKQAFDPKDNPFYKKGG*

*QLVKAVRVEKTQESGVLLNKKNAYTIADNGDMVRVDVFCKVDKKG*

*KNQYFIVPIYAWQVAENILPDIDCKGYRIDDSYTFCFSLHKYDLI*

-continued

*AFQKDEKSKVEFAYYINCDSSNGRFYLAWHDKGSKEQQFRISTQN*

*LVLIQKYQVNELGKEIRPCRLKKRPPVR**ED*KRPAATKKAGQAKKK*

KYPYDVPDYAGYPYDVPDYAGSYPYDVPDYAAA*PAAKKKKLD**

Recombinant Nme2Cas9
SV40 NLS (yellow-BOLD); Nucleoplasmin-like NLS
(red-underline); Linker (magenta-bold
italics) and Nme2Cas9 (italics).

(SEQ ID NO: 734)

PKKKRKVNA*MAAFKPNPINYILGLDIGIASVGWAMVEIDEEENPI*

*RLIDLGVRVFERAEVPKTGDSLAMARRLARSVRRLTRRRAHRLLR*

*ARRLLKREGVLQAADFDENGLIKSLPNTPWQLRAAALDRKLTPLE*

*WSAVLLHLIKHRGYLSQRKNEGETADKELGALLKGVANNAHALQT*

*GDFRTPAELALNKFEKESGHIRNQRGDYSHTFSRKDLQAELILLF*

*EKQKEFGNPHVSGGLKEGIETLLMTQRPALSGDAVQKMLGHCTFE*

*PAEPKAAKNTYTAERFIWLTKLNNLRILEQGSERPLTDTERATLM*

*DEPYRKSKLTYAQARKLLGLEDTAFFKGLRYGKDNAEASTLMEMK*

*AYHAISRALEKEGLKDKKSPLNLSSELQDEIGTAFSLFKTDEDIT*

*GRLKDRVQPEILEALLKHISFDKFVQISLKALRRIVPLMEQGKRY*

*DEACAEIYGDHYGKKNTEEKIYLPPIPADEIRNPVVLRALSQARK*

*VINGVVRRYGSPARIHIETAREVGKSFKDRKEIEKRQEENRKDRE*

*KAAAKFREYFPNFVGEPKSKDILKLRLYEQQHGKCLYSGKEINLV*

*RLNEKGYVEIDHALPFSRTWDDSFNNKVLVLGSENQNKGNQTPYE*

*YFNGKDNSREWQEFKARVETSRFPRSKKQRILLQKFDEDGFKECN*

*LNDTRYVNRFLCQFVADHILLTGKGKRRVFASNGQITNLLRGFWG*

*LRKVRAENDRHHALDAVVVACSTVAMQQKITRFVRYKEMNAFDGK*

*TIDKETGKVLHQKTHFPQPWEFFAQEVMIRVFGKPDGKPEFEEAD*

*TPEKLRTLLAEKLSSRPEAVHEYVTPLFVSRAPNRKMSGAHKDTL*

*RSAKRFVKHNEKISVKRVWLTEIKLADLENMVNYKNGREIELYEA*

*LKARLEAYGGNAKQAFDPKDNPFYKKGGQLVKAVRVEKTQESGVL*

*LNKKNAYTIADNGDMVRVDVFCKVDKKGKNQYFIVPIYAWQVAEN*

*ILPDIDCKGYRIDDSYTFCFSLHKYDLIAFQKDEKSKVEFAYYIN*

*CDSSNGRFYLAWHDKGSKEQQFRISTQNLVLIQKYQVNELGKEIR*

*PCRLKKRPPVR**GGGGSGGGGSGGGGS*PAAKKKKLD*GGGGS*KRPAAT

KKAGQAKKK*

Recombinant Nme2Cas9 for use in mammalian cell RNP delivery:
SV40 NLS (yellow-BOLD); Nucleoplasmin-like NLS
(red-underline); Linker (magenta-bold
italics) and Nme2Cas9 (italics).

(SEQ ID NO: 735)

PKKKRKVNA*MAAFKPNPINYILGLDIGIASVGWAMVEIDEEENPI*

*RLIDLGVRVFERAEVPKTGDSLAMARRLARSVRRLTRRRAHRLLR*

*ARRLLKREGVLQAADFDENGLIKSLPNTPWQLRAAALDRKLTPLE*

*WSAVLLHLIKHRGYLSQRKNEGETADKELGALLKGVANNAHALQT*

*GDFRTPAELALNKFEKESGHIRNQRGDYSHTFSRKDLQAELILLF*

*EKQKEFGNPHVSGGLKEGIETLLMTQRPALSGDAVQKMLGHCTFE*

*PAEPKAAKNTYTAERFIWLTKLNNLRILEQGSERPLTDTERATLM*

-continued

```
DEPYRKSKLTYAQARKLLGLEDTAFFKGLRYGKDNAEASTLMEMK

AYHAISRALEKEGLKDKKSPLNLSSELQDEIGTAFSLFKTDEDIT

GRLKDRVQPEILEALLKHISFDKFVQISLKALRRIVPLMEQGKRY

DEACAEIYGDHYGKKNTEEKIYLPPIPADEIRNPVVLRALSQARK

VINGVVRRYGSPARIHIETAREVGKSFKDRKEIEKRQEENRKDRE

KAAAKFREYFPNFVGEPKSKDILKLRLYEQQHGKCLYSGKEINLV

RLNEKGYVEIDHALPFSRTIFDDSFNNKVLVLGSENQNKGNQTPY

EYFNGKDNSREWQEFKARVETSRFPRSKKQRILLQKFDEDGFKEC

NLNDTRYVNRFLCQFVADHILLTGKGKRRVFASNGQITNLLRGFW

GLRKVRAENDRHHALDAVVVACSTVAMQQKITRFVRYKEMNAFDG

KTIDKETGKVLHQKTHFPQPWEFFAQEVMIRVFGKPDGKPEFEEA

DTPEKLRTLLAEKLSSRPEAVHEYVTPLFVSRAPNRKMSGAHKDT

LRSAKRFVKHNEKISVKRVWLTEIKLADLENMVNYKNGREIELYE

ALKARLEAYGGNAKQAFDPKDNPFYKKGGQLVKAVRVEKTQESGV

LLNKKNAYTIADNGDIVIVRVDVFCKVDKKGKNQYFIVPIYAWQV

AENILPDIDCKGYRIDDSYTFCFSLHKYDLIAFQKDEKSKVEFAY

YINCDSSNGRFYLAWHDKGSKEQQFRISTQNLVLIQKYQVNELGK

EIRPCRLKKRPPVRGGGGSGGGGSGGGGSPAAKKKKLDGGGKRPA

ATKKAGQAKKKK*
```

9. Therapeutic Applications

Although compact Cas9 orthologs have been previously validated for genome editing, including via single-AAV delivery, their longer PAMs have restricted therapeutic development due to target site frequencies that are lower than that of the more widely adopted SpyCas9. In addition, SauCas9 and its KKH variant with relaxed PAM requirements (Kleinstiver et al., 2015) are prone to off-target editing with some sgRNAs (Friedland et al., 2015; Kleinstiver et al., 2015). These limitations are exacerbated with target loci that require editing within a narrow sequence window, or that require precise segmental deletion. We have identified Nme2Cas9 as a compact and highly accurate Cas9 with a less restrictive dinucleotide PAM for genome editing by AAV delivery in vivo. The development of Nme2Cas9 greatly expands the genomic scope of in vivo editing, especially via viral vector delivery. The Nme2Cas9 all-in-one AAV delivery platform established in this study can in principle be used to target as wide a range of sites as SpyCas9 (due to the identical densities of optimal N$_4$CC and NGG PAMs), but without the need to deliver two separate vectors to the same target cells. The availability of a catalytically dead version of Nme2Cas9 (dNme2Cas9) also promises to expand the scope of applications such as CRISPRi, CRISPRa, base editing, and related approaches (Dominguez et al., 2016; Komor et al., 2017). Moreover, Nme2Cas9's hyper-accuracy enables precise editing of target genes, potentially ameliorating safety issues resulting from off-target activities. Perhaps counterintuitively, the higher target site density of Nme2Cas9 (compared to that of Nme1Cas9) does not lead to a relative increase in off-target editing for the former. Similar results have been reported recently with SpyCas9 variants evolved to have shorter PAMs (Hu et al., 2018). Type II-C Cas9 orthologs are generally slower nucleases in vitro than SpyCas9 (Ma et al., 2015; Mir et al., 2018); interestingly, enzymological principles indicate that a reduced apparent k$_{cat}$ (within limits) can improve on-vs. off-target specificity for RNA-guided nucleases (Bisaria et al., 2017).

The discovery of Nme2Cas9 and Nme3Cas9 hinged on unexplored Cas9s that are highly related (outside of the PID) to an ortholog that was previously validated for human genome editing (Esvelt et al., 2013; Hou et al., 2013; Lee et al., 2016; Amrani et al., 2018). The relatedness of Nme2Cas9 and Nme3Cas9 to Nme1Cas9 brought an added benefit, namely that they use the exact same sgRNA scaffold, circumventing the need to identify and validate functional tracrRNA sequences for each. In the context of natural CRISPR immunity, the accelerated evolution of novel PAM specificities could reflect selective pressure to restore targeting of phages and MGEs that have escaped interference through PAM mutations (Deveau et al., 2008; Paez-Espino et al., 2015). Our observation that AcrIIC5$_{Smu}$ inhibits Nme1Cas9 but not Nme2Cas9 suggests a second, non-mutually-exclusive basis for accelerated PID variation, namely evasion of anti-CRISPR inhibition. We also speculate that accelerated variability may not be restricted to PIDs, perhaps resulting from selective pressures to evade anti-CRISPRs that bind other Cas9 domains. Cas9 inhibitors such as AcrIIC1 that bind more conserved regions of Cas9 likely present fewer routes toward mutational escape and therefore exhibit a broader inhibitory spectrum (Harrington et al., 2017a). Whatever the sources of selective pressure driving Acr and Cas9 co-evolution, the availability of validated inhibitors of Nme2Cas9 (e.g. AcrIIC1-4) provides opportunities for additional levels of control over its activities.

The approach used in this study (i.e. searching for rapidly-evolving domains within Cas9) can be implemented elsewhere, especially with bacterial species that are well-sampled at the level of genome sequence. This approach could also be applied to other CRISPR-Cas effector proteins such as Cas12 and Cas13 that have also been developed for genome or transcriptome engineering and other applications. This strategy could be especially compelling with Cas proteins that are closely related to orthologs with proven efficacy in heterologous contexts (e.g. in eukaryotic cells), as was the case for Nme1Cas9. The application of this approach to meningococcal Cas9 orthologs yielded a new genome editing platform, Nme2Cas9, with a unique combination of characteristics (compact size, dinucleotide PAM, hyper-accuracy, single-AAV deliverability, and Acr susceptibility) that promise to accelerate the development of genome editing tools for both general and therapeutic applications.

TABLE 3

The following presents exemplary sequences for plasmids and oligos as disclosed herein.

Exemplary Plasmids

| Plasmid # | Name | Insert description | Back bone | Purpose | Insert Sequence | SEQ ID NO: | |
|---|---|---|---|---|---|---|---|
| 1 | pAE70 | Nme3Cas9 PID on Nme1Cas9 | pMCSG 7 | Bacterial expression of Nme1Cas9 with Nme3Cas9 PID | Seeexamples herein. | | |
| 2 | pAE71 | Nme2Cas9 PID on Nme1Cas9 | pMCSG 7 | Bacterial expression of Nme1Cas9 with Nme2Cas9 PID | Seeexamples herein. | | |
| 3 | Pae113 | Nme2TLR1 | pLKO | Targeting TLR2.0 with Nme2Cas9 | GTCACCTGCCTCGT GGAATACGG | 736 | 504 |
| 4 | pAE114 | Nme2TLR2 | pLKO | Targeting TLR2.0 with Nme2Cas9 | GCACCTGCCTCGTG GAATACGGT | 737 | 505 |
| 5 | pAE115 | Nme2TLR5 | pLKO | Targeting TLR2.0 with Nme2Cas9 | GTTCAGCGTGTCCG GCTTTGGC | 738 | 506 |
| 6 | pAE116 | Nme2TLR11 | pLKO | Targeting TLR2.0 wath Nme2Cas9 | GTGGTGAGCAAGG GCGAGGAGCTG | 739 | 507 |
| 7 | pAE117 | Nme2TLR12 | pLKO | Targeting TLR2.0 with Nme2Cas9 | GGGCGAGGAGCTG TTCACCGGGGT | 740 | 508 |
| 8 | pAE118 | Nme2TLR13 | pLKO | Targeting TLR2.0 with Nme2Cas9 | GTGAACTTGTGGCC GTTTACGTCG | 741 | 509 |
| 9 | pAE119 | Nme2TLR14 | pLKO | Targeting TLR2.0 with Nme2Cas9 | GCGTCCAGCTCGAC CAGGATGGGC | 742 | 510 |
| 10 | pAE120 | Nme2TLR15 | pLKO | Targeting TLR2.0 with Nme2Cas9 | GCGGTGAACAGCT CCTCGCCCTTG | 743 | 511 |
| 11 | pAE121 | Nme2TLR16 | pLKO | Targeting TLR2.0 with Nme2Cas9 | GGGCACCACCCCG GTGAACAGCTC | 744 | 512 |
| 12 | pAE122 | Nme2TLR17 | pLKO | Targeting TLR2.0 with Nme2Cas9 | GGCACCACCCCGGT GAACAGCTCC | 745 | 513 |
| 13 | pAE123 | Nme2TLR18 | pLKO | Targeting TLR2.0 with Nme2Cas9 | GGGATGGGCACCA CCCCGGTGAAC | 746 | 514 |
| 14 | pAE124 | Nme2TLR19 | pLKO | Targeting TLR2.0 with Nme2Cas9 | GCGTGTCCGGCTTT GGCGAGACAA | 747 | 515 |
| 15 | pAE125 | Nme2TLR20 | pLKO | Targeting TLR2.0 with Nme2Cas9 | GTCCGGCTTTGGCG AGACAAATCA | 748 | 516 |
| 16 | pAE126 | Nme2TLR21 | pLKO | Targeting TLR2.0 with Nme2Cas9 | GATCACCTGCCTCG TGGAATACGG | 749 | 517 |

TABLE 3-continued

The following presents exemplary sequences for plasmids and oligos as disclosed herein.

| 17 | pAE149 | Nme2TLR22 | pLKO | Targeting TLR2.0 with Nme2Cas9 | GACGCTGAACTTGT GGCCGTTTAC | 750 | 518 |
| 18 | pAE150 | Nme2TLR23 | pLKO | Targeting TLR2.0 with Nme2Cas9 | GCCAAAGCCGGAC ACGCTGAACTT | 751 | 519 |
| 19 | pAE193 | Nme2TLR13 with23nt spacer | pLKO | Targeting TLR2.0 with Nme2Cas9 | GGAACTTGTGGCCG TTTACGTCG | 752 | 520 |
| 20 | pAE194 | Nme2TLR13 with 22 nt spacer | pLKO | Targeting TLR2.0 with Nme2Cas9 | GAACTTGTGGCCGT TTACGTCG | 753 | 521 |
| 21 | pAE195 | Nme2TLR13 with 21 nt spacer | pLKO | Targeting TLR2.0 with Nme2Cas9 | GACTTGTGGCCGTT TACGTCG | 754 | 522 |
| 22 | pAE196 | Nme2TLR13 with 20nt spacer | pLKO | Targeting TLR2.0 with Nme2Cas9 | GCTTGTGGCCGTTT ACGTCG | 755 | 523 |
| 23 | pAE197 | Nme2TLR13 with 19nt spacer | pLKO | Targeting TLR2.0 with Nme2Cas9 | GTTGTGGCCGTTTA CGTCG | 756 | 524 |
| 24 | pAE213 | Nme2TLR21 with G22 spacer | pLKO | Targeting TLR2.0 with Nme2Cas9 | GTCACCTGCCTCGT GGAATACGG | 757 | 525 |
| 25 | pAE214 | Nme2TLR21 with G21 spacer | pLKO | Targeting TLR2.0 with Nme2Cas9 | GCACCTGCCTCGTG GAATACGG | 758 | 526 |
| 26 | pAE215 | Nme2TLR21 with G20 spacer | pLKO | Targeting TLR2.0 with Nme2Cas9 | GACCTGCCTCGTGG AATACGG | 759 | 527 |
| 27 | pAE216 | Nme2TLR21 with G19 spacer | pLKO | Targeting TLR2.0 with Nme2Cas9 | GCCTGCCTCGTGGA ATACGG | 760 | 528 |
| 28 | pAE90 | Nme2TS1 | pLKO | Targeting AAVS1 with Nme2Cas9 | GGTTCTGGGTACTT TTATCTGTCC | 761 | 529 |
| 29 | pAE93 | Nme2TS4 | pLKO | Targeting AA VS1 with Nme2Cas9 | GTCTGCCTAACAGG AGGTGGGGGT | 762 | |
| 30 | pAE94 | Nme2TS5 | pLKO | Targeting AAVS1 with Nme2Cas9 | GAATATCAGGAGA CTAGGAAGGAG | 763 | |
| 31 | pAE129 | Nme2TS6 | pLKO | Targeting LINC01588 with Nme2Cas9 | GCCTCCCTGCAGGG CTGCTCCC | 764 | |
| 32 | pAE130 | Nme2TS10 | pLKO | Targeting AAVS1 with Nme2Cas9 | GAGCTAGTCTTCTT CCTCCAACCC | 765 | |
| 33 | pAE131 | Nme2TS11 | pLKO | Targeting AAVS1 with Nme2Cas9 | GATCTGTCCCCTCC ACCCCACAGT | 766 | |
| 34 | pAE132 | Nme2TS12 | pLKO | Targeting AAVS1 with Nme2Cas9 | GGCCCAAATGAAA GGAGTGAGAGG | 767 | |
| 35 | pAE133 | Nme2TS13 | pLKO | Targeting AAVS1 with Nme2Cas9 | GCATCCTCTTGCTT TCTTTGCCTG | 768 | |
| 36 | pAE136 | Nme2TS16 | pLKO | Targeting LINC01588 with Nme2Cas9 | GGAGTCGCCAGAG GCCGGTGGTGG | 769 | |
| 37 | pAE137 | Nme2TS17 | pLKO | Targeting LINC01588 with Nme2Cas9 | GCCCAGCGGCCGG ATATCAGCTGC | 770 | |

TABLE 3-continued

The following presents exemplary sequences for plasmids and oligos as disclosed herein.

| 38 | pAE138 | Nme2TS18 | pLKO | Targeting CYBB with Nme2Cas9 | GGAAGGGAACATA TTACTATTGC | 771 |
|----|--------|----------|------|-----------------------------|--------------------------|-----|
| 39 | pAE139 | Nme2TS19 | pLKO | Targeting CYBB with Nme2Cas9 | GTGGAGTGGCCTGC TATCAGCTAC | 772 |
| 40 | pAE140 | Nme2TS20 | pLKO | Targeting CYBB with Nme2Cas9 | GAGGAAGGGAACA TATTACTATTG | 773 |
| 41 | pAE141 | Nme2TS21 | pLKO | Targeting CYBB with Nme2Cas9 | GTGAATTCTCATCA GCTAAAATGC | 774 |
| 42 | pAE144 | Nme2TS25 | pLKO | Targeting VEGFA with Nme2Cas9 | GCTCACTCACCCAC ACAGACACAC | 775 |
| 43 | pAE145 | Nme2TS26 | pLKO | Targeting CFTR with Nme2Cas9 | GGAAGAATTTCATT CTGTTCTCAG | 776 |
| 44 | pAE146 | Nme2TS27 | pLKO | Targeting CFTR with Nme2Cas9 | GCTCAGTTTTCCTG GATTATGCCT | 777 |
| 45 | pAE152 | Mme2TS31 | pLKO | Targeting VEGFA with Nme2Cas9 | GCGTTGGAGCGGG GAGAAGGCCAG | 778 |
| 46 | pAE153 | Nme2TS34 | pLKO | Targeting LINC01588 with Nme2Cas9 | GGGCCGCGGAGAT AGCTGCAGGGC | 779 |
| 47 | pAE154 | Nme2TS35 | pLKO | Targeting LINC01588 with Nme2Cas9 | GCCCACCCGGCGG CGCCTCCCTGC | 780 |
| 48 | pAE155 | Nme2TS36 | pLKO | Targeting UNC01588 with Nme2Cas9 | GCGTGGCAGCTGAT ATCCGGCCGC | 781 |
| 49 | pAE 156 | Nme2TS37 | pLKO | Targeting LINC01588 with Nme2Cas9 | GCCGCGGCGCGAC GTGGAGCCAGC | 782 |
| 50 | pAE157 | Nme2TS38 | pLKO | Targeting LINC01588 with Nme2Cas9 | GTGCTCCCCAGCCC AAACCGCCGC | 783 |
| 51 | pAE159 | Nme2TS41 | pLKO | Targeting AGA with Nme2Cas9 | GTCAGATTGGCTTG CTCGGAATTG | 784 |
| 52 | pAEl 85 | Nme2TS44 | pLKO | Targeting VEGFA with Nme2Cas9 | GCTGGGTGAATGG AGCGAGCAGCG | 785 |
| 53 | pAE186 | Nme2TS45 | pLKO | Targeting VEGFA with Nme2Cas9 | GTCCTGGAGTGACC CCTGGCCTTC | 786 |
| 54 | pAE187 | Nme2TS46 | pLKO | Targeting VEGFA with Nme2Cas9 | GATCCTGGAGTGAC CCCTGGCCTT | 787 |
| 55 | pAE188 | Nme2TS47 | pLKO | Targeting VEGFA with Nme2Cas9 | GTGTGTCCCTCTCC CCACCCGTCC | 788 |
| 56 | pAE189 | Nme2TS48 | pLKO | Targeting VEGFA with Nme2Cas9 | GTTGGAGCGGGGA GAAGGCCAGGG | 789 |
| 57 | pAE 190 | Nme2TS49 | pLKO | Targeting VEGFA with Nme2Cas9 | GCGTTGGAGCGGG GAGAAGGCCAG | 790 |
| 58 | pAE191 | Nme2TS50 | pLKO | Targeting AGA with Nme2Cas9 | GTACCCTCCAATAA TTTGGCTGGC | 791 |

TABLE 3-continued

The following presents exemplary sequences for plasmids and oligos as disclosed herein.

| 59 | pAE192 | Nme2TS51 | pLKO | Targeting AGA with Mme2Cas9 | GATAATTTGGCTGG CAATTCCGAG | 792 |
| 60 | pAE232 | TS64_FancJ1 | pLKO | Targeting FANCJ with Nme2Cas9 | GAAAATTGTGATTT CCAGATCCAC | 793 |
| 61 | pAE233 | TS65_FancJ2 | pLKO | Targeting FANCJ with Nme2Cas9 | GAGCAGAAAAAAT TGTGATTTCC | 794 |
| 62 | pAE200 | Nme2TS58 (Nme2DS1) | pLKO | Targeting DS in VEGFA with Nme2Cas9 | GCAGGGGCCAGGT GTCCTTCTCTG | 795 |
| 63 | pAE201 | Nme2TS59 (Nme2DS2) | pLKO | Targeting DS in VEGFA with Nme2Cas9 | GAATGGCAGGCGG AGGTTGTACTG | 796 |
| 64 | pAE202 | Nme2TS60 (Nme2DS3) | pLKO | Targeting DS in VEGFA with Nme2Cas9 | GAGTGAGAGAGTG AGAGAGAGACA | 797 |
| 65 | pAE203 | Nme2TS61 (Nme2DS4) | pLKO | Targeting DS in VEGFA with Nme2Cas9 | GTGAGCAGGCACC TGTGCCAACAT | 798 |
| 66 | pAE204 | Nme2TS62 (Nme2DS5) | pLKO | Targeting DS in VEGFA with Nme2Cas9 | GCGTGGGGGCTCC GTGCCCCACGC | 799 |
| 67 | pAE205 | Nme2TS63 (Nme2DS6) | pLKO | Targeting DS in VEGFA with Nme2Cas9 | GCATGGGCAGGGG CTGGGGTGCAC | 800 |
| 68 | pAE207 | SpyDS1 | pLKO | Targeting DS in VEGFA with SpyCas9 | GGGCCAGGTGTCCT TCTCTG | 801 |
| 69 | pAE208 | SpyDS2 | pLKO | Targeting DS in VEGFA with SpyCas9 | GGCAGGCGGAGGT TGTACTG | 802 |
| 70 | pAE209 | SpyDS3 | pLKO | Targeting DS in VEGFA with SpyCas9 | GAGAGAGTGAGAG AGAGACA | 803 |
| 71 | pAE210 | SpyDS4 | pLKO | Targeting DS in VEGFA with SpyCas9 | GCAGGCACCTGTGC CAACAT | 804 |
| 72 | pAE211 | SpyDS5 | pLKO | Targeting DS in VEGFA with SpyCas9 | GGGGGCTCCGTGCC CCACGC | 805 |
| 73 | pAE212 | SpyDS6 | pLKO | Targeting DS in VEGFA with SpyCas9 | GGGCAGGGGCTGG GGTGCAC | 806 |
| 74 | pAE169 | hDeCas9 Wt in AAV backbone | AAV | Nme2Cas9 all-in-one AAV expression with sgRNA cassette | See examples herein. | |
| 75 | pAE217 | hDeCas9 wt in pMSCG7 backbone | pMCSG 7 | wildtype Nme2Cas9 for bacterial expression | See examples herein. | |

TABLE 3-continued

The following presents exemplary sequences for plasmids and oligos as disclosed herein.

| 76 | pAE107 | 2xNLS Nme2Cas9 with HA | pCdest | Nme2Cas9 CMV- driven expression plasmid | See examples herein. |
| 77 | pAE127 | hDemonCas9 3XNLS in pMSCG7 | pMSCG 7 | Targeting endogenous loci with Nme2Cas9 | See examples herein. |
| 78 | pAM172 | hNme2Cas9 4X NLS with 3XHA | pCVL | Lentivector containing UCOE, SFFV driven Nme2Cas9 and Puro | See examples herein. |
| 79 | pAM174 | nickase hNme2Cas9 D16A 4X NLS with 3XHA | pCVL | Lentivector containing UCOE, SFFV driven Nme2Cas9 and Puro | See examples herein. |
| 80 | pAM175 | nickase hNme2Cas9 H588A4X NLS with 3XHA | pCVL | Lentivector containing UCOE, SFFV driven Nme2Cas9 and Puro | See examples herein. |
| 81 | pAM177 | dead hNme2Cas9 4X NLS with 3XHA | pCVL | Lentivector containing UCOE, SFFV driven Nme2Cas9 and Puro | See examples herein. |

Exemplary oligonucleotides

| Number | Name | Sequence | Purpose | SEQ ID NO: |
|---|---|---|---|---|
| 1 | AAVS1_T1DE1_FW | TGGCTTAGCACCTCTCCAT | TIDE analysis | 807 575 |
| 2 | LINC01588_TIDE_ FW | AGAGGAGCCTTCTGACTGCT GCAGA | TIDE analysis | 808 576 |
| 3 | AAVS1_TIDE2_FW | TCCGTCTTCCTCCACTCC | TIDE analysis | 809 577 |
| 4 | NTS55_TIDE_FW | TAGAGAACTGGGTAGTGTG | TIDE analysis | 810 578 |
| 5 | VEGF_TIDE3_FW | GTACATGAAGCAACTCCAGT CCCA | TIDE analysis | 811 579 |
| 6 | hCFTR_TIDE1_FW | TGGTGATTATGGGAGAACTG GAGC | TIDE analysis | 812 580 |
| 7 | AGA_TIDE1_FW | GGCATAAGGAAATCGAAGGT C | TIDE analysis | 813 581 |
| 8 | VEGF_TIDE4_FW | ACACGGGCAGCATGGGAATA GTC | TIDE analysis | 814 582 |
| 9 | VEGF_TIDE5_FW | CCTGTGTGGCTTTGCTTTGGT CG | TIDE analysis | 815 583 |
| 10 | VEGF_TIDE6_FW | GGAGGAAGAGTAGCTCGCCG AGG | TIDE analysis | 816 584 |
| 11 | VEGF_TIDE7FW | AGGGAGAGGGAAGTGTGGG GAAGG | TIDE analysis | 817 585 |
| 12 | AAVS1_TIDE1_RV | AGAACTCAGGACCAACTTAT TCTG | TIDE analysis | 818 586 |
| 13 | LINC01588_ TIDE_RV | ATGACAGACACAACCAGAGG GCA | TIDE analysis | 819 587 |
| 14 | AAVS1_TIDE2_RV | TAGGAAGGAGGAGGCCTAAG | TIDE analysis | 820 588 |
| 15 | NTS55_TIDE_RV | CCAATATTGCATGGGATGG | TIDE analysis | 821 589 |

TABLE 3-continued

The following presents exemplary sequences for plasmids and oligos as disclosed herein.

| 16 | VEGFT_IDE3RV | ATCAAATTCCAGCACCGAGC GC | TIDE analysis | 822 | 590 |
|----|--------------|-------------------------|---------------|-----|-----|
| 17 | hCFTR_TIDE1_RV | ACCATTGAGGACGTTTGTCTC AC | TIDE analysis | 823 | 591 |
| 18 | AGA_TIDE1_RV | CATGTCCTCAAGTCAAGAAC AAG | TIDE analysis | 824 | 592 |
| 19 | VEGF_TIDE4_RV | GCTAGGGGAGAGTCCCACTG TCCA | TIDE analysis | 825 | 593 |
| 20 | VEGF_TIDE5_RV | GTAGGGTGTGATGGGAGGCT AAGC | TIDE analysis | 826 | 594 |
| 21 | VEGF_TIDE6_RV | AGACCGAGTGGCAGTGACAG CAAG | TIDE analysis | 827 | 595 |
| 22 | VEGF_T1DE7_RV | GTCTTCCTGCTCTGTGCGCAC GAC | TIDE analysis | 828 | 596 |
| 23 | RandomPAM_FW | TAGCGGCCGCTCATGCGCGG CGCATTACCTTTACNNNNNN NNNNGGAT CCTCTAGAGTCG | Protospacer with randomized PAM | 829 | 597 |
| 24 | RandomPAM_RV | ACAGGAAACAGCTATGACCA TGAAAGCTTGCATGCCTGCA GGTCGACTCTA GAGGATC | Protospacer with randomized PAM | 830 | 598 |
| 25 | DS2_ON_FW1 | ctacacgacgctcttccgatctCCTGGAG CGTGTACGTTGG | Targeted Deep Seq | 831 | 599 |
| 26 | SpyDS2_OT1_FW1 | ctacacgacgctcttccgatctCCTGTGG TCCCAGCTACTTG | Targeted Deep Seq | 832 | 600 |
| 27 | SpyDS2_OT2_FW1 | ctacacgacgctcttccgatctATCTGCG ATGTCCTCGAGG | Targeted Deep Seq | 833 | 601 |
| 28 | SpyDS2_OT3_FW1 | ctacacgacgctcttccgatctTGGTGTG CGCCTCTAACG | Targeted Deep Seq | 834 | 602 |
| 29 | SpyDS2_OT4_FW1 | ctacacgacgctcttccgatctGGAGTCT TGCTTTGTCACTCAGA | Targeted Deep Seq | 835 | 603 |
| 30 | SpyDS2_OT5_FW1 | ctacacgacgctcttccgatctAGCCTAG ACCCAGTCCCAT | Targeted Deep Seq | 836 | 604 |
| 31 | SpyDS2_OT6_FW1 | ctacacgacgctcttccgatctGCTGGGC ATAGTAGTGGACT | Targeted Deep Seq | 837 | 605 |
| 32 | SpyDS2_OT7_FW1 | ctacacgacgctcttccgatctTGGGGAG GCTGAGACACGA | Targeted Deep Seq | 838 | 606 |
| 33 | SpyDS2_OT8_FW1 | ctacacgacgctcttccgatctCTTGGGA GGCTGAGGCAAG | Targeted Deep Seq | 839 | 608 |
| 34 | DS2_ON_RV1 | agacgtgtgctcttccgatctCAGGAGG ATGAGAGCCAGG | Targeted Deep Seq | 840 | 609 |
| 35 | SpyDS2_OT1_RV1 | agacgtgtgctcttccgatctCAGGGTCT CACTCTATCACCCA | Targeted Deep Seq | 841 | 610 |
| 36 | SpyDS2_OT2_RV1 | agacgtgtgctcttccgatctACTGAATG GGTTGAACTTGGC | Targeted Deep Seq | 842 | 612 |
| 37 | SpyDS2_OT3_RV1 | agacgtgtgctcttccgatctGAGACAG AATCTTGCTCTGTCTCC | Targeted Deep Seq | 843 | 613 |
| 38 | SpyDS2_OT4_RV1 | agacgtgtgctcttccgatctTCCCAGCT ACTTGGGAGGC | Targeted Deep Seq | 844 | 612 |
| 39 | SpyDS2_OT5_RV1 | agacgtgtgctcttccgatctCCTGCCCA AATAGGGAAGCAG | Targeted Deep Seq | 845 | 614 |
| 40 | SpyDS2_OT6_RV1 | agacgtgtgctcttccgatctTGGCGCCT TAGTCTCTGCTAC | Targeted Deep Seq | 846 | 615 |

TABLE 3-continued

The following presents exemplary sequences for plasmids and oligos as disclosed herein.

| 41 | SpyDS2_OT7_RV1 | agacgtgtgctcttccgatctGCATGAGA CACAGTTTCACTCTG | Targeted Deep Seq | 847 | 616 |
|---|---|---|---|---|---|
| 42 | SpyDS2_OT8_RV1 | agacgtgtgctcttccgatctGAGAGAGT CTCACTGCGTTGC | Targeted Deep Seq | 848 | 617 |
| 43 | DS4_ON_FW3 | ctacacgacgctcttccgatctTCTCTCA CCCACTGGGCAC | Targeted Deep Seq | 849 | 618 |
| 44 | DS4_ON_RV3 | agacgtgtgctcttccgatctGCTTCCAG ACGAGTGCAGA | Targeted Deep Seq | 850 | 619 |
| 45 | SpyDS4_OT1_FW1 | ctacacgacgctcttccgatctAAGTTTT CAAACCAGAAGAACTACGAC | Targeted Deep Seq | 851 | 620 |
| 46 | SpyDS4_OT2_FW1 | ctacacgacgctcttccgatctCCGGTAT AAGTCCTGGAGCG | Targeted Deep Seq | 852 | 621 |
| 47 | SpyDS4_OT3_FW1 | ctacacgacgctcttccgatctGCCAGGG AGCAATGGCAG | Targeted Deep Seq | 853 | 622 |
| 48 | SpyDS4_OT6_FW1 | ctacacgacgctcttccgatctCCTCGAA TTCCACGGGGTT | Targeted Deep Seq | 854 | 623 |
| 49 | DS16_ON_FW1 | ctacacgacgctcttccgatctGTTGGTG GGAGGGAAGTGAG | Targeted Deep Seq | 855 | 624 |
| 50 | SpyDS6_OT1_FW1 | ctacacgacgctcttccgatctGATGGCG GTTGTAGCGGC | Targeted Deep Seq | 856 | 625 |
| 51 | SpyDS6_OT2_FW1 | ctacacgacgctcttccgatctCACATAA ACCTATGTTTCAGCAGA | Targeted Deep Seq | 857 | 626 |
| 52 | SpyDS6_OT3_FW1 | ctacacgacgctcttccgatctGCTAGTT GGATTGAAGCAGGGT | Targeted Deep Seq | 858 | 627 |
| 53 | SpyDS6_OT4_FW1 | ctacacgacgctcttccgatctTTGAGTG CGGCAGCTTCC | Targeted Deep Seq | 859 | 628 |
| 54 | SpyDS6_OT6_FW1 | CtacacgacgctcttccgatctATAACCC TCCCAGGCAAAGTC | Targeted Deep Seq | 860 | 629 |
| 55 | SpyDS6_OT7_FW1 | ctacacgacgctcttccgatctAGCCTGC ACATCTGAGCTC | Targeted Deep Seq | 861 | 630 |
| 56 | SpyDS6_OT8_FW1 | ctacacgacgctcttccgatctGGAGCAT TGAAGTGCCTGG | Targeted Deep Seq | 862 | 631 |
| 57 | DeDS6_ON_RV1 | agacgtgtgctcttccgatctCAGCCTGG GACCACTGA | Targeted Deep Seq | 863 | 632 |
| 58 | SpyDS6_OT1_RV1 | agacgtgtgctcttccgatctCATCCTCG ACAGTCGCGG | Targeted Deep Seq | 864 | 633 |
| 59 | SpyDS6_OT2_RV1 | agacgtgtgctcttccgatctGACTGATC AAGTAGAATACTCATGGG | Targeted Deep Seq | 865 | 634 |
| 60 | SpyDS6_OT3_RV1 | agacgtgtgctcttccgatctCCCTGCCA GCACTGAAGC | Targeted Deep Seq | 866 | 635 |
| 61 | SpyDS6_OT4_Rv1 | agacgtgtgctcttccgatctGGTTCCTA TCTTTCTAGACCAGGAGT | Targeted Deep Seq | 867 | 636 |
| 62 | SpyDS6_OT6_RV1 | agacgtgtgctcttccgatctAGTGTGGA GGGCTCAGGG | Targeted Deep Seq | 868 | 637 |
| 63 | SpyDS6_OT7_RV1 | agacgtgtgctcttccgatctGATGGGCA GAGGAAGGCAA | Targeted Deep Seq | 869 | 638 |
| 64 | SpyDS6_OT8_RV1 | agacgtgtgctcttccgatctTCACTCTC ATGAGCGTCCCA | Targeted Deep Seq | 870 | 639 |
| 65 | Nme2DS2_OT1_FW1 | ctacacgacgctcttccgatctAAGGTTC CTTGCGGTTCGC | Targeted Deep Seq | 871 | 640 |
| 66 | Nme2DS2_OT1_RV1 | agacgtgtgctcttccgatctCGCTGCCA TTGCTCCCT | Targeted Deep Seq | 872 | 641 |

TABLE 3-continued

The following presents exemplary sequences for plasmids and oligos as disclosed herein.

| 67 | Nme2DS6_OT1_FW1 | ctacacgacgctcttccgatctTCTCGCA CATTCTTCACGTCC | Targeted Deep Seq | 873 | 642 |
| 68 | Nme2DS6_OT1_RV1 | agacgtgtgctcttccgatctAGGAACCT TCCCGACTTAGGG | Targeted Deep Seq | 874 | 643 |
| 69 | Rosa26_ON_FW1 | ctacacgacgctcttccgatctCCCGCCC ATCTTCTAGAAAGAC | Targeted Deep Seq | 875 | 644 |
| 70 | Rosa26_OT1_FW1 | ctacacgacgctcttccgatctTGCCAGG TGAGGGACTGG | Targeted Deep Seq | 876 | 645 |
| 71 | Rosa26_ON_RV1 | agacgtgtgctcttccgatctTCTGGGAG TTCTCTGCTGCC | Targeted Deep Seq | 877 | 646 |
| 72 | Rosa26_OT1_RV1 | agacgtgtgctcttccgatctTGCCCAAC CTTAGCAAGGAG | Targeted Deep Seq | 878 | 647 |
| 73 | pCSK9_ON_FW2 | ctacacgacgctcttccgatcttacct tggagcaacggcg | Targeted Deep Seq | 879 | 648 |
| 74 | PCSK9_ON_RV2 | agacgtgtgctcttccgatctcccagga cgaggatggag | Targeted Deep Seq | 880 | 649 |
| 75 | Tyr_500_FW3 | GATAGTCACTCCAGGGGTTG | TIDE analysis | 881 | 650 |
| 76 | Tyr_500_RV3 | GTGGTGAACCAATCAGTCCT | TIDE analysis | 882 | 651 |

RNP Delivery for Mammalian Genome Editing

For RNP experiments, the Neon electroporation system was used exactly as described (Amrani et al., 2018). Briefly, 40 picomoles of 3×NLS-Nme2Cas9 along with 50 picomoles of T7-transcribed sgRNA was assembled in buffer R and electroporated using 10 µL Neon tips. After electroporation, cells were plated in pre-warmed 24-well plates containing the appropriate culture media without antibiotics. Electroporation parameters (voltage, width, number of pulses) were 1150 V, 20 ms, 2 pulses for HEK293T cells; 1000 V, 50 ms, 1 pulse for K562 cells.

In Vivo AAV8.Nme2Cas9+sgRNA Delivery and Liver Tissue Processing

For the AAV8 vector injections, 8-week-old female C57BL/6NJ mice were injected with $4\times10^{11}$ genome copies per mouse via tail vein, with the sgRNA targeting a validated site in either Pcsk9 or Rosa26. Mice were sacrificed 28 days after vector administration and liver tissues were collected for analysis. Liver tissues were fixed in 4% formalin overnight, embedded in paraffin, sectioned and stained with hematoxylin and eosin (H&E). Blood was drawn from the facial vein at 0, 14 and 28 days post injection, and serum was isolated using a serum separator (BD, Cat. No. 365967) and stored at −80° C. until assay. Serum cholesterol level was measured using the Infinity™ colorimetric endpoint assay (Thermo-Scientific) following the manufacturer's protocol and as previously described (Ibraheim et al., 2018). For the anti-PCSK9 Western blot, 40 µg of protein from tissue or 2 ng of Recombinant Mouse PCSK9 Protein (R&D Systems, 9258-SE-020) were loaded onto a MiniPROTEAN® TGX™ Precast Gel (Bio-Rad). The separated bands were transferred onto a PVDF membrane and blocked with 5% Blocking-Grade Blocker solution (Bio-Rad) for 2 hours at room temperature. Next, the membrane was incubated with rabbit anti-GAPDH (Abcam ab9485, 1:2,000) or goat anti- PCSK9 (R&D Systems AF3985, 1:400) antibodies overnight. Membranes were washed in TBST and incubated with horseradish peroxidase (HRP)-conjugated goat anti-rabbit (Bio-Rad 1706515, 1:4,000), and donkey anti-goat (R&D Systems HAF109, 1:2,000) secondary antibodies for 2 hours at room temperature. The membranes were washed again in TBST and visualized using Clarity™ western ECL substrate (Bio-Rad) using an M35A XOMAT Processor (Kodak).

Ex Vivo AAV6.Nme2Cas9 Delivery in Mouse Zygotes

Zygotes were incubated in 15 µl drops of KSOM (Potassium-Supplemented Simplex Optimized Medium, Millipore, Cat. No. MR-106-D) containing $3\times10^9$ or $3\times10^8$ GCs of AAV6.Nme2Cas9.sgTyr vector for 5-6 h (4 zygotes in each drop). After incubation, zygotes were rinsed in M2 and transferred to fresh KSOM for overnight culture. The next day, the embryos that advanced to 2-cell stage were transferred into the oviduct of pseudopregnant recipients and allowed to develop to term.

Experimental

Example I

Discovery of Cas9 Orthologs with Differentially Diverged PIDs

Nme1Cas9 peptide sequence was used as a query in BLAST searches to find all Cas9 orthologs in *Neisseria meningitidis* species. Orthologs with >80% identity to Nme1Cas9 were selected for the remainder of this study. The PIDs were then aligned with that of Nme1Cas9 (residues 820-1082) using ClustalW2 and those with clusters of mutations in the PID were selected for further analysis. An unrooted phylogenetic tree of NmeCas9 orthologs was constructed using FigTree (http://tree.bio.ed.ac.uk/software/figtree/).

Example II

Cloning, Expression and Purification of Cas9 and Acr Orthologs

Examples of plasmids and oligonucleotides used in this study are listed in Table 3. The PIDs of Nme2Cas9 and Nme3Cas9 were ordered as gBlocks (IDT) to replace the PID of Nme1Cas9 using Gibson Assembly (NEB) in the bacterial expression plasmid pMSCG7 (Zhang et al., 2015), which encodes Nme1Cas9 with a 6×His tag. The construct was transformed into *E. coli*, expressed and purified as previously described (Pawluk et al., 2016). Briefly, Rosetta (DE3) cells containing the respective Cas9 plasmids were grown at 37° C. to an $OD_{600}$ of 0.6 and protein expression was induced by 1 mM IPTG for 16 hr at 18° C. Cells were harvested and lysed by sonication in lysis buffer [50 mM Tris-HCl (pH 7.5), 500 mM NaCl, 5 mM imidazole, 1 mM DTT] supplemented with 1 mg/mL Lysozyme and protease inhibitor cocktail (Sigma). The lysate was then run through a $Ni^{2+}$-NTA agarose column (Qiagen), and the bound protein was eluted with 300 mM imidazole and dialyzed into storage buffer [20 mM HEPES-NaOH (pH 7.5), 250 mM NaCl, 1 mM DTT]. For Acr proteins, 6×His-tagged proteins were expressed in *E. coli* strain BL21 Rosetta (DE3). Cells were grown at 37° C. to an optical density ($OD_{600}$) of 0.6 in a shaking incubator. The bacterial cultures were cooled to 18° C., and protein expression was induced by adding 1 mM IPTG for overnight expression. The next day, cells were harvested and resuspended in lysis buffer supplemented with 1 mg/mL Lysozyme and protease inhibitor cocktail (Sigma) and protein was purified using the same protocol as for Cas9. The 6×His tag was removed by incubation of the resin-bound protein with Tobacco Etch Virus (TEV) protease overnight at 4° C. to isolate untagged Acrs.

Example III

In Vitro PAM Discovery Assay

A dsDNA target library with randomized PAM sequences was generated by overlapping PCR, with the forward primer containing the 10-nt randomized PAM region. The library was gel-purified and subjected to in vitro cleavage reaction by purified Cas9 along with T7-transcribed sgRNAs. 300 nM Cas9: sgRNA complex was used to cleave 300 nM of the target fragment in 1×NEBuffer 3.1 (NEB) at 37° C. for 1 hr. The reaction was then treated with proteinase K at 50° C. for 10 minutes and run on a 4% agarose/1×TAE gel. The cleavage product was excised, eluted, and cloned using a previously described protocol (Zhang et al., 2012), with modifications. Briefly, DNA ends were repaired, non-templated 2'-deoxyadenosine tails were added, and Y-shaped adapters were ligated. After PCR, the product was quantitated with KAPA Library Quantification Kit and sequenced using a NextSeq 500 (Illumina) to obtain 75 nt paired-end reads. Sequences were analyzed with custom scripts and R.

Example IV

Transfections and Mammalian Genome Editing

Human codon-optimized Nme2Cas9 was cloned by Gibson Assembly into the pCDest2 plasmid backbone previously used for Nme1Cas9 and SpyCas9 expression (Pawluk et al., 2016; Amrani et al., 2018). Transfection of HEK293T and HEK293T-TLR2.0 cells was performed as previously described (Amrani et al., 2018). For Hepa1-6 transfections, Lipofectamine LTX was used to transfect 500 ng of all-in-one AAV.sgRNA.Nme2Cas9 plasmid in 24-well plates (~$10^5$ cells/well), using cells that had been cultured 24 hours before transfection. For K562 cells stably expressing Nme2Cas9 delivered via lentivector (see below), 50,000-150,000 cells were electroporated with 500 ng sgRNA plasmid using 10 μL Neon tips. To measure indels in all cells 72 hr after transfections, cells were harvested and genomic DNA was extracted using the DNaesy Blood and Tissue kit (Qiagen). The targeted locus was amplified by PCR, Sanger-sequenced (Genewiz), and analyzed by TIDE (Brinkman et al., 2014) using the Desktop Genetics web-based interface (http://tide.deskgen.com).

Example V

Lentiviral Transduction of K562 Cells to Stably Express Nme2Cas9

K562 cells stably expressing Nme2Cas9 were generated as previously described for Nme1Cas9 (Amrani et al., 2018). For lentivirus production, the lentiviral vector was co-transfected into HEK293T cells along with the packaging plasmids (Addgene 12260 & 12259) in 6-well plates using TransIT-LT1 transfection reagent (Mirus Bio). After 24 hours, culture media was aspirated from the transfected cells and replaced with 1 mL of fresh DMEM. The next day, the supernatant containing the virus was collected and filtered through a 0.45 μm filter. 10 μL of the undiluted supernatant along with 2.5 ug of Polybrene was used to transduce ~106 K562 cells in 6-well plates. The transduced cells were selected using media supplemented with 2.5 pg/mL puromycin.

Example VI

RNP Delivery for Mammalian Genome Editing

For RNP experiments, the Neon electroporation system was used exactly as described (Amrani et al., 2018). Briefly, 40 picomoles of 3×NLS-Nme2Cas9 along with 50 picomoles of T7-transcribed sgRNA was assembled in buffer R and electroporated using 10 μL Neon tips. After electroporation, cells were plated in pre-warmed 24-well plates containing the appropriate culture media without antibiotics. Electroporation parameters (voltage, width, number of pulses) were 1150 V, 20 ms, 2 pulses for HEK293T cells; 1000 V, 50 ms, 1 pulse for K562 cells.

Example VII

GUIDE-Seq

GUIDE-seq experiments were performed as described previously (Tsai et al., 2014), with minor modifications (Bolukbasi et al., 2015a). Briefly, HEK293T cells were transfected with 200 ng of Cas9 plasmid, 200 ng of sgRNA plasmid, and 7.5 pmol of annealed GUIDE-seq oligonucleotides using Polyfect (Qiagen). Alternatively, Hepa1-6 cells were transfected as described above. Genomic DNA was extracted with a DNeasy Blood and Tissue kit (Qiagen) 72 h after transfection according to the manufacturer's protocol. Library preparation and sequencing were performed exactly as described previously (Bolukbasi et al., 2015a). For analysis, all sequences with up to ten mismatches with the target site, as well as a C in the fifth PAM position (N$_4$CN), were considered potential off-target sites. Data were analyzed using the Bioconductor package GUIDEseq version 1.1.17 (Zhu et al., 2017).

Example VIII

Targeted Deep Sequencing and Analysis

We used targeted deep sequencing to confirm the results of GUIDE-seq and to measure indel rates with maximal accuracy. We used two-step PCR amplification to produce DNA fragments for each on- and off-target site. For SpyCas9 editing at DS2 and DS6, we selected the top off-target sites based on GUIDE-seq read counts. For SpyCas9 editing at DS4, fewer candidate off-target sites were identified by GUIDE-seq, and only those with NGG (DS4|OT1, DS4|OT3, DS4|OT6) or NGC (DS4|OT2) PAMs were examined by sequencing. In the first step, we used locus-specific primers bearing universal overhangs with ends complementary to the adapters. In the first step, 2×PCR master mix (NEB) was used to generate fragments bearing the overhangs. In the second step, the purified PCR products were amplified with a universal forward primer and indexed reverse primers. Full-size products (~250 bp) were gel-purified and sequenced on an Illumina MiSeq in paired-end mode. MiSeq data analysis was performed as previously described (Pinello et al., 2016; Ibraheim et al., 2018).

Example IX

Off-Target Analysis Using CRISPRseek

Global off-target predictions for TS25 and TS47 were performed using the Bioconductor package CRISPRseek. Minor changes were made to accommodate characteristics of Nme2Cas9 not shared with SpyCas9. Specifically, we used the following changes to: gRNA.size=24, PAM= "NNNNCC", PAM.size=6, RNA.PAM.pattern= "NNNNCN", and candidate off-target sites with fewer than 6 mismatches were collected. The top potential off-target sites based on the numbers and positions of mismatches were selected. Genomic DNA from cells targeted by each respective sgRNA was used to amplify each candidate off-target locus and then analyzed by TIDE.

Example X

Mouse Strains and Embryo Collection

All animal experiments were conducted under the guidance of the Institutional Animal Care and Use Committee (IACUC) of the University of Massachusetts Medical School. C57BL/6NJ (Stock No. 005304). Mice were obtained from The Jackson Laboratory. All animals were maintained in a 12 h light cycle. The middle of the light cycle of the day when a mating plug was observed was considered embryonic day 0.5 (E0.5) of gestation. Zygotes were collected at E0.5 by tearing the ampulla with forceps and incubation in M2 medium containing hyaluronidase to remove cumulus cells.

Example XI

In Vivo AAV8.Nme2Cas9+sgRNA Delivery and Liver Tissue Processing

For the AAV8 vector injections, 8-week-old female C57BL/6NJ mice were injected with 4×10$^{11}$ genome copies per mouse via tail vein, with the sgRNA targeting a validated site in either Pcsk9 or Rosa26. Mice were sacrificed 28 days after vector administration and liver tissues were collected for analysis. Liver tissues were fixed in 4% formalin overnight, embedded in paraffin, sectioned and stained with hematoxylin and eosin (H&E). Blood was drawn from the facial vein at 0, 14 and 28 days post injection, and serum was isolated using a serum separator (BD, Cat. No. 365967) and stored at −80° C. until assay. Serum cholesterol level was measured using the Infinity™ colorimetric endpoint assay (Thermo-Scientific) following the manufacturer's protocol and as previously described (Ibraheim et al., 2018). For the anti-PCSK9 Western blot, 40 µg of protein from tissue or 2 ng of Recombinant Mouse PCSK9 Protein (R&D Systems, 9258-SE-020) were loaded onto a MiniPROTEAN® TGX™ Precast Gel (Bio-Rad). The separated bands were transferred onto a PVDF membrane and blocked with 5% Blocking-Grade Blocker solution (Bio-Rad) for 2 hours at room temperature. Next, the membrane was incubated with rabbit anti-GAPDH (Abcam ab9485, 1:2,000) or goat anti-PCSK9 (R&D Systems AF3985, 1:400) antibodies overnight. Membranes were washed in TBST and incubated with horseradish peroxidase (HRP)-conjugated goat anti-rabbit (Bio-Rad 1706515, 1:4,000), and donkey anti-goat (R&D Systems HAF109, 1:2,000) secondary antibodies for 2 hours at room temperature. The membranes were washed again in TBST and visualized using Clarity™ western ECL substrate (Bio-Rad) using an M35A XOMAT Processor (Kodak).

Example XII

Ex Vivo AAV6.Nme2Cas9 Delivery in Mouse Zygotes

Zygotes were incubated in 15 µl drops of KSOM (Potassium-Supplemented Simplex Optimized Medium, Millipore, Cat. No. MR-106-D) containing 3×10$^9$ or 3×10$^8$ GCs of AAV6.Nme2Cas9.sgTyr vector for 5-6 h (4 zygotes in each drop). After incubation, zygotes were rinsed in M2 and transferred to fresh KSOM for overnight culture. The next day, the embryos that advanced to 2-cell stage were transferred into the oviduct of pseudopregnant recipients and allowed to develop to term.

References, each of which are herein incorporated by reference in their entirety:

Amrani, N., Gao, X. D., Liu, P., Edraki, A., Mir, A., Ibraheim, R., Gupta, A., Sasaki, K. E., Wu, T., Donohoue, P. D., et al. (2018). NmeCas9 is an intrinsically high-fidelity genome editing platform. BioRxiv, https://doi.org/10.1101/172650.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Bisaria, N., Jarmoskaite, I., and Herschlag, D. (2017). Lessons from Enzyme Kinetics Reveal Specificity Principles for RNA-Guided Nucleases in RNA Interference and CRISPR-Based Genome Editing. Cell Syst. 4, 21-29.

Bolukbasi, M. F., Gupta, A., Oikemus, S., Derr, A. G., Garber, M., Brodsky, M. H., Zhu, L. J., and Wolfe, S. A. (2015a). DNA-binding-domain fusions enhance the targeting range and precision of Cas9. Nat. Methods 12, 1150-1156.

Bolukbasi, M. F., Gupta, A., and Wolfe, S. A. (2015b). Creating and evaluating accurate CRISPR-Cas9 scalpels for genomic surgery. Nat. Methods 13, 41-50.

Brinkman, E. K., Chen, T., Amendola, M., and van Steensel, B. (2014). Easy quantitative assessment of genome editing by sequence trace decomposition. Nucleic Acids Res. 42, e168.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Casini, A., Olivieri, M., Petris, G., Montagna, C., Reginato, G., Maule, G., Lorenzin, F., Prandi, D., Romanel, A., Demichelis, F., et al. (2018). A highly specific SpCas9 variant is identified by in vivo screening in yeast. Nat. Biotechnol. 36, 265-271.

Certo, M. T., Ryu, B. Y., Annis, J. E., Garibov, M., Jarjour, J., Rawlings, D. J., and Scharenberg, A. M. (2011). Tracking genome engineering outcome at individual DNA breakpoints. Nat. Methods 8, 671-676.

Chen, J. S., Dagdas, Y. S., Kleinstiver, B. P., Welch, M. M., Sousa, A. A., Harrington, L. B., Sternberg, S. H., Joung, J. K., Yildiz, A., and Doudna, J. A. (2017). Enhanced proofreading governs CRISPR-Cas9 targeting accuracy. Nature 550, 407-410.

Cho, S. W., Kim, S., Kim, J. M., and Kim, J. S. (2013). Targeted genome engineering in human cells with the Cas9 RNA-guided endonuclease. Nat. Biotechnol. 31, 230-232.

Cho, S. W., Kim, S., Kim, Y., Kweon, J., Kim, H. S., Bae, S., and Kim, J. S. (2014). Analysis of off-target effects of CRISPR/Cas-derived RNA-guided endonucleases and nickases. Genome Res. 24, 132-141.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Deveau, H., Barrangou, R., Garneau, J. E., Labonte, J., Fremaux, C., Boyaval, P., Romero, D. A., Horvath, P., and Moineau, S. (2008). Phage response to CRISPR-encoded resistance in Streptococcus thermophilus. J. Bacteriol. 190, 1390-1400.

Dominguez, A. A., Lim, W. A., and Qi, L. S. (2016). Beyond editing: repurposing CRISPR-Cas9 for precision genome regulation and interrogation. Nat. Rev. Mol. Cell Biol. 17, 5-15.

Dong, Guo, M., Wang, S., Zhu, Y., Wang, S., Xiong, Z., Yang, J., Xu, Z., and Huang, Z. (2017). Structural basis of CRISPR-SpyCas9 inhibition by an anti-CRISPR protein. Nature 546, 436-439.

Esvelt, K. M., Mali, P., Braff, J. L., Moosburner, M., Yaung, S. J., and Church, G. M. (2013). Orthogonal Cas9 proteins for RNA-guided gene regulation and editing. Nat. Methods 10, 1116-1121.

Fonfara, I., Le Rhun, A., Chylinski, K., Makarova, K. S., Lecrivain, A. L., Bzdrenga, J., Koonin, E. V., and Charpentier, E. (2014). Phylogeny of Cas9 determines functional exchangeability of dual-RNA and Cas9 among orthologous type II CRISPR-Cas systems. Nucleic Acids Res. 42, 2577-2590.

Friedland, A. E., Baral, R., Singhal, P., Loveluck, K., Shen, S., Sanchez, M., Marco, E., Gotta, G. M., Maeder, M. L., Kennedy, E. M., et al. (2015). Characterization of Staphylococcus aureus Cas9: a smaller Cas9 for all-in-one adeno-associated virus delivery and paired nickase applications. Genome Biol. 16, 257.

Friedrich, G., and Soriano, P. (1991). Promoter traps in embryonic stem cells: a genetic screen to identify and mutate developmental genes in mice. Genes Dev. 5, 1513-1523.

Fu, Y., Sander, J. D., Reyon, D., Cascio, V. M., and Joung, J. K. (2014). Improving CRISPR-Cas nuclease specificity using truncated guide RNAs. Nat. Biotechnol. 32, 279-284.

Gallagher, D. N., and Haber, J. E. (2018). Repair of a Site-Specific DNA Cleavage: Old-School Lessons for Cas9-Mediated Gene Editing. ACS Chem. Biol. 13, 397-405.

Garneau, J. E., Dupuis, M. E., Villion, M., Romero, D. A., Barrangou, R., Boyaval, P., Fremaux, C., Horvath, P., Magadan, A. H., and Moineau, S. (2010). The CRISPR/Cas bacterial immune system cleaves bacteriophage and plasmid DNA. Nature 468, 67-71.

Gasiunas, G., Barrangou, R., Horvath, P., and Siksnys, V. (2012). Cas9-crRNA ribonucleoprotein complex mediates specific DNA cleavage for adaptive immunity in bacteria. Proc. Natl. Acad. Sci. USA 109, E2579-2586.

Gaudelli, N. M., Komor, A. C., Rees, H. A., Packer, M. S., Badran, A. H., Bryson, D. I., and Liu, D. R. (2017). Programmable base editing of A*T to G*C in genomic DNA without DNA cleavage. Nature 551, 464-471.

Ghanta, K., Dokshin, G., Mir, A., Krishnamurthy, P., Gneid, H., Edraki, A., Watts, J., Sontheimer, E., and Mello, C. (2018). 5' Modifications Improve Potency and Efficacy of DNA Donors for Precision Genome Editing. Biorxiv 354480.

Gorski, S. A., Vogel, J., and Doudna, J. A. (2017). RNA-based recognition and targeting: sowing the seeds of specificity. Nat. Rev. Mol. Cell Biol. 18, 215-228.

Harrington, L. B., Doxzen, K. W., Ma, E., Liu, J. J., Knott, G. J., Edraki, A., Garcia, B., Amrani, N., Chen, J. S., Cofsky, J. C., et al. (2017a). A Broad-Spectrum Inhibitor of CRISPR-Cas9. Cell 170, 1224-1233.

Harrington, L. B., Paez-Espino, D., Staahl, B. T., Chen, J. S., Ma, E., Kyrpides, N.C., and Doudna, J. A. (2017b). A thermostable Cas9 with increased lifetime in human plasma. Nat. Commun. 8, 1424.

Hou, Z., Zhang, Y., Propson, N. E., Howden, S. E., Chu, L. F., Sontheimer, E. J., and Thomson, J. A. (2013). Efficient genome engineering in human pluripotent stem cells using Cas9 from Neisseria meningitidis. Proc. Natl. Acad. Sci. USA 110, 15644-15649.

Hu, J. H., Miller, S. M., Geurts, M. H., Tang, W., Chen, L., Sun, N., Zeina, C. M., Gao, X., Rees, H. A., Lin, Z., et al. (2018). Evolved Cas9 variants with broad PAM compatibility and high DNA specificity. Nature 556, 57-63.

Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPR-Cas system. Nat. Biotechnol. 31, 227-229.

Hynes, A. P., Rousseau, G. M., Lemay, M.-L., Horvath, P., Romero, D. A., Fremaux, C., and Moineau, S. (2017). An anti-CRISPR from a virulent streptococcal phage inhibits Streptococcus pyogenes Cas9. Nat. Microbiol. 2, 1374-1380.

Ibraheim, R., Song, C.-Q., Mir, A., Amrani, N., Xue, W., and Sontheimer, E. J. (2018). All-in-One Adeno-associated Virus Delivery and Genome Editing by Neisseria meningitidis Cas9 in vivo. BioRxiv, https://doi.org/10.1101/295055.

Jiang, F., and Doudna, J. A. (2017). CRISPR-Cas9 Structures and Mechanisms. Annu. Rev. Biophys. 46, 505-529.

Jiang, W., Bikard, D., Cox, D., Zhang, F., and Marraffini, L. A. (2013). RNA-guided editing of bacterial genomes using CRISPR-Cas systems. Nat. Biotechnol. 31, 233-239.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jinek, M., East, A., Cheng, A., Lin, S., Ma, E., and Doudna, J. (2013). RNA-programmed genome editing in human cells. eLife 2, e00471.

Karvelis, T., Gasiunas, G., Young, J., Bigelyte, G., Silanskas, A., Cigan, M., and Siksnys, V. (2015). Rapid characterization of CRISPR-Cas9 protospacer adjacent motif sequence elements. Genome Biol. 16, 253.

Keeler, A. M., ElMallah, M. K., and Flotte, T. R. (2017). Gene Therapy 2017: Progress and Future Directions. Clin. Transl. Sci. 10, 242-248.

Kim, E., Koo, T., Park, S. W., Kim, D., Kim, K.-E., Kim, K., Cho, H.-Y., Song, D. W., Lee, K. J., Jung, M. H., et al. (2017). In vivo genome editing with a small Cas9 ortholog derived from *Campylobacter jejuni*. Nat. Commun. 8, 14500.

Kim, S., Kim, D., Cho, S. W., Kim, J., and Kim, J. S. (2014). Highly efficient RNA-guided genome editing in human cells via delivery of purified Cas9 ribonucleoproteins. Genome Res. 24, 1012-1019.

Kim, B., Komor, A., Levy, J., Packer, M., Zhao, K., and Liu, D. (2017). Increasing the genome-targeting scope and precision of base editing with engineered Cas9-cytidine deaminase fusions. Nature Biotechnology 35.

Kleinstiver, B. P., Prew, M. S., Tsai, S. Q., Nguyen, N. T., Topkar, V. V., Zheng, Z., and Joung, J. K. (2015). Broadening the targeting range of *Staphylococcus aureus* CRISPR-Cas9 by modifying PAM recognition. Nat. Biotechnol. 33, 1293-1298.

Kluesner, M., Nedveck, D., Lahr, W., Garbe, J., Abrahante, J., Webber, B., and Moriarity, B. (2018). EditR: A Method to Quantify Base Editing from Sanger Sequencing. The CRISPR Journal 1, 239-250.

Koblan, L., Doman, J., Wilson, C., Levy, J., Tay, T., Newby, G., Maianti, J., Raguram, A., and Liu, D. (2018). Improving cytidine and adenine base editors by expression optimization and ancestral reconstruction. Nat Biotechnol 36, 843.

Komor, A. C., Badran, A. H., and Liu, D. R. (2017). CRISPR-Based Technologies for the Manipulation of Eukaryotic Genomes. Cell 168, 20-36.

Komor, A. C., Kim, Y. B., Packer, M. S., Zuris, J. A., and Liu, D. R. (2016). Programmable editing of a target base in genomic DNA without double-stranded DNA cleavage. Nature 533, 420-424.

Lee, C. M., Cradick, T. J., and Bao, G. (2016). The *Neisseria meningitidis* CRISPR-Cas9 system enables specific genome editing in mammalian cells. Mol. Ther. 24, 645-654.

Lee, J., Mir, A., Edraki, A., Garcia, B., Amrani, N., Lou, H. E., Gainetdinov, I., Pawluk, A., Ibraheim, R., Gao, X. D., et al. (2018). Potent Cas9 inhibition in bacterial and human cells by new anti-CRISPR protein families. BioRxiv, https://www.biorxiv.org/content/early/2018/2006/2020/350504.

Ma, E., Harrington, L. B., O'Connell, M. R., Zhou, K., and Doudna, J. A. (2015). Single-Stranded DNA Cleavage by Divergent CRISPR-Cas9 Enzymes. Mol. Cell 60, 398-407.

Mali, P., Aach, J., Stranges, P. B., Esvelt, K. M., Moosburner, M., Kosuri, S., Yang, L., and Church, G. M. (2013a). CAS9 transcriptional activators for target specificity screening and paired nickases for cooperative genome engineering. Nat. Biotechnol. 31, 833-838.

Mali, P., Yang, L., Esvelt, K. M., Aach, J., Guell, M., DiCarlo, J. E., Norville, J. E., and Church, G. M. (2013b). RNA-guided human genome engineering via Cas9. Science 339, 823-826.

Marraffini, L. A., and Sontheimer, E. J. (2008). CRISPR interference limits horizontal gene transfer in staphylococci by targeting DNA. Science 322, 1843-1845.

Mir, A., Edraki, A., Lee, J., and Sontheimer, E. J. (2018). Type II-C CRISPR-Cas9 biology, mechanism and application. ACS Chem. Biol. 13, 357-365.

Mojica, F. J., Diez-Villasenor, C., Garcia-Martinez, J., and Almendros, C. (2009). Short motif sequences determine the targets of the prokaryotic CRISPR defence system. Microbiology 155, 733-740.

Paez-Espino, D., Sharon, I., Morovic, W., Stahl, B., Thomas, B. C., Barrangou, R., and Banfield, J. F. (2015). CRISPR immunity drives rapid phage genome evolution in *Streptococcus thermophilus*. mBio 6.

Pawluk, A., Amrani, N., Zhang, Y., Garcia, B., Hidalgo-Reyes, Y., Lee, J., Edraki, A., Shah, M., Sontheimer, E. J., Maxwell, K. L., et al. (2016). Naturally occurring off-switches for CRISPR-Cas9. Cell 167, 1829-1838e1829.

Pawluk, A., Bondy-Denomy, J., Cheung, V. H., Maxwell, K. L., and Davidson, A. R. (2014). A new group of phage anti-CRISPR genes inhibits the type I-E CRISPR-Cas system of *Pseudomonas aeruginosa*. mBio 5, e00896.

Pinello, L., Canver, M. C., Hoban, M. D., Orkin, S. H., Kohn, D. B., Bauer, D. E., and Yuan, G•C. (2016). Analyzing CRISPR genome-editing experiments with CRISPResso. Nat. Biotechnol. 34, 695-697.

Racanelli, V., and Rehermann, B. (2006). The liver as an immunological organ. Hepatology 43, S54-62.

Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using *Staphylococcus aureus* Cas9. Nature 520, 186-191.

Ran, F. A., Hsu, P. D., Lin, C. Y., Gootenberg, J. S., Konermann, S., Trevino, A. E., Scott, D. A., Inoue, A., Matoba, S., Zhang, Y., et al. (2013). Double nicking by RNA-guided CRISPR Cas9 for enhanced genome editing specificity. Cell 154, 1380-1389.

Rashid, S., Curtis, D. E., Garuti, R., Anderson, N. N., Bashmakov, Y., Ho, Y. K., Hammer, R. E., Moon, Y. A., and Horton, J. D. (2005). Decreased plasma cholesterol and hypersensitivity to statins in mice lacking Pcsk9. Proc. Natl. Acad. Sci. USA 102, 5374-5379.

Rauch, B. J., Silvis, M. R., Hultquist, J. F., Waters, C. S., McGregor, M. J., Krogan, N. J., and Bondy-Denomy, J. (2017). Inhibition of CRISPR-Cas9 with Bacteriophage Proteins. Cell 168, 150-158e110.

Sapranauskas, R., Gasiunas, G., Fremaux, C., Barrangou, R., Horvath, P., and Siksnys, V. (2011). The *Streptococcus thermophilus* CRISPR/Cas system provides immunity in *Escherichia coli*. Nucleic Acids Res. 39, 9275-9282.

Schumann, K., Lin, S., Boyer, E., Simeonov, D. R., Subramaniam, M., Gate, R. E., Haliburton, G. E., Ye, C. J., Bluestone, J. A., Doudna, J. A., et al. (2015). Generation of knock-in primary human T cells using Cas9 ribonucleoproteins. Proc. Natl. Acad. Sci. USA 112, 10437-10442.

Shin, J., Jiang, F., Liu, J. J., Bray, N. L., Rauch, B. J., Baik, S. H., Nogales, E., Bondy-Denomy, J., Corn, J. E., and Doudna, J. A. (2017). Disabling Cas9 by an anti-CRISPR DNA mimic. Sci. Adv. 3, e1701620.

Tsai, S. Q., and Joung, J. K. (2016). Defining and improving the genome-wide specificities of CRISPR-Cas9 nucleases. Nat. Rev. Genet. 17, 300-312.

Tsai, S. Q., Zheng, Z., Nguyen, N. T., Liebers, M., Topkar, V. V., Thapar, V., Wyvekens, N., Khayter, C., Iafrate, A. J., Le, L. P., et al. (2014). GUIDE-seq enables genome-wide profiling of off-target cleavage by CRISPR-Cas nucleases. Nat. Biotechnol. 33, 187-197.

Tycko, J., Myer, V. E., and Hsu, P. D. (2016). Methods for optimizing CRISPR-Cas9 genome editing specificity. Mol. Cell 63, 355-370.

Yang, H., and Patel, D. J. (2017). Inhibition Mechanism of an Anti-CRISPR Suppressor AcrIIA4 Targeting SpyCas9. Mol Cell 67, 117-127e115.

Yin, H., Song, C. Q., Suresh, S., Kwan, S. Y., Wu, Q., Walsh, S., Ding, J., Bogorad, R. L., Zhu, L. J., Wolfe, S. A., et al. (2018). Partial DNA-guided Cas9 enables genome editing with reduced off-target activity. Nat. Chem. Biol. 14, 311-316.

Yokoyama, T., Silversides, D. W., Waymire, K. G., Kwon, B. S., Takeuchi, T., and Overbeek, P. A. (1990). Conserved cysteine to serine mutation in tyrosinase is responsible for the classical albino mutation in laboratory mice. Nucleic Acids Res. 18, 7293-7298.

Yoon, Y., Wang, D., Tai, P. W. L., Riley, J., Gao, G., and Rivera-Perez, J. A. (2018). Streamlined ex vivo and in vivo genome editing in mouse embryos using recombinant adeno-associated viruses. Nat. Commun. 9, 412.

Zhang, Y., Heidrich, N., Ampattu, B. J., Gunderson, C. W., Seifert, H. S., Schoen, C., Vogel, J., and Sontheimer, E. J. (2013). Processing-independent CRISPR RNAs limit natural transformation in Neisseria meningitidis. Mol. Cell 50, 488-503.

Zhang, Y., Rajan, R., Seifert, H. S., Mondragón, A., and Sontheimer, E. J. (2015). DNase H activity of Neisseria meningitidis Cas9. Mol. Cell 60, 242-255.

Zhang, Z., Theurkauf, W. E., Weng, Z., and Zamore, P. D. (2012). Strand-specific libraries for high throughput RNA sequencing (RNA-Seq) prepared without poly (A) selection. Silence 3, 9.

Zhu, L. J., Holmes, B. R., Aronin, N., and Brodsky, M. H. (2014). CRISPRseek: a bioconductor package to identify target-specific guide RNAs for CRISPR-Cas9 genome-editing systems. PLOS One 9, e108424.

Zhu, L. J., Lawrence, M., Gupta, A., Pagés, H., Kucukural, A., Garber, M., and Wolfe, S. A. (2017). GUIDEseq: a bioconductor package to analyze GUIDE-Seq datasets for CRISPR-Cas nucleases. BMC Genomics 18, 379.

Zuris, J. A., Thompson, D. B., Shu, Y., Guilinger, J. P., Bessen, J. L., Hu, J. H., Maeder, M. L., Joung, J. K., Chen, Z.-Y., and Liu, D. R. (2015). Cationic lipid-mediated delivery of proteins enables efficient protein-based genome editing in vitro and in vivo. Nat. Biotechnol. 33, 73-80.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in biological control, biochemistry, molecular biology, entomology, plankton, fishery systems, and fresh water ecology, or related fields are intended to be within the scope of the following claims.

---

We claim:

1. A mutated Nme2Cas9 protein comprising a fused nucleotide deaminase and a binding region for an $N_4CC$ nucleotide sequence.

2. The protein of claim 1, further comprising a nuclear localization signal protein.

3. The protein of claim 1, wherein said nucleotide deaminase is a cytidine deaminase.

4. The protein of claim 1, wherein said nucleotide deaminase is an adenosine deaminase.

5. The protein of claim 1, further comprising a uracil glycosylase inhibitor.

6. The protein of claim 2, wherein said nuclear localization signal protein is selected from a nucleoplasmin and an SV40.

7. The protein of claim 1, wherein said binding region is a protospacer accessory motif interacting domain.

8. The protein of claim 1, wherein said mutated Nme2Cas9 protein comprises a D16A mutation.

9. An adeno-associated virus comprising the mutated Nme2Cas9 protein of claim 1.

10. The virus of claim 9, wherein said virus is an adeno-associated virus 8.

11. The virus of claim 9, wherein said virus is an adeno-associated virus 6.

5

\* \* \* \* \*

SEQUENCE LISTING

```
<160> NUMBER OF SEQ ID NOS: 971

<210> SEQ ID NO 1
<211> LENGTH: 1425
<212> TYPE: PRT
<213> ORGANISM: Artificial Sequence
<220> FEATURE:
<223> OTHER INFORMATION: Synthetic

<400> SEQUENCE: 1

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Tyr Ser Pro Cys Gly Glu Cys
                85                  90                  95

Ser Arg Ala Ile Thr Glu Phe Leu Ser Arg Tyr Pro His Val Thr Leu
```

-continued

```
                 100                 105                 110

Phe Ile Tyr Ile Ala Arg Leu Tyr His His Ala Asp Pro Glu Asn Arg
         115                 120                 125

Gln Gly Leu Arg Asp Leu Ile Ser Ser Gly Val Thr Ile Gln Ile Met
         130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                 165                 170                 175

Leu Tyr Val Leu Glu Leu Tyr Cys Ile Ile Leu Gly Leu Pro Pro Cys
                 180                 185                 190

Leu Asn Ile Leu Arg Arg Lys Gln Pro Gln Leu Thr Phe Phe Thr Ile
         195                 200                 205

Ala Leu Gln Ser Cys His Tyr Gln Arg Leu Pro Pro His Ile Leu Trp
         210                 215                 220

Ala Thr Gly Leu Lys Ser Gly Ser Glu Thr Pro Gly Thr Ser Glu Ser
225                 230                 235                 240

Ala Thr Pro Glu Ser Met Ala Ala Phe Lys Pro Asn Pro Ile Asn Tyr
                 245                 250                 255

Ile Leu Gly Leu Ala Ile Gly Ile Ala Ser Val Gly Trp Ala Met Val
                 260                 265                 270

Glu Ile Asp Glu Glu Glu Asn Pro Ile Arg Leu Ile Asp Leu Gly Val
                 275                 280                 285

Arg Val Phe Glu Arg Ala Glu Val Pro Lys Thr Gly Asp Ser Leu Ala
         290                 295                 300

Met Ala Arg Arg Leu Ala Arg Ser Val Arg Arg Leu Thr Arg Arg Arg
305                 310                 315                 320

Ala His Arg Leu Leu Arg Ala Arg Arg Leu Leu Lys Arg Glu Gly Val
                 325                 330                 335

Leu Gln Ala Ala Asp Phe Asp Glu Asn Gly Leu Ile Lys Ser Leu Pro
                 340                 345                 350

Asn Thr Pro Trp Gln Leu Arg Ala Ala Ala Leu Asp Arg Lys Leu Thr
                 355                 360                 365

Pro Leu Glu Trp Ser Ala Val Leu Leu His Leu Ile Lys His Arg Gly
         370                 375                 380

Tyr Leu Ser Gln Arg Lys Asn Glu Gly Glu Thr Ala Asp Lys Glu Leu
385                 390                 395                 400

Gly Ala Leu Leu Lys Gly Val Ala Asn Asn Ala His Ala Leu Gln Thr
                 405                 410                 415

Gly Asp Phe Arg Thr Pro Ala Glu Leu Ala Leu Asn Lys Phe Glu Lys
                 420                 425                 430

Glu Ser Gly His Ile Arg Asn Gln Arg Gly Asp Tyr Ser His Thr Phe
                 435                 440                 445

Ser Arg Lys Asp Leu Gln Ala Glu Leu Ile Leu Leu Phe Glu Lys Gln
         450                 455                 460

Lys Glu Phe Gly Asn Pro His Val Ser Gly Gly Leu Lys Glu Gly Ile
465                 470                 475                 480

Glu Thr Leu Leu Met Thr Gln Arg Pro Ala Leu Ser Gly Asp Ala Val
                 485                 490                 495

Gln Lys Met Leu Gly His Cys Thr Phe Glu Pro Ala Glu Pro Lys Ala
                 500                 505                 510

Ala Lys Asn Thr Tyr Thr Ala Glu Arg Phe Ile Trp Leu Thr Lys Leu
         515                 520                 525
```

-continued

```
Asn Asn Leu Arg Ile Leu Glu Gln Gly Ser Glu Arg Pro Leu Thr Asp
    530                 535                 540

Thr Glu Arg Ala Thr Leu Met Asp Glu Pro Tyr Arg Lys Ser Lys Leu
545                 550                 555                 560

Thr Tyr Ala Gln Ala Arg Lys Leu Leu Gly Leu Glu Asp Thr Ala Phe
                565                 570                 575

Phe Lys Gly Leu Arg Tyr Gly Lys Asp Asn Ala Glu Ala Ser Thr Leu
                580                 585                 590

Met Glu Met Lys Ala Tyr His Ala Ile Ser Arg Ala Leu Glu Lys Glu
                595                 600                 605

Gly Leu Lys Asp Lys Lys Ser Pro Leu Asn Leu Ser Ser Glu Leu Gln
    610                 615                 620

Asp Glu Ile Gly Thr Ala Phe Ser Leu Phe Lys Thr Asp Glu Asp Ile
625                 630                 635                 640

Thr Gly Arg Leu Lys Asp Arg Val Gln Pro Glu Ile Leu Glu Ala Leu
                645                 650                 655

Leu Lys His Ile Ser Phe Asp Lys Phe Val Gln Ile Ser Leu Lys Ala
                660                 665                 670

Leu Arg Arg Ile Val Pro Leu Met Glu Gln Gly Lys Arg Tyr Asp Glu
                675                 680                 685

Ala Cys Ala Glu Ile Tyr Gly Asp His Tyr Gly Lys Lys Asn Thr Glu
    690                 695                 700

Glu Lys Ile Tyr Leu Pro Pro Ile Pro Ala Asp Glu Ile Arg Asn Pro
705                 710                 715                 720

Val Val Leu Arg Ala Leu Ser Gln Ala Arg Lys Val Ile Asn Gly Val
                725                 730                 735

Val Arg Arg Tyr Gly Ser Pro Ala Arg Ile His Ile Glu Thr Ala Arg
                740                 745                 750

Glu Val Gly Lys Ser Phe Lys Asp Arg Lys Glu Ile Glu Lys Arg Gln
                755                 760                 765

Glu Glu Asn Arg Lys Asp Arg Glu Lys Ala Ala Ala Lys Phe Arg Glu
    770                 775                 780

Tyr Phe Pro Asn Phe Val Gly Glu Pro Lys Ser Lys Asp Ile Leu Lys
785                 790                 795                 800

Leu Arg Leu Tyr Glu Gln Gln His Gly Lys Cys Leu Tyr Ser Gly Lys
                805                 810                 815

Glu Ile Asn Leu Val Arg Leu Asn Glu Lys Gly Tyr Val Glu Ile Asp
                820                 825                 830

Ala Ala Leu Pro Phe Ser Arg Thr Trp Asp Asp Ser Phe Asn Asn Lys
                835                 840                 845

Val Leu Val Leu Gly Ser Glu Asn Gln Asn Lys Gly Asn Gln Thr Pro
    850                 855                 860

Tyr Glu Tyr Phe Asn Gly Lys Asp Asn Ser Arg Glu Trp Gln Glu Phe
865                 870                 875                 880

Lys Ala Arg Val Glu Thr Ser Arg Phe Pro Arg Ser Lys Lys Gln Arg
                885                 890                 895

Ile Leu Leu Gln Lys Phe Asp Glu Asp Gly Phe Lys Glu Cys Asn Leu
                900                 905                 910

Asn Asp Thr Arg Tyr Val Asn Arg Phe Leu Cys Gln Phe Val Ala Asp
    915                 920                 925

His Ile Leu Leu Thr Gly Lys Gly Lys Arg Arg Val Phe Ala Ser Asn
    930                 935                 940
```

-continued

```
Gly Gln Ile Thr Asn Leu Leu Arg Gly Phe Trp Gly Leu Arg Lys Val
945                 950                 955                 960

Arg Ala Glu Asn Asp Arg His His Ala Leu Asp Ala Val Val Val Ala
                965                 970                 975

Cys Ser Thr Val Ala Met Gln Gln Lys Ile Thr Arg Phe Val Arg Tyr
                980                 985                 990

Lys Glu Met Asn Ala Phe Asp Gly  Lys Thr Ile Asp Lys  Glu Thr Gly
        995                 1000                1005

Lys Val  Leu His Gln Lys Thr  His Phe Pro Gln Pro  Trp Glu Phe
    1010                1015                1020

Phe Ala  Gln Glu Val Met Ile  Arg Val Phe Gly Lys  Pro Asp Gly
    1025                1030                1035

Lys Pro  Glu Phe Glu Glu Ala  Asp Thr Pro Glu Lys  Leu Arg Thr
    1040                1045                1050

Leu Leu  Ala Glu Lys Leu Ser  Ser Arg Pro Glu Ala  Val His Glu
    1055                1060                1065

Tyr Val  Thr Pro Leu Phe Val  Ser Arg Ala Pro Asn  Arg Lys Met
    1070                1075                1080

Ser Gly  Ala His Lys Asp Thr  Leu Arg Ser Ala Lys  Arg Phe Val
    1085                1090                1095

Lys His  Asn Glu Lys Ile Ser  Val Lys Arg Val Trp  Leu Thr Glu
    1100                1105                1110

Ile Lys  Leu Ala Asp Leu Glu  Asn Met Val Asn Tyr  Lys Asn Gly
    1115                1120                1125

Arg Glu  Ile Glu Leu Tyr Glu  Ala Leu Lys Ala Arg  Leu Glu Ala
    1130                1135                1140

Tyr Gly  Gly Asn Ala Lys Gln  Ala Phe Asp Pro Lys  Asp Asn Pro
    1145                1150                1155

Phe Tyr  Lys Lys Gly Gly Gln  Leu Val Lys Ala Val  Arg Val Glu
    1160                1165                1170

Lys Thr  Gln Glu Ser Gly Val  Leu Leu Asn Lys Lys  Asn Ala Tyr
    1175                1180                1185

Thr Ile  Ala Asp Asn Gly Asp  Met Val Arg Val Asp  Val Phe Cys
    1190                1195                1200

Lys Val  Asp Lys Lys Gly Lys  Asn Gln Tyr Phe Ile  Val Pro Ile
    1205                1210                1215

Tyr Ala  Trp Gln Val Ala Glu  Asn Ile Leu Pro Asp  Ile Asp Cys
    1220                1225                1230

Lys Gly  Tyr Arg Ile Asp Asp  Ser Tyr Thr Phe Cys  Phe Ser Leu
    1235                1240                1245

His Lys  Tyr Asp Leu Ile Ala  Phe Gln Lys Asp Glu  Lys Ser Lys
    1250                1255                1260

Val Glu  Phe Ala Tyr Tyr Ile  Asn Cys Asp Ser Ser  Asn Gly Arg
    1265                1270                1275

Phe Tyr  Leu Ala Trp His Asp  Lys Gly Ser Lys Glu  Gln Gln Phe
    1280                1285                1290

Arg Ile  Ser Thr Gln Asn Leu  Val Leu Ile Gln Lys  Tyr Gln Val
    1295                1300                1305

Asn Glu  Leu Gly Lys Glu Ile  Arg Pro Cys Arg Leu  Lys Lys Arg
    1310                1315                1320

Pro Pro  Val Arg Ser Gly Gly  Ser Thr Asn Leu Ser  Asp Ile Ile
    1325                1330                1335

Glu Lys  Glu Thr Gly Lys Gln  Leu Val Ile Gln Glu  Ser Ile Leu
```

-continued

```
        1340              1345              1350

Met Leu  Pro Glu Glu Val Glu  Glu Val Ile Gly Asn  Lys Pro Glu
    1355              1360              1365

Ser Asp  Ile Leu Val His Thr  Ala Tyr Asp Glu Ser  Thr Asp Glu
    1370              1375              1380

Asn Val  Met Leu Leu Thr Ser  Asp Ala Pro Glu Tyr  Lys Pro Trp
    1385              1390              1395

Ala Leu  Val Ile Gln Asp Ser  Asn Gly Glu Asn Lys  Ile Lys Met
    1400              1405              1410

Leu Ser  Gly Gly Ser Pro Lys  Lys Lys Arg Lys Val
    1415              1420              1425

<210> SEQ ID NO 2
<211> LENGTH: 1425
<212> TYPE: PRT
<213> ORGANISM: Artificial Sequence
<220> FEATURE:
<223> OTHER INFORMATION: Synthetic

<400> SEQUENCE: 2

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Tyr Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Glu Asn Arg
            115                 120                 125

Gln Gly Leu Arg Asp Leu Ile Ser Ser Gly Val Thr Ile Gln Ile Met
        130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
        210                 215                 220

Ala Thr Gly Leu Lys Ser Gly Ser Glu Thr Pro Gly Thr Ser Glu Ser
225                 230                 235                 240

Ala Thr Pro Glu Ser Met Ala Ala Phe Lys Pro Asn Pro Ile Asn Tyr
                245                 250                 255

Ile Leu Gly Leu Ala Ile Gly Ile Ala Ser Val Gly Trp Ala Met Val
            260                 265                 270

Glu Ile Asp Glu Glu Glu Asn Pro Ile Arg Leu Ile Asp Leu Gly Val
```

```
                275                 280                 285

Arg Val Phe Glu Arg Ala Glu Val Pro Lys Thr Gly Asp Ser Leu Ala
    290                 295                 300

Met Ala Arg Arg Leu Ala Arg Ser Val Arg Arg Leu Thr Arg Arg Arg
305                 310                 315                 320

Ala His Arg Leu Leu Arg Ala Arg Arg Leu Leu Lys Arg Glu Gly Val
                325                 330                 335

Leu Gln Ala Ala Asp Phe Asp Glu Asn Gly Leu Ile Lys Ser Leu Pro
                340                 345                 350

Asn Thr Pro Trp Gln Leu Arg Ala Ala Ala Leu Asp Arg Lys Leu Thr
                355                 360                 365

Pro Leu Glu Trp Ser Ala Val Leu Leu His Leu Ile Lys His Arg Gly
    370                 375                 380

Tyr Leu Ser Gln Arg Lys Asn Glu Gly Glu Thr Ala Asp Lys Glu Leu
385                 390                 395                 400

Gly Ala Leu Leu Lys Gly Val Ala Asn Asn Ala His Ala Leu Gln Thr
                405                 410                 415

Gly Asp Phe Arg Thr Pro Ala Glu Leu Ala Leu Asn Lys Phe Glu Lys
                420                 425                 430

Glu Ser Gly His Ile Arg Asn Gln Arg Gly Asp Tyr Ser His Thr Phe
                435                 440                 445

Ser Arg Lys Asp Leu Gln Ala Glu Leu Ile Leu Leu Phe Glu Lys Gln
    450                 455                 460

Lys Glu Phe Gly Asn Pro His Val Ser Gly Gly Leu Lys Glu Gly Ile
465                 470                 475                 480

Glu Thr Leu Leu Met Thr Gln Arg Pro Ala Leu Ser Gly Asp Ala Val
                485                 490                 495

Gln Lys Met Leu Gly His Cys Thr Phe Glu Pro Ala Glu Pro Lys Ala
                500                 505                 510

Ala Lys Asn Thr Tyr Thr Ala Glu Arg Phe Ile Trp Leu Thr Lys Leu
                515                 520                 525

Asn Asn Leu Arg Ile Leu Glu Gln Gly Ser Glu Arg Pro Leu Thr Asp
    530                 535                 540

Thr Glu Arg Ala Thr Leu Met Asp Glu Pro Tyr Arg Lys Ser Lys Leu
545                 550                 555                 560

Thr Tyr Ala Gln Ala Arg Lys Leu Leu Gly Leu Glu Asp Thr Ala Phe
                565                 570                 575

Phe Lys Gly Leu Arg Tyr Gly Lys Asp Asn Ala Glu Ala Ser Thr Leu
                580                 585                 590

Met Glu Met Lys Ala Tyr His Ala Ile Ser Arg Ala Leu Glu Lys Glu
                595                 600                 605

Gly Leu Lys Asp Lys Lys Ser Pro Leu Asn Leu Ser Ser Glu Leu Gln
    610                 615                 620

Asp Glu Ile Gly Thr Ala Phe Ser Leu Phe Lys Thr Asp Glu Asp Ile
625                 630                 635                 640

Thr Gly Arg Leu Lys Asp Arg Val Gln Pro Glu Ile Leu Glu Ala Leu
                645                 650                 655

Leu Lys His Ile Ser Phe Asp Lys Phe Val Gln Ile Ser Leu Lys Ala
                660                 665                 670

Leu Arg Arg Ile Val Pro Leu Met Glu Gln Gly Lys Arg Tyr Asp Glu
                675                 680                 685

Ala Cys Ala Glu Ile Tyr Gly Asp His Tyr Gly Lys Lys Asn Thr Glu
    690                 695                 700
```

-continued

```
Glu Lys Ile Tyr Leu Pro Pro Ile Pro Ala Asp Glu Ile Arg Asn Pro
705             710             715             720

Val Val Leu Arg Ala Leu Ser Gln Ala Arg Lys Val Ile Asn Gly Val
            725             730             735

Val Arg Arg Tyr Gly Ser Pro Ala Arg Ile His Ile Glu Thr Ala Arg
            740             745             750

Glu Val Gly Lys Ser Phe Lys Asp Arg Lys Glu Ile Glu Lys Arg Gln
            755             760             765

Glu Glu Asn Arg Lys Asp Arg Glu Lys Ala Ala Ala Lys Phe Arg Glu
            770             775             780

Tyr Phe Pro Asn Phe Val Gly Glu Pro Lys Ser Lys Asp Ile Leu Lys
785             790             795             800

Leu Arg Leu Tyr Glu Gln Gln His Gly Lys Cys Leu Tyr Ser Gly Lys
                805             810             815

Glu Ile Asn Leu Val Arg Leu Asn Glu Lys Gly Tyr Val Glu Ile Asp
            820             825             830

Ala Ala Leu Pro Phe Ser Arg Thr Trp Asp Asp Ser Phe Asn Asn Lys
            835             840             845

Val Leu Val Leu Gly Ser Glu Asn Gln Asn Lys Gly Asn Gln Thr Pro
            850             855             860

Tyr Glu Tyr Phe Asn Gly Lys Asp Asn Ser Arg Glu Trp Gln Glu Phe
865             870             875             880

Lys Ala Arg Val Glu Thr Ser Arg Phe Pro Arg Ser Lys Lys Gln Arg
                885             890             895

Ile Leu Leu Gln Lys Phe Asp Glu Asp Gly Phe Lys Glu Cys Asn Leu
                900             905             910

Asn Asp Thr Arg Tyr Val Asn Arg Phe Leu Cys Gln Phe Val Ala Asp
            915             920             925

His Ile Leu Leu Thr Gly Lys Gly Lys Arg Arg Val Phe Ala Ser Asn
            930             935             940

Gly Gln Ile Thr Asn Leu Leu Arg Gly Phe Trp Gly Leu Arg Lys Val
945             950             955             960

Arg Ala Glu Asn Asp Arg His His Ala Leu Asp Ala Val Val Val Ala
                965             970             975

Cys Ser Thr Val Ala Met Gln Gln Lys Ile Thr Arg Phe Val Arg Tyr
            980             985             990

Lys Glu Met Asn Ala Phe Asp Gly  Lys Thr Ile Asp Lys  Glu Thr Gly
            995             1000            1005

Lys Val  Leu His Gln Lys Thr  His Phe Pro Gln Pro  Trp Glu Phe
    1010            1015            1020

Phe Ala  Gln Glu Val Met Ile  Arg Val Phe Gly Lys  Pro Asp Gly
    1025            1030            1035

Lys Pro  Glu Phe Glu Glu Ala  Asp Thr Pro Glu Lys  Leu Arg Thr
    1040            1045            1050

Leu Leu  Ala Glu Lys Leu Ser  Ser Arg Pro Glu Ala  Val His Glu
    1055            1060            1065

Tyr Val  Thr Pro Leu Phe Val  Ser Arg Ala Pro Asn  Arg Lys Met
    1070            1075            1080

Ser Gly  Ala His Lys Asp Thr  Leu Arg Ser Ala Lys  Arg Phe Val
    1085            1090            1095

Lys His  Asn Glu Lys Ile Ser  Val Lys Arg Val Trp  Leu Thr Glu
    1100            1105            1110
```

```
Ile Lys Leu Ala Asp Leu Glu  Asn Met Val Asn Tyr  Lys Asn Gly
    1115              1120              1125

Arg Glu  Ile Glu Leu Tyr Glu  Ala Leu Lys Ala Arg  Leu Glu Ala
    1130              1135              1140

Tyr Gly  Gly Asn Ala Lys Gln  Ala Phe Asp Pro Lys  Asp Asn Pro
    1145              1150              1155

Phe Tyr  Lys Lys Gly Gly Gln  Leu Val Lys Ala Val  Arg Val Glu
    1160              1165              1170

Lys Thr  Gln Glu Ser Gly Val  Leu Leu Asn Lys Lys  Asn Ala Tyr
    1175              1180              1185

Thr Ile  Ala Asp Asn Gly Asp  Met Val Arg Val Asp  Val Phe Cys
    1190              1195              1200

Lys Val  Asp Lys Lys Gly Lys  Asn Gln Tyr Phe Ile  Val Pro Ile
    1205              1210              1215

Tyr Ala  Trp Gln Val Ala Glu  Asn Ile Leu Pro Asp  Ile Asp Cys
    1220              1225              1230

Lys Gly  Tyr Arg Ile Asp Asp  Ser Tyr Thr Phe Cys  Phe Ser Leu
    1235              1240              1245

His Lys  Tyr Asp Leu Ile Ala  Phe Gln Lys Asp Glu  Lys Ser Lys
    1250              1255              1260

Val Glu  Phe Ala Tyr Tyr Ile  Asn Cys Asp Ser Ser  Asn Gly Arg
    1265              1270              1275

Phe Tyr  Leu Ala Trp His Asp  Lys Gly Ser Lys Glu  Gln Gln Phe
    1280              1285              1290

Arg Ile  Ser Thr Gln Asn Leu  Val Leu Ile Gln Lys  Tyr Gln Val
    1295              1300              1305

Asn Glu  Leu Gly Lys Glu Ile  Arg Pro Cys Arg Leu  Lys Lys Arg
    1310              1315              1320

Pro Pro  Val Arg Ser Gly Gly  Ser Thr Asn Leu Ser  Asp Ile Ile
    1325              1330              1335

Glu Lys  Glu Thr Gly Lys Gln  Leu Val Ile Gln Glu  Ser Ile Leu
    1340              1345              1350

Met Leu  Pro Glu Glu Val Glu  Glu Val Ile Gly Asn  Lys Pro Glu
    1355              1360              1365

Ser Asp  Ile Leu Val His Thr  Ala Tyr Asp Glu Ser  Thr Asp Glu
    1370              1375              1380

Asn Val  Met Leu Leu Thr Ser  Asp Ala Pro Glu Tyr  Lys Pro Trp
    1385              1390              1395

Ala Leu  Val Ile Gln Asp Ser  Asn Gly Glu Asn Lys  Ile Lys Met
    1400              1405              1410

Leu Ser  Gly Gly Ser Pro Lys  Lys Lys Arg Lys Val
    1415              1420              1425

<210> SEQ ID NO 3
<211> LENGTH: 1497
<212> TYPE: PRT
<213> ORGANISM: Artificial Sequence
<220> FEATURE:
<223> OTHER INFORMATION: Synthetic

<400> SEQUENCE: 3

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
        20                  25                  30
```

```
Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
            115                 120                 125

Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
            165                 170                 175

Gly Ser Glu Thr Pro Gly Thr Ser Glu Ser Ala Thr Pro Glu Ser Ser
            180                 185                 190

Gly Gly Ser Ser Gly Gly Ser Ser Glu Val Glu Phe Ser His Glu Tyr
            195                 200                 205

Trp Met Arg His Ala Leu Thr Leu Ala Lys Arg Ala Arg Asp Glu Arg
        210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
            245                 250                 255

Glu Ile Met Ala Leu Arg Gln Gly Gly Leu Val Met Gln Asn Tyr Arg
            260                 265                 270

Leu Ile Asp Ala Thr Leu Tyr Val Thr Phe Glu Pro Cys Val Met Cys
        275                 280                 285

Ala Gly Ala Met Ile His Ser Arg Ile Gly Arg Val Val Phe Gly Val
        290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
            325                 330                 335

Asp Glu Cys Ala Ala Leu Leu Cys Tyr Phe Phe Arg Met Pro Arg Gln
            340                 345                 350

Val Phe Asn Ala Gln Lys Lys Ala Gln Ser Ser Thr Asp Ser Gly Gly
            355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Met Ala Ala
385                 390                 395                 400

Phe Lys Pro Asn Pro Ile Asn Tyr Ile Leu Gly Leu Ala Ile Gly Ile
            405                 410                 415

Ala Ser Val Gly Trp Ala Met Val Glu Ile Asp Glu Glu Glu Asn Pro
            420                 425                 430

Ile Arg Leu Ile Asp Leu Gly Val Arg Val Phe Glu Arg Ala Glu Val
            435                 440                 445

Pro Lys Thr Gly Asp Ser Leu Ala Met Ala Arg Arg Leu Ala Arg Ser
```

```
           450                 455                 460

Val Arg Arg Leu Thr Arg Arg Arg Ala His Arg Leu Leu Arg Ala Arg
465                 470                 475                 480

Arg Leu Leu Lys Arg Glu Gly Val Leu Gln Ala Ala Asp Phe Asp Glu
                485                 490                 495

Asn Gly Leu Ile Lys Ser Leu Pro Asn Thr Pro Trp Gln Leu Arg Ala
                500                 505                 510

Ala Ala Leu Asp Arg Lys Leu Thr Pro Leu Glu Trp Ser Ala Val Leu
                515                 520                 525

Leu His Leu Ile Lys His Arg Gly Tyr Leu Ser Gln Arg Lys Asn Glu
                530                 535                 540

Gly Glu Thr Ala Asp Lys Glu Leu Gly Ala Leu Leu Lys Gly Val Ala
545                 550                 555                 560

Asn Asn Ala His Ala Leu Gln Thr Gly Asp Phe Arg Thr Pro Ala Glu
                565                 570                 575

Leu Ala Leu Asn Lys Phe Glu Lys Glu Ser Gly His Ile Arg Asn Gln
                580                 585                 590

Arg Gly Asp Tyr Ser His Thr Phe Ser Arg Lys Asp Leu Gln Ala Glu
                595                 600                 605

Leu Ile Leu Leu Phe Glu Lys Gln Lys Glu Phe Gly Asn Pro His Val
                610                 615                 620

Ser Gly Gly Leu Lys Glu Gly Ile Glu Thr Leu Leu Met Thr Gln Arg
625                 630                 635                 640

Pro Ala Leu Ser Gly Asp Ala Val Gln Lys Met Leu Gly His Cys Thr
                645                 650                 655

Phe Glu Pro Ala Glu Pro Lys Ala Ala Lys Asn Thr Tyr Thr Ala Glu
                660                 665                 670

Arg Phe Ile Trp Leu Thr Lys Leu Asn Asn Leu Arg Ile Leu Glu Gln
                675                 680                 685

Gly Ser Glu Arg Pro Leu Thr Asp Thr Glu Arg Ala Thr Leu Met Asp
                690                 695                 700

Glu Pro Tyr Arg Lys Ser Lys Leu Thr Tyr Ala Gln Ala Arg Lys Leu
705                 710                 715                 720

Leu Gly Leu Glu Asp Thr Ala Phe Phe Lys Gly Leu Arg Tyr Gly Lys
                725                 730                 735

Asp Asn Ala Glu Ala Ser Thr Leu Met Glu Met Lys Ala Tyr His Ala
                740                 745                 750

Ile Ser Arg Ala Leu Glu Lys Glu Gly Leu Lys Asp Lys Lys Ser Pro
                755                 760                 765

Leu Asn Leu Ser Ser Glu Leu Gln Asp Glu Ile Gly Thr Ala Phe Ser
                770                 775                 780

Leu Phe Lys Thr Asp Glu Asp Ile Thr Gly Arg Leu Lys Asp Arg Val
785                 790                 795                 800

Gln Pro Glu Ile Leu Glu Ala Leu Leu Lys His Ile Ser Phe Asp Lys
                805                 810                 815

Phe Val Gln Ile Ser Leu Lys Ala Leu Arg Arg Ile Val Pro Leu Met
                820                 825                 830

Glu Gln Gly Lys Arg Tyr Asp Glu Ala Cys Ala Glu Ile Tyr Gly Asp
                835                 840                 845

His Tyr Gly Lys Lys Asn Thr Glu Glu Lys Ile Tyr Leu Pro Pro Ile
                850                 855                 860

Pro Ala Asp Glu Ile Arg Asn Pro Val Val Leu Arg Ala Leu Ser Gln
865                 870                 875                 880
```

-continued

```
Ala Arg Lys Val Ile Asn Gly Val Val Arg Arg Tyr Gly Ser Pro Ala
                885                890                895

Arg Ile His Ile Glu Thr Ala Arg Glu Val Gly Lys Ser Phe Lys Asp
            900                905                910

Arg Lys Glu Ile Glu Lys Arg Gln Glu Glu Asn Arg Lys Asp Arg Glu
        915                920                925

Lys Ala Ala Ala Lys Phe Arg Glu Tyr Phe Pro Asn Phe Val Gly Glu
    930                935                940

Pro Lys Ser Lys Asp Ile Leu Lys Leu Arg Leu Tyr Glu Gln Gln His
945                950                955                960

Gly Lys Cys Leu Tyr Ser Gly Lys Glu Ile Asn Leu Val Arg Leu Asn
                965                970                975

Glu Lys Gly Tyr Val Glu Ile Asp His Ala Leu Pro Phe Ser Arg Thr
            980                985                990

Trp Asp Asp Ser Phe Asn Asn Lys  Val Leu Val Leu Gly  Ser Glu Asn
        995                1000                1005

Gln Asn  Lys Gly Asn Gln Thr  Pro Tyr Glu Tyr Phe  Asn Gly Lys
    1010                1015                1020

Asp Asn  Ser Arg Glu Trp Gln  Glu Phe Lys Ala Arg  Val Glu Thr
    1025                1030                1035

Ser Arg  Phe Pro Arg Ser Lys  Lys Gln Arg Ile Leu  Leu Gln Lys
    1040                1045                1050

Phe Asp  Glu Asp Gly Phe Lys  Glu Cys Asn Leu Asn  Asp Thr Arg
    1055                1060                1065

Tyr Val  Asn Arg Phe Leu Cys  Gln Phe Val Ala Asp  His Ile Leu
    1070                1075                1080

Leu Thr  Gly Lys Gly Lys Arg  Arg Val Phe Ala Ser  Asn Gly Gln
    1085                1090                1095

Ile Thr  Asn Leu Leu Arg Gly  Phe Trp Gly Leu Arg  Lys Val Arg
    1100                1105                1110

Ala Glu  Asn Asp Arg His His  Ala Leu Asp Ala Val  Val Val Ala
    1115                1120                1125

Cys Ser  Thr Val Ala Met Gln  Gln Lys Ile Thr Arg  Phe Val Arg
    1130                1135                1140

Tyr Lys  Glu Met Asn Ala Phe  Asp Gly Lys Thr Ile  Asp Lys Glu
    1145                1150                1155

Thr Gly  Lys Val Leu His Gln  Lys Thr His Phe Pro  Gln Pro Trp
    1160                1165                1170

Glu Phe  Phe Ala Gln Glu Val  Met Ile Arg Val Phe  Gly Lys Pro
    1175                1180                1185

Asp Gly  Lys Pro Glu Phe Glu  Glu Ala Asp Thr Pro  Glu Lys Leu
    1190                1195                1200

Arg Thr  Leu Leu Ala Glu Lys  Leu Ser Ser Arg Pro  Glu Ala Val
    1205                1210                1215

His Glu  Tyr Val Thr Pro Leu  Phe Val Ser Arg Ala  Pro Asn Arg
    1220                1225                1230

Lys Met  Ser Gly Ala His Lys  Asp Thr Leu Arg Ser  Ala Lys Arg
    1235                1240                1245

Phe Val  Lys His Asn Glu Lys  Ile Ser Val Lys Arg  Val Trp Leu
    1250                1255                1260

Thr Glu  Ile Lys Leu Ala Asp  Leu Glu Asn Met Val  Asn Tyr Lys
    1265                1270                1275
```

```
Asn Gly  Arg Glu Ile Glu Leu  Tyr Glu Ala Leu Lys  Ala Arg Leu
    1280                1285                1290

Glu Ala  Tyr Gly Gly Asn Ala  Lys Gln Ala Phe Asp  Pro Lys Asp
    1295                1300                1305

Asn Pro  Phe Tyr Lys Lys Gly  Gly Gln Leu Val Lys  Ala Val Arg
    1310                1315                1320

Val Glu  Lys Thr Gln Glu Ser  Gly Val Leu Leu Asn  Lys Lys Asn
    1325                1330                1335

Ala Tyr  Thr Ile Ala Asp Asn  Gly Asp Met Val Arg  Val Asp Val
    1340                1345                1350

Phe Cys  Lys Val Asp Lys Lys  Gly Lys Asn Gln Tyr  Phe Ile Val
    1355                1360                1365

Pro Ile  Tyr Ala Trp Gln Val  Ala Glu Asn Ile Leu  Pro Asp Ile
    1370                1375                1380

Asp Cys  Lys Gly Tyr Arg Ile  Asp Asp Ser Tyr Thr  Phe Cys Phe
    1385                1390                1395

Ser Leu  His Lys Tyr Asp Leu  Ile Ala Phe Gln Lys  Asp Glu Lys
    1400                1405                1410

Ser Lys  Val Glu Phe Ala Tyr  Tyr Ile Asn Cys Asp  Ser Ser Asn
    1415                1420                1425

Gly Arg  Phe Tyr Leu Ala Trp  His Asp Lys Gly Ser  Lys Glu Gln
    1430                1435                1440

Gln Phe  Arg Ile Ser Thr Gln  Asn Leu Val Leu Ile  Gln Lys Tyr
    1445                1450                1455

Gln Val  Asn Glu Leu Gly Lys  Glu Ile Arg Pro Cys  Arg Leu Lys
    1460                1465                1470

Lys Arg  Pro Pro Val Arg Glu  Asp Lys Arg Pro Ala  Ala Thr Lys
    1475                1480                1485

Lys Ala  Gly Gln Ala Lys Lys  Lys Lys
    1490                1495
```

```
<210> SEQ ID NO 4
<211> LENGTH: 1497
<212> TYPE: PRT
<213> ORGANISM: Artificial Sequence
<220> FEATURE:
<223> OTHER INFORMATION: Synthetic

<400> SEQUENCE: 4
```

```
Met Ser Glu Val Glu Phe Ser His Glu Tyr Trp Met Arg His Ala Leu
1               5               10              15

Thr Leu Ala Lys Arg Ala Trp Asp Glu Arg Glu Val Pro Val Gly Ala
            20              25              30

Val Leu Val His Asn Asn Arg Val Ile Gly Glu Gly Trp Asn Arg Pro
        35              40              45

Ile Gly Arg His Asp Pro Thr Ala His Ala Glu Ile Met Ala Leu Arg
    50              55              60

Gln Gly Gly Leu Val Met Gln Asn Tyr Arg Leu Ile Asp Ala Thr Leu
65              70              75              80

Tyr Val Thr Leu Glu Pro Cys Val Met Cys Ala Gly Ala Met Ile His
            85              90              95

Ser Arg Ile Gly Arg Val Val Phe Gly Ala Arg Asp Ala Lys Thr Gly
            100             105             110

Ala Ala Gly Ser Leu Met Asp Val Leu His His Pro Gly Met Asn His
        115             120             125
```

-continued

```
Arg Val Glu Ile Thr Glu Gly Ile Leu Ala Asp Glu Cys Ala Ala Leu
    130                 135                 140

Leu Ser Asp Phe Phe Arg Met Arg Arg Gln Glu Ile Lys Ala Gln Lys
145                 150                 155                 160

Lys Ala Gln Ser Ser Thr Asp Ser Gly Gly Ser Ser Gly Gly Ser Ser
                165                 170                 175

Gly Ser Glu Thr Pro Gly Thr Ser Glu Ser Ala Thr Pro Glu Ser Ser
                180                 185                 190

Gly Gly Ser Ser Gly Gly Ser Ser Glu Val Glu Phe Ser His Glu Tyr
                195                 200                 205

Trp Met Arg His Ala Leu Thr Leu Ala Lys Arg Ala Arg Asp Glu Arg
    210                 215                 220

Glu Val Pro Val Gly Ala Val Leu Val Leu Asn Asn Arg Val Ile Gly
225                 230                 235                 240

Glu Gly Trp Asn Arg Ala Ile Gly Leu His Asp Pro Thr Ala His Ala
                245                 250                 255

Glu Ile Met Ala Leu Arg Gln Gly Gly Leu Val Met Gln Asn Tyr Arg
                260                 265                 270

Leu Ile Asp Ala Thr Leu Tyr Val Thr Phe Glu Pro Cys Val Met Cys
                275                 280                 285

Ala Gly Ala Met Ile His Ser Arg Ile Gly Arg Val Val Phe Gly Val
    290                 295                 300

Arg Asn Ala Lys Thr Gly Ala Ala Gly Ser Leu Met Asp Val Leu His
305                 310                 315                 320

Tyr Pro Gly Met Asn His Arg Val Glu Ile Thr Glu Gly Ile Leu Ala
                325                 330                 335

Asp Glu Cys Ala Ala Leu Leu Cys Tyr Phe Phe Arg Met Pro Arg Gln
                340                 345                 350

Val Phe Asn Ala Gln Lys Lys Ala Gln Ser Ser Thr Asp Ser Gly Gly
                355                 360                 365

Ser Ser Gly Gly Ser Ser Gly Ser Glu Thr Pro Gly Thr Ser Glu Ser
    370                 375                 380

Ala Thr Pro Glu Ser Ser Gly Gly Ser Ser Gly Gly Ser Met Ala Ala
385                 390                 395                 400

Phe Lys Pro Asn Pro Ile Asn Tyr Ile Leu Gly Leu Ala Ile Gly Ile
                405                 410                 415

Ala Ser Val Gly Trp Ala Met Val Glu Ile Asp Glu Glu Glu Asn Pro
                420                 425                 430

Ile Arg Leu Ile Asp Leu Gly Val Arg Val Phe Glu Arg Ala Glu Val
                435                 440                 445

Pro Lys Thr Gly Asp Ser Leu Ala Met Ala Arg Arg Leu Ala Arg Ser
    450                 455                 460

Val Arg Arg Leu Thr Arg Arg Arg Ala His Arg Leu Leu Arg Ala Arg
465                 470                 475                 480

Arg Leu Leu Lys Arg Glu Gly Val Leu Gln Ala Ala Asp Phe Asp Glu
                485                 490                 495

Asn Gly Leu Ile Lys Ser Leu Pro Asn Thr Pro Trp Gln Leu Arg Ala
                500                 505                 510

Ala Ala Leu Asp Arg Lys Leu Thr Pro Leu Glu Trp Ser Ala Val Leu
                515                 520                 525

Leu His Leu Ile Lys His Arg Gly Tyr Leu Ser Gln Arg Lys Asn Glu
    530                 535                 540

Gly Glu Thr Ala Asp Lys Glu Leu Gly Ala Leu Leu Lys Gly Val Ala
```

```
545                550                555                560

Asn Asn Ala His Ala Leu Gln Thr Gly Asp Phe Arg Thr Pro Ala Glu
            565                570                575

Leu Ala Leu Asn Lys Phe Glu Lys Glu Ser Gly His Ile Arg Asn Gln
            580                585                590

Arg Gly Asp Tyr Ser His Thr Phe Ser Arg Lys Asp Leu Gln Ala Glu
            595                600                605

Leu Ile Leu Leu Phe Glu Lys Gln Lys Glu Phe Gly Asn Pro His Val
    610                615                620

Ser Gly Gly Leu Lys Glu Gly Ile Glu Thr Leu Leu Met Thr Gln Arg
625                630                635                640

Pro Ala Leu Ser Gly Asp Ala Val Gln Lys Met Leu Gly His Cys Thr
            645                650                655

Phe Glu Pro Ala Glu Pro Lys Ala Ala Lys Asn Thr Tyr Thr Ala Glu
            660                665                670

Arg Phe Ile Trp Leu Thr Lys Leu Asn Asn Leu Arg Ile Leu Glu Gln
            675                680                685

Gly Ser Glu Arg Pro Leu Thr Asp Thr Glu Arg Ala Thr Leu Met Asp
    690                695                700

Glu Pro Tyr Arg Lys Ser Lys Leu Thr Tyr Ala Gln Ala Arg Lys Leu
705                710                715                720

Leu Gly Leu Glu Asp Thr Ala Phe Phe Lys Gly Leu Arg Tyr Gly Lys
            725                730                735

Asp Asn Ala Glu Ala Ser Thr Leu Met Glu Met Lys Ala Tyr His Ala
            740                745                750

Ile Ser Arg Ala Leu Glu Lys Glu Gly Leu Lys Asp Lys Lys Ser Pro
            755                760                765

Leu Asn Leu Ser Ser Glu Leu Gln Asp Glu Ile Gly Thr Ala Phe Ser
    770                775                780

Leu Phe Lys Thr Asp Glu Asp Ile Thr Gly Arg Leu Lys Asp Arg Val
785                790                795                800

Gln Pro Glu Ile Leu Glu Ala Leu Leu Lys His Ile Ser Phe Asp Lys
            805                810                815

Phe Val Gln Ile Ser Leu Lys Ala Leu Arg Arg Ile Val Pro Leu Met
            820                825                830

Glu Gln Gly Lys Arg Tyr Asp Glu Ala Cys Ala Glu Ile Tyr Gly Asp
            835                840                845

His Tyr Gly Lys Lys Asn Thr Glu Glu Lys Ile Tyr Leu Pro Pro Ile
    850                855                860

Pro Ala Asp Glu Ile Arg Asn Pro Val Val Leu Arg Ala Leu Ser Gln
865                870                875                880

Ala Arg Lys Val Ile Asn Gly Val Val Arg Arg Tyr Gly Ser Pro Ala
            885                890                895

Arg Ile His Ile Glu Thr Ala Arg Glu Val Gly Lys Ser Phe Lys Asp
            900                905                910

Arg Lys Glu Ile Glu Lys Arg Gln Glu Glu Asn Arg Lys Asp Arg Glu
            915                920                925

Lys Ala Ala Ala Lys Phe Arg Glu Tyr Phe Pro Asn Phe Val Gly Glu
    930                935                940

Pro Lys Ser Lys Asp Ile Leu Lys Leu Arg Leu Tyr Glu Gln Gln His
945                950                955                960

Gly Lys Cys Leu Tyr Ser Gly Lys Glu Ile Asn Leu Val Arg Leu Asn
            965                970                975
```

Glu Lys Gly Tyr Val Glu Ile Asp His Ala Leu Pro Phe Ser Arg Thr
        980                 985                 990

Trp Asp Asp Ser Phe Asn Asn Lys  Val Leu Val Leu Gly  Ser Glu Asn
        995                 1000                1005

Gln Asn  Lys Gly Asn Gln Thr  Pro Tyr Glu Tyr Phe  Asn Gly Lys
    1010                1015                1020

Asp Asn  Ser Arg Glu Trp Gln  Glu Phe Lys Ala Arg  Val Glu Thr
    1025                1030                1035

Ser Arg  Phe Pro Arg Ser Lys  Lys Gln Arg Ile Leu  Leu Gln Lys
    1040                1045                1050

Phe Asp  Glu Asp Gly Phe Lys  Glu Cys Asn Leu Asn  Asp Thr Arg
    1055                1060                1065

Tyr Val  Asn Arg Phe Leu Cys  Gln Phe Val Ala Asp  His Ile Leu
    1070                1075                1080

Leu Thr  Gly Lys Gly Lys Arg  Arg Val Phe Ala Ser  Asn Gly Gln
    1085                1090                1095

Ile Thr  Asn Leu Leu Arg Gly  Phe Trp Gly Leu Arg  Lys Val Arg
    1100                1105                1110

Ala Glu  Asn Asp Arg His His  Ala Leu Asp Ala Val  Val Val Ala
    1115                1120                1125

Cys Ser  Thr Val Ala Met Gln  Gln Lys Ile Thr Arg  Phe Val Arg
    1130                1135                1140

Tyr Lys  Glu Met Asn Ala Phe  Asp Gly Lys Thr Ile  Asp Lys Glu
    1145                1150                1155

Thr Gly  Lys Val Leu His Gln  Lys Thr His Phe Pro  Gln Pro Trp
    1160                1165                1170

Glu Phe  Phe Ala Gln Glu Val  Met Ile Arg Val Phe  Gly Lys Pro
    1175                1180                1185

Asp Gly  Lys Pro Glu Phe Glu  Glu Ala Asp Thr Pro  Glu Lys Leu
    1190                1195                1200

Arg Thr  Leu Leu Ala Glu Lys  Leu Ser Ser Arg Pro  Glu Ala Val
    1205                1210                1215

His Glu  Tyr Val Thr Pro Leu  Phe Val Ser Arg Ala  Pro Asn Arg
    1220                1225                1230

Lys Met  Ser Gly Ala His Lys  Asp Thr Leu Arg Ser  Ala Lys Arg
    1235                1240                1245

Phe Val  Lys His Asn Glu Lys  Ile Ser Val Lys Arg  Val Trp Leu
    1250                1255                1260

Thr Glu  Ile Lys Leu Ala Asp  Leu Glu Asn Met Val  Asn Tyr Lys
    1265                1270                1275

Asn Gly  Arg Glu Ile Glu Leu  Tyr Glu Ala Leu Lys  Ala Arg Leu
    1280                1285                1290

Glu Ala  Tyr Gly Gly Asn Ala  Lys Gln Ala Phe Asp  Pro Lys Asp
    1295                1300                1305

Asn Pro  Phe Tyr Lys Lys Gly  Gly Gln Leu Val Lys  Ala Val Arg
    1310                1315                1320

Val Glu  Lys Thr Gln Glu Ser  Gly Val Leu Leu Asn  Lys Lys Asn
    1325                1330                1335

Ala Tyr  Thr Ile Ala Asp Asn  Gly Asp Met Val Arg  Val Asp Val
    1340                1345                1350

Phe Cys  Lys Val Asp Lys Lys  Gly Lys Asn Gln Tyr  Phe Ile Val
    1355                1360                1365

-continued

```
Pro Ile  Tyr Ala Trp Gln Val  Ala Glu Asn Ile Leu  Pro Asp Ile
    1370              1375              1380

Asp Cys  Lys Gly Tyr Arg Ile  Asp Asp Ser Tyr Thr  Phe Cys Phe
    1385              1390              1395

Ser Leu  His Lys Tyr Asp Leu  Ile Ala Phe Gln Lys  Asp Glu Lys
    1400              1405              1410

Ser Lys  Val Glu Phe Ala Tyr  Tyr Ile Asn Cys Asp  Ser Ser Asn
    1415              1420              1425

Gly Arg  Phe Tyr Leu Ala Trp  His Asp Lys Gly Ser  Lys Glu Gln
    1430              1435              1440

Gln Phe  Arg Ile Ser Thr Gln  Asn Leu Val Leu Ile  Gln Lys Tyr
    1445              1450              1455

Gln Val  Asn Glu Leu Gly Lys  Glu Ile Arg Pro Cys  Arg Leu Lys
    1460              1465              1470

Lys Arg  Pro Pro Val Arg Glu  Asp Lys Arg Pro Ala  Ala Thr Lys
    1475              1480              1485

Lys Ala  Gly Gln Ala Lys Lys  Lys Lys
    1490              1495
```

```
<210> SEQ ID NO 5
<211> LENGTH: 1524
<212> TYPE: PRT
<213> ORGANISM: Artificial Sequence
<220> FEATURE:
<223> OTHER INFORMATION: Synthetic

<400> SEQUENCE: 5
```

```
Met Lys Arg Thr Ala Asp Gly Ser Glu Phe Glu Ser Pro Lys Lys Lys
1               5                   10                  15

Arg Lys Val Ser Glu Val Glu Phe Ser His Glu Tyr Trp Met Arg His
            20                  25                  30

Ala Leu Thr Leu Ala Lys Arg Ala Trp Asp Glu Arg Glu Val Pro Val
        35                  40                  45

Gly Ala Val Leu Val His Asn Asn Arg Val Ile Gly Glu Gly Trp Asn
    50                  55                  60

Arg Pro Ile Gly Arg His Asp Pro Thr Ala His Ala Glu Ile Met Ala
65                  70                  75                  80

Leu Arg Gln Gly Gly Leu Val Met Gln Asn Tyr Arg Leu Ile Asp Ala
                85                  90                  95

Thr Leu Tyr Val Thr Leu Glu Pro Cys Val Met Cys Ala Gly Ala Met
            100                 105                 110

Ile His Ser Arg Ile Gly Arg Val Val Phe Gly Ala Arg Asp Ala Lys
        115                 120                 125

Thr Gly Ala Ala Gly Ser Leu Met Asp Val Leu His His Pro Gly Met
    130                 135                 140

Asn His Arg Val Glu Ile Thr Glu Gly Ile Leu Ala Asp Glu Cys Ala
145                 150                 155                 160

Ala Leu Leu Ser Asp Phe Phe Arg Met Arg Arg Gln Glu Ile Lys Ala
                165                 170                 175

Gln Lys Lys Ala Gln Ser Ser Thr Asp Ser Gly Gly Ser Ser Gly Gly
            180                 185                 190

Ser Ser Gly Ser Glu Thr Pro Gly Thr Ser Glu Ser Ala Thr Pro Glu
        195                 200                 205

Ser Ser Gly Gly Ser Ser Gly Gly Ser Ser Glu Val Glu Phe Ser His
    210                 215                 220
```

-continued

```
Glu Tyr Trp Met Arg His Ala Leu Thr Leu Ala Lys Arg Ala Arg Asp
225                 230                 235                 240

Glu Arg Glu Val Pro Val Gly Ala Val Leu Val Leu Asn Asn Arg Val
                245                 250                 255

Ile Gly Glu Gly Trp Asn Arg Ala Ile Gly Leu His Asp Pro Thr Ala
                260                 265                 270

His Ala Glu Ile Met Ala Leu Arg Gln Gly Gly Leu Val Met Gln Asn
                275                 280                 285

Tyr Arg Leu Ile Asp Ala Thr Leu Tyr Val Thr Phe Glu Pro Cys Val
        290                 295                 300

Met Cys Ala Gly Ala Met Ile His Ser Arg Ile Gly Arg Val Val Phe
305                 310                 315                 320

Gly Val Arg Asn Ala Lys Thr Gly Ala Ala Gly Ser Leu Met Asp Val
                325                 330                 335

Leu His Tyr Pro Gly Met Asn His Arg Val Glu Ile Thr Glu Gly Ile
                340                 345                 350

Leu Ala Asp Glu Cys Ala Ala Leu Leu Cys Tyr Phe Phe Arg Met Pro
        355                 360                 365

Arg Gln Val Phe Asn Ala Gln Lys Lys Ala Gln Ser Ser Thr Asp Ser
        370                 375                 380

Gly Gly Ser Ser Gly Gly Ser Ser Gly Ser Glu Thr Pro Gly Thr Ser
385                 390                 395                 400

Glu Ser Ala Thr Pro Glu Ser Ser Gly Gly Ser Ser Gly Gly Ser Met
                405                 410                 415

Ala Ala Phe Lys Pro Asn Pro Ile Asn Tyr Ile Leu Gly Leu Ala Ile
                420                 425                 430

Gly Ile Ala Ser Val Gly Trp Ala Met Val Glu Ile Asp Glu Glu Glu
        435                 440                 445

Asn Pro Ile Arg Leu Ile Asp Leu Gly Val Arg Val Phe Glu Arg Ala
        450                 455                 460

Glu Val Pro Lys Thr Gly Asp Ser Leu Ala Met Ala Arg Arg Leu Ala
465                 470                 475                 480

Arg Ser Val Arg Arg Leu Thr Arg Arg Arg Ala His Arg Leu Leu Arg
                485                 490                 495

Ala Arg Arg Leu Leu Lys Arg Glu Gly Val Leu Gln Ala Ala Asp Phe
        500                 505                 510

Asp Glu Asn Gly Leu Ile Lys Ser Leu Pro Asn Thr Pro Trp Gln Leu
        515                 520                 525

Arg Ala Ala Ala Leu Asp Arg Lys Leu Thr Pro Leu Glu Trp Ser Ala
        530                 535                 540

Val Leu Leu His Leu Ile Lys His Arg Gly Tyr Leu Ser Gln Arg Lys
545                 550                 555                 560

Asn Glu Gly Glu Thr Ala Asp Lys Glu Leu Gly Ala Leu Leu Lys Gly
                565                 570                 575

Val Ala Asn Asn Ala His Ala Leu Gln Thr Gly Asp Phe Arg Thr Pro
        580                 585                 590

Ala Glu Leu Ala Leu Asn Lys Phe Glu Lys Glu Ser Gly His Ile Arg
        595                 600                 605

Asn Gln Arg Gly Asp Tyr Ser His Thr Phe Ser Arg Lys Asp Leu Gln
        610                 615                 620

Ala Glu Leu Ile Leu Leu Phe Glu Lys Gln Lys Glu Phe Gly Asn Pro
625                 630                 635                 640

His Val Ser Gly Gly Leu Lys Glu Gly Ile Glu Thr Leu Leu Met Thr
```

-continued

```
             645              650              655

Gln Arg Pro Ala Leu Ser Gly Asp Ala Val Gln Lys Met Leu Gly His
            660              665              670

Cys Thr Phe Glu Pro Ala Glu Pro Lys Ala Ala Lys Asn Thr Tyr Thr
            675              680              685

Ala Glu Arg Phe Ile Trp Leu Thr Lys Leu Asn Asn Leu Arg Ile Leu
        690              695              700

Glu Gln Gly Ser Glu Arg Pro Leu Thr Asp Thr Glu Arg Ala Thr Leu
705              710              715              720

Met Asp Glu Pro Tyr Arg Lys Ser Lys Leu Thr Tyr Ala Gln Ala Arg
                725              730              735

Lys Leu Leu Gly Leu Glu Asp Thr Ala Phe Phe Lys Gly Leu Arg Tyr
            740              745              750

Gly Lys Asp Asn Ala Glu Ala Ser Thr Leu Met Glu Met Lys Ala Tyr
            755              760              765

His Ala Ile Ser Arg Ala Leu Glu Lys Glu Gly Leu Lys Asp Lys Lys
        770              775              780

Ser Pro Leu Asn Leu Ser Ser Glu Leu Gln Asp Glu Ile Gly Thr Ala
785              790              795              800

Phe Ser Leu Phe Lys Thr Asp Glu Asp Ile Thr Gly Arg Leu Lys Asp
                805              810              815

Arg Val Gln Pro Glu Ile Leu Glu Ala Leu Leu Lys His Ile Ser Phe
            820              825              830

Asp Lys Phe Val Gln Ile Ser Leu Lys Ala Leu Arg Arg Ile Val Pro
            835              840              845

Leu Met Glu Gln Gly Lys Arg Tyr Asp Glu Ala Cys Ala Glu Ile Tyr
        850              855              860

Gly Asp His Tyr Gly Lys Lys Asn Thr Glu Glu Lys Ile Tyr Leu Pro
865              870              875              880

Pro Ile Pro Ala Asp Glu Ile Arg Asn Pro Val Val Leu Arg Ala Leu
                885              890              895

Ser Gln Ala Arg Lys Val Ile Asn Gly Val Val Arg Arg Tyr Gly Ser
            900              905              910

Pro Ala Arg Ile His Ile Glu Thr Ala Arg Glu Val Gly Lys Ser Phe
            915              920              925

Lys Asp Arg Lys Glu Ile Glu Lys Arg Gln Glu Glu Asn Arg Lys Asp
        930              935              940

Arg Glu Lys Ala Ala Ala Lys Phe Arg Glu Tyr Phe Pro Asn Phe Val
945              950              955              960

Gly Glu Pro Lys Ser Lys Asp Ile Leu Lys Leu Arg Leu Tyr Glu Gln
                965              970              975

Gln His Gly Lys Cys Leu Tyr Ser Gly Lys Glu Ile Asn Leu Val Arg
            980              985              990

Leu Asn Glu Lys Gly Tyr Val Glu Ile Asp His Ala Leu Pro Phe Ser
        995              1000              1005

Arg Thr Trp Asp Asp Ser Phe Asn Asn Lys Val Leu Val Leu Gly
    1010              1015              1020

Ser Glu Asn Gln Asn Lys Gly Asn Gln Thr Pro Tyr Glu Tyr Phe
    1025              1030              1035

Asn Gly Lys Asp Asn Ser Arg Glu Trp Gln Glu Phe Lys Ala Arg
    1040              1045              1050

Val Glu Thr Ser Arg Phe Pro Arg Ser Lys Lys Gln Arg Ile Leu
    1055              1060              1065
```

```
Leu Gln Lys Phe Asp Glu Asp  Gly Phe Lys Glu Cys  Asn Leu Asn
    1070            1075           1080

Asp Thr Arg Tyr Val Asn Arg  Phe Leu Cys Gln Phe  Val Ala Asp
    1085            1090           1095

His Ile Leu Leu Thr Gly Lys  Gly Lys Arg Arg Val  Phe Ala Ser
    1100            1105           1110

Asn Gly Gln Ile Thr Asn Leu  Leu Arg Gly Phe Trp  Gly Leu Arg
    1115            1120           1125

Lys Val Arg Ala Glu Asn Asp  Arg His His Ala Leu  Asp Ala Val
    1130            1135           1140

Val Val Ala Cys Ser Thr Val  Ala Met Gln Gln Lys  Ile Thr Arg
    1145            1150           1155

Phe Val Arg Tyr Lys Glu Met  Asn Ala Phe Asp Gly  Lys Thr Ile
    1160            1165           1170

Asp Lys Glu Thr Gly Lys Val  Leu His Gln Lys Thr  His Phe Pro
    1175            1180           1185

Gln Pro Trp Glu Phe Phe Ala  Gln Glu Val Met Ile  Arg Val Phe
    1190            1195           1200

Gly Lys Pro Asp Gly Lys Pro  Glu Phe Glu Glu Ala  Asp Thr Pro
    1205            1210           1215

Glu Lys Leu Arg Thr Leu Leu  Ala Glu Lys Leu Ser  Ser Arg Pro
    1220            1225           1230

Glu Ala Val His Glu Tyr Val  Thr Pro Leu Phe Val  Ser Arg Ala
    1235            1240           1245

Pro Asn Arg Lys Met Ser Gly  Ala His Lys Asp Thr  Leu Arg Ser
    1250            1255           1260

Ala Lys Arg Phe Val Lys His  Asn Glu Lys Ile Ser  Val Lys Arg
    1265            1270           1275

Val Trp Leu Thr Glu Ile Lys  Leu Ala Asp Leu Glu  Asn Met Val
    1280            1285           1290

Asn Tyr Lys Asn Gly Arg Glu  Ile Glu Leu Tyr Glu  Ala Leu Lys
    1295            1300           1305

Ala Arg Leu Glu Ala Tyr Gly  Gly Asn Ala Lys Gln  Ala Phe Asp
    1310            1315           1320

Pro Lys Asp Asn Pro Phe Tyr  Lys Lys Gly Gly Gln  Leu Val Lys
    1325            1330           1335

Ala Val Arg Val Glu Lys Thr  Gln Glu Ser Gly Val  Leu Leu Asn
    1340            1345           1350

Lys Lys Asn Ala Tyr Thr Ile  Ala Asp Asn Gly Asp  Met Val Arg
    1355            1360           1365

Val Asp Val Phe Cys Lys Val  Asp Lys Lys Gly Lys  Asn Gln Tyr
    1370            1375           1380

Phe Ile Val Pro Ile Tyr Ala  Trp Gln Val Ala Glu  Asn Ile Leu
    1385            1390           1395

Pro Asp Ile Asp Cys Lys Gly  Tyr Arg Ile Asp Asp  Ser Tyr Thr
    1400            1405           1410

Phe Cys Phe Ser Leu His Lys  Tyr Asp Leu Ile Ala  Phe Gln Lys
    1415            1420           1425

Asp Glu Lys Ser Lys Val Glu  Phe Ala Tyr Tyr Ile  Asn Cys Asp
    1430            1435           1440

Ser Ser Asn Gly Arg Phe Tyr  Leu Ala Trp His Asp  Lys Gly Ser
    1445            1450           1455
```

```
Lys Glu  Gln Gln Phe Arg Ile  Ser Thr Gln Asn Leu  Val Leu Ile
    1460              1465              1470

Gln Lys  Tyr Gln Val Asn Glu  Leu Gly Lys Glu Ile  Arg Pro Cys
    1475              1480              1485

Arg Leu  Lys Lys Arg Pro Pro  Val Arg Glu Asp Lys  Arg Pro Ala
    1490              1495              1500

Ala Thr  Lys Lys Ala Gly Gln  Ala Lys Lys Lys  Phe Glu Pro
    1505              1510              1515

Lys Lys  Lys Arg Lys Val
    1520

<210> SEQ ID NO 6
<211> LENGTH: 1697
<212> TYPE: PRT
<213> ORGANISM: Artificial Sequence
<220> FEATURE:
<223> OTHER INFORMATION: Synthetic

<400> SEQUENCE: 6

Pro Ala Ala Lys Arg Val Lys Leu Asp Gly Gly Ser Gly Gly Gly Ser
1                5               10              15

Gly Gly Gly Ser Gly Pro Ala Ala Lys Arg Val Lys Leu Asp Gly Gly
           20              25              30

Ser Gly Gly Gly Ser Gly Gly Ser Gly Pro Leu Glu Pro Lys Lys
        35              40              45

Lys Arg Lys Val Pro Trp Ser Ser Glu Thr Gly Pro Val Ala Val Asp
    50              55              60

Pro Thr Leu Arg Arg Arg Ile Glu Pro His Glu Phe Glu Val Phe Phe
65              70              75              80

Asp Pro Arg Glu Leu Arg Lys Glu Thr Cys Leu Leu Tyr Glu Ile Asn
            85              90              95

Trp Gly Gly Arg His Ser Ile Trp Arg His Thr Ser Gln Asn Thr Asn
            100             105             110

Lys His Val Glu Val Asn Phe Ile Glu Lys Phe Thr Thr Glu Arg Tyr
        115             120             125

Phe Cys Pro Asn Thr Arg Cys Ser Ile Thr Trp Phe Leu Ser Trp Ser
    130             135             140

Pro Cys Gly Glu Cys Ser Arg Ala Ile Thr Glu Phe Leu Ser Arg Tyr
145             150             155             160

Pro His Val Thr Leu Phe Ile Tyr Ile Ala Arg Leu Tyr His His Ala
            165             170             175

Asp Pro Arg Asn Arg Gln Gly Leu Arg Asp Leu Ile Ser Ser Gly Val
            180             185             190

Thr Ile Gln Ile Met Thr Glu Gln Glu Ser Gly Tyr Cys Trp Arg Asn
        195             200             205

Phe Val Asn Tyr Ser Pro Ser Asn Glu Ala His Trp Pro Arg Tyr Pro
    210             215             220

His Leu Trp Val Arg Leu Tyr Val Leu Glu Leu Tyr Cys Ile Ile Leu
225             230             235             240

Gly Leu Pro Pro Cys Leu Asn Ile Leu Arg Arg Lys Gln Pro Gln Leu
            245             250             255

Thr Phe Phe Thr Ile Ala Leu Gln Ser Cys His Tyr Gln Arg Leu Pro
            260             265             270

Pro His Ile Leu Trp Ala Thr Gly Leu Lys Ser Gly Gly Ser Ser Gly
        275             280             285
```

-continued

```
Gly Ser Ser Gly Ser Glu Thr Pro Gly Thr Ser Glu Ser Ala Thr Pro
    290                 295                 300

Glu Ser Ser Gly Gly Ser Ser Gly Gly Ser Ile Asp Lys Leu Ala Ala
305                 310                 315                 320

Phe Lys Pro Asn Pro Ile Asn Tyr Ile Leu Gly Leu Ala Ile Gly Ile
                325                 330                 335

Ala Ser Val Gly Trp Ala Met Val Glu Ile Asp Glu Glu Glu Asn Pro
                340                 345                 350

Ile Arg Leu Ile Asp Leu Gly Val Arg Val Phe Glu Arg Ala Glu Val
            355                 360                 365

Pro Lys Thr Gly Asp Ser Leu Ala Met Ala Arg Arg Leu Ala Arg Ser
    370                 375                 380

Val Arg Arg Leu Thr Arg Arg Arg Ala His Arg Leu Leu Arg Ala Arg
385                 390                 395                 400

Arg Leu Leu Lys Arg Glu Gly Val Leu Gln Ala Ala Asp Phe Asp Glu
                405                 410                 415

Asn Gly Leu Ile Lys Ser Leu Pro Asn Thr Pro Trp Gln Leu Arg Ala
                420                 425                 430

Ala Ala Leu Asp Arg Lys Leu Thr Pro Leu Glu Trp Ser Ala Val Leu
                435                 440                 445

Leu His Leu Ile Lys His Arg Gly Tyr Leu Ser Gln Arg Lys Asn Glu
    450                 455                 460

Gly Glu Thr Ala Asp Lys Glu Leu Gly Ala Leu Leu Lys Gly Val Ala
465                 470                 475                 480

Asn Asn Ala His Ala Leu Gln Thr Gly Asp Phe Arg Thr Pro Ala Glu
                485                 490                 495

Leu Ala Leu Asn Lys Phe Glu Lys Glu Ser Gly His Ile Arg Asn Gln
                500                 505                 510

Arg Gly Asp Tyr Ser His Thr Phe Ser Arg Lys Asp Leu Gln Ala Glu
            515                 520                 525

Leu Ile Leu Leu Phe Glu Lys Gln Lys Glu Phe Gly Asn Pro His Val
    530                 535                 540

Ser Gly Gly Leu Lys Glu Gly Ile Glu Thr Leu Leu Met Thr Gln Arg
545                 550                 555                 560

Pro Ala Leu Ser Gly Asp Ala Val Gln Lys Met Leu Gly His Cys Thr
                565                 570                 575

Phe Glu Pro Ala Glu Pro Lys Ala Ala Lys Asn Thr Tyr Thr Ala Glu
                580                 585                 590

Arg Phe Ile Trp Leu Thr Lys Leu Asn Asn Leu Arg Ile Leu Glu Gln
            595                 600                 605

Gly Ser Glu Arg Pro Leu Thr Asp Thr Glu Arg Ala Thr Leu Met Asp
    610                 615                 620

Glu Pro Tyr Arg Lys Ser Lys Leu Thr Tyr Ala Gln Ala Arg Lys Leu
625                 630                 635                 640

Leu Gly Leu Glu Asp Thr Ala Phe Phe Lys Gly Leu Arg Tyr Gly Lys
                645                 650                 655

Asp Asn Ala Glu Ala Ser Thr Leu Met Glu Met Lys Ala Tyr His Ala
                660                 665                 670

Ile Ser Arg Ala Leu Glu Lys Glu Gly Leu Lys Asp Lys Lys Ser Pro
            675                 680                 685

Leu Asn Leu Ser Ser Glu Leu Gln Asp Glu Ile Gly Thr Ala Phe Ser
    690                 695                 700

Leu Phe Lys Thr Asp Glu Asp Ile Thr Gly Arg Leu Lys Asp Arg Val
```

-continued

```
705                 710                 715                 720
Gln Pro Glu Ile Leu Glu Ala Leu Leu Lys His Ile Ser Phe Asp Lys
                725                 730                 735
Phe Val Gln Ile Ser Leu Lys Ala Leu Arg Arg Ile Val Pro Leu Met
                740                 745                 750
Glu Gln Gly Lys Arg Tyr Asp Glu Ala Cys Ala Glu Ile Tyr Gly Asp
                755                 760                 765
His Tyr Gly Lys Lys Asn Thr Glu Glu Lys Ile Tyr Leu Pro Pro Ile
                770                 775                 780
Pro Ala Asp Glu Ile Arg Asn Pro Val Val Leu Arg Ala Leu Ser Gln
785                 790                 795                 800
Ala Arg Lys Val Ile Asn Gly Val Val Arg Arg Tyr Gly Ser Pro Ala
                805                 810                 815
Arg Ile His Ile Glu Thr Ala Arg Glu Val Gly Lys Ser Phe Lys Asp
                820                 825                 830
Arg Lys Glu Ile Glu Lys Arg Gln Glu Glu Asn Arg Lys Asp Arg Glu
                835                 840                 845
Lys Ala Ala Ala Lys Phe Arg Glu Tyr Phe Pro Asn Phe Val Gly Glu
            850                 855                 860
Pro Lys Ser Lys Asp Ile Leu Lys Leu Arg Leu Tyr Glu Gln Gln His
865                 870                 875                 880
Gly Lys Cys Leu Tyr Ser Gly Lys Glu Ile Asn Leu Val Arg Leu Asn
                885                 890                 895
Glu Lys Gly Tyr Val Glu Ile Asp His Ala Leu Pro Phe Ser Arg Thr
                900                 905                 910
Trp Asp Asp Ser Phe Asn Asn Lys Val Leu Val Leu Gly Ser Glu Asn
                915                 920                 925
Gln Asn Lys Gly Asn Gln Thr Pro Tyr Glu Tyr Phe Asn Gly Lys Asp
            930                 935                 940
Asn Ser Arg Glu Trp Gln Glu Phe Lys Ala Arg Val Glu Thr Ser Arg
945                 950                 955                 960
Phe Pro Arg Ser Lys Lys Gln Arg Ile Leu Leu Gln Lys Phe Asp Glu
                965                 970                 975
Asp Gly Phe Lys Glu Cys Asn Leu Asn Asp Thr Arg Tyr Val Asn Arg
            980                 985                 990
Phe Leu Cys Gln Phe Val Ala Asp  His Ile Leu Leu Thr  Gly Lys Gly
            995                 1000                 1005
Lys Arg  Arg Val Phe Ala Ser  Asn Gly Gln Ile Thr  Asn Leu Leu
    1010                 1015                 1020
Arg Gly  Phe Trp Gly Leu Arg  Lys Val Arg Ala Glu  Asn Asp Arg
    1025                 1030                 1035
His His  Ala Leu Asp Ala Val  Val Val Ala Cys Ser  Thr Val Ala
    1040                 1045                 1050
Met Gln  Gln Lys Ile Thr Arg  Phe Val Arg Tyr Lys  Glu Met Asn
    1055                 1060                 1065
Ala Phe  Asp Gly Lys Thr Ile  Asp Lys Glu Thr Gly  Lys Val Leu
    1070                 1075                 1080
His Gln  Lys Thr His Phe Pro  Gln Pro Trp Glu Phe  Phe Ala Gln
    1085                 1090                 1095
Glu Val  Met Ile Arg Val Phe  Gly Lys Pro Asp Gly  Lys Pro Glu
    1100                 1105                 1110
Phe Glu  Glu Ala Asp Thr Pro  Glu Lys Leu Arg Thr  Leu Leu Ala
    1115                 1120                 1125
```

-continued

```
Glu Lys Leu Ser Ser Arg Pro  Glu Ala Val His Glu  Tyr Val Thr
    1130            1135            1140

Pro Leu Phe Val Ser Arg Ala  Pro Asn Arg Lys Met  Ser Gly Ala
    1145            1150            1155

His Lys Asp Thr Leu Arg Ser  Ala Lys Arg Phe Val  Lys His Asn
    1160            1165            1170

Glu Lys Ile Ser Val Lys Arg  Val Trp Leu Thr Glu  Ile Lys Leu
    1175            1180            1185

Ala Asp Leu Glu Asn Met Val  Asn Tyr Lys Asn Gly  Arg Glu Ile
    1190            1195            1200

Glu Leu Tyr Glu Ala Leu Lys  Ala Arg Leu Glu Ala  Tyr Gly Gly
    1205            1210            1215

Asn Ala Lys Gln Ala Phe Asp  Pro Lys Asp Asn Pro  Phe Tyr Lys
    1220            1225            1230

Lys Gly Gly Gln Leu Val Lys  Ala Val Arg Val Glu  Lys Thr Gln
    1235            1240            1245

Glu Ser Gly Val Leu Leu Asn  Lys Lys Asn Ala Tyr  Thr Ile Ala
    1250            1255            1260

Asp Asn Gly Asp Met Val Arg  Val Asp Val Phe Cys  Lys Val Asp
    1265            1270            1275

Lys Lys Gly Lys Asn Gln Tyr  Phe Ile Val Pro Ile  Tyr Ala Trp
    1280            1285            1290

Gln Val Ala Glu Asn Ile Leu  Pro Asp Ile Asp Cys  Lys Gly Tyr
    1295            1300            1305

Arg Ile Asp Asp Ser Tyr Thr  Phe Cys Phe Ser Leu  His Lys Tyr
    1310            1315            1320

Asp Leu Ile Ala Phe Gln Lys  Asp Glu Lys Ser Lys  Val Glu Phe
    1325            1330            1335

Ala Tyr Tyr Ile Asn Cys Asp  Ser Ser Asn Gly Arg  Phe Tyr Leu
    1340            1345            1350

Ala Trp His Asp Lys Gly Ser  Lys Glu Gln Gln Phe  Arg Ile Ser
    1355            1360            1365

Thr Gln Asn Leu Val Leu Ile  Gln Lys Tyr Gln Val  Asn Glu Leu
    1370            1375            1380

Gly Lys Glu Ile Arg Pro Cys  Arg Leu Lys Lys Arg  Pro Pro Val
    1385            1390            1395

Arg Val Tyr Pro Tyr Asp Val  Pro Asp Tyr Ala Gly  Tyr Pro Tyr
    1400            1405            1410

Asp Val Pro Asp Tyr Ala Gly  Ser Tyr Pro Tyr Asp  Val Pro Asp
    1415            1420            1425

Tyr Ala Gly Ser Ala Ala Pro  Ala Ala Lys Lys Lys  Lys Leu Asp
    1430            1435            1440

Phe Glu Ser Gly Glu Phe Leu  Gln Pro Gly Ile Asp  Leu Ser Gln
    1445            1450            1455

Leu Gly Gly Asp Ser Gly Gly  Ser Gly Gly Ser Gly  Gly Ser Thr
    1460            1465            1470

Asn Leu Ser Asp Ile Ile Glu  Lys Glu Thr Gly Lys  Gln Leu Val
    1475            1480            1485

Ile Gln Glu Ser Ile Leu Met  Leu Pro Glu Glu Val  Glu Glu Val
    1490            1495            1500

Ile Gly Asn Lys Pro Glu Ser  Asp Ile Leu Val His  Thr Ala Tyr
    1505            1510            1515
```

-continued

```
Asp Glu  Ser Thr Asp Glu Asn  Val Met Leu Leu Thr  Ser Asp Ala
    1520              1525              1530

Pro Glu  Tyr Lys Pro Trp Ala  Leu Val Ile Gln Asp  Ser Asn Gly
    1535              1540              1545

Glu Asn  Lys Ile Lys Met Leu  Ser Gly Gly Ser Gly  Gly Ser Gly
    1550              1555              1560

Gly Ser  Thr Asn Leu Ser Asp  Ile Ile Glu Lys Glu  Thr Gly Lys
    1565              1570              1575

Gln Leu  Val Ile Gln Glu Ser  Ile Leu Met Leu Pro  Glu Glu Val
    1580              1585              1590

Glu Glu  Val Ile Gly Asn Lys  Pro Glu Ser Asp Ile  Leu Val His
    1595              1600              1605

Thr Ala  Tyr Asp Glu Ser Thr  Asp Glu Asn Val Met  Leu Leu Thr
    1610              1615              1620

Ser Asp  Ala Pro Glu Tyr Lys  Pro Trp Ala Leu Val  Ile Gln Asp
    1625              1630              1635

Ser Asn  Gly Glu Asn Lys Ile  Lys Met Leu Ser Gly  Gly Ser Pro
    1640              1645              1650

Lys Lys  Lys Arg Lys Val Ser  Arg Gly Ser Ala Ala  Pro Ala Ala
    1655              1660              1665

Lys Arg  Val Lys Leu Asp Gly  Gly Ser Gly Gly Gly  Ser Gly Gly
    1670              1675              1680

Gly Ser  Gly Ser Gly Pro Ala  Ala Lys Arg Val Lys  Leu Asp
    1685              1690              1695

<210> SEQ ID NO 7
<211> LENGTH: 1641
<212> TYPE: PRT
<213> ORGANISM: Artificial Sequence
<220> FEATURE:
<223> OTHER INFORMATION: Synthetic

<400> SEQUENCE: 7

Pro Ala Ala Lys Arg Val Lys Leu Asp Gly Gly Ser Gly Gly Gly Ser
1               5                   10                  15

Gly Gly Gly Ser Gly Pro Ala Ala Lys Arg Val Lys Leu Asp Gly Gly
            20                  25                  30

Ser Gly Gly Gly Ser Gly Gly Gly Ser Gly Pro Leu Glu Pro Lys Lys
        35                  40                  45

Lys Arg Lys Val Ser Glu Val Glu Phe Ser His Glu Tyr Trp Met Arg
    50                  55                  60

His Ala Leu Thr Leu Ala Lys Arg Ala Trp Asp Glu Arg Glu Val Pro
65                  70                  75                  80

Val Gly Ala Val Leu Val His Asn Asn Arg Val Ile Gly Glu Gly Trp
                85                  90                  95

Asn Arg Pro Ile Gly Arg His Asp Pro Thr Ala His Ala Glu Ile Met
            100                 105                 110

Ala Leu Arg Gln Gly Gly Leu Val Met Gln Asn Tyr Arg Leu Ile Asp
        115                 120                 125

Ala Thr Leu Tyr Val Thr Leu Glu Pro Cys Val Met Cys Ala Gly Ala
    130                 135                 140

Met Ile His Ser Arg Ile Gly Arg Val Val Phe Gly Ala Arg Asp Ala
145                 150                 155                 160

Lys Thr Gly Ala Ala Gly Ser Leu Met Asp Val Leu His His Pro Gly
                165                 170                 175
```

-continued

```
Met Asn His Arg Val Glu Ile Thr Glu Gly Ile Leu Ala Asp Glu Cys
            180             185             190

Ala Ala Leu Leu Ser Asp Phe Phe Arg Met Arg Arg Gln Glu Ile Lys
            195             200             205

Ala Gln Lys Lys Ala Gln Ser Ser Thr Asp Ser Gly Gly Ser Ser Gly
    210             215             220

Gly Ser Ser Gly Ser Glu Thr Pro Gly Thr Ser Glu Ser Ala Thr Pro
225             230             235             240

Glu Ser Ser Gly Gly Ser Ser Gly Gly Ser Ser Glu Val Glu Phe Ser
            245             250             255

His Glu Tyr Trp Met Arg His Ala Leu Thr Leu Ala Lys Arg Ala Arg
            260             265             270

Asp Glu Arg Glu Val Pro Val Gly Ala Val Leu Val Leu Asn Asn Arg
            275             280             285

Val Ile Gly Glu Gly Trp Asn Arg Ala Ile Gly Leu His Asp Pro Thr
    290             295             300

Ala His Ala Glu Ile Met Ala Leu Arg Gln Gly Gly Leu Val Met Gln
305             310             315             320

Asn Tyr Arg Leu Ile Asp Ala Thr Leu Tyr Val Thr Phe Glu Pro Cys
            325             330             335

Val Met Cys Ala Gly Ala Met Ile His Ser Arg Ile Gly Arg Val Val
            340             345             350

Phe Gly Val Arg Asn Ala Lys Thr Gly Ala Ala Gly Ser Leu Met Asp
            355             360             365

Val Leu His Tyr Pro Gly Met Asn His Arg Val Glu Ile Thr Glu Gly
            370             375             380

Ile Leu Ala Asp Glu Cys Ala Ala Leu Leu Cys Tyr Phe Phe Arg Met
385             390             395             400

Pro Arg Gln Val Phe Asn Ala Gln Lys Lys Ala Gln Ser Ser Thr Asp
            405             410             415

Ser Gly Gly Ser Ser Gly Gly Ser Ser Gly Ser Glu Thr Pro Gly Thr
            420             425             430

Ser Glu Ser Ala Thr Pro Glu Ser Ser Gly Gly Ser Ser Gly Gly Ser
            435             440             445

Met Ala Ala Phe Lys Pro Asn Pro Ile Asn Tyr Asp Ile Asp Lys Leu
    450             455             460

Ala Ala Phe Lys Pro Asn Pro Ile Asn Tyr Ile Leu Gly Leu Ala Ile
465             470             475             480

Gly Ile Ala Ser Val Gly Trp Ala Met Val Glu Ile Asp Glu Glu Glu
            485             490             495

Asn Pro Ile Arg Leu Ile Asp Leu Gly Val Arg Val Phe Glu Arg Ala
            500             505             510

Glu Val Pro Lys Thr Gly Asp Ser Leu Ala Met Ala Arg Arg Leu Ala
            515             520             525

Arg Ser Val Arg Arg Leu Thr Arg Arg Arg Ala His Arg Leu Leu Arg
    530             535             540

Ala Arg Arg Leu Leu Lys Arg Glu Gly Val Leu Gln Ala Ala Asp Phe
545             550             555             560

Asp Glu Asn Gly Leu Ile Lys Ser Leu Pro Asn Thr Pro Trp Gln Leu
            565             570             575

Arg Ala Ala Ala Leu Asp Arg Lys Leu Thr Pro Leu Glu Trp Ser Ala
            580             585             590

Val Leu Leu His Leu Ile Lys His Arg Gly Tyr Leu Ser Gln Arg Lys
```

-continued

```
          595                   600                   605

Asn Glu Gly Glu Thr Ala Asp Lys Glu Leu Gly Ala Leu Leu Lys Gly
    610                   615                   620

Val Ala Asn Asn Ala His Ala Leu Gln Thr Gly Asp Phe Arg Thr Pro
625                   630                   635                   640

Ala Glu Leu Ala Leu Asn Lys Phe Glu Lys Glu Ser Gly His Ile Arg
                    645                   650                   655

Asn Gln Arg Gly Asp Tyr Ser His Thr Phe Ser Arg Lys Asp Leu Gln
                    660                   665                   670

Ala Glu Leu Ile Leu Leu Phe Glu Lys Gln Lys Glu Phe Gly Asn Pro
                    675                   680                   685

His Val Ser Gly Gly Leu Lys Glu Gly Ile Glu Thr Leu Leu Met Thr
                    690                   695                   700

Gln Arg Pro Ala Leu Ser Gly Asp Ala Val Gln Lys Met Leu Gly His
705                   710                   715                   720

Cys Thr Phe Glu Pro Ala Glu Pro Lys Ala Ala Lys Asn Thr Tyr Thr
                    725                   730                   735

Ala Glu Arg Phe Ile Trp Leu Thr Lys Leu Asn Asn Leu Arg Ile Leu
                    740                   745                   750

Glu Gln Gly Ser Glu Arg Pro Leu Thr Asp Thr Glu Arg Ala Thr Leu
                    755                   760                   765

Met Asp Glu Pro Tyr Arg Lys Ser Lys Leu Thr Tyr Ala Gln Ala Arg
                    770                   775                   780

Lys Leu Leu Gly Leu Glu Asp Thr Ala Phe Phe Lys Gly Leu Arg Tyr
785                   790                   795                   800

Gly Lys Asp Asn Ala Glu Ala Ser Thr Leu Met Glu Met Lys Ala Tyr
                    805                   810                   815

His Ala Ile Ser Arg Ala Leu Glu Lys Glu Gly Leu Lys Asp Lys Lys
                    820                   825                   830

Ser Pro Leu Asn Leu Ser Ser Glu Leu Gln Asp Glu Ile Gly Thr Ala
                    835                   840                   845

Phe Ser Leu Phe Lys Thr Asp Glu Asp Ile Thr Gly Arg Leu Lys Asp
    850                   855                   860

Arg Val Gln Pro Glu Ile Leu Glu Ala Leu Leu Lys His Ile Ser Phe
865                   870                   875                   880

Asp Lys Phe Val Gln Ile Ser Leu Lys Ala Leu Arg Arg Ile Val Pro
                    885                   890                   895

Leu Met Glu Gln Gly Lys Arg Tyr Asp Glu Ala Cys Ala Glu Ile Tyr
                    900                   905                   910

Gly Asp His Tyr Gly Lys Lys Asn Thr Glu Glu Lys Ile Tyr Leu Pro
                    915                   920                   925

Pro Ile Pro Ala Asp Glu Ile Arg Asn Pro Val Val Leu Arg Ala Leu
    930                   935                   940

Ser Gln Ala Arg Lys Val Ile Asn Gly Val Val Arg Arg Tyr Gly Ser
945                   950                   955                   960

Pro Ala Arg Ile His Ile Glu Thr Ala Arg Glu Val Gly Lys Ser Phe
                    965                   970                   975

Lys Asp Arg Lys Glu Ile Glu Lys Arg Gln Glu Glu Asn Arg Lys Asp
                    980                   985                   990

Arg Glu Lys Ala Ala Ala Lys Phe  Arg Glu Tyr Phe Pro  Asn Phe Val
                    995                   1000                   1005

Gly Glu  Pro Lys Ser Lys Asp  Ile Leu Lys Leu Arg  Leu Tyr Glu
    1010                   1015                   1020
```

-continued

```
Gln Gln His Gly Lys Cys Leu  Tyr Ser Gly Lys Glu  Ile Asn Leu
    1025            1030           1035

Val Arg Leu Asn Glu Lys Gly  Tyr Val Glu Ile Asp  His Ala Leu
    1040            1045           1050

Pro Phe Ser Arg Thr Trp Asp  Asp Ser Phe Asn Asn  Lys Val Leu
    1055            1060           1065

Val Leu Gly Ser Glu Asn Gln  Asn Lys Gly Asn Gln  Thr Pro Tyr
    1070            1075           1080

Glu Tyr Phe Asn Gly Lys Asp  Asn Ser Arg Glu Trp  Gln Glu Phe
    1085            1090           1095

Lys Ala Arg Val Glu Thr Ser  Arg Phe Pro Arg Ser  Lys Lys Gln
    1100            1105           1110

Arg Ile Leu Leu Gln Lys Phe  Asp Glu Asp Gly Phe  Lys Glu Cys
    1115            1120           1125

Asn Leu Asn Asp Thr Arg Tyr  Val Asn Arg Phe Leu  Cys Gln Phe
    1130            1135           1140

Val Ala Asp His Ile Leu Leu  Thr Gly Lys Gly Lys  Arg Arg Val
    1145            1150           1155

Phe Ala Ser Asn Gly Gln Ile  Thr Asn Leu Leu Arg  Gly Phe Trp
    1160            1165           1170

Gly Leu Arg Lys Val Arg Ala  Glu Asn Asp Arg His  His Ala Leu
    1175            1180           1185

Asp Ala Val Val Val Ala Cys  Ser Thr Val Ala Met  Gln Gln Lys
    1190            1195           1200

Ile Thr Arg Phe Val Arg Tyr  Lys Glu Met Asn Ala  Phe Asp Gly
    1205            1210           1215

Lys Thr Ile Asp Lys Glu Thr  Gly Lys Val Leu His  Gln Lys Thr
    1220            1225           1230

His Phe Pro Gln Pro Trp Glu  Phe Phe Ala Gln Glu  Val Met Ile
    1235            1240           1245

Arg Val Phe Gly Lys Pro Asp  Gly Lys Pro Glu Phe  Glu Glu Ala
    1250            1255           1260

Asp Thr Pro Glu Lys Leu Arg  Thr Leu Leu Ala Glu  Lys Leu Ser
    1265            1270           1275

Ser Arg Pro Glu Ala Val His  Glu Tyr Val Thr Pro  Leu Phe Val
    1280            1285           1290

Ser Arg Ala Pro Asn Arg Lys  Met Ser Gly Ala His  Lys Asp Thr
    1295            1300           1305

Leu Arg Ser Ala Lys Arg Phe  Val Lys His Asn Glu  Lys Ile Ser
    1310            1315           1320

Val Lys Arg Val Trp Leu Thr  Glu Ile Lys Leu Ala  Asp Leu Glu
    1325            1330           1335

Asn Met Val Asn Tyr Lys Asn  Gly Arg Glu Ile Glu  Leu Tyr Glu
    1340            1345           1350

Ala Leu Lys Ala Arg Leu Glu  Ala Tyr Gly Gly Asn  Ala Lys Gln
    1355            1360           1365

Ala Phe Asp Pro Lys Asp Asn  Pro Phe Tyr Lys Lys  Gly Gly Gln
    1370            1375           1380

Leu Val Lys Ala Val Arg Val  Glu Lys Thr Gln Glu  Ser Gly Val
    1385            1390           1395

Leu Leu Asn Lys Lys Asn Ala  Tyr Thr Ile Ala Asp  Asn Gly Asp
    1400            1405           1410
```

-continued

```
Met Val  Arg Val Asp Val Phe  Cys Lys Val Asp Lys  Lys Gly Lys
    1415              1420              1425

Asn Gln  Tyr Phe Ile Val Pro  Ile Tyr Ala Trp Gln  Val Ala Glu
    1430              1435              1440

Asn Ile  Leu Pro Asp Ile Asp  Cys Lys Gly Tyr Arg  Ile Asp Asp
    1445              1450              1455

Ser Tyr  Thr Phe Cys Phe Ser  Leu His Lys Tyr Asp  Leu Ile Ala
    1460              1465              1470

Phe Gln  Lys Asp Glu Lys Ser  Lys Val Glu Phe Ala  Tyr Tyr Ile
    1475              1480              1485

Asn Cys  Asp Ser Ser Asn Gly  Arg Phe Tyr Leu Ala  Trp His Asp
    1490              1495              1500

Lys Gly  Ser Lys Glu Gln Gln  Phe Arg Ile Ser Thr  Gln Asn Leu
    1505              1510              1515

Val Leu  Ile Gln Lys Tyr Gln  Val Asn Glu Leu Gly  Lys Glu Ile
    1520              1525              1530

Arg Pro  Cys Arg Leu Lys Lys  Arg Pro Pro Val Arg  Val Tyr Pro
    1535              1540              1545

Tyr Asp  Val Pro Asp Tyr Ala  Gly Tyr Pro Tyr Asp  Val Pro Asp
    1550              1555              1560

Tyr Ala  Gly Ser Tyr Pro Tyr  Asp Val Pro Asp Tyr  Ala Gly Ser
    1565              1570              1575

Ala Ala  Pro Ala Ala Lys Lys  Lys Lys Leu Asp Phe  Glu Ser Gly
    1580              1585              1590

Glu Phe  Leu Gln Pro Gly Gly  Ser Thr Ser Ser Arg  Gly Ser Ala
    1595              1600              1605

Ala Pro  Ala Ala Lys Arg Val  Lys Leu Asp Gly Gly  Ser Gly Gly
    1610              1615              1620

Gly Ser  Gly Gly Gly Ser Gly  Ser Gly Pro Ala Ala  Lys Arg Val
    1625              1630              1635

Lys Leu  Asp
    1640
```

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
ggttctgggt acttttatct gtcc                                                24

<210> SEQ ID NO 9
<211> LENGTH: 8
<212> TYPE: DNA
<213> ORGANISM: Artificial Sequence
<220> FEATURE:
<223> OTHER INFORMATION: Synthetic

<400> SEQUENCE: 9 cctccacc                                                                   8

<210> SEQ ID NO 10
<211> LENGTH: 19
<212> TYPE: DNA
<213> ORGANISM: Artificial Sequence
<220> FEATURE:
<223> OTHER INFORMATION: Synthetic -continued

<400> SEQUENCE: 10
tggcttagca cctctccat                                                    19

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
agaactcagg accaacttat tctg                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
gtctgcctaa caggaggtgg gggt                                              24

<210> SEQ ID NO 13
<211> LENGTH: 8
<212> TYPE: DNA
<213> ORGANISM: Artificial Sequence
<220> FEATURE:
<223> OTHER INFORMATION: Synthetic

<400> SEQUENCE: 13 tagacgaa                                                                8

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
tggcttagca cctctccat                                                    19

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
agaactcagg accaacttat tctg                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
gaatatcagg agactaggaa ggag                                              24

<210> SEQ ID NO 17

-continued

```
<211> LENGTH: 8
<212> TYPE: DNA
<213> ORGANISM: Artificial Sequence
<220> FEATURE:
<223> OTHER INFORMATION: Synthetic

<400> SEQUENCE: 17 gaggccta                                                              8

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18
tggcttagca cctctccat                                                  19

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
agaactcagg accaacttat tctg                                            24

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
gcctccctgc agggctgctc cc                                              22

<210> SEQ ID NO 21
<211> LENGTH: 8
<212> TYPE: DNA
<213> ORGANISM: Artificial Sequence
<220> FEATURE:
<223> OTHER INFORMATION: Synthetic

<400> SEQUENCE: 21 cagcccaa                                                              8

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
aggagccttc tgactgctgc a                                               21

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
```

```
atgacagaca caaccagagg gca                                            23

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
gagctagtct tcttcctcca accc                                           24

<210> SEQ ID NO 25
<211> LENGTH: 8
<212> TYPE: DNA
<213> ORGANISM: Artificial Sequence
<220> FEATURE:
<223> OTHER INFORMATION: Synthetic

<400> SEQUENCE: 25 gggcccta                                                              8

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
tggcttagca cctctccat                                                 19

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
agaactcagg accaacttat tctg                                           24

<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
gatctgtccc ctccacccca cagt                                           24

<210> SEQ ID NO 29
<211> LENGTH: 8
<212> TYPE: DNA
<213> ORGANISM: Artificial Sequence
<220> FEATURE:
<223> OTHER INFORMATION: Synthetic

<400> SEQUENCE: 29 ggggccac                                                              8

<210> SEQ ID NO 30
<211> LENGTH: 19
<212> TYPE: DNA
```

<213> ORGANISM: Artificial Sequence
<220> FEATURE:
<223> OTHER INFORMATION: Synthetic

<400> SEQUENCE: 30
tggcttagca cctctccat                                                                    19

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
agaactcagg accaacttat tctg                                                               24

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
ggcccaaatg aaaggagtga gagg                                                               24

<210> SEQ ID NO 33
<211> LENGTH: 8
<212> TYPE: DNA
<213> ORGANISM: Artificial Sequence
<220> FEATURE:
<223> OTHER INFORMATION: Synthetic

<400> SEQUENCE: 33 tgacccga                                                                                 8

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
tccgtcttcc tccactcc                                                                      18

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
taggaaggag gaggcctaag                                                                    20

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
gcatcctctt gctttctttg cctg                                                               24

```
<210> SEQ ID NO 37
<211> LENGTH: 8
<212> TYPE: DNA
<213> ORGANISM: Artificial Sequence
<220> FEATURE:
<223> OTHER INFORMATION: Synthetic

<400> SEQUENCE: 37 gacacccc                                                                  8

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38
tccgtcttcc tccactcc                                                      18

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
taggaaggag gaggcctaag                                                    20

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
ggagtcgcca gaggccggtg gtgg                                               24

<210> SEQ ID NO 41
<211> LENGTH: 8
<212> TYPE: DNA
<213> ORGANISM: Artificial Sequence
<220> FEATURE:
<223> OTHER INFORMATION: Synthetic

<400> SEQUENCE: 41 atttcctc                                                                  8

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
aggagccttc tgactgctgc a                                                  21

<210> SEQ ID NO 43
<211> LENGTH: 23
<212> TYPE: DNA
<213> ORGANISM: Artificial Sequence
<220> FEATURE:
```

<223> OTHER INFORMATION: Synthetic

<400> SEQUENCE: 43
atgacagaca caaccagagg gca                                                                                23

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
gcccagcggc cggatatcag ctgc                                                                               24

<210> SEQ ID NO 45
<211> LENGTH: 8
<212> TYPE: DNA
<213> ORGANISM: Artificial Sequence
<220> FEATURE:
<223> OTHER INFORMATION: Synthetic

<400> SEQUENCE: 45 cacgcccg                                                                                                 8

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
aggagccttc tgactgctgc a                                                                                  21

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
atgacagaca caaccagagg gca                                                                                23

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
ggaagggaac atattactat tgc                                                                                23

<210> SEQ ID NO 49
<211> LENGTH: 8
<212> TYPE: DNA
<213> ORGANISM: Artificial Sequence
<220> FEATURE:
<223> OTHER INFORMATION: Synthetic

<400> SEQUENCE: 49 tttccctc                                                                                                 8

-continued

```
<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
tagagaactg ggtagtgtg                                                  19

<210> SEQ ID NO 51
<211> LENGTH: 19
<212> TYPE: DNA
<213> ORGANISM: Artificial Sequence
<220> FEATURE:
<223> OTHER INFORMATION: Synthetic

<400> SEQUENCE: 51
ccaatattgc atgggatgg                                                  19

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
gtggagtggc ctgctatcag ctac                                            24

<210> SEQ ID NO 53
<211> LENGTH: 8
<212> TYPE: DNA
<213> ORGANISM: Artificial Sequence
<220> FEATURE:
<223> OTHER INFORMATION: Synthetic

<400> SEQUENCE: 53 ctatccaa                                                              8

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
tagagaactg ggtagtgtg                                                  19

<210> SEQ ID NO 55
<211> LENGTH: 19
<212> TYPE: DNA
<213> ORGANISM: Artificial Sequence
<220> FEATURE:
<223> OTHER INFORMATION: Synthetic

<400> SEQUENCE: 55
ccaatattgc atgggatgg                                                  19

<210> SEQ ID NO 56
<211> LENGTH: 24
<212> TYPE: DNA
<213> ORGANISM: Artificial Sequence
<220> FEATURE:
<223> OTHER INFORMATION: Synthetic
```

-continued

<400> SEQUENCE: 56
gaggaaggga acatattact attg                                                    24

<210> SEQ ID NO 57
<211> LENGTH: 8
<212> TYPE: DNA
<213> ORGANISM: Artificial Sequence
<220> FEATURE:
<223> OTHER INFORMATION: Synthetic

<400> SEQUENCE: 57 ctttccct                                                                      8

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
tagagaactg ggtagtgtg                                                          19

<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
ccaatattgc atgggatgg                                                          19

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60
gtgaattctc atcagctaaa atgc                                                    24

<210> SEQ ID NO 61
<211> LENGTH: 8
<212> TYPE: DNA
<213> ORGANISM: Artificial Sequence
<220> FEATURE:
<223> OTHER INFORMATION: Synthetic

<400> SEQUENCE: 61 caagcctt                                                                      8

<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
tagagaactg ggtagtgtg                                                          19

<210> SEQ ID NO 63
<211> LENGTH: 19

-continued

```
<212> TYPE: DNA
<213> ORGANISM: Artificial Sequence
<220> FEATURE:
<223> OTHER INFORMATION: Synthetic

<400> SEQUENCE: 63
ccaatattgc atgggatgg                                           19

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gctcactcac ccacacagac acac                                     24

<210> SEQ ID NO 65
<211> LENGTH: 8
<212> TYPE: DNA
<213> ORGANISM: Artificial Sequence
<220> FEATURE:
<223> OTHER INFORMATION: Synthetic

<400> SEQUENCE: 65 acgtcctc                                                        8

<210> SEQ ID NO 66
<211> LENGTH: 22
<212> TYPE: DNA
<213> ORGANISM: Artificial Sequence
<220> FEATURE:
<223> OTHER INFORMATION: Synthetic

<400> SEQUENCE: 66
tacatgaagc aactccagtc cc                                        22

<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
atcaaattcc agcaccgagc gc                                        22

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
ggaagaattt cattctgttc tcag                                      24

<210> SEQ ID NO 69
<211> LENGTH: 8
<212> TYPE: DNA
<213> ORGANISM: Artificial Sequence
<220> FEATURE:
<223> OTHER INFORMATION: Synthetic

<400> SEQUENCE: 69
``` ttttcctg                                                          8

<210> SEQ ID NO 70
<211> LENGTH: 22
<212> TYPE: DNA
<213> ORGANISM: Artificial Sequence
<220> FEATURE:
<223> OTHER INFORMATION: Synthetic

<400> SEQUENCE: 70
ggtgattatg ggagaactgg ag                                          22

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
accattgagg acgtttgtct cac                                         23

<210> SEQ ID NO 72
<211> LENGTH: 24
<212> TYPE: DNA
<213> ORGANISM: Artificial Sequence
<220> FEATURE:
<223> OTHER INFORMATION: Synthetic

<400> SEQUENCE: 72
gctcagtttt cctggattat gcct                                        24

<210> SEQ ID NO 73
<211> LENGTH: 8
<212> TYPE: DNA
<213> ORGANISM: Artificial Sequence
<220> FEATURE:
<223> OTHER INFORMATION: Synthetic

<400> SEQUENCE: 73 ggcaccat                                                          8

<210> SEQ ID NO 74
<211> LENGTH: 22
<212> TYPE: DNA
<213> ORGANISM: Artificial Sequence
<220> FEATURE:
<223> OTHER INFORMATION: Synthetic

<400> SEQUENCE: 74
ggtgattatg ggagaactgg ag                                          22

<210> SEQ ID NO 75
<211> LENGTH: 23
<212> TYPE: DNA
<213> ORGANISM: Artificial Sequence
<220> FEATURE:
<223> OTHER INFORMATION: Synthetic

<400> SEQUENCE: 75
accattgagg acgtttgtct cac                                         23

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
gcgttggagc ggggagaagg ccag                                              24

<210> SEQ ID NO 77
<211> LENGTH: 8
<212> TYPE: DNA
<213> ORGANISM: Artificial Sequence
<220> FEATURE:
<223> OTHER INFORMATION: Synthetic

<400> SEQUENCE: 77 gggtcact                                                                8

<210> SEQ ID NO 78
<211> LENGTH: 22
<212> TYPE: DNA
<213> ORGANISM: Artificial Sequence
<220> FEATURE:
<223> OTHER INFORMATION: Synthetic

<400> SEQUENCE: 78
tacatgaagc aactccagtc cc                                                22

<210> SEQ ID NO 79
<211> LENGTH: 22
<212> TYPE: DNA
<213> ORGANISM: Artificial Sequence
<220> FEATURE:
<223> OTHER INFORMATION: Synthetic

<400> SEQUENCE: 79
atcaaattcc agcaccgagc gc                                                22

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80
gggccgcgga gatagctgca gggc                                              24

<210> SEQ ID NO 81
<211> LENGTH: 8
<212> TYPE: DNA
<213> ORGANISM: Artificial Sequence
<220> FEATURE:
<223> OTHER INFORMATION: Synthetic

<400> SEQUENCE: 81 ggggcccc                                                                8

<210> SEQ ID NO 82
<211> LENGTH: 21
<212> TYPE: DNA
<213> ORGANISM: Artificial Sequence
<220> FEATURE:
<223> OTHER INFORMATION: Synthetic

<400> SEQUENCE: 82
aggagccttc tgactgctgc a                                                 21

-continued

```
<210> SEQ ID NO 83
<211> LENGTH: 23
<212> TYPE: DNA
<213> ORGANISM: Artificial Sequence
<220> FEATURE:
<223> OTHER INFORMATION: Synthetic

<400> SEQUENCE: 83
atgacagaca caaccagagg gca                                               23

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84
gcccacccgg cggcgcctcc ctgc                                              24

<210> SEQ ID NO 85
<211> LENGTH: 8
<212> TYPE: DNA
<213> ORGANISM: Artificial Sequence
<220> FEATURE:
<223> OTHER INFORMATION: Synthetic

<400> SEQUENCE: 85 agggctgc                                                                8

<210> SEQ ID NO 86
<211> LENGTH: 21
<212> TYPE: DNA
<213> ORGANISM: Artificial Sequence
<220> FEATURE:
<223> OTHER INFORMATION: Synthetic

<400> SEQUENCE: 86
aggagccttc tgactgctgc a                                                 21

<210> SEQ ID NO 87
<211> LENGTH: 23
<212> TYPE: DNA
<213> ORGANISM: Artificial Sequence
<220> FEATURE:
<223> OTHER INFORMATION: Synthetic

<400> SEQUENCE: 87
atgacagaca caaccagagg gca                                               23

<210> SEQ ID NO 88
<211> LENGTH: 24
<212> TYPE: DNA
<213> ORGANISM: Artificial Sequence
<220> FEATURE:
<223> OTHER INFORMATION: Synthetic

<400> SEQUENCE: 88
gcgtggcagc tgatatccgg ccgc                                              24

<210> SEQ ID NO 89
<211> LENGTH: 8
<212> TYPE: DNA
<213> ORGANISM: Artificial Sequence
<220> FEATURE:
<223> OTHER INFORMATION: Synthetic
```

-continued

```
<400> SEQUENCE: 89 tgggcgtc                                                                 8

<210> SEQ ID NO 90
<211> LENGTH: 21
<212> TYPE: DNA
<213> ORGANISM: Artificial Sequence
<220> FEATURE:
<223> OTHER INFORMATION: Synthetic

<400> SEQUENCE: 90
aggagccttc tgactgctgc a                                                 21

<210> SEQ ID NO 91
<211> LENGTH: 23
<212> TYPE: DNA
<213> ORGANISM: Artificial Sequence
<220> FEATURE:
<223> OTHER INFORMATION: Synthetic

<400> SEQUENCE: 91
atgacagaca caaccagagg gca                                               23

<210> SEQ ID NO 92
<211> LENGTH: 24
<212> TYPE: DNA
<213> ORGANISM: Artificial Sequence
<220> FEATURE:
<223> OTHER INFORMATION: Synthetic

<400> SEQUENCE: 92
gccgcggcgc gacgtggagc cagc                                             24

<210> SEQ ID NO 93
<211> LENGTH: 8
<212> TYPE: DNA
<213> ORGANISM: Artificial Sequence
<220> FEATURE:
<223> OTHER INFORMATION: Synthetic

<400> SEQUENCE: 93 cccgcaaa                                                                 8

<210> SEQ ID NO 94
<211> LENGTH: 21
<212> TYPE: DNA
<213> ORGANISM: Artificial Sequence
<220> FEATURE:
<223> OTHER INFORMATION: Synthetic

<400> SEQUENCE: 94
aggagccttc tgactgctgc a                                                 21

<210> SEQ ID NO 95
<211> LENGTH: 23
<212> TYPE: DNA
<213> ORGANISM: Artificial Sequence
<220> FEATURE:
<223> OTHER INFORMATION: Synthetic

<400> SEQUENCE: 95
atgacagaca caaccagagg gca                                               23

<210> SEQ ID NO 96
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 96
gtgctcccca gcccaaaccg ccgc                                            24

<210> SEQ ID NO 97
<211> LENGTH: 8
<212> TYPE: DNA
<213> ORGANISM: Artificial Sequence
<220> FEATURE:
<223> OTHER INFORMATION: Synthetic

<400> SEQUENCE: 97 ggcgcgac                                                             8

<210> SEQ ID NO 98
<211> LENGTH: 21
<212> TYPE: DNA
<213> ORGANISM: Artificial Sequence
<220> FEATURE:
<223> OTHER INFORMATION: Synthetic

<400> SEQUENCE: 98
aggagccttc tgactgctgc a                                              21

<210> SEQ ID NO 99
<211> LENGTH: 23
<212> TYPE: DNA
<213> ORGANISM: Artificial Sequence
<220> FEATURE:
<223> OTHER INFORMATION: Synthetic

<400> SEQUENCE: 99
atgacagaca caaccagagg gca                                            23

<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100
gtcagattgg cttgctcgga attg                                           24

<210> SEQ ID NO 101
<211> LENGTH: 8
<212> TYPE: DNA
<213> ORGANISM: Artificial Sequence
<220> FEATURE:
<223> OTHER INFORMATION: Synthetic

<400> SEQUENCE: 101 ccagccaa                                                             8

<210> SEQ ID NO 102
<211> LENGTH: 21
<212> TYPE: DNA
<213> ORGANISM: Artificial Sequence
<220> FEATURE:
<223> OTHER INFORMATION: Synthetic

<400> SEQUENCE: 102
```
ggcataagga aatcgaaggt c 21

<210> SEQ ID NO 103
<211> LENGTH: 23
<212> TYPE: DNA
<213> ORGANISM: Artificial Sequence
<220> FEATURE:
<223> OTHER INFORMATION: Synthetic

<400> SEQUENCE: 103
catgtcctca agtcaagaac aag 23

<210> SEQ ID NO 104
<211> LENGTH: 24
<212> TYPE: DNA
<213> ORGANISM: Artificial Sequence
<220> FEATURE:
<223> OTHER INFORMATION: Synthetic

<400> SEQUENCE: 104
gctgggtgaa tggagcgagc agcg 24

<210> SEQ ID NO 105
<211> LENGTH: 8
<212> TYPE: DNA
<213> ORGANISM: Artificial Sequence
<220> FEATURE:
<223> OTHER INFORMATION: Synthetic

<400> SEQUENCE: 105 tcttcgag 8

<210> SEQ ID NO 106
<211> LENGTH: 22
<212> TYPE: DNA
<213> ORGANISM: Artificial Sequence
<220> FEATURE:
<223> OTHER INFORMATION: Synthetic

<400> SEQUENCE: 106
tacatgaagc aactccagtc cc 22

<210> SEQ ID NO 107
<211> LENGTH: 22
<212> TYPE: DNA
<213> ORGANISM: Artificial Sequence
<220> FEATURE:
<223> OTHER INFORMATION: Synthetic

<400> SEQUENCE: 107
atcaaattcc agcaccgagc gc 22

<210> SEQ ID NO 108
<211> LENGTH: 24
<212> TYPE: DNA
<213> ORGANISM: Artificial Sequence
<220> FEATURE:
<223> OTHER INFORMATION: Synthetic

<400> SEQUENCE: 108
gtcctggagt gacccctggc cttc 24

<210> SEQ ID NO 109
<211> LENGTH: 8
<212> TYPE: DNA

<213> ORGANISM: Artificial Sequence
<220> FEATURE:
<223> OTHER INFORMATION: Synthetic

<400> SEQUENCE: 109 tccccgct                                                                    8

<210> SEQ ID NO 110
<211> LENGTH: 22
<212> TYPE: DNA
<213> ORGANISM: Artificial Sequence
<220> FEATURE:
<223> OTHER INFORMATION: Synthetic

<400> SEQUENCE: 110
tacatgaagc aactccagtc cc                                                    22

<210> SEQ ID NO 111
<211> LENGTH: 22
<212> TYPE: DNA
<213> ORGANISM: Artificial Sequence
<220> FEATURE:
<223> OTHER INFORMATION: Synthetic

<400> SEQUENCE: 111
atcaaattcc agcaccgagc gc                                                    22

<210> SEQ ID NO 112
<211> LENGTH: 24
<212> TYPE: DNA
<213> ORGANISM: Artificial Sequence
<220> FEATURE:
<223> OTHER INFORMATION: Synthetic

<400> SEQUENCE: 112
gatcctggag tgacccctgg cctt                                                  24

<210> SEQ ID NO 113
<211> LENGTH: 8
<212> TYPE: DNA
<213> ORGANISM: Artificial Sequence
<220> FEATURE:
<223> OTHER INFORMATION: Synthetic

<400> SEQUENCE: 113 ctccccgc                                                                    8

<210> SEQ ID NO 114
<211> LENGTH: 22
<212> TYPE: DNA
<213> ORGANISM: Artificial Sequence
<220> FEATURE:
<223> OTHER INFORMATION: Synthetic

<400> SEQUENCE: 114
tacatgaagc aactccagtc cc                                                    22

<210> SEQ ID NO 115
<211> LENGTH: 22
<212> TYPE: DNA
<213> ORGANISM: Artificial Sequence
<220> FEATURE:
<223> OTHER INFORMATION: Synthetic

<400> SEQUENCE: 115
atcaaattcc agcaccgagc gc                                                    22

-continued

```
<210> SEQ ID NO 116
<211> LENGTH: 24
<212> TYPE: DNA
<213> ORGANISM: Artificial Sequence
<220> FEATURE:
<223> OTHER INFORMATION: Synthetic

<400> SEQUENCE: 116
gtgtgtccct ctccccaccc gtcc                                         24

<210> SEQ ID NO 117
<211> LENGTH: 8
<212> TYPE: DNA
<213> ORGANISM: Artificial Sequence
<220> FEATURE:
<223> OTHER INFORMATION: Synthetic

<400> SEQUENCE: 117 ctgtccgg                                                            8

<210> SEQ ID NO 118
<211> LENGTH: 22
<212> TYPE: DNA
<213> ORGANISM: Artificial Sequence
<220> FEATURE:
<223> OTHER INFORMATION: Synthetic

<400> SEQUENCE: 118
tacatgaagc aactccagtc cc                                           22

<210> SEQ ID NO 119
<211> LENGTH: 22
<212> TYPE: DNA
<213> ORGANISM: Artificial Sequence
<220> FEATURE:
<223> OTHER INFORMATION: Synthetic

<400> SEQUENCE: 119
atcaaattcc agcaccgagc gc                                           22

<210> SEQ ID NO 120
<211> LENGTH: 24
<212> TYPE: DNA
<213> ORGANISM: Artificial Sequence
<220> FEATURE:
<223> OTHER INFORMATION: Synthetic

<400> SEQUENCE: 120
gttggagcgg ggagaaggcc aggg                                         24

<210> SEQ ID NO 121
<211> LENGTH: 8
<212> TYPE: DNA
<213> ORGANISM: Artificial Sequence
<220> FEATURE:
<223> OTHER INFORMATION: Synthetic

<400> SEQUENCE: 121 gtcactcc                                                            8

<210> SEQ ID NO 122
<211> LENGTH: 22
<212> TYPE: DNA
<213> ORGANISM: Artificial Sequence
<220> FEATURE:
```

```
<223> OTHER INFORMATION: Synthetic

<400> SEQUENCE: 122
tacatgaagc aactccagtc cc                                            22

<210> SEQ ID NO 123
<211> LENGTH: 22
<212> TYPE: DNA
<213> ORGANISM: Artificial Sequence
<220> FEATURE:
<223> OTHER INFORMATION: Synthetic

<400> SEQUENCE: 123
atcaaattcc agcaccgagc gc                                            22

<210> SEQ ID NO 124
<211> LENGTH: 24
<212> TYPE: DNA
<213> ORGANISM: Artificial Sequence
<220> FEATURE:
<223> OTHER INFORMATION: Synthetic

<400> SEQUENCE: 124
gcgttggagc ggggagaagg ccag                                          24

<210> SEQ ID NO 125
<211> LENGTH: 8
<212> TYPE: DNA
<213> ORGANISM: Artificial Sequence
<220> FEATURE:
<223> OTHER INFORMATION: Synthetic

<400> SEQUENCE: 125 gggtcact                                                            8

<210> SEQ ID NO 126
<211> LENGTH: 22
<212> TYPE: DNA
<213> ORGANISM: Artificial Sequence
<220> FEATURE:
<223> OTHER INFORMATION: Synthetic

<400> SEQUENCE: 126
tacatgaagc aactccagtc cc                                            22

<210> SEQ ID NO 127
<211> LENGTH: 22
<212> TYPE: DNA
<213> ORGANISM: Artificial Sequence
<220> FEATURE:
<223> OTHER INFORMATION: Synthetic

<400> SEQUENCE: 127
atcaaattcc agcaccgagc gc                                            22

<210> SEQ ID NO 128
<211> LENGTH: 24
<212> TYPE: DNA
<213> ORGANISM: Artificial Sequence
<220> FEATURE:
<223> OTHER INFORMATION: Synthetic

<400> SEQUENCE: 128
gtaccctcca ataatttggc tggc                                          24
```

-continued

```
<210> SEQ ID NO 129
<211> LENGTH: 8
<212> TYPE: DNA
<213> ORGANISM: Artificial Sequence
<220> FEATURE:
<223> OTHER INFORMATION: Synthetic

<400> SEQUENCE: 129 aattccga                                                               8

<210> SEQ ID NO 130
<211> LENGTH: 21
<212> TYPE: DNA
<213> ORGANISM: Artificial Sequence
<220> FEATURE:
<223> OTHER INFORMATION: Synthetic

<400> SEQUENCE: 130
ggcataagga aatcgaaggt c                                                21

<210> SEQ ID NO 131
<211> LENGTH: 23
<212> TYPE: DNA
<213> ORGANISM: Artificial Sequence
<220> FEATURE:
<223> OTHER INFORMATION: Synthetic

<400> SEQUENCE: 131
catgtcctca agtcaagaac aag                                              23

<210> SEQ ID NO 132
<211> LENGTH: 24
<212> TYPE: DNA
<213> ORGANISM: Artificial Sequence
<220> FEATURE:
<223> OTHER INFORMATION: Synthetic

<400> SEQUENCE: 132
gataatttgg ctggcaattc cgag                                             24

<210> SEQ ID NO 133
<211> LENGTH: 8
<212> TYPE: DNA
<213> ORGANISM: Artificial Sequence
<220> FEATURE:
<223> OTHER INFORMATION: Synthetic

<400> SEQUENCE: 133 caagccaa                                                               8

<210> SEQ ID NO 134
<211> LENGTH: 21
<212> TYPE: DNA
<213> ORGANISM: Artificial Sequence
<220> FEATURE:
<223> OTHER INFORMATION: Synthetic

<400> SEQUENCE: 134
ggcataagga aatcgaaggt c                                                21

<210> SEQ ID NO 135
<211> LENGTH: 23
<212> TYPE: DNA
<213> ORGANISM: Artificial Sequence
<220> FEATURE:
<223> OTHER INFORMATION: Synthetic
```

<400> SEQUENCE: 135
catgtcctca agtcaagaac aag                                                                23

<210> SEQ ID NO 136
<211> LENGTH: 24
<212> TYPE: DNA
<213> ORGANISM: Artificial Sequence
<220> FEATURE:
<223> OTHER INFORMATION: Synthetic

<400> SEQUENCE: 136
gcaggggcca ggtgtccttc tctg                                                               24

<210> SEQ ID NO 137
<211> LENGTH: 8
<212> TYPE: DNA
<213> ORGANISM: Artificial Sequence
<220> FEATURE:
<223> OTHER INFORMATION: Synthetic

<400> SEQUENCE: 137 ggggcctc                                                                                 8

<210> SEQ ID NO 138
<211> LENGTH: 21
<212> TYPE: DNA
<213> ORGANISM: Artificial Sequence
<220> FEATURE:
<223> OTHER INFORMATION: Synthetic

<400> SEQUENCE: 138
cacgggcagc atgggaatag t                                                                  21

<210> SEQ ID NO 139
<211> LENGTH: 24
<212> TYPE: DNA
<213> ORGANISM: Artificial Sequence
<220> FEATURE:
<223> OTHER INFORMATION: Synthetic

<400> SEQUENCE: 139
gctaggggag agtcccactg tcca                                                               24

<210> SEQ ID NO 140
<211> LENGTH: 24
<212> TYPE: DNA
<213> ORGANISM: Artificial Sequence
<220> FEATURE:
<223> OTHER INFORMATION: Synthetic

<400> SEQUENCE: 140
gaatggcagg cggaggttgt actg                                                               24

<210> SEQ ID NO 141
<211> LENGTH: 8
<212> TYPE: DNA
<213> ORGANISM: Artificial Sequence
<220> FEATURE:
<223> OTHER INFORMATION: Synthetic

<400> SEQUENCE: 141 ggggccag                                                                                 8

<210> SEQ ID NO 142
<211> LENGTH: 21

-continued

```
<212> TYPE: DNA
<213> ORGANISM: Artificial Sequence
<220> FEATURE:
<223> OTHER INFORMATION: Synthetic

<400> SEQUENCE: 142
ctgtgtggct ttgctttggt c                                        21

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
gtagggtgtg atgggaggct aagc                                     24

<210> SEQ ID NO 144
<211> LENGTH: 24
<212> TYPE: DNA
<213> ORGANISM: Artificial Sequence
<220> FEATURE:
<223> OTHER INFORMATION: Synthetic

<400> SEQUENCE: 144
gagtgagaga gtgagagaga gaca                                     24

<210> SEQ ID NO 145
<211> LENGTH: 8
<212> TYPE: DNA
<213> ORGANISM: Artificial Sequence
<220> FEATURE:
<223> OTHER INFORMATION: Synthetic

<400> SEQUENCE: 145 cgggccag                                                       8

<210> SEQ ID NO 146
<211> LENGTH: 21
<212> TYPE: DNA
<213> ORGANISM: Artificial Sequence
<220> FEATURE:
<223> OTHER INFORMATION: Synthetic

<400> SEQUENCE: 146
ctgtgtggct ttgctttggt c                                        21

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
gtagggtgtg atgggaggct aagc                                     24

<210> SEQ ID NO 148
<211> LENGTH: 24
<212> TYPE: DNA
<213> ORGANISM: Artificial Sequence
<220> FEATURE:
<223> OTHER INFORMATION: Synthetic

<400> SEQUENCE: 148
```
gtgagcaggc acctgtgcca acat                                                24

<210> SEQ ID NO 149
<211> LENGTH: 8
<212> TYPE: DNA
<213> ORGANISM: Artificial Sequence
<220> FEATURE:
<223> OTHER INFORMATION: Synthetic

<400> SEQUENCE: 149 gggcccgc                                                                  8

<210> SEQ ID NO 150
<211> LENGTH: 21
<212> TYPE: DNA
<213> ORGANISM: Artificial Sequence
<220> FEATURE:
<223> OTHER INFORMATION: Synthetic

<400> SEQUENCE: 150
ctgtgtggct ttgctttggt c                                                   21

<210> SEQ ID NO 151
<211> LENGTH: 24
<212> TYPE: DNA
<213> ORGANISM: Artificial Sequence
<220> FEATURE:
<223> OTHER INFORMATION: Synthetic

<400> SEQUENCE: 151
gtagggtgtg atgggaggct aagc                                                24

<210> SEQ ID NO 152
<211> LENGTH: 24
<212> TYPE: DNA
<213> ORGANISM: Artificial Sequence
<220> FEATURE:
<223> OTHER INFORMATION: Synthetic

<400> SEQUENCE: 152
gcgtgggggc tccgtgcccc acgc                                                24

<210> SEQ ID NO 153
<211> LENGTH: 8
<212> TYPE: DNA
<213> ORGANISM: Artificial Sequence
<220> FEATURE:
<223> OTHER INFORMATION: Synthetic

<400> SEQUENCE: 153 gggtccat                                                                  8

<210> SEQ ID NO 154
<211> LENGTH: 21
<212> TYPE: DNA
<213> ORGANISM: Artificial Sequence
<220> FEATURE:
<223> OTHER INFORMATION: Synthetic

<400> SEQUENCE: 154
gaggaagagt agctcgccga g                                                   21

<210> SEQ ID NO 155
<211> LENGTH: 24
<212> TYPE: DNA
<213> ORGANISM: Artificial Sequence
<220> FEATURE:
<223> OTHER INFORMATION: Synthetic

<400> SEQUENCE: 155
agaccgagtg gcagtgacag caag                                                        24

<210> SEQ ID NO 156
<211> LENGTH: 24
<212> TYPE: DNA
<213> ORGANISM: Artificial Sequence
<220> FEATURE:
<223> OTHER INFORMATION: Synthetic

<400> SEQUENCE: 156
gcatgggcag gggctggggt gcac                                                        24

<210> SEQ ID NO 157
<211> LENGTH: 8
<212> TYPE: DNA
<213> ORGANISM: Artificial Sequence
<220> FEATURE:
<223> OTHER INFORMATION: Synthetic

<400> SEQUENCE: 157 aggcccag                                                                          8

<210> SEQ ID NO 158
<211> LENGTH: 22
<212> TYPE: DNA
<213> ORGANISM: Artificial Sequence
<220> FEATURE:
<223> OTHER INFORMATION: Synthetic

<400> SEQUENCE: 158
gggagaggga agtgtgggga ag                                                          22

<210> SEQ ID NO 159
<211> LENGTH: 24
<212> TYPE: DNA
<213> ORGANISM: Artificial Sequence
<220> FEATURE:
<223> OTHER INFORMATION: Synthetic

<400> SEQUENCE: 159
gtcttcctgc tctgtgcgca cgac                                                        24

<210> SEQ ID NO 160
<211> LENGTH: 24
<212> TYPE: DNA
<213> ORGANISM: Artificial Sequence
<220> FEATURE:
<223> OTHER INFORMATION: Synthetic

<400> SEQUENCE: 160
gaaaattgtg atttccagat ccac                                                        24

<210> SEQ ID NO 161
<211> LENGTH: 8
<212> TYPE: DNA
<213> ORGANISM: Artificial Sequence
<220> FEATURE:
<223> OTHER INFORMATION: Synthetic

<400> SEQUENCE: 161 aagcccaa                                                                          8

```
<210> SEQ ID NO 162
<211> LENGTH: 21
<212> TYPE: DNA
<213> ORGANISM: Artificial Sequence
<220> FEATURE:
<223> OTHER INFORMATION: Synthetic

<400> SEQUENCE: 162
ttgggggctc taagttatgt a                                                    21

<210> SEQ ID NO 163
<211> LENGTH: 23
<212> TYPE: DNA
<213> ORGANISM: Artificial Sequence
<220> FEATURE:
<223> OTHER INFORMATION: Synthetic

<400> SEQUENCE: 163
cttcatctgt atcttcagga tca                                                  23

<210> SEQ ID NO 164
<211> LENGTH: 23
<212> TYPE: DNA
<213> ORGANISM: Artificial Sequence
<220> FEATURE:
<223> OTHER INFORMATION: Synthetic

<400> SEQUENCE: 164
gagcagaaaa aattgtgatt tcc                                                  23

<210> SEQ ID NO 165
<211> LENGTH: 8
<212> TYPE: DNA
<213> ORGANISM: Artificial Sequence
<220> FEATURE:
<223> OTHER INFORMATION: Synthetic

<400> SEQUENCE: 165 agatccac                                                                    8

<210> SEQ ID NO 166
<211> LENGTH: 21
<212> TYPE: DNA
<213> ORGANISM: Artificial Sequence
<220> FEATURE:
<223> OTHER INFORMATION: Synthetic

<400> SEQUENCE: 166
ttgggggctc taagttatgt a                                                    21

<210> SEQ ID NO 167
<211> LENGTH: 23
<212> TYPE: DNA
<213> ORGANISM: Artificial Sequence
<220> FEATURE:
<223> OTHER INFORMATION: Synthetic

<400> SEQUENCE: 167
cttcatctgt atcttcagga tca                                                  23

<210> SEQ ID NO 168
<211> LENGTH: 23
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (21)..(21)
<223> OTHER INFORMATION: n is a, c, g, t or u

<400> SEQUENCE: 168
ggcaggcgga ggttgtactg ngg                                           23

<210> SEQ ID NO 169
<211> LENGTH: 23
<212> TYPE: DNA
<213> ORGANISM: Artificial Sequence
<220> FEATURE:
<223> OTHER INFORMATION: Synthetic

<400> SEQUENCE: 169
ggcaggcgga ggttgtactg ggg                                           23

<210> SEQ ID NO 170
<211> LENGTH: 23
<212> TYPE: DNA
<213> ORGANISM: Artificial Sequence
<220> FEATURE:
<223> OTHER INFORMATION: Synthetic

<400> SEQUENCE: 170
ggaaggcgga agttgtactg agg                                           23

<210> SEQ ID NO 171
<211> LENGTH: 23
<212> TYPE: DNA
<213> ORGANISM: Artificial Sequence
<220> FEATURE:
<223> OTHER INFORMATION: Synthetic

<400> SEQUENCE: 171
ggcaggcgga ggttgtagtg ggg                                           23

<210> SEQ ID NO 172
<211> LENGTH: 23
<212> TYPE: DNA
<213> ORGANISM: Artificial Sequence
<220> FEATURE:
<223> OTHER INFORMATION: Synthetic

<400> SEQUENCE: 172
aggaggcgga ggttgcactg agg                                           23

<210> SEQ ID NO 173
<211> LENGTH: 23
<212> TYPE: DNA
<213> ORGANISM: Artificial Sequence
<220> FEATURE:
<223> OTHER INFORMATION: Synthetic

<400> SEQUENCE: 173
gggaggtgga ggttgtactg agg                                           23

<210> SEQ ID NO 174
<211> LENGTH: 23
<212> TYPE: DNA
<213> ORGANISM: Artificial Sequence
<220> FEATURE:
<223> OTHER INFORMATION: Synthetic

<400> SEQUENCE: 174
```

-continued

```
ggcagggggga agctgtactg tgg                                            23

<210> SEQ ID NO 175
<211> LENGTH: 23
<212> TYPE: DNA
<213> ORGANISM: Artificial Sequence
<220> FEATURE:
<223> OTHER INFORMATION: Synthetic

<400> SEQUENCE: 175
aggaggcgga ggttgcactg agg                                             23

<210> SEQ ID NO 176
<211> LENGTH: 23
<212> TYPE: DNA
<213> ORGANISM: Artificial Sequence
<220> FEATURE:
<223> OTHER INFORMATION: Synthetic

<400> SEQUENCE: 176
aggaggcgga ggttgtactg agc                                             23

<210> SEQ ID NO 177
<211> LENGTH: 23
<212> TYPE: DNA
<213> ORGANISM: Artificial Sequence
<220> FEATURE:
<223> OTHER INFORMATION: Synthetic

<400> SEQUENCE: 177
gggaggcgga ggttgtaatg agg                                             23

<210> SEQ ID NO 178
<211> LENGTH: 23
<212> TYPE: DNA
<213> ORGANISM: Artificial Sequence
<220> FEATURE:
<223> OTHER INFORMATION: Synthetic

<400> SEQUENCE: 178
ggcaagagga ggttggactg ggg                                             23

<210> SEQ ID NO 179
<211> LENGTH: 23
<212> TYPE: DNA
<213> ORGANISM: Artificial Sequence
<220> FEATURE:
<223> OTHER INFORMATION: Synthetic

<400> SEQUENCE: 179
aggaggcgga ggttgcactg agg                                             23

<210> SEQ ID NO 180
<211> LENGTH: 23
<212> TYPE: DNA
<213> ORGANISM: Artificial Sequence
<220> FEATURE:
<223> OTHER INFORMATION: Synthetic

<400> SEQUENCE: 180
gggaggcgga ggttgtagtg agg                                             23

<210> SEQ ID NO 181
<211> LENGTH: 23
<212> TYPE: DNA
<213> ORGANISM: Artificial Sequence
```

<220> FEATURE:
<223> OTHER INFORMATION: Synthetic

<400> SEQUENCE: 181
aggaagcgga ggttgtaatg agg                                                                23

<210> SEQ ID NO 182
<211> LENGTH: 23
<212> TYPE: DNA
<213> ORGANISM: Artificial Sequence
<220> FEATURE:
<223> OTHER INFORMATION: Synthetic

<400> SEQUENCE: 182
aggaggcgga ggttgtaatg agg                                                                23

<210> SEQ ID NO 183
<211> LENGTH: 23
<212> TYPE: DNA
<213> ORGANISM: Artificial Sequence
<220> FEATURE:
<223> OTHER INFORMATION: Synthetic

<400> SEQUENCE: 183
gggaggcgga ggttgtagtg agg                                                                23

<210> SEQ ID NO 184
<211> LENGTH: 23
<212> TYPE: DNA
<213> ORGANISM: Artificial Sequence
<220> FEATURE:
<223> OTHER INFORMATION: Synthetic

<400> SEQUENCE: 184
tccaggtgga ggctgtactg agg                                                                23

<210> SEQ ID NO 185
<211> LENGTH: 23
<212> TYPE: DNA
<213> ORGANISM: Artificial Sequence
<220> FEATURE:
<223> OTHER INFORMATION: Synthetic

<400> SEQUENCE: 185
aggaggcaga ggttgcactg ggg                                                                23

<210> SEQ ID NO 186
<211> LENGTH: 23
<212> TYPE: DNA
<213> ORGANISM: Artificial Sequence
<220> FEATURE:
<223> OTHER INFORMATION: Synthetic

<400> SEQUENCE: 186
gggaggcgga ggatgtaatg agg                                                                23

<210> SEQ ID NO 187
<211> LENGTH: 23
<212> TYPE: DNA
<213> ORGANISM: Artificial Sequence
<220> FEATURE:
<223> OTHER INFORMATION: Synthetic

<400> SEQUENCE: 187
cacaggcaga ggttgtactg agc                                                                23

```
<210> SEQ ID NO 188
<211> LENGTH: 23
<212> TYPE: DNA
<213> ORGANISM: Artificial Sequence
<220> FEATURE:
<223> OTHER INFORMATION: Synthetic

<400> SEQUENCE: 188
aggaggcgga ggttgtagtg agg                                                         23

<210> SEQ ID NO 189
<211> LENGTH: 23
<212> TYPE: DNA
<213> ORGANISM: Artificial Sequence
<220> FEATURE:
<223> OTHER INFORMATION: Synthetic

<400> SEQUENCE: 189
gggaggcgga ggttgtagtg agg                                                         23

<210> SEQ ID NO 190
<211> LENGTH: 23
<212> TYPE: DNA
<213> ORGANISM: Artificial Sequence
<220> FEATURE:
<223> OTHER INFORMATION: Synthetic

<400> SEQUENCE: 190
aggaggcaga ggttgaactg agg                                                         23

<210> SEQ ID NO 191
<211> LENGTH: 23
<212> TYPE: DNA
<213> ORGANISM: Artificial Sequence
<220> FEATURE:
<223> OTHER INFORMATION: Synthetic

<400> SEQUENCE: 191
ggcaagggga agttgtactg tgg                                                         23

<210> SEQ ID NO 192
<211> LENGTH: 23
<212> TYPE: DNA
<213> ORGANISM: Artificial Sequence
<220> FEATURE:
<223> OTHER INFORMATION: Synthetic

<400> SEQUENCE: 192
gggaggcaga ggttgcactg agg                                                         23

<210> SEQ ID NO 193
<211> LENGTH: 23
<212> TYPE: DNA
<213> ORGANISM: Artificial Sequence
<220> FEATURE:
<223> OTHER INFORMATION: Synthetic

<400> SEQUENCE: 193
gagaggcgga ggttgcactg agg                                                         23

<210> SEQ ID NO 194
<211> LENGTH: 23
<212> TYPE: DNA
<213> ORGANISM: Artificial Sequence
<220> FEATURE:
<223> OTHER INFORMATION: Synthetic
```

<400> SEQUENCE: 194
aggaggcgga ggttgcactg agg                                    23

<210> SEQ ID NO 195
<211> LENGTH: 23
<212> TYPE: DNA
<213> ORGANISM: Artificial Sequence
<220> FEATURE:
<223> OTHER INFORMATION: Synthetic

<400> SEQUENCE: 195
aggaggcaga ggttgcactg agg                                    23

<210> SEQ ID NO 196
<211> LENGTH: 23
<212> TYPE: DNA
<213> ORGANISM: Artificial Sequence
<220> FEATURE:
<223> OTHER INFORMATION: Synthetic

<400> SEQUENCE: 196
gggaggcaga ggttgcactg agg                                    23

<210> SEQ ID NO 197
<211> LENGTH: 23
<212> TYPE: DNA
<213> ORGANISM: Artificial Sequence
<220> FEATURE:
<223> OTHER INFORMATION: Synthetic

<400> SEQUENCE: 197
cagaggcgga ggttgtagtg agg                                    23

<210> SEQ ID NO 198
<211> LENGTH: 23
<212> TYPE: DNA
<213> ORGANISM: Artificial Sequence
<220> FEATURE:
<223> OTHER INFORMATION: Synthetic

<400> SEQUENCE: 198
agcaggtaga ggttggactg agg                                    23

<210> SEQ ID NO 199
<211> LENGTH: 23
<212> TYPE: DNA
<213> ORGANISM: Artificial Sequence
<220> FEATURE:
<223> OTHER INFORMATION: Synthetic

<400> SEQUENCE: 199
aggaggcgga ggttgtagtg agg                                    23

<210> SEQ ID NO 200
<211> LENGTH: 23
<212> TYPE: DNA
<213> ORGANISM: Artificial Sequence
<220> FEATURE:
<223> OTHER INFORMATION: Synthetic

<400> SEQUENCE: 200
gggaggcaga ggttgcactg agg                                    23

<210> SEQ ID NO 201

```
<211> LENGTH: 23
<212> TYPE: DNA
<213> ORGANISM: Artificial Sequence
<220> FEATURE:
<223> OTHER INFORMATION: Synthetic

<400> SEQUENCE: 201
aggaggcgga ggttgcactg agg                                            23

<210> SEQ ID NO 202
<211> LENGTH: 23
<212> TYPE: DNA
<213> ORGANISM: Artificial Sequence
<220> FEATURE:
<223> OTHER INFORMATION: Synthetic

<400> SEQUENCE: 202
tggaggcgga ggttgtactg agc                                            23

<210> SEQ ID NO 203
<211> LENGTH: 23
<212> TYPE: DNA
<213> ORGANISM: Artificial Sequence
<220> FEATURE:
<223> OTHER INFORMATION: Synthetic

<400> SEQUENCE: 203
aggaggcaga ggttgcactg agg                                            23

<210> SEQ ID NO 204
<211> LENGTH: 23
<212> TYPE: DNA
<213> ORGANISM: Artificial Sequence
<220> FEATURE:
<223> OTHER INFORMATION: Synthetic

<400> SEQUENCE: 204
gggaggcgga ggttgtagtg agg                                            23

<210> SEQ ID NO 205
<211> LENGTH: 23
<212> TYPE: DNA
<213> ORGANISM: Artificial Sequence
<220> FEATURE:
<223> OTHER INFORMATION: Synthetic

<400> SEQUENCE: 205
aggaggcaga ggttgtactg agc                                            23

<210> SEQ ID NO 206
<211> LENGTH: 23
<212> TYPE: DNA
<213> ORGANISM: Artificial Sequence
<220> FEATURE:
<223> OTHER INFORMATION: Synthetic

<400> SEQUENCE: 206
aggaggcgga ggttgtagtg agg                                            23

<210> SEQ ID NO 207
<211> LENGTH: 23
<212> TYPE: DNA
<213> ORGANISM: Artificial Sequence
<220> FEATURE:
<223> OTHER INFORMATION: Synthetic

<400> SEQUENCE: 207
```
gggaggcgga ggttgtactg agc                                          23

<210> SEQ ID NO 208
<211> LENGTH: 23
<212> TYPE: DNA
<213> ORGANISM: Artificial Sequence
<220> FEATURE:
<223> OTHER INFORMATION: Synthetic

<400> SEQUENCE: 208
gggaggtgga ggttgcactg agg                                          23

<210> SEQ ID NO 209
<211> LENGTH: 23
<212> TYPE: DNA
<213> ORGANISM: Artificial Sequence
<220> FEATURE:
<223> OTHER INFORMATION: Synthetic

<400> SEQUENCE: 209
gggaggcgga ggttgtagtg agg                                          23

<210> SEQ ID NO 210
<211> LENGTH: 23
<212> TYPE: DNA
<213> ORGANISM: Artificial Sequence
<220> FEATURE:
<223> OTHER INFORMATION: Synthetic

<400> SEQUENCE: 210
aggaggcgga ggttgtagtg agg                                          23

<210> SEQ ID NO 211
<211> LENGTH: 23
<212> TYPE: DNA
<213> ORGANISM: Artificial Sequence
<220> FEATURE:
<223> OTHER INFORMATION: Synthetic

<400> SEQUENCE: 211
gggaggcgga ggttgtagtg agg                                          23

<210> SEQ ID NO 212
<211> LENGTH: 23
<212> TYPE: DNA
<213> ORGANISM: Artificial Sequence
<220> FEATURE:
<223> OTHER INFORMATION: Synthetic

<400> SEQUENCE: 212
aggaggcgga ggttgtactg agc                                          23

<210> SEQ ID NO 213
<211> LENGTH: 23
<212> TYPE: DNA
<213> ORGANISM: Artificial Sequence
<220> FEATURE:
<223> OTHER INFORMATION: Synthetic

<400> SEQUENCE: 213
agaaggcgga ggttgtagtg agg                                          23

<210> SEQ ID NO 214
<211> LENGTH: 23
<212> TYPE: DNA

-continued

```
<213> ORGANISM: Artificial Sequence
<220> FEATURE:
<223> OTHER INFORMATION: Synthetic

<400> SEQUENCE: 214
aggaggcgga ggttgtagtg agg                                              23

<210> SEQ ID NO 215
<211> LENGTH: 23
<212> TYPE: DNA
<213> ORGANISM: Artificial Sequence
<220> FEATURE:
<223> OTHER INFORMATION: Synthetic

<400> SEQUENCE: 215
aggaggcgga ggctgcactg agg                                              23

<210> SEQ ID NO 216
<211> LENGTH: 23
<212> TYPE: DNA
<213> ORGANISM: Artificial Sequence
<220> FEATURE:
<223> OTHER INFORMATION: Synthetic

<400> SEQUENCE: 216
gggaggcgga ggttgtagtg agg                                              23

<210> SEQ ID NO 217
<211> LENGTH: 23
<212> TYPE: DNA
<213> ORGANISM: Artificial Sequence
<220> FEATURE:
<223> OTHER INFORMATION: Synthetic

<400> SEQUENCE: 217
gggaggcgga ggttgcactg agg                                              23

<210> SEQ ID NO 218
<211> LENGTH: 23
<212> TYPE: DNA
<213> ORGANISM: Artificial Sequence
<220> FEATURE:
<223> OTHER INFORMATION: Synthetic

<400> SEQUENCE: 218
gggaggcaga ggttgcactg agg                                              23

<210> SEQ ID NO 219
<211> LENGTH: 23
<212> TYPE: DNA
<213> ORGANISM: Artificial Sequence
<220> FEATURE:
<223> OTHER INFORMATION: Synthetic

<400> SEQUENCE: 219
aggaggcaga ggttgtaatg agg                                              23

<210> SEQ ID NO 220
<211> LENGTH: 23
<212> TYPE: DNA
<213> ORGANISM: Artificial Sequence
<220> FEATURE:
<223> OTHER INFORMATION: Synthetic

<400> SEQUENCE: 220
gggaggcgga ggttgtagtg agg                                              23
```

-continued

```
<210> SEQ ID NO 221
<211> LENGTH: 23
<212> TYPE: DNA
<213> ORGANISM: Artificial Sequence
<220> FEATURE:
<223> OTHER INFORMATION: Synthetic

<400> SEQUENCE: 221
ggaaggcgga ggttgtagtg agg                                             23

<210> SEQ ID NO 222
<211> LENGTH: 23
<212> TYPE: DNA
<213> ORGANISM: Artificial Sequence
<220> FEATURE:
<223> OTHER INFORMATION: Synthetic

<400> SEQUENCE: 222
aggaggcaga ggttgtactg agc                                             23

<210> SEQ ID NO 223
<211> LENGTH: 23
<212> TYPE: DNA
<213> ORGANISM: Artificial Sequence
<220> FEATURE:
<223> OTHER INFORMATION: Synthetic

<400> SEQUENCE: 223
gggaggcaga ggttgtactg agc                                             23

<210> SEQ ID NO 224
<211> LENGTH: 23
<212> TYPE: DNA
<213> ORGANISM: Artificial Sequence
<220> FEATURE:
<223> OTHER INFORMATION: Synthetic

<400> SEQUENCE: 224
ggaaggtgaa ggctgtactg cgg                                             23

<210> SEQ ID NO 225
<211> LENGTH: 23
<212> TYPE: DNA
<213> ORGANISM: Artificial Sequence
<220> FEATURE:
<223> OTHER INFORMATION: Synthetic

<400> SEQUENCE: 225
agaaggcaga ggttgcactg agg                                             23

<210> SEQ ID NO 226
<211> LENGTH: 23
<212> TYPE: DNA
<213> ORGANISM: Artificial Sequence
<220> FEATURE:
<223> OTHER INFORMATION: Synthetic

<400> SEQUENCE: 226
agtaggcaga ggttgcactg agg                                             23

<210> SEQ ID NO 227
<211> LENGTH: 23
<212> TYPE: DNA
<213> ORGANISM: Artificial Sequence
<220> FEATURE:
```

<223> OTHER INFORMATION: Synthetic

<400> SEQUENCE: 227
gggaggcaga ggttgtactg agc                                        23

<210> SEQ ID NO 228
<211> LENGTH: 23
<212> TYPE: DNA
<213> ORGANISM: Artificial Sequence
<220> FEATURE:
<223> OTHER INFORMATION: Synthetic

<400> SEQUENCE: 228
gggaggcgga ggttgtactg agc                                        23

<210> SEQ ID NO 229
<211> LENGTH: 23
<212> TYPE: DNA
<213> ORGANISM: Artificial Sequence
<220> FEATURE:
<223> OTHER INFORMATION: Synthetic

<400> SEQUENCE: 229
aggaggcaga ggttgtaatg agg                                        23

<210> SEQ ID NO 230
<211> LENGTH: 23
<212> TYPE: DNA
<213> ORGANISM: Artificial Sequence
<220> FEATURE:
<223> OTHER INFORMATION: Synthetic

<400> SEQUENCE: 230
aggaggcgga ggttgtagtg agg                                        23

<210> SEQ ID NO 231
<211> LENGTH: 23
<212> TYPE: DNA
<213> ORGANISM: Artificial Sequence
<220> FEATURE:
<223> OTHER INFORMATION: Synthetic

<400> SEQUENCE: 231
gggaggcaga ggttgtactg agc                                        23

<210> SEQ ID NO 232
<211> LENGTH: 23
<212> TYPE: DNA
<213> ORGANISM: Artificial Sequence
<220> FEATURE:
<223> OTHER INFORMATION: Synthetic

<400> SEQUENCE: 232
gccaggcggg tgctgtactg ggg                                        23

<210> SEQ ID NO 233
<211> LENGTH: 23
<212> TYPE: DNA
<213> ORGANISM: Artificial Sequence
<220> FEATURE:
<223> OTHER INFORMATION: Synthetic

<400> SEQUENCE: 233
aggaggcgga ggttgtactg ggc                                        23

-continued

```
<210> SEQ ID NO 234
<211> LENGTH: 23
<212> TYPE: DNA
<213> ORGANISM: Artificial Sequence
<220> FEATURE:
<223> OTHER INFORMATION: Synthetic

<400> SEQUENCE: 234
tggaggcgga ggttgtactg agc                                      23

<210> SEQ ID NO 235
<211> LENGTH: 23
<212> TYPE: DNA
<213> ORGANISM: Artificial Sequence
<220> FEATURE:
<223> OTHER INFORMATION: Synthetic

<400> SEQUENCE: 235
gggaggtgga ggttgtactg agc                                      23

<210> SEQ ID NO 236
<211> LENGTH: 23
<212> TYPE: DNA
<213> ORGANISM: Artificial Sequence
<220> FEATURE:
<223> OTHER INFORMATION: Synthetic

<400> SEQUENCE: 236
aggaggtgga ggttgtaatg agg                                      23

<210> SEQ ID NO 237
<211> LENGTH: 23
<212> TYPE: DNA
<213> ORGANISM: Artificial Sequence
<220> FEATURE:
<223> OTHER INFORMATION: Synthetic

<400> SEQUENCE: 237
aggaggcgga ggttgtagtg agg                                      23

<210> SEQ ID NO 238
<211> LENGTH: 23
<212> TYPE: DNA
<213> ORGANISM: Artificial Sequence
<220> FEATURE:
<223> OTHER INFORMATION: Synthetic

<400> SEQUENCE: 238
gggaggcaga ggttgtactg agc                                      23

<210> SEQ ID NO 239
<211> LENGTH: 23
<212> TYPE: DNA
<213> ORGANISM: Artificial Sequence
<220> FEATURE:
<223> OTHER INFORMATION: Synthetic

<400> SEQUENCE: 239
aggaggcaga ggttgcactg agg                                      23

<210> SEQ ID NO 240
<211> LENGTH: 23
<212> TYPE: DNA
<213> ORGANISM: Artificial Sequence
<220> FEATURE:
<223> OTHER INFORMATION: Synthetic
```

-continued

```
<400> SEQUENCE: 240
gggaggcaga ggttgtagtg agg                                              23

<210> SEQ ID NO 241
<211> LENGTH: 23
<212> TYPE: DNA
<213> ORGANISM: Artificial Sequence
<220> FEATURE:
<223> OTHER INFORMATION: Synthetic

<400> SEQUENCE: 241
gggaggcgga ggttgtactg agc                                              23

<210> SEQ ID NO 242
<211> LENGTH: 23
<212> TYPE: DNA
<213> ORGANISM: Artificial Sequence
<220> FEATURE:
<223> OTHER INFORMATION: Synthetic

<400> SEQUENCE: 242
ggtaggcaaa ggttgtacca ggg                                              23

<210> SEQ ID NO 243
<211> LENGTH: 23
<212> TYPE: DNA
<213> ORGANISM: Artificial Sequence
<220> FEATURE:
<223> OTHER INFORMATION: Synthetic

<400> SEQUENCE: 243
gggaggcgga ggttgtagtg agg                                              23

<210> SEQ ID NO 244
<211> LENGTH: 23
<212> TYPE: DNA
<213> ORGANISM: Artificial Sequence
<220> FEATURE:
<223> OTHER INFORMATION: Synthetic

<400> SEQUENCE: 244
aggaggcaga ggttgtactg agc                                              23

<210> SEQ ID NO 245
<211> LENGTH: 23
<212> TYPE: DNA
<213> ORGANISM: Artificial Sequence
<220> FEATURE:
<223> OTHER INFORMATION: Synthetic

<400> SEQUENCE: 245
gggaggcaga ggttgtagtg agg                                              23

<210> SEQ ID NO 246
<211> LENGTH: 23
<212> TYPE: DNA
<213> ORGANISM: Artificial Sequence
<220> FEATURE:
<223> OTHER INFORMATION: Synthetic

<400> SEQUENCE: 246
gggaggcgga ggttgtagtg agg                                              23

<210> SEQ ID NO 247
<211> LENGTH: 23
```

-continued

```
<212> TYPE: DNA
<213> ORGANISM: Artificial Sequence
<220> FEATURE:
<223> OTHER INFORMATION: Synthetic

<400> SEQUENCE: 247
gggaggcaga ggttgtagtg agg                                        23

<210> SEQ ID NO 248
<211> LENGTH: 23
<212> TYPE: DNA
<213> ORGANISM: Artificial Sequence
<220> FEATURE:
<223> OTHER INFORMATION: Synthetic

<400> SEQUENCE: 248
gggaggcgga ggttgtactg agc                                        23

<210> SEQ ID NO 249
<211> LENGTH: 23
<212> TYPE: DNA
<213> ORGANISM: Artificial Sequence
<220> FEATURE:
<223> OTHER INFORMATION: Synthetic

<400> SEQUENCE: 249
gggaggtgga ggttgcactg agg                                        23

<210> SEQ ID NO 250
<211> LENGTH: 23
<212> TYPE: DNA
<213> ORGANISM: Artificial Sequence
<220> FEATURE:
<223> OTHER INFORMATION: Synthetic

<400> SEQUENCE: 250
cagaggcaga ggttgtactg agc                                        23

<210> SEQ ID NO 251
<211> LENGTH: 23
<212> TYPE: DNA
<213> ORGANISM: Artificial Sequence
<220> FEATURE:
<223> OTHER INFORMATION: Synthetic

<400> SEQUENCE: 251
gggaggcaga ggttgtactg agt                                        23

<210> SEQ ID NO 252
<211> LENGTH: 23
<212> TYPE: DNA
<213> ORGANISM: Artificial Sequence
<220> FEATURE:
<223> OTHER INFORMATION: Synthetic

<400> SEQUENCE: 252
gggaggcaga ggttgtactg agc                                        23

<210> SEQ ID NO 253
<211> LENGTH: 23
<212> TYPE: DNA
<213> ORGANISM: Artificial Sequence
<220> FEATURE:
<223> OTHER INFORMATION: Synthetic

<400> SEQUENCE: 253
```

-continued agaaggcgga ggttgtagtg agg                                              23

<210> SEQ ID NO 254
<211> LENGTH: 23
<212> TYPE: DNA
<213> ORGANISM: Artificial Sequence
<220> FEATURE:
<223> OTHER INFORMATION: Synthetic

<400> SEQUENCE: 254
cgtctgcgag ggtactagtg aga                                              23

<210> SEQ ID NO 255
<211> LENGTH: 23
<212> TYPE: DNA
<213> ORGANISM: Artificial Sequence
<220> FEATURE:
<223> OTHER INFORMATION: Synthetic

<400> SEQUENCE: 255
gggaggcaga ggttgtactg agc                                              23

<210> SEQ ID NO 256
<211> LENGTH: 23
<212> TYPE: DNA
<213> ORGANISM: Artificial Sequence
<220> FEATURE:
<223> OTHER INFORMATION: Synthetic

<400> SEQUENCE: 256
gggagacgga ggttgtagtg agg                                              23

<210> SEQ ID NO 257
<211> LENGTH: 23
<212> TYPE: DNA
<213> ORGANISM: Artificial Sequence
<220> FEATURE:
<223> OTHER INFORMATION: Synthetic

<400> SEQUENCE: 257
aggaggcaga ggttgtactg agc                                              23

<210> SEQ ID NO 258
<211> LENGTH: 23
<212> TYPE: DNA
<213> ORGANISM: Artificial Sequence
<220> FEATURE:
<223> OTHER INFORMATION: Synthetic

<400> SEQUENCE: 258
aggaggcgga ggttgtactg agc                                              23

<210> SEQ ID NO 259
<211> LENGTH: 23
<212> TYPE: DNA
<213> ORGANISM: Artificial Sequence
<220> FEATURE:
<223> OTHER INFORMATION: Synthetic

<400> SEQUENCE: 259
agaaggcaga ggttgtactg agc                                              23

<210> SEQ ID NO 260
<211> LENGTH: 23
<212> TYPE: DNA
<213> ORGANISM: Artificial Sequence -continued

```
<220> FEATURE:
<223> OTHER INFORMATION: Synthetic

<400> SEQUENCE: 260
gccaggctga ggatgtactg tgg                                              23

<210> SEQ ID NO 261
<211> LENGTH: 23
<212> TYPE: DNA
<213> ORGANISM: Artificial Sequence
<220> FEATURE:
<223> OTHER INFORMATION: Synthetic

<400> SEQUENCE: 261
aggaggcgga ggttgtactg agc                                              23

<210> SEQ ID NO 262
<211> LENGTH: 23
<212> TYPE: DNA
<213> ORGANISM: Artificial Sequence
<220> FEATURE:
<223> OTHER INFORMATION: Synthetic

<400> SEQUENCE: 262
gggaggcaga ggttgtagtg agg                                              23

<210> SEQ ID NO 263
<211> LENGTH: 4
<212> TYPE: DNA
<213> ORGANISM: Artificial Sequence
<220> FEATURE:
<223> OTHER INFORMATION: Synthetic

<400> SEQUENCE: 263 agaa                                                                    4

<210> SEQ ID NO 264
<211> LENGTH: 4
<212> TYPE: DNA
<213> ORGANISM: Artificial Sequence
<220> FEATURE:
<223> OTHER INFORMATION: Synthetic

<400> SEQUENCE: 264 tctc                                                                    4

<210> SEQ ID NO 265
<211> LENGTH: 4
<212> TYPE: DNA
<213> ORGANISM: Artificial Sequence
<220> FEATURE:
<223> OTHER INFORMATION: Synthetic

<400> SEQUENCE: 265 agac                                                                    4

<210> SEQ ID NO 266
<211> LENGTH: 4
<212> TYPE: DNA
<213> ORGANISM: Artificial Sequence
<220> FEATURE:
<223> OTHER INFORMATION: Synthetic

<400> SEQUENCE: 266 agaa                                                                    4
```

-continued

```
<210> SEQ ID NO 267
<211> LENGTH: 4
<212> TYPE: DNA
<213> ORGANISM: Artificial Sequence
<220> FEATURE:
<223> OTHER INFORMATION: Synthetic

<400> SEQUENCE: 267 agac                                                                    4

<210> SEQ ID NO 268
<211> LENGTH: 4
<212> TYPE: DNA
<213> ORGANISM: Artificial Sequence
<220> FEATURE:
<223> OTHER INFORMATION: Synthetic

<400> SEQUENCE: 268 cagg                                                                    4

<210> SEQ ID NO 269
<211> LENGTH: 4
<212> TYPE: DNA
<213> ORGANISM: Artificial Sequence
<220> FEATURE:
<223> OTHER INFORMATION: Synthetic

<400> SEQUENCE: 269 atag                                                                    4

<210> SEQ ID NO 270
<211> LENGTH: 4
<212> TYPE: DNA
<213> ORGANISM: Artificial Sequence
<220> FEATURE:
<223> OTHER INFORMATION: Synthetic

<400> SEQUENCE: 270 agac                                                                    4

<210> SEQ ID NO 271
<211> LENGTH: 4
<212> TYPE: DNA
<213> ORGANISM: Artificial Sequence
<220> FEATURE:
<223> OTHER INFORMATION: Synthetic

<400> SEQUENCE: 271 agcc                                                                    4

<210> SEQ ID NO 272
<211> LENGTH: 4
<212> TYPE: DNA
<213> ORGANISM: Artificial Sequence
<220> FEATURE:
<223> OTHER INFORMATION: Synthetic

<400> SEQUENCE: 272 agaa                                                                    4

<210> SEQ ID NO 273
<211> LENGTH: 4
<212> TYPE: DNA
<213> ORGANISM: Artificial Sequence
<220> FEATURE:
<223> OTHER INFORMATION: Synthetic
```

-continued

```
<400> SEQUENCE: 273 atac                                                               4

<210> SEQ ID NO 274
<211> LENGTH: 4
<212> TYPE: DNA
<213> ORGANISM: Artificial Sequence
<220> FEATURE:
<223> OTHER INFORMATION: Synthetic

<400> SEQUENCE: 274 aaac                                                               4

<210> SEQ ID NO 275
<211> LENGTH: 4
<212> TYPE: DNA
<213> ORGANISM: Artificial Sequence
<220> FEATURE:
<223> OTHER INFORMATION: Synthetic

<400> SEQUENCE: 275 atac                                                               4

<210> SEQ ID NO 276
<211> LENGTH: 4
<212> TYPE: DNA
<213> ORGANISM: Artificial Sequence
<220> FEATURE:
<223> OTHER INFORMATION: Synthetic

<400> SEQUENCE: 276 agaa                                                               4

<210> SEQ ID NO 277
<211> LENGTH: 4
<212> TYPE: DNA
<213> ORGANISM: Artificial Sequence
<220> FEATURE:
<223> OTHER INFORMATION: Synthetic

<400> SEQUENCE: 277 cgtc                                                               4

<210> SEQ ID NO 278
<211> LENGTH: 4
<212> TYPE: DNA
<213> ORGANISM: Artificial Sequence
<220> FEATURE:
<223> OTHER INFORMATION: Synthetic

<400> SEQUENCE: 278 agta                                                               4

<210> SEQ ID NO 279
<211> LENGTH: 4
<212> TYPE: DNA
<213> ORGANISM: Artificial Sequence
<220> FEATURE:
<223> OTHER INFORMATION: Synthetic

<400> SEQUENCE: 279 agac                                                               4

<210> SEQ ID NO 280
```

<211> LENGTH: 5
<212> TYPE: DNA
<213> ORGANISM: Artificial Sequence
<220> FEATURE:
<223> OTHER INFORMATION: Synthetic

<400> SEQUENCE: 280 taaca                                                                            5

<210> SEQ ID NO 281
<211> LENGTH: 5
<212> TYPE: DNA
<213> ORGANISM: Artificial Sequence
<220> FEATURE:
<223> OTHER INFORMATION: Synthetic

<400> SEQUENCE: 281 taaca                                                                            5

<210> SEQ ID NO 282
<211> LENGTH: 9
<212> TYPE: DNA
<213> ORGANISM: Artificial Sequence
<220> FEATURE:
<223> OTHER INFORMATION: Synthetic

<400> SEQUENCE: 282 ctctagacg                                                                        9

<210> SEQ ID NO 283
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 283
gcaggcacct gtgccaacat ngg                                                        23

<210> SEQ ID NO 284
<211> LENGTH: 23
<212> TYPE: DNA
<213> ORGANISM: Artificial Sequence
<220> FEATURE:
<223> OTHER INFORMATION: Synthetic

<400> SEQUENCE: 284
gcaggcacct gtgccaacat ggg                                                        23

<210> SEQ ID NO 285
<211> LENGTH: 23
<212> TYPE: DNA
<213> ORGANISM: Artificial Sequence
<220> FEATURE:
<223> OTHER INFORMATION: Synthetic

<400> SEQUENCE: 285
acaggcactg atgccaactt tgg                                                        23

<210> SEQ ID NO 286
<211> LENGTH: 23
<212> TYPE: DNA
<213> ORGANISM: Artificial Sequence
<220> FEATURE:
<223> OTHER INFORMATION: Synthetic

<400> SEQUENCE: 286
taatgccctg gagcctccct ggc                                                              23

<210> SEQ ID NO 287
<211> LENGTH: 23
<212> TYPE: DNA
<213> ORGANISM: Artificial Sequence
<220> FEATURE:
<223> OTHER INFORMATION: Synthetic

<400> SEQUENCE: 287
gcagggcgcg ccgagagcag cgg                                                              23

<210> SEQ ID NO 288
<211> LENGTH: 23
<212> TYPE: DNA
<213> ORGANISM: Artificial Sequence
<220> FEATURE:
<223> OTHER INFORMATION: Synthetic

<400> SEQUENCE: 288
ccagccaccc agcccctcct ccc                                                              23

<210> SEQ ID NO 289
<211> LENGTH: 23
<212> TYPE: DNA
<213> ORGANISM: Artificial Sequence
<220> FEATURE:
<223> OTHER INFORMATION: Synthetic

<400> SEQUENCE: 289
gtaagcatat gatagtccat ttt                                                              23

<210> SEQ ID NO 290
<211> LENGTH: 23
<212> TYPE: DNA
<213> ORGANISM: Artificial Sequence
<220> FEATURE:
<223> OTHER INFORMATION: Synthetic

<400> SEQUENCE: 290
ccgcgtccct gcgcaaaccc agg                                                              23

<210> SEQ ID NO 291
<211> LENGTH: 23
<212> TYPE: DNA
<213> ORGANISM: Artificial Sequence
<220> FEATURE:
<223> OTHER INFORMATION: Synthetic

<400> SEQUENCE: 291
gtgcacccct gctcctaccc ccc                                                              23

<210> SEQ ID NO 292
<211> LENGTH: 23
<212> TYPE: DNA
<213> ORGANISM: Artificial Sequence
<220> FEATURE:
<223> OTHER INFORMATION: Synthetic

<400> SEQUENCE: 292
ccagggagca atggcagcgc gcc                                                              23

<210> SEQ ID NO 293
<211> LENGTH: 23
<212> TYPE: DNA
<213> ORGANISM: Artificial Sequence
<220> FEATURE:
<223> OTHER INFORMATION: Synthetic

<400> SEQUENCE: 293
ggcggaagtt gtactgaggt gag                                                               23

<210> SEQ ID NO 294
<211> LENGTH: 23
<212> TYPE: DNA
<213> ORGANISM: Artificial Sequence
<220> FEATURE:
<223> OTHER INFORMATION: Synthetic

<400> SEQUENCE: 294
gcaggaactg gagtgcacag gtg                                                               23

<210> SEQ ID NO 295
<211> LENGTH: 5
<212> TYPE: DNA
<213> ORGANISM: Artificial Sequence
<220> FEATURE:
<223> OTHER INFORMATION: Synthetic

<400> SEQUENCE: 295 atgat                                                                                   5

<210> SEQ ID NO 296
<211> LENGTH: 10
<212> TYPE: DNA
<213> ORGANISM: Artificial Sequence
<220> FEATURE:
<223> OTHER INFORMATION: Synthetic

<400> SEQUENCE: 296
tatctgatcc                                                                              10

<210> SEQ ID NO 297
<211> LENGTH: 10
<212> TYPE: DNA
<213> ORGANISM: Artificial Sequence
<220> FEATURE:
<223> OTHER INFORMATION: Synthetic

<400> SEQUENCE: 297
gcggccaggg                                                                              10

<210> SEQ ID NO 298
<211> LENGTH: 9
<212> TYPE: DNA
<213> ORGANISM: Artificial Sequence
<220> FEATURE:
<223> OTHER INFORMATION: Synthetic

<400> SEQUENCE: 298 cccagcctc                                                                               9

<210> SEQ ID NO 299
<211> LENGTH: 10
<212> TYPE: DNA
<213> ORGANISM: Artificial Sequence
<220> FEATURE:
<223> OTHER INFORMATION: Synthetic

<400> SEQUENCE: 299
tataatagtc                                                                                                    10

<210> SEQ ID NO 300
<211> LENGTH: 9
<212> TYPE: DNA
<213> ORGANISM: Artificial Sequence
<220> FEATURE:
<223> OTHER INFORMATION: Synthetic

<400> SEQUENCE: 300 cgctccacc                                                                                                      9

<210> SEQ ID NO 301
<211> LENGTH: 10
<212> TYPE: DNA
<213> ORGANISM: Artificial Sequence
<220> FEATURE:
<223> OTHER INFORMATION: Synthetic

<400> SEQUENCE: 301
tgcaccttcc                                                                                                    10

<210> SEQ ID NO 302
<211> LENGTH: 9
<212> TYPE: DNA
<213> ORGANISM: Artificial Sequence
<220> FEATURE:
<223> OTHER INFORMATION: Synthetic

<400> SEQUENCE: 302 cggaagggc                                                                                                      9

<210> SEQ ID NO 303
<211> LENGTH: 10
<212> TYPE: DNA
<213> ORGANISM: Artificial Sequence
<220> FEATURE:
<223> OTHER INFORMATION: Synthetic

<400> SEQUENCE: 303
gcagtatggg                                                                                                    10

<210> SEQ ID NO 304
<211> LENGTH: 8
<212> TYPE: DNA
<213> ORGANISM: Artificial Sequence
<220> FEATURE:
<223> OTHER INFORMATION: Synthetic

<400> SEQUENCE: 304 atgatgcg                                                                                                       8

<210> SEQ ID NO 305
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 305

-continued gggcaggggc tggggtgcac ngg                                                              23

<210> SEQ ID NO 306
<211> LENGTH: 23
<212> TYPE: DNA
<213> ORGANISM: Artificial Sequence
<220> FEATURE:
<223> OTHER INFORMATION: Synthetic

<400> SEQUENCE: 306
cggcaggggc tgaggggcac tgg                                                              23

<210> SEQ ID NO 307
<211> LENGTH: 23
<212> TYPE: DNA
<213> ORGANISM: Artificial Sequence
<220> FEATURE:
<223> OTHER INFORMATION: Synthetic

<400> SEQUENCE: 307
gggtaggagc aggggtgcac tgg                                                              23

<210> SEQ ID NO 308
<211> LENGTH: 23
<212> TYPE: DNA
<213> ORGANISM: Artificial Sequence
<220> FEATURE:
<223> OTHER INFORMATION: Synthetic

<400> SEQUENCE: 308
gggcaggggc tggggtgcac agg                                                              23

<210> SEQ ID NO 309
<211> LENGTH: 23
<212> TYPE: DNA
<213> ORGANISM: Artificial Sequence
<220> FEATURE:
<223> OTHER INFORMATION: Synthetic

<400> SEQUENCE: 309
gggcaggaac tggagtgcac agg                                                              23

<210> SEQ ID NO 310
<211> LENGTH: 23
<212> TYPE: DNA
<213> ORGANISM: Artificial Sequence
<220> FEATURE:
<223> OTHER INFORMATION: Synthetic

<400> SEQUENCE: 310
gggcaggaac tggagtgcac agg                                                              23

<210> SEQ ID NO 311
<211> LENGTH: 23
<212> TYPE: DNA
<213> ORGANISM: Artificial Sequence
<220> FEATURE:
<223> OTHER INFORMATION: Synthetic

<400> SEQUENCE: 311
cagcaggggc tggggtgcac agg                                                              23

<210> SEQ ID NO 312
<211> LENGTH: 23
<212> TYPE: DNA
<213> ORGANISM: Artificial Sequence -continued

```
<220> FEATURE:
<223> OTHER INFORMATION: Synthetic

<400> SEQUENCE: 312
gggaagggcc tggggtacac ggg                                              23

<210> SEQ ID NO 313
<211> LENGTH: 23
<212> TYPE: DNA
<213> ORGANISM: Artificial Sequence
<220> FEATURE:
<223> OTHER INFORMATION: Synthetic

<400> SEQUENCE: 313
gggccggggc aggggtgcac agg                                              23

<210> SEQ ID NO 314
<211> LENGTH: 23
<212> TYPE: DNA
<213> ORGANISM: Artificial Sequence
<220> FEATURE:
<223> OTHER INFORMATION: Synthetic

<400> SEQUENCE: 314
agacaggggc cggggtgcac agg                                              23

<210> SEQ ID NO 315
<211> LENGTH: 23
<212> TYPE: DNA
<213> ORGANISM: Artificial Sequence
<220> FEATURE:
<223> OTHER INFORMATION: Synthetic

<400> SEQUENCE: 315
gggcaggaac tggagtgcac cgg                                              23

<210> SEQ ID NO 316
<211> LENGTH: 23
<212> TYPE: DNA
<213> ORGANISM: Artificial Sequence
<220> FEATURE:
<223> OTHER INFORMATION: Synthetic

<400> SEQUENCE: 316
aggcaggaac tggagtgcac ggg                                              23

<210> SEQ ID NO 317
<211> LENGTH: 23
<212> TYPE: DNA
<213> ORGANISM: Artificial Sequence
<220> FEATURE:
<223> OTHER INFORMATION: Synthetic

<400> SEQUENCE: 317
aggcaggaac tggagtgcac agg                                              23

<210> SEQ ID NO 318
<211> LENGTH: 23
<212> TYPE: DNA
<213> ORGANISM: Artificial Sequence
<220> FEATURE:
<223> OTHER INFORMATION: Synthetic

<400> SEQUENCE: 318
aggaagggac tggggtgcac tgg                                              23
```

```
<210> SEQ ID NO 319
<211> LENGTH: 23
<212> TYPE: DNA
<213> ORGANISM: Artificial Sequence
<220> FEATURE:
<223> OTHER INFORMATION: Synthetic

<400> SEQUENCE: 319
aggcaggaac tggagtgcac agg                                              23

<210> SEQ ID NO 320
<211> LENGTH: 23
<212> TYPE: DNA
<213> ORGANISM: Artificial Sequence
<220> FEATURE:
<223> OTHER INFORMATION: Synthetic

<400> SEQUENCE: 320
aggtgggggc tggggtgcac agg                                              23

<210> SEQ ID NO 321
<211> LENGTH: 23
<212> TYPE: DNA
<213> ORGANISM: Artificial Sequence
<220> FEATURE:
<223> OTHER INFORMATION: Synthetic

<400> SEQUENCE: 321
aggcaggaac tggggtgcac ggg                                              23

<210> SEQ ID NO 322
<211> LENGTH: 23
<212> TYPE: DNA
<213> ORGANISM: Artificial Sequence
<220> FEATURE:
<223> OTHER INFORMATION: Synthetic

<400> SEQUENCE: 322
tggcaggggc aggggtgaac tgg                                              23

<210> SEQ ID NO 323
<211> LENGTH: 23
<212> TYPE: DNA
<213> ORGANISM: Artificial Sequence
<220> FEATURE:
<223> OTHER INFORMATION: Synthetic

<400> SEQUENCE: 323
gggcaggaac tggagtgcac ggg                                              23

<210> SEQ ID NO 324
<211> LENGTH: 23
<212> TYPE: DNA
<213> ORGANISM: Artificial Sequence
<220> FEATURE:
<223> OTHER INFORMATION: Synthetic

<400> SEQUENCE: 324
ggccaggggc tggggagcac agg                                              23

<210> SEQ ID NO 325
<211> LENGTH: 23
<212> TYPE: DNA
<213> ORGANISM: Artificial Sequence
<220> FEATURE:
<223> OTHER INFORMATION: Synthetic
```

-continued

```
<400> SEQUENCE: 325
gggcagggct gggggtgcac agg                                          23

<210> SEQ ID NO 326
<211> LENGTH: 23
<212> TYPE: DNA
<213> ORGANISM: Artificial Sequence
<220> FEATURE:
<223> OTHER INFORMATION: Synthetic

<400> SEQUENCE: 326
tgggtggggc tggggtgcac tgg                                          23

<210> SEQ ID NO 327
<211> LENGTH: 23
<212> TYPE: DNA
<213> ORGANISM: Artificial Sequence
<220> FEATURE:
<223> OTHER INFORMATION: Synthetic

<400> SEQUENCE: 327 gggaggggggc tggggagcac agg                                         23

<210> SEQ ID NO 328
<211> LENGTH: 23
<212> TYPE: DNA
<213> ORGANISM: Artificial Sequence
<220> FEATURE:
<223> OTHER INFORMATION: Synthetic

<400> SEQUENCE: 328
gggcaggaac tggagtacac ggg                                          23

<210> SEQ ID NO 329
<211> LENGTH: 23
<212> TYPE: DNA
<213> ORGANISM: Artificial Sequence
<220> FEATURE:
<223> OTHER INFORMATION: Synthetic

<400> SEQUENCE: 329
gagaaggagc tggggagcac tgg                                          23

<210> SEQ ID NO 330
<211> LENGTH: 23
<212> TYPE: DNA
<213> ORGANISM: Artificial Sequence
<220> FEATURE:
<223> OTHER INFORMATION: Synthetic

<400> SEQUENCE: 330
gggcaggaac tggagtgcac cag                                          23

<210> SEQ ID NO 331
<211> LENGTH: 23
<212> TYPE: DNA
<213> ORGANISM: Artificial Sequence
<220> FEATURE:
<223> OTHER INFORMATION: Synthetic

<400> SEQUENCE: 331
gggcaagggc aggggtgcac cag                                          23

<210> SEQ ID NO 332
```

-continued

```
<211> LENGTH: 23
<212> TYPE: DNA
<213> ORGANISM: Artificial Sequence
<220> FEATURE:
<223> OTHER INFORMATION: Synthetic

<400> SEQUENCE: 332
aagaaggggc aagggtgcac agg                                           23

<210> SEQ ID NO 333
<211> LENGTH: 23
<212> TYPE: DNA
<213> ORGANISM: Artificial Sequence
<220> FEATURE:
<223> OTHER INFORMATION: Synthetic

<400> SEQUENCE: 333
ggccaggagc aggggtgcac ggg                                           23

<210> SEQ ID NO 334
<211> LENGTH: 23
<212> TYPE: DNA
<213> ORGANISM: Artificial Sequence
<220> FEATURE:
<223> OTHER INFORMATION: Synthetic

<400> SEQUENCE: 334
tggcagcggc tggggagcac tgg                                           23

<210> SEQ ID NO 335
<211> LENGTH: 23
<212> TYPE: DNA
<213> ORGANISM: Artificial Sequence
<220> FEATURE:
<223> OTHER INFORMATION: Synthetic

<400> SEQUENCE: 335
gggcgtgggc aggggtgcac tgg                                           23

<210> SEQ ID NO 336
<211> LENGTH: 23
<212> TYPE: DNA
<213> ORGANISM: Artificial Sequence
<220> FEATURE:
<223> OTHER INFORMATION: Synthetic

<400> SEQUENCE: 336
gggcagtggc tggggtgcat tgg                                           23

<210> SEQ ID NO 337
<211> LENGTH: 23
<212> TYPE: DNA
<213> ORGANISM: Artificial Sequence
<220> FEATURE:
<223> OTHER INFORMATION: Synthetic

<400> SEQUENCE: 337
ggccaggagc tggggtgctc agg                                           23

<210> SEQ ID NO 338
<211> LENGTH: 23
<212> TYPE: DNA
<213> ORGANISM: Artificial Sequence
<220> FEATURE:
<223> OTHER INFORMATION: Synthetic

<400> SEQUENCE: 338
```

```
cctcaggggc tggggtgaac agg                                        23

<210> SEQ ID NO 339
<211> LENGTH: 23
<212> TYPE: DNA
<213> ORGANISM: Artificial Sequence
<220> FEATURE:
<223> OTHER INFORMATION: Synthetic

<400> SEQUENCE: 339
tggcagggtc tggggtgcac aga                                        23

<210> SEQ ID NO 340
<211> LENGTH: 23
<212> TYPE: DNA
<213> ORGANISM: Artificial Sequence
<220> FEATURE:
<223> OTHER INFORMATION: Synthetic

<400> SEQUENCE: 340
gagcagggtc tggggtgcat ggg                                        23

<210> SEQ ID NO 341
<211> LENGTH: 23
<212> TYPE: DNA
<213> ORGANISM: Artificial Sequence
<220> FEATURE:
<223> OTHER INFORMATION: Synthetic

<400> SEQUENCE: 341
gagcagggac tgagggcac agg                                         23

<210> SEQ ID NO 342
<211> LENGTH: 23
<212> TYPE: DNA
<213> ORGANISM: Artificial Sequence
<220> FEATURE:
<223> OTHER INFORMATION: Synthetic

<400> SEQUENCE: 342
gagcaggggc tgggggcac tgg                                         23

<210> SEQ ID NO 343
<211> LENGTH: 23
<212> TYPE: DNA
<213> ORGANISM: Artificial Sequence
<220> FEATURE:
<223> OTHER INFORMATION: Synthetic

<400> SEQUENCE: 343
tggcaggggt aagggtgcac tgg                                        23

<210> SEQ ID NO 344

<400> SEQUENCE: 344

000

<210> SEQ ID NO 345
<211> LENGTH: 23
<212> TYPE: DNA
<213> ORGANISM: Artificial Sequence
<220> FEATURE:
<223> OTHER INFORMATION: Synthetic

<400> SEQUENCE: 345
```

-continued

```
agacagaggc tggagtgcac tgg                                               23

<210> SEQ ID NO 346
<211> LENGTH: 23
<212> TYPE: DNA
<213> ORGANISM: Artificial Sequence
<220> FEATURE:
<223> OTHER INFORMATION: Synthetic

<400> SEQUENCE: 346
aggcaggggc tggagttcac agg                                               23

<210> SEQ ID NO 347
<211> LENGTH: 23
<212> TYPE: DNA
<213> ORGANISM: Artificial Sequence
<220> FEATURE:
<223> OTHER INFORMATION: Synthetic

<400> SEQUENCE: 347
aggaagggac cagggtgcac cag                                               23

<210> SEQ ID NO 348
<211> LENGTH: 23
<212> TYPE: DNA
<213> ORGANISM: Artificial Sequence
<220> FEATURE:
<223> OTHER INFORMATION: Synthetic

<400> SEQUENCE: 348
ggccaggagc aggggtgcac agg                                               23

<210> SEQ ID NO 349
<211> LENGTH: 23
<212> TYPE: DNA
<213> ORGANISM: Artificial Sequence
<220> FEATURE:
<223> OTHER INFORMATION: Synthetic

<400> SEQUENCE: 349
gggccggggc tggggtgcca ggg                                               23

<210> SEQ ID NO 350
<211> LENGTH: 23
<212> TYPE: DNA
<213> ORGANISM: Artificial Sequence
<220> FEATURE:
<223> OTHER INFORMATION: Synthetic

<400> SEQUENCE: 350 gggcggggc tggggagcac agg                                                23

<210> SEQ ID NO 351
<211> LENGTH: 23
<212> TYPE: DNA
<213> ORGANISM: Artificial Sequence
<220> FEATURE:
<223> OTHER INFORMATION: Synthetic

<400> SEQUENCE: 351
aggcaggagc cagggtgcag agg                                               23

<210> SEQ ID NO 352
<211> LENGTH: 23
<212> TYPE: DNA
```

-continued

```
<213> ORGANISM: Artificial Sequence
<220> FEATURE:
<223> OTHER INFORMATION: Synthetic

<400> SEQUENCE: 352
gggcagaggc tggagtgccc agg                                         23

<210> SEQ ID NO 353
<211> LENGTH: 23
<212> TYPE: DNA
<213> ORGANISM: Artificial Sequence
<220> FEATURE:
<223> OTHER INFORMATION: Synthetic

<400> SEQUENCE: 353
ggacaggggc aggggtgccc ggg                                         23

<210> SEQ ID NO 354
<211> LENGTH: 23
<212> TYPE: DNA
<213> ORGANISM: Artificial Sequence
<220> FEATURE:
<223> OTHER INFORMATION: Synthetic

<400> SEQUENCE: 354
agggaggggc tggggtgcac gga                                         23

<210> SEQ ID NO 355
<211> LENGTH: 23
<212> TYPE: DNA
<213> ORGANISM: Artificial Sequence
<220> FEATURE:
<223> OTHER INFORMATION: Synthetic

<400> SEQUENCE: 355
gggcaggaac tggagtgcat agg                                         23

<210> SEQ ID NO 356
<211> LENGTH: 23
<212> TYPE: DNA
<213> ORGANISM: Artificial Sequence
<220> FEATURE:
<223> OTHER INFORMATION: Synthetic

<400> SEQUENCE: 356
aggcaggaac tggagtgcac aag                                         23

<210> SEQ ID NO 357
<211> LENGTH: 23
<212> TYPE: DNA
<213> ORGANISM: Artificial Sequence
<220> FEATURE:
<223> OTHER INFORMATION: Synthetic

<400> SEQUENCE: 357
gggcagaggc tagggtgcag tgg                                         23

<210> SEQ ID NO 358
<211> LENGTH: 23
<212> TYPE: DNA
<213> ORGANISM: Artificial Sequence
<220> FEATURE:
<223> OTHER INFORMATION: Synthetic

<400> SEQUENCE: 358
aggtaggggt tgggggcac agg                                          23
```

<210> SEQ ID NO 359
<211> LENGTH: 23
<212> TYPE: DNA
<213> ORGANISM: Artificial Sequence
<220> FEATURE:
<223> OTHER INFORMATION: Synthetic

<400> SEQUENCE: 359
gggcagaagc aggggtgctc agg                                              23

<210> SEQ ID NO 360
<211> LENGTH: 23
<212> TYPE: DNA
<213> ORGANISM: Artificial Sequence
<220> FEATURE:
<223> OTHER INFORMATION: Synthetic

<400> SEQUENCE: 360
ggggaggggt gggggtgcac cgg                                              23

<210> SEQ ID NO 361
<211> LENGTH: 23
<212> TYPE: DNA
<213> ORGANISM: Artificial Sequence
<220> FEATURE:
<223> OTHER INFORMATION: Synthetic

<400> SEQUENCE: 361
gagcaggggc tgggggcac tgg                                               23

<210> SEQ ID NO 362
<211> LENGTH: 23
<212> TYPE: DNA
<213> ORGANISM: Artificial Sequence
<220> FEATURE:
<223> OTHER INFORMATION: Synthetic

<400> SEQUENCE: 362
gggcagaggc tggagtgccc agg                                              23

<210> SEQ ID NO 363
<211> LENGTH: 23
<212> TYPE: DNA
<213> ORGANISM: Artificial Sequence
<220> FEATURE:
<223> OTHER INFORMATION: Synthetic

<400> SEQUENCE: 363
gggtgggggc tggggtgccc agg                                              23

<210> SEQ ID NO 364
<211> LENGTH: 23
<212> TYPE: DNA
<213> ORGANISM: Artificial Sequence
<220> FEATURE:
<223> OTHER INFORMATION: Synthetic

<400> SEQUENCE: 364
gggcaagggc aggggtgccc tgg                                              23

<210> SEQ ID NO 365
<211> LENGTH: 23
<212> TYPE: DNA
<213> ORGANISM: Artificial Sequence
<220> FEATURE:

```
<223> OTHER INFORMATION: Synthetic

<400> SEQUENCE: 365
gagagggagc tggggtgcac ggg                                            23

<210> SEQ ID NO 366
<211> LENGTH: 23
<212> TYPE: DNA
<213> ORGANISM: Artificial Sequence
<220> FEATURE:
<223> OTHER INFORMATION: Synthetic

<400> SEQUENCE: 366
aggcagggac tgaggtgcat agg                                            23

<210> SEQ ID NO 367
<211> LENGTH: 23
<212> TYPE: DNA
<213> ORGANISM: Artificial Sequence
<220> FEATURE:
<223> OTHER INFORMATION: Synthetic

<400> SEQUENCE: 367
gggccagggc tgaggtgcac agg                                            23

<210> SEQ ID NO 368
<211> LENGTH: 23
<212> TYPE: DNA
<213> ORGANISM: Artificial Sequence
<220> FEATURE:
<223> OTHER INFORMATION: Synthetic

<400> SEQUENCE: 368
tgggaggggc tagagtgcac agg                                            23

<210> SEQ ID NO 369
<211> LENGTH: 23
<212> TYPE: DNA
<213> ORGANISM: Artificial Sequence
<220> FEATURE:
<223> OTHER INFORMATION: Synthetic

<400> SEQUENCE: 369
ccgcaggggc tgggatgctg ggg                                            23

<210> SEQ ID NO 370

<400> SEQUENCE: 370

000

<210> SEQ ID NO 371
<211> LENGTH: 23
<212> TYPE: DNA
<213> ORGANISM: Artificial Sequence
<220> FEATURE:
<223> OTHER INFORMATION: Synthetic

<400> SEQUENCE: 371
gaggaggggc tggggtgccc tgg                                            23

<210> SEQ ID NO 372
<211> LENGTH: 23
<212> TYPE: DNA
<213> ORGANISM: Artificial Sequence
<220> FEATURE:
```

-continued

```
<223> OTHER INFORMATION: Synthetic

<400> SEQUENCE: 372
gggcaaaggc cggggtgccc agg                                           23

<210> SEQ ID NO 373
<211> LENGTH: 23
<212> TYPE: DNA
<213> ORGANISM: Artificial Sequence
<220> FEATURE:
<223> OTHER INFORMATION: Synthetic

<400> SEQUENCE: 373
aggcgggggc tgggggggctc ggg                                          23

<210> SEQ ID NO 374
<211> LENGTH: 23
<212> TYPE: DNA
<213> ORGANISM: Artificial Sequence
<220> FEATURE:
<223> OTHER INFORMATION: Synthetic

<400> SEQUENCE: 374
aggcaggggc cagggtccac agg                                           23

<210> SEQ ID NO 375

<400> SEQUENCE: 375

000

<210> SEQ ID NO 376
<211> LENGTH: 23
<212> TYPE: DNA
<213> ORGANISM: Artificial Sequence
<220> FEATURE:
<223> OTHER INFORMATION: Synthetic

<400> SEQUENCE: 376
gggttggggt tggggtgcac agg                                           23

<210> SEQ ID NO 377
<211> LENGTH: 23
<212> TYPE: DNA
<213> ORGANISM: Artificial Sequence
<220> FEATURE:
<223> OTHER INFORMATION: Synthetic

<400> SEQUENCE: 377
aggcaggggc cggggtgcgc agg                                           23

<210> SEQ ID NO 378
<211> LENGTH: 23
<212> TYPE: DNA
<213> ORGANISM: Artificial Sequence
<220> FEATURE:
<223> OTHER INFORMATION: Synthetic

<400> SEQUENCE: 378
gggcacagac tggggtgcat tgg                                           23

<210> SEQ ID NO 379
<211> LENGTH: 23
<212> TYPE: DNA
<213> ORGANISM: Artificial Sequence
<220> FEATURE:
```

-continued

<223> OTHER INFORMATION: Synthetic

<400> SEQUENCE: 379
gggctggggc tgaggtgcgc cgg                                              23

<210> SEQ ID NO 380
<211> LENGTH: 23
<212> TYPE: DNA
<213> ORGANISM: Artificial Sequence
<220> FEATURE:
<223> OTHER INFORMATION: Synthetic

<400> SEQUENCE: 380
aggcaggggc tggggggcaa ggg                                              23

<210> SEQ ID NO 381
<211> LENGTH: 23
<212> TYPE: DNA
<213> ORGANISM: Artificial Sequence
<220> FEATURE:
<223> OTHER INFORMATION: Synthetic

<400> SEQUENCE: 381
gagcgggagc tggggggcac agg                                              23

<210> SEQ ID NO 382
<211> LENGTH: 23
<212> TYPE: DNA
<213> ORGANISM: Artificial Sequence
<220> FEATURE:
<223> OTHER INFORMATION: Synthetic

<400> SEQUENCE: 382
gggcagggac tggggtgctt agg                                              23

<210> SEQ ID NO 383
<211> LENGTH: 23
<212> TYPE: DNA
<213> ORGANISM: Artificial Sequence
<220> FEATURE:
<223> OTHER INFORMATION: Synthetic

<400> SEQUENCE: 383
gggaaggggc tggagggcac agg                                              23

<210> SEQ ID NO 384
<211> LENGTH: 23
<212> TYPE: DNA
<213> ORGANISM: Artificial Sequence
<220> FEATURE:
<223> OTHER INFORMATION: Synthetic

<400> SEQUENCE: 384
gggcagggga aggggtggac tgg                                              23

<210> SEQ ID NO 385
<211> LENGTH: 23
<212> TYPE: DNA
<213> ORGANISM: Artificial Sequence
<220> FEATURE:
<223> OTHER INFORMATION: Synthetic

<400> SEQUENCE: 385
agacaggggc tggagtgcag tgg                                              23

-continued

```
<210> SEQ ID NO 386
<211> LENGTH: 23
<212> TYPE: DNA
<213> ORGANISM: Artificial Sequence
<220> FEATURE:
<223> OTHER INFORMATION: Synthetic

<400> SEQUENCE: 386
gggcagaggc tggagtgcaa tgg                                                    23

<210> SEQ ID NO 387
<211> LENGTH: 23
<212> TYPE: DNA
<213> ORGANISM: Artificial Sequence
<220> FEATURE:
<223> OTHER INFORMATION: Synthetic

<400> SEQUENCE: 387
gggctggggc tggggagcag ggg                                                    23

<210> SEQ ID NO 388
<211> LENGTH: 23
<212> TYPE: DNA
<213> ORGANISM: Artificial Sequence
<220> FEATURE:
<223> OTHER INFORMATION: Synthetic

<400> SEQUENCE: 388
aggaaagggc tggagtgcag ggg                                                    23

<210> SEQ ID NO 389
<211> LENGTH: 23
<212> TYPE: DNA
<213> ORGANISM: Artificial Sequence
<220> FEATURE:
<223> OTHER INFORMATION: Synthetic

<400> SEQUENCE: 389
gggcaggaac tggagtgcac cag                                                    23

<210> SEQ ID NO 390
<211> LENGTH: 23
<212> TYPE: DNA
<213> ORGANISM: Artificial Sequence
<220> FEATURE:
<223> OTHER INFORMATION: Synthetic

<400> SEQUENCE: 390
aggcaggaac tggagtgcac aag                                                    23

<210> SEQ ID NO 391
<211> LENGTH: 23
<212> TYPE: DNA
<213> ORGANISM: Artificial Sequence
<220> FEATURE:
<223> OTHER INFORMATION: Synthetic

<400> SEQUENCE: 391
aggcagagcc tggggtgcag ggg                                                    23

<210> SEQ ID NO 392
<211> LENGTH: 23
<212> TYPE: DNA
<213> ORGANISM: Artificial Sequence
<220> FEATURE:
<223> OTHER INFORMATION: Synthetic
```

-continued

<400> SEQUENCE: 392
gggcagggcc aggggagcac agg                                                          23

<210> SEQ ID NO 393
<211> LENGTH: 23
<212> TYPE: DNA
<213> ORGANISM: Artificial Sequence
<220> FEATURE:
<223> OTHER INFORMATION: Synthetic

<400> SEQUENCE: 393
agccaggggc tgggggaac agg                                                           23

<210> SEQ ID NO 394
<211> LENGTH: 23
<212> TYPE: DNA
<213> ORGANISM: Artificial Sequence
<220> FEATURE:
<223> OTHER INFORMATION: Synthetic

<400> SEQUENCE: 394 gggcaggggga tggggtgcag tgg                                                         23

<210> SEQ ID NO 395
<211> LENGTH: 23
<212> TYPE: DNA
<213> ORGANISM: Artificial Sequence
<220> FEATURE:
<223> OTHER INFORMATION: Synthetic

<400> SEQUENCE: 395
aggcaaggcc tggggtgccc agg                                                          23

<210> SEQ ID NO 396
<211> LENGTH: 23
<212> TYPE: DNA
<213> ORGANISM: Artificial Sequence
<220> FEATURE:
<223> OTHER INFORMATION: Synthetic

<400> SEQUENCE: 396
gggctggggc tggggagcac ggg                                                          23

<210> SEQ ID NO 397
<211> LENGTH: 23
<212> TYPE: DNA
<213> ORGANISM: Artificial Sequence
<220> FEATURE:
<223> OTHER INFORMATION: Synthetic

<400> SEQUENCE: 397
gagaaggggc tgggaagcac agg                                                          23

<210> SEQ ID NO 398
<211> LENGTH: 23
<212> TYPE: DNA
<213> ORGANISM: Artificial Sequence
<220> FEATURE:
<223> OTHER INFORMATION: Synthetic

<400> SEQUENCE: 398
aggcaggaac tggagtgcac aag                                                          23

<210> SEQ ID NO 399
<211> LENGTH: 23

-continued

```
<212> TYPE: DNA
<213> ORGANISM: Artificial Sequence
<220> FEATURE:
<223> OTHER INFORMATION: Synthetic

<400> SEQUENCE: 399
ggggaggggc tggggtgcca ggg                                              23

<210> SEQ ID NO 400
<211> LENGTH: 23
<212> TYPE: DNA
<213> ORGANISM: Artificial Sequence
<220> FEATURE:
<223> OTHER INFORMATION: Synthetic

<400> SEQUENCE: 400
aggaaggggc tgggaaaac agg                                               23

<210> SEQ ID NO 401
<211> LENGTH: 23
<212> TYPE: DNA
<213> ORGANISM: Artificial Sequence
<220> FEATURE:
<223> OTHER INFORMATION: Synthetic

<400> SEQUENCE: 401
ccccaggggc tggggtgcct ggg                                              23

<210> SEQ ID NO 402
<211> LENGTH: 23
<212> TYPE: DNA
<213> ORGANISM: Artificial Sequence
<220> FEATURE:
<223> OTHER INFORMATION: Synthetic

<400> SEQUENCE: 402
aagcagaggc tgaagtgcac agg                                              23

<210> SEQ ID NO 403
<211> LENGTH: 23
<212> TYPE: DNA
<213> ORGANISM: Artificial Sequence
<220> FEATURE:
<223> OTHER INFORMATION: Synthetic

<400> SEQUENCE: 403
aggcaggaac tagagtgcac agg                                              23

<210> SEQ ID NO 404
<211> LENGTH: 23
<212> TYPE: DNA
<213> ORGANISM: Artificial Sequence
<220> FEATURE:
<223> OTHER INFORMATION: Synthetic

<400> SEQUENCE: 404
gggcaggggg tggggtccac agg                                              23

<210> SEQ ID NO 405

<400> SEQUENCE: 405

000

<210> SEQ ID NO 406
<211> LENGTH: 23
```

```
<212> TYPE: DNA
<213> ORGANISM: Artificial Sequence
<220> FEATURE:
<223> OTHER INFORMATION: Synthetic

<400> SEQUENCE: 406
ggggaggggc tggggagcac gga                                              23

<210> SEQ ID NO 407
<211> LENGTH: 23
<212> TYPE: DNA
<213> ORGANISM: Artificial Sequence
<220> FEATURE:
<223> OTHER INFORMATION: Synthetic

<400> SEQUENCE: 407
aggcagaggc tggagtggac cgg                                              23

<210> SEQ ID NO 408
<211> LENGTH: 23
<212> TYPE: DNA
<213> ORGANISM: Artificial Sequence
<220> FEATURE:
<223> OTHER INFORMATION: Synthetic

<400> SEQUENCE: 408
gggtaggggc tgggggatac cgg                                              23

<210> SEQ ID NO 409
<211> LENGTH: 23
<212> TYPE: DNA
<213> ORGANISM: Artificial Sequence
<220> FEATURE:
<223> OTHER INFORMATION: Synthetic

<400> SEQUENCE: 409
gggaagggtc tggagtccac tgg                                              23

<210> SEQ ID NO 410
<211> LENGTH: 23
<212> TYPE: DNA
<213> ORGANISM: Artificial Sequence
<220> FEATURE:
<223> OTHER INFORMATION: Synthetic

<400> SEQUENCE: 410
gggcaggaac tagagtgcac ggg                                              23

<210> SEQ ID NO 411
<211> LENGTH: 23
<212> TYPE: DNA
<213> ORGANISM: Artificial Sequence
<220> FEATURE:
<223> OTHER INFORMATION: Synthetic

<400> SEQUENCE: 411
gggcagggac tggggtgctc tgg                                              23

<210> SEQ ID NO 412
<211> LENGTH: 23
<212> TYPE: DNA
<213> ORGANISM: Artificial Sequence
<220> FEATURE:
<223> OTHER INFORMATION: Synthetic

<400> SEQUENCE: 412
```

-continued

```
gagtagggc aggggtgctc tgg                                               23

<210> SEQ ID NO 413
<211> LENGTH: 23
<212> TYPE: DNA
<213> ORGANISM: Artificial Sequence
<220> FEATURE:
<223> OTHER INFORMATION: Synthetic

<400> SEQUENCE: 413
aggaagggcc tggggtgcac aga                                              23

<210> SEQ ID NO 414
<211> LENGTH: 23
<212> TYPE: DNA
<213> ORGANISM: Artificial Sequence
<220> FEATURE:
<223> OTHER INFORMATION: Synthetic

<400> SEQUENCE: 414 ggccagggc tggggtgcac ggt                                               23

<210> SEQ ID NO 415
<211> LENGTH: 23
<212> TYPE: DNA
<213> ORGANISM: Artificial Sequence
<220> FEATURE:
<223> OTHER INFORMATION: Synthetic

<400> SEQUENCE: 415 aggcagggc cagggtgcat ggg                                               23

<210> SEQ ID NO 416
<211> LENGTH: 23
<212> TYPE: DNA
<213> ORGANISM: Artificial Sequence
<220> FEATURE:
<223> OTHER INFORMATION: Synthetic

<400> SEQUENCE: 416
gggcagagga tggggtgcag ggg                                              23

<210> SEQ ID NO 417
<211> LENGTH: 23
<212> TYPE: DNA
<213> ORGANISM: Artificial Sequence
<220> FEATURE:
<223> OTHER INFORMATION: Synthetic

<400> SEQUENCE: 417 cggcagggc tggagtgcag tgg                                               23

<210> SEQ ID NO 418
<211> LENGTH: 23
<212> TYPE: DNA
<213> ORGANISM: Artificial Sequence
<220> FEATURE:
<223> OTHER INFORMATION: Synthetic

<400> SEQUENCE: 418
aggcaggatc tggagtgcac agg                                              23

<210> SEQ ID NO 419
<211> LENGTH: 23
<212> TYPE: DNA
<213> ORGANISM: Artificial Sequence
```

<220> FEATURE:
<223> OTHER INFORMATION: Synthetic

<400> SEQUENCE: 419
agacaggagc tggagtgcac aag                                                   23

<210> SEQ ID NO 420
<211> LENGTH: 23
<212> TYPE: DNA
<213> ORGANISM: Artificial Sequence
<220> FEATURE:
<223> OTHER INFORMATION: Synthetic

<400> SEQUENCE: 420
tggcaggggc aggatgctc tgg                                                    23

<210> SEQ ID NO 421
<211> LENGTH: 23
<212> TYPE: DNA
<213> ORGANISM: Artificial Sequence
<220> FEATURE:
<223> OTHER INFORMATION: Synthetic

<400> SEQUENCE: 421
cctcaggggt tgggatgcac tgg                                                   23

<210> SEQ ID NO 422
<211> LENGTH: 23
<212> TYPE: DNA
<213> ORGANISM: Artificial Sequence
<220> FEATURE:
<223> OTHER INFORMATION: Synthetic

<400> SEQUENCE: 422
gagcagggtc aggggtgcag agg                                                   23

<210> SEQ ID NO 423
<211> LENGTH: 23
<212> TYPE: DNA
<213> ORGANISM: Artificial Sequence
<220> FEATURE:
<223> OTHER INFORMATION: Synthetic

<400> SEQUENCE: 423
caggagtggc tggggtgcac agg                                                   23

<210> SEQ ID NO 424
<211> LENGTH: 23
<212> TYPE: DNA
<213> ORGANISM: Artificial Sequence
<220> FEATURE:
<223> OTHER INFORMATION: Synthetic

<400> SEQUENCE: 424
gggcctgggc tgagatgcac ggg                                                   23

<210> SEQ ID NO 425
<211> LENGTH: 23
<212> TYPE: DNA
<213> ORGANISM: Artificial Sequence
<220> FEATURE:
<223> OTHER INFORMATION: Synthetic

<400> SEQUENCE: 425
acgcaggggc tagggagcac aag                                                   23

```
<210> SEQ ID NO 426
<211> LENGTH: 23
<212> TYPE: DNA
<213> ORGANISM: Artificial Sequence
<220> FEATURE:
<223> OTHER INFORMATION: Synthetic

<400> SEQUENCE: 426
gggctggggc tggggaggac ggg                                          23

<210> SEQ ID NO 427
<211> LENGTH: 23
<212> TYPE: DNA
<213> ORGANISM: Artificial Sequence
<220> FEATURE:
<223> OTHER INFORMATION: Synthetic

<400> SEQUENCE: 427
gggcagggat tgggggcac agg                                           23

<210> SEQ ID NO 428
<211> LENGTH: 23
<212> TYPE: DNA
<213> ORGANISM: Artificial Sequence
<220> FEATURE:
<223> OTHER INFORMATION: Synthetic

<400> SEQUENCE: 428
agggaggggc cgggctgcac tgg                                          23

<210> SEQ ID NO 429
<211> LENGTH: 4
<212> TYPE: DNA
<213> ORGANISM: Artificial Sequence
<220> FEATURE:
<223> OTHER INFORMATION: Synthetic

<400> SEQUENCE: 429 aaaa                                                               4

<210> SEQ ID NO 430
<211> LENGTH: 4
<212> TYPE: DNA
<213> ORGANISM: Artificial Sequence
<220> FEATURE:
<223> OTHER INFORMATION: Synthetic

<400> SEQUENCE: 430 aaaa                                                               4

<210> SEQ ID NO 431
<211> LENGTH: 4
<212> TYPE: DNA
<213> ORGANISM: Artificial Sequence
<220> FEATURE:
<223> OTHER INFORMATION: Synthetic

<400> SEQUENCE: 431 aaaa                                                               4

<210> SEQ ID NO 432
<211> LENGTH: 4
<212> TYPE: DNA
<213> ORGANISM: Artificial Sequence
<220> FEATURE:
<223> OTHER INFORMATION: Synthetic
```

```
<400> SEQUENCE: 432 aaaa                                                          4

<210> SEQ ID NO 433
<211> LENGTH: 4
<212> TYPE: DNA
<213> ORGANISM: Artificial Sequence
<220> FEATURE:
<223> OTHER INFORMATION: Synthetic

<400> SEQUENCE: 433 aaaa                                                          4

<210> SEQ ID NO 434
<211> LENGTH: 5
<212> TYPE: DNA
<213> ORGANISM: Artificial Sequence
<220> FEATURE:
<223> OTHER INFORMATION: Synthetic

<400> SEQUENCE: 434 aaaaa                                                         5

<210> SEQ ID NO 435
<211> LENGTH: 4
<212> TYPE: DNA
<213> ORGANISM: Artificial Sequence
<220> FEATURE:
<223> OTHER INFORMATION: Synthetic

<400> SEQUENCE: 435 ccta                                                          4

<210> SEQ ID NO 436
<211> LENGTH: 4
<212> TYPE: DNA
<213> ORGANISM: Artificial Sequence
<220> FEATURE:
<223> OTHER INFORMATION: Synthetic

<400> SEQUENCE: 436 ccta                                                          4

<210> SEQ ID NO 437
<211> LENGTH: 4
<212> TYPE: DNA
<213> ORGANISM: Artificial Sequence
<220> FEATURE:
<223> OTHER INFORMATION: Synthetic

<400> SEQUENCE: 437 ttaa                                                          4

<210> SEQ ID NO 438
<211> LENGTH: 4
<212> TYPE: DNA
<213> ORGANISM: Artificial Sequence
<220> FEATURE:
<223> OTHER INFORMATION: Synthetic

<400> SEQUENCE: 438 aaaa                                                          4

<210> SEQ ID NO 439
```

```
<211> LENGTH: 5
<212> TYPE: DNA
<213> ORGANISM: Artificial Sequence
<220> FEATURE:
<223> OTHER INFORMATION: Synthetic

<400> SEQUENCE: 439 aaaca                                                                    5

<210> SEQ ID NO 440
<211> LENGTH: 5
<212> TYPE: DNA
<213> ORGANISM: Artificial Sequence
<220> FEATURE:
<223> OTHER INFORMATION: Synthetic

<400> SEQUENCE: 440 aacag                                                                    5

<210> SEQ ID NO 441
<211> LENGTH: 4
<212> TYPE: DNA
<213> ORGANISM: Artificial Sequence
<220> FEATURE:
<223> OTHER INFORMATION: Synthetic

<400> SEQUENCE: 441 aaat                                                                     4

<210> SEQ ID NO 442
<211> LENGTH: 4
<212> TYPE: DNA
<213> ORGANISM: Artificial Sequence
<220> FEATURE:
<223> OTHER INFORMATION: Synthetic

<400> SEQUENCE: 442 aaaa                                                                     4

<210> SEQ ID NO 443
<211> LENGTH: 4
<212> TYPE: DNA
<213> ORGANISM: Artificial Sequence
<220> FEATURE:
<223> OTHER INFORMATION: Synthetic

<400> SEQUENCE: 443 attg                                                                     4

<210> SEQ ID NO 444
<211> LENGTH: 4
<212> TYPE: DNA
<213> ORGANISM: Artificial Sequence
<220> FEATURE:
<223> OTHER INFORMATION: Synthetic

<400> SEQUENCE: 444 aaat                                                                     4

<210> SEQ ID NO 445
<211> LENGTH: 4
<212> TYPE: DNA
<213> ORGANISM: Artificial Sequence
<220> FEATURE:
<223> OTHER INFORMATION: Synthetic

<400> SEQUENCE: 445
```

-continued

```
aaga                                                              4

<210> SEQ ID NO 446
<211> LENGTH: 4
<212> TYPE: DNA
<213> ORGANISM: Artificial Sequence
<220> FEATURE:
<223> OTHER INFORMATION: Synthetic

<400> SEQUENCE: 446 aaat                                                              4

<210> SEQ ID NO 447
<211> LENGTH: 4
<212> TYPE: DNA
<213> ORGANISM: Artificial Sequence
<220> FEATURE:
<223> OTHER INFORMATION: Synthetic

<400> SEQUENCE: 447 tgaa                                                              4

<210> SEQ ID NO 448
<211> LENGTH: 4
<212> TYPE: DNA
<213> ORGANISM: Artificial Sequence
<220> FEATURE:
<223> OTHER INFORMATION: Synthetic

<400> SEQUENCE: 448 aacc                                                              4

<210> SEQ ID NO 449
<211> LENGTH: 4
<212> TYPE: DNA
<213> ORGANISM: Artificial Sequence
<220> FEATURE:
<223> OTHER INFORMATION: Synthetic

<400> SEQUENCE: 449 aggt                                                              4

<210> SEQ ID NO 450
<211> LENGTH: 4
<212> TYPE: DNA
<213> ORGANISM: Artificial Sequence
<220> FEATURE:
<223> OTHER INFORMATION: Synthetic

<400> SEQUENCE: 450 acac                                                              4

<210> SEQ ID NO 451
<211> LENGTH: 4
<212> TYPE: DNA
<213> ORGANISM: Artificial Sequence
<220> FEATURE:
<223> OTHER INFORMATION: Synthetic

<400> SEQUENCE: 451 caat                                                              4

<210> SEQ ID NO 452
<211> LENGTH: 4
<212> TYPE: DNA
```

-continued

```
<213> ORGANISM: Artificial Sequence
<220> FEATURE:
<223> OTHER INFORMATION: Synthetic

<400> SEQUENCE: 452 agag                                                              4

<210> SEQ ID NO 453
<211> LENGTH: 4
<212> TYPE: DNA
<213> ORGANISM: Artificial Sequence
<220> FEATURE:
<223> OTHER INFORMATION: Synthetic

<400> SEQUENCE: 453 aaag                                                              4

<210> SEQ ID NO 454
<211> LENGTH: 5
<212> TYPE: DNA
<213> ORGANISM: Artificial Sequence
<220> FEATURE:
<223> OTHER INFORMATION: Synthetic

<400> SEQUENCE: 454 aaaag                                                             5

<210> SEQ ID NO 455
<211> LENGTH: 4
<212> TYPE: DNA
<213> ORGANISM: Artificial Sequence
<220> FEATURE:
<223> OTHER INFORMATION: Synthetic

<400> SEQUENCE: 455 aaaa                                                              4

<210> SEQ ID NO 456
<211> LENGTH: 4
<212> TYPE: DNA
<213> ORGANISM: Artificial Sequence
<220> FEATURE:
<223> OTHER INFORMATION: Synthetic

<400> SEQUENCE: 456 aacg                                                              4

<210> SEQ ID NO 457
<211> LENGTH: 4
<212> TYPE: DNA
<213> ORGANISM: Artificial Sequence
<220> FEATURE:
<223> OTHER INFORMATION: Synthetic

<400> SEQUENCE: 457 acga                                                              4

<210> SEQ ID NO 458
<211> LENGTH: 4
<212> TYPE: DNA
<213> ORGANISM: Artificial Sequence
<220> FEATURE:
<223> OTHER INFORMATION: Synthetic

<400> SEQUENCE: 458 aacc                                                              4
```

```
<210> SEQ ID NO 459
<211> LENGTH: 4
<212> TYPE: DNA
<213> ORGANISM: Artificial Sequence
<220> FEATURE:
<223> OTHER INFORMATION: Synthetic

<400> SEQUENCE: 459 aaaa                                                                  4

<210> SEQ ID NO 460
<211> LENGTH: 4
<212> TYPE: DNA
<213> ORGANISM: Artificial Sequence
<220> FEATURE:
<223> OTHER INFORMATION: Synthetic

<400> SEQUENCE: 460 aaaa                                                                  4

<210> SEQ ID NO 461
<211> LENGTH: 5
<212> TYPE: DNA
<213> ORGANISM: Artificial Sequence
<220> FEATURE:
<223> OTHER INFORMATION: Synthetic

<400> SEQUENCE: 461 aaaaa                                                                 5

<210> SEQ ID NO 462
<211> LENGTH: 5
<212> TYPE: DNA
<213> ORGANISM: Artificial Sequence
<220> FEATURE:
<223> OTHER INFORMATION: Synthetic

<400> SEQUENCE: 462 cccct                                                                 5

<210> SEQ ID NO 463
<211> LENGTH: 5
<212> TYPE: DNA
<213> ORGANISM: Artificial Sequence
<220> FEATURE:
<223> OTHER INFORMATION: Synthetic

<400> SEQUENCE: 463 aaaaa                                                                 5

<210> SEQ ID NO 464
<211> LENGTH: 5
<212> TYPE: DNA
<213> ORGANISM: Artificial Sequence
<220> FEATURE:
<223> OTHER INFORMATION: Synthetic

<400> SEQUENCE: 464 aaaaa                                                                 5

<210> SEQ ID NO 465
<211> LENGTH: 4
<212> TYPE: DNA
<213> ORGANISM: Artificial Sequence
<220> FEATURE:
```

-continued

```
<223> OTHER INFORMATION: Synthetic

<400> SEQUENCE: 465 aaag                                                              4

<210> SEQ ID NO 466
<211> LENGTH: 4
<212> TYPE: DNA
<213> ORGANISM: Artificial Sequence
<220> FEATURE:
<223> OTHER INFORMATION: Synthetic

<400> SEQUENCE: 466 tgat                                                              4

<210> SEQ ID NO 467
<211> LENGTH: 4
<212> TYPE: DNA
<213> ORGANISM: Artificial Sequence
<220> FEATURE:
<223> OTHER INFORMATION: Synthetic

<400> SEQUENCE: 467 atac                                                              4

<210> SEQ ID NO 468
<211> LENGTH: 4
<212> TYPE: DNA
<213> ORGANISM: Artificial Sequence
<220> FEATURE:
<223> OTHER INFORMATION: Synthetic

<400> SEQUENCE: 468 aaaa                                                              4

<210> SEQ ID NO 469
<211> LENGTH: 4
<212> TYPE: DNA
<213> ORGANISM: Artificial Sequence
<220> FEATURE:
<223> OTHER INFORMATION: Synthetic

<400> SEQUENCE: 469 atat                                                              4

<210> SEQ ID NO 470
<211> LENGTH: 4
<212> TYPE: DNA
<213> ORGANISM: Artificial Sequence
<220> FEATURE:
<223> OTHER INFORMATION: Synthetic

<400> SEQUENCE: 470 acat                                                              4

<210> SEQ ID NO 471
<211> LENGTH: 4
<212> TYPE: DNA
<213> ORGANISM: Artificial Sequence
<220> FEATURE:
<223> OTHER INFORMATION: Synthetic

<400> SEQUENCE: 471 aata                                                              4
```

-continued

```
<210> SEQ ID NO 472
<211> LENGTH: 4
<212> TYPE: DNA
<213> ORGANISM: Artificial Sequence
<220> FEATURE:
<223> OTHER INFORMATION: Synthetic

<400> SEQUENCE: 472 aaaa                                                                    4

<210> SEQ ID NO 473
<211> LENGTH: 4
<212> TYPE: DNA
<213> ORGANISM: Artificial Sequence
<220> FEATURE:
<223> OTHER INFORMATION: Synthetic

<400> SEQUENCE: 473 taat                                                                    4

<210> SEQ ID NO 474
<211> LENGTH: 5
<212> TYPE: DNA
<213> ORGANISM: Artificial Sequence
<220> FEATURE:
<223> OTHER INFORMATION: Synthetic

<400> SEQUENCE: 474 cctta                                                                   5

<210> SEQ ID NO 475
<211> LENGTH: 4
<212> TYPE: DNA
<213> ORGANISM: Artificial Sequence
<220> FEATURE:
<223> OTHER INFORMATION: Synthetic

<400> SEQUENCE: 475 atag                                                                    4

<210> SEQ ID NO 476
<211> LENGTH: 4
<212> TYPE: DNA
<213> ORGANISM: Artificial Sequence
<220> FEATURE:
<223> OTHER INFORMATION: Synthetic

<400> SEQUENCE: 476 cagt                                                                    4

<210> SEQ ID NO 477
<211> LENGTH: 4
<212> TYPE: DNA
<213> ORGANISM: Artificial Sequence
<220> FEATURE:
<223> OTHER INFORMATION: Synthetic

<400> SEQUENCE: 477 ctaa                                                                    4

<210> SEQ ID NO 478
<211> LENGTH: 4
<212> TYPE: DNA
<213> ORGANISM: Artificial Sequence
<220> FEATURE:
<223> OTHER INFORMATION: Synthetic
```

-continued

```
<400> SEQUENCE: 478 acaa                                                              4

<210> SEQ ID NO 479
<211> LENGTH: 4
<212> TYPE: DNA
<213> ORGANISM: Artificial Sequence
<220> FEATURE:
<223> OTHER INFORMATION: Synthetic

<400> SEQUENCE: 479 agcc                                                              4

<210> SEQ ID NO 480
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 480
gaatggcagg cggaggttgt actgnnnncc nn                              32

<210> SEQ ID NO 481
<211> LENGTH: 32
<212> TYPE: DNA
<213> ORGANISM: Artificial Sequence
<220> FEATURE:
<223> OTHER INFORMATION: Synthetic

<400> SEQUENCE: 481
gaatggcagg cggaggttgt actgggggcc ag                             32

<210> SEQ ID NO 482
<211> LENGTH: 32
<212> TYPE: DNA
<213> ORGANISM: Artificial Sequence
<220> FEATURE:
<223> OTHER INFORMATION: Synthetic

<400> SEQUENCE: 482
aaacggaagc cgcacgtctc actagtaccc tc                             32

<210> SEQ ID NO 483
<211> LENGTH: 10
<212> TYPE: DNA
<213> ORGANISM: Artificial Sequence
<220> FEATURE:
<223> OTHER INFORMATION: Synthetic

<400> SEQUENCE: 483
acacccctca                                                      10

<210> SEQ ID NO 484
<211> LENGTH: 8
<212> TYPE: DNA
<213> ORGANISM: Artificial Sequence
<220> FEATURE:
<223> OTHER INFORMATION: Synthetic
```

<400> SEQUENCE: 484 gggggccag                                                               8

<210> SEQ ID NO 485
<211> LENGTH: 8
<212> TYPE: DNA
<213> ORGANISM: Artificial Sequence
<220> FEATURE:
<223> OTHER INFORMATION: Synthetic

<400> SEQUENCE: 485 gtaccctc                                                                8

<210> SEQ ID NO 486
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 486
gtgagcaggc acctgtgcca acatnnnncc nn                                     32

<210> SEQ ID NO 487
<211> LENGTH: 32
<212> TYPE: DNA
<213> ORGANISM: Artificial Sequence
<220> FEATURE:
<223> OTHER INFORMATION: Synthetic

<400> SEQUENCE: 487
gtgagcaggc acctgtgcca acatgggccc gc                                     32

<210> SEQ ID NO 488
<211> LENGTH: 8
<212> TYPE: DNA
<213> ORGANISM: Artificial Sequence
<220> FEATURE:
<223> OTHER INFORMATION: Synthetic

<400> SEQUENCE: 488 gggcccgc                                                                8

<210> SEQ ID NO 489
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 489
gcatgggcag gggctggggt gcacnnnncc nn                                    32

<210> SEQ ID NO 490
<211> LENGTH: 32
<212> TYPE: DNA
<213> ORGANISM: Artificial Sequence
<220> FEATURE:
<223> OTHER INFORMATION: Synthetic

<400> SEQUENCE: 490
gcatgggcag gggctggggt gcacaggccc ag                                    32

<210> SEQ ID NO 491
<211> LENGTH: 32
<212> TYPE: DNA
<213> ORGANISM: Artificial Sequence
<220> FEATURE:
<223> OTHER INFORMATION: Synthetic

<400> SEQUENCE: 491
gcaggaagcg tcgccggggg gcccacaagg gt                                    32

<210> SEQ ID NO 492
<211> LENGTH: 10
<212> TYPE: DNA
<213> ORGANISM: Artificial Sequence
<220> FEATURE:
<223> OTHER INFORMATION: Synthetic

<400> SEQUENCE: 492
gaagctccgc                                                             10

<210> SEQ ID NO 493
<211> LENGTH: 8
<212> TYPE: DNA
<213> ORGANISM: Artificial Sequence
<220> FEATURE:
<223> OTHER INFORMATION: Synthetic

<400> SEQUENCE: 493 aggcccag                                                                8

<210> SEQ ID NO 494
<211> LENGTH: 8
<212> TYPE: DNA
<213> ORGANISM: Artificial Sequence
<220> FEATURE:
<223> OTHER INFORMATION: Synthetic

<400> SEQUENCE: 494 acaagggt                                                                8

<210> SEQ ID NO 495
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 495

-continued

```
tgaggaccgc cctgggcctg ggagnnncc nn                                    32

<210> SEQ ID NO 496
<211> LENGTH: 32
<212> TYPE: DNA
<213> ORGANISM: Artificial Sequence
<220> FEATURE:
<223> OTHER INFORMATION: Synthetic

<400> SEQUENCE: 496
tgaggaccgc cctgggcctg ggagaatccc tt                                   32

<210> SEQ ID NO 497
<211> LENGTH: 32
<212> TYPE: DNA
<213> ORGANISM: Artificial Sequence
<220> FEATURE:
<223> OTHER INFORMATION: Synthetic

<400> SEQUENCE: 497
gaaggaccac cctaggcctg ggagactccc tc                                   32

<210> SEQ ID NO 498
<211> LENGTH: 4
<212> TYPE: DNA
<213> ORGANISM: Artificial Sequence
<220> FEATURE:
<223> OTHER INFORMATION: Synthetic

<400> SEQUENCE: 498 gaaa                                                                  4

<210> SEQ ID NO 499
<211> LENGTH: 8
<212> TYPE: DNA
<213> ORGANISM: Artificial Sequence
<220> FEATURE:
<223> OTHER INFORMATION: Synthetic

<400> SEQUENCE: 499 aatcccctt                                                             8

<210> SEQ ID NO 500
<211> LENGTH: 8
<212> TYPE: DNA
<213> ORGANISM: Artificial Sequence
<220> FEATURE:
<223> OTHER INFORMATION: Synthetic

<400> SEQUENCE: 500 actccctc                                                              8

<210> SEQ ID NO 501
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
```

-continued

<400> SEQUENCE: 501
ggcctggctg atgaggccgc acatnnnncc nn                                    32

<210> SEQ ID NO 502
<211> LENGTH: 32
<212> TYPE: DNA
<213> ORGANISM: Artificial Sequence
<220> FEATURE:
<223> OTHER INFORMATION: Synthetic

<400> SEQUENCE: 502
ggcctggctg atgaggccgc acatgtggcc ac                                    32

<210> SEQ ID NO 503
<211> LENGTH: 8
<212> TYPE: DNA
<213> ORGANISM: Artificial Sequence
<220> FEATURE:
<223> OTHER INFORMATION: Synthetic

<400> SEQUENCE: 503 gtggccac                                                                8

<210> SEQ ID NO 504
<211> LENGTH: 23
<212> TYPE: DNA
<213> ORGANISM: Artificial Sequence
<220> FEATURE:
<223> OTHER INFORMATION: Synthetic

<400> SEQUENCE: 504
gtcacctgcc tcgtggaata cgg                                              23

<210> SEQ ID NO 505
<211> LENGTH: 23
<212> TYPE: DNA
<213> ORGANISM: Artificial Sequence
<220> FEATURE:
<223> OTHER INFORMATION: Synthetic

<400> SEQUENCE: 505
gcacctgcct cgtggaatac ggt                                              23

<210> SEQ ID NO 506
<211> LENGTH: 22
<212> TYPE: DNA
<213> ORGANISM: Artificial Sequence
<220> FEATURE:
<223> OTHER INFORMATION: Synthetic

<400> SEQUENCE: 506
gttcagcgtg tccggctttg gc                                               22

<210> SEQ ID NO 507
<211> LENGTH: 24
<212> TYPE: DNA
<213> ORGANISM: Artificial Sequence
<220> FEATURE:
<223> OTHER INFORMATION: Synthetic

<400> SEQUENCE: 507
gtggtgagca agggcgagga gctg                                             24

<210> SEQ ID NO 508
<211> LENGTH: 24

-continued

```
<212> TYPE: DNA
<213> ORGANISM: Artificial Sequence
<220> FEATURE:
<223> OTHER INFORMATION: Synthetic

<400> SEQUENCE: 508
gggcgaggag ctgttcaccg gggt                                              24

<210> SEQ ID NO 509
<211> LENGTH: 24
<212> TYPE: DNA
<213> ORGANISM: Artificial Sequence
<220> FEATURE:
<223> OTHER INFORMATION: Synthetic

<400> SEQUENCE: 509
gtgaacttgt ggccgtttac gtcg                                              24

<210> SEQ ID NO 510
<211> LENGTH: 24
<212> TYPE: DNA
<213> ORGANISM: Artificial Sequence
<220> FEATURE:
<223> OTHER INFORMATION: Synthetic

<400> SEQUENCE: 510
gcgtccagct cgaccaggat gggc                                              24

<210> SEQ ID NO 511
<211> LENGTH: 24
<212> TYPE: DNA
<213> ORGANISM: Artificial Sequence
<220> FEATURE:
<223> OTHER INFORMATION: Synthetic

<400> SEQUENCE: 511
gcggtgaaca gctcctcgcc cttg                                              24

<210> SEQ ID NO 512
<211> LENGTH: 24
<212> TYPE: DNA
<213> ORGANISM: Artificial Sequence
<220> FEATURE:
<223> OTHER INFORMATION: Synthetic

<400> SEQUENCE: 512
gggcaccacc ccggtgaaca gctc                                              24

<210> SEQ ID NO 513
<211> LENGTH: 24
<212> TYPE: DNA
<213> ORGANISM: Artificial Sequence
<220> FEATURE:
<223> OTHER INFORMATION: Synthetic

<400> SEQUENCE: 513
ggcaccaccc cggtgaacag ctcc                                              24

<210> SEQ ID NO 514
<211> LENGTH: 24
<212> TYPE: DNA
<213> ORGANISM: Artificial Sequence
<220> FEATURE:
<223> OTHER INFORMATION: Synthetic

<400> SEQUENCE: 514
```

```
gggatgggca ccaccccggt gaac                                    24
```

<210> SEQ ID NO 515
<211> LENGTH: 24
<212> TYPE: DNA
<213> ORGANISM: Artificial Sequence
<220> FEATURE:
<223> OTHER INFORMATION: Synthetic

<400> SEQUENCE: 515

```
gcgtgtccgg ctttggcgag acaa                                    24
```

<210> SEQ ID NO 516
<211> LENGTH: 24
<212> TYPE: DNA
<213> ORGANISM: Artificial Sequence
<220> FEATURE:
<223> OTHER INFORMATION: Synthetic

<400> SEQUENCE: 516

```
gtccggcttt ggcgagacaa atca                                    24
```

<210> SEQ ID NO 517
<211> LENGTH: 24
<212> TYPE: DNA
<213> ORGANISM: Artificial Sequence
<220> FEATURE:
<223> OTHER INFORMATION: Synthetic

<400> SEQUENCE: 517

```
gatcacctgc ctcgtggaat acgg                                    24
```

<210> SEQ ID NO 518
<211> LENGTH: 24
<212> TYPE: DNA
<213> ORGANISM: Artificial Sequence
<220> FEATURE:
<223> OTHER INFORMATION: Synthetic

<400> SEQUENCE: 518

```
gacgctgaac ttgtggccgt ttac                                    24
```

<210> SEQ ID NO 519
<211> LENGTH: 24
<212> TYPE: DNA
<213> ORGANISM: Artificial Sequence
<220> FEATURE:
<223> OTHER INFORMATION: Synthetic

<400> SEQUENCE: 519

```
gccaaagccg gacacgctga actt                                    24
```

<210> SEQ ID NO 520
<211> LENGTH: 23
<212> TYPE: DNA
<213> ORGANISM: Artificial Sequence
<220> FEATURE:
<223> OTHER INFORMATION: Synthetic

<400> SEQUENCE: 520

```
ggaacttgtg gccgtttacg tcg                                     23
```

<210> SEQ ID NO 521
<211> LENGTH: 22
<212> TYPE: DNA
<213> ORGANISM: Artificial Sequence -continued
<220> FEATURE:
<223> OTHER INFORMATION: Synthetic

<400> SEQUENCE: 521
gaacttgtgg ccgtttacgt cg                                          22

<210> SEQ ID NO 522
<211> LENGTH: 21
<212> TYPE: DNA
<213> ORGANISM: Artificial Sequence
<220> FEATURE:
<223> OTHER INFORMATION: Synthetic

<400> SEQUENCE: 522
gacttgtggc cgtttacgtc g                                           21

<210> SEQ ID NO 523
<211> LENGTH: 20
<212> TYPE: DNA
<213> ORGANISM: Artificial Sequence
<220> FEATURE:
<223> OTHER INFORMATION: Synthetic

<400> SEQUENCE: 523
gcttgtggcc gtttacgtcg                                             20

<210> SEQ ID NO 524
<211> LENGTH: 19
<212> TYPE: DNA
<213> ORGANISM: Artificial Sequence
<220> FEATURE:
<223> OTHER INFORMATION: Synthetic

<400> SEQUENCE: 524
gttgtggccg tttacgtcg                                              19

<210> SEQ ID NO 525
<211> LENGTH: 23
<212> TYPE: DNA
<213> ORGANISM: Artificial Sequence
<220> FEATURE:
<223> OTHER INFORMATION: Synthetic

<400> SEQUENCE: 525
gtcacctgcc tcgtggaata cgg                                         23

<210> SEQ ID NO 526
<211> LENGTH: 22
<212> TYPE: DNA
<213> ORGANISM: Artificial Sequence
<220> FEATURE:
<223> OTHER INFORMATION: Synthetic

<400> SEQUENCE: 526
gcacctgcct cgtggaatac gg                                          22

<210> SEQ ID NO 527
<211> LENGTH: 21
<212> TYPE: DNA
<213> ORGANISM: Artificial Sequence
<220> FEATURE:
<223> OTHER INFORMATION: Synthetic

<400> SEQUENCE: 527
gacctgcctc gtggaatacg g                                           21

-continued

```
<210> SEQ ID NO 528
<211> LENGTH: 20
<212> TYPE: DNA
<213> ORGANISM: Artificial Sequence
<220> FEATURE:
<223> OTHER INFORMATION: Synthetic

<400> SEQUENCE: 528
gcctgcctcg tggaatacgg                                               20

<210> SEQ ID NO 529
<211> LENGTH: 24
<212> TYPE: DNA
<213> ORGANISM: Artificial Sequence
<220> FEATURE:
<223> OTHER INFORMATION: Synthetic

<400> SEQUENCE: 529
ggttctgggt acttttatct gtcc                                          24

<210> SEQ ID NO 530
<211> LENGTH: 24
<212> TYPE: DNA
<213> ORGANISM: Artificial Sequence
<220> FEATURE:
<223> OTHER INFORMATION: Synthetic

<400> SEQUENCE: 530
gtctgcctaa caggaggtgg gggt                                          24

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531
gaatatcagg agactaggaa ggag                                          24

<210> SEQ ID NO 532
<211> LENGTH: 22
<212> TYPE: DNA
<213> ORGANISM: Artificial Sequence
<220> FEATURE:
<223> OTHER INFORMATION: Synthetic

<400> SEQUENCE: 532
gcctccctgc agggctgctc cc                                            22

<210> SEQ ID NO 533
<211> LENGTH: 24
<212> TYPE: DNA
<213> ORGANISM: Artificial Sequence
<220> FEATURE:
<223> OTHER INFORMATION: Synthetic

<400> SEQUENCE: 533
gagctagtct tcttcctcca accc                                          24

<210> SEQ ID NO 534
<211> LENGTH: 24
<212> TYPE: DNA
<213> ORGANISM: Artificial Sequence
<220> FEATURE:
<223> OTHER INFORMATION: Synthetic
```

-continued

```
<400> SEQUENCE: 534
gatctgtccc ctccacccca cagt                                          24

<210> SEQ ID NO 535
<211> LENGTH: 24
<212> TYPE: DNA
<213> ORGANISM: Artificial Sequence
<220> FEATURE:
<223> OTHER INFORMATION: Synthetic

<400> SEQUENCE: 535
ggcccaaatg aaaggagtga gagg                                          24

<210> SEQ ID NO 536
<211> LENGTH: 24
<212> TYPE: DNA
<213> ORGANISM: Artificial Sequence
<220> FEATURE:
<223> OTHER INFORMATION: Synthetic

<400> SEQUENCE: 536
gcatcctctt gctttctttg cctg                                          24

<210> SEQ ID NO 537
<211> LENGTH: 24
<212> TYPE: DNA
<213> ORGANISM: Artificial Sequence
<220> FEATURE:
<223> OTHER INFORMATION: Synthetic

<400> SEQUENCE: 537
ggagtcgcca gaggccggtg gtgg                                          24

<210> SEQ ID NO 538
<211> LENGTH: 24
<212> TYPE: DNA
<213> ORGANISM: Artificial Sequence
<220> FEATURE:
<223> OTHER INFORMATION: Synthetic

<400> SEQUENCE: 538
gcccagcggc cggatatcag ctgc                                          24

<210> SEQ ID NO 539
<211> LENGTH: 23
<212> TYPE: DNA
<213> ORGANISM: Artificial Sequence
<220> FEATURE:
<223> OTHER INFORMATION: Synthetic

<400> SEQUENCE: 539
ggaagggaac atattactat tgc                                           23

<210> SEQ ID NO 540
<211> LENGTH: 24
<212> TYPE: DNA
<213> ORGANISM: Artificial Sequence
<220> FEATURE:
<223> OTHER INFORMATION: Synthetic

<400> SEQUENCE: 540
gtggagtggc ctgctatcag ctac                                          24

<210> SEQ ID NO 541
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 541
gaggaaggga acatattact attg                                              24

<210> SEQ ID NO 542
<211> LENGTH: 24
<212> TYPE: DNA
<213> ORGANISM: Artificial Sequence
<220> FEATURE:
<223> OTHER INFORMATION: Synthetic

<400> SEQUENCE: 542
gtgaattctc atcagctaaa atgc                                              24

<210> SEQ ID NO 543
<211> LENGTH: 24
<212> TYPE: DNA
<213> ORGANISM: Artificial Sequence
<220> FEATURE:
<223> OTHER INFORMATION: Synthetic

<400> SEQUENCE: 543
gctcactcac ccacacagac acac                                              24

<210> SEQ ID NO 544
<211> LENGTH: 24
<212> TYPE: DNA
<213> ORGANISM: Artificial Sequence
<220> FEATURE:
<223> OTHER INFORMATION: Synthetic

<400> SEQUENCE: 544
ggaagaattt cattctgttc tcag                                              24

<210> SEQ ID NO 545
<211> LENGTH: 24
<212> TYPE: DNA
<213> ORGANISM: Artificial Sequence
<220> FEATURE:
<223> OTHER INFORMATION: Synthetic

<400> SEQUENCE: 545
gctcagtttt cctggattat gcct                                              24

<210> SEQ ID NO 546
<211> LENGTH: 24
<212> TYPE: DNA
<213> ORGANISM: Artificial Sequence
<220> FEATURE:
<223> OTHER INFORMATION: Synthetic

<400> SEQUENCE: 546
gcgttggagc ggggagaagg ccag                                              24

<210> SEQ ID NO 547
<211> LENGTH: 24
<212> TYPE: DNA
<213> ORGANISM: Artificial Sequence
<220> FEATURE:
<223> OTHER INFORMATION: Synthetic

<400> SEQUENCE: 547
```

-continued gggccgcgga gatagctgca gggc                                          24

<210> SEQ ID NO 548
<211> LENGTH: 24
<212> TYPE: DNA
<213> ORGANISM: Artificial Sequence
<220> FEATURE:
<223> OTHER INFORMATION: Synthetic

<400> SEQUENCE: 548
gcccacccgg cggcgcctcc ctgc                                          24

<210> SEQ ID NO 549
<211> LENGTH: 24
<212> TYPE: DNA
<213> ORGANISM: Artificial Sequence
<220> FEATURE:
<223> OTHER INFORMATION: Synthetic

<400> SEQUENCE: 549
gcgtggcagc tgatatccgg ccgc                                          24

<210> SEQ ID NO 550
<211> LENGTH: 24
<212> TYPE: DNA
<213> ORGANISM: Artificial Sequence
<220> FEATURE:
<223> OTHER INFORMATION: Synthetic

<400> SEQUENCE: 550
gccgcggcgc gacgtggagc cagc                                          24

<210> SEQ ID NO 551
<211> LENGTH: 24
<212> TYPE: DNA
<213> ORGANISM: Artificial Sequence
<220> FEATURE:
<223> OTHER INFORMATION: Synthetic

<400> SEQUENCE: 551
gtgctcccca gcccaaaccg ccgc                                          24

<210> SEQ ID NO 552
<211> LENGTH: 24
<212> TYPE: DNA
<213> ORGANISM: Artificial Sequence
<220> FEATURE:
<223> OTHER INFORMATION: Synthetic

<400> SEQUENCE: 552
gtcagattgg cttgctcgga attg                                          24

<210> SEQ ID NO 553
<211> LENGTH: 24
<212> TYPE: DNA
<213> ORGANISM: Artificial Sequence
<220> FEATURE:
<223> OTHER INFORMATION: Synthetic

<400> SEQUENCE: 553
gctgggtgaa tggagcgagc agcg                                          24

<210> SEQ ID NO 554
<211> LENGTH: 24
<212> TYPE: DNA

-continued

<213> ORGANISM: Artificial Sequence
<220> FEATURE:
<223> OTHER INFORMATION: Synthetic

<400> SEQUENCE: 554
gtcctggagt gacccctggc cttc                                               24

<210> SEQ ID NO 555
<211> LENGTH: 24
<212> TYPE: DNA
<213> ORGANISM: Artificial Sequence
<220> FEATURE:
<223> OTHER INFORMATION: Synthetic

<400> SEQUENCE: 555
gatcctggag tgacccctgg cctt                                               24

<210> SEQ ID NO 556
<211> LENGTH: 24
<212> TYPE: DNA
<213> ORGANISM: Artificial Sequence
<220> FEATURE:
<223> OTHER INFORMATION: Synthetic

<400> SEQUENCE: 556
gtgtgtccct ctccccaccc gtcc                                               24

<210> SEQ ID NO 557
<211> LENGTH: 24
<212> TYPE: DNA
<213> ORGANISM: Artificial Sequence
<220> FEATURE:
<223> OTHER INFORMATION: Synthetic

<400> SEQUENCE: 557
gttggagcgg ggagaaggcc aggg                                               24

<210> SEQ ID NO 558
<211> LENGTH: 24
<212> TYPE: DNA
<213> ORGANISM: Artificial Sequence
<220> FEATURE:
<223> OTHER INFORMATION: Synthetic

<400> SEQUENCE: 558
gcgttggagc ggggagaagg ccag                                               24

<210> SEQ ID NO 559
<211> LENGTH: 24
<212> TYPE: DNA
<213> ORGANISM: Artificial Sequence
<220> FEATURE:
<223> OTHER INFORMATION: Synthetic

<400> SEQUENCE: 559
gtaccctcca ataatttggc tggc                                               24

<210> SEQ ID NO 560
<211> LENGTH: 24
<212> TYPE: DNA
<213> ORGANISM: Artificial Sequence
<220> FEATURE:
<223> OTHER INFORMATION: Synthetic

<400> SEQUENCE: 560
gataatttgg ctggcaattc cgag                                               24

-continued

```
<210> SEQ ID NO 561
<211> LENGTH: 24
<212> TYPE: DNA
<213> ORGANISM: Artificial Sequence
<220> FEATURE:
<223> OTHER INFORMATION: Synthetic

<400> SEQUENCE: 561
gaaaattgtg atttccagat ccac                                         24

<210> SEQ ID NO 562
<211> LENGTH: 23
<212> TYPE: DNA
<213> ORGANISM: Artificial Sequence
<220> FEATURE:
<223> OTHER INFORMATION: Synthetic

<400> SEQUENCE: 562
gagcagaaaa aattgtgatt tcc                                          23

<210> SEQ ID NO 563
<211> LENGTH: 24
<212> TYPE: DNA
<213> ORGANISM: Artificial Sequence
<220> FEATURE:
<223> OTHER INFORMATION: Synthetic

<400> SEQUENCE: 563
gcaggggcca ggtgtccttc tctg                                         24

<210> SEQ ID NO 564
<211> LENGTH: 24
<212> TYPE: DNA
<213> ORGANISM: Artificial Sequence
<220> FEATURE:
<223> OTHER INFORMATION: Synthetic

<400> SEQUENCE: 564
gaatggcagg cggaggttgt actg                                         24

<210> SEQ ID NO 565
<211> LENGTH: 24
<212> TYPE: DNA
<213> ORGANISM: Artificial Sequence
<220> FEATURE:
<223> OTHER INFORMATION: Synthetic

<400> SEQUENCE: 565
gagtgagaga gtgagagaga gaca                                         24

<210> SEQ ID NO 566
<211> LENGTH: 24
<212> TYPE: DNA
<213> ORGANISM: Artificial Sequence
<220> FEATURE:
<223> OTHER INFORMATION: Synthetic

<400> SEQUENCE: 566
gtgagcaggc acctgtgcca acat                                         24

<210> SEQ ID NO 567
<211> LENGTH: 24
<212> TYPE: DNA
<213> ORGANISM: Artificial Sequence
<220> FEATURE:
```

-continued

```
<223> OTHER INFORMATION: Synthetic

<400> SEQUENCE: 567
gcgtgggggc tccgtgcccc acgc                                              24

<210> SEQ ID NO 568
<211> LENGTH: 24
<212> TYPE: DNA
<213> ORGANISM: Artificial Sequence
<220> FEATURE:
<223> OTHER INFORMATION: Synthetic

<400> SEQUENCE: 568
gcatgggcag gggctggggt gcac                                              24

<210> SEQ ID NO 569
<211> LENGTH: 20
<212> TYPE: DNA
<213> ORGANISM: Artificial Sequence
<220> FEATURE:
<223> OTHER INFORMATION: Synthetic

<400> SEQUENCE: 569
gggccaggtg tccttctctg                                                   20

<210> SEQ ID NO 570
<211> LENGTH: 20
<212> TYPE: DNA
<213> ORGANISM: Artificial Sequence
<220> FEATURE:
<223> OTHER INFORMATION: Synthetic

<400> SEQUENCE: 570
ggcaggcgga ggttgtactg                                                   20

<210> SEQ ID NO 571
<211> LENGTH: 20
<212> TYPE: DNA
<213> ORGANISM: Artificial Sequence
<220> FEATURE:
<223> OTHER INFORMATION: Synthetic

<400> SEQUENCE: 571
gagagagtga gagagagaca                                                   20

<210> SEQ ID NO 572
<211> LENGTH: 20
<212> TYPE: DNA
<213> ORGANISM: Artificial Sequence
<220> FEATURE:
<223> OTHER INFORMATION: Synthetic

<400> SEQUENCE: 572
gcaggcacct gtgccaacat                                                   20

<210> SEQ ID NO 573
<211> LENGTH: 20
<212> TYPE: DNA
<213> ORGANISM: Artificial Sequence
<220> FEATURE:
<223> OTHER INFORMATION: Synthetic

<400> SEQUENCE: 573
gggggctccg tgccccacgc                                                   20
```

-continued

```
<210> SEQ ID NO 574
<211> LENGTH: 20
<212> TYPE: DNA
<213> ORGANISM: Artificial Sequence
<220> FEATURE:
<223> OTHER INFORMATION: Synthetic

<400> SEQUENCE: 574
gggcaggggc tggggtgcac                                                  20

<210> SEQ ID NO 575
<211> LENGTH: 19
<212> TYPE: DNA
<213> ORGANISM: Artificial Sequence
<220> FEATURE:
<223> OTHER INFORMATION: Synthetic

<400> SEQUENCE: 575
tggcttagca cctctccat                                                   19

<210> SEQ ID NO 576
<211> LENGTH: 25
<212> TYPE: DNA
<213> ORGANISM: Artificial Sequence
<220> FEATURE:
<223> OTHER INFORMATION: Synthetic

<400> SEQUENCE: 576
agaggagcct tctgactgct gcaga                                            25

<210> SEQ ID NO 577
<211> LENGTH: 18
<212> TYPE: DNA
<213> ORGANISM: Artificial Sequence
<220> FEATURE:
<223> OTHER INFORMATION: Synthetic

<400> SEQUENCE: 577
tccgtcttcc tccactcc                                                    18

<210> SEQ ID NO 578
<211> LENGTH: 19
<212> TYPE: DNA
<213> ORGANISM: Artificial Sequence
<220> FEATURE:
<223> OTHER INFORMATION: Synthetic

<400> SEQUENCE: 578
tagagaactg ggtagtgtg                                                   19

<210> SEQ ID NO 579
<211> LENGTH: 24
<212> TYPE: DNA
<213> ORGANISM: Artificial Sequence
<220> FEATURE:
<223> OTHER INFORMATION: Synthetic

<400> SEQUENCE: 579
gtacatgaag caactccagt ccca                                             24

<210> SEQ ID NO 580
<211> LENGTH: 24
<212> TYPE: DNA
<213> ORGANISM: Artificial Sequence
<220> FEATURE:
<223> OTHER INFORMATION: Synthetic
```

-continued

<400> SEQUENCE: 580
tggtgattat gggagaactg gagc                                     24

<210> SEQ ID NO 581
<211> LENGTH: 21
<212> TYPE: DNA
<213> ORGANISM: Artificial Sequence
<220> FEATURE:
<223> OTHER INFORMATION: Synthetic

<400> SEQUENCE: 581
ggcataagga aatcgaaggt c                                        21

<210> SEQ ID NO 582
<211> LENGTH: 23
<212> TYPE: DNA
<213> ORGANISM: Artificial Sequence
<220> FEATURE:
<223> OTHER INFORMATION: Synthetic

<400> SEQUENCE: 582
acacgggcag catgggaata gtc                                      23

<210> SEQ ID NO 583
<211> LENGTH: 23
<212> TYPE: DNA
<213> ORGANISM: Artificial Sequence
<220> FEATURE:
<223> OTHER INFORMATION: Synthetic

<400> SEQUENCE: 583
cctgtgtggc tttgctttgg tcg                                      23

<210> SEQ ID NO 584
<211> LENGTH: 23
<212> TYPE: DNA
<213> ORGANISM: Artificial Sequence
<220> FEATURE:
<223> OTHER INFORMATION: Synthetic

<400> SEQUENCE: 584
ggaggaagag tagctcgccg agg                                      23

<210> SEQ ID NO 585
<211> LENGTH: 24
<212> TYPE: DNA
<213> ORGANISM: Artificial Sequence
<220> FEATURE:
<223> OTHER INFORMATION: Synthetic

<400> SEQUENCE: 585
agggagaggg aagtgtgggg aagg                                     24

<210> SEQ ID NO 586
<211> LENGTH: 24
<212> TYPE: DNA
<213> ORGANISM: Artificial Sequence
<220> FEATURE:
<223> OTHER INFORMATION: Synthetic

<400> SEQUENCE: 586
agaactcagg accaacttat tctg                                     24

<210> SEQ ID NO 587
<211> LENGTH: 23

```
<212> TYPE: DNA
<213> ORGANISM: Artificial Sequence
<220> FEATURE:
<223> OTHER INFORMATION: Synthetic

<400> SEQUENCE: 587
atgacagaca caaccagagg gca                                                    23

<210> SEQ ID NO 588
<211> LENGTH: 20
<212> TYPE: DNA
<213> ORGANISM: Artificial Sequence
<220> FEATURE:
<223> OTHER INFORMATION: Synthetic

<400> SEQUENCE: 588
taggaaggag gaggcctaag                                                        20

<210> SEQ ID NO 589
<211> LENGTH: 19
<212> TYPE: DNA
<213> ORGANISM: Artificial Sequence
<220> FEATURE:
<223> OTHER INFORMATION: Synthetic

<400> SEQUENCE: 589
ccaatattgc atgggatgg                                                         19

<210> SEQ ID NO 590
<211> LENGTH: 22
<212> TYPE: DNA
<213> ORGANISM: Artificial Sequence
<220> FEATURE:
<223> OTHER INFORMATION: Synthetic

<400> SEQUENCE: 590
atcaaattcc agcaccgagc gc                                                     22

<210> SEQ ID NO 591
<211> LENGTH: 23
<212> TYPE: DNA
<213> ORGANISM: Artificial Sequence
<220> FEATURE:
<223> OTHER INFORMATION: Synthetic

<400> SEQUENCE: 591
accattgagg acgtttgtct cac                                                    23

<210> SEQ ID NO 592
<211> LENGTH: 23
<212> TYPE: DNA
<213> ORGANISM: Artificial Sequence
<220> FEATURE:
<223> OTHER INFORMATION: Synthetic

<400> SEQUENCE: 592
catgtcctca agtcaagaac aag                                                    23

<210> SEQ ID NO 593
<211> LENGTH: 24
<212> TYPE: DNA
<213> ORGANISM: Artificial Sequence
<220> FEATURE:
<223> OTHER INFORMATION: Synthetic

<400> SEQUENCE: 593
```

-continued

```
gctaggggag agtcccactg tcca                                           24

<210> SEQ ID NO 594
<211> LENGTH: 24
<212> TYPE: DNA
<213> ORGANISM: Artificial Sequence
<220> FEATURE:
<223> OTHER INFORMATION: Synthetic

<400> SEQUENCE: 594
gtagggtgtg atgggaggct aagc                                           24

<210> SEQ ID NO 595
<211> LENGTH: 24
<212> TYPE: DNA
<213> ORGANISM: Artificial Sequence
<220> FEATURE:
<223> OTHER INFORMATION: Synthetic

<400> SEQUENCE: 595
agaccgagtg gcagtgacag caag                                           24

<210> SEQ ID NO 596
<211> LENGTH: 24
<212> TYPE: DNA
<213> ORGANISM: Artificial Sequence
<220> FEATURE:
<223> OTHER INFORMATION: Synthetic

<400> SEQUENCE: 596
gtcttcctgc tctgtgcgca cgac                                           24

<210> SEQ ID NO 597
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(44)
<223> OTHER INFORMATION: n is a, c, g, or t

<400> SEQUENCE: 597
tagcggccgc tcatgcgcgg cgcattacct ttacnnnnnn nnnnggatcc tctagagtcg     60

<210> SEQ ID NO 598
<211> LENGTH: 58
<212> TYPE: DNA
<213> ORGANISM: Artificial Sequence
<220> FEATURE:
<223> OTHER INFORMATION: Synthetic

<400> SEQUENCE: 598
acaggaaaca gctatgacca tgaaagcttg catgcctgca ggtcgactct agaggatc       58

<210> SEQ ID NO 599
<211> LENGTH: 41
<212> TYPE: DNA
<213> ORGANISM: Artificial Sequence
<220> FEATURE:
<223> OTHER INFORMATION: Synthetic

<400> SEQUENCE: 599
ctacacgacg ctcttccgat ctcctggagc gtgtacgttg g                        41
```

-continued

```
<210> SEQ ID NO 600
<211> LENGTH: 42
<212> TYPE: DNA
<213> ORGANISM: Artificial Sequence
<220> FEATURE:
<223> OTHER INFORMATION: Synthetic

<400> SEQUENCE: 600
ctacacgacg ctcttccgat ctcctgtggt cccagctact tg                42

<210> SEQ ID NO 601
<211> LENGTH: 41
<212> TYPE: DNA
<213> ORGANISM: Artificial Sequence
<220> FEATURE:
<223> OTHER INFORMATION: Synthetic

<400> SEQUENCE: 601
ctacacgacg ctcttccgat ctatctgcga tgtcctcgag g                 41

<210> SEQ ID NO 602
<211> LENGTH: 40
<212> TYPE: DNA
<213> ORGANISM: Artificial Sequence
<220> FEATURE:
<223> OTHER INFORMATION: Synthetic

<400> SEQUENCE: 602
ctacacgacg ctcttccgat cttggtgtgc gcctctaacg                   40

<210> SEQ ID NO 603
<211> LENGTH: 45
<212> TYPE: DNA
<213> ORGANISM: Artificial Sequence
<220> FEATURE:
<223> OTHER INFORMATION: Synthetic

<400> SEQUENCE: 603
ctacacgacg ctcttccgat ctggagtctt gctttgtcac tcaga            45

<210> SEQ ID NO 604
<211> LENGTH: 41
<212> TYPE: DNA
<213> ORGANISM: Artificial Sequence
<220> FEATURE:
<223> OTHER INFORMATION: Synthetic

<400> SEQUENCE: 604
ctacacgacg ctcttccgat ctagcctaga cccagtccca t                 41

<210> SEQ ID NO 605
<211> LENGTH: 42
<212> TYPE: DNA
<213> ORGANISM: Artificial Sequence
<220> FEATURE:
<223> OTHER INFORMATION: Synthetic

<400> SEQUENCE: 605
ctacacgacg ctcttccgat ctgctgggca tagtagtgga ct                42

<210> SEQ ID NO 606
<211> LENGTH: 41
<212> TYPE: DNA
<213> ORGANISM: Artificial Sequence
<220> FEATURE:
<223> OTHER INFORMATION: Synthetic
```

<400> SEQUENCE: 606
ctacacgacg ctcttccgat cttggggagg ctgagacacg a                      41

<210> SEQ ID NO 607

<400> SEQUENCE: 607

000

<210> SEQ ID NO 608
<211> LENGTH: 41
<212> TYPE: DNA
<213> ORGANISM: Artificial Sequence
<220> FEATURE:
<223> OTHER INFORMATION: Synthetic

<400> SEQUENCE: 608
ctacacgacg ctcttccgat ctcttgggag gctgaggcaa g                      41

<210> SEQ ID NO 609
<211> LENGTH: 40
<212> TYPE: DNA
<213> ORGANISM: Artificial Sequence
<220> FEATURE:
<223> OTHER INFORMATION: Synthetic

<400> SEQUENCE: 609
agacgtgtgc tcttccgatc tcaggaggat gagagccagg                        40

<210> SEQ ID NO 610
<211> LENGTH: 43
<212> TYPE: DNA
<213> ORGANISM: Artificial Sequence
<220> FEATURE:
<223> OTHER INFORMATION: Synthetic

<400> SEQUENCE: 610
agacgtgtgc tcttccgatc tcagggtctc actctatcac cca                    43

<210> SEQ ID NO 611
<211> LENGTH: 42
<212> TYPE: DNA
<213> ORGANISM: Artificial Sequence
<220> FEATURE:
<223> OTHER INFORMATION: Synthetic

<400> SEQUENCE: 611
agacgtgtgc tcttccgatc tactgaatgg gttgaacttg gc                     42

<210> SEQ ID NO 612
<211> LENGTH: 45
<212> TYPE: DNA
<213> ORGANISM: Artificial Sequence
<220> FEATURE:
<223> OTHER INFORMATION: Synthetic

<400> SEQUENCE: 612
agacgtgtgc tcttccgatc tgagacagaa tcttgctctg tctcc                  45

<210> SEQ ID NO 613
<211> LENGTH: 40
<212> TYPE: DNA
<213> ORGANISM: Artificial Sequence
<220> FEATURE:
<223> OTHER INFORMATION: Synthetic -continued

<400> SEQUENCE: 613
agacgtgtgc tcttccgatc ttcccagcta cttgggaggc                              40

<210> SEQ ID NO 614
<211> LENGTH: 42
<212> TYPE: DNA
<213> ORGANISM: Artificial Sequence
<220> FEATURE:
<223> OTHER INFORMATION: Synthetic

<400> SEQUENCE: 614
agacgtgtgc tcttccgatc tcctgcccaa atagggaagc ag                           42

<210> SEQ ID NO 615
<211> LENGTH: 42
<212> TYPE: DNA
<213> ORGANISM: Artificial Sequence
<220> FEATURE:
<223> OTHER INFORMATION: Synthetic

<400> SEQUENCE: 615
agacgtgtgc tcttccgatc ttggcgcctt agtctctgct ac                           42

<210> SEQ ID NO 616
<211> LENGTH: 44
<212> TYPE: DNA
<213> ORGANISM: Artificial Sequence
<220> FEATURE:
<223> OTHER INFORMATION: Synthetic

<400> SEQUENCE: 616
agacgtgtgc tcttccgatc tgcatgagac acagtttcac tctg                         44

<210> SEQ ID NO 617
<211> LENGTH: 42
<212> TYPE: DNA
<213> ORGANISM: Artificial Sequence
<220> FEATURE:
<223> OTHER INFORMATION: Synthetic

<400> SEQUENCE: 617
agacgtgtgc tcttccgatc tgagagagtc tcactgcgtt gc                           42

<210> SEQ ID NO 618
<211> LENGTH: 41
<212> TYPE: DNA
<213> ORGANISM: Artificial Sequence
<220> FEATURE:
<223> OTHER INFORMATION: Synthetic

<400> SEQUENCE: 618
ctacacgacg ctcttccgat cttctctcac ccactgggca c                           41

<210> SEQ ID NO 619
<211> LENGTH: 40
<212> TYPE: DNA
<213> ORGANISM: Artificial Sequence
<220> FEATURE:
<223> OTHER INFORMATION: Synthetic

<400> SEQUENCE: 619
agacgtgtgc tcttccgatc tgcttccaga cgagtgcaga                              40

<210> SEQ ID NO 620
<211> LENGTH: 49

-continued

```
<212> TYPE: DNA
<213> ORGANISM: Artificial Sequence
<220> FEATURE:
<223> OTHER INFORMATION: Synthetic

<400> SEQUENCE: 620
ctacacgacg ctcttccgat ctaagttttc aaaccagaag aactacgac                49

<210> SEQ ID NO 621
<211> LENGTH: 42
<212> TYPE: DNA
<213> ORGANISM: Artificial Sequence
<220> FEATURE:
<223> OTHER INFORMATION: Synthetic

<400> SEQUENCE: 621
ctacacgacg ctcttccgat ctccggtata agtcctggag cg                       42

<210> SEQ ID NO 622
<211> LENGTH: 40
<212> TYPE: DNA
<213> ORGANISM: Artificial Sequence
<220> FEATURE:
<223> OTHER INFORMATION: Synthetic

<400> SEQUENCE: 622
ctacacgacg ctcttccgat ctgccaggga gcaatggcag                          40

<210> SEQ ID NO 623
<211> LENGTH: 41
<212> TYPE: DNA
<213> ORGANISM: Artificial Sequence
<220> FEATURE:
<223> OTHER INFORMATION: Synthetic

<400> SEQUENCE: 623
ctacacgacg ctcttccgat ctcctcgaat tccacggggt t                        41

<210> SEQ ID NO 624
<211> LENGTH: 42
<212> TYPE: DNA
<213> ORGANISM: Artificial Sequence
<220> FEATURE:
<223> OTHER INFORMATION: Synthetic

<400> SEQUENCE: 624
ctacacgacg ctcttccgat ctgttggtgg gagggaagtg ag                       42

<210> SEQ ID NO 625
<211> LENGTH: 40
<212> TYPE: DNA
<213> ORGANISM: Artificial Sequence
<220> FEATURE:
<223> OTHER INFORMATION: Synthetic

<400> SEQUENCE: 625
ctacacgacg ctcttccgat ctgatggcgg ttgtagcggc                          40

<210> SEQ ID NO 626
<211> LENGTH: 46
<212> TYPE: DNA
<213> ORGANISM: Artificial Sequence
<220> FEATURE:
<223> OTHER INFORMATION: Synthetic

<400> SEQUENCE: 626
```

-continued

```
ctacacgacg ctcttccgat ctcacataaa cctatgtttc agcaga                    46

<210> SEQ ID NO 627
<211> LENGTH: 44
<212> TYPE: DNA
<213> ORGANISM: Artificial Sequence
<220> FEATURE:
<223> OTHER INFORMATION: Synthetic

<400> SEQUENCE: 627
ctacacgacg ctcttccgat ctgctagttg gattgaagca gggt                      44

<210> SEQ ID NO 628
<211> LENGTH: 40
<212> TYPE: DNA
<213> ORGANISM: Artificial Sequence
<220> FEATURE:
<223> OTHER INFORMATION: Synthetic

<400> SEQUENCE: 628
ctacacgacg ctcttccgat ctttgagtgc ggcagcttcc                           40

<210> SEQ ID NO 629
<211> LENGTH: 43
<212> TYPE: DNA
<213> ORGANISM: Artificial Sequence
<220> FEATURE:
<223> OTHER INFORMATION: Synthetic

<400> SEQUENCE: 629
ctacacgacg ctcttccgat ctataaccct cccaggcaaa gtc                       43

<210> SEQ ID NO 630
<211> LENGTH: 41
<212> TYPE: DNA
<213> ORGANISM: Artificial Sequence
<220> FEATURE:
<223> OTHER INFORMATION: Synthetic

<400> SEQUENCE: 630
ctacacgacg ctcttccgat ctagcctgca catctgagct c                         41

<210> SEQ ID NO 631
<211> LENGTH: 41
<212> TYPE: DNA
<213> ORGANISM: Artificial Sequence
<220> FEATURE:
<223> OTHER INFORMATION: Synthetic

<400> SEQUENCE: 631
ctacacgacg ctcttccgat ctggagcatt gaagtgcctg g                         41

<210> SEQ ID NO 632
<211> LENGTH: 38
<212> TYPE: DNA
<213> ORGANISM: Artificial Sequence
<220> FEATURE:
<223> OTHER INFORMATION: Synthetic

<400> SEQUENCE: 632
agacgtgtgc tcttccgatc tcagcctggg accactga                             38

<210> SEQ ID NO 633
<211> LENGTH: 39
<212> TYPE: DNA
<213> ORGANISM: Artificial Sequence
```

-continued

<220> FEATURE:
<223> OTHER INFORMATION: Synthetic

<400> SEQUENCE: 633
agacgtgtgc tcttccgatc tcatcctcga cagtcgcgg                              39

<210> SEQ ID NO 634
<211> LENGTH: 47
<212> TYPE: DNA
<213> ORGANISM: Artificial Sequence
<220> FEATURE:
<223> OTHER INFORMATION: Synthetic

<400> SEQUENCE: 634
agacgtgtgc tcttccgatc tgactgatca agtagaatac tcatggg                    47

<210> SEQ ID NO 635
<211> LENGTH: 39
<212> TYPE: DNA
<213> ORGANISM: Artificial Sequence
<220> FEATURE:
<223> OTHER INFORMATION: Synthetic

<400> SEQUENCE: 635
agacgtgtgc tcttccgatc tccctgccag cactgaagc                              39

<210> SEQ ID NO 636
<211> LENGTH: 47
<212> TYPE: DNA
<213> ORGANISM: Artificial Sequence
<220> FEATURE:
<223> OTHER INFORMATION: Synthetic

<400> SEQUENCE: 636
agacgtgtgc tcttccgatc tggttcctat ctttctagac caggagt                    47

<210> SEQ ID NO 637
<211> LENGTH: 39
<212> TYPE: DNA
<213> ORGANISM: Artificial Sequence
<220> FEATURE:
<223> OTHER INFORMATION: Synthetic

<400> SEQUENCE: 637
agacgtgtgc tcttccgatc tagtgtggag ggctcaggg                              39

<210> SEQ ID NO 638
<211> LENGTH: 40
<212> TYPE: DNA
<213> ORGANISM: Artificial Sequence
<220> FEATURE:
<223> OTHER INFORMATION: Synthetic

<400> SEQUENCE: 638
agacgtgtgc tcttccgatc tgatgggcag aggaaggcaa                            40

<210> SEQ ID NO 639
<211> LENGTH: 41
<212> TYPE: DNA
<213> ORGANISM: Artificial Sequence
<220> FEATURE:
<223> OTHER INFORMATION: Synthetic

<400> SEQUENCE: 639
agacgtgtgc tcttccgatc ttcactctca tgagcgtccc a                          41

-continued

```
<210> SEQ ID NO 640
<211> LENGTH: 41
<212> TYPE: DNA
<213> ORGANISM: Artificial Sequence
<220> FEATURE:
<223> OTHER INFORMATION: Synthetic

<400> SEQUENCE: 640
ctacacgacg ctcttccgat ctaaggttcc ttgcggttcg c                         41

<210> SEQ ID NO 641
<211> LENGTH: 38
<212> TYPE: DNA
<213> ORGANISM: Artificial Sequence
<220> FEATURE:
<223> OTHER INFORMATION: Synthetic

<400> SEQUENCE: 641
agacgtgtgc tcttccgatc tcgctgccat tgctccct                            38

<210> SEQ ID NO 642
<211> LENGTH: 43
<212> TYPE: DNA
<213> ORGANISM: Artificial Sequence
<220> FEATURE:
<223> OTHER INFORMATION: Synthetic

<400> SEQUENCE: 642
ctacacgacg ctcttccgat cttctcgcac attcttcacg tcc                      43

<210> SEQ ID NO 643
<211> LENGTH: 42
<212> TYPE: DNA
<213> ORGANISM: Artificial Sequence
<220> FEATURE:
<223> OTHER INFORMATION: Synthetic

<400> SEQUENCE: 643
agacgtgtgc tcttccgatc taggaacctt cccgacttag gg                       42

<210> SEQ ID NO 644
<211> LENGTH: 44
<212> TYPE: DNA
<213> ORGANISM: Artificial Sequence
<220> FEATURE:
<223> OTHER INFORMATION: Synthetic

<400> SEQUENCE: 644
ctacacgacg ctcttccgat ctcccgccca tcttctagaa agac                     44

<210> SEQ ID NO 645
<211> LENGTH: 40
<212> TYPE: DNA
<213> ORGANISM: Artificial Sequence
<220> FEATURE:
<223> OTHER INFORMATION: Synthetic

<400> SEQUENCE: 645
ctacacgacg ctcttccgat cttgccaggt gagggactgg                          40

<210> SEQ ID NO 646
<211> LENGTH: 41
<212> TYPE: DNA
<213> ORGANISM: Artificial Sequence
<220> FEATURE:
<223> OTHER INFORMATION: Synthetic
```

-continued

<400> SEQUENCE: 646
agacgtgtgc tcttccgatc ttctgggagt tctctgctgc c                         41

<210> SEQ ID NO 647
<211> LENGTH: 41
<212> TYPE: DNA
<213> ORGANISM: Artificial Sequence
<220> FEATURE:
<223> OTHER INFORMATION: Synthetic

<400> SEQUENCE: 647
agacgtgtgc tcttccgatc ttgcccaacc ttagcaagga g                         41

<210> SEQ ID NO 648
<211> LENGTH: 40
<212> TYPE: DNA
<213> ORGANISM: Artificial Sequence
<220> FEATURE:
<223> OTHER INFORMATION: Synthetic

<400> SEQUENCE: 648
ctacacgacg ctcttccgat cttaccttgg agcaacggcg                           40

<210> SEQ ID NO 649
<211> LENGTH: 39
<212> TYPE: DNA
<213> ORGANISM: Artificial Sequence
<220> FEATURE:
<223> OTHER INFORMATION: Synthetic

<400> SEQUENCE: 649
agacgtgtgc tcttccgatc tcccaggacg aggatggag                            39

<210> SEQ ID NO 650
<211> LENGTH: 20
<212> TYPE: DNA
<213> ORGANISM: Artificial Sequence
<220> FEATURE:
<223> OTHER INFORMATION: Synthetic

<400> SEQUENCE: 650
gatagtcact ccaggggttg                                                 20

<210> SEQ ID NO 651
<211> LENGTH: 20
<212> TYPE: DNA
<213> ORGANISM: Artificial Sequence
<220> FEATURE:
<223> OTHER INFORMATION: Synthetic

<400> SEQUENCE: 651
gtggtgaacc aatcagtcct                                                 20

<210> SEQ ID NO 652
<211> LENGTH: 60
<212> TYPE: PRT
<213> ORGANISM: Artificial Sequence
<220> FEATURE:
<223> OTHER INFORMATION: Synthetic

<400> SEQUENCE: 652

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu

-continued

```
                  20              25              30

Glu Asn Pro Ile Arg Leu Ile Asp Leu Gly Val Arg Val Phe Glu Arg
        35              40              45

Ala Glu Val Pro Lys Thr Gly Asp Ser Leu Ala Met
    50              55              60
```

<210> SEQ ID NO 653
<211> LENGTH: 60
<212> TYPE: PRT
<213> ORGANISM: Artificial Sequence
<220> FEATURE:
<223> OTHER INFORMATION: Synthetic

<400> SEQUENCE: 653

```
Ala Arg Arg Leu Ala Arg Ser Val Arg Arg Leu Thr Arg Arg Arg Ala
1               5               10              15

His Arg Leu Leu Arg Thr Arg Arg Leu Leu Lys Arg Glu Gly Val Leu
            20              25              30

Gln Ala Ala Asn Phe Asp Glu Asn Gly Leu Ile Lys Ser Leu Pro Asn
        35              40              45

Thr Pro Trp Gln Leu Arg Ala Ala Ala Leu Asp Arg
    50              55              60
```

<210> SEQ ID NO 654
<211> LENGTH: 60
<212> TYPE: PRT
<213> ORGANISM: Artificial Sequence
<220> FEATURE:
<223> OTHER INFORMATION: Synthetic

<400> SEQUENCE: 654

```
Ala Arg Arg Leu Ala Arg Ser Val Arg Arg Leu Thr Arg Arg Arg Ala
1               5               10              15

His Arg Leu Leu Arg Ala Arg Arg Leu Leu Lys Arg Glu Gly Val Leu
            20              25              30

Gln Ala Ala Asp Phe Asp Glu Asn Gly Leu Ile Lys Ser Leu Pro Asn
        35              40              45

Thr Pro Trp Gln Leu Arg Ala Ala Ala Leu Asp Arg
    50              55              60
```

<210> SEQ ID NO 655
<211> LENGTH: 60
<212> TYPE: PRT
<213> ORGANISM: Artificial Sequence
<220> FEATURE:
<223> OTHER INFORMATION: Synthetic

<400> SEQUENCE: 655

```
Lys Leu Thr Pro Leu Glu Trp Ser Ala Val Leu Leu His Leu Ile Lys
1               5               10              15

His Arg Gly Tyr Leu Ser Gln Arg Lys Asn Glu Gly Glu Thr Ala Asp
            20              25              30

Lys Glu Leu Gly Ala Leu Leu Lys Gly Val Ala Gly Asn Ala His Ala
        35              40              45

Leu Gln Thr Gly Asp Phe Arg Thr Pro Ala Glu Leu
    50              55              60
```

<210> SEQ ID NO 656
<211> LENGTH: 60
<212> TYPE: PRT
<213> ORGANISM: Artificial Sequence -continued
<220> FEATURE:
<223> OTHER INFORMATION: Synthetic

<400> SEQUENCE: 656

```
Lys Leu Thr Pro Leu Glu Trp Ser Ala Val Leu Leu His Leu Ile Lys
1               5                   10                  15

His Arg Gly Tyr Leu Ser Gln Arg Lys Asn Glu Gly Glu Thr Ala Asp
            20                  25                  30

Lys Glu Leu Gly Ala Leu Leu Lys Gly Val Ala Asn Asn Ala His Ala
        35                  40                  45

Leu Gln Thr Gly Asp Phe Arg Thr Pro Ala Glu Leu
    50                  55                  60
```

<210> SEQ ID NO 657
<211> LENGTH: 60
<212> TYPE: PRT
<213> ORGANISM: Artificial Sequence
<220> FEATURE:
<223> OTHER INFORMATION: Synthetic

<400> SEQUENCE: 657

```
Ala Leu Asn Lys Phe Glu Lys Glu Ser Gly His Ile Arg Asn Gln Arg
1               5                   10                  15

Ser Asp Tyr Ser His Thr Phe Ser Arg Lys Asp Leu Gln Ala Glu Leu
            20                  25                  30

Ile Leu Leu Phe Glu Lys Gln Lys Glu Phe Gly Asn Pro His Val Ser
        35                  40                  45

Gly Gly Leu Lys Glu Gly Ile Glu Thr Leu Leu Met
    50                  55                  60
```

<210> SEQ ID NO 658
<211> LENGTH: 60
<212> TYPE: PRT
<213> ORGANISM: Artificial Sequence
<220> FEATURE:
<223> OTHER INFORMATION: Synthetic

<400> SEQUENCE: 658

```
Ala Leu Asn Lys Phe Glu Lys Glu Ser Gly His Ile Arg Asn Gln Arg
1               5                   10                  15

Gly Asp Tyr Ser His Thr Phe Ser Arg Lys Asp Leu Gln Ala Glu Leu
            20                  25                  30

Ile Leu Leu Phe Glu Lys Gln Lys Glu Phe Gly Asn Pro His Val Ser
        35                  40                  45

Gly Gly Leu Lys Glu Gly Ile Glu Thr Leu Leu Met
    50                  55                  60
```

<210> SEQ ID NO 659
<211> LENGTH: 60
<212> TYPE: PRT
<213> ORGANISM: Artificial Sequence
<220> FEATURE:
<223> OTHER INFORMATION: Synthetic

<400> SEQUENCE: 659

```
Thr Gln Arg Pro Ala Leu Ser Gly Asp Ala Val Gln Lys Met Leu Gly
1               5                   10                  15

His Cys Thr Phe Glu Pro Ala Glu Pro Lys Ala Ala Lys Asn Thr Tyr
            20                  25                  30

Thr Ala Glu Arg Phe Ile Trp Leu Thr Lys Leu Asn Asn Leu Arg Ile
        35                  40                  45
```

```
Leu Glu Gln Gly Ser Glu Arg Pro Leu Thr Asp Thr
    50                  55                  60

<210> SEQ ID NO 660
<211> LENGTH: 60
<212> TYPE: PRT
<213> ORGANISM: Artificial Sequence
<220> FEATURE:
<223> OTHER INFORMATION: Synthetic

<400> SEQUENCE: 660

Thr Gln Arg Pro Ala Leu Ser Gly Asp Ala Val Gln Lys Met Leu Gly
1               5                   10                  15

His Cys Thr Phe Glu Pro Ala Glu Pro Lys Ala Ala Lys Asn Thr Tyr
                20                  25                  30

Thr Ala Glu Arg Phe Ile Trp Leu Thr Lys Leu Asn Asn Leu Arg Ile
        35                  40                  45

Leu Glu Gln Gly Ser Glu Arg Pro Leu Thr Asp Thr
    50                  55                  60

<210> SEQ ID NO 661
<211> LENGTH: 60
<212> TYPE: PRT
<213> ORGANISM: Artificial Sequence
<220> FEATURE:
<223> OTHER INFORMATION: Synthetic

<400> SEQUENCE: 661

Glu Arg Ala Thr Leu Met Asp Glu Pro Tyr Arg Lys Ser Lys Leu Thr
1               5                   10                  15

Tyr Ala Gln Ala Arg Lys Leu Leu Gly Leu Glu Asp Thr Ala Phe Phe
                20                  25                  30

Lys Gly Leu Arg Tyr Gly Lys Asp Asn Ala Glu Ala Ser Thr Leu Met
        35                  40                  45

Glu Met Lys Ala Tyr His Ala Ile Ser Arg Ala Leu
    50                  55                  60

<210> SEQ ID NO 662
<211> LENGTH: 60
<212> TYPE: PRT
<213> ORGANISM: Artificial Sequence
<220> FEATURE:
<223> OTHER INFORMATION: Synthetic

<400> SEQUENCE: 662

Glu Arg Ala Thr Leu Met Asp Glu Pro Tyr Arg Lys Ser Lys Leu Thr
1               5                   10                  15

Tyr Ala Gln Ala Arg Lys Leu Leu Gly Leu Glu Asp Thr Ala Phe Phe
                20                  25                  30

Lys Gly Leu Arg Tyr Gly Lys Asp Asn Ala Glu Ala Ser Thr Leu Met
        35                  40                  45

Glu Met Lys Ala Tyr His Ala Ile Ser Arg Ala Leu
    50                  55                  60

<210> SEQ ID NO 663
<211> LENGTH: 60
<212> TYPE: PRT
<213> ORGANISM: Artificial Sequence
<220> FEATURE:
<223> OTHER INFORMATION: Synthetic

<400> SEQUENCE: 663
```

-continued

```
Glu Lys Glu Gly Leu Lys Asp Lys Lys Ser Pro Leu Asn Leu Ser Pro
1               5                   10                  15

Glu Leu Gln Asp Glu Ile Gly Thr Ala Phe Ser Leu Phe Lys Thr Asp
                20                  25                  30

Glu Asp Ile Thr Gly Arg Leu Lys Asp Arg Ile Gln Pro Glu Ile Leu
        35                  40                  45

Glu Ala Leu Leu Lys His Ile Ser Phe Asp Lys Phe
    50                  55                  60
```

<210> SEQ ID NO 664
<211> LENGTH: 60
<212> TYPE: PRT
<213> ORGANISM: Artificial Sequence
<220> FEATURE:
<223> OTHER INFORMATION: Synthetic

<400> SEQUENCE: 664

```
Glu Lys Glu Gly Leu Lys Asp Lys Lys Ser Pro Leu Asn Leu Ser Ser
1               5                   10                  15

Glu Leu Gln Asp Glu Ile Gly Thr Ala Phe Ser Leu Phe Lys Thr Asp
                20                  25                  30

Glu Asp Ile Thr Gly Arg Leu Lys Asp Arg Val Gln Pro Glu Ile Leu
        35                  40                  45

Glu Ala Leu Leu Lys His Ile Ser Phe Asp Lys Phe
    50                  55                  60
```

<210> SEQ ID NO 665
<211> LENGTH: 60
<212> TYPE: PRT
<213> ORGANISM: Artificial Sequence
<220> FEATURE:
<223> OTHER INFORMATION: Synthetic

<400> SEQUENCE: 665

```
Val Gln Ile Ser Leu Lys Ala Leu Arg Arg Ile Val Pro Leu Met Glu
1               5                   10                  15

Gln Gly Lys Arg Tyr Asp Glu Ala Cys Ala Glu Ile Tyr Gly Asp His
                20                  25                  30

Tyr Gly Lys Lys Asn Thr Glu Glu Lys Ile Tyr Leu Pro Pro Ile Pro
        35                  40                  45

Ala Asp Glu Ile Arg Asn Pro Val Val Leu Arg Ala
    50                  55                  60
```

<210> SEQ ID NO 666
<211> LENGTH: 60
<212> TYPE: PRT
<213> ORGANISM: Artificial Sequence
<220> FEATURE:
<223> OTHER INFORMATION: Synthetic

<400> SEQUENCE: 666

```
Val Gln Ile Ser Leu Lys Ala Leu Arg Arg Ile Val Pro Leu Met Glu
1               5                   10                  15

Gln Gly Lys Arg Tyr Asp Glu Ala Cys Ala Glu Ile Tyr Gly Asp His
                20                  25                  30

Tyr Gly Lys Lys Asn Thr Glu Glu Lys Ile Tyr Leu Pro Pro Ile Pro
        35                  40                  45

Ala Asp Glu Ile Arg Asn Pro Val Val Leu Arg Ala
    50                  55                  60
```

<210> SEQ ID NO 667
<211> LENGTH: 60
<212> TYPE: PRT
<213> ORGANISM: Artificial Sequence
<220> FEATURE:
<223> OTHER INFORMATION: Synthetic

<400> SEQUENCE: 667

Leu Ser Gln Ala Arg Lys Val Ile Asn Gly Val Val Arg Arg Tyr Gly
1               5                   10                  15

Ser Pro Ala Arg Ile His Ile Glu Thr Ala Arg Glu Val Gly Lys Ser
            20                  25                  30

Phe Lys Asp Arg Lys Glu Ile Glu Lys Arg Gln Glu Glu Asn Arg Lys
        35                  40                  45

Asp Arg Glu Lys Ala Ala Ala Lys Phe Arg Glu Tyr
    50                  55                  60

<210> SEQ ID NO 668
<211> LENGTH: 60
<212> TYPE: PRT
<213> ORGANISM: Artificial Sequence
<220> FEATURE:
<223> OTHER INFORMATION: Synthetic

<400> SEQUENCE: 668

Leu Ser Gln Ala Arg Lys Val Ile Asn Gly Val Val Arg Arg Tyr Gly
1               5                   10                  15

Ser Pro Ala Arg Ile His Ile Glu Thr Ala Arg Glu Val Gly Lys Ser
            20                  25                  30

Phe Lys Asp Arg Lys Glu Ile Glu Lys Arg Gln Glu Glu Asn Arg Lys
        35                  40                  45

Asp Arg Glu Lys Ala Ala Ala Lys Phe Arg Glu Tyr
    50                  55                  60

<210> SEQ ID NO 669
<211> LENGTH: 60
<212> TYPE: PRT
<213> ORGANISM: Artificial Sequence
<220> FEATURE:
<223> OTHER INFORMATION: Synthetic

<400> SEQUENCE: 669

Phe Pro Asn Phe Val Gly Glu Pro Lys Ser Lys Asp Ile Leu Lys Leu
1               5                   10                  15

Arg Leu Tyr Glu Gln Gln His Gly Lys Cys Leu Tyr Ser Gly Lys Glu
            20                  25                  30

Ile Asn Leu Gly Arg Leu Asn Glu Lys Gly Tyr Val Glu Ile Asp His
        35                  40                  45

Ala Leu Pro Phe Ser Arg Thr Trp Asp Asp Ser Phe
    50                  55                  60

<210> SEQ ID NO 670
<211> LENGTH: 60
<212> TYPE: PRT
<213> ORGANISM: Artificial Sequence
<220> FEATURE:
<223> OTHER INFORMATION: Synthetic

<400> SEQUENCE: 670

Phe Pro Asn Phe Val Gly Glu Pro Lys Ser Lys Asp Ile Leu Lys Leu
1               5                   10                  15

-continued

Arg Leu Tyr Glu Gln Gln His Gly Lys Cys Leu Tyr Ser Gly Lys Glu
            20                      25                  30

Ile Asn Leu Val Arg Leu Asn Glu Lys Gly Tyr Val Glu Ile Asp His
        35                      40                  45

Ala Leu Pro Phe Ser Arg Thr Trp Asp Asp Ser Phe
    50                      55                  60

<210> SEQ ID NO 671
<211> LENGTH: 60
<212> TYPE: PRT
<213> ORGANISM: Artificial Sequence
<220> FEATURE:
<223> OTHER INFORMATION: Synthetic

<400> SEQUENCE: 671

Asn Asn Lys Val Leu Val Leu Gly Ser Glu Asn Gln Asn Lys Gly Asn
1                   5                   10                  15

Gln Thr Pro Tyr Glu Tyr Phe Asn Gly Lys Asp Asn Ser Arg Glu Trp
            20                      25                  30

Gln Glu Phe Lys Ala Arg Val Glu Thr Ser Arg Phe Pro Arg Ser Lys
        35                      40                  45

Lys Gln Arg Ile Leu Leu Gln Lys Phe Asp Glu Asp
    50                      55                  60

<210> SEQ ID NO 672
<211> LENGTH: 60
<212> TYPE: PRT
<213> ORGANISM: Artificial Sequence
<220> FEATURE:
<223> OTHER INFORMATION: Synthetic

<400> SEQUENCE: 672

Asn Asn Lys Val Leu Val Leu Gly Ser Glu Asn Gln Asn Lys Gly Asn
1                   5                   10                  15

Gln Thr Pro Tyr Glu Tyr Phe Asn Gly Lys Asp Asn Ser Arg Glu Trp
            20                      25                  30

Gln Glu Phe Lys Ala Arg Val Glu Thr Ser Arg Phe Pro Arg Ser Lys
        35                      40                  45

Lys Gln Arg Ile Leu Leu Gln Lys Phe Asp Glu Asp
    50                      55                  60

<210> SEQ ID NO 673
<211> LENGTH: 60
<212> TYPE: PRT
<213> ORGANISM: Artificial Sequence
<220> FEATURE:
<223> OTHER INFORMATION: Synthetic

<400> SEQUENCE: 673

Gly Phe Lys Glu Arg Asn Leu Asn Asp Thr Arg Tyr Val Asn Arg Phe
1                   5                   10                  15

Leu Cys Gln Phe Val Ala Asp Arg Met Arg Leu Thr Gly Lys Gly Lys
            20                      25                  30

Lys Arg Val Phe Ala Ser Asn Gly Gln Ile Thr Asn Leu Leu Arg Gly
        35                      40                  45

Phe Trp Gly Leu Arg Lys Val Arg Ala Glu Asn Asp
    50                      55                  60

<210> SEQ ID NO 674
<211> LENGTH: 60
<212> TYPE: PRT

-continued

```
<213> ORGANISM: Artificial Sequence
<220> FEATURE:
<223> OTHER INFORMATION: Synthetic

<400> SEQUENCE: 674

Gly Phe Lys Glu Cys Asn Leu Asn Asp Thr Arg Tyr Val Asn Arg Phe
1               5                   10                  15

Leu Cys Gln Phe Val Ala Asp His Ile Leu Leu Thr Gly Lys Gly Lys
            20                  25                  30

Arg Arg Val Phe Ala Ser Asn Gly Gln Ile Thr Asn Leu Leu Arg Gly
        35                  40                  45

Phe Trp Gly Leu Arg Lys Val Arg Ala Glu Asn Asp
    50                  55                  60

<210> SEQ ID NO 675
<211> LENGTH: 60
<212> TYPE: PRT
<213> ORGANISM: Artificial Sequence
<220> FEATURE:
<223> OTHER INFORMATION: Synthetic

<400> SEQUENCE: 675

Arg His His Ala Leu Asp Ala Val Val Val Ala Cys Ser Thr Val Ala
1               5                   10                  15

Met Gln Gln Lys Ile Thr Arg Phe Val Arg Tyr Lys Glu Met Asn Ala
            20                  25                  30

Phe Asp Gly Lys Thr Ile Asp Lys Glu Thr Gly Glu Val Leu His Gln
        35                  40                  45

Lys Thr His Phe Pro Gln Pro Trp Glu Phe Phe Ala
    50                  55                  60

<210> SEQ ID NO 676
<211> LENGTH: 60
<212> TYPE: PRT
<213> ORGANISM: Artificial Sequence
<220> FEATURE:
<223> OTHER INFORMATION: Synthetic

<400> SEQUENCE: 676

Arg His His Ala Leu Asp Ala Val Val Val Ala Cys Ser Thr Val Ala
1               5                   10                  15

Met Gln Gln Lys Ile Thr Arg Phe Val Arg Tyr Lys Glu Met Asn Ala
            20                  25                  30

Phe Asp Gly Lys Thr Ile Asp Lys Glu Thr Gly Lys Val Leu His Gln
        35                  40                  45

Lys Thr His Phe Pro Gln Pro Trp Glu Phe Phe Ala
    50                  55                  60

<210> SEQ ID NO 677
<211> LENGTH: 60
<212> TYPE: PRT
<213> ORGANISM: Artificial Sequence
<220> FEATURE:
<223> OTHER INFORMATION: Synthetic

<400> SEQUENCE: 677

Gln Glu Val Met Ile Arg Val Phe Gly Lys Pro Asp Gly Lys Pro Glu
1               5                   10                  15

Phe Glu Glu Ala Asp Thr Leu Glu Lys Leu Arg Thr Leu Leu Ala Glu
            20                  25                  30

Lys Leu Ser Ser Arg Pro Glu Ala Val His Glu Tyr Val Thr Pro Leu
```

-continued

```
            35                  40                  45

Phe Val Ser Arg Ala Pro Asn Arg Lys Met Ser Gly
    50                  55                  60

<210> SEQ ID NO 678
<211> LENGTH: 60
<212> TYPE: PRT
<213> ORGANISM: Artificial Sequence
<220> FEATURE:
<223> OTHER INFORMATION: Synthetic

<400> SEQUENCE: 678

Gln Glu Val Met Ile Arg Val Phe Gly Lys Pro Asp Gly Lys Pro Glu
1               5                  10                  15

Phe Glu Glu Ala Asp Thr Pro Glu Lys Leu Arg Thr Leu Leu Ala Glu
            20                  25                  30

Lys Leu Ser Ser Arg Pro Glu Ala Val His Glu Tyr Val Thr Pro Leu
        35                  40                  45

Phe Val Ser Arg Ala Pro Asn Arg Lys Met Ser Gly
    50                  55                  60

<210> SEQ ID NO 679
<211> LENGTH: 55
<212> TYPE: PRT
<213> ORGANISM: Artificial Sequence
<220> FEATURE:
<223> OTHER INFORMATION: Synthetic

<400> SEQUENCE: 679

Gln Gly His Met Glu Thr Val Lys Ser Ala Lys Arg Leu Asp Glu Gly
1               5                  10                  15

Val Ser Val Leu Arg Val Pro Leu Thr Gln Leu Lys Leu Lys Asp Leu
            20                  25                  30

Glu Lys Met Val Asn Arg Glu Arg Glu Pro Lys Leu Tyr Glu Ala Leu
        35                  40                  45

Lys Ala Arg Leu Glu Ala His
    50                  55

<210> SEQ ID NO 680
<211> LENGTH: 59
<212> TYPE: PRT
<213> ORGANISM: Artificial Sequence
<220> FEATURE:
<223> OTHER INFORMATION: Synthetic

<400> SEQUENCE: 680

Ala His Lys Asp Thr Leu Arg Ser Ala Lys Arg Phe Val Lys His Asn
1               5                  10                  15

Glu Lys Ile Ser Val Lys Arg Val Trp Leu Thr Glu Ile Lys Leu Ala
            20                  25                  30

Asp Leu Glu Asn Met Val Asn Tyr Lys Asn Gly Arg Glu Ile Glu Leu
        35                  40                  45

Tyr Glu Ala Leu Lys Ala Arg Leu Glu Ala Tyr
    50                  55

<210> SEQ ID NO 681
<211> LENGTH: 55
<212> TYPE: PRT
<213> ORGANISM: Artificial Sequence
<220> FEATURE:
<223> OTHER INFORMATION: Synthetic
```

<400> SEQUENCE: 681

Lys Asp Asp Pro Ala Lys Ala Phe Ala Glu Pro Phe Tyr Lys Tyr Asp
1               5                   10                  15

Lys Ala Gly Asn Arg Thr Gln Gln Val Lys Ala Val Arg Val Glu Gln
                20                  25                  30

Val Gln Lys Thr Gly Val Trp Val Arg Asn His Asn Gly Ile Ala Asp
            35                  40                  45

Asn Ala Thr Met Val Arg Val
        50                  55

<210> SEQ ID NO 682
<211> LENGTH: 55
<212> TYPE: PRT
<213> ORGANISM: Artificial Sequence
<220> FEATURE:
<223> OTHER INFORMATION: Synthetic

<400> SEQUENCE: 682

Gly Gly Asn Ala Lys Gln Ala Phe Asp Pro Lys Asp Asn Pro Phe Tyr
1               5                   10                  15

Lys Lys Gly Gly Gln Leu Val Lys Ala Val Arg Val Glu Lys Thr Gln
                20                  25                  30

Glu Ser Gly Val Leu Leu Asn Lys Lys Asn Ala Tyr Thr Ile Ala Asp
            35                  40                  45

Asn Gly Asp Met Val Arg Val
        50                  55

<210> SEQ ID NO 683
<211> LENGTH: 55
<212> TYPE: PRT
<213> ORGANISM: Artificial Sequence
<220> FEATURE:
<223> OTHER INFORMATION: Synthetic

<400> SEQUENCE: 683

Asp Val Phe Glu Lys Gly Asp Lys Tyr Tyr Leu Val Pro Ile Tyr Ser
1               5                   10                  15

Trp Gln Val Ala Lys Gly Ile Leu Pro Asp Arg Ala Val Val Gln Gly
                20                  25                  30

Lys Asp Glu Glu Asp Trp Gln Leu Ile Asp Asp Ser Phe Asn Phe Lys
            35                  40                  45

Phe Ser Leu His Pro Asn Asp
        50                  55

<210> SEQ ID NO 684
<211> LENGTH: 53
<212> TYPE: PRT
<213> ORGANISM: Artificial Sequence
<220> FEATURE:
<223> OTHER INFORMATION: Synthetic

<400> SEQUENCE: 684

Asp Val Phe Cys Lys Val Asp Lys Lys Gly Lys Asn Gln Tyr Phe Ile
1               5                   10                  15

Val Pro Ile Tyr Ala Trp Gln Val Ala Glu Asn Ile Leu Pro Asp Ile
                20                  25                  30

Asp Cys Lys Gly Tyr Arg Ile Asp Asp Ser Tyr Thr Phe Cys Phe Ser
            35                  40                  45

Leu His Lys Tyr Asp
        50

<210> SEQ ID NO 685
<211> LENGTH: 58
<212> TYPE: PRT
<213> ORGANISM: Artificial Sequence
<220> FEATURE:
<223> OTHER INFORMATION: Synthetic

<400> SEQUENCE: 685

Leu Val Glu Val Ile Thr Lys Lys Ala Arg Met Phe Gly Tyr Phe Ala
1               5                   10                  15

Ser Cys His Arg Gly Thr Gly Asn Ile Asn Ile Arg Ile His Asp Leu
            20                  25                  30

Asp His Lys Ile Gly Lys Asn Gly Ile Leu Glu Gly Ile Gly Val Lys
        35                  40                  45

Thr Ala Leu Ser Phe Gln Lys Tyr Gln Ile
    50                  55

<210> SEQ ID NO 686
<211> LENGTH: 56
<212> TYPE: PRT
<213> ORGANISM: Artificial Sequence
<220> FEATURE:
<223> OTHER INFORMATION: Synthetic

<400> SEQUENCE: 686

Leu Ile Ala Phe Gln Lys Asp Glu Lys Ser Lys Val Glu Phe Ala Tyr
1               5                   10                  15

Tyr Ile Asn Cys Asp Ser Ser Asn Gly Arg Phe Tyr Leu Ala Trp His
            20                  25                  30

Asp Lys Gly Ser Lys Glu Gln Gln Phe Arg Ile Ser Thr Gln Asn Leu
        35                  40                  45

Val Leu Ile Gln Lys Tyr Gln Val
    50                  55

<210> SEQ ID NO 687
<211> LENGTH: 19
<212> TYPE: PRT
<213> ORGANISM: Artificial Sequence
<220> FEATURE:
<223> OTHER INFORMATION: Synthetic

<400> SEQUENCE: 687

Asp Glu Leu Gly Lys Glu Ile Arg Pro Cys Arg Leu Lys Lys Arg Pro
1               5                   10                  15

Pro Val Arg

<210> SEQ ID NO 688
<211> LENGTH: 19
<212> TYPE: PRT
<213> ORGANISM: Artificial Sequence
<220> FEATURE:
<223> OTHER INFORMATION: Synthetic

<400> SEQUENCE: 688

Asn Glu Leu Gly Lys Glu Ile Arg Pro Cys Arg Leu Lys Lys Arg Pro
1               5                   10                  15

Pro Val Arg

<210> SEQ ID NO 689
<211> LENGTH: 50
<212> TYPE: PRT

-continued

<213> ORGANISM: Artificial Sequence
<220> FEATURE:
<223> OTHER INFORMATION: Synthetic

<400> SEQUENCE: 689

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu
    50

<210> SEQ ID NO 690
<211> LENGTH: 50
<212> TYPE: PRT
<213> ORGANISM: Artificial Sequence
<220> FEATURE:
<223> OTHER INFORMATION: Synthetic

<400> SEQUENCE: 690

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu
    50

<210> SEQ ID NO 691
<211> LENGTH: 50
<212> TYPE: PRT
<213> ORGANISM: Artificial Sequence
<220> FEATURE:
<223> OTHER INFORMATION: Synthetic

<400> SEQUENCE: 691

Val Pro Lys Thr Gly Asp Ser Leu Ala Met Ala Arg Arg Leu Ala Arg
1               5                   10                  15

Ser Val Arg Arg Leu Thr Arg Arg Ala His Arg Leu Leu Arg Thr
            20                  25                  30

Arg Arg Leu Leu Lys Arg Glu Gly Val Leu Gln Ala Ala Asn Phe Asp
        35                  40                  45

Glu Asn
    50

<210> SEQ ID NO 692
<211> LENGTH: 50
<212> TYPE: PRT
<213> ORGANISM: Artificial Sequence
<220> FEATURE:
<223> OTHER INFORMATION: Synthetic

<400> SEQUENCE: 692

Val Pro Lys Thr Gly Asp Ser Leu Ala Met Ala Arg Arg Leu Ala Arg
1               5                   10                  15

Ser Val Arg Arg Leu Thr Arg Arg Ala His Arg Leu Leu Arg Ala
            20                  25                  30

Arg Arg Leu Leu Lys Arg Glu Gly Val Leu Gln Ala Ala Asp Phe Asp

-continued

```
           35              40              45

Glu Asn
    50

<210> SEQ ID NO 693
<211> LENGTH: 50
<212> TYPE: PRT
<213> ORGANISM: Artificial Sequence
<220> FEATURE:
<223> OTHER INFORMATION: Synthetic

<400> SEQUENCE: 693

Gly Leu Ile Lys Ser Leu Pro Asn Thr Pro Trp Gln Leu Arg Ala Ala
1               5                   10                  15

Ala Leu Asp Arg Lys Leu Thr Pro Leu Glu Trp Ser Ala Val Leu Leu
            20                  25                  30

His Leu Ile Lys His Arg Gly Tyr Leu Ser Gln Arg Lys Asn Glu Gly
        35                  40                  45

Glu Thr
    50

<210> SEQ ID NO 694
<211> LENGTH: 50
<212> TYPE: PRT
<213> ORGANISM: Artificial Sequence
<220> FEATURE:
<223> OTHER INFORMATION: Synthetic

<400> SEQUENCE: 694

Gly Leu Ile Lys Ser Leu Pro Asn Thr Pro Trp Gln Leu Arg Ala Ala
1               5                   10                  15

Ala Leu Asp Arg Lys Leu Thr Pro Leu Glu Trp Ser Ala Val Leu Leu
            20                  25                  30

His Leu Ile Lys His Arg Gly Tyr Leu Ser Gln Arg Lys Asn Glu Gly
        35                  40                  45

Glu Thr
    50

<210> SEQ ID NO 695
<211> LENGTH: 50
<212> TYPE: PRT
<213> ORGANISM: Artificial Sequence
<220> FEATURE:
<223> OTHER INFORMATION: Synthetic

<400> SEQUENCE: 695

Ala Asp Lys Glu Leu Gly Ala Leu Leu Lys Gly Val Ala Gly Asn Ala
1               5                   10                  15

His Ala Leu Gln Thr Gly Asp Phe Arg Thr Pro Ala Glu Leu Ala Leu
            20                  25                  30

Asn Lys Phe Glu Lys Glu Ser Gly His Ile Arg Asn Gln Arg Ser Asp
        35                  40                  45

Tyr Ser
    50

<210> SEQ ID NO 696
<211> LENGTH: 50
<212> TYPE: PRT
<213> ORGANISM: Artificial Sequence
<220> FEATURE:
<223> OTHER INFORMATION: Synthetic
```

```
<400> SEQUENCE: 696

Ala Asp Lys Glu Leu Gly Ala Leu Leu Lys Gly Val Ala Asp Asn Ala
1               5                   10                  15

His Ala Leu Gln Thr Gly Asp Phe Arg Thr Pro Ala Glu Leu Ala Leu
            20                  25                  30

Asn Lys Phe Glu Lys Glu Cys Gly His Ile Arg Asn Gln Arg Gly Asp
        35                  40                  45

Tyr Ser
    50

<210> SEQ ID NO 697
<211> LENGTH: 50
<212> TYPE: PRT
<213> ORGANISM: Artificial Sequence
<220> FEATURE:
<223> OTHER INFORMATION: Synthetic

<400> SEQUENCE: 697

His Thr Phe Ser Arg Lys Asp Leu Gln Ala Glu Leu Ile Leu Leu Phe
1               5                   10                  15

Glu Lys Gln Lys Glu Phe Gly Asn Pro His Val Ser Gly Gly Leu Lys
            20                  25                  30

Glu Gly Ile Glu Thr Leu Leu Met Thr Gln Arg Pro Ala Leu Ser Gly
        35                  40                  45

Asp Ala
    50

<210> SEQ ID NO 698
<211> LENGTH: 50
<212> TYPE: PRT
<213> ORGANISM: Artificial Sequence
<220> FEATURE:
<223> OTHER INFORMATION: Synthetic

<400> SEQUENCE: 698

His Thr Phe Ser Arg Lys Asp Leu Gln Ala Glu Leu Asn Leu Leu Phe
1               5                   10                  15

Glu Lys Gln Lys Glu Phe Gly Asn Pro His Val Ser Gly Gly Leu Lys
            20                  25                  30

Glu Gly Ile Glu Thr Leu Leu Met Thr Gln Arg Pro Ala Leu Ser Gly
        35                  40                  45

Asp Ala
    50

<210> SEQ ID NO 699
<211> LENGTH: 50
<212> TYPE: PRT
<213> ORGANISM: Artificial Sequence
<220> FEATURE:
<223> OTHER INFORMATION: Synthetic

<400> SEQUENCE: 699

Val Gln Lys Met Leu Gly His Cys Thr Phe Glu Pro Ala Glu Pro Lys
1               5                   10                  15

Ala Ala Lys Asn Thr Tyr Thr Ala Glu Arg Phe Ile Trp Leu Thr Lys
            20                  25                  30

Leu Asn Asn Leu Arg Ile Leu Glu Gln Gly Ser Glu Arg Pro Leu Thr
        35                  40                  45

Asp Thr
    50
```

-continued

```
<210> SEQ ID NO 700
<211> LENGTH: 50
<212> TYPE: PRT
<213> ORGANISM: Artificial Sequence
<220> FEATURE:
<223> OTHER INFORMATION: Synthetic

<400> SEQUENCE: 700

Val Gln Lys Met Leu Gly His Cys Thr Phe Glu Pro Ala Glu Pro Lys
1               5                   10                  15

Ala Ala Lys Asn Thr Tyr Thr Ala Glu Arg Phe Ile Trp Leu Thr Lys
            20                  25                  30

Leu Asn Asn Leu Arg Ile Leu Glu Gln Gly Ser Glu Arg Pro Leu Thr
        35                  40                  45

Asp Thr
    50

<210> SEQ ID NO 701
<211> LENGTH: 50
<212> TYPE: PRT
<213> ORGANISM: Artificial Sequence
<220> FEATURE:
<223> OTHER INFORMATION: Synthetic

<400> SEQUENCE: 701

Glu Arg Ala Thr Leu Met Asp Glu Pro Tyr Arg Lys Ser Lys Leu Thr
1               5                   10                  15

Tyr Ala Gln Ala Arg Lys Leu Leu Gly Leu Glu Asp Thr Ala Phe Phe
            20                  25                  30

Lys Gly Leu Arg Tyr Gly Lys Asp Asn Ala Glu Ala Ser Thr Leu Met
        35                  40                  45

Glu Met
    50

<210> SEQ ID NO 702
<211> LENGTH: 50
<212> TYPE: PRT
<213> ORGANISM: Artificial Sequence
<220> FEATURE:
<223> OTHER INFORMATION: Synthetic

<400> SEQUENCE: 702

Glu Arg Ala Thr Leu Met Asp Glu Pro Tyr Arg Lys Ser Lys Leu Thr
1               5                   10                  15

Tyr Ala Gln Ala Arg Lys Leu Leu Ser Leu Glu Asp Thr Ala Phe Phe
            20                  25                  30

Lys Gly Leu Arg Tyr Gly Lys Asp Asn Ala Glu Ala Ser Thr Leu Met
        35                  40                  45

Glu Met
    50

<210> SEQ ID NO 703
<211> LENGTH: 50
<212> TYPE: PRT
<213> ORGANISM: Artificial Sequence
<220> FEATURE:
<223> OTHER INFORMATION: Synthetic

<400> SEQUENCE: 703

Lys Ala Tyr His Ala Ile Ser Arg Ala Leu Glu Lys Glu Gly Leu Lys
1               5                   10                  15
```

-continued

```
Asp Lys Lys Ser Pro Leu Asn Leu Ser Pro Glu Leu Gln Asp Glu Ile
            20                  25                  30

Gly Thr Ala Phe Ser Leu Phe Lys Thr Asp Glu Asp Ile Thr Gly Arg
            35                  40                  45

Leu Lys
    50

<210> SEQ ID NO 704
<211> LENGTH: 50
<212> TYPE: PRT
<213> ORGANISM: Artificial Sequence
<220> FEATURE:
<223> OTHER INFORMATION: Synthetic

<400> SEQUENCE: 704

Lys Ala Tyr His Thr Ile Ser Arg Ala Leu Glu Lys Glu Gly Leu Lys
1               5                  10                  15

Asp Lys Lys Ser Pro Leu Asn Leu Ser Pro Glu Leu Gln Asp Glu Ile
            20                  25                  30

Gly Thr Ala Phe Ser Leu Phe Lys Thr Asp Glu Asp Ile Thr Gly Arg
            35                  40                  45

Leu Lys
    50

<210> SEQ ID NO 705
<211> LENGTH: 50
<212> TYPE: PRT
<213> ORGANISM: Artificial Sequence
<220> FEATURE:
<223> OTHER INFORMATION: Synthetic

<400> SEQUENCE: 705

Asp Arg Ile Gln Pro Glu Ile Leu Glu Ala Leu Leu Lys His Ile Ser
1               5                  10                  15

Phe Asp Lys Phe Val Gln Ile Ser Leu Lys Ala Leu Arg Arg Ile Val
            20                  25                  30

Pro Leu Met Glu Gln Gly Lys Arg Tyr Asp Glu Ala Cys Ala Glu Ile
            35                  40                  45

Tyr Gly
    50

<210> SEQ ID NO 706
<211> LENGTH: 50
<212> TYPE: PRT
<213> ORGANISM: Artificial Sequence
<220> FEATURE:
<223> OTHER INFORMATION: Synthetic

<400> SEQUENCE: 706

Asp Arg Ile Gln Pro Glu Ile Leu Glu Ala Leu Leu Lys His Ile Ser
1               5                  10                  15

Phe Asp Lys Phe Val Gln Ile Ser Leu Lys Ala Leu Arg Arg Ile Val
            20                  25                  30

Pro Leu Met Glu Gln Gly Lys Arg Tyr Asp Glu Ala Cys Ala Glu Ile
            35                  40                  45

Tyr Gly
    50

<210> SEQ ID NO 707
<211> LENGTH: 50
```

-continued

```
<212> TYPE: PRT
<213> ORGANISM: Artificial Sequence
<220> FEATURE:
<223> OTHER INFORMATION: Synthetic

<400> SEQUENCE: 707

Asp His Tyr Gly Lys Lys Asn Thr Glu Glu Lys Ile Tyr Leu Pro Pro
1               5                   10                  15

Ile Pro Ala Asp Glu Ile Arg Asn Pro Val Val Leu Arg Ala Leu Ser
            20                  25                  30

Gln Ala Arg Lys Val Ile Asn Gly Val Val Arg Arg Tyr Gly Ser Pro
        35                  40                  45

Ala Arg
    50

<210> SEQ ID NO 708
<211> LENGTH: 50
<212> TYPE: PRT
<213> ORGANISM: Artificial Sequence
<220> FEATURE:
<223> OTHER INFORMATION: Synthetic

<400> SEQUENCE: 708

Asp His Tyr Gly Lys Lys Asn Thr Glu Glu Lys Ile Tyr Leu Pro Pro
1               5                   10                  15

Ile Pro Ala Asp Glu Ile Arg Asn Pro Val Val Leu Arg Ala Leu Ser
            20                  25                  30

Gln Ala Arg Lys Val Ile Asn Gly Val Val Arg Arg Tyr Gly Ser Pro
        35                  40                  45

Ala Arg
    50

<210> SEQ ID NO 709
<211> LENGTH: 50
<212> TYPE: PRT
<213> ORGANISM: Artificial Sequence
<220> FEATURE:
<223> OTHER INFORMATION: Synthetic

<400> SEQUENCE: 709

Ile His Ile Glu Thr Ala Arg Glu Val Gly Lys Ser Phe Lys Asp Arg
1               5                   10                  15

Lys Glu Ile Glu Lys Arg Gln Glu Glu Asn Arg Lys Asp Arg Glu Lys
            20                  25                  30

Ala Ala Ala Lys Phe Arg Glu Tyr Phe Pro Asn Phe Val Gly Glu Pro
        35                  40                  45

Lys Ser
    50

<210> SEQ ID NO 710
<211> LENGTH: 50
<212> TYPE: PRT
<213> ORGANISM: Artificial Sequence
<220> FEATURE:
<223> OTHER INFORMATION: Synthetic

<400> SEQUENCE: 710

Ile His Ile Glu Thr Ala Arg Glu Val Gly Lys Ser Phe Lys Asp Arg
1               5                   10                  15

Lys Glu Ile Glu Lys Arg Gln Glu Glu Asn Arg Lys Asp Arg Glu Lys
            20                  25                  30
```

-continued

```
Ala Ala Ala Lys Phe Arg Glu Tyr Phe Pro Asn Phe Val Gly Glu Pro
        35                  40                  45

Lys Ser
    50

<210> SEQ ID NO 711
<211> LENGTH: 50
<212> TYPE: PRT
<213> ORGANISM: Artificial Sequence
<220> FEATURE:
<223> OTHER INFORMATION: Synthetic

<400> SEQUENCE: 711

Lys Asp Ile Leu Lys Leu Arg Leu Tyr Glu Gln Gln His Gly Lys Cys
1               5                   10                  15

Leu Tyr Ser Gly Lys Glu Ile Asn Leu Gly Arg Leu Asn Glu Lys Gly
            20                  25                  30

Tyr Val Glu Ile Asp His Ala Leu Pro Phe Ser Arg Thr Trp Asp Asp
        35                  40                  45

Ser Phe
    50

<210> SEQ ID NO 712
<211> LENGTH: 50
<212> TYPE: PRT
<213> ORGANISM: Artificial Sequence
<220> FEATURE:
<223> OTHER INFORMATION: Synthetic

<400> SEQUENCE: 712

Lys Asp Ile Leu Lys Leu Arg Leu Tyr Glu Gln Gln His Gly Lys Cys
1               5                   10                  15

Leu Tyr Ser Gly Lys Glu Ile Asn Leu Gly Arg Leu Asn Glu Lys Gly
            20                  25                  30

Tyr Val Glu Ile Asp His Ala Leu Pro Phe Ser Arg Thr Trp Asp Asp
        35                  40                  45

Ser Phe
    50

<210> SEQ ID NO 713
<211> LENGTH: 50
<212> TYPE: PRT
<213> ORGANISM: Artificial Sequence
<220> FEATURE:
<223> OTHER INFORMATION: Synthetic

<400> SEQUENCE: 713

Asn Asn Lys Val Leu Val Leu Gly Ser Glu Asn Gln Asn Lys Gly Asn
1               5                   10                  15

Gln Thr Pro Tyr Glu Tyr Phe Asn Gly Lys Asp Asn Ser Arg Glu Trp
            20                  25                  30

Gln Glu Phe Lys Ala Arg Val Glu Thr Ser Arg Phe Pro Arg Ser Lys
        35                  40                  45

Lys Gln
    50

<210> SEQ ID NO 714
<211> LENGTH: 50
<212> TYPE: PRT
<213> ORGANISM: Artificial Sequence
<220> FEATURE:
<223> OTHER INFORMATION: Synthetic
```

-continued

<400> SEQUENCE: 714

Asn Asn Lys Val Leu Val Leu Gly Ser Glu Asn Gln Asn Lys Gly Asn
1               5                   10                  15

Gln Thr Pro Tyr Glu Tyr Phe Asn Gly Lys Asp Asn Ser Arg Glu Trp
                20                  25                  30

Gln Glu Phe Lys Ala Arg Val Glu Thr Ser Arg Phe Pro Arg Ser Lys
        35                  40                  45

Lys Gln
    50

<210> SEQ ID NO 715
<211> LENGTH: 50
<212> TYPE: PRT
<213> ORGANISM: Artificial Sequence
<220> FEATURE:
<223> OTHER INFORMATION: Synthetic

<400> SEQUENCE: 715

Arg Ile Leu Leu Gln Lys Phe Asp Glu Asp Gly Phe Lys Glu Arg Asn
1               5                   10                  15

Leu Asn Asp Thr Arg Tyr Val Asn Arg Phe Leu Cys Gln Phe Val Ala
                20                  25                  30

Asp Arg Met Arg Leu Thr Gly Lys Gly Lys Lys Arg Val Phe Ala Ser
        35                  40                  45

Asn Gly
    50

<210> SEQ ID NO 716
<211> LENGTH: 50
<212> TYPE: PRT
<213> ORGANISM: Artificial Sequence
<220> FEATURE:
<223> OTHER INFORMATION: Synthetic

<400> SEQUENCE: 716

Arg Ile Leu Leu Gln Lys Phe Asp Glu Asp Gly Phe Lys Glu Arg Asn
1               5                   10                  15

Leu Asn Asp Thr Arg Tyr Val Asn Arg Phe Leu Cys Gln Phe Val Ala
                20                  25                  30

Asp Arg Met Arg Leu Thr Gly Lys Gly Lys Lys Arg Val Phe Ala Ser
        35                  40                  45

Asn Gly
    50

<210> SEQ ID NO 717
<211> LENGTH: 50
<212> TYPE: PRT
<213> ORGANISM: Artificial Sequence
<220> FEATURE:
<223> OTHER INFORMATION: Synthetic

<400> SEQUENCE: 717

Gln Ile Thr Asn Leu Leu Arg Gly Phe Trp Gly Leu Arg Lys Val Arg
1               5                   10                  15

Ala Glu Asn Asp Arg His His Ala Leu Asp Ala Val Val Val Ala Cys
                20                  25                  30

Ser Thr Val Ala Met Gln Gln Lys Ile Thr Arg Phe Val Arg Tyr Lys
        35                  40                  45

Glu Met

-continued
─────────────────────────────────────────────────────────────

```
     50

<210> SEQ ID NO 718
<211> LENGTH: 50
<212> TYPE: PRT
<213> ORGANISM: Artificial Sequence
<220> FEATURE:
<223> OTHER INFORMATION: Synthetic

<400> SEQUENCE: 718

Gln Ile Thr Asn Leu Leu Arg Gly Phe Trp Gly Leu Arg Lys Val Arg
1               5                   10                  15

Ala Glu Asn Asp Arg His His Ala Leu Asp Ala Val Val Val Ala Cys
            20                  25                  30

Ser Thr Val Ala Met Gln Gln Lys Ile Thr Arg Phe Val Arg Tyr Lys
        35                  40                  45

Glu Met
    50

<210> SEQ ID NO 719
<211> LENGTH: 50
<212> TYPE: PRT
<213> ORGANISM: Artificial Sequence
<220> FEATURE:
<223> OTHER INFORMATION: Synthetic

<400> SEQUENCE: 719

Asn Ala Phe Asp Gly Lys Thr Ile Asp Lys Glu Thr Gly Glu Val Leu
1               5                   10                  15

His Gln Lys Thr His Phe Pro Gln Pro Trp Glu Phe Phe Ala Gln Glu
            20                  25                  30

Val Met Ile Arg Val Phe Gly Lys Pro Asp Gly Lys Pro Glu Phe Glu
        35                  40                  45

Glu Ala
    50

<210> SEQ ID NO 720
<211> LENGTH: 50
<212> TYPE: PRT
<213> ORGANISM: Artificial Sequence
<220> FEATURE:
<223> OTHER INFORMATION: Synthetic

<400> SEQUENCE: 720

Asn Ala Phe Asp Gly Lys Thr Ile Asp Lys Glu Thr Gly Glu Val Leu
1               5                   10                  15

His Gln Lys Thr His Phe Pro Gln Pro Trp Glu Phe Phe Ala Gln Glu
            20                  25                  30

Val Met Ile Arg Val Phe Gly Lys Pro Asp Gly Lys Pro Glu Phe Glu
        35                  40                  45

Glu Ala
    50

<210> SEQ ID NO 721
<211> LENGTH: 50
<212> TYPE: PRT
<213> ORGANISM: Artificial Sequence
<220> FEATURE:
<223> OTHER INFORMATION: Synthetic

<400> SEQUENCE: 721

Asp Thr Leu Glu Lys Leu Arg Thr Leu Leu Ala Glu Lys Leu Ser Ser
```

-continued

```
1               5                   10                  15

Arg Pro Glu Ala Val His Glu Tyr Val Thr Pro Leu Phe Val Ser Arg
            20                  25                  30

Ala Pro Asn Arg Lys Met Ser Gly Gln Gly His Met Glu Thr Val Lys
        35                  40                  45

Ser Ala
    50

<210> SEQ ID NO 722
<211> LENGTH: 50
<212> TYPE: PRT
<213> ORGANISM: Artificial Sequence
<220> FEATURE:
<223> OTHER INFORMATION: Synthetic

<400> SEQUENCE: 722

Asp Thr Pro Glu Lys Leu Arg Thr Leu Leu Ala Glu Lys Leu Ser Ser
1               5                   10                  15

Arg Pro Glu Ala Val His Glu Tyr Val Thr Pro Leu Phe Val Ser Arg
            20                  25                  30

Ala Pro Asn Arg Lys Met Ser Gly Gln Gly His Met Glu Thr Val Lys
        35                  40                  45

Ser Ala
    50

<210> SEQ ID NO 723
<211> LENGTH: 50
<212> TYPE: PRT
<213> ORGANISM: Artificial Sequence
<220> FEATURE:
<223> OTHER INFORMATION: Synthetic

<400> SEQUENCE: 723

Lys Arg Leu Asp Glu Gly Val Ser Val Leu Arg Val Pro Leu Thr Gln
1               5                   10                  15

Leu Lys Leu Lys Asp Leu Glu Lys Met Val Asn Arg Glu Arg Glu Pro
            20                  25                  30

Lys Leu Tyr Glu Ala Leu Lys Ala Arg Leu Glu Ala His Lys Asp Asp
        35                  40                  45

Pro Ala
    50

<210> SEQ ID NO 724
<211> LENGTH: 50
<212> TYPE: PRT
<213> ORGANISM: Artificial Sequence
<220> FEATURE:
<223> OTHER INFORMATION: Synthetic

<400> SEQUENCE: 724

Lys Arg Leu Asp Glu Gly Val Ser Val Leu Arg Val Pro Leu Thr Gln
1               5                   10                  15

Leu Lys Leu Lys Asp Leu Glu Lys Met Val Asn Arg Glu Arg Glu Pro
            20                  25                  30

Lys Leu Tyr Glu Ala Leu Lys Ala Arg Leu Glu Ala His Lys Asp Asp
        35                  40                  45

Pro Ala
    50

<210> SEQ ID NO 725
```

-continued

```
<211> LENGTH: 50
<212> TYPE: PRT
<213> ORGANISM: Artificial Sequence
<220> FEATURE:
<223> OTHER INFORMATION: Synthetic

<400> SEQUENCE: 725

Lys Ala Phe Ala Glu Pro Phe Tyr Lys Tyr Asp Lys Ala Gly Asn Arg
1               5                   10                  15

Thr Gln Gln Val Lys Ala Val Arg Val Glu Gln Val Gln Lys Thr Gly
                20                  25                  30

Val Trp Val Arg Asn His Asn Gly Ile Ala Asp Asn Ala Thr Met Val
        35                  40                  45

Arg Val
    50

<210> SEQ ID NO 726
<211> LENGTH: 50
<212> TYPE: PRT
<213> ORGANISM: Artificial Sequence
<220> FEATURE:
<223> OTHER INFORMATION: Synthetic

<400> SEQUENCE: 726

Lys Ala Phe Ala Glu Pro Phe Tyr Lys Tyr Asp Lys Ala Gly Asn Arg
1               5                   10                  15

Thr Gln Gln Val Lys Ala Val Arg Val Glu Gln Val Gln Lys Thr Gly
                20                  25                  30

Val Trp Val Arg Asn His Asn Gly Ile Ala Asp Asn Ala Thr Met Val
        35                  40                  45

Arg Val
    50

<210> SEQ ID NO 727
<211> LENGTH: 50
<212> TYPE: PRT
<213> ORGANISM: Artificial Sequence
<220> FEATURE:
<223> OTHER INFORMATION: Synthetic

<400> SEQUENCE: 727

Asp Val Phe Glu Lys Gly Asp Lys Tyr Tyr Leu Val Pro Ile Tyr Ser
1               5                   10                  15

Trp Gln Val Ala Lys Gly Ile Leu Pro Asp Arg Ala Val Val Gln Gly
                20                  25                  30

Lys Asp Glu Glu Asp Trp Gln Leu Ile Asp Asp Ser Phe Asn Phe Lys
        35                  40                  45

Phe Ser
    50

<210> SEQ ID NO 728
<211> LENGTH: 50
<212> TYPE: PRT
<213> ORGANISM: Artificial Sequence
<220> FEATURE:
<223> OTHER INFORMATION: Synthetic

<400> SEQUENCE: 728

Asp Val Phe Glu Lys Gly Asp Lys Tyr Tyr Leu Val Pro Ile Tyr Ser
1               5                   10                  15

Trp Gln Val Ala Lys Gly Ile Leu Pro Asp Arg Ala Val Val Ala Tyr
                20                  25                  30
```

-continued

```
Ala Asp Glu Glu Asp Trp Thr Val Ile Asp Glu Ser Phe Arg Phe Lys
        35                  40                  45

Phe Val
    50
```

<210> SEQ ID NO 729
<211> LENGTH: 50
<212> TYPE: PRT
<213> ORGANISM: Artificial Sequence
<220> FEATURE:
<223> OTHER INFORMATION: Synthetic

<400> SEQUENCE: 729

```
Leu His Pro Asn Asp Leu Val Glu Val Ile Thr Lys Lys Ala Arg Met
1               5                   10                  15

Phe Gly Tyr Phe Ala Ser Cys His Arg Gly Thr Gly Asn Ile Asn Ile
            20                  25                  30

Arg Ile His Asp Leu Asp His Lys Ile Gly Lys Asn Gly Ile Leu Glu
        35                  40                  45

Gly Ile
    50
```

<210> SEQ ID NO 730
<211> LENGTH: 32
<212> TYPE: PRT
<213> ORGANISM: Artificial Sequence
<220> FEATURE:
<223> OTHER INFORMATION: Synthetic

<400> SEQUENCE: 730

```
Gly Val Lys Thr Ala Leu Ser Phe Gln Lys Tyr Gln Ile Asp Glu Leu
1               5                   10                  15

Gly Lys Glu Ile Arg Pro Cys Arg Leu Lys Lys Arg Pro Pro Val Arg
            20                  25                  30
```

<210> SEQ ID NO 731
<211> LENGTH: 32
<212> TYPE: PRT
<213> ORGANISM: Artificial Sequence
<220> FEATURE:
<223> OTHER INFORMATION: Synthetic

<400> SEQUENCE: 731

```
Gly Val Lys Thr Ala Leu Ser Phe Gln Lys Tyr Gln Ile Asp Glu Met
1               5                   10                  15

Gly Lys Glu Ile Arg Pro Cys Arg Leu Lys Lys Arg Pro Pro Val Arg
            20                  25                  30
```

<210> SEQ ID NO 732
<211> LENGTH: 1140
<212> TYPE: PRT
<213> ORGANISM: Artificial Sequence
<220> FEATURE:
<223> OTHER INFORMATION: Synthetic

<400> SEQUENCE: 732

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45
```

-continued

```
Ala Glu Val Pro Lys Thr Gly Asp Ser Leu Ala Met Ala Arg Arg Leu
    50              55              60

Ala Arg Ser Val Arg Arg Leu Thr Arg Arg Arg Ala His Arg Leu Leu
65              70              75              80

Arg Ala Arg Arg Leu Leu Lys Arg Glu Gly Val Leu Gln Ala Ala Asp
                85              90              95

Phe Asp Glu Asn Gly Leu Ile Lys Ser Leu Pro Asn Thr Pro Trp Gln
            100             105             110

Leu Arg Ala Ala Ala Leu Asp Arg Lys Leu Thr Pro Leu Glu Trp Ser
        115             120             125

Ala Val Leu Leu His Leu Ile Lys His Arg Gly Tyr Leu Ser Gln Arg
    130             135             140

Lys Asn Glu Gly Glu Thr Ala Asp Lys Glu Leu Gly Ala Leu Leu Lys
145             150             155             160

Gly Val Ala Asn Asn Ala His Ala Leu Gln Thr Gly Asp Phe Arg Thr
                165             170             175

Pro Ala Glu Leu Ala Leu Asn Lys Phe Glu Lys Glu Ser Gly His Ile
            180             185             190

Arg Asn Gln Arg Gly Asp Tyr Ser His Thr Phe Ser Arg Lys Asp Leu
        195             200             205

Gln Ala Glu Leu Ile Leu Leu Phe Glu Lys Gln Lys Glu Phe Gly Asn
    210             215             220

Pro His Val Ser Gly Gly Leu Lys Glu Gly Ile Glu Thr Leu Leu Met
225             230             235             240

Thr Gln Arg Pro Ala Leu Ser Gly Asp Ala Val Gln Lys Met Leu Gly
                245             250             255

His Cys Thr Phe Glu Pro Ala Glu Pro Lys Ala Ala Lys Asn Thr Tyr
            260             265             270

Thr Ala Glu Arg Phe Ile Trp Leu Thr Lys Leu Asn Asn Leu Arg Ile
        275             280             285

Leu Glu Gln Gly Ser Glu Arg Pro Leu Thr Asp Thr Glu Arg Ala Thr
    290             295             300

Leu Met Asp Glu Pro Tyr Arg Lys Ser Lys Leu Thr Tyr Ala Gln Ala
305             310             315             320

Arg Lys Leu Leu Gly Leu Glu Asp Thr Ala Phe Phe Lys Gly Leu Arg
                325             330             335

Tyr Gly Lys Asp Asn Ala Glu Ala Ser Thr Leu Met Glu Met Lys Ala
            340             345             350

Tyr His Ala Ile Ser Arg Ala Leu Glu Lys Glu Gly Leu Lys Asp Lys
        355             360             365

Lys Ser Pro Leu Asn Leu Ser Ser Glu Leu Gln Asp Glu Ile Gly Thr
    370             375             380

Ala Phe Ser Leu Phe Lys Thr Asp Glu Asp Ile Thr Gly Arg Leu Lys
385             390             395             400

Asp Arg Val Gln Pro Glu Ile Leu Glu Ala Leu Leu Lys His Ile Ser
                405             410             415

Phe Asp Lys Phe Val Gln Ile Ser Leu Lys Ala Leu Arg Arg Ile Val
            420             425             430

Pro Leu Met Glu Gln Gly Lys Arg Tyr Asp Glu Ala Cys Ala Glu Ile
        435             440             445

Tyr Gly Asp His Tyr Gly Lys Lys Asn Thr Glu Glu Lys Ile Tyr Leu
    450             455             460
```

-continued

```
Pro Pro Ile Pro Ala Asp Glu Ile Arg Asn Pro Val Val Leu Arg Ala
465             470             475             480

Leu Ser Gln Ala Arg Lys Val Ile Asn Gly Val Val Arg Arg Tyr Gly
            485             490             495

Ser Pro Ala Arg Ile His Ile Glu Thr Ala Arg Glu Val Gly Lys Ser
            500             505             510

Phe Lys Asp Arg Lys Glu Ile Glu Lys Arg Gln Glu Glu Asn Arg Lys
            515             520             525

Asp Arg Glu Lys Ala Ala Ala Lys Phe Arg Glu Tyr Phe Pro Asn Phe
    530             535             540

Val Gly Glu Pro Lys Ser Lys Asp Ile Leu Lys Leu Arg Leu Tyr Glu
545             550             555             560

Gln Gln His Gly Lys Cys Leu Tyr Ser Gly Lys Glu Ile Asn Leu Val
            565             570             575

Arg Leu Asn Glu Lys Gly Tyr Val Glu Ile Asp His Ala Leu Pro Phe
            580             585             590

Ser Arg Thr Trp Asp Asp Ser Phe Asn Asn Lys Val Leu Val Leu Gly
            595             600             605

Ser Glu Asn Gln Asn Lys Gly Asn Gln Thr Pro Tyr Glu Tyr Phe Asn
    610             615             620

Gly Lys Asp Asn Ser Arg Glu Trp Gln Glu Phe Lys Ala Arg Val Glu
625             630             635             640

Thr Ser Arg Phe Pro Arg Ser Lys Lys Gln Arg Ile Leu Leu Gln Lys
            645             650             655

Phe Asp Glu Asp Gly Phe Lys Glu Cys Asn Leu Asn Asp Thr Arg Tyr
            660             665             670

Val Asn Arg Phe Leu Cys Gln Phe Val Ala Asp His Ile Leu Leu Thr
            675             680             685

Gly Lys Gly Lys Arg Arg Val Phe Ala Ser Asn Gly Gln Ile Thr Asn
    690             695             700

Leu Leu Arg Gly Phe Trp Gly Leu Arg Lys Val Arg Ala Glu Asn Asp
705             710             715             720

Arg His His Ala Leu Asp Ala Val Val Val Ala Cys Ser Thr Val Ala
            725             730             735

Met Gln Gln Lys Ile Thr Arg Phe Val Arg Tyr Lys Glu Met Asn Ala
            740             745             750

Phe Asp Gly Lys Thr Ile Asp Lys Glu Thr Gly Lys Val Leu His Gln
            755             760             765

Lys Thr His Phe Pro Gln Pro Trp Glu Phe Phe Ala Gln Glu Val Met
    770             775             780

Ile Arg Val Phe Gly Lys Pro Asp Gly Lys Pro Glu Phe Glu Glu Ala
785             790             795             800

Asp Thr Pro Glu Lys Leu Arg Thr Leu Leu Ala Glu Lys Leu Ser Ser
            805             810             815

Arg Pro Glu Ala Val His Glu Tyr Val Thr Pro Leu Phe Val Ser Arg
            820             825             830

Ala Pro Asn Arg Lys Met Ser Gly Ala His Lys Asp Thr Leu Arg Ser
    835             840             845

Ala Lys Arg Phe Val Lys His Asn Glu Lys Ile Ser Val Lys Arg Val
    850             855             860

Trp Leu Thr Glu Ile Lys Leu Ala Asp Leu Glu Asn Met Val Asn Tyr
865             870             875             880

Lys Asn Gly Arg Glu Ile Glu Leu Tyr Glu Ala Leu Lys Ala Arg Leu
```

-continued

```
          885              890              895

Glu Ala Tyr Gly Gly Asn Ala Lys Gln Ala Phe Asp Pro Lys Asp Asn
          900              905              910

Pro Phe Tyr Lys Lys Gly Gly Gln Leu Val Lys Ala Val Arg Val Glu
          915              920              925

Lys Thr Gln Glu Ser Gly Val Leu Leu Asn Lys Lys Asn Ala Tyr Thr
     930              935              940

Ile Ala Asp Asn Gly Asp Met Val Arg Val Asp Val Phe Cys Lys Val
945              950              955              960

Asp Lys Lys Gly Lys Asn Gln Tyr Phe Ile Val Pro Ile Tyr Ala Trp
          965              970              975

Gln Val Ala Glu Asn Ile Leu Pro Asp Ile Asp Cys Lys Gly Tyr Arg
          980              985              990

Ile Asp Asp Ser Tyr Thr Phe Cys  Phe Ser Leu His Lys  Tyr Asp Leu
          995              1000              1005

Ile Ala  Phe Gln Lys Asp Glu  Lys Ser Lys Val Glu  Phe Ala Tyr
     1010              1015              1020

Tyr Ile  Asn Cys Asp Ser Ser  Asn Gly Arg Phe Tyr  Leu Ala Trp
     1025              1030              1035

His Asp  Lys Gly Ser Lys Glu  Gln Gln Phe Arg Ile  Ser Thr Gln
     1040              1045              1050

Asn Leu  Val Leu Ile Gln Lys  Tyr Gln Val Asn Glu  Leu Gly Lys
     1055              1060              1065

Glu Ile  Arg Pro Cys Arg Leu  Lys Lys Arg Pro Pro  Val Arg Gly
     1070              1075              1080

Thr Gly  Gly Pro Lys Lys Lys  Arg Lys Val Tyr Pro  Tyr Asp Val
     1085              1090              1095

Pro Asp  Tyr Ala Gly Tyr Pro  Tyr Asp Val Pro Asp  Tyr Ala Gly
     1100              1105              1110

Ser Tyr  Pro Tyr Asp Val Pro  Asp Tyr Ala Gly Ser  Ala Ala Pro
     1115              1120              1125

Ala Ala  Lys Lys Lys Lys Leu  Asp Phe Glu Ser Gly
     1130              1135              1140
```

```
<210> SEQ ID NO 733
<211> LENGTH: 1168
<212> TYPE: PRT
<213> ORGANISM: Artificial Sequence
<220> FEATURE:
<223> OTHER INFORMATION: Synthetic

<400> SEQUENCE: 733

Met Val Pro Lys Lys Lys Arg Lys Val Glu Asp Lys Arg Pro Ala Ala
1               5               10              15

Thr Lys Lys Ala Gly Gln Ala Lys Lys Lys Lys Met Ala Ala Phe Lys
          20              25              30

Pro Asn Pro Ile Asn Tyr Ile Leu Gly Leu Asp Ile Gly Ile Ala Ser
          35              40              45

Val Gly Trp Ala Met Val Glu Ile Asp Glu Glu Glu Asn Pro Ile Arg
     50              55              60

Leu Ile Asp Leu Gly Val Arg Val Phe Glu Arg Ala Glu Val Pro Lys
65              70              75              80

Thr Gly Asp Ser Leu Ala Met Ala Arg Arg Leu Ala Arg Ser Val Arg
          85              90              95

Arg Leu Thr Arg Arg Arg Ala His Arg Leu Leu Arg Ala Arg Arg Leu
```

-continued

```
               100             105             110

Leu Lys Arg Glu Gly Val Leu Gln Ala Ala Asp Phe Asp Glu Asn Gly
            115             120             125

Leu Ile Lys Ser Leu Pro Asn Thr Pro Trp Gln Leu Arg Ala Ala Ala
        130             135             140

Leu Asp Arg Lys Leu Thr Pro Leu Glu Trp Ser Ala Val Leu Leu His
145             150             155             160

Leu Ile Lys His Arg Gly Tyr Leu Ser Gln Arg Lys Asn Glu Gly Glu
                165             170             175

Thr Ala Asp Lys Glu Leu Gly Ala Leu Leu Lys Gly Val Ala Asn Asn
                180             185             190

Ala His Ala Leu Gln Thr Gly Asp Phe Arg Thr Pro Ala Glu Leu Ala
        195             200             205

Leu Asn Lys Phe Glu Lys Glu Ser Gly His Ile Arg Asn Gln Arg Gly
        210             215             220

Asp Tyr Ser His Thr Phe Ser Arg Lys Asp Leu Gln Ala Glu Leu Ile
225             230             235             240

Leu Leu Phe Glu Lys Gln Lys Glu Phe Gly Asn Pro His Val Ser Gly
                245             250             255

Gly Leu Lys Glu Gly Ile Glu Thr Leu Leu Met Thr Gln Arg Pro Ala
                260             265             270

Leu Ser Gly Asp Ala Val Gln Lys Met Leu Gly His Cys Thr Phe Glu
                275             280             285

Pro Ala Glu Pro Lys Ala Ala Lys Asn Thr Tyr Thr Ala Glu Arg Phe
        290             295             300

Ile Trp Leu Thr Lys Leu Asn Asn Leu Arg Ile Leu Glu Gln Gly Ser
305             310             315             320

Glu Arg Pro Leu Thr Asp Thr Glu Arg Ala Thr Leu Met Asp Glu Pro
                325             330             335

Tyr Arg Lys Ser Lys Leu Thr Tyr Ala Gln Ala Arg Lys Leu Leu Gly
                340             345             350

Leu Glu Asp Thr Ala Phe Phe Lys Gly Leu Arg Tyr Gly Lys Asp Asn
                355             360             365

Ala Glu Ala Ser Thr Leu Met Glu Met Lys Ala Tyr His Ala Ile Ser
        370             375             380

Arg Ala Leu Glu Lys Glu Gly Leu Lys Asp Lys Lys Ser Pro Leu Asn
385             390             395             400

Leu Ser Ser Glu Leu Gln Asp Glu Ile Gly Thr Ala Phe Ser Leu Phe
                405             410             415

Lys Thr Asp Glu Asp Ile Thr Gly Arg Leu Lys Asp Arg Val Gln Pro
                420             425             430

Glu Ile Leu Glu Ala Leu Leu Lys His Ile Ser Phe Asp Lys Phe Val
                435             440             445

Gln Ile Ser Leu Lys Ala Leu Arg Arg Ile Val Pro Leu Met Glu Gln
        450             455             460

Gly Lys Arg Tyr Asp Glu Ala Cys Ala Glu Ile Tyr Gly Asp His Tyr
465             470             475             480

Gly Lys Lys Asn Thr Glu Glu Lys Ile Tyr Leu Pro Pro Ile Pro Ala
                485             490             495

Asp Glu Ile Arg Asn Pro Val Val Leu Arg Ala Leu Ser Gln Ala Arg
                500             505             510

Lys Val Ile Asn Gly Val Val Arg Arg Tyr Gly Ser Pro Ala Arg Ile
                515             520             525
```

-continued

```
His Ile Glu Thr Ala Arg Glu Val Gly Lys Ser Phe Lys Asp Arg Lys
    530                 535                 540

Glu Ile Glu Lys Arg Gln Glu Asn Arg Lys Asp Arg Glu Lys Ala
545                 550                 555                 560

Ala Ala Lys Phe Arg Glu Tyr Phe Pro Asn Phe Val Gly Glu Pro Lys
                565                 570                 575

Ser Lys Asp Ile Leu Lys Leu Arg Leu Tyr Glu Gln Gln His Gly Lys
                580                 585                 590

Cys Leu Tyr Ser Gly Lys Glu Ile Asn Leu Val Arg Leu Asn Glu Lys
                595                 600                 605

Gly Tyr Val Glu Ile Asp His Ala Leu Pro Phe Ser Arg Thr Trp Asp
    610                 615                 620

Asp Ser Phe Asn Asn Lys Val Leu Val Leu Gly Ser Glu Asn Gln Asn
625                 630                 635                 640

Lys Gly Asn Gln Thr Pro Tyr Glu Tyr Phe Asn Gly Lys Asp Asn Ser
                645                 650                 655

Arg Glu Trp Gln Glu Phe Lys Ala Arg Val Glu Thr Ser Arg Phe Pro
                660                 665                 670

Arg Ser Lys Lys Gln Arg Ile Leu Leu Gln Lys Phe Asp Glu Asp Gly
                675                 680                 685

Phe Lys Glu Cys Asn Leu Asn Asp Thr Arg Tyr Val Asn Arg Phe Leu
    690                 695                 700

Cys Gln Phe Val Ala Asp His Ile Leu Leu Thr Gly Lys Gly Lys Arg
705                 710                 715                 720

Arg Val Phe Ala Ser Asn Gly Gln Ile Thr Asn Leu Leu Arg Gly Phe
                725                 730                 735

Trp Gly Leu Arg Lys Val Arg Ala Glu Asn Asp Arg His His Ala Leu
                740                 745                 750

Asp Ala Val Val Val Ala Cys Ser Thr Val Ala Met Gln Gln Lys Ile
                755                 760                 765

Thr Arg Phe Val Arg Tyr Lys Glu Met Asn Ala Phe Asp Gly Lys Thr
    770                 775                 780

Ile Asp Lys Glu Thr Gly Lys Val Leu His Gln Lys Thr His Phe Pro
785                 790                 795                 800

Gln Pro Trp Glu Phe Phe Ala Gln Glu Val Met Ile Arg Val Phe Gly
                805                 810                 815

Lys Pro Asp Gly Lys Pro Glu Phe Glu Glu Ala Asp Thr Pro Glu Lys
                820                 825                 830

Leu Arg Thr Leu Leu Ala Glu Lys Leu Ser Ser Arg Pro Glu Ala Val
                835                 840                 845

His Glu Tyr Val Thr Pro Leu Phe Val Ser Arg Ala Pro Asn Arg Lys
    850                 855                 860

Met Ser Gly Ala His Lys Asp Thr Leu Arg Ser Ala Lys Arg Phe Val
865                 870                 875                 880

Lys His Asn Glu Lys Ile Ser Val Lys Arg Val Trp Leu Thr Glu Ile
                885                 890                 895

Lys Leu Ala Asp Leu Glu Asn Met Val Asn Tyr Lys Asn Gly Arg Glu
                900                 905                 910

Ile Glu Leu Tyr Glu Ala Leu Lys Ala Arg Leu Glu Ala Tyr Gly Gly
                915                 920                 925

Asn Ala Lys Gln Ala Phe Asp Pro Lys Asp Asn Pro Phe Tyr Lys Lys
    930                 935                 940
```

```
Gly Gly Gln Leu Val Lys Ala Val Arg Val Glu Lys Thr Gln Glu Ser
945             950             955             960

Gly Val Leu Leu Asn Lys Lys Asn Ala Tyr Thr Ile Ala Asp Asn Gly
                965             970             975

Asp Met Val Arg Val Asp Val Phe Cys Lys Val Asp Lys Lys Gly Lys
            980             985             990

Asn Gln Tyr Phe Ile Val Pro Ile  Tyr Ala Trp Gln Val  Ala Glu Asn
        995             1000            1005

Ile Leu  Pro Asp Ile Asp Cys  Lys Gly Tyr Arg Ile  Asp Asp Ser
    1010            1015            1020

Tyr Thr  Phe Cys Phe Ser Leu  His Lys Tyr Asp Leu  Ile Ala Phe
    1025            1030            1035

Gln Lys  Asp Glu Lys Ser Lys  Val Glu Phe Ala Tyr  Tyr Ile Asn
    1040            1045            1050

Cys Asp  Ser Ser Asn Gly Arg  Phe Tyr Leu Ala Trp  His Asp Lys
    1055            1060            1065

Gly Ser  Lys Glu Gln Gln Phe  Arg Ile Ser Thr Gln  Asn Leu Val
    1070            1075            1080

Leu Ile  Gln Lys Tyr Gln Val  Asn Glu Leu Gly Lys  Glu Ile Arg
    1085            1090            1095

Pro Cys  Arg Leu Lys Lys Arg  Pro Pro Val Arg Glu  Asp Lys Arg
    1100            1105            1110

Pro Ala  Ala Thr Lys Lys Ala  Gly Gln Ala Lys Lys  Lys Lys Tyr
    1115            1120            1125

Pro Tyr  Asp Val Pro Asp Tyr  Ala Gly Tyr Pro Tyr  Asp Val Pro
    1130            1135            1140

Asp Tyr  Ala Gly Ser Tyr Pro  Tyr Asp Val Pro Asp  Tyr Ala Ala
    1145            1150            1155

Ala Pro  Ala Ala Lys Lys Lys  Lys Leu Asp
    1160            1165
```

<210> SEQ ID NO 734
<211> LENGTH: 1135
<212> TYPE: PRT
<213> ORGANISM: Artificial Sequence
<220> FEATURE:
<223> OTHER INFORMATION: Synthetic

<400> SEQUENCE: 734

```
Pro Lys Lys Lys Arg Lys Val Asn Ala Met Ala Ala Phe Lys Pro Asn
1               5               10              15

Pro Ile Asn Tyr Ile Leu Gly Leu Asp Ile Gly Ile Ala Ser Val Gly
            20              25              30

Trp Ala Met Val Glu Ile Asp Glu Glu Glu Asn Pro Ile Arg Leu Ile
        35              40              45

Asp Leu Gly Val Arg Val Phe Glu Arg Ala Glu Val Pro Lys Thr Gly
    50              55              60

Asp Ser Leu Ala Met Ala Arg Arg Leu Ala Arg Ser Val Arg Arg Leu
65              70              75              80

Thr Arg Arg Arg Ala His Arg Leu Leu Arg Ala Arg Arg Leu Leu Lys
                85              90              95

Arg Glu Gly Val Leu Gln Ala Ala Asp Phe Asp Glu Asn Gly Leu Ile
            100             105             110

Lys Ser Leu Pro Asn Thr Pro Trp Gln Leu Arg Ala Ala Ala Leu Asp
        115             120             125
```

-continued

```
Arg Lys Leu Thr Pro Leu Glu Trp Ser Ala Val Leu Leu His Leu Ile
    130             135             140

Lys His Arg Gly Tyr Leu Ser Gln Arg Lys Asn Glu Gly Glu Thr Ala
145             150             155             160

Asp Lys Glu Leu Gly Ala Leu Leu Lys Gly Val Ala Asn Asn Ala His
            165             170             175

Ala Leu Gln Thr Gly Asp Phe Arg Thr Pro Ala Glu Leu Ala Leu Asn
            180             185             190

Lys Phe Glu Lys Glu Ser Gly His Ile Arg Asn Gln Arg Gly Asp Tyr
            195             200             205

Ser His Thr Phe Ser Arg Lys Asp Leu Gln Ala Glu Leu Ile Leu Leu
    210             215             220

Phe Glu Lys Gln Lys Glu Phe Gly Asn Pro His Val Ser Gly Gly Leu
225             230             235             240

Lys Glu Gly Ile Glu Thr Leu Leu Met Thr Gln Arg Pro Ala Leu Ser
            245             250             255

Gly Asp Ala Val Gln Lys Met Leu Gly His Cys Thr Phe Glu Pro Ala
            260             265             270

Glu Pro Lys Ala Ala Lys Asn Thr Tyr Thr Ala Glu Arg Phe Ile Trp
    275             280             285

Leu Thr Lys Leu Asn Asn Leu Arg Ile Leu Glu Gln Gly Ser Glu Arg
    290             295             300

Pro Leu Thr Asp Thr Glu Arg Ala Thr Leu Met Asp Glu Pro Tyr Arg
305             310             315             320

Lys Ser Lys Leu Thr Tyr Ala Gln Ala Arg Lys Leu Leu Gly Leu Glu
            325             330             335

Asp Thr Ala Phe Phe Lys Gly Leu Arg Tyr Gly Lys Asp Asn Ala Glu
            340             345             350

Ala Ser Thr Leu Met Glu Met Lys Ala Tyr His Ala Ile Ser Arg Ala
            355             360             365

Leu Glu Lys Glu Gly Leu Lys Asp Lys Lys Ser Pro Leu Asn Leu Ser
    370             375             380

Ser Glu Leu Gln Asp Glu Ile Gly Thr Ala Phe Ser Leu Phe Lys Thr
385             390             395             400

Asp Glu Asp Ile Thr Gly Arg Leu Lys Asp Arg Val Gln Pro Glu Ile
            405             410             415

Leu Glu Ala Leu Leu Lys His Ile Ser Phe Asp Lys Phe Val Gln Ile
            420             425             430

Ser Leu Lys Ala Leu Arg Arg Ile Val Pro Leu Met Glu Gln Gly Lys
            435             440             445

Arg Tyr Asp Glu Ala Cys Ala Glu Ile Tyr Gly Asp His Tyr Gly Lys
    450             455             460

Lys Asn Thr Glu Glu Lys Ile Tyr Leu Pro Pro Ile Pro Ala Asp Glu
465             470             475             480

Ile Arg Asn Pro Val Val Leu Arg Ala Leu Ser Gln Ala Arg Lys Val
            485             490             495

Ile Asn Gly Val Val Arg Arg Tyr Gly Ser Pro Ala Arg Ile His Ile
            500             505             510

Glu Thr Ala Arg Glu Val Gly Lys Ser Phe Lys Asp Arg Lys Glu Ile
            515             520             525

Glu Lys Arg Gln Glu Glu Asn Arg Lys Asp Arg Glu Lys Ala Ala Ala
    530             535             540

Lys Phe Arg Glu Tyr Phe Pro Asn Phe Val Gly Glu Pro Lys Ser Lys
```

-continued

```
545              550              555              560

Asp Ile Leu Lys Leu Arg Leu Tyr Glu Gln Gln His Gly Lys Cys Leu
             565              570              575

Tyr Ser Gly Lys Glu Ile Asn Leu Val Arg Leu Asn Glu Lys Gly Tyr
             580              585              590

Val Glu Ile Asp His Ala Leu Pro Phe Ser Arg Thr Trp Asp Asp Ser
             595              600              605

Phe Asn Asn Lys Val Leu Val Leu Gly Ser Glu Asn Gln Asn Lys Gly
    610              615              620

Asn Gln Thr Pro Tyr Glu Tyr Phe Asn Gly Lys Asp Asn Ser Arg Glu
625              630              635              640

Trp Gln Glu Phe Lys Ala Arg Val Glu Thr Ser Arg Phe Pro Arg Ser
             645              650              655

Lys Lys Gln Arg Ile Leu Leu Gln Lys Phe Asp Glu Asp Gly Phe Lys
             660              665              670

Glu Cys Asn Leu Asn Asp Thr Arg Tyr Val Asn Arg Phe Leu Cys Gln
             675              680              685

Phe Val Ala Asp His Ile Leu Leu Thr Gly Lys Gly Lys Arg Arg Val
    690              695              700

Phe Ala Ser Asn Gly Gln Ile Thr Asn Leu Leu Arg Gly Phe Trp Gly
705              710              715              720

Leu Arg Lys Val Arg Ala Glu Asn Asp Arg His His Ala Leu Asp Ala
             725              730              735

Val Val Val Ala Cys Ser Thr Val Ala Met Gln Gln Lys Ile Thr Arg
             740              745              750

Phe Val Arg Tyr Lys Glu Met Asn Ala Phe Asp Gly Lys Thr Ile Asp
             755              760              765

Lys Glu Thr Gly Lys Val Leu His Gln Lys Thr His Phe Pro Gln Pro
    770              775              780

Trp Glu Phe Phe Ala Gln Glu Val Met Ile Arg Val Phe Gly Lys Pro
785              790              795              800

Asp Gly Lys Pro Glu Phe Glu Glu Ala Asp Thr Pro Glu Lys Leu Arg
             805              810              815

Thr Leu Leu Ala Glu Lys Leu Ser Ser Arg Pro Glu Ala Val His Glu
             820              825              830

Tyr Val Thr Pro Leu Phe Val Ser Arg Ala Pro Asn Arg Lys Met Ser
             835              840              845

Gly Ala His Lys Asp Thr Leu Arg Ser Ala Lys Arg Phe Val Lys His
    850              855              860

Asn Glu Lys Ile Ser Val Lys Arg Val Trp Leu Thr Glu Ile Lys Leu
865              870              875              880

Ala Asp Leu Glu Asn Met Val Asn Tyr Lys Asn Gly Arg Glu Ile Glu
             885              890              895

Leu Tyr Glu Ala Leu Lys Ala Arg Leu Glu Ala Tyr Gly Gly Asn Ala
             900              905              910

Lys Gln Ala Phe Asp Pro Lys Asp Asn Pro Phe Tyr Lys Lys Gly Gly
             915              920              925

Gln Leu Val Lys Ala Val Arg Val Glu Lys Thr Gln Glu Ser Gly Val
    930              935              940

Leu Leu Asn Lys Lys Asn Ala Tyr Thr Ile Ala Asp Asn Gly Asp Met
945              950              955              960

Val Arg Val Asp Val Phe Cys Lys Val Asp Lys Lys Gly Lys Asn Gln
             965              970              975
```

-continued

```
Tyr Phe Ile Val Pro Ile Tyr Ala Trp Gln Val Ala Glu Asn Ile Leu
          980                 985                 990

Pro Asp Ile Asp Cys Lys Gly Tyr  Arg Ile Asp Asp Ser  Tyr Thr Phe
          995                1000                1005

Cys Phe  Ser Leu His Lys Tyr  Asp Leu Ile Ala Phe  Gln Lys Asp
    1010                1015                1020

Glu Lys  Ser Lys Val Glu Phe  Ala Tyr Tyr Ile Asn  Cys Asp Ser
    1025                1030                1035

Ser Asn  Gly Arg Phe Tyr Leu  Ala Trp His Asp Lys  Gly Ser Lys
    1040                1045                1050

Glu Gln  Gln Phe Arg Ile Ser  Thr Gln Asn Leu Val  Leu Ile Gln
    1055                1060                1065

Lys Tyr  Gln Val Asn Glu Leu  Gly Lys Glu Ile Arg  Pro Cys Arg
    1070                1075                1080

Leu Lys  Lys Arg Pro Pro Val  Arg Gly Gly Gly Gly  Ser Gly Gly
    1085                1090                1095

Gly Gly  Ser Gly Gly Gly Gly  Ser Pro Ala Ala Lys  Lys Lys Lys
    1100                1105                1110

Leu Asp  Gly Gly Gly Ser Lys  Arg Pro Ala Ala Thr  Lys Lys Ala
    1115                1120                1125

Gly Gln  Ala Lys Lys Lys Lys
    1130                1135

<210> SEQ ID NO 735
<211> LENGTH: 1135
<212> TYPE: PRT
<213> ORGANISM: Artificial Sequence
<220> FEATURE:
<223> OTHER INFORMATION: Synthetic

<400> SEQUENCE: 735

Pro Lys Lys Arg Lys Val Asn Ala Met Ala Ala Phe Lys Pro Asn
1               5                   10                  15

Pro Ile Asn Tyr Ile Leu Gly Leu Asp Ile Gly Ile Ala Ser Val Gly
            20                  25                  30

Trp Ala Met Val Glu Ile Asp Glu Glu Glu Asn Pro Ile Arg Leu Ile
            35                  40                  45

Asp Leu Gly Val Arg Val Phe Glu Arg Ala Glu Val Pro Lys Thr Gly
    50                  55                  60

Asp Ser Leu Ala Met Ala Arg Arg Leu Ala Arg Ser Val Arg Arg Leu
65                  70                  75                  80

Thr Arg Arg Arg Ala His Arg Leu Leu Arg Ala Arg Arg Leu Leu Lys
                85                  90                  95

Arg Glu Gly Val Leu Gln Ala Ala Asp Phe Asp Glu Asn Gly Leu Ile
            100                 105                 110

Lys Ser Leu Pro Asn Thr Pro Trp Gln Leu Arg Ala Ala Ala Leu Asp
    115                 120                 125

Arg Lys Leu Thr Pro Leu Glu Trp Ser Ala Val Leu Leu His Leu Ile
    130                 135                 140

Lys His Arg Gly Tyr Leu Ser Gln Arg Lys Asn Glu Gly Glu Thr Ala
145                 150                 155                 160

Asp Lys Glu Leu Gly Ala Leu Leu Lys Gly Val Ala Asn Asn Ala His
            165                 170                 175

Ala Leu Gln Thr Gly Asp Phe Arg Thr Pro Ala Glu Leu Ala Leu Asn
            180                 185                 190
```

-continued

```
Lys Phe Glu Lys Glu Ser Gly His Ile Arg Asn Gln Arg Gly Asp Tyr
        195             200             205

Ser His Thr Phe Ser Arg Lys Asp Leu Gln Ala Glu Leu Ile Leu Leu
        210             215             220

Phe Glu Lys Gln Lys Glu Phe Gly Asn Pro His Val Ser Gly Gly Leu
225             230             235             240

Lys Glu Gly Ile Glu Thr Leu Leu Met Thr Gln Arg Pro Ala Leu Ser
            245             250             255

Gly Asp Ala Val Gln Lys Met Leu Gly His Cys Thr Phe Glu Pro Ala
            260             265             270

Glu Pro Lys Ala Ala Lys Asn Thr Tyr Thr Ala Glu Arg Phe Ile Trp
        275             280             285

Leu Thr Lys Leu Asn Asn Leu Arg Ile Leu Glu Gln Gly Ser Glu Arg
        290             295             300

Pro Leu Thr Asp Thr Glu Arg Ala Thr Leu Met Asp Glu Pro Tyr Arg
305             310             315             320

Lys Ser Lys Leu Thr Tyr Ala Gln Ala Arg Lys Leu Leu Gly Leu Glu
            325             330             335

Asp Thr Ala Phe Phe Lys Gly Leu Arg Tyr Gly Lys Asp Asn Ala Glu
            340             345             350

Ala Ser Thr Leu Met Glu Met Lys Ala Tyr His Ala Ile Ser Arg Ala
            355             360             365

Leu Glu Lys Glu Gly Leu Lys Asp Lys Lys Ser Pro Leu Asn Leu Ser
        370             375             380

Ser Glu Leu Gln Asp Glu Ile Gly Thr Ala Phe Ser Leu Phe Lys Thr
385             390             395             400

Asp Glu Asp Ile Thr Gly Arg Leu Lys Asp Arg Val Gln Pro Glu Ile
            405             410             415

Leu Glu Ala Leu Leu Lys His Ile Ser Phe Asp Lys Phe Val Gln Ile
            420             425             430

Ser Leu Lys Ala Leu Arg Arg Ile Val Pro Leu Met Glu Gln Gly Lys
        435             440             445

Arg Tyr Asp Glu Ala Cys Ala Glu Ile Tyr Gly Asp His Tyr Gly Lys
        450             455             460

Lys Asn Thr Glu Glu Lys Ile Tyr Leu Pro Pro Ile Pro Ala Asp Glu
465             470             475             480

Ile Arg Asn Pro Val Val Leu Arg Ala Leu Ser Gln Ala Arg Lys Val
            485             490             495

Ile Asn Gly Val Val Arg Arg Tyr Gly Ser Pro Ala Arg Ile His Ile
            500             505             510

Glu Thr Ala Arg Glu Val Gly Lys Ser Phe Lys Asp Arg Lys Glu Ile
            515             520             525

Glu Lys Arg Gln Glu Glu Asn Arg Lys Asp Arg Glu Lys Ala Ala Ala
        530             535             540

Lys Phe Arg Glu Tyr Phe Pro Asn Phe Val Gly Glu Pro Lys Ser Lys
545             550             555             560

Asp Ile Leu Lys Leu Arg Leu Tyr Glu Gln Gln His Gly Lys Cys Leu
            565             570             575

Tyr Ser Gly Lys Glu Ile Asn Leu Val Arg Leu Asn Glu Lys Gly Tyr
            580             585             590

Val Glu Ile Asp His Ala Leu Pro Phe Ser Arg Thr Trp Asp Asp Ser
            595             600             605
```

-continued

```
Phe Asn Asn Lys Val Leu Val Leu Gly Ser Glu Asn Gln Asn Lys Gly
    610             615                 620

Asn Gln Thr Pro Tyr Glu Tyr Phe Asn Gly Lys Asp Asn Ser Arg Glu
625             630                 635                 640

Trp Gln Glu Phe Lys Ala Arg Val Glu Thr Ser Arg Phe Pro Arg Ser
                645                 650                 655

Lys Lys Gln Arg Ile Leu Leu Gln Lys Phe Asp Glu Asp Gly Phe Lys
                660                 665                 670

Glu Cys Asn Leu Asn Asp Thr Arg Tyr Val Asn Arg Phe Leu Cys Gln
            675                 680                 685

Phe Val Ala Asp His Ile Leu Leu Thr Gly Lys Gly Lys Arg Arg Val
    690                 695                 700

Phe Ala Ser Asn Gly Gln Ile Thr Asn Leu Leu Arg Gly Phe Trp Gly
705                 710                 715                 720

Leu Arg Lys Val Arg Ala Glu Asn Asp Arg His His Ala Leu Asp Ala
                725                 730                 735

Val Val Val Ala Cys Ser Thr Val Ala Met Gln Gln Lys Ile Thr Arg
                740                 745                 750

Phe Val Arg Tyr Lys Glu Met Asn Ala Phe Asp Gly Lys Thr Ile Asp
            755                 760                 765

Lys Glu Thr Gly Lys Val Leu His Gln Lys Thr His Phe Pro Gln Pro
    770                 775                 780

Trp Glu Phe Phe Ala Gln Glu Val Met Ile Arg Val Phe Gly Lys Pro
785                 790                 795                 800

Asp Gly Lys Pro Glu Phe Glu Glu Ala Asp Thr Pro Glu Lys Leu Arg
                805                 810                 815

Thr Leu Leu Ala Glu Lys Leu Ser Ser Arg Pro Glu Ala Val His Glu
                820                 825                 830

Tyr Val Thr Pro Leu Phe Val Ser Arg Ala Pro Asn Arg Lys Met Ser
            835                 840                 845

Gly Ala His Lys Asp Thr Leu Arg Ser Ala Lys Arg Phe Val Lys His
    850                 855                 860

Asn Glu Lys Ile Ser Val Lys Arg Val Trp Leu Thr Glu Ile Lys Leu
865                 870                 875                 880

Ala Asp Leu Glu Asn Met Val Asn Tyr Lys Asn Gly Arg Glu Ile Glu
                885                 890                 895

Leu Tyr Glu Ala Leu Lys Ala Arg Leu Glu Ala Tyr Gly Gly Asn Ala
                900                 905                 910

Lys Gln Ala Phe Asp Pro Lys Asp Asn Pro Phe Tyr Lys Lys Gly Gly
            915                 920                 925

Gln Leu Val Lys Ala Val Arg Val Glu Lys Thr Gln Glu Ser Gly Val
    930                 935                 940

Leu Leu Asn Lys Lys Asn Ala Tyr Thr Ile Ala Asp Asn Gly Asp Met
945                 950                 955                 960

Val Arg Val Asp Val Phe Cys Lys Val Asp Lys Lys Gly Lys Asn Gln
                965                 970                 975

Tyr Phe Ile Val Pro Ile Tyr Ala Trp Gln Val Ala Glu Asn Ile Leu
            980                 985                 990

Pro Asp Ile Asp Cys Lys Gly Tyr  Arg Ile Asp Asp Ser  Tyr Thr Phe
            995                 1000                1005

Cys Phe  Ser Leu His Lys Tyr  Asp Leu Ile Ala Phe  Gln Lys Asp
    1010                1015                1020

Glu Lys  Ser Lys Val Glu Phe  Ala Tyr Tyr Ile Asn  Cys Asp Ser
```

-continued

```
    1025                1030                1035

Ser Asn  Gly Arg Phe Tyr Leu  Ala Trp His Asp Lys  Gly Ser Lys
    1040                1045                1050

Glu Gln  Gln Phe Arg Ile Ser  Thr Gln Asn Leu Val  Leu Ile Gln
    1055                1060                1065

Lys Tyr  Gln Val Asn Glu Leu  Gly Lys Glu Ile Arg  Pro Cys Arg
    1070                1075                1080

Leu Lys  Lys Arg Pro Pro Val  Arg Gly Gly Gly Gly  Ser Gly Gly
    1085                1090                1095

Gly Gly  Ser Gly Gly Gly Gly  Ser Pro Ala Ala Lys  Lys Lys Lys
    1100                1105                1110

Leu Asp  Gly Gly Gly Ser Lys  Arg Pro Ala Ala Thr  Lys Lys Ala
    1115                1120                1125

Gly Gln  Ala Lys Lys Lys Lys
    1130                1135
```

```
<210> SEQ ID NO 736
<211> LENGTH: 23
<212> TYPE: DNA
<213> ORGANISM: Artificial Sequence
<220> FEATURE:
<223> OTHER INFORMATION: Synthetic

<400> SEQUENCE: 736
gtcacctgcc tcgtggaata cgg                                        23

<210> SEQ ID NO 737
<211> LENGTH: 23
<212> TYPE: DNA
<213> ORGANISM: Artificial Sequence
<220> FEATURE:
<223> OTHER INFORMATION: Synthetic

<400> SEQUENCE: 737
gcacctgcct cgtggaatac ggt                                        23

<210> SEQ ID NO 738
<211> LENGTH: 22
<212> TYPE: DNA
<213> ORGANISM: Artificial Sequence
<220> FEATURE:
<223> OTHER INFORMATION: Synthetic

<400> SEQUENCE: 738
gttcagcgtg tccggctttg gc                                         22

<210> SEQ ID NO 739
<211> LENGTH: 24
<212> TYPE: DNA
<213> ORGANISM: Artificial Sequence
<220> FEATURE:
<223> OTHER INFORMATION: Synthetic

<400> SEQUENCE: 739
gtggtgagca agggcgagga gctg                                       24

<210> SEQ ID NO 740
<211> LENGTH: 24
<212> TYPE: DNA
<213> ORGANISM: Artificial Sequence
<220> FEATURE:
<223> OTHER INFORMATION: Synthetic
```

-continued

```
<400> SEQUENCE: 740
gggcgaggag ctgttcaccg gggt                                             24

<210> SEQ ID NO 741
<211> LENGTH: 24
<212> TYPE: DNA
<213> ORGANISM: Artificial Sequence
<220> FEATURE:
<223> OTHER INFORMATION: Synthetic

<400> SEQUENCE: 741
gggcgaggag ctgttcaccg gggt                                             24

<210> SEQ ID NO 742
<211> LENGTH: 24
<212> TYPE: DNA
<213> ORGANISM: Artificial Sequence
<220> FEATURE:
<223> OTHER INFORMATION: Synthetic

<400> SEQUENCE: 742
gcgtccagct cgaccaggat gggc                                             24

<210> SEQ ID NO 743
<211> LENGTH: 24
<212> TYPE: DNA
<213> ORGANISM: Artificial Sequence
<220> FEATURE:
<223> OTHER INFORMATION: Synthetic

<400> SEQUENCE: 743
gcggtgaaca gctcctcgcc cttg                                             24

<210> SEQ ID NO 744
<211> LENGTH: 24
<212> TYPE: DNA
<213> ORGANISM: Artificial Sequence
<220> FEATURE:
<223> OTHER INFORMATION: Synthetic

<400> SEQUENCE: 744
gggcaccacc ccggtgaaca gctc                                             24

<210> SEQ ID NO 745
<211> LENGTH: 24
<212> TYPE: DNA
<213> ORGANISM: Artificial Sequence
<220> FEATURE:
<223> OTHER INFORMATION: Synthetic

<400> SEQUENCE: 745
ggcaccaccc cggtgaacag ctcc                                             24

<210> SEQ ID NO 746
<211> LENGTH: 24
<212> TYPE: DNA
<213> ORGANISM: Artificial Sequence
<220> FEATURE:
<223> OTHER INFORMATION: Synthetic

<400> SEQUENCE: 746
gggatgggca ccaccccggt gaac                                             24

<210> SEQ ID NO 747
<211> LENGTH: 24
```

<212> TYPE: DNA
<213> ORGANISM: Artificial Sequence
<220> FEATURE:
<223> OTHER INFORMATION: Synthetic

<400> SEQUENCE: 747
gcgtgtccgg ctttggcgag acaa                                              24

<210> SEQ ID NO 748
<211> LENGTH: 24
<212> TYPE: DNA
<213> ORGANISM: Artificial Sequence
<220> FEATURE:
<223> OTHER INFORMATION: Synthetic

<400> SEQUENCE: 748
gtccggcttt ggcgagacaa atca                                              24

<210> SEQ ID NO 749
<211> LENGTH: 24
<212> TYPE: DNA
<213> ORGANISM: Artificial Sequence
<220> FEATURE:
<223> OTHER INFORMATION: Synthetic

<400> SEQUENCE: 749
gatcacctgc ctcgtggaat acgg                                              24

<210> SEQ ID NO 750
<211> LENGTH: 24
<212> TYPE: DNA
<213> ORGANISM: Artificial Sequence
<220> FEATURE:
<223> OTHER INFORMATION: Synthetic

<400> SEQUENCE: 750
gatcacctgc ctcgtggaat acgg                                              24

<210> SEQ ID NO 751
<211> LENGTH: 24
<212> TYPE: DNA
<213> ORGANISM: Artificial Sequence
<220> FEATURE:
<223> OTHER INFORMATION: Synthetic

<400> SEQUENCE: 751
gccaaagccg gacacgctga actt                                              24

<210> SEQ ID NO 752
<211> LENGTH: 23
<212> TYPE: DNA
<213> ORGANISM: Artificial Sequence
<220> FEATURE:
<223> OTHER INFORMATION: Synthetic

<400> SEQUENCE: 752
ggaacttgtg gccgtttacg tcg                                               23

<210> SEQ ID NO 753
<211> LENGTH: 22
<212> TYPE: DNA
<213> ORGANISM: Artificial Sequence
<220> FEATURE:
<223> OTHER INFORMATION: Synthetic

<400> SEQUENCE: 753

-continued gaacttgtgg ccgtttacgt cg                                          22

<210> SEQ ID NO 754
<211> LENGTH: 21
<212> TYPE: DNA
<213> ORGANISM: Artificial Sequence
<220> FEATURE:
<223> OTHER INFORMATION: Synthetic

<400> SEQUENCE: 754
gacttgtggc cgtttacgtc g                                           21

<210> SEQ ID NO 755
<211> LENGTH: 20
<212> TYPE: DNA
<213> ORGANISM: Artificial Sequence
<220> FEATURE:
<223> OTHER INFORMATION: Synthetic

<400> SEQUENCE: 755
gcttgtggcc gtttacgtcg                                             20

<210> SEQ ID NO 756
<211> LENGTH: 19
<212> TYPE: DNA
<213> ORGANISM: Artificial Sequence
<220> FEATURE:
<223> OTHER INFORMATION: Synthetic

<400> SEQUENCE: 756
gttgtggccg tttacgtcg                                              19

<210> SEQ ID NO 757
<211> LENGTH: 23
<212> TYPE: DNA
<213> ORGANISM: Artificial Sequence
<220> FEATURE:
<223> OTHER INFORMATION: Synthetic

<400> SEQUENCE: 757
gtcacctgcc tcgtggaata cgg                                         23

<210> SEQ ID NO 758
<211> LENGTH: 22
<212> TYPE: DNA
<213> ORGANISM: Artificial Sequence
<220> FEATURE:
<223> OTHER INFORMATION: Synthetic

<400> SEQUENCE: 758
gcacctgcct cgtggaatac gg                                          22

<210> SEQ ID NO 759
<211> LENGTH: 21
<212> TYPE: DNA
<213> ORGANISM: Artificial Sequence
<220> FEATURE:
<223> OTHER INFORMATION: Synthetic

<400> SEQUENCE: 759
gacctgcctc gtggaatacg g                                           21

<210> SEQ ID NO 760
<211> LENGTH: 20
<212> TYPE: DNA
<213> ORGANISM: Artificial Sequence -continued

```
<220> FEATURE:
<223> OTHER INFORMATION: Synthetic

<400> SEQUENCE: 760
gcctgcctcg tggaatacgg                                            20

<210> SEQ ID NO 761
<211> LENGTH: 24
<212> TYPE: DNA
<213> ORGANISM: Artificial Sequence
<220> FEATURE:
<223> OTHER INFORMATION: Synthetic

<400> SEQUENCE: 761
ggttctgggt acttttatct gtcc                                       24

<210> SEQ ID NO 762
<211> LENGTH: 24
<212> TYPE: DNA
<213> ORGANISM: Artificial Sequence
<220> FEATURE:
<223> OTHER INFORMATION: Synthetic

<400> SEQUENCE: 762
gtctgcctaa caggaggtgg gggt                                       24

<210> SEQ ID NO 763
<211> LENGTH: 24
<212> TYPE: DNA
<213> ORGANISM: Artificial Sequence
<220> FEATURE:
<223> OTHER INFORMATION: Synthetic

<400> SEQUENCE: 763
gaatatcagg agactaggaa ggag                                       24

<210> SEQ ID NO 764
<211> LENGTH: 22
<212> TYPE: DNA
<213> ORGANISM: Artificial Sequence
<220> FEATURE:
<223> OTHER INFORMATION: Synthetic

<400> SEQUENCE: 764
gcctccctgc agggctgctc cc                                         22

<210> SEQ ID NO 765
<211> LENGTH: 24
<212> TYPE: DNA
<213> ORGANISM: Artificial Sequence
<220> FEATURE:
<223> OTHER INFORMATION: Synthetic

<400> SEQUENCE: 765
gagctagtct tcttcctcca accc                                       24

<210> SEQ ID NO 766
<211> LENGTH: 24
<212> TYPE: DNA
<213> ORGANISM: Artificial Sequence
<220> FEATURE:
<223> OTHER INFORMATION: Synthetic

<400> SEQUENCE: 766
gatctgtccc ctccacccca cagt                                       24
```

-continued

```
<210> SEQ ID NO 767
<211> LENGTH: 24
<212> TYPE: DNA
<213> ORGANISM: Artificial Sequence
<220> FEATURE:
<223> OTHER INFORMATION: Synthetic

<400> SEQUENCE: 767
gatctgtccc ctccacccca cagt                                                     24

<210> SEQ ID NO 768
<211> LENGTH: 24
<212> TYPE: DNA
<213> ORGANISM: Artificial Sequence
<220> FEATURE:
<223> OTHER INFORMATION: Synthetic

<400> SEQUENCE: 768
gcatcctctt gctttctttg cctg                                                     24

<210> SEQ ID NO 769
<211> LENGTH: 24
<212> TYPE: DNA
<213> ORGANISM: Artificial Sequence
<220> FEATURE:
<223> OTHER INFORMATION: Synthetic

<400> SEQUENCE: 769
ggagtcgcca gaggccggtg gtgg                                                     24

<210> SEQ ID NO 770
<211> LENGTH: 24
<212> TYPE: DNA
<213> ORGANISM: Artificial Sequence
<220> FEATURE:
<223> OTHER INFORMATION: Synthetic

<400> SEQUENCE: 770
gcccagcggc cggatatcag ctgc                                                     24

<210> SEQ ID NO 771
<211> LENGTH: 23
<212> TYPE: DNA
<213> ORGANISM: Artificial Sequence
<220> FEATURE:
<223> OTHER INFORMATION: Synthetic

<400> SEQUENCE: 771
ggaagggaac atattactat tgc                                                      23

<210> SEQ ID NO 772
<211> LENGTH: 24
<212> TYPE: DNA
<213> ORGANISM: Artificial Sequence
<220> FEATURE:
<223> OTHER INFORMATION: Synthetic

<400> SEQUENCE: 772
gtggagtggc ctgctatcag ctac                                                     24

<210> SEQ ID NO 773
<211> LENGTH: 24
<212> TYPE: DNA
<213> ORGANISM: Artificial Sequence
<220> FEATURE:
<223> OTHER INFORMATION: Synthetic
```

<400> SEQUENCE: 773
gaggaaggga acatattact attg                                                      24

<210> SEQ ID NO 774
<211> LENGTH: 24
<212> TYPE: DNA
<213> ORGANISM: Artificial Sequence
<220> FEATURE:
<223> OTHER INFORMATION: Synthetic

<400> SEQUENCE: 774
gtgaattctc atcagctaaa atgc                                                      24

<210> SEQ ID NO 775
<211> LENGTH: 24
<212> TYPE: DNA
<213> ORGANISM: Artificial Sequence
<220> FEATURE:
<223> OTHER INFORMATION: Synthetic

<400> SEQUENCE: 775
gctcactcac ccacacagac acac                                                      24

<210> SEQ ID NO 776
<211> LENGTH: 24
<212> TYPE: DNA
<213> ORGANISM: Artificial Sequence
<220> FEATURE:
<223> OTHER INFORMATION: Synthetic

<400> SEQUENCE: 776
ggaagaattt cattctgttc tcag                                                      24

<210> SEQ ID NO 777
<211> LENGTH: 24
<212> TYPE: DNA
<213> ORGANISM: Artificial Sequence
<220> FEATURE:
<223> OTHER INFORMATION: Synthetic

<400> SEQUENCE: 777
gctcagtttt cctggattat gcct                                                      24

<210> SEQ ID NO 778
<211> LENGTH: 24
<212> TYPE: DNA
<213> ORGANISM: Artificial Sequence
<220> FEATURE:
<223> OTHER INFORMATION: Synthetic

<400> SEQUENCE: 778
gcgttggagc ggggagaagg ccag                                                      24

<210> SEQ ID NO 779
<211> LENGTH: 24
<212> TYPE: DNA
<213> ORGANISM: Artificial Sequence
<220> FEATURE:
<223> OTHER INFORMATION: Synthetic

<400> SEQUENCE: 779
gggccgcgga gatagctgca gggc                                                      24

<210> SEQ ID NO 780

-continued

```
<211> LENGTH: 24
<212> TYPE: DNA
<213> ORGANISM: Artificial Sequence
<220> FEATURE:
<223> OTHER INFORMATION: Synthetic

<400> SEQUENCE: 780
gcccacccgg cggcgcctcc ctgc                                          24

<210> SEQ ID NO 781
<211> LENGTH: 24
<212> TYPE: DNA
<213> ORGANISM: Artificial Sequence
<220> FEATURE:
<223> OTHER INFORMATION: Synthetic

<400> SEQUENCE: 781
gcgtggcagc tgatatccgg ccgc                                          24

<210> SEQ ID NO 782
<211> LENGTH: 24
<212> TYPE: DNA
<213> ORGANISM: Artificial Sequence
<220> FEATURE:
<223> OTHER INFORMATION: Synthetic

<400> SEQUENCE: 782
gccgcggcgc gacgtggagc cagc                                          24

<210> SEQ ID NO 783
<211> LENGTH: 24
<212> TYPE: DNA
<213> ORGANISM: Artificial Sequence
<220> FEATURE:
<223> OTHER INFORMATION: Synthetic

<400> SEQUENCE: 783
gtgctcccca gcccaaaccg ccgc                                          24

<210> SEQ ID NO 784
<211> LENGTH: 24
<212> TYPE: DNA
<213> ORGANISM: Artificial Sequence
<220> FEATURE:
<223> OTHER INFORMATION: Synthetic

<400> SEQUENCE: 784
gtcagattgg cttgctcgga attg                                          24

<210> SEQ ID NO 785
<211> LENGTH: 24
<212> TYPE: DNA
<213> ORGANISM: Artificial Sequence
<220> FEATURE:
<223> OTHER INFORMATION: Synthetic

<400> SEQUENCE: 785
gctgggtgaa tggagcgagc agcg                                          24

<210> SEQ ID NO 786
<211> LENGTH: 24
<212> TYPE: DNA
<213> ORGANISM: Artificial Sequence
<220> FEATURE:
<223> OTHER INFORMATION: Synthetic

<400> SEQUENCE: 786
```
gtcctggagt gacccctggc cttc                                                     24

<210> SEQ ID NO 787
<211> LENGTH: 24
<212> TYPE: DNA
<213> ORGANISM: Artificial Sequence
<220> FEATURE:
<223> OTHER INFORMATION: Synthetic

<400> SEQUENCE: 787
gatcctggag tgacccctgg cctt                                                     24

<210> SEQ ID NO 788
<211> LENGTH: 24
<212> TYPE: DNA
<213> ORGANISM: Artificial Sequence
<220> FEATURE:
<223> OTHER INFORMATION: Synthetic

<400> SEQUENCE: 788
gtgtgtccct ctccccaccc gtcc                                                     24

<210> SEQ ID NO 789
<211> LENGTH: 24
<212> TYPE: DNA
<213> ORGANISM: Artificial Sequence
<220> FEATURE:
<223> OTHER INFORMATION: Synthetic

<400> SEQUENCE: 789
gttggagcgg ggagaaggcc aggg                                                     24

<210> SEQ ID NO 790
<211> LENGTH: 24
<212> TYPE: DNA
<213> ORGANISM: Artificial Sequence
<220> FEATURE:
<223> OTHER INFORMATION: Synthetic

<400> SEQUENCE: 790
gcgttggagc ggggagaagg ccag                                                     24

<210> SEQ ID NO 791
<211> LENGTH: 24
<212> TYPE: DNA
<213> ORGANISM: Artificial Sequence
<220> FEATURE:
<223> OTHER INFORMATION: Synthetic

<400> SEQUENCE: 791
gtaccctcca ataatttggc tggc                                                     24

<210> SEQ ID NO 792
<211> LENGTH: 24
<212> TYPE: DNA
<213> ORGANISM: Artificial Sequence
<220> FEATURE:
<223> OTHER INFORMATION: Synthetic

<400> SEQUENCE: 792
gataatttgg ctggcaattc cgag                                                     24

<210> SEQ ID NO 793
<211> LENGTH: 24
<212> TYPE: DNA

-continued

```
<213> ORGANISM: Artificial Sequence
<220> FEATURE:
<223> OTHER INFORMATION: Synthetic

<400> SEQUENCE: 793
gaaaattgtg atttccagat ccac                                           24

<210> SEQ ID NO 794
<211> LENGTH: 23
<212> TYPE: DNA
<213> ORGANISM: Artificial Sequence
<220> FEATURE:
<223> OTHER INFORMATION: Synthetic

<400> SEQUENCE: 794
gagcagaaaa aattgtgatt tcc                                            23

<210> SEQ ID NO 795
<211> LENGTH: 24
<212> TYPE: DNA
<213> ORGANISM: Artificial Sequence
<220> FEATURE:
<223> OTHER INFORMATION: Synthetic

<400> SEQUENCE: 795
gcagggccca ggtgtccttc tctg                                           24

<210> SEQ ID NO 796
<211> LENGTH: 24
<212> TYPE: DNA
<213> ORGANISM: Artificial Sequence
<220> FEATURE:
<223> OTHER INFORMATION: Synthetic

<400> SEQUENCE: 796
gaatggcagg cggaggttgt actg                                           24

<210> SEQ ID NO 797
<211> LENGTH: 24
<212> TYPE: DNA
<213> ORGANISM: Artificial Sequence
<220> FEATURE:
<223> OTHER INFORMATION: Synthetic

<400> SEQUENCE: 797
gagtgagaga gtgagagaga gaca                                           24

<210> SEQ ID NO 798
<211> LENGTH: 24
<212> TYPE: DNA
<213> ORGANISM: Artificial Sequence
<220> FEATURE:
<223> OTHER INFORMATION: Synthetic

<400> SEQUENCE: 798
gtgagcaggc acctgtgcca acat                                           24

<210> SEQ ID NO 799
<211> LENGTH: 24
<212> TYPE: DNA
<213> ORGANISM: Artificial Sequence
<220> FEATURE:
<223> OTHER INFORMATION: Synthetic

<400> SEQUENCE: 799
gcgtgggggc tccgtgcccc acgc                                           24
```

-continued

```
<210> SEQ ID NO 800
<211> LENGTH: 24
<212> TYPE: DNA
<213> ORGANISM: Artificial Sequence
<220> FEATURE:
<223> OTHER INFORMATION: Synthetic

<400> SEQUENCE: 800
gcatgggcag gggctggggt gcac                                             24

<210> SEQ ID NO 801
<211> LENGTH: 20
<212> TYPE: DNA
<213> ORGANISM: Artificial Sequence
<220> FEATURE:
<223> OTHER INFORMATION: Synthetic

<400> SEQUENCE: 801
gggccaggtg tccttctctg                                                  20

<210> SEQ ID NO 802
<211> LENGTH: 20
<212> TYPE: DNA
<213> ORGANISM: Artificial Sequence
<220> FEATURE:
<223> OTHER INFORMATION: Synthetic

<400> SEQUENCE: 802
ggcaggcgga ggttgtactg                                                  20

<210> SEQ ID NO 803
<211> LENGTH: 20
<212> TYPE: DNA
<213> ORGANISM: Artificial Sequence
<220> FEATURE:
<223> OTHER INFORMATION: Synthetic

<400> SEQUENCE: 803
gagagagtga gagagagaca                                                  20

<210> SEQ ID NO 804
<211> LENGTH: 20
<212> TYPE: DNA
<213> ORGANISM: Artificial Sequence
<220> FEATURE:
<223> OTHER INFORMATION: Synthetic

<400> SEQUENCE: 804
gcaggcacct gtgccaacat                                                  20

<210> SEQ ID NO 805
<211> LENGTH: 20
<212> TYPE: DNA
<213> ORGANISM: Artificial Sequence
<220> FEATURE:
<223> OTHER INFORMATION: Synthetic

<400> SEQUENCE: 805
gggggctccg tgccccacgc                                                  20

<210> SEQ ID NO 806
<211> LENGTH: 20
<212> TYPE: DNA
<213> ORGANISM: Artificial Sequence
<220> FEATURE:
```

-continued

<223> OTHER INFORMATION: Synthetic

<400> SEQUENCE: 806
gggcaggggc tggggtgcac                                                    20

<210> SEQ ID NO 807
<211> LENGTH: 19
<212> TYPE: DNA
<213> ORGANISM: Artificial Sequence
<220> FEATURE:
<223> OTHER INFORMATION: Synthetic

<400> SEQUENCE: 807
tggcttagca cctctccat                                                     19

<210> SEQ ID NO 808
<211> LENGTH: 25
<212> TYPE: DNA
<213> ORGANISM: Artificial Sequence
<220> FEATURE:
<223> OTHER INFORMATION: Synthetic

<400> SEQUENCE: 808
agaggagcct tctgactgct gcaga                                              25

<210> SEQ ID NO 809
<211> LENGTH: 18
<212> TYPE: DNA
<213> ORGANISM: Artificial Sequence
<220> FEATURE:
<223> OTHER INFORMATION: Synthetic

<400> SEQUENCE: 809
tccgtcttcc tccactcc                                                      18

<210> SEQ ID NO 810
<211> LENGTH: 19
<212> TYPE: DNA
<213> ORGANISM: Artificial Sequence
<220> FEATURE:
<223> OTHER INFORMATION: Synthetic

<400> SEQUENCE: 810
tagagaactg ggtagtgtg                                                     19

<210> SEQ ID NO 811
<211> LENGTH: 24
<212> TYPE: DNA
<213> ORGANISM: Artificial Sequence
<220> FEATURE:
<223> OTHER INFORMATION: Synthetic

<400> SEQUENCE: 811
gtacatgaag caactccagt ccca                                               24

<210> SEQ ID NO 812
<211> LENGTH: 24
<212> TYPE: DNA
<213> ORGANISM: Artificial Sequence
<220> FEATURE:
<223> OTHER INFORMATION: Synthetic

<400> SEQUENCE: 812
tggtgattat gggagaactg gagc                                               24

-continued

```
<210> SEQ ID NO 813
<211> LENGTH: 21
<212> TYPE: DNA
<213> ORGANISM: Artificial Sequence
<220> FEATURE:
<223> OTHER INFORMATION: Synthetic

<400> SEQUENCE: 813
ggcataagga aatcgaaggt c                                          21

<210> SEQ ID NO 814
<211> LENGTH: 23
<212> TYPE: DNA
<213> ORGANISM: Artificial Sequence
<220> FEATURE:
<223> OTHER INFORMATION: Synthetic

<400> SEQUENCE: 814
acacgggcag catgggaata gtc                                        23

<210> SEQ ID NO 815
<211> LENGTH: 23
<212> TYPE: DNA
<213> ORGANISM: Artificial Sequence
<220> FEATURE:
<223> OTHER INFORMATION: Synthetic

<400> SEQUENCE: 815
cctgtgtggc tttgctttgg tcg                                        23

<210> SEQ ID NO 816
<211> LENGTH: 23
<212> TYPE: DNA
<213> ORGANISM: Artificial Sequence
<220> FEATURE:
<223> OTHER INFORMATION: Synthetic

<400> SEQUENCE: 816
ggaggaagag tagctcgccg agg                                        23

<210> SEQ ID NO 817
<211> LENGTH: 24
<212> TYPE: DNA
<213> ORGANISM: Artificial Sequence
<220> FEATURE:
<223> OTHER INFORMATION: Synthetic

<400> SEQUENCE: 817
agggagaggg aagtgtgggg aagg                                       24

<210> SEQ ID NO 818
<211> LENGTH: 24
<212> TYPE: DNA
<213> ORGANISM: Artificial Sequence
<220> FEATURE:
<223> OTHER INFORMATION: Synthetic

<400> SEQUENCE: 818
agaactcagg accaacttat tctg                                       24

<210> SEQ ID NO 819
<211> LENGTH: 23
<212> TYPE: DNA
<213> ORGANISM: Artificial Sequence
<220> FEATURE:
<223> OTHER INFORMATION: Synthetic
```

-continued

```
<400> SEQUENCE: 819
atgacagaca caaccagagg gca                                          23

<210> SEQ ID NO 820
<211> LENGTH: 20
<212> TYPE: DNA
<213> ORGANISM: Artificial Sequence
<220> FEATURE:
<223> OTHER INFORMATION: Synthetic

<400> SEQUENCE: 820
taggaaggag gaggcctaag                                              20

<210> SEQ ID NO 821
<211> LENGTH: 19
<212> TYPE: DNA
<213> ORGANISM: Artificial Sequence
<220> FEATURE:
<223> OTHER INFORMATION: Synthetic

<400> SEQUENCE: 821
ccaatattgc atgggatgg                                               19

<210> SEQ ID NO 822
<211> LENGTH: 22
<212> TYPE: DNA
<213> ORGANISM: Artificial Sequence
<220> FEATURE:
<223> OTHER INFORMATION: Synthetic

<400> SEQUENCE: 822
atcaaattcc agcaccgagc gc                                           22

<210> SEQ ID NO 823
<211> LENGTH: 23
<212> TYPE: DNA
<213> ORGANISM: Artificial Sequence
<220> FEATURE:
<223> OTHER INFORMATION: Synthetic

<400> SEQUENCE: 823
accattgagg acgtttgtct cac                                          23

<210> SEQ ID NO 824
<211> LENGTH: 23
<212> TYPE: DNA
<213> ORGANISM: Artificial Sequence
<220> FEATURE:
<223> OTHER INFORMATION: Synthetic

<400> SEQUENCE: 824
catgtcctca agtcaagaac aag                                          23

<210> SEQ ID NO 825
<211> LENGTH: 24
<212> TYPE: DNA
<213> ORGANISM: Artificial Sequence
<220> FEATURE:
<223> OTHER INFORMATION: Synthetic

<400> SEQUENCE: 825
gctaggggag agtcccactg tcca                                         24

<210> SEQ ID NO 826
<211> LENGTH: 24
```

<212> TYPE: DNA
<213> ORGANISM: Artificial Sequence
<220> FEATURE:
<223> OTHER INFORMATION: Synthetic

<400> SEQUENCE: 826
gtagggtgtg atgggaggct aagc                                            24

<210> SEQ ID NO 827
<211> LENGTH: 24
<212> TYPE: DNA
<213> ORGANISM: Artificial Sequence
<220> FEATURE:
<223> OTHER INFORMATION: Synthetic

<400> SEQUENCE: 827
agaccgagtg gcagtgacag caag                                            24

<210> SEQ ID NO 828
<211> LENGTH: 24
<212> TYPE: DNA
<213> ORGANISM: Artificial Sequence
<220> FEATURE:
<223> OTHER INFORMATION: Synthetic

<400> SEQUENCE: 828
gtcttcctgc tctgtgcgca cgac                                            24

<210> SEQ ID NO 829
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(44)
<223> OTHER INFORMATION: n is a, c, g, or t

<400> SEQUENCE: 829
tagcggccgc tcatgcgcgg cgcattacct ttacnnnnnn nnnnggatcc tctagagtcg      60

<210> SEQ ID NO 830
<211> LENGTH: 58
<212> TYPE: DNA
<213> ORGANISM: Artificial Sequence
<220> FEATURE:
<223> OTHER INFORMATION: Synthetic

<400> SEQUENCE: 830
acaggaaaca gctatgacca tgaaagcttg catgcctgca ggtcgactct agaggatc        58

<210> SEQ ID NO 831
<211> LENGTH: 41
<212> TYPE: DNA
<213> ORGANISM: Artificial Sequence
<220> FEATURE:
<223> OTHER INFORMATION: Synthetic

<400> SEQUENCE: 831
ctacacgacg ctcttccgat ctcctggagc gtgtacgttg g                         41

<210> SEQ ID NO 832
<211> LENGTH: 42
<212> TYPE: DNA
<213> ORGANISM: Artificial Sequence
<220> FEATURE:

```
<223> OTHER INFORMATION: Synthetic

<400> SEQUENCE: 832
ctacacgacg ctcttccgat ctcctgtggt cccagctact tg                        42

<210> SEQ ID NO 833
<211> LENGTH: 41
<212> TYPE: DNA
<213> ORGANISM: Artificial Sequence
<220> FEATURE:
<223> OTHER INFORMATION: Synthetic

<400> SEQUENCE: 833
ctacacgacg ctcttccgat ctatctgcga tgtcctcgag g                         41

<210> SEQ ID NO 834
<211> LENGTH: 40
<212> TYPE: DNA
<213> ORGANISM: Artificial Sequence
<220> FEATURE:
<223> OTHER INFORMATION: Synthetic

<400> SEQUENCE: 834
ctacacgacg ctcttccgat cttggtgtgc gcctctaacg                           40

<210> SEQ ID NO 835
<211> LENGTH: 45
<212> TYPE: DNA
<213> ORGANISM: Artificial Sequence
<220> FEATURE:
<223> OTHER INFORMATION: Synthetic

<400> SEQUENCE: 835
ctacacgacg ctcttccgat ctggagtctt gctttgtcac tcaga                     45

<210> SEQ ID NO 836
<211> LENGTH: 41
<212> TYPE: DNA
<213> ORGANISM: Artificial Sequence
<220> FEATURE:
<223> OTHER INFORMATION: Synthetic

<400> SEQUENCE: 836
ctacacgacg ctcttccgat ctagcctaga cccagtccca t                         41

<210> SEQ ID NO 837
<211> LENGTH: 42
<212> TYPE: DNA
<213> ORGANISM: Artificial Sequence
<220> FEATURE:
<223> OTHER INFORMATION: Synthetic

<400> SEQUENCE: 837
ctacacgacg ctcttccgat ctgctgggca tagtagtgga ct                        42

<210> SEQ ID NO 838
<211> LENGTH: 41
<212> TYPE: DNA
<213> ORGANISM: Artificial Sequence
<220> FEATURE:
<223> OTHER INFORMATION: Synthetic

<400> SEQUENCE: 838
ctacacgacg ctcttccgat cttggggagg ctgagacacg a                         41
```

-continued

```
<210> SEQ ID NO 839
<211> LENGTH: 41
<212> TYPE: DNA
<213> ORGANISM: Artificial Sequence
<220> FEATURE:
<223> OTHER INFORMATION: Synthetic

<400> SEQUENCE: 839
ctacacgacg ctcttccgat ctcttgggag gctgaggcaa g                          41

<210> SEQ ID NO 840
<211> LENGTH: 40
<212> TYPE: DNA
<213> ORGANISM: Artificial Sequence
<220> FEATURE:
<223> OTHER INFORMATION: Synthetic

<400> SEQUENCE: 840
agacgtgtgc tcttccgatc tcaggaggat gagagccagg                            40

<210> SEQ ID NO 841
<211> LENGTH: 43
<212> TYPE: DNA
<213> ORGANISM: Artificial Sequence
<220> FEATURE:
<223> OTHER INFORMATION: Synthetic

<400> SEQUENCE: 841
agacgtgtgc tcttccgatc tcagggtctc actctatcac cca                        43

<210> SEQ ID NO 842
<211> LENGTH: 42
<212> TYPE: DNA
<213> ORGANISM: Artificial Sequence
<220> FEATURE:
<223> OTHER INFORMATION: Synthetic

<400> SEQUENCE: 842
agacgtgtgc tcttccgatc tactgaatgg gttgaacttg gc                         42

<210> SEQ ID NO 843
<211> LENGTH: 45
<212> TYPE: DNA
<213> ORGANISM: Artificial Sequence
<220> FEATURE:
<223> OTHER INFORMATION: Synthetic

<400> SEQUENCE: 843
agacgtgtgc tcttccgatc tgagacagaa tcttgctctg tctcc                      45

<210> SEQ ID NO 844
<211> LENGTH: 40
<212> TYPE: DNA
<213> ORGANISM: Artificial Sequence
<220> FEATURE:
<223> OTHER INFORMATION: Synthetic

<400> SEQUENCE: 844
agacgtgtgc tcttccgatc ttcccagcta cttgggaggc                            40

<210> SEQ ID NO 845
<211> LENGTH: 42
<212> TYPE: DNA
<213> ORGANISM: Artificial Sequence
<220> FEATURE:
<223> OTHER INFORMATION: Synthetic
```

-continued

```
<400> SEQUENCE: 845
agacgtgtgc tcttccgatc tcctgcccaa atagggaagc ag                          42

<210> SEQ ID NO 846
<211> LENGTH: 42
<212> TYPE: DNA
<213> ORGANISM: Artificial Sequence
<220> FEATURE:
<223> OTHER INFORMATION: Synthetic

<400> SEQUENCE: 846
agacgtgtgc tcttccgatc ttggcgcctt agtctctgct ac                          42

<210> SEQ ID NO 847
<211> LENGTH: 44
<212> TYPE: DNA
<213> ORGANISM: Artificial Sequence
<220> FEATURE:
<223> OTHER INFORMATION: Synthetic

<400> SEQUENCE: 847
agacgtgtgc tcttccgatc tgcatgagac acagtttcac tctg                        44

<210> SEQ ID NO 848
<211> LENGTH: 42
<212> TYPE: DNA
<213> ORGANISM: Artificial Sequence
<220> FEATURE:
<223> OTHER INFORMATION: Synthetic

<400> SEQUENCE: 848
agacgtgtgc tcttccgatc tgagagagtc tcactgcgtt gc                          42

<210> SEQ ID NO 849
<211> LENGTH: 41
<212> TYPE: DNA
<213> ORGANISM: Artificial Sequence
<220> FEATURE:
<223> OTHER INFORMATION: Synthetic

<400> SEQUENCE: 849
ctacacgacg ctcttccgat cttctctcac ccactgggca c                           41

<210> SEQ ID NO 850
<211> LENGTH: 40
<212> TYPE: DNA
<213> ORGANISM: Artificial Sequence
<220> FEATURE:
<223> OTHER INFORMATION: Synthetic

<400> SEQUENCE: 850
agacgtgtgc tcttccgatc tgcttccaga cgagtgcaga                             40

<210> SEQ ID NO 851
<211> LENGTH: 49
<212> TYPE: DNA
<213> ORGANISM: Artificial Sequence
<220> FEATURE:
<223> OTHER INFORMATION: Synthetic

<400> SEQUENCE: 851
ctacacgacg ctcttccgat ctaagttttc aaaccagaag aactacgac                   49

<210> SEQ ID NO 852
<211> LENGTH: 42
```

-continued

```
<212> TYPE: DNA
<213> ORGANISM: Artificial Sequence
<220> FEATURE:
<223> OTHER INFORMATION: Synthetic

<400> SEQUENCE: 852
ctacacgacg ctcttccgat ctccggtata agtcctggag cg                         42

<210> SEQ ID NO 853
<211> LENGTH: 42
<212> TYPE: DNA
<213> ORGANISM: Artificial Sequence
<220> FEATURE:
<223> OTHER INFORMATION: Synthetic

<400> SEQUENCE: 853
ctacacgacg ctcttccgat ctccggtata agtcctggag cg                         42

<210> SEQ ID NO 854
<211> LENGTH: 41
<212> TYPE: DNA
<213> ORGANISM: Artificial Sequence
<220> FEATURE:
<223> OTHER INFORMATION: Synthetic

<400> SEQUENCE: 854
ctacacgacg ctcttccgat ctcctcgaat tccacggggt t                          41

<210> SEQ ID NO 855
<211> LENGTH: 42
<212> TYPE: DNA
<213> ORGANISM: Artificial Sequence
<220> FEATURE:
<223> OTHER INFORMATION: Synthetic

<400> SEQUENCE: 855
ctacacgacg ctcttccgat ctgttggtgg gagggaagtg ag                         42

<210> SEQ ID NO 856
<211> LENGTH: 40
<212> TYPE: DNA
<213> ORGANISM: Artificial Sequence
<220> FEATURE:
<223> OTHER INFORMATION: Synthetic

<400> SEQUENCE: 856
ctacacgacg ctcttccgat ctgatggcgg ttgtagcggc                            40

<210> SEQ ID NO 857
<211> LENGTH: 46
<212> TYPE: DNA
<213> ORGANISM: Artificial Sequence
<220> FEATURE:
<223> OTHER INFORMATION: Synthetic

<400> SEQUENCE: 857
ctacacgacg ctcttccgat ctcacataaa cctatgtttc agcaga                     46

<210> SEQ ID NO 858
<211> LENGTH: 44
<212> TYPE: DNA
<213> ORGANISM: Artificial Sequence
<220> FEATURE:
<223> OTHER INFORMATION: Synthetic

<400> SEQUENCE: 858
```

-continued

```
ctacacgacg ctcttccgat ctgctagttg gattgaagca gggt                      44

<210> SEQ ID NO 859
<211> LENGTH: 40
<212> TYPE: DNA
<213> ORGANISM: Artificial Sequence
<220> FEATURE:
<223> OTHER INFORMATION: Synthetic

<400> SEQUENCE: 859
ctacacgacg ctcttccgat ctttgagtgc ggcagcttcc                           40

<210> SEQ ID NO 860
<211> LENGTH: 43
<212> TYPE: DNA
<213> ORGANISM: Artificial Sequence
<220> FEATURE:
<223> OTHER INFORMATION: Synthetic

<400> SEQUENCE: 860
ctacacgacg ctcttccgat ctataaccct cccaggcaaa gtc                       43

<210> SEQ ID NO 861
<211> LENGTH: 41
<212> TYPE: DNA
<213> ORGANISM: Artificial Sequence
<220> FEATURE:
<223> OTHER INFORMATION: Synthetic

<400> SEQUENCE: 861
ctacacgacg ctcttccgat ctagcctgca catctgagct c                         41

<210> SEQ ID NO 862
<211> LENGTH: 41
<212> TYPE: DNA
<213> ORGANISM: Artificial Sequence
<220> FEATURE:
<223> OTHER INFORMATION: Synthetic

<400> SEQUENCE: 862
ctacacgacg ctcttccgat ctggagcatt gaagtgcctg g                         41

<210> SEQ ID NO 863
<211> LENGTH: 41
<212> TYPE: DNA
<213> ORGANISM: Artificial Sequence
<220> FEATURE:
<223> OTHER INFORMATION: Synthetic

<400> SEQUENCE: 863
ctacacgacg ctcttccgat ctggagcatt gaagtgcctg g                         41

<210> SEQ ID NO 864
<211> LENGTH: 39
<212> TYPE: DNA
<213> ORGANISM: Artificial Sequence
<220> FEATURE:
<223> OTHER INFORMATION: Synthetic

<400> SEQUENCE: 864
agacgtgtgc tcttccgatc tcatcctcga cagtcgcgg                            39

<210> SEQ ID NO 865
<211> LENGTH: 47
<212> TYPE: DNA
<213> ORGANISM: Artificial Sequence
```

-continued

```
<220> FEATURE:
<223> OTHER INFORMATION: Synthetic

<400> SEQUENCE: 865
agacgtgtgc tcttccgatc tgactgatca agtagaatac tcatggg                 47

<210> SEQ ID NO 866
<211> LENGTH: 39
<212> TYPE: DNA
<213> ORGANISM: Artificial Sequence
<220> FEATURE:
<223> OTHER INFORMATION: Synthetic

<400> SEQUENCE: 866
agacgtgtgc tcttccgatc tccctgccag cactgaagc                          39

<210> SEQ ID NO 867
<211> LENGTH: 47
<212> TYPE: DNA
<213> ORGANISM: Artificial Sequence
<220> FEATURE:
<223> OTHER INFORMATION: Synthetic

<400> SEQUENCE: 867
agacgtgtgc tcttccgatc tggttcctat ctttctagac caggagt                 47

<210> SEQ ID NO 868
<211> LENGTH: 39
<212> TYPE: DNA
<213> ORGANISM: Artificial Sequence
<220> FEATURE:
<223> OTHER INFORMATION: Synthetic

<400> SEQUENCE: 868
agacgtgtgc tcttccgatc tagtgtggag ggctcaggg                          39

<210> SEQ ID NO 869
<211> LENGTH: 40
<212> TYPE: DNA
<213> ORGANISM: Artificial Sequence
<220> FEATURE:
<223> OTHER INFORMATION: Synthetic

<400> SEQUENCE: 869
agacgtgtgc tcttccgatc tgatgggcag aggaaggcaa                         40

<210> SEQ ID NO 870
<211> LENGTH: 41
<212> TYPE: DNA
<213> ORGANISM: Artificial Sequence
<220> FEATURE:
<223> OTHER INFORMATION: Synthetic

<400> SEQUENCE: 870
agacgtgtgc tcttccgatc ttcactctca tgagcgtccc a                       41

<210> SEQ ID NO 871
<211> LENGTH: 41
<212> TYPE: DNA
<213> ORGANISM: Artificial Sequence
<220> FEATURE:
<223> OTHER INFORMATION: Synthetic

<400> SEQUENCE: 871
ctacacgacg ctcttccgat ctaaggttcc ttgcggttcg c                       41
```

-continued

```
<210> SEQ ID NO 872
<211> LENGTH: 38
<212> TYPE: DNA
<213> ORGANISM: Artificial Sequence
<220> FEATURE:
<223> OTHER INFORMATION: Synthetic

<400> SEQUENCE: 872
agacgtgtgc tcttccgatc tcgctgccat tgctccct                            38

<210> SEQ ID NO 873
<211> LENGTH: 43
<212> TYPE: DNA
<213> ORGANISM: Artificial Sequence
<220> FEATURE:
<223> OTHER INFORMATION: Synthetic

<400> SEQUENCE: 873
ctacacgacg ctcttccgat cttctcgcac attcttcacg tcc                      43

<210> SEQ ID NO 874
<211> LENGTH: 42
<212> TYPE: DNA
<213> ORGANISM: Artificial Sequence
<220> FEATURE:
<223> OTHER INFORMATION: Synthetic

<400> SEQUENCE: 874
agacgtgtgc tcttccgatc taggaacctt cccgacttag gg                       42

<210> SEQ ID NO 875
<211> LENGTH: 44
<212> TYPE: DNA
<213> ORGANISM: Artificial Sequence
<220> FEATURE:
<223> OTHER INFORMATION: Synthetic

<400> SEQUENCE: 875
ctacacgacg ctcttccgat ctcccgccca tcttctagaa agac                     44

<210> SEQ ID NO 876
<211> LENGTH: 40
<212> TYPE: DNA
<213> ORGANISM: Artificial Sequence
<220> FEATURE:
<223> OTHER INFORMATION: Synthetic

<400> SEQUENCE: 876
ctacacgacg ctcttccgat cttgccaggt gagggactgg                          40

<210> SEQ ID NO 877
<211> LENGTH: 41
<212> TYPE: DNA
<213> ORGANISM: Artificial Sequence
<220> FEATURE:
<223> OTHER INFORMATION: Synthetic

<400> SEQUENCE: 877
agacgtgtgc tcttccgatc ttctgggagt tctctgctgc c                        41

<210> SEQ ID NO 878
<211> LENGTH: 41
<212> TYPE: DNA
<213> ORGANISM: Artificial Sequence
<220> FEATURE:
<223> OTHER INFORMATION: Synthetic
```

<400> SEQUENCE: 878
agacgtgtgc tcttccgatc ttgcccaacc ttagcaagga g                          41

<210> SEQ ID NO 879
<211> LENGTH: 40
<212> TYPE: DNA
<213> ORGANISM: Artificial Sequence
<220> FEATURE:
<223> OTHER INFORMATION: Synthetic

<400> SEQUENCE: 879
ctacacgacg ctcttccgat cttaccttgg agcaacggcg                            40

<210> SEQ ID NO 880
<211> LENGTH: 39
<212> TYPE: DNA
<213> ORGANISM: Artificial Sequence
<220> FEATURE:
<223> OTHER INFORMATION: Synthetic

<400> SEQUENCE: 880
agacgtgtgc tcttccgatc tcccaggacg aggatggag                             39

<210> SEQ ID NO 881
<211> LENGTH: 20
<212> TYPE: DNA
<213> ORGANISM: Artificial Sequence
<220> FEATURE:
<223> OTHER INFORMATION: Synthetic

<400> SEQUENCE: 881
gatagtcact ccaggggttg                                                  20

<210> SEQ ID NO 882
<211> LENGTH: 20
<212> TYPE: DNA
<213> ORGANISM: Artificial Sequence
<220> FEATURE:
<223> OTHER INFORMATION: Synthetic

<400> SEQUENCE: 882
gtggtgaacc aatcagtcct                                                  20

<210> SEQ ID NO 883
<211> LENGTH: 60
<212> TYPE: PRT
<213> ORGANISM: Artificial Sequence
<220> FEATURE:
<223> OTHER INFORMATION: Synthetic

<400> SEQUENCE: 883

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met
    50                  55                  60

<210> SEQ ID NO 884
<211> LENGTH: 49
<212> TYPE: PRT

-continued

```
<213> ORGANISM: Artificial Sequence
<220> FEATURE:
<223> OTHER INFORMATION: Synthetic

<400> SEQUENCE: 884

Leu Tyr Ser Asn Asp Leu Ile Lys Val Gln Leu Lys Lys Asp Ser Phe
1               5                   10                  15

Leu Gly Tyr Phe Ser Gly Leu Asp Arg Ala Thr Gly Ala Ile Ser Leu
            20                  25                  30

Arg Glu His Asp Leu Glu Lys Ser Lys Gly Lys Asp Gly Met His Arg
        35                  40                  45

Ile

<210> SEQ ID NO 885
<211> LENGTH: 30
<212> TYPE: DNA
<213> ORGANISM: Artificial Sequence
<220> FEATURE:
<223> OTHER INFORMATION: Synthetic

<400> SEQUENCE: 885
tccagctcga ccaggatggg caccacccg                                     30

<210> SEQ ID NO 886
<211> LENGTH: 30
<212> TYPE: DNA
<213> ORGANISM: Artificial Sequence
<220> FEATURE:
<223> OTHER INFORMATION: Synthetic

<400> SEQUENCE: 886
tccagctcga ccaggatggg caccacccg                                     30

<210> SEQ ID NO 887
<211> LENGTH: 30
<212> TYPE: DNA
<213> ORGANISM: Artificial Sequence
<220> FEATURE:
<223> OTHER INFORMATION: Synthetic

<400> SEQUENCE: 887
ttcagctcga ccaggatggg caccacccg                                     30

<210> SEQ ID NO 888
<211> LENGTH: 30
<212> TYPE: DNA
<213> ORGANISM: Artificial Sequence
<220> FEATURE:
<223> OTHER INFORMATION: Synthetic

<400> SEQUENCE: 888
tccagcttga ccaggatggg caccacccg                                     30

<210> SEQ ID NO 889
<211> LENGTH: 30
<212> TYPE: DNA
<213> ORGANISM: Artificial Sequence
<220> FEATURE:
<223> OTHER INFORMATION: Synthetic

<400> SEQUENCE: 889
ttcagcttga ccaggatggg caccacccg                                     30

<210> SEQ ID NO 890
```

-continued

```
<211> LENGTH: 30
<212> TYPE: DNA
<213> ORGANISM: Artificial Sequence
<220> FEATURE:
<223> OTHER INFORMATION: Synthetic

<400> SEQUENCE: 890
ggtcgagctg gacggcgacg taaacggcca                                    30

<210> SEQ ID NO 891
<211> LENGTH: 30
<212> TYPE: DNA
<213> ORGANISM: Artificial Sequence
<220> FEATURE:
<223> OTHER INFORMATION: Synthetic

<400> SEQUENCE: 891
ggtcgagctg gacggcgacg taaacggcca                                    30

<210> SEQ ID NO 892
<211> LENGTH: 30
<212> TYPE: DNA
<213> ORGANISM: Artificial Sequence
<220> FEATURE:
<223> OTHER INFORMATION: Synthetic

<400> SEQUENCE: 892
ggttgagctg gacggcgacg taaacggcca                                    30

<210> SEQ ID NO 893
<211> LENGTH: 30
<212> TYPE: DNA
<213> ORGANISM: Artificial Sequence
<220> FEATURE:
<223> OTHER INFORMATION: Synthetic

<400> SEQUENCE: 893
agttcatctg caccaccggc aagctgcccg                                    30

<210> SEQ ID NO 894
<211> LENGTH: 30
<212> TYPE: DNA
<213> ORGANISM: Artificial Sequence
<220> FEATURE:
<223> OTHER INFORMATION: Synthetic

<400> SEQUENCE: 894
agttcatctg caccaccggc aagctgcccg                                    30

<210> SEQ ID NO 895
<211> LENGTH: 30
<212> TYPE: DNA
<213> ORGANISM: Artificial Sequence
<220> FEATURE:
<223> OTHER INFORMATION: Synthetic

<400> SEQUENCE: 895
agtttatctg caccaccggc aagctgcccg                                    30

<210> SEQ ID NO 896
<211> LENGTH: 30
<212> TYPE: DNA
<213> ORGANISM: Artificial Sequence
<220> FEATURE:
<223> OTHER INFORMATION: Synthetic

<400> SEQUENCE: 896
```

```
agttcatttg caccaccggc aagctgcccg                                       30

<210> SEQ ID NO 897
<211> LENGTH: 30
<212> TYPE: DNA
<213> ORGANISM: Artificial Sequence
<220> FEATURE:
<223> OTHER INFORMATION: Synthetic

<400> SEQUENCE: 897
cgtgccctgg cccaccctcg tgaccaccct                                       30

<210> SEQ ID NO 898
<211> LENGTH: 30
<212> TYPE: DNA
<213> ORGANISM: Artificial Sequence
<220> FEATURE:
<223> OTHER INFORMATION: Synthetic

<400> SEQUENCE: 898
cgtgccctgg cccaccctcg tgaccaccct                                       30

<210> SEQ ID NO 899
<211> LENGTH: 30
<212> TYPE: DNA
<213> ORGANISM: Artificial Sequence
<220> FEATURE:
<223> OTHER INFORMATION: Synthetic

<400> SEQUENCE: 899
cgtgccttgg cccaccctcg tgaccaccct                                       30

<210> SEQ ID NO 900
<211> LENGTH: 30
<212> TYPE: DNA
<213> ORGANISM: Artificial Sequence
<220> FEATURE:
<223> OTHER INFORMATION: Synthetic

<400> SEQUENCE: 900
ggcctttccc tgtagccctg gggggagcca                                       30

<210> SEQ ID NO 901
<211> LENGTH: 30
<212> TYPE: DNA
<213> ORGANISM: Artificial Sequence
<220> FEATURE:
<223> OTHER INFORMATION: Synthetic

<400> SEQUENCE: 901
ggcctttccc tgtagccctg gggggagcca                                       30

<210> SEQ ID NO 902
<211> LENGTH: 30
<212> TYPE: DNA
<213> ORGANISM: Artificial Sequence
<220> FEATURE:
<223> OTHER INFORMATION: Synthetic

<400> SEQUENCE: 902
ggccttttcc tgtagccctg gggggagcca                                       30

<210> SEQ ID NO 903
<211> LENGTH: 30
<212> TYPE: DNA
```

<213> ORGANISM: Artificial Sequence
<220> FEATURE:
<223> OTHER INFORMATION: Synthetic

<400> SEQUENCE: 903
ggcctttttc tgtagccctg gggggagcca                                          30

<210> SEQ ID NO 904
<211> LENGTH: 30
<212> TYPE: DNA
<213> ORGANISM: Artificial Sequence
<220> FEATURE:
<223> OTHER INFORMATION: Synthetic

<400> SEQUENCE: 904
ggcctttacc tgtagccctg gggggagcca                                          30

<210> SEQ ID NO 905
<211> LENGTH: 30
<212> TYPE: DNA
<213> ORGANISM: Artificial Sequence
<220> FEATURE:
<223> OTHER INFORMATION: Synthetic

<400> SEQUENCE: 905
ggcctttttt tgtagccctg gggggagcca                                          30

<210> SEQ ID NO 906
<211> LENGTH: 30
<212> TYPE: DNA
<213> ORGANISM: Artificial Sequence
<220> FEATURE:
<223> OTHER INFORMATION: Synthetic

<400> SEQUENCE: 906
ggcctttgcc tgtagccctg gggggagcca                                          30

<210> SEQ ID NO 907
<211> LENGTH: 30
<212> TYPE: DNA
<213> ORGANISM: Artificial Sequence
<220> FEATURE:
<223> OTHER INFORMATION: Synthetic

<400> SEQUENCE: 907 ggcctttttct tgtagccctg gggggagcca                                         30

<210> SEQ ID NO 908
<211> LENGTH: 29
<212> TYPE: DNA
<213> ORGANISM: Artificial Sequence
<220> FEATURE:
<223> OTHER INFORMATION: Synthetic

<400> SEQUENCE: 908
ggcctttcct gtagccctgg gggagcca                                            29

<210> SEQ ID NO 909
<211> LENGTH: 30
<212> TYPE: DNA
<213> ORGANISM: Artificial Sequence
<220> FEATURE:
<223> OTHER INFORMATION: Synthetic

<400> SEQUENCE: 909
ggcctttcct tgtagccctg gggggagcca                                          30

```
<210> SEQ ID NO 910
<211> LENGTH: 30
<212> TYPE: DNA
<213> ORGANISM: Artificial Sequence
<220> FEATURE:
<223> OTHER INFORMATION: Synthetic

<400> SEQUENCE: 910
ggcctttctc tgtagccctg gggggagcca                                   30

<210> SEQ ID NO 911
<211> LENGTH: 30
<212> TYPE: DNA
<213> ORGANISM: Artificial Sequence
<220> FEATURE:
<223> OTHER INFORMATION: Synthetic

<400> SEQUENCE: 911
cagggctaca gggaaaggcc gaggaaacct                                   30

<210> SEQ ID NO 912
<211> LENGTH: 30
<212> TYPE: DNA
<213> ORGANISM: Artificial Sequence
<220> FEATURE:
<223> OTHER INFORMATION: Synthetic

<400> SEQUENCE: 912
cagggctaca gggaaaggcc gaggaaacct                                   30

<210> SEQ ID NO 913
<211> LENGTH: 30
<212> TYPE: DNA
<213> ORGANISM: Artificial Sequence
<220> FEATURE:
<223> OTHER INFORMATION: Synthetic

<400> SEQUENCE: 913
cagggctgca gggaaaggcc gaggaaacct                                   30

<210> SEQ ID NO 914
<211> LENGTH: 30
<212> TYPE: DNA
<213> ORGANISM: Artificial Sequence
<220> FEATURE:
<223> OTHER INFORMATION: Synthetic

<400> SEQUENCE: 914
cagggctaca gggaaaggcc gaggaaacct                                   30

<210> SEQ ID NO 915
<211> LENGTH: 30
<212> TYPE: DNA
<213> ORGANISM: Artificial Sequence
<220> FEATURE:
<223> OTHER INFORMATION: Synthetic

<400> SEQUENCE: 915
cagggctaca gggaaaggcc gaggaaacct                                   30

<210> SEQ ID NO 916
<211> LENGTH: 30
<212> TYPE: DNA
<213> ORGANISM: Artificial Sequence
<220> FEATURE:
```

<223> OTHER INFORMATION: Synthetic

<400> SEQUENCE: 916
cagggctgca gggaaaggcc gaggaaacct                    30

<210> SEQ ID NO 917
<211> LENGTH: 40
<212> TYPE: DNA
<213> ORGANISM: Artificial Sequence
<220> FEATURE:
<223> OTHER INFORMATION: Synthetic

<400> SEQUENCE: 917
aacgactgga gcagtaatgc ctggtggccc agcttcctct         40

<210> SEQ ID NO 918
<211> LENGTH: 40
<212> TYPE: DNA
<213> ORGANISM: Artificial Sequence
<220> FEATURE:
<223> OTHER INFORMATION: Synthetic

<400> SEQUENCE: 918
aacgactgga gcggtaatgc ctggtggccc agcttcctct         40

<210> SEQ ID NO 919
<211> LENGTH: 24
<212> TYPE: DNA
<213> ORGANISM: Artificial Sequence
<220> FEATURE:
<223> OTHER INFORMATION: Synthetic

<400> SEQUENCE: 919
gtgaacttgt ggccgtttac gtcg                          24

<210> SEQ ID NO 920
<211> LENGTH: 24
<212> TYPE: DNA
<213> ORGANISM: Artificial Sequence
<220> FEATURE:
<223> OTHER INFORMATION: Synthetic

<400> SEQUENCE: 920
gtgaacttgt ggccgtttac gtcc                          24

<210> SEQ ID NO 921
<211> LENGTH: 24
<212> TYPE: DNA
<213> ORGANISM: Artificial Sequence
<220> FEATURE:
<223> OTHER INFORMATION: Synthetic

<400> SEQUENCE: 921
gtgaacttgt ggccgtttac gtgg                          24

<210> SEQ ID NO 922
<211> LENGTH: 24
<212> TYPE: DNA
<213> ORGANISM: Artificial Sequence
<220> FEATURE:
<223> OTHER INFORMATION: Synthetic

<400> SEQUENCE: 922
gtgaacttgt ggccgtttac gacg                          24

-continued

```
<210> SEQ ID NO 923
<211> LENGTH: 24
<212> TYPE: DNA
<213> ORGANISM: Artificial Sequence
<220> FEATURE:
<223> OTHER INFORMATION: Synthetic

<400> SEQUENCE: 923
gtgaacttgt ggccgtttac ctcg                                          24

<210> SEQ ID NO 924
<211> LENGTH: 24
<212> TYPE: DNA
<213> ORGANISM: Artificial Sequence
<220> FEATURE:
<223> OTHER INFORMATION: Synthetic

<400> SEQUENCE: 924
gtgaacttgt ggccgtttag gtcg                                          24

<210> SEQ ID NO 925
<211> LENGTH: 24
<212> TYPE: DNA
<213> ORGANISM: Artificial Sequence
<220> FEATURE:
<223> OTHER INFORMATION: Synthetic

<400> SEQUENCE: 925
gtgaacttgt ggccgttttc gtcg                                          24

<210> SEQ ID NO 926
<211> LENGTH: 24
<212> TYPE: DNA
<213> ORGANISM: Artificial Sequence
<220> FEATURE:
<223> OTHER INFORMATION: Synthetic

<400> SEQUENCE: 926
gtgaacttgt ggccgttaac gtcg                                          24

<210> SEQ ID NO 927
<211> LENGTH: 24
<212> TYPE: DNA
<213> ORGANISM: Artificial Sequence
<220> FEATURE:
<223> OTHER INFORMATION: Synthetic

<400> SEQUENCE: 927
gtgaacttgt ggccgtatac gtcg                                          24

<210> SEQ ID NO 928
<211> LENGTH: 24
<212> TYPE: DNA
<213> ORGANISM: Artificial Sequence
<220> FEATURE:
<223> OTHER INFORMATION: Synthetic

<400> SEQUENCE: 928
gtgaacttgt ggccgattac gtcg                                          24

<210> SEQ ID NO 929
<211> LENGTH: 24
<212> TYPE: DNA
<213> ORGANISM: Artificial Sequence
<220> FEATURE:
<223> OTHER INFORMATION: Synthetic
```

-continued

```
<400> SEQUENCE: 929
gtgaacttgt ggccctttac gtcg                                             24

<210> SEQ ID NO 930
<211> LENGTH: 24
<212> TYPE: DNA
<213> ORGANISM: Artificial Sequence
<220> FEATURE:
<223> OTHER INFORMATION: Synthetic

<400> SEQUENCE: 930
gtgaacttgt ggcggtttac gtcg                                             24

<210> SEQ ID NO 931
<211> LENGTH: 24
<212> TYPE: DNA
<213> ORGANISM: Artificial Sequence
<220> FEATURE:
<223> OTHER INFORMATION: Synthetic

<400> SEQUENCE: 931
gtgaacttgt gggcgtttac gtcg                                             24

<210> SEQ ID NO 932
<211> LENGTH: 24
<212> TYPE: DNA
<213> ORGANISM: Artificial Sequence
<220> FEATURE:
<223> OTHER INFORMATION: Synthetic

<400> SEQUENCE: 932
gtgaacttgt gcccgtttac gtcg                                             24

<210> SEQ ID NO 933
<211> LENGTH: 24
<212> TYPE: DNA
<213> ORGANISM: Artificial Sequence
<220> FEATURE:
<223> OTHER INFORMATION: Synthetic

<400> SEQUENCE: 933
gtgaacttgt cgccgtttac gtcg                                             24

<210> SEQ ID NO 934
<211> LENGTH: 24
<212> TYPE: DNA
<213> ORGANISM: Artificial Sequence
<220> FEATURE:
<223> OTHER INFORMATION: Synthetic

<400> SEQUENCE: 934
gtgaacttga ggccgtttac gtcg                                             24

<210> SEQ ID NO 935
<211> LENGTH: 24
<212> TYPE: DNA
<213> ORGANISM: Artificial Sequence
<220> FEATURE:
<223> OTHER INFORMATION: Synthetic

<400> SEQUENCE: 935
gtgaacttct ggccgtttac gtcg                                             24

<210> SEQ ID NO 936
<211> LENGTH: 24
```

-continued

```
<212> TYPE: DNA
<213> ORGANISM: Artificial Sequence
<220> FEATURE:
<223> OTHER INFORMATION: Synthetic

<400> SEQUENCE: 936
gtgaactagt ggccgtttac gtcg                                          24

<210> SEQ ID NO 937
<211> LENGTH: 24
<212> TYPE: DNA
<213> ORGANISM: Artificial Sequence
<220> FEATURE:
<223> OTHER INFORMATION: Synthetic

<400> SEQUENCE: 937
gtgaacatgt ggccgtttac gtcg                                          24

<210> SEQ ID NO 938
<211> LENGTH: 24
<212> TYPE: DNA
<213> ORGANISM: Artificial Sequence
<220> FEATURE:
<223> OTHER INFORMATION: Synthetic

<400> SEQUENCE: 938
gtgaagttgt ggccgtttac gtcg                                          24

<210> SEQ ID NO 939
<211> LENGTH: 24
<212> TYPE: DNA
<213> ORGANISM: Artificial Sequence
<220> FEATURE:
<223> OTHER INFORMATION: Synthetic

<400> SEQUENCE: 939
gtgatcttgt ggccgtttac gtcg                                          24

<210> SEQ ID NO 940
<211> LENGTH: 24
<212> TYPE: DNA
<213> ORGANISM: Artificial Sequence
<220> FEATURE:
<223> OTHER INFORMATION: Synthetic

<400> SEQUENCE: 940
gtgtacttgt ggccgtttac gtcg                                          24

<210> SEQ ID NO 941
<211> LENGTH: 24
<212> TYPE: DNA
<213> ORGANISM: Artificial Sequence
<220> FEATURE:
<223> OTHER INFORMATION: Synthetic

<400> SEQUENCE: 941
gtcaacttgt ggccgtttac gtcg                                          24

<210> SEQ ID NO 942
<211> LENGTH: 24
<212> TYPE: DNA
<213> ORGANISM: Artificial Sequence
<220> FEATURE:
<223> OTHER INFORMATION: Synthetic

<400> SEQUENCE: 942
```

-continued

```
gagaacttgt ggccgtttac gtcg                                            24

<210> SEQ ID NO 943
<211> LENGTH: 30
<212> TYPE: DNA
<213> ORGANISM: Artificial Sequence
<220> FEATURE:
<223> OTHER INFORMATION: Synthetic

<400> SEQUENCE: 943
ctcactcacc cacacagaca cacacgtcct                                      30

<210> SEQ ID NO 944
<211> LENGTH: 30
<212> TYPE: DNA
<213> ORGANISM: Artificial Sequence
<220> FEATURE:
<223> OTHER INFORMATION: Synthetic

<400> SEQUENCE: 944
cacacacacc cacacagaca cacccccccc                                      30

<210> SEQ ID NO 945
<211> LENGTH: 30
<212> TYPE: DNA
<213> ORGANISM: Artificial Sequence
<220> FEATURE:
<223> OTHER INFORMATION: Synthetic

<400> SEQUENCE: 945
ctccctcaca cacacagaca cacacctccc                                      30

<210> SEQ ID NO 946
<211> LENGTH: 30
<212> TYPE: DNA
<213> ORGANISM: Artificial Sequence
<220> FEATURE:
<223> OTHER INFORMATION: Synthetic

<400> SEQUENCE: 946
cacacacaca cacacagaca cacacacccc                                      30

<210> SEQ ID NO 947
<211> LENGTH: 31
<212> TYPE: DNA
<213> ORGANISM: Artificial Sequence
<220> FEATURE:
<223> OTHER INFORMATION: Synthetic

<400> SEQUENCE: 947
gtgtgtccct ctccccaccc gtccctgtcc g                                    31

<210> SEQ ID NO 948
<211> LENGTH: 31
<212> TYPE: DNA
<213> ORGANISM: Artificial Sequence
<220> FEATURE:
<223> OTHER INFORMATION: Synthetic

<400> SEQUENCE: 948
ttgtctccct gtccccaccc gtccccttca g                                    31

<210> SEQ ID NO 949
<211> LENGTH: 31
<212> TYPE: DNA
<213> ORGANISM: Artificial Sequence
```

<220> FEATURE:
<223> OTHER INFORMATION: Synthetic

<400> SEQUENCE: 949
ctgcctccct ctgcccaccc gtccttccca c                                         31

<210> SEQ ID NO 950
<211> LENGTH: 31
<212> TYPE: DNA
<213> ORGANISM: Artificial Sequence
<220> FEATURE:
<223> OTHER INFORMATION: Synthetic

<400> SEQUENCE: 950
ctgtgcctct ctccccaccc ttccacaccc t                                         31

<210> SEQ ID NO 951
<211> LENGTH: 31
<212> TYPE: DNA
<213> ORGANISM: Artificial Sequence
<220> FEATURE:
<223> OTHER INFORMATION: Synthetic

<400> SEQUENCE: 951
gctcatcccc ctccccaccc gtcctcgccc g                                         31

<210> SEQ ID NO 952

<400> SEQUENCE: 952

000

<210> SEQ ID NO 953
<211> LENGTH: 31
<212> TYPE: DNA
<213> ORGANISM: Artificial Sequence
<220> FEATURE:
<223> OTHER INFORMATION: Synthetic

<400> SEQUENCE: 953
tgaggaccgc cctgggcctg ggagaatccc t                                         31

<210> SEQ ID NO 954
<211> LENGTH: 31
<212> TYPE: DNA
<213> ORGANISM: Artificial Sequence
<220> FEATURE:
<223> OTHER INFORMATION: Synthetic

<400> SEQUENCE: 954
gaaggaccac cctaggcctg ggagactccc t                                         31

<210> SEQ ID NO 955
<211> LENGTH: 100
<212> TYPE: DNA
<213> ORGANISM: Artificial Sequence
<220> FEATURE:
<223> OTHER INFORMATION: Synthetic

<400> SEQUENCE: 955
tcctatggtg tctagaatgg tgagcaaggg cgaggaggac aacatggcca tcatcaagga         60
gttcatgcgc ttcaaggtgc acatggaggg ctccgtgaac                              100

<210> SEQ ID NO 956
<211> LENGTH: 100

-continued

```
<212> TYPE: DNA
<213> ORGANISM: Artificial Sequence
<220> FEATURE:
<223> OTHER INFORMATION: Synthetic

<400> SEQUENCE: 956
aggataccac agatcttacc actcgttccc gctcctcctg ttgtaccggt agtagttcct      60
caagtacgcg aagttccacg tgtacctccc gaggcacttg                           100

<210> SEQ ID NO 957
<211> LENGTH: 33
<212> TYPE: PRT
<213> ORGANISM: Artificial Sequence
<220> FEATURE:
<223> OTHER INFORMATION: Synthetic

<400> SEQUENCE: 957

Pro Met Val Ser Arg Met Val Ser Lys Gly Glu Glu Asp Asn Met Ala
1               5                   10                  15

Ile Ile Lys Glu Phe Met Arg Phe Lys Val His Met Glu Gly Ser Val
            20                  25                  30

Asn

<210> SEQ ID NO 958
<211> LENGTH: 100
<212> TYPE: DNA
<213> ORGANISM: Artificial Sequence
<220> FEATURE:
<223> OTHER INFORMATION: Synthetic

<400> SEQUENCE: 958
ggccacgagt tcgagatcga gggtgagggt gagggccgac cctacgaggg cacctagacc      60
gccaagctga aggtgaccaa gggcggaccc ctgcccttcg                           100

<210> SEQ ID NO 959
<211> LENGTH: 98
<212> TYPE: DNA
<213> ORGANISM: Artificial Sequence
<220> FEATURE:
<223> OTHER INFORMATION: Synthetic

<400> SEQUENCE: 959
ccggtgctca agctctagct cccactccca ctcccggctg ggatgctccc gtggatctgg      60
cggttcgact tccactggtt cccgcctggg acggaagc                             98

<210> SEQ ID NO 960
<211> LENGTH: 32
<212> TYPE: PRT
<213> ORGANISM: Artificial Sequence
<220> FEATURE:
<223> OTHER INFORMATION: Synthetic

<400> SEQUENCE: 960

Gly His Glu Phe Glu Ile Glu Gly Glu Gly Glu Gly Arg Pro Tyr Glu
1               5                   10                  15

Gly Thr Thr Ala Lys Leu Lys Val Thr Lys Gly Gly Pro Leu Pro Phe
            20                  25                  30

<210> SEQ ID NO 961
<211> LENGTH: 100
<212> TYPE: DNA
<213> ORGANISM: Artificial Sequence
<220> FEATURE:
```

-continued

<223> OTHER INFORMATION: Synthetic

<400> SEQUENCE: 961
cccgagcagg gccgcatgac caacaagatg aagagcacca aaggcgccct gaccttcagc          60
ccctacctgc tgagccacgt gatgggccac ggcttctacc                                100

<210> SEQ ID NO 962
<211> LENGTH: 100
<212> TYPE: DNA
<213> ORGANISM: Artificial Sequence
<220> FEATURE:
<223> OTHER INFORMATION: Synthetic

<400> SEQUENCE: 962
gggctcgtcc cggcgtactg gttgttctac ttctcgtggt ttccgcggga ctggaagtcg          60
gggatggacg actcggtgca ctacccggtg ccgaagatgg                                100

<210> SEQ ID NO 963
<211> LENGTH: 33
<212> TYPE: PRT
<213> ORGANISM: Artificial Sequence
<220> FEATURE:
<223> OTHER INFORMATION: Synthetic

<400> SEQUENCE: 963

Pro Glu Gln Gly Arg Met Thr Asn Lys Met Lys Ser Thr Lys Gly Ala
1               5                   10                  15

Leu Thr Phe Ser Pro Tyr Leu Leu Ser His Val Met Gly His Gly Phe
            20                  25                  30

Tyr

<210> SEQ ID NO 964
<211> LENGTH: 100
<212> TYPE: DNA
<213> ORGANISM: Artificial Sequence
<220> FEATURE:
<223> OTHER INFORMATION: Synthetic

<400> SEQUENCE: 964
acttcggcac ctaccccagc gggtacgaga accccttcct gcacgccatc aacaacggcg          60
gctacaccaa cacccgcatc gagaagtacg aggacggcgg                                100

<210> SEQ ID NO 965
<211> LENGTH: 100
<212> TYPE: DNA
<213> ORGANISM: Artificial Sequence
<220> FEATURE:
<223> OTHER INFORMATION: Synthetic

<400> SEQUENCE: 965
tgaagccgtg gatggggtcg cccatgctct gggggaagga cgtgcggtag ttgttgccgc          60
cgatgtggtt gtgggcgtag ctcttcatgc tcctgccgcc                                100

<210> SEQ ID NO 966
<211> LENGTH: 34
<212> TYPE: PRT
<213> ORGANISM: Artificial Sequence
<220> FEATURE:
<223> OTHER INFORMATION: Synthetic

<400> SEQUENCE: 966

His Phe Gly Thr Tyr Pro Ser Gly Tyr Glu Asn Pro Phe Leu His Ala

-continued

```
1            5              10             15

Ile Asn Asn Gly Gly Tyr Thr Asn Thr Arg Ile Glu Lys Tyr Glu Asp
          20              25             30

Gly Gly
```

<210> SEQ ID NO 967
<211> LENGTH: 29
<212> TYPE: DNA
<213> ORGANISM: Artificial Sequence
<220> FEATURE:
<223> OTHER INFORMATION: Synthetic

<400> SEQUENCE: 967
gactcttctg catgggtgat gtcaatgcc                                    29

<210> SEQ ID NO 968
<211> LENGTH: 29
<212> TYPE: DNA
<213> ORGANISM: Artificial Sequence
<220> FEATURE:
<223> OTHER INFORMATION: Synthetic

<400> SEQUENCE: 968
ccgccagaac cgagccggct actcggccc                                    29

<210> SEQ ID NO 969
<211> LENGTH: 39
<212> TYPE: DNA
<213> ORGANISM: Artificial Sequence
<220> FEATURE:
<223> OTHER INFORMATION: Synthetic

<400> SEQUENCE: 969
cacacactca ctcacccaca cagacacaca cgtcctcac                         39

<210> SEQ ID NO 970
<211> LENGTH: 39
<212> TYPE: DNA
<213> ORGANISM: Artificial Sequence
<220> FEATURE:
<223> OTHER INFORMATION: Synthetic

<400> SEQUENCE: 970
gtgtgtgagt gagtgggtgt gtctgtgtgt gcaggagtg                         39

<210> SEQ ID NO 971
<211> LENGTH: 29
<212> TYPE: DNA
<213> ORGANISM: Artificial Sequence
<220> FEATURE:
<223> OTHER INFORMATION: Synthetic

<400> SEQUENCE: 971
gcucacucac ccacacagac acacguugu                                    29